(12) United States Patent
Hoveyda et al.

(10) Patent No.: US 9,938,253 B2
(45) Date of Patent: Apr. 10, 2018

(54) CATALYSTS FOR EFFICIENT Z-SELECTIVE METATHESIS

(71) Applicant: Trustees of Boston College, Chestnut Hill, MA (US)

(72) Inventors: Amir H. Hoveyda, Lincoln, MA (US); R. Kashif M. Khan, Boston, MA (US); Sebastian Torker, Brighton, MA (US); Ming Joo Koh, Chestnut Hill, MA (US)

(73) Assignee: Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 14/303,523

(22) Filed: Jun. 12, 2014

(65) Prior Publication Data

US 2014/0371454 A1    Dec. 18, 2014

Related U.S. Application Data

(60) Provisional application No. 61/834,050, filed on Jun. 12, 2013.

(51) Int. Cl.
| | | |
|---|---|---|
| C07F 15/00 | (2006.01) | |
| B01J 31/12 | (2006.01) | |
| C07D 333/56 | (2006.01) | |
| C07F 7/08 | (2006.01) | |
| C07C 41/30 | (2006.01) | |
| C07C 231/12 | (2006.01) | |
| C07C 29/32 | (2006.01) | |
| C07D 209/12 | (2006.01) | |
| C07C 45/68 | (2006.01) | |
| C07C 51/353 | (2006.01) | |
| C07B 37/08 | (2006.01) | |
| C07C 6/06 | (2006.01) | |
| C08G 61/08 | (2006.01) | |
| C07F 5/02 | (2006.01) | |
| B01J 31/22 | (2006.01) | |

(52) U.S. Cl.
CPC .......... *C07D 333/56* (2013.01); *B01J 31/226* (2013.01); *B01J 31/2273* (2013.01); *B01J 31/2278* (2013.01); *C07B 37/08* (2013.01); *C07C 6/06* (2013.01); *C07C 29/32* (2013.01); *C07C 41/30* (2013.01); *C07C 45/68* (2013.01); *C07C 51/353* (2013.01); *C07C 231/12* (2013.01); *C07D 209/12* (2013.01); *C07F 5/025* (2013.01); *C07F 7/0818* (2013.01); *C07F 15/0046* (2013.01); *C08G 61/08* (2013.01); *B01J 2231/543* (2013.01); *B01J 2531/821* (2013.01); *C07B 2200/09* (2013.01); *C07C 2601/08* (2017.05); *C07C 2601/14* (2017.05); *C08G 2261/3324* (2013.01); *C08G 2261/418* (2013.01)

(58) Field of Classification Search
USPC ........... 548/103; 549/3, 206; 546/2; 502/155
See application file for complete search history.

(56) References Cited

U.S. PATENT DOCUMENTS

| | | |
|---|---|---|
| 5,811,515 A | 9/1998 | Grubbs et al. |
| 6,867,303 B2 | 3/2005 | Grela |
| 6,921,735 B2 | 7/2005 | Hoveyda et al. |
| 7,094,898 B2 | 8/2006 | Fogg et al. |
| 7,632,772 B2 | 12/2009 | Zhan |
| 8,049,025 B2 | 11/2011 | Zhan |
| 8,067,623 B2 | 11/2011 | Lee |
| 8,288,576 B2 | 10/2012 | Zhan |
| 8,394,965 B2 | 3/2013 | Mauduit et al. |
| 8,586,757 B2 | 11/2013 | Mauduit et al. |
| 8,895,771 B2 | 11/2014 | Abraham et al. |
| 2007/0043180 A1 | 2/2007 | Zhan |
| 2008/0021219 A1 | 1/2008 | Puentener et al. |
| 2008/0064891 A1 | 3/2008 | Lee |
| 2009/0259065 A1 | 10/2009 | Abraham et al. |
| 2010/0145086 A1 | 6/2010 | Schrodi et al. |
| 2013/0023665 A1 | 1/2013 | Jensen et al. |
| 2013/0231499 A1 | 9/2013 | Grubbs et al. |
| 2014/0106960 A1 | 4/2014 | Endo et al. |
| 2014/0329017 A1 | 11/2014 | Wang et al. |

FOREIGN PATENT DOCUMENTS

| | | |
|---|---|---|
| WO | WO-02/14376 | 2/2002 |
| WO | WO-2008/065187 | 6/2008 |

OTHER PUBLICATIONS

Adlhart, C. and Chen, P. J., Mechanism and Activity of Ruthenium Olefin Metathesis Catalysts: The Role of Ligands and Substrates from a Theoretical Perspective, Am. Chem. Soc., 126: 3496-3510 (2004).

Anderson, D. R. et al., Kinetic Selectivity of Olefin Metathesis Catalysts Bearing Cyclic (Alkyl)(Amino) Carbenes, Organometallics, 27: 563-566 (2008).

Andrae, D. et al., Energy-adjusted ab initio pseudopotentials for the second and third row transition elements, Theor. Chim. Acta, 77: 123-141 (1990).

Bahri-Laleh, N. et al., The intriguing modeling of cis-trans selectivity in ruthenium-catalyzed olefin metathesis, Beilstein J. Org. Chem., 7: 40-45 (2011).

Barbasiewicz, M. et al., Structure and Activity Peculiarities of Ruthenium Quinoline and Quinoxaline Complexes: Novel Metathesis Catalysts, Organometallics, 25: 3599-3604 (2006).

(Continued)

*Primary Examiner* — Charanjit Aulakh
(74) *Attorney, Agent, or Firm* — Stoel Rives LLP

(57) ABSTRACT

The present application provides, among other things, compounds and methods for metathesis reactions. In some embodiments, provided compounds promote highly efficient and highly Z-selective metathesis. In some embodiments, provided compounds and methods are particularly useful for producing allyl alcohols. In some embodiments, provided compounds have the structure of formula I. In some embodiments, provided compounds comprise ruthenium, and a ligand bonded to ruthenium through a sulfur atom.

16 Claims, 28 Drawing Sheets

(56) References Cited

OTHER PUBLICATIONS

Becke, A. D., Density-functional exchange-energy approximation with correct asymptotic behavior, Phys. Rev. A, 38(6): 3098-3100 (1988).
Benitez, D. and Goddard, W. A., The Isomerization Equilibrium between Cis and Trans Chloride Ruthenium Olefin Metathesis Catalysts from Quantum Mechanics Calculations, J. Am. Chem. Soc., 127: 12218-12219 (2005).
Benitez, D. et al., Relevance of cis- and trans-dichloride Ru intermediates in Grubbs-II olefin metathesis catalysis (H2IMesCl2Ru=CHR), Chem. Commun., 6194-6196 (2008).
Borre, E. et al., Design of a library of Hoveyda-Grubbs type olefin metathesis catalysts, Chemistry Today 27(5): 74-78 (2009).
Carpino, L. A. and Barr, D. E., 7-Azabenzonorbornadiene, J. Org. Chem. , 31: 764-767 (1966).
Correa, A. and Cavallo, L., The Elusive mechanism of olefin metathesis promoted by (NHC)Ru-Based catalyst: A Trade between Steric, Electric and Solvent Effects, J. Am. Chem. Soc., 128, 13352-13353 (2006).
Cramer, C. J. and Truhlar, D. G., Density functional theory for transition metals and transition metal chemistry, Phys. Chem. Chem. Phys., 11: 10757-10816 (2009).
Dias, E. L. et al., Well-Defined Ruthenium Olefin Metathesis Catalysts Mechanism and Activity, J. Am. Chem. Soc., 119, 3887-3897 (1997).
Diesendruck, C. E. et al., Predicting the Cis-Trans Dichloro Configuration of Group 15-16 Chelated Ruthenium Olefin Metathesis Complexes: A DFT and Experimental Study, Inorg. Chem., 48: 10819-10825 (2009).
Donohoe, T. J. et al., Heteroaromatic Synthesis via Olefin Cross-Metathesis: Entry to Polysubstituted Pyridines, Org. Lett., 13: 1036-1039 (2011).
Endo, K. and Grubbs, R.H., Chelated ruthenium catalysts for Z-selective olefin metathesis, Journal of the American Chemical Society, 133: 8525-8527 (2011).
Flook, M. M. et al., Z-Selective Olefin Metathesis Processes Catalyzed by a Molybdenum Hexaisopropylterphenoxide Monopyrrolide Complex, J. Am. Chem. Soc., 131: 7962-7963 (2009).
Furstner, A., Teaching Metathesis "Simple" Stereochemistry, Science, 341: 1357-1364 (2013).
Fuwa, H. et al., A Concise Total Synthesis of (+)-Neopeltolide, Angew. Chem. Int. Ed., 49: 3041-3044 (2010).
Garber, S. B. et al., Efficient ad Recyclable Monomeric and Dendritic Ru-Based Metathesis Catalysts, J. Am. Chem. Soc., 122: 8168-8179 (2000).
Hartung, J. and Grubbs, R. H., Highly Z-Selective and Enantioselective Ring-Opening/Cross-Metathesis Catalyzed by a Resolved Sterogenic-at-Ru Complex, J. Am. Chem. Soc., 135: 10183-10185 (2013).
Herbert, M.B. et al., Concise Syntheses of Insect Pheromones Using Z-Selective Cross Metathesis, Angew. Chem. Int. Ed., 52: 310-314 (2012).
Hoveyda, A.H. and A. R. Zhugralin, The remarkable metal-catalysed olefin metathesis reaction, Nature, 450: 243-251 (2007).
Hoveyda, A.H. et al., Catalytic Enantioselective Olefin Metathesis in Natural Product Synthesis. Chiral Metal-Based Complexes that Deliver High Enantioselectivity and More, Angew. Chem., Int. Ed., 49: 34-44 (2010).
Hoveyda, A.H. et al., H-Bonding as a Control Element in Steroselective Ru-Catalyzed Olefin Metathesis, J. Am. Chem. Soc., 131: 8378-8379 (2009).
Hoveyda, A.H. et al., Ru complexes bearing bidentate carbenes: from innocent curiosity to uniquely effective catalysts for olefin metathesis, Org. Biomol. Chem., 2: 8-23 (2004).
Hoye, T. R. and Zhao, H., Some Allylic Substituent Effects in Ring-Closing Metathesis Reactions: Allylic Alcohol Activation, Org. Lett., 1: 1123-1125 (1999).
Ibrahem, I. et al., Highly Z- and Enantioselective Ring-Opening/Cross-Metathesis Reactions Catalyzed by Sterogenic-at-Mo Adamantylimido Complexes, J. Am. Chem. Soc., 131: 3844-3845 (2009).
International Search Report for PCT/US2014/042195, 5 pages (dated Sep. 29, 2014).
Jiang, J. et al., Highly Z-Selective Metathesis Homocoupling of Terminal Olefins, J. Am. Chem. Soc., 131: 16630-16631 (2009).
Kaur, S. et al., Sythesis and Cationic Photopolymerization of 1-Butenyl and 1-Pentenyl Ethers, J. Polym. Sci. A: Polym. Chem., 37: 199-209 (1999).
Keitz, B. K. et al., Z-Selective Homodimerization of Terminal Olefins with a Ruthenium Metathesis Catalyst, J. Am. Chem. Soc., 133: 9686-9688 (2011).
Keitz, B.K. et al., Improved ruthenium catalysts for Z-selective ole fin metathesis, Journal of the American Chemical Society, 134: 693-699 (2012).
Khan, R. K. M. et al., Synthesis, Isolation, Characterization, and Reactivity of High-Energy Sterogenic-at-Ru Carbenes: Stereochemical Inversion through Olefin Metathesis and Other Pathways, J. Am. Chem. Soc., 134: 12774-12779 (2012).
Khan, R. K. M. et al., Z- and Enantioselective ring-Opening/Cross-Metathesis with Enol Ethers Catalyzed by Sterogenic-at-Ru Carbenes: Reactivity, Selectivity, and Curtin-Hammett Kinetics, J. Am. Chem. Soc., 134: 12438-12441 (2012).
Khan, R.K.M. et al., Reactivity and Selectivity Differences between Catecholate and Catechothiolate Ru Complexes. Implication s Regarding Design of Steroselective Olefin Metathesis Catalysts, Journal of the American Chemical Society, 136: 14337-14340 (2014).
Doppiu, A. et al., Synthesis Optimization and Catalytic Activity Screening of Industrially Relevant Ruthenium-Based Metathesis Catalysts, Top Catal, 57: 1351-1358 (2014).
Khan, R.K.M. et al., Readily accessible and easily modifiable Ru-based catalysts for efficient and Z-selective ring-opening metathesis polymerization and ring-opening/cross-metathesis, Journal of the American Chemical Society, 135: 10258-10261 (2013).
Miller, S.J. and Grubbs, R.H., Synthesis of Conformationally Restricted Amino Acids and Peptides Employing Olefin Metathesis, J. Am. Chem. Soc., 117(21): 5855-5856 (1995).
Kiesewetter, E.T. et al., Synthesis of Z-(Pinacolato)allylboron and Z-(Pinacolato)alkenylboron Compounds through Steroselective Catalytic Cross-Metathesis, J. Am. Chem. Soc., 135: 6026-6029 (2013).
Koh, M. et al., Broadly Applicable Z- and Diastereoselective Ring-Opening/Cross-Metathesis Catalyzed by a Dithiolate Ru Complex, Angew.Chem. Int. Ed., 53: 1968-1972 (2014).
Konning, D. et al., One-Pot Oxidation/Isomerization of Z-Allylic Alcohols with Oxygen as Stoichiometric Oxidant, Org. Lett., 14(20): 5258-5261 (2012).
Ledoux, N. et al., Comparative Investigation of Hoveyda-Grubbs Catalysts bearing Modified N-Heterocyclic Carbene Ligands, Adv. Synth. Catal., 349: 1692-1700 (2007).
Lin, Y.A. et al., Olefin Cross-Metathesis on Proteins: Investigation of Allylic Chalcogen Effects and Guiding Principles in Metathesis Partner Selections, J. Am. Chem. Soc., 132: 16805-16811 (2010).
Liu, P. et al., Z-selectivity in olefin metathesis with chelate Ru catalysts: computational studies of mechanism and selectivity, Journal of the American Chemical Society, 134: 1464-1467 (2012).
Lozano-Vila, A. M. et al., Ruthenium-Based Olefin Metathesis Catalysts Derived from Alkynes, Chem. Rev., 110: 4865-4909 (2010).
Mann, T. J. et al., Catalytic Z-Selective Cross-Metathesis with Secondary Silyl- and Benzyl-Protected Allylic Ethers: Mechanistic Aspects and Applications to Natural Product Synthesis, Angew. Chem. Int. Ed., 53: 8395-8400 (2013).
Marrocchi, A. et al., High pressure and thermal Diels-Alder reaction of 2-vinyl-benzo[b]furan and 2-vinyl0benzo[b]thiophene. Synthesis of new condensed heterocycles, Tetrahedron, 57: 4959-4965 (2001).
Meek, S. et al., The Significance of Degenerate Processes to Enanticselective Olefin Metathesis Reactions Promoted by Sterogenic-at-Mo Complexes, J. Am. Chem. Soc., 131: 16407-16409 (2009).

(56) References Cited

OTHER PUBLICATIONS

Meek, S. J. et al., Catalytic Z-selective olefin cross-metathesis for natural product synthesis, Nature, 471: 461-466 (2011).
Mlynarski, S. N. et al., Direct Sterospecific Amination of Alkyl and Aryl Pinacol Boronates, J. Am. Chem. Soc., 134: 16449-16451 (2012).
Monfette, S. and Fogg, D. E. et al., Ruthenium Metathesis Catalysts Containing Chelating Aryloxide Ligands, Organometallics, 25: 1940-1944 (2006).
Monfette, S. et al., Dissecting out the effect of Ru-Oar bonding in a five-coordinate complex of ruthenium (II)1, Can. J. Chem., 87: 361-367 (2009).
Monfette, S. et al., Electronic Effects of the Anionic Ligand in Ruthenium-Catalyzed Olefin Metathesis, Organometallics, 28: 944-946 (2009).
Nicolai, S., et al., Pd(0)-Catalyzed Alkene Oxy- and Aminoalkynylation with Aliphatic Bromoacetylenes, J. Org. Chem., 78: 3783-3801 (2013).
Occhipinti, G. et al., Simple and Highly Z-Selective Ruthenium-Based Olefin Metathesis Catalyst, J. Am. Chem. Soc., 135: 3331-3334 (2013).
Peeck, L. H. et al., Switched Stereocontrol in Grubbs-Hoveyda Complex Catalyzed ROMP Utilizing Proton-Switched NHC Ligands, Organometallics, 29: 4339-4345 (2010).
Perdew, J. P. and Yue, W., Accurate and simple density functional for the electronic exchange energy: Generalized gradient approximation, Phys. Rev. B, 33(12): 8800-8802 (1986).
Pirrung, M.C. and Webster, N. J. G., Mechanism of Intramolecular Photocycloadditions of Cyclooctenones, J. Org. Chem., 52: 3603-3613 (1987).
Poater, A. et al., Mechanistic Insights into the cis-trans Isomerization of Ruthenium Complexes Relevant to Catalysis of Olefin Metathesis, Chem. Eur. J., 16: 14354-14364 (2010).
Rosebrugh, L. E. et al., Highly Active Ruthenium Metathesis Catalysts Exhibiting Unprecedented Activity and Z-Selectivity, J. Am. Chem. Soc., 135: 1276-1279 (2013).
Rosen, E. L. et al., Olefin Metathesis Catalysts Containing Acyclic Diaminocarbenes, Organometallics, 29: 250-256 (2010).
Rubin, M. and Gevorgyan, V., Simple Large-Scale Preparation of 3,3-Disubstituted Cyclopropenes: Easy Access to Stereodefined Cyclopropylmetals via Transition Metal-Catalyzed Hydrometalation, Synthesis, 5:796-800 (2004).
Samojlowicz, C. et al., Ruthenium-Based Olefin Metathesis Catalysts Bearing N-Heterocyclic Carbene Ligands, Chem. Rev., 109: 3708-3742 (2009).
Sanford, M. S. et al., Mechanism and Activity of Ruthenium Olefin Metathesis Catalysts, J. Am. Chem. Soc., 123: 6543-6554 (2001).
Scalmani, G. and Frisch, M. J. Continuous surface charge polarizable continuum models of solvation. I. General formalism, J.,Chem. Phys., 132: 114110 (2010).
Schreiner, E. N. N. et al., Dynamical magnetostructural properties of Anabaena ferredoxin, Proc. Nat. Acad. Sci., 104(52): 20725-20730 (2007).
Schrock, R. R. and Hoveyda, A. H., Molybdenum and Tungsten Imido Alkylidene Complexes as Efficient Olefin-Metathesis Catalysts, Angew. Chem., Int. Ed., 42: 4592-4633 (2003).
Siau, W-Y. et al., Stereoselective Synthesis of Z-Alkenes, Top Curr. Chem., 327: 33-58 (2012).
Slugovc, C. et al., "Second Generation" Ruthenium Carbene Complexes with a cis-Dichloro Arrangement, Organometallics, 23: 3622-3626 (2004).
Straub, B. F., Ligand Influence on Metathesis Activity of Ruthenium Carbene Catalysts: a DFT Stufy, Adv. Synth. Catal., 349: 204-214 (2007).
Sugihara, J. M. and Bowman, C. M., Cyclic Benzeneboronate Esters, J. Am. Chem. Soc. 80: 2443-2446 (1958).
Torker, S. et al., Building Stereoselectivity into a Chemoselective Ring-Opening Metathesis Polymerization Catalyst for Alternating Copolymerization, Angew. Chem., Int. Ed. 49: 3762-3766 (2010).
Torker, S., et al., The Influence of Anionic Ligands on Stereoisomerism of Ru Carbenes and Their Importance to Efficiency and Selectivity of Catalytic Olefin Metathesis Reactions, J. Am. Chem. Soc., 136: 3439-3455 (2014).
Townsend, E. M. et al., Z-Selective Metathesis Homocoupling of 1,3-Dienes by Molybdenum and Tungsten Monoaryloxide Pyrrolide (MAP) Complexes, J. Am. Chem. Soc., 134: 11334-11337 (2012).
Tsogoeva, S. B. et al., Asymmetric Organocatalysis with Novel Chiral Thiourea Derivatives: Bifunctional Catalysts for the Strecker and Nitro-Michael Reactions, Eur. J. Org. Chem., 4995-5000 (2005).
Tzur, E. et al., Studies on Electronic Effects in O-, N- and S-Chelated Ruthenium Olefin-Metathesis Catalysts, Chem. Eur. J., 16: 8726-8737 (2010).
Ung, T. et al., Latent Ruthenium Olefin Metathesis Catalysts that Contain an N-Heterocycli Carbene Ligand, Organometallics, 23: 5399-5401 (2004).
Vehlow, K. et al., Ruthenium Metathesis Catalysts with Saturated Unsymmetrical N-Heterocyclic Carbene Ligands, Organometallics, 25(1): 25-28 (2006).
Vougioukalakis, G. C. and Grubbs, R. H., Ruthenium-Based Heterocyclic Carbene-Coordinated Olefin Metathesis Catalysts, Chem. Rev., 110: 1746-1787 (2010).
Vougioukalakis, G. C. and Grubbs, R. H., Synthesis and Activity of Ruthenium Olefin Metathesis Catalysts Coordinated with Thiazol-2-ylidene Ligands, J. Am. Chem. Soc., 130: 2234-2245 (2008).
Vyboishchikov, S. F. et al., Mechanism of Olefin Metathesis with Catalysis by Ruthenium Carbene Complexes: Density Functional Studies on Model Systems, Chem. Eur. J., 8: 3962-3975 (2002).
Wang, C. et al., Mo-Based Complexes with Two Aryloxides and a Pentafluoroimido Ligand: Catalysts for Efficient Z-Selective Synthesis of a Macrocyclic Trisubstituted Alkene by Ring-Closing Metathesis, Angew. Chem. Int. Ed., 52(7): 1939-1943 (2013).
Waser, J. et al., Hydrazines and Azides via the Metal-Catalyzed Hydrohydrazination and Hydroazidation of Olefins, J. Am. Chem. Soc., 128: 11693-11712 (2006).
Wennmohs, F. et al., Theoretical investigation of weak hydrogen bonds to sulfur, J. Chem. Phys., 119: 3208-3218 (2003).
Written Opinion for PCT/US2014/042195, 7 pages (dated Sep. 29, 2014).
Yu, M. et al., Catalytic Enantioselective Allylation of Carbonyl Compounds and Imines, Nature, 479: 88-93 (2011).
Yu, M. et al., Enol Ethers as Substrates for Efficient Z- and Enantioselective Ring-Opening/Cross-Metathesis Reactions Promoted by Stereogenic-at-Mo Complexes: Utility in Chemical Synthesis and Mechanistic Attributes, J. Am. Chem. Soc., 134: 2788-2799 (2012).
Zhou, P. et al., Geometric characteristics of hydrogen bonds, involving sulfur atoms in proteins, Proteins: Struct., Funct., Bioinf., 76: 151-163 (2008).
Ackerman, et al., "Ruthenium Carbene Complexes with Imidazol-S-Ylidene Ligands: Syntheses of Conduritol Derivatives Reveals Superior RCT Activity", Tetrahedron 56, 2000, 2195-2202.
Arisawa, et al., "Selective Isomerization of a Terminal Olefin Catalyzed by a Ruthenium complex: The Synthesis of Indoles Through Ring-Closing Metathesis", Agnew. Chem. Int. Ed. 41, 2002, 4732-4734.
Bielawski, et al., "Living Ring-Opening Metathesis Polymerization", Progress in Polymer Science 32, 2007, 1-29.
Bielawski, et al., "Tandem Catalysis: Three Mechanistically Distinct Reactions from a Single Ruthenium Complex", Journal of the American Chemical Society 122, 2000, 12872-12873.
Burdett, et al., "Renewable Monomer Feedstocks via Olefin Metathesis: Fundamental Mechanistic Studies of Methyl Oleate Ethenolysis with the First-Generation Grubbs Catalyst", Organometallics, 23(9), 2004, 2027-47.
Cadot, et al., "Olefin Isomerization by a Ruthenium Carbenoid Complex. Cleavage of Allyl and Homoallyl Groups", Tetrahedron Lett. 43, 2002, 1839-1841.
De La Mata, et al., "Synthesis and Reactions of Tungsten Oxo Vinylalkylidene Complexes: Reactions of WCl2(O) (PX3) (X=OMe, R) Precursors with 3,3-Diphenylcyclopropene", Organometallics, 15(2), 1996, 577-584.

(56) References Cited

OTHER PUBLICATIONS

Dinger, et al., "High Turnover Numbers with Ruthenium-Based Metathesis Catalysts", Adv. Synth. Catal., 344(6-7), 2002, 671-7.
Forman, et al., "A Stable Ruthenium Catalyst for Productive Olefin Metathesis", Organometallics, 23(21), 2004, 4824-7.
Furstner, et al., "Cationic Ruthenium Allenylidene Complexes as Catalysts for Ring Closing Olefin Metathesis", Chemistry, 6(10), 2000, 1847-57.
Grubbs, et al., "Efficacy of New Retinoids in the Prevention of Mammary Cancers and Correlations with Short-Term Biomarkers", Carcinogenesis, 27(6), 2009, 1232-1239.
Grubbs, "Olefin-Metathesis Catalysts for the Preparation of Molecules and Materials", (Nobel Lecture) Agnew. Chem. Int. Ed. Engl., 45, 2006, 3760-5.
Grubbs, et al., "Ring-Closing Metathesis and Related Processes in Organic Synthesis", Am. Chem. Res. 28, 1995, 446-452.
Gurjar, et al., "Temperature-Dependent Isomerisation Versus Net Fragmentation of Secondary Allylic Alcohols with Grubbs' Catalyst", Tetrahedron Lett. 42, 2001, 3633-3636.
Heeres, et al., "Combined Dehydration/(Transfer)-Hydrogenation of C6-Sugars (D-Glucose and D-Fructose) γ-Valerolactone Using Ruthenium Catalysts", Green Chem. 11, 2009, 1247-1255.
Hesek, et al., "The First Asymmetric Synthesis of Chiral Ruthenium Tris(Bipyridine) from Racemic Ruthenium Bis (Bipyridine) Complexes", Tetrahedron Lett. 41(5), 2000, 2617-20.
Hudej, et al., "The Influence of Electroporation on Cytotoxicity of Anticancer Ruthenium(III) Complex KP1339 In Vitro and In Vivo", Anticancer Research 30(6), 2010, 2055-2064.
Jing, et al., "Ruthenium Salen/Phenyltrimethylammonium Tribromide Catalyzed Coupling Reaction of Carbon Dioxide and Epoxides", Catalysis Communications, 8(11), 2007, 1630-1634.
Khan, et al., "Readily Accessible and Easily Modifiable Ru-based Catalysts for Efficient and Z-Selective Ring-Opening Metathesis Polymerization and Ring-Opening/Cross Metathesis", Journal of the American Chemical Society, vol. 135, 2013, pp. 10258-10261.
Li, et al., "Enantioselective Intramolecular Cyclopropanation of Cis-Alkenes by Chiral Ruthenium(II) Shiff Base Catalysts and Crystal Structures of (Shiff Base) Ruthenium Complexes Containing Carbene, PPh3, and CO Ligands", Organometallics, 25, 2006, 1676-1688.
Liu, et al., "Z-Selectivity in Olefin Metathesis with Chelated Ru Catalysts: Computational Studies of Mechanism and Selectivity", Journal of the American Chemical Society, vol. 134, 2012, pp. 1464-1467.
Miller, et al., "Axial Ligand Effects: Utilization of Chiral Sulf-Oxide Additives for the Induction of Asymmetry in (Salen) Ruthenium(II) Olefin Cyclopropanation Catalysts", Angewandte Chemie International Edition, 44, 2005, 3885-3889.
Pezet, et al., "Highly diastereoselective preparation of ruthenium bis(diimine) sulfoxide complexes: new concept in the preparation of optically active octahedral ruthenium complexes", Organometallics 19(20), 2000, pp. 4008-4015.
Rademaker-Lakhal, et al., "A Phase I and Pharmacological Study with Imidazolium Trans-DMSO-Imidazole-Tetrachlororuthenate, A Novel Ruthenium Anticancer Agent", Clinical Cancer Research, 10(11), 2004, 3717-3727.
Rosebrugh, et al., "Synthesis of Highly Cis, Syndiotactic Polymers via Ring-Opening Metathesis Polymerization Using Ruthenium Metathesis Catalysts", Journal of American Chemical Society, 135(27), 2013, 10032-10035.
Scholl, et al., "Increased Ring Closing Metathesis Activity of Ruthenium-Based Olefin Metathesis Catalysts Coordinated with Imidazolin-2-Ylidene Ligands", Tetrahedron Lett. 40, 1999, 2247.
Scholl, et al., "Synthesis and Activity of a New Generation of Ruthenium-Based Olefin Metathesis Catalysts Coordinated with 1,3-Dimesityl-4,5-Dihydroimidazol-2-Ylidine Ligands", Org. Lett. 1, 1999, 953-956.
Schrodi, et al., "Ruthenium Olefin Metathesis Catalysts for the Ethenolysis of Renewable Feedstocks", Clean: Soil, Air, Water 36, 2008, 669-673.
Solladie-Cavallo, et al., "Heterogeneous Hydrogenation of Substituted Phenols Over Al2O3 Supported Ruthenium", J. Mol. Catalysis A: Chemical, 273, 2007, 92-98.
Sutton, et al., "New Tandem Catalysis: Preparation of Cyclic Enol Ethers Through a Ruthenium-Catalyzed Ring-Closing Metathesis-Olefin Isomerization Sequence", J. Am. Chem. Soc., 124, 2002, 13390-13391.
Vinokurov, et al., "A New, Highly Active Bimetallic grubbs-Hoveyda-Blechert-Precatalyst for Alkene Metathesis", Organometallics, 27, 2008, 1878-1886.
Yi, et al., "The ruthenium acetylide catalyzed cross-coupling reaction of terminal and internal alkynes: isolation of a catalytically active-agostic intermediate species", Organometallics 17(15), 1998, pp. 3158-3160.
Monfette, et al., "Expanding the "ROMP Toolbox" for Tissue Engineering: Assessing the Design Criteria for Ru-Pseudohalide Initiators", Polymer Preprints, vol. 51, No. 1, Jan. 1, 2011 (Jan. 1, 2011), XP55307883, Jan. 1, 2011.

Ru Complex 1

Ru Complex 5

Ru Complex 6a

Ru Complex 6b

*E* isomer of ROCM product 11a

*Z* isomer of ROCM product 11a a.

b.

CN-group of neighboring complex

Ru center of adjacentcomplex

CATALYSTS FOR EFFICIENT Z-SELECTIVE METATHESIS

CROSS-REFERENCE TO RELATED APPLICATIONS

The present application claims priority to U.S. Provisional Application Ser. No. 61/834,050, filed Jun. 12, 2013, the entirety of which is incorporated herein by reference.

STATEMENT REGARDING FEDERALLY SPONSORED RESEARCH OR DEVELOPMENT

This invention was made with government support under Grant No. CHE-1111074 awarded by the National Science Foundation. The US government has certain rights in the invention.

FIELD OF THE INVENTION

The present invention generally relates to metathesis reactions.

BACKGROUND

Catalytic metathesis has transformed chemical synthesis and offers exceptionally efficient pathways for the synthesis of many commercially important chemicals, including but not limited to biologically active molecules, oleochemicals, renewables, fine chemicals, and polymeric materials. There remains an unmet need for improved methods and catalysts for metathesis reactions, for example, in terms of better catalyst stability and/or activity, efficiency and stereoselectivity.

SUMMARY

The present invention, among other things, provides new compounds for promoting metathesis reactions. In some embodiments, the present invention provides a compound having the structure of formula I:

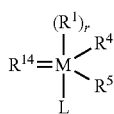

I wherein:
M is a metal selected from Group VIII;
each of $R^1$ and L is independently a neutral ligand;
r is 1-3;
each of $R^4$ and $R^5$ is independently bonded to M through an oxygen, nitrogen, sulfur, phosphorus or selenium atom;
$R^{14}$ is a carbene;
$R^4$ and $R^5$ are taken together to form a bidentate ligand, or $R^4$ and $R^5$ are taken together with one or more of $R^1$, L and $R^{14}$ to form a polydentate ligand;
two or more of $R^1$, L and $R^{14}$ are optionally taken together to form a bidentate or polydentate ligand; and
each of $R^1$, $R^4$, $R^5$, L and $R^{14}$ is independently and optionally linked to a tag or support.

In some embodiments, a provided compound of formula I has the structure of formula I-a:

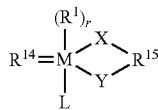

I-a wherein:
M is a metal selected from Group VIII;
each of $R^1$ and L is independently a neutral ligand;
r is 1-3;
each of X and Y is independently —O—, —S—, —Se—, —OC(O)—, —OC(S)—, —SC(O)—, —SC(S)—, —P($R^x$)—, —P(O)($R^x$)—, or —N($R^x$)—;
$R^{14}$ is a carbene;
$R^{15}$ is —$B^x$—, or an optionally substituted bivalent $C_{1-20}$ aliphatic or $C_{1-20}$ heteroaliphatic group, wherein 0-6 methylene units are optionally and independently replaced by —O—, —N(R')—, —S—, —C(O)—, —OC(O)—, —C(O)O—, —OC(O)O—, —C(S)—, —OC(S)—, —SC(O)—, —SC(S)—, —S(O)—, —S(O)$_2$—, —OS(O)$_2$O—, —N(R')C(O)—, —C(O)N(R')—, —N(R')C(O)O—, —OC(O)N(R')—, —N(R')C(O)N(R')—, —P($R^x$)—, —P(O)($R^x$)—, or -$Cy^1$-;
each -$Cy^1$- is independently:
  a bivalent optionally substituted monocyclic ring independently selected from phenylene, a 3-8 membered saturated or partially unsaturated carbocyclylene, a 5-6 membered heteroarylene having 1-4 heteroatoms independently selected from nitrogen, oxygen, or sulfur, or a 3-8 membered saturated or partially unsaturated heterocyclylene having 1-4 heteroatoms independently selected from nitrogen, oxygen, or sulfur; or
  a bivalent optionally substituted bicyclic or polycyclic ring independently selected from an 8-14 membered arylene, a 7-14 membered saturated or partially unsaturated carbocyclylene, an 8-14 membered heteroarylene having 1-5 heteroatoms independently selected from nitrogen, oxygen, or sulfur, or a 7-14 membered saturated or partially unsaturated heterocyclylene having 1-5 heteroatoms selected from nitrogen, oxygen, or sulfur;

$B^x$ is:

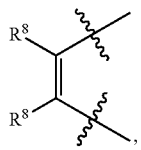

B1

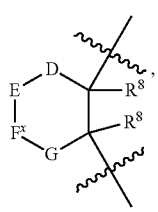

B2

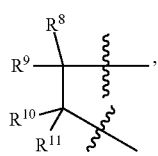

B3

-continued

B4
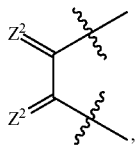

B5
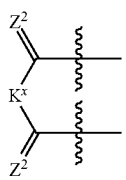

B6
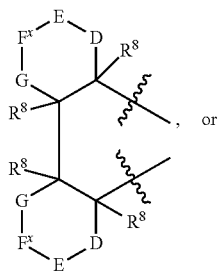, or

B7
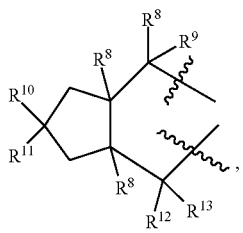

wherein:
each $Z^2$ is independently $=C(R^x)_2$, $=O$, $=S$, $=Se$, $=N(R^x)$, $=P(R^x)$, $=C=O$, $=C=S$, $=S=O$, or $=Se=O$;
each of D, E, $F^x$, G is independently $-N(R^8)-$, $-C(R^8)_2-$, $-S-$, $-O-$, $-P(R^8)-$, $-Se-$, $-C(O)-$, $-S(O)-$, or $-Se(O)-$;
each of $R^8$, $R^9$, $R^{10}$, $R^{11}$, $R^{12}$, and $R^{13}$ is independently $R^x$, or
  one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ on the same atom to form a $=C(R^x)_2$, $=N(R^x)$, $=P(R^x)$, $=O$, $=S$, or $=Se$ group; or
  one $R^8$, $R^9$, R, $R^{11}$, $R^{12}$, or $R^{13}$ is independently taken together with another $R^8$, $R^9$, $R^{10}$, $R^{11}$, $R^{12}$, or $R^{13}$ on an adjacent atom to form a double bond; or
  one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms; and
$K^x$ is an optionally substituted bivalent $C_{1-20}$ aliphatic or $C_{1-20}$ heteroaliphatic group, wherein 0-6 methylene units are optionally and independently replaced by $-O-$, $-N(R')-$, $-S-$, $-C(O)-$, $-OC(O)-$, $-C(O)O-$, $-OC(O)O-$, $-C(S)-$, $-OC(S)-$, $-SC(O)-$, $-SC(S)-$, $-S(O)-$, $-S(O)_2-$, $-OS(O)_2O-$, $-N(R')C(O)-$, $-C(O)N(R')-$, $-N(R')C(O)O-$, $-OC(O)N(R')-$, $-N(R')C(O)N(R')-$, $-P(R^x)-$, $-P(O)(R^x)-$, or -$Cy^1$-;

each $R^x$ is independently halogen, R, $-CN$, $-C(O)N(R')_2$, $-C(O)R$, $-C(O)OR$, $-OR$, $-OC(O)R$, $-OC(O)OR$, $-OC(O)N(R')_2$, $-OSi(R)_3$, $-N(R')_2$, $-N(R')_3^+$, $-NR'C(O)R$, $-NR'C(O)OR$, $-NR'C(O)N(R')_2$, $-NR'SO_2R$, $-NR'SO_2N(R')_2$, $-NR'OR$, $-NO_2$, $-Si(R)_3$, $-P(R)_2$, $-P(O)(R)_2$, $-P(O)(OR)_2$, $-SR$, $-SC(O)R$, $-S(O)R$, $-SO_2R$, $-SO_3R$, $-SO_2N(R')_2$, or $-SeR$;
each $R^x$ is independently R, $-C(O)R$, $-C(O)N(R)_2$, $-C(O)OR$, $-SO_2R$, $-SO_2N(R)_2$, $-P(O)(OR)_2$, or $-OR$; and
each R is independently hydrogen or an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:
  two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;
two or more of $R^1$, $-X-R^{15}-Y-$, L and $R^{14}$ are optionally taken together to form a bidentate or polydentate ligand; and
each of $R^1$, X, $R^{15}$, Y, L and $R^{14}$ is independently and optionally linked to a tag or support.

In some embodiments, a provide compound of formula I has the structure of formula I-b:

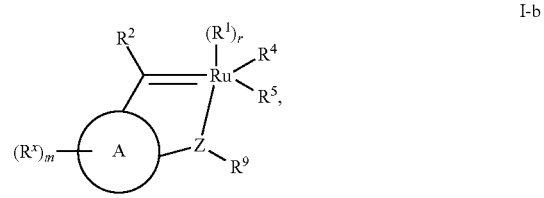

I-b wherein:
$R^1$ is a neutral ligand;
r is 1-3;
each of $R^2$ and $R^9$ is independently $R^x$;
Ring A is an optionally substituted ring selected from phenyl, an 8-14 membered bicyclic or polycyclic aryl ring, a 5-6 membered monocyclic heteroaryl ring having 1-4 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur;
each $R^x$ is independently halogen, R, $-CN$, $-C(O)N(R')_2$, $-C(O)R$, $-C(O)OR$, $-OR$, $-OC(O)R$, $-OC(O)OR$, $-OC(O)N(R')_2$, $-OSi(R)_3$, $-N(R')_2$, $-N(R')_3^+$, $-NR'C(O)R$, $-NR'C(O)OR$, $-NR'C(O)N(R')_2$, $-NR'SO_2R$, $-NR'SO_2N(R')_2$, $-NR'OR$, $-NO_2$, $-Si$ (R)$_3$, —P(R)$_2$, —P(O)(R)$_2$, —P(O)(OR)$_2$, —SR, —SC(O)R, —S(O)R, —SO$_2$R, —SO$_3$R, —SO$_2$N(R')$_2$, or —SeR;

m is 0-6;

Z is —O—, —S—, —Se—, —N(R$^x$)—, —N=, —P(R$^x$)—, —C(O)—, —C(S)—, —S(O)—, or —Se(O)—, or —Z—R$^9$ is halogen;

each of R$^4$ and R$^5$ is independently bonded to M through an oxygen, nitrogen, sulfur, phosphorus or selenium atom;

R$^4$ and R$^5$ are taken together to form a bidentate ligand, or R$^4$ and R$^5$ are taken together with one or more of R$^1$ and

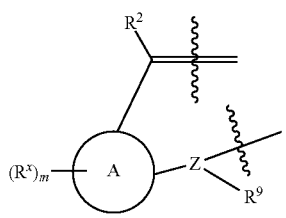

to form a polydentate ligand;

each R is independently R, —C(O)R, —C(O)N(R)$_2$, —C(O)OR, —SO$_2$R, —SO$_2$N(R)$_2$, —P(O)(OR)$_2$, or —OR;

each R is independently hydrogen or an optionally substituted group selected from C$_{1-20}$ aliphatic, C$_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;

two or more of R$^1$, R$^2$, and

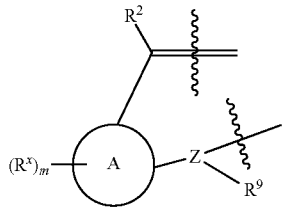

are optionally taken together to form a bidentate or polydentate ligand; and each of R$^1$, R$^2$, Ring A, R$^x$, Z, R$^9$, R$^4$ and R$^5$ is independently and optionally linked to a tag or support.

In some embodiments, a compound of formula I has the structure of formula I-c:

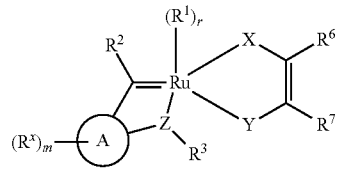

I-c wherein:

R$^1$ is a neutral ligand;

r is 1-3;

R$^2$ is R$^x$;

R$^3$ is hydrogen or an optionally substituted group selected from C$_{1-20}$ aliphatic, C$_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur;

Ring A is an optionally substituted ring selected from phenyl, an 8-14 membered bicyclic or polycyclic aryl ring, a 5-6 membered monocyclic heteroaryl ring having 1-4 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur;

each R$^x$ is independently halogen, R, —CN, —C(O)N(R')$_2$, —C(O)R, —C(O)OR, —OR, —OC(O)R, —OC(O)OR, —OC(O)N(R')$_2$, —OSi(R)$_3$, —N(R')$_2$, —N(R')$_3^+$, —NR'C(O)R, —NR'C(O)OR, —NR'C(O)N(R')$_2$, —NR'SO$_2$R, —NR'SO$_2$N(R')$_2$, —NR'OR, —NO$_2$, —Si(R)$_3$, —P(R)$_2$, —P(O)(R)$_2$, —P(O)(OR)$_2$, —SR, —SC(O)R, —S(O)R, —SO$_2$R, —SO$_3$R, —SO$_2$N(R')$_2$, or —SeR;

m is 0-6;

Z is —O—, —S—, —Se—, —N(R$^x$)—, —N=, —P(R$^x$)—, —C(O)—, —C(S)—, —S(O)—, or —Se(O)—, or —Z—R$^3$ is halogen;

each of X and Y is independently —O—, —S—, —Se—, —OC(O)—, —OC(S)—, —SC(O)—, —SC(S)—, —P(R$^x$)—, —P(O)(R$^x$)—, or —N(R$^x$)—;

each of R$^6$ and R$^7$ is independently R, —CN, halogen, —OR, —OC(O)R, —OSi(R)$_3$, —SR, —S(O)R, —S(O)$_2$R, —NO$_2$, —N(R')$_2$, —NR'C(O)R, —NR'C(O)OR, —NR'C(O)N(R')$_2$, —NR'SO$_2$R, —NR'SO$_2$N(R')$_2$, —NR'OR, —SeR, —Si(R)$_3$, or:

R$^6$ and R$^7$ are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur;

each R' is independently R, —C(O)R, —C(O)N(R)$_2$, —C(O)OR, —SO$_2$R, —SO$_2$N(R)$_2$, —P(O)(OR)$_2$, or —OR; and each R is independently hydrogen or an optionally substituted group selected from C$_{1-20}$ aliphatic, C$_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;

two or more of $R^1$,

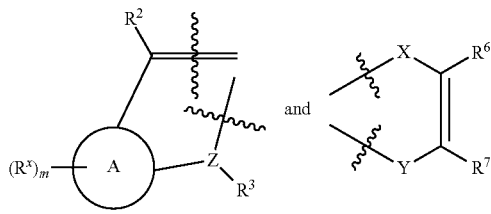

are optionally taken together to form a bidentate or polydentate ligand; and each of $R^1$, $R^2$, Ring A, $R^x$, Z, $R^3$, X, Y, $R^6$ and $R^7$ is independently and optionally linked to a tag or support.

In some embodiments, a provided compound of formula I has the structure of formula I':

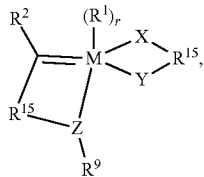

wherein:

each variable is independently as defined above and described herein;

two or more of $R^1$,

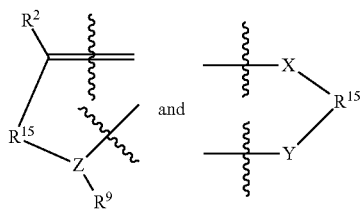

are optionally taken together to form a bidentate or polydentate ligand;

each of $R^1$, $R^2$, $R^{15}$, Z, $R^9$, X, Y or $R^{15}$ is independently and optionally linked to a tag or support.

In some embodiments, a provided compound of formula I has the structure of formula I':

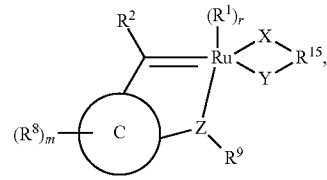

wherein:

Ring C is an optionally substituted group selected from phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each of r, $R^1$, $R^2$, $R^8$, m, Z, $R^9$, X, Y and $R^{15}$ is independently as defined above and described herein;

two or more of $R^1$,

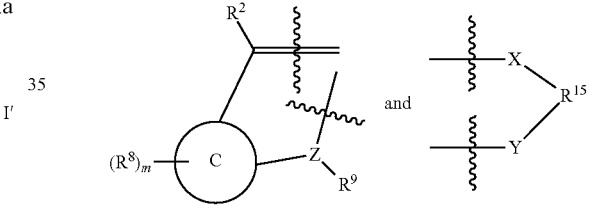

are optionally taken together to form a bidentate or polydentate ligand; and each of $R^1$, $R^2$, Ring C', $R^8$, Z, $R^9$, X, Y and $R^{15}$ is independently and optionally linked to a tag or support.

In some embodiments, the present invention provides a method for preparing a compound of formula I. In some embodiments, a provided method comprises providing a compound of formula II:

wherein:

each of $R^{4'}$ and $R^{5'}$ is independently halogen or —OR; and each of $R^1$, L, and $R^{14}$ is independently as defined above and described herein.

In some embodiments, r is 1.

In some other embodiments, the present invention provides methods for metathesis reactions. In some embodiments, a provided method comprises providing a compound provided by this invention. In some embodiments, a provided method produces a product with Z-selectivity. In some embodiments, a provided method produces a product with high efficiency. In some embodiments, a metathesis reaction is cross metathesis. In some embodiments, a metathesis reaction is ring-opening metathesis polymerization (ROMP). In some embodiments a metathesis reaction is ring-opening cross metathesis (ROCM). In some embodiments, a provided method produces a product with exceptionally high Z selectivity (typically >98:2 Z:E) and efficiency. In some embodiments, a provided method proceeds with catalyst loading (e.g., the loading of a compound of formula I) below 1% percent. In some embodiments, a provided method proceeds with catalyst loading below 0.1% percent. In some embodiments, a provided method proceeds with catalyst loading below 0.01% percent. In some embodiments, a provided method has a catalyst TON (e.g., TON of a compound of formula I) of about 5,000 or more. In some embodiments, a provided method has a catalyst TON of about 10,000 or more. In some embodiments, a provided method has a catalyst TON of about 15,000 or more. In some embodiments, a provided method has a catalyst TON of about 20,000 or more. In some embodiments, a provided method has a catalyst TON of about 25,000 or more. In some embodiments, a provided method has a catalyst TON of about 30,000 or more. In some embodiments, a provided method has a catalyst TON of about 35,000 or more. In some embodiments, a provided method has a catalyst TON of about 40,000 or more. In some embodiments, a metathesis reaction in a provided method proceeds at about room temperature and achieves complete conversion with catalyst (or catalyst precursor; e.g., a compound of formula I) loadings as low as 0.002 mol % and turnover numbers of up to 43,000.

BRIEF DESCRIPTION OF THE DRAWING

FIG. 6. $^1$H NMR of complex 6a.
FIG. 7. $^{13}$C NMR of complex 6a.
FIG. 24. X-ray structure of complex B-1a.
FIG. 40. HPLC analysis of compound C31a.

DETAILED DESCRIPTION OF CERTAIN EMBODIMENTS

1. General Description of Certain Embodiments of the Invention

Reliable access to Z alkenes has important implications to various branches of chemistry and its related disciplines and industries (For a recent comprehensive review on synthesis of Z alkenes, see: Siau, W-Y.; Zhang, Y.; Zhao, Y. *Top. Curr. Chem.* 2012, 327, 33), rendering it critical that entities that contain such function groups are made available by reliable, efficient, selective and catalytic processes. Discovery of efficient olefin metathesis catalysts that deliver effective control of high levels of stereoselectivity is therefore a central objective of research in modern chemistry (for a brief overview of challenging problems in catalytic olefin metathesis, see: (a) Zhugralin, A. R.; Hoveyda, A. H. *Nature* 2007, 450, 243. For selected reviews on various aspects of catalytic olefin metathesis, see: (b) Schrock, R. R.; Hoveyda, A. H. *Angew. Chem., Int. Ed.* 2003, 42, 4592-4633. (c) *Handbook of Metathesis* (Grubbs, R. H., Ed.), Wiley-VCH, Weinheim, Germany, 2003. (d) Hoveyda, A. H.; Gillingham, D. G.; Van Veldhuizen, J. J.; Kataoka, O.; Garber, S. B.; Kingsbury, K. S.; Harrity, J. P. A. *Org. Biomol. Chem.* 2004, 2, 8-23. (e) Samojlowicz, C.; Bieniek, M.; Grela, K. *Chem. Rev.* 2009, 109, 3708-3742. (f) Vougioukalakis, G. C.; Grubbs, R. H. *Chem. Rev.* 2010, 110, 1746-1787. (g) Lozano-Vila, A. M.; Monsaert, S.; Bajek, A.; Verpoort, F. *Chem. Rev.* 2010, 110, 4865-4909). However, Z-olefins are typically the higher energy isomers and olefin metathesis is a reversible process; accordingly, isomerization of the kinetically generated product to the thermodynamically favored E alkenes a complication and the design of efficient catalysts that furnish Z olefins with high selectivity is challenging. The first advance in this area arrived in the form of Z-selective olefin metathesis reactions facilitated by Mo- and W-based monoaryloxide pyrrolide alkylidenes ((a) Ibrahem, I.; Yu, M.; Schrock, R. R.; Hoveyda, A. H. *J. Am. Chem. Soc.* 2009, 131, 3844. (b) Flook, M. M., Jiang, A. J.; Schrock, R. R.; Müller, P.; Hoveyda, A. H. *J. Am. Chem. Soc.* 2009, 131, 7962. (c) Meek, S. J.; O'Brien, R. V.; Llaveria, J.; Schrock, R. R.; Hoveyda, A. H. *Nature* 2011, 471, 461.

Figure 1:
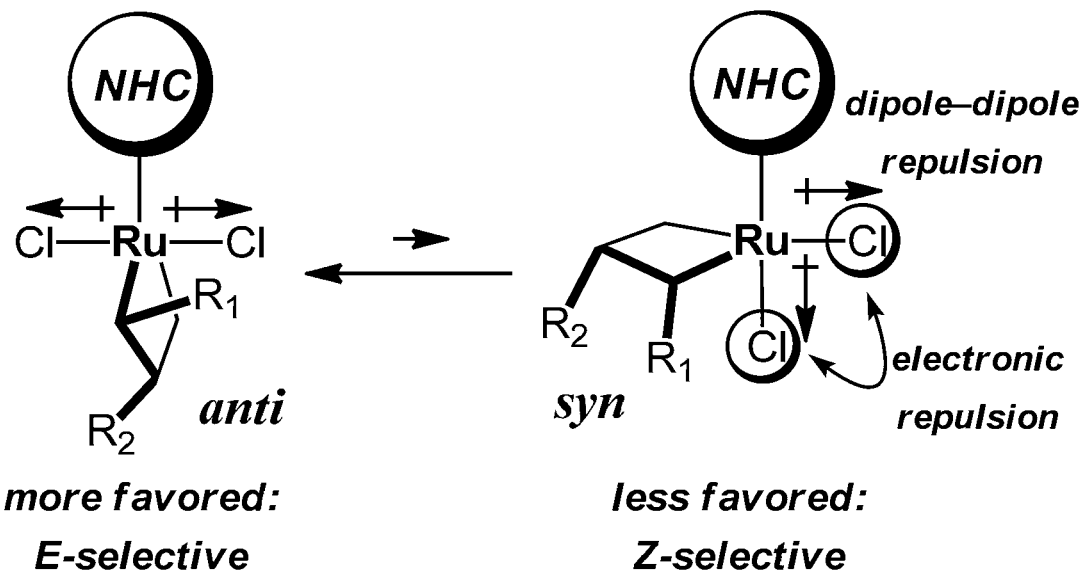
FIG. 1. Previously known Ru-catalysts favor E-selectivity.

(d) Yu, M.; Wang, C.; Kyle, A. F.; Jakubec, P.; Dixon, D. J.; Schrock, R. R.; Hoveyda, A. H. *Nature* 2011, 479, 88. (e) Yu, M.; Ibrahem, I.; Hasegawa, M.; Schrock, R. R.; Hoveyda, A. H. *J. Am. Chem. Soc.* 2012, 134, 2788. (f) Townsend, E. M.; Schrock, R. R.; Hoveyda, A. H. *J. Am. Chem. Soc.* 2012, 134, 11334. (g) Wang, C.; Haeffner, F.; Schrock, R. R.; Hoveyda, A. H. *Angew. Chem., Int. Ed.* 2013, 52, 1939), along with applications to several complex molecule natural products ((a) Meek, S. J.; O'Brien, R. V.; Llaveria, J.; Schrock, R. R.; Hoveyda, A. H. *Nature* 2011, 471, 461. (b) Yu, M.; Wang, C.; Kyle, A. F.; Jakubec, P.; Dixon, D. J.; Schrock, R. R.; Hoveyda, A. H. *Nature* 2011, 479, 88. (c) Wang, C.; Haeffner, F.; Schrock, R. R.; Hoveyda, A. H. *Angew. Chem., Int. Ed.* 2013, 52, 1939. (d) Yu, M.; Wang, C.; Kyle, A. F.; Jakubec, P.; Dixon, D. J.; Schrock, R. R.; Hoveyda, A. H. *Nature* 2011, 479, 88). Subsequent investigations has led to the development of Ru-based catalysts with a bidentate N-heterocyclic carbene (NHC) ligand ((a) Endo, K.; Grubbs, R. H. *J. Am. Chem. Soc.* 2011, 133, 8525. (b) Keitz, B. K.; Endo, K.; Herbert, M. B.; Grubbs, R. H. *J. Am. Chem. Soc.* 2011, 133, 9686. (c) Keitz, B. K.; Endo, K.; Patel, P. R.; Herbert, M. B.; Grubbs, R. H. *J. Am. Chem. Soc.* 2012, 134, 693. (d) Liu, P.; Xu, X.; Dong, X.; Keitz, B. K.; Herbert, M. B.; Grubbs, R. H.; Houk, K. N. *J. Am. Chem. Soc.* 2012, 134, 1464); the latter complexes furnish moderate to high degrees of Z selectivity for reactions of unhindered terminal alkenes (e.g., without a secondary allylic substituent). Additionally, a monothiolate Ru chloride was recently shown to promote homodimerization of similar types of terminal olefins with moderate Z:E ratios (Occhipinti, G.; Hansen, F. R.; Tornroos, K. W.; Jensen, V. R. *J. Am. Chem. Soc.* 2013, 135, 3331); nonetheless, in the majority of cases, substantial amounts of E isomers are generated at higher conversions, and/or improved stereoselectivity is achieved at the expense of diminished catalytic activity. It is accepted by a person having ordinary skill in the art that known Ru-catalysts tend to favor the production of E double bonds (E-selective). While not wishing to be limited by theory, a generally accepted model for the observed E-selectivity of known Ru-catalysts is depicted in FIG. 1.

The present invention, among other things, provides compounds for promoting metathesis reactions with high stereoselectivity and/or efficiency. In some embodiments, the present invention provides compounds for promoting metathesis reactions with high stereoselectivity. In some embodiments, the present invention provides compounds for promoting metathesis reactions with high Z-selectivity. In some embodiments, the present invention provides compounds for promoting metathesis reactions with high efficiency. In some embodiments, the present invention provides compounds that promote metathesis reactions with high Z selectivity and/or efficiency.

In some embodiments, the present invention provides a compound of formula I:

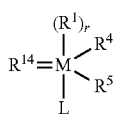

I wherein each variable is independently as defined above and described herein. In some embodiments, a compound of formula I has the structure of

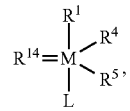

wherein each variable is independently as defined above and described herein.

In some embodiments, a provided compound of formula I has the structure of formula I-a:

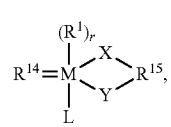

I-a wherein each variable is independently as defined above and described herein. In some embodiments, a compound of formula I-a has the structure of

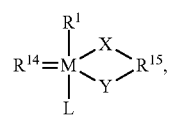

wherein each variable is independently as defined above and described herein.

In some embodiments, $R^{14}$ and L are covalently linked. In some embodiments, $R^{14}$ and L are taken together to form a bidentate ligand. In some embodiments, $R^{14}$ and L are taken together with one or more of $R^1$, $R^4$ and $R^5$ to form a polydentate ligand.

In some embodiments, a provided compound of formula I has the structure of formula I':

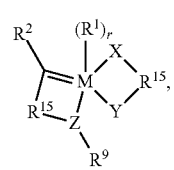

I' wherein each variable is independently as defined above and described herein. In some embodiments, a compound of formula I' has the structure of:

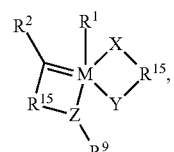

wherein each variable is independently as defined above and described herein.

In some embodiments, a provided compound of formula I has the structure of formula I'':

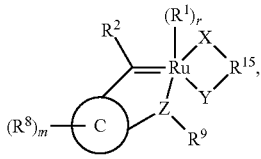

wherein each variable is independently as defined above and described herein. In some embodiments, a compound of formula I″ has the structure of:

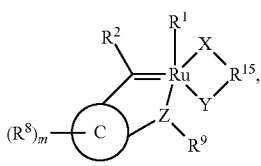

wherein each variable is independently as defined above and described herein.

In some embodiments, a provide compound of formula I has the structure of formula I-b:

I-b

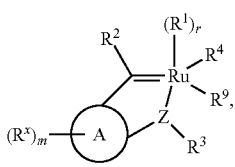

wherein each variable is independently as defined above and described herein. In some embodiments, a provide compound of formula I-b has the structure of:

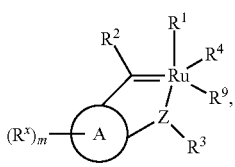

wherein each variable is independently as defined above and described herein.

In some embodiments, a compound of formula I has the structure of formula I-c:

I-c

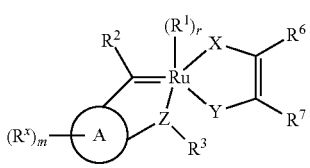

wherein each variable is independently as defined above and described herein. In some embodiments, a compound of formula I-c has the structure of:

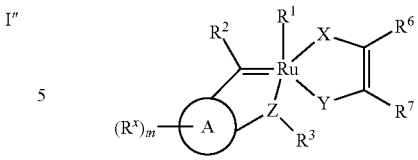

wherein each variable is independently as defined above and described herein.

In some embodiments, the present invention provides a method for preparing a compound having the structure of formula I, comprising providing a compound of formula II:

II

wherein each variable is independently as defined above and described herein.

In some other embodiments, the present invention provides methods for metathesis reactions. In some embodiments, a provided method comprises providing a compound provided by this invention. In some embodiments, the present invention provides a method for performing a metathesis reaction, comprising providing a compound having the structure of formula I. In some embodiments, a metathesis reaction is olefin metathesis. In some embodiments, a metathesis reaction is cross metathesis. In some embodiments, a metathesis reaction is ring-opening metathesis polymerization (ROMP). In some embodiments, a metathesis reaction is ring-opening cross metathesis (ROCM). In some embodiments, a metathesis reaction is ring closing metathesis. In some embodiments, a provided method produces a product with unexpected selectivity and/or efficiency. In some embodiments, a provided method produces a product with unexpected selectivity. In some embodiments, a provided method produces a metathesis product with high Z selectivity (e.g., greater than about 98:2). In some embodiments, a provided method produces a product with unexpected efficiency (e.g., complete conversion with catalyst loadings as low as 0.002 mol %/turn over number (TON) up to 43,000). In some embodiments, concentration of a compound of formula I in a reaction of a provided method is no more than about 100 ppm. In some embodiments, concentration of a compound of formula I in a metathesis reaction of a provided method is about 50 ppm or less. In some embodiments, the loading of a compound of formula I in a metathesis reaction of a provided method is about 0.1 mol % or less. In some embodiments, the loading of a compound of formula I in a metathesis reaction of a provided method is about 0.1 mol % or less, relative to an olefin in a metathesis reaction. In some embodiments, the loading of a compound of formula I in a metathesis reaction of a provided method is about 0.05 mol % or less. In some embodiments, the loading of a compound of formula I in a metathesis reaction of a provided method is about 0.01 mol % or less. In some embodiments, the loading of a compound of formula I in a metathesis reaction of a provided method is about 0.005 mol % or less. In some embodiments, the TON of a compound of formula I in a metathesis reaction of a provided method is greater than about 1,000. In some embodiments, the TON of a compound of formula I in a metathesis reaction of a provided method is greater than about 5,000. In some embodiments, the TON of a compound of formula I in a metathesis reaction of a provided method is greater than about 10,000. In some embodiments, the TON of a compound of formula I in a metathesis reaction of a provided method is greater than about 20,000. In some embodiments, the TON of a compound of formula I in a metathesis reaction of a provided method is greater than about 30,000. In some embodiments, the TON of a compound of formula I in a metathesis reaction of a provided method is greater than about 40,000. In some embodiments, the TON of a compound of formula I in a metathesis reaction of a provided method is up to 43,000. In some embodiments, a provided method produces a product with unexpected selectivity and efficiency. In some embodiments, a provided method produces a metathesis product with high Z selectivity (e.g., greater than about 98:2) and high efficiency (e.g., complete conversion with catalyst loadings as low as 0.002 mol %/turn over number (TON) up to 43,000). In some embodiments, a substrate of a metathesis reaction of a provided method comprises an unprotected hydroxyl group. In some embodiments, a substrate of a metathesis reaction of a provided method comprises a sterically hindered olefin (e.g., vinylcyclohexane) wherein the olefin is one of the two unsaturated bonds involved in the metathesis reaction.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 93$^{rd}$ Ed. Additionally, general principles of organic chemistry are described in "Organic Chemistry", 2$^{nd}$ Ed, Thomas N. Sorrell, University Science Books, Sausalito: 2005, and "March's Advanced Organic Chemistry", 6$^{th}$ Ed., Smith, M. B. and March, J., John Wiley & Sons, New York: 2007, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, phosphorus, selenium and the like). Examples of heteroalkyl groups include, but are not limited to, alkoxy, poly(ethylene glycol)-, alkyl-substituted amino, tetrahydrofuranyl, piperidinyl, morpholinyl, etc. In some embodiments, a heteroatom may be oxidized (e.g., —S(O)—, —S(O)$_2$—, —N(O)—, —P(O)— and the like).

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, selenium, nitrogen, phosphorus, or silicon (including, any oxidized form of nitrogen, sulfur, selenium, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogen atoms of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —(CH$_2$)$_{0-4}$SR°; —(CH$_2$)$_{0-4}$S(O)R°; —O(CH$_2$)$_{0-4}$R°; —O—(CH$_2$)$_{0-4}$C(O)OR°; —(CH$_2$)$_{0-4}$CH(OR°)$_2$; —(CH$_2$)$_{0-4}$Ph, which may be substituted with R°; —(CH$_2$)$_{0-4}$(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —P(O)(OR°)R°; —P(O)(OR°)$_2$; —OP(O)R°$_2$; —OP(O)(OR°)R°; —OP(O)(OR°)$_2$; —PR°$_2$; —P(OR°)R°; —P(OR°)$_2$; —OPR°$_2$; —OP(OR°)R°; —OP(OR°)$_2$; —SiR°$_3$; —OSiR°$_3$; —SeR°; —(CH$_2$)$_{0-4}$SeSeR°; —(C$_{1-4}$ straight or branched alkylene)O—N(R°)$_2$; or —(C$_{1-4}$ straight or branched alkylene)C(O)O—N(R°)$_2$; wherein each R° may be substituted as defined below and is independently hydrogen, C$_{1-6}$ aliphatic, —CH$_2$Ph, —O(CH$_2$)$_{0-1}$Ph, —CH$_2$(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-6 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•$$_2$, —NO$_2$, —SiR$^•$$_3$, —OSiR$^•$$_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•$$_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_1$-aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•$$_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In certain embodiments, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral product. Such metal complexes may exhibit improved catalytic activity and stereoselectivity, relative to previous systems, and may reduce undesired side reactions (e.g., dimerization or oligomerization of the metal complex).

The term "chiral" is given its ordinary meaning in the art and refers to a molecule that is not superimposable with its mirror image, wherein the resulting non-superimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, a ligand may be either monodentate or polydentate. In some embodiments, a ligand is monodentate. In some embodiments, a ligand is bidentate. In some embodiments, a ligand is tridentate. In some embodiments, two or more monodentate ligands are taken together to form a polydentate ligand. A ligand may have hapticity of more than one. In some cases, a ligand has a hapticity of 1 to 10. In some embodiments, a ligand has a hapticity of 1. In some embodiments, a ligand has a hapticity of 2. In some embodiments, a ligand has a hapticity of 3. In some embodiments, a ligand has a hapticity of 4. In some embodiments, a ligand has a hapticity of 5. In some embodiments, a ligand has a hapticity of 6. For a ligand having hapticity greater than one, as sometimes done in the art, a single bond may be drawn between the ligand and the metal. In some cases, a ligand is alkylidene. In some cases, a ligand is a nitrogen-containing ligand. In some cases, a ligand is an oxygen-containing ligand. In some cases, a ligand is a phosphorus-containing ligand. In some embodiments, a ligand comprises an unsaturated bond, and the unsaturated bond is coordinated to a metal. In some embodiments, a ligand comprises a carbon-carbon double bond, and the double bond is coordinated to a metal. In some embodiments, a ligand is an olefin. When an olefin double bond is coordinated to a metal, the chemical bonding between the olefin and the metal can either be depicted as a 3-membered ring wherein the ring members comprises the metal and both carbon atoms of the double bond, or as a single bond between the metal and the double bond.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Ru metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In some embodiments, the nitrogen-containing ligand may be chiral and the precatalyst may be provided as a racemic mixture or a purified stereoisomer.

In some embodiments, a nitrogen-containing ligand may also describe a ligand precursor comprising at least one hydrogen atom directly bonded to a nitrogen atom, wherein deprotonation of the at least one hydrogen atom results in a negatively charged nitrogen atom, which may coordinate to a metal atom. Exemplary such precursors include but are not limited to amines, amides, and pyrrole and its derivatives thereof. A nitrogen-containing ligand may be a heteroaryl or heteroalkyl group comprising at least one nitrogen ring atom. In some cases, the nitrogen atom may be positioned on a substituent of an alkyl, heteroalkyl, aryl, or heteroaryl group. For example, a nitrogen-containing ligand may be an amine- or amide-substituted aryl group, wherein the amine or amide group is deprotonated upon coordination to the metal center.

In some embodiments, a nitrogen-containing ligand is a neutral ligand. In some embodiments, a nitrogen-containing ligand is pyridine. As exemplified in the examples, pyridine can bond to M, e.g., Ru, through its nitrogen atom.

As used herein, the term "oxygen-containing ligand" may be used to refer to ligands comprising at least one oxygen atom. In some cases, the oxygen atom binds to the metal atom thereby forming an ether-linkage. In other cases, the oxygen-containing ligand may bind the metal center via a different atom. The term "oxygen-containing ligand" may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

In some embodiments, an oxygen-containing ligand may also describe a ligand precursor comprising at least one hydroxyl group (e.g., a hydroxyl-containing ligand), wherein deprotonation of the hydroxyl group results in a negatively charged oxygen atom, which may coordinate to a metal atom. An oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, an oxygen-containing ligand may be a hydroxy-substituted aryl group, wherein the hydroxyl group is deprotonated upon coordination to the metal center. In some embodiments, an oxygen-containing ligand is a neutral ligand.

As used herein, the term "phosphorus-containing ligand" may be used to refer to ligands comprising at least one phosphorus atom. In some cases, the phosphorus atom binds to the metal. In other cases, the phosphorus-containing ligand may bind to the metal center via a different atom (i.e., an atom other than the phosphorous). The phosphorus-containing ligand may have phosphorus atom of various oxidation states. In some cases the phosphorus-containing ligand is phosphine. In some cases the phosphorus-containing ligand is phosphite. In some cases the phosphorus-containing ligand is phosphate. The phosphorus-containing ligand may be either monodentate or polydentate. In some cases, two or more phosphorus atoms bind to the metal. In some cases, one or more phosphorus atoms together with one or more non-phosphorus atoms bind to the metal. In some embodiments, a phosphorus-containing ligand is a neutral ligand.

As defined herein, a "metal complex" is any complex used to form a provided precursor complex or any complex generated from a provided precursor complex (e.g., for use as a catalyst in a reaction such as a metathesis reaction). In some embodiments, a metal complex is a compound having the structure of formula I described herein.

As used herein, the term "electron-withdrawing group" is given its ordinary meaning in the art and refers to an atom or group that draws electron density from a neighboring atom or group, usually by resonance and/or inductive effects. In some embodiments, an electron-withdrawing group withdraws electron density from an aromatic ring system by resonance and/or inductive effects. In some embodiments, an electron-withdrawing group withdraws electron density from an aromatic ring system by resonance and inductive effects. In some embodiments, an electron-withdrawing group lowers the electron density of an aromatic ring system such as phenyl. Exemplary electron-withdrawing groups are extensively described in the art, including but not limited to halogen, carbonyl moieties (e.g., aldehyde and ketone groups), —COOH and its derivatives (e.g., ester and amide moieties), protonated amines, quaternary ammonium groups, —CN, —NO$_2$, —S(O)—, and —S(O)$_2$—. In some embodiments, an electron-withdrawing group is halogen. In some embodiments, an electron-withdrawing group is —F. In some embodiments, an electron-withdrawing group is —Cl. In some embodiments, an electron-withdrawing group is —Br. In some embodiments, an electron-withdrawing group is —I. In some embodiments, hydrogen is used as reference and regarded as having no effect. In contrast to an electron-withdrawing group, an electron-donating group is given its ordinary meaning in the art and refers to an atom or group that contributes to increase electron density of a neighboring atom or group.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in Protecting Groups in Organic Synthesis, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxycarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

As used herein, the term "metathesis reaction" is given its ordinary meaning in the art and refers to a chemical reaction in which two reacting species exchange partners in the presence of a transition-metal catalyst. In some cases, a byproduct of a metathesis reaction may be ethylene. A metathesis reaction may involve reaction between species comprising, for example, olefins and/or alkynes. Examples of different kinds of metathesis reactions include cross metathesis, ring-closing metathesis, ring-opening metathesis, acyclic diene metathesis, alkyne metathesis, enyne metathesis, ring-opening metathesis polymerization (ROMP), and the like. A metathesis reaction may occur between two substrates which are not joined by a bond (e.g., intermolecular metathesis reaction) or between two portions of a single substrate (e.g., intramolecular metathesis reaction).

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}C$- or $^{13}C$- or $^{14}C$-enriched carbon are within the scope of this invention. Such compounds are useful, for example, as analytical tools or probes in biological assays.

As used herein and in the claims, the singular forms "a", "an", and "the" include the plural reference unless the context clearly indicates otherwise. Thus, for example, a reference to "a compound" includes a plurality of such compounds.

3. Description of Certain Embodiments of the Invention

In some embodiments, the present invention provides compounds and methods for metathesis reactions. In some embodiments, the present invention provides a compound having the structure of formula I. In some embodiments, a compound of formula I has the structure of formula I', I", I-a, I-b, I-c, I-d, I-e, I-f, or I-g.

As generally defined above, M is a metal selected from Group VIII. In some embodiments, M is Fe. In some embodiments, M is Ru. In some embodiments, M is Os.

As generally defined above, $R^1$ is a neutral ligand. In some embodiments, $R^1$ is optionally taken together with one or more of other $R^1$ groups, $R^4$, $R^5$, $R^{14}$ and L to form a bidentate or polydentate ligand. In some embodiments, $R^1$ is optionally taken together with one or more of $R^4$, $R^5$, $R^{14}$ and L to form a bidentate or polydentate ligand. In some embodiments, $R^1$ is optionally linked to a tag or sold support. In some embodiments, $R^1$ is optionally linked to a tag. In some embodiments, $R^1$ is optionally linked to a support.

In some embodiments, $R^1$ is a neutral phosphorus-containing ligand, wherein $R^1$ is bonded to Ru through a phosphorus atom. In some embodiments, $R^1$ is a phosphine ligand. In some embodiments, $R^1$ is a phosphite ligand. In some embodiments, $R^1$ is a phosphoramidite. In some embodiments, $R^1$ has the structure of $P(R^x)_3$, wherein each $R^x$ is independently as defined above and described herein. In some embodiments, $R^1$ has the structure of $P(R)_3$, wherein each R is independently as defined above and described herein. In some embodiments, $R^1$ is tricyclohexylphosphine ($PCy_3$). In some embodiments, $R^1$ is $PPh_3$.

In some embodiments, $R^1$ is a nitrile. In some embodiments, $R^1$ is a nitrile coordinated to M through the nitrogen atom of the nitrile group. In some embodiments, $R^1$ is $R^8$—CN.

In some embodiments, $R^1$ is a carbene. In some embodiments, $R^1$ is a carbene forming a single bond with M. Exemplary carbenes are widely known in the art, including but not limited to those described in de Fremont, P. et al, *Coordination Chemistry Reviews* 253 (2009), 862-892, Colacino, E. et al, *Coordination Chemistry Reviews* 251 (2007), 726-764, Herrmann, W. A., *Angew. Chem. Int. Ed.* 2002, 41, 1290-1309, Samojlowicz, C.; Bieniek, M.; Grela, K. Ruthenium-based olefin metathesis catalysts bearing N-heterocyclic carbene ligands, *Chem. Rev.* 2009, 109, 3708-3742, Vougioukalakis, G. C.; Grubbs, R. H. Ruthenium-based heterocyclic carbene-coordinated olefin metathesis catalysts, *Chem. Rev.* 2010, 110, 1746-1787, and Lozano-Vila, A. M.; Monsaert, S.; Bajek, A.; Verpoort, F. *Chem. Rev.* 2010, 110, 4865-4909.

In some embodiments, $R^1$ is $(R^x)_2C$:, wherein each $R^x$ is independently as defined above and described herein. In some embodiments, at least one $R^x$ is connected to the carbon atom through a heteroatom. In some embodiments, each $R^x$ is connected to the carbon atom through a heteroatom. In some embodiments, at least one $R^x$ is connected to the carbon atom through a nitrogen atom. In some embodiments, at least one $R^x$ is connected to the carbon atom through an oxygen atom. In some embodiments, at least one $R^x$ is connected to the carbon atom through a sulfur atom. In some embodiments, at least one $R^x$ is connected to the carbon atom through a phosphorus atom. In some embodiments, at least one $R^x$ is connected to the carbon atom through a silicon atom. In some embodiments, each $R^x$ is connected to the carbon atom through a nitrogen, oxygen, silicon, sulfur, or phosphorus atom.

In some embodiments, $R^1$ is a carbene having the structure of

wherein each $R^x$ is independently as defined above and described herein. In some embodiments, $R^1$ is a carbene having the structure of

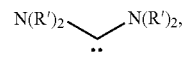

wherein each R' is independently as defined above and described herein. In some embodiments, each R' is independently optionally substituted $C_{1-20}$ aliphatic. In some embodiments, each R' is independently optionally substituted $C_{1-20}$ alkyl. In some embodiments, each R' is independently optionally substituted $C_{1-6}$ alkyl. In some embodiments, each R' is independently optionally substituted secondary or tertiary $C_{1-6}$ alkyl. In some embodiments, each R' is independently optionally substituted secondary $C_{1-6}$ alkyl. In some embodiments, each R' is isopropyl. In some embodiments, $R^1$ is

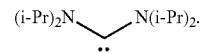

In some embodiments, each R' is independently optionally substituted tertiary $C_{1-6}$ alkyl.

In some embodiments, $R^1$ is an optionally substituted saturated or unsaturated cyclic carbene. In some embodiments, $R^1$ is an optionally substituted saturated or unsaturated cyclic carbene comprising 0-5 heteroatoms. In some embodiments, $R^1$ is an optionally substituted 3-10 membered, saturated or unsaturated cyclic carbene comprising 0-5 heteroatoms. In some embodiments, $R^1$ is an optionally substituted 3-10 membered, saturated or unsaturated cyclic carbene comprising 0-5 heteroatoms independently selected from nitrogen, phosphorus, oxygen or sulfur.

In some embodiments, $R^1$ is a carbene having the structure of

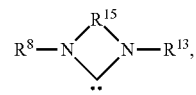

wherein each variable is independently as defined above and described herein.

In some embodiments, $R^1$ is an optionally substituted 3-8 membered cyclic carbene. In some embodiments, $R^1$ is an optionally substituted group having the structure of:

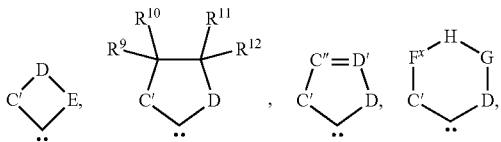 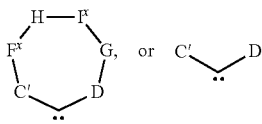

wherein:

each of C, D, E, $F^x$, G, H, $I^x$ is independently —N(R$^8$)—, —C(R$^8$)$_2$—, —S—, —O—, —P(R$^8$)—, —Se—, —C(O)—, —S(O)—, or —Se(O)—;

each of C″ and D′ is independently —N=, —P=, or —C(R$^8$)=;

each of R$^8$, R$^9$, R$^{10}$, R$^{11}$, R$^{12}$, and R$^{13}$ is independently R$^x$, or
- one R$^8$, R$^9$, R$^{10}$, R$^{11}$, R$^{12}$, or R$^{13}$ is independently taken together with another R$^8$, R$^9$, R$^{10}$, R$^{11}$, R$^{12}$, or R$^{13}$ on the same atom to form a =C(R$^x$)$_2$, =N(R$^x$), =P(R$^x$), =O, =S, or =Se group; or
- one R$^8$, R$^9$, R$^{10}$, R$^{11}$, R$^{12}$, or R$^{13}$ is independently taken together with another R$^8$, R$^9$, R$^{10}$, R$^{11}$, R$^{12}$, or R$^{13}$ on an adjacent atom to form a double bond; or
- one R$^8$, R$^9$, R$^{10}$, R$^{11}$, R$^{12}$, or R$^{13}$ is independently taken together with another R$^8$, R$^9$, R$^{10}$, R$^{11}$, R$^{12}$, or R$^{13}$ and their intervening atoms to form an optionally substituted 3-10 membered, saturated, partially unsaturated, or aryl ring having, in addition to the intervening atoms, 0-4 heteroatoms; and each $R^x$ is independently as defined above and described herein.

In some embodiments, $R^1$ is

In some embodiments, $R^1$ is

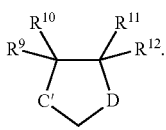

In some embodiments, $R^1$ is

In some embodiments, $R^1$ is

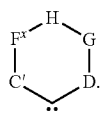

In some embodiments, $R^1$ is

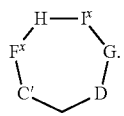

In some embodiments, $R^1$ is

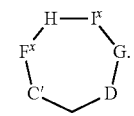

In some embodiments, $R^1$ is an optionally substituted group having the structure of:

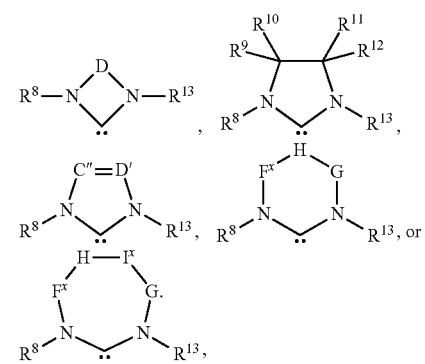

wherein each variable is independently as defined above and described herein. In some embodiments, $R^1$ is

In some embodiments, $R^1$ is

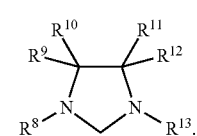

In some embodiments, $R^1$ is

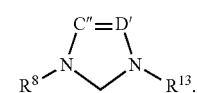

In some embodiments, $R^1$ is

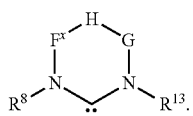

In some embodiments, $R^1$ is

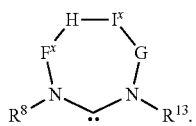

In some embodiments, $R^1$ is an optionally substituted saturated or unsaturated cyclic carbene having 0-5 heteroatoms independently selected from nitrogen, oxygen, or sulfur. In some embodiments, $R^1$ is an optionally substituted saturated or unsaturated cyclic carbene having 0-5 heteroatoms independently selected from nitrogen or sulfur. In some embodiments, $R^1$ is an optionally substituted saturated or unsaturated cyclic carbene having 0-5 heteroatoms independently selected from nitrogen or oxygen. In some embodiments, $R^1$ is an optionally substituted saturated or unsaturated cyclic carbene having 0-5 heteroatoms independently selected from oxygen or sulfur. In some embodiments, $R^1$ is an optionally substituted saturated or unsaturated cyclic carbene having 1-5 nitrogen atoms.

In some embodiments, $R^1$ is an N-heterocyclic carbenes (NHC). Exemplary N-heterocyclic carbene are widely known in the art, including but not limited to those described in de Fremont, P. et al, *Coordination Chemistry Reviews* 253 (2009), 862-892, Colacino, E. et al, *Coordination Chemistry Reviews* 251 (2007), 726-764, Herrmann, W. A., *Angew. Chem. Int. Ed.* 2002, 41, 1290-1309, Samojlowicz, C.; Bieniek, M.; Grela, K. Ruthenium-based olefin metathesis catalysts bearing N-heterocyclic carbene ligands, *Chem. Rev.* 2009, 109, 3708-3742, Vougioukalakis, G. C.; Grubbs, R. H. Ruthenium-based heterocyclic carbene-coordinated olefin metathesis catalysts, *Chem. Rev.* 2010, 110, 1746-1787, and Lozano-Vila, A. M.; Monsaert, S.; Bajek, A.; Verpoort, F. *Chem. Rev.* 2010, 110, 4865-4909.

In some embodiments, $R^1$ is an optionally substituted saturated or unsaturated cyclic carbene having 1-5 nitrogen atoms. In some embodiments, $R^1$ is an optionally substituted 3-10 membered, saturated or unsaturated cyclic carbene having 1-5 nitrogen atoms. In some embodiments, $R^1$ is an optionally substituted 4-membered, saturated or unsaturated cyclic carbene having 1-5 nitrogen atoms. In some embodiments, $R^1$ is an optionally substituted 5-membered, saturated or unsaturated cyclic carbene having 1-5 nitrogen atoms. In some embodiments, $R^1$ is an optionally substituted 6-membered, saturated or unsaturated cyclic carbene having 1-5 nitrogen atoms. In some embodiments, $R^1$ is an optionally substituted 7-membered, saturated or unsaturated cyclic carbene having 1-5 nitrogen atoms. In some embodiments, $R^1$ is an optionally substituted 8-membered, saturated or unsaturated cyclic carbene having 1-5 nitrogen atoms. In some embodiments, $R^1$ is an optionally substituted 9-membered, saturated or unsaturated cyclic carbene having 1-5 nitrogen atoms. In some embodiments, $R^1$ is an optionally substituted 10-membered, saturated or unsaturated cyclic carbene having 1-5 nitrogen atoms.

In some embodiments, $R^1$ is an optionally substituted 4-membered saturated or unsaturated cyclic carbene having 1-5 nitrogen atoms. In some embodiments, $R^1$ is an optionally substituted saturated or unsaturated 4-membered ring carbene having two nitrogen atoms. In some embodiments, $R^1$ is an optionally substituted saturated 4-membered ring carbene having two nitrogen atoms. In some embodiments, $R^1$ is a substituted saturated 4-membered ring carbene having two nitrogen atoms. In some embodiments, $R^1$ is an optionally substituted unsaturated 4-membered ring carbene having two nitrogen atoms. In some embodiments, $R^1$ is a substituted unsaturated 4-membered ring carbene having two nitrogen atoms. In some embodiments, $R^1$ has the structure of

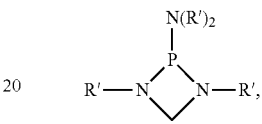

wherein each R' is independently as defined above and described herein. In some embodiments, R' has the structure of

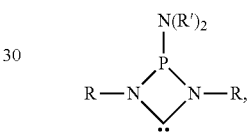

wherein each R is independently as defined above and described herein. In some embodiments, $R^1$ has the structure of

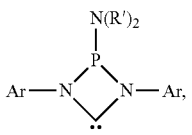

wherein each R is independently as defined above and described herein, and each Ar is independently an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, $R^1$ has the structure of


wherein each R is independently as defined above and described herein, and each Ar is independently optionally substituted phenyl. In some embodiments, $R^1$ has the structure of

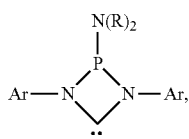

wherein each R is independently optionally substituted $C_{1-20}$ aliphatic, and each Ar is independently optionally substituted phenyl. In some embodiments, $R^1$ has the structure of

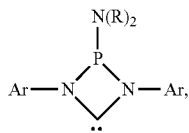

wherein each R is independently optionally substituted $C_{1-6}$ aliphatic, and each Ar is independently optionally substituted phenyl. In some embodiments, $R^1$ has the structure of

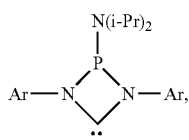

wherein each Ar is independently optionally substituted phenyl. In some embodiments, $R^1$ has the structure of

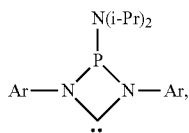

wherein each Ar is 2,6-diisopropylphenyl. In some embodiments, $R^1$ is

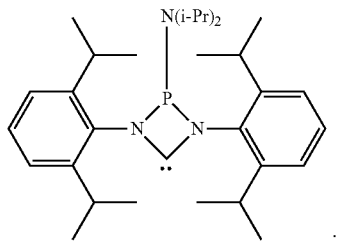

In some embodiments, $R^1$ is optionally substituted

In some embodiments, $R^1$ is optionally substituted

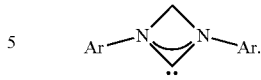

In some embodiments, $R^1$ is optionally substituted

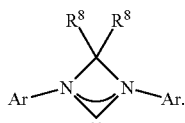

In some embodiments, $R^1$ is an optionally substituted 5-membered saturated or unsaturated cyclic carbene having 1-5 nitrogen atoms. In some embodiments, $R^1$ is an optionally substituted saturated or unsaturated 5-membered ring carbene having two nitrogen atoms. In some embodiments, $R^1$ is an optionally substituted saturated 5-membered ring carbene having two nitrogen atoms. In some embodiments, $R^1$ is a substituted saturated 5-membered ring carbene having two nitrogen atoms. In some embodiments, $R^1$ is an optionally substituted unsaturated 5-membered ring carbene having two nitrogen atoms. In some embodiments, $R^1$ is a substituted unsaturated 5-membered ring carbene having two nitrogen atoms. In some embodiments, $R^1$ is an optionally substituted group selected from

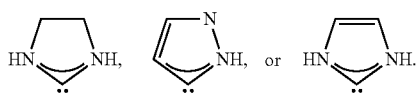

In some embodiments, $R^1$ is an NHC having the structure of

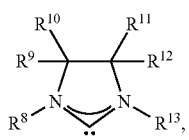

wherein each variable is independently as defined above and described herein. In some embodiments, $R^1$ is an NHC having the structure of

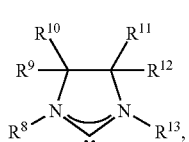

wherein $R^8$ and $R^{13}$ are different. In some embodiments, $R^1$ is an NHC having the structure of

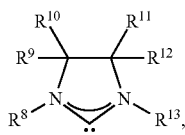

wherein $R^8$ and $R^{13}$ are the same. In some embodiments, $R^1$ is an NHC having the structure of

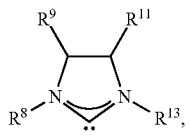

wherein each variable is independently as defined above and described herein. In some embodiments, $R^1$ is an NHC having the structure of

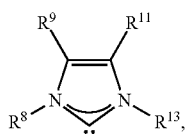

wherein each variable is independently as defined above and described herein. In some embodiments, $R^1$ is an NHC having the structure of

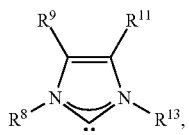

wherein $R^8$ and $R^{13}$ are the same. In some embodiments, $R^1$ is an NHC having the structure of

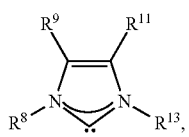

wherein $R^8$ and $R^{13}$ are different. In some embodiments, $R^1$ is optionally substituted

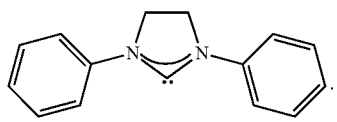

In some embodiments, $R^1$ is optionally substituted

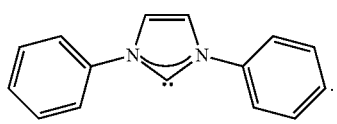

In some embodiments, $R^1$ is

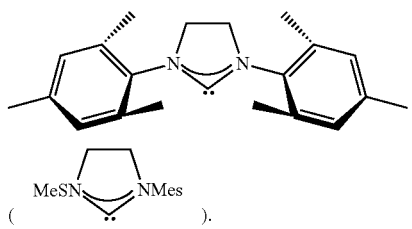

In some embodiments, $R^1$ is

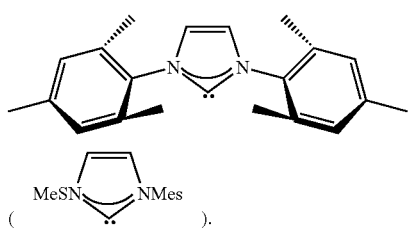

In some embodiments, $R^1$ is

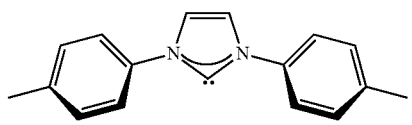

In some embodiments, $R^1$ is

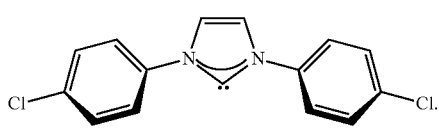

In some embodiments, $R^1$ is

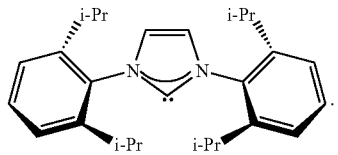

In some embodiments, $R^1$ is

In some embodiments, $R^1$ is

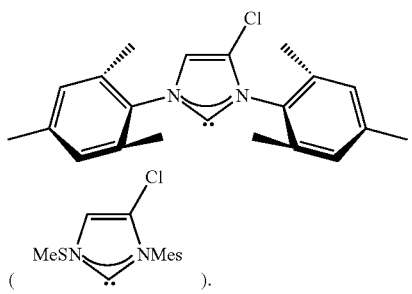

In some embodiments, $R^1$ is

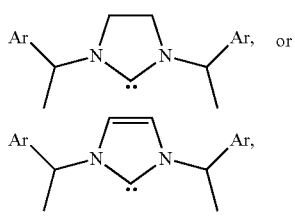

wherein each Ar is independently an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, $R^1$ is

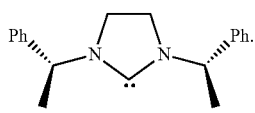

In some embodiments, $R^1$ is

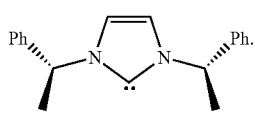

In some embodiments, $R^1$ is

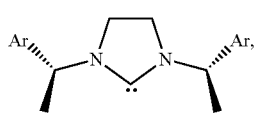

wherein Ar is naphthyl. In some embodiments, $R^1$ is

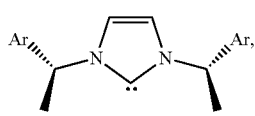

wherein Ar is naphthyl. In some embodiments, $R^1$ is

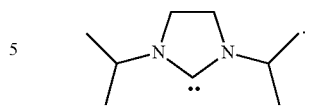

In some embodiments, $R^1$ is

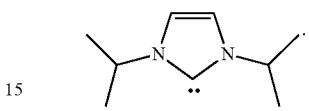

In some embodiments, $R^1$ is

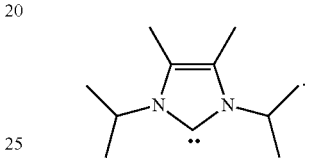

In some embodiments, $R^1$ is

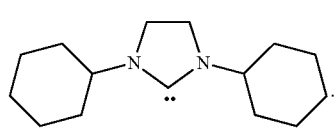 [SMILES: C1CCC(N2CCN(C3CCCCC3)C2)CC1]

In some embodiments, $R^1$ is

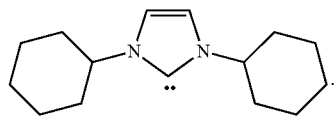

In some embodiments, $R^1$ is

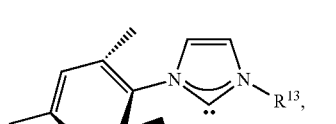

wherein $R^{13}$ is as defined above and described herein. In some embodiments, $R^1$ is

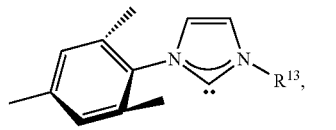

wherein $R^{13}$ is optionally substituted $C_{1-20}$ aliphatic. In some embodiments, $R^1$ is

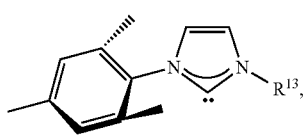

wherein R[13] is selected from —(CH$_2$)$_3$CH=CH$_2$, —(CH$_2$)$_4$CH=CH$_2$, —(CH$_2$)$_6$CH=CH$_2$, —(CH$_2$)$_2$O(t-BuSi(CH$_3$)$_2$), —(CH$_2$)$_2$OSi(CH$_3$)$_3$, —(CH$_2$)$_3$OSi(CH$_3$)$_3$, —(CH$_2$)$_6$OSi(CH$_3$)$_3$, —(CH$_2$)$_2$C(CH$_3$)$_2$O Si(CH$_3$)$_3$, —CH$_2$CH$_2$(CF$_2$)$_5$CF$_3$, —CH(CH$_3$)COEt, —(CH$_2$)$_5$CN, —(CH$_2$)$_2$OH, —(CH$_2$)$_3$OH, —(CH$_2$)$_6$OH, or —(CH$_2$)$_2$C(CH$_3$)$_2$OH. In some embodiments, R[1] is

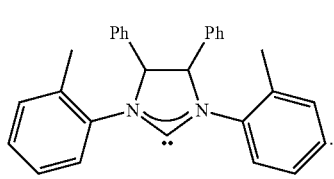

wherein Ad is adamantyl. In some embodiments, R[1] is

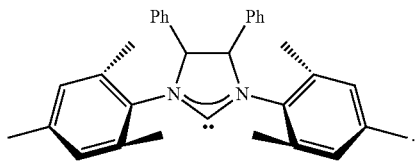

In some embodiments, R[1] is

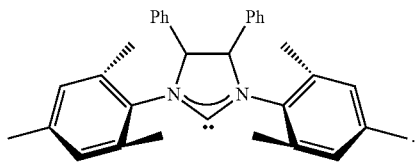

In some embodiments, R[1] is

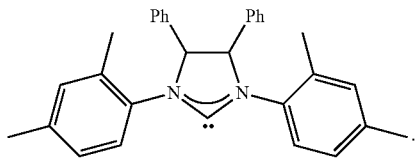

In some embodiments, R[1] is

In some embodiments, R[1] is

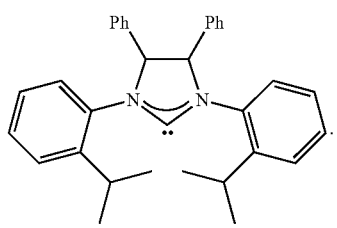 [SMILES: CC(C)c1ccccc1N1CN(c2ccccc2C(C)C)C(c2ccccc2)C1c1ccccc1]

In some embodiments, R[1] is

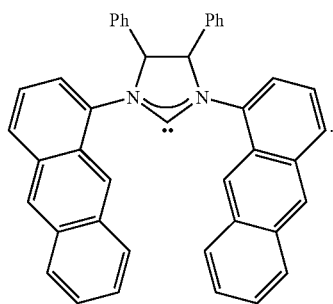 [SMILES: c1ccc(C2C(c3ccccc3)N(c3cccc4cc5ccccc5cc34)CN2c2cccc3cc4ccccc4cc23)cc1]

In some embodiments, R[1] is

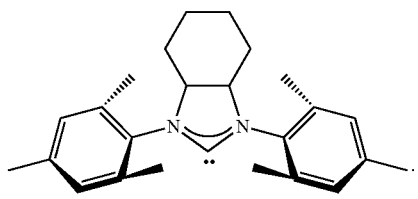

In some embodiments, R[1] is

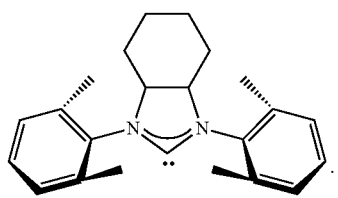

In some embodiments, R[1] is

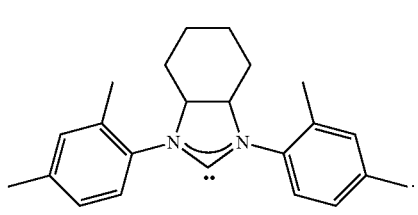

In some embodiments, $R^1$ is

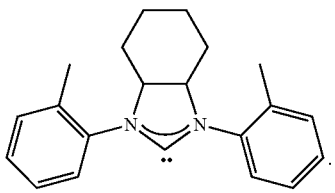 [SMILES: Cc1ccccc1N1CN(c2ccccc2C)C2CCCCC21]

In some embodiments, $R^1$ is

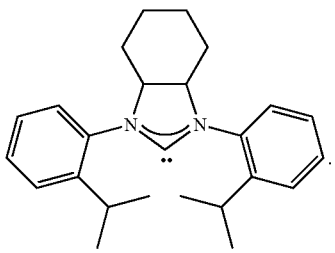 [SMILES: CC(C)c1ccccc1N1CN(c2ccccc2C(C)C)C2CCCCC21]

In some embodiments, $R^1$ is

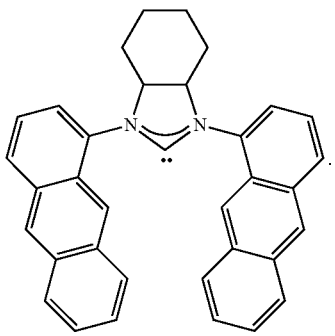 [SMILES: c1ccc2cc3c(N4CN(c5cccc6cc7ccccc7cc56)C5CCCCC54)cccc3cc2c1]

In some embodiments, $R^1$ is

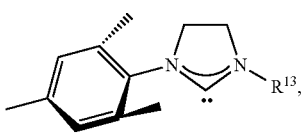

wherein $R^{13}$ is selected from —(CH$_2$)$_3$CH=CH$_2$, —(CH$_2$)$_4$CH=CH$_2$, —(CH$_2$)$_6$CH=CH$_2$, —(CH$_2$)$_2$O(t-BuSi(CH$_3$)$_2$), —(CH$_2$)$_2$OSi(CH$_3$)$_3$, —(CH$_2$)$_3$OSi(CH$_3$)$_3$, —(CH$_2$)$_6$OSi(CH$_3$)$_3$, —(CH$_2$)$_2$C(CH$_3$)$_2$OSi(CH$_3$)$_3$, —CH$_2$CH$_2$(CF$_2$)$_5$CF$_3$, —CH(CH$_3$)COEt, —(CH$_2$)$_5$CN, —(CH$_2$)$_2$OH, —(CH$_2$)$_2$OCH$_3$, —CH$_2$MeS, —(CH$_2$)$_3$OH, —(CH$_2$)$_6$OH, —(CH$_2$)$_2$C(CH$_3$)$_2$OH, adamantyl, MeAd, t-Bu, Mes, cyclohexyl, —(CH$_2$)$_7$CH$_3$, —CH$_3$, —CH$_2$CH$_3$, or isopinocampheyl. In some embodiments, $R^1$ is

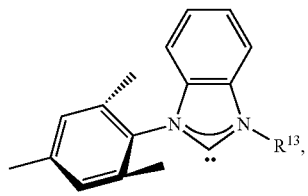

wherein $R^{13}$ is selected from —(CH$_2$)$_3$CH=CH$_2$, —(CH$_2$)$_4$CH=CH$_2$, —(CH$_2$)$_6$CH=CH$_2$, —(CH$_2$)$_2$O(t-BuSi(CH$_3$)$_2$), —(CH$_2$)$_2$OSi(CH$_3$)$_3$, —(CH$_2$)$_3$OSi(CH$_3$)$_3$, —(CH$_2$)$_6$OSi(CH$_3$)$_3$, —(CH$_2$)$_2$C(CH$_3$)$_2$OSi(CH$_3$)$_3$, —CH$_2$CH$_2$(CF$_2$)$_5$CF$_3$, —CH(CH$_3$)COEt, —(CH$_2$)$_5$CN, —(CH$_2$)$_2$OH, —(CH$_2$)$_2$OCH$_3$, —CH$_2$Mes, —(CH$_2$)$_3$OH, —(CH$_2$)$_6$OH, —(CH$_2$)$_2$C(CH$_3$)$_2$OH, adamantyl, MeAd, t-Bu, Mes, cyclohexyl, —(CH$_2$)$_7$CH$_3$, —CH$_3$, —CH$_2$CH$_3$, or isopinocampheyl. In some embodiments, $R^1$ is

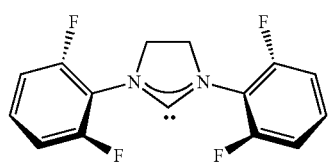

In some embodiments, $R^1$ is

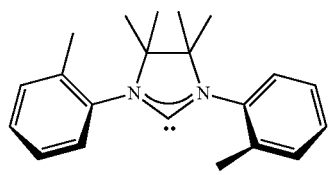

In some embodiments, $R^1$ is

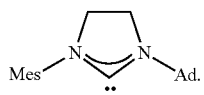

In some embodiments, $R^1$ is

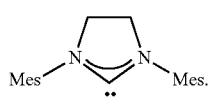

In some embodiments, $R^1$ is

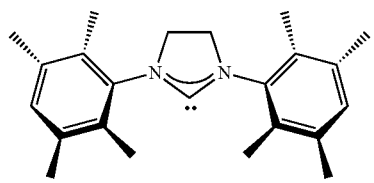

In some embodiments, $R^1$ is an optionally substituted saturated or unsaturated 5-membered ring carbene having three nitrogen atoms. In some embodiments, $R^1$ is an optionally substituted saturated 5-membered ring carbene having three nitrogen atoms. In some embodiments, $R^1$ is a substituted saturated 5-membered ring carbene having three nitrogen atoms. In some embodiments, $R^1$ is an optionally substituted unsaturated 5-membered ring carbene having three nitrogen atoms. In some embodiments, $R^1$ is an optionally substituted group selected from

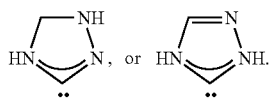

In some embodiments, $R^1$ has the structure of

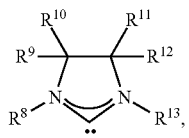

wherein each variable is independently as defined above and described herein. In some embodiments, $R^1$ has the structure of

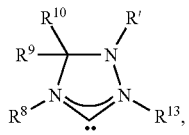

wherein $R^8$ and $R^{13}$ are the same. In some embodiments, $R^1$ has the structure of

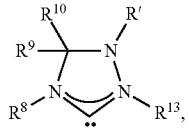

wherein $R^8$ and $R^{13}$ are different. In some embodiments, $R^1$ has the structure of

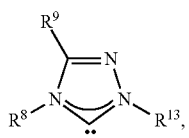

wherein each variable is independently as defined above and described herein. In some embodiments, $R^1$ has the structure of

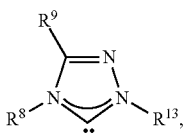

wherein $R^8$ and $R^{13}$ are the same. In some embodiments, $R^1$ has the structure of

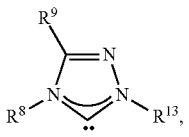

wherein $R^8$ and $R^{13}$ are different. In some embodiments, $R^1$ has the structure of

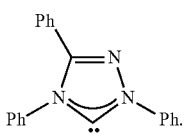

In some embodiments, $R^1$ is

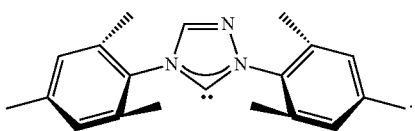

In some embodiments, $R^1$ is an optionally substituted 6-membered saturated or unsaturated cyclic carbene having 1-5 nitrogen atoms. In some embodiments, $R^1$ is an optionally substituted saturated or unsaturated 6-membered ring carbene having two nitrogen atoms. In some embodiments, $R^1$ is an optionally substituted saturated 6-membered ring carbene having two nitrogen atoms. In some embodiments, $R^1$ is a substituted saturated 6-membered ring carbene having two nitrogen atoms. In some embodiments, $R^1$ is an optionally substituted unsaturated 6-membered ring carbene having two nitrogen atoms. In some embodiments, $R^1$ is a substituted unsaturated 6-membered ring carbene having two nitrogen atoms. In some embodiments, $R^1$ is optionally substituted

In some embodiments, $R^1$ is

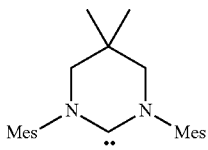

In some embodiments, $R^1$ is an optionally substituted 7-membered saturated or unsaturated cyclic carbene having 1-5 nitrogen atoms. In some embodiments, $R^1$ is an optionally substituted saturated or unsaturated 7-membered ring carbene having two nitrogen atoms. In some embodiments, $R^1$ is an optionally substituted saturated 7-membered ring carbene having two nitrogen atoms. In some embodiments, $R^1$ is a substituted saturated 7-membered ring carbene having two nitrogen atoms. In some embodiments, $R^1$ is an optionally substituted unsaturated 7-membered ring carbene having two nitrogen atoms. In some embodiments, $R^1$ is a substituted unsaturated 7-membered ring carbene having two nitrogen atoms. In some embodiments, $R^1$ is optionally substituted

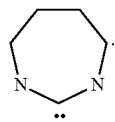

In some embodiments, $R^1$ is

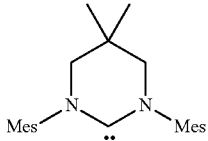

Exemplary NHCs as $R^1$ are depicted below:
4-Membered Ring NHC:

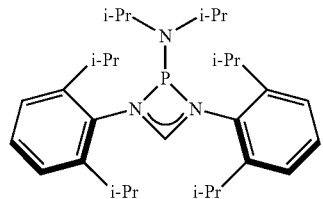

5-Membered Ring NHC with Saturated Backbone (X is a Monovalent Anion):

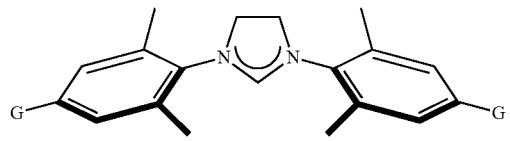

G = H, Me, OMe, SiMe$_3$, NEt$_2$, SMe, F, Cl, Br, I

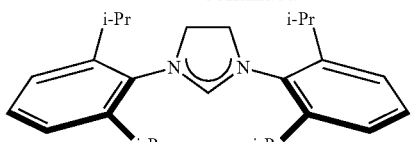

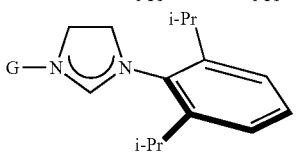

G = Me, Cy

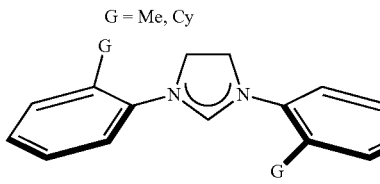

G = H, F, Me, Et, i-Pr, t-Bu, Ph, o-Tolyl

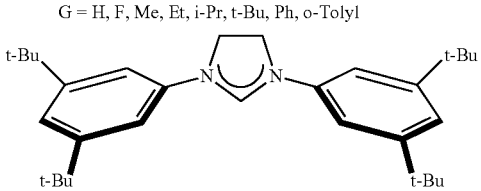

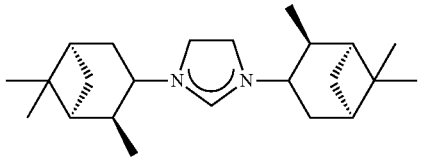

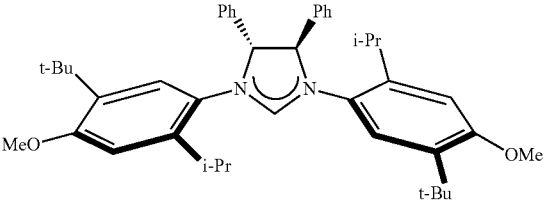

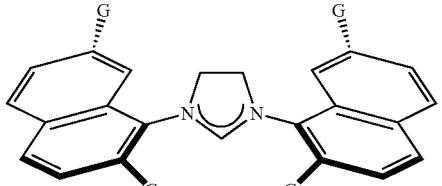

G = H, Me, Et, i-Pr, t-Bu

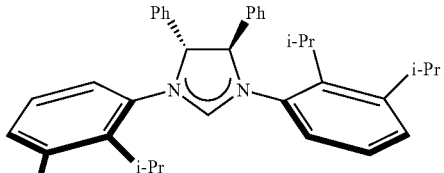

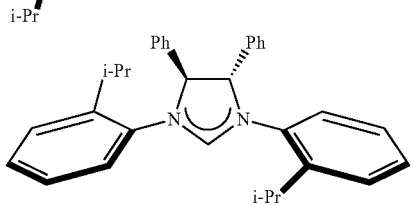

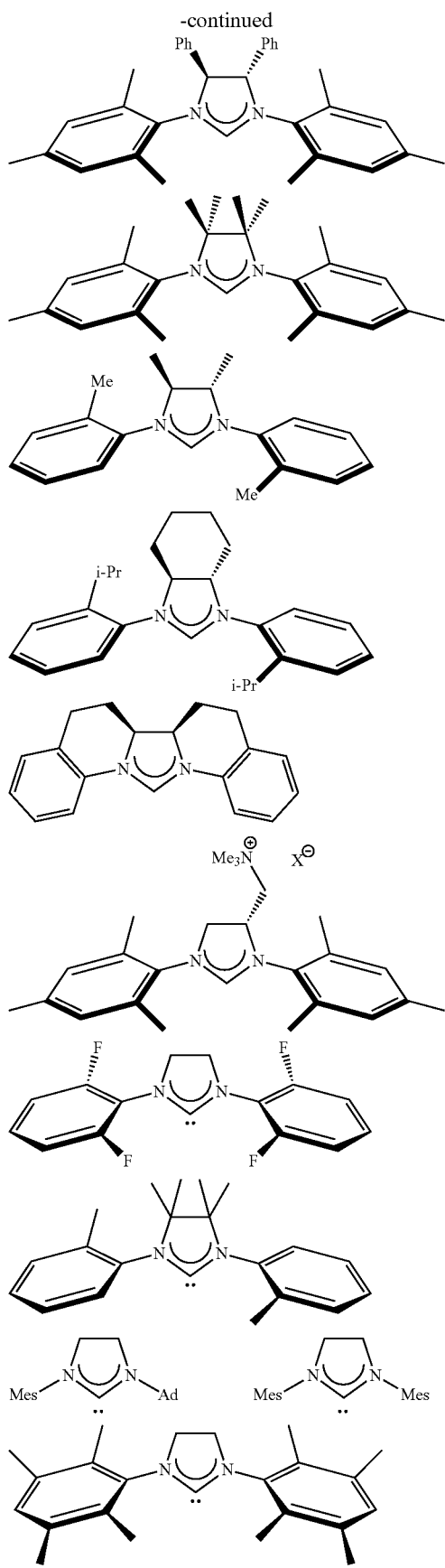
5-Membered Ring Cyclic Alkylamino Carbenes:
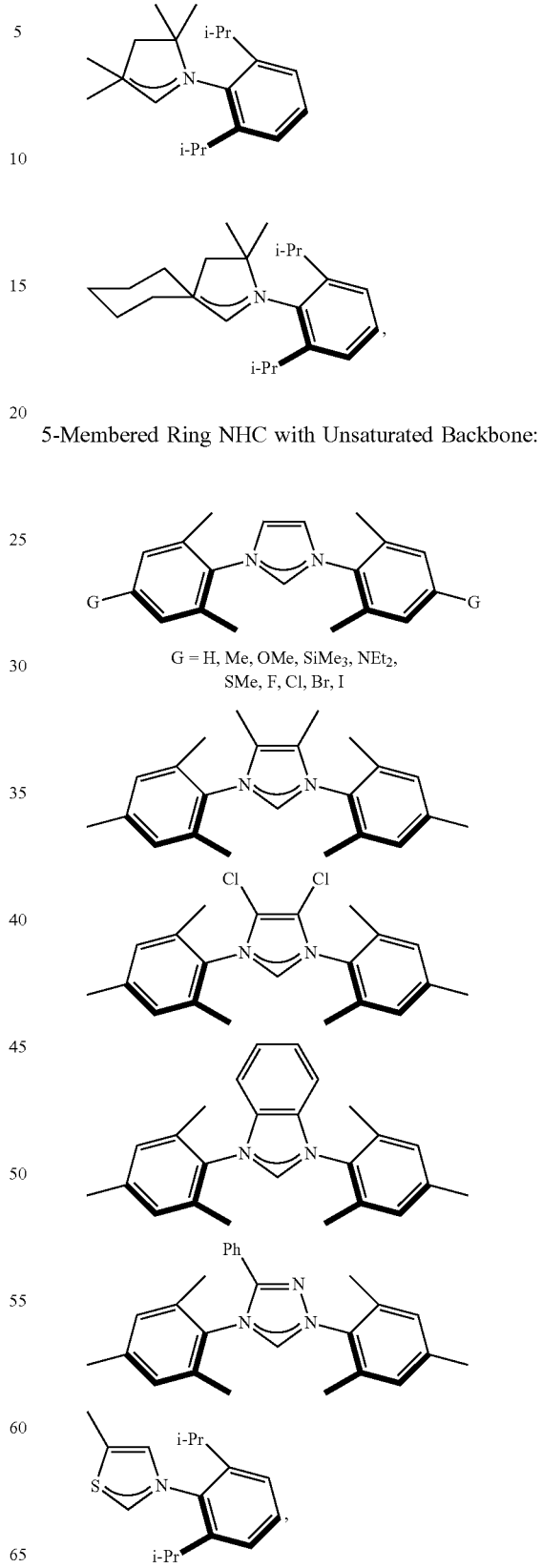
5-Membered Ring NHC with Unsaturated Backbone:
G = H, Me, OMe, SiMe₃, NEt₂, SMe, F, Cl, Br, I 6-Membered Ring NHC:

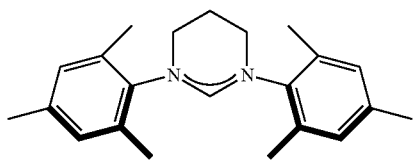

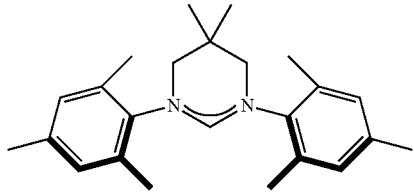

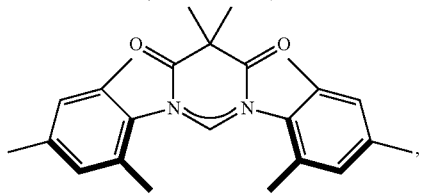

7-Membered Ring NHC:

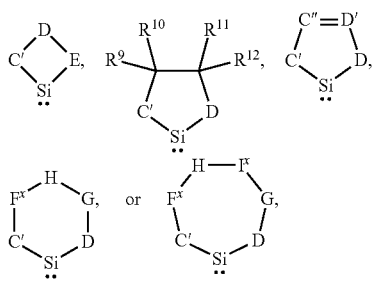

In some embodiments, $R^1$ is silylene.

In some embodiments, $R^1$ is $(R^x)_2Si:$, wherein each $R^x$ is independently as defined above and described herein. In some embodiments, at least one of $R^x$ is connected the silicon atom through a heteroatom.

In some embodiments, $R^1$ is an optionally substituted 3-8 membered cyclic silylene. In some embodiments, $R^1$ is an optionally substituted group having the structure of:

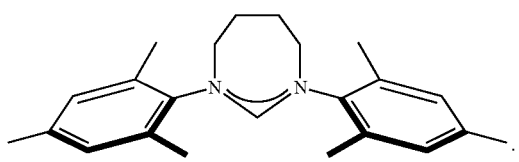

wherein each variable is independently as defined above and described herein. In some embodiments, $R^1$ is

In some embodiments, $R^1$ is

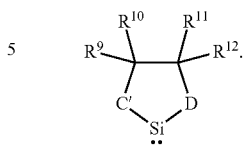

In some embodiments, $R^1$ is

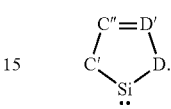

In some embodiments, $R^1$ is

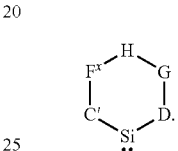

In some embodiments, $R^1$ is

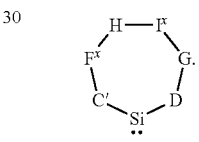

In some embodiments, $R^1$ is a silylene having the structure of

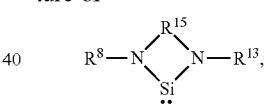

wherein each variable is independently as defined above and described herein.

In some embodiments, $R^1$ is an optionally substituted group having the structure of:

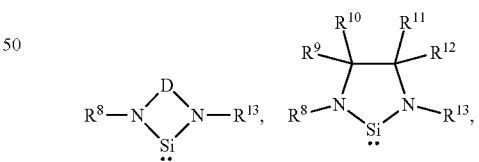

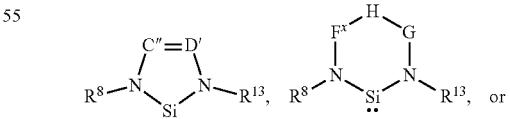

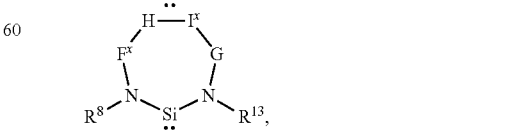

wherein each variable is independently as defined above and described herein. In some embodiments, $R^1$ is In some embodiments, $R^1$ is

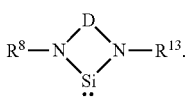

In some embodiments, $R^1$ is

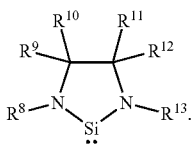

In some embodiments, $R^1$ is

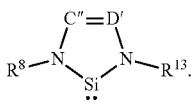

In some embodiments, $R^1$ is

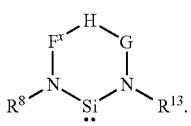

In some embodiments, $R^1$ is

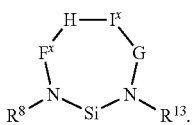

In some embodiments, each $R^1$ is the same. In some embodiments, at least one $R^1$ is different from the others. In some embodiments, one or more $R^1$ are taken together to form a bidentate or polydentate ligand.

In some embodiments, at least one $R^1$ is a phosphine. In some embodiments, at least one $R^1$ is a carbene or silylene. In some embodiments, at least one $R^1$ is a carbene. In some embodiments, at least one $R^1$ is an NHC. In some embodiments, at least one $R^1$ is a silylene.

As generally defined above, r is 1-3. In some embodiments, r is 1, 2 or 3. In some embodiments, r is 1. In some embodiments, r is 2. In some embodiments, r is 3.

As defined generally above, R is hydrogen or an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur.

In some embodiments, R is hydrogen.

In some embodiments, R is an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur.

In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl.

In some embodiments, R is optionally substituted $C_{3-20}$ cycloaliphatic. In some embodiments, R is optionally substituted $C_{3-10}$ cycloaliphatic. In some embodiments, R is optionally substituted cyclohexyl. In some embodiments, R is cyclohexyl. In some embodiments, R is

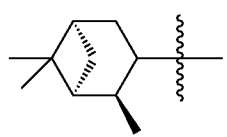

In some embodiments, R is

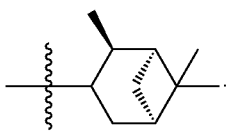 [SMILES: *C1C[C@H]2C[C@@H]([C@@H]1C)C2(C)C]

In some embodiments, R is adamantyl.

In some embodiments, R is $C_{1-20}$ heteroaliphatic. In some embodiments, R is $C_{1-20}$ heteroaliphatic having 1-6 heteroatoms independently selected from nitrogen, sulfur, phosphorus or selenium. In some embodiments, R is $C_{1-20}$ heteroaliphatic having 1-6 heteroatoms independently selected from nitrogen, sulfur, phosphorus or selenium, optionally including one or more oxidized forms of nitrogen, sulfur, phosphorus or selenium. In some embodiments, R is $C_{1-20}$ heteroaliphatic comprising 1-6 groups independently selected from

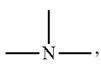

—N=, =N—, —S—, —S(O)—, —S(O)$_2$—, —O—, =O,

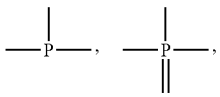

—Se—, and —Se(O)—.

In some embodiments, R is optionally substituted phenyl. In some embodiments, R is optionally substituted phenyl wherein one or more substituents are halogen. In some embodiments, R is optionally substituted phenyl wherein one or more substituents are —F. In some embodiments, R is optionally substituted phenyl wherein one or more substituents are —Cl. In some embodiments, R is optionally substituted phenyl wherein one or more substituents are —Br. In some embodiments, R is optionally substituted phenyl wherein one or more substituents are —I. In some embodiments, R is phenyl. In some embodiments, R is mesityl. In some embodiments, R is 2,6-diflurophenyl. In some embodiments, R is tolyl. In some embodiments, R is o-tolyl. In some embodiments, R is 4-fluorophenyl. In some embodiments, R is 2,6-diisopropylphenyl. In some embodiments, R is 2,4-diisopropylphenyl. In some embodiments, R is 2-isopropylphenyl. In some embodiments, R is 2,6-dimethylphenyl. In some embodiments, R is 2,6-dimethyl-4-methoxyphenyl. In some embodiments, R is 2,6-dimethyl-4-trimethylsilylphenyl. In some embodiments, R is 2,6-dimethyl-4-diethylaminophenyl. In some embodiments, R is 2,6-dimethyl-4-methylthiophenyl. In some embodiments, R is 2,6-dimethyl-4-fluorophenyl. In some embodiments, R is 2,6-dimethyl-4-chlorophenyl. In some embodiments, R is 2,6-dimethyl-4-bromophenyl. In some embodiments, R is 2,6-dimethyl-4-iodophenyl. In some embodiments, R is 2-fluorophenyl. In some embodiments, R is 2-methylphenyl. In some embodiments, R is 2-ethylphenyl. In some embodiments, R is 2-isopropylphenyl. In some embodiments, R is 2-tert-butylphenyl. In some embodiments, R is 2-phenylphenyl. In some embodiments, R is 2-(o-tolyl)phenyl. In some embodiments, R is 3,5-di-tert-butylpheyl. In some embodiments, R is 2-isopropyl-4-methoxy-5-tert-butylphenyl. In some embodiments, R is 2,3-diisopropylphenyl. In some embodiments, R is 2,3,5,6-tetramethylphenyl.

In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl. In some embodiments, R is

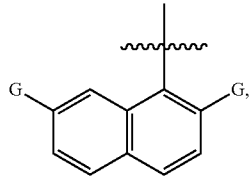

wherein G is hydrogen, methyl, ethyl, isopropyl or tert-butyl.

In some embodiments, R is optionally substituted biaryl wherein each aryl group is independently an optionally substituted group selected from phenyl, a 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur. In some embodiments, R is optionally substituted biaryl wherein each aryl group is independently an optionally substituted group selected from phenyl, a 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is optionally substituted phenyl. In some embodiments, R is optionally substituted biaryl wherein each aryl group is independently an optionally substituted group selected from phenyl, a 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is an optionally substituted 5-6 membered monocyclic heteroaryl ring having 1-4 heteroatoms independently selected from nitrogen, oxygen, or sulfur. In some embodiments, R is optionally substituted biaryl wherein each aryl group is independently an optionally substituted group selected from phenyl, a 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is an optionally substituted 8-10 membered bicyclic aryl ring. In some embodiments, R is optionally substituted biaryl wherein each aryl group is independently an optionally substituted group selected from phenyl, a 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is optionally substituted naphthyl. In some embodiments, R is optionally substituted biaryl wherein each aryl group is independently an optionally substituted group selected from phenyl, a 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is an optionally substituted 8-10 membered bicyclic heteroaryl ring having 1-5 heteroatoms independently selected from nitrogen, oxygen, or sulfur. In some embodiments, R is optionally substituted biaryl wherein each aryl group is independently optionally substituted phenyl. In some embodiments, R is optionally substituted biaryl wherein each aryl group is independently optionally substituted phenyl, or an optionally substituted 5-6 membered monocyclic heteroaryl ring having 1-4 heteroatoms independently selected from nitrogen, oxygen. In some embodiments, R is optionally substituted biaryl wherein each aryl group is independently an optionally substituted 8-10 membered bicyclic aryl ring. In some embodiments, R is optionally substituted biaryl wherein one aryl group is optionally substituted naphthyl, and the other aryl group is independently an optionally substituted 8-10 membered bicyclic aryl ring. In some embodiments, R is optionally substituted biaryl wherein each aryl group is optionally substituted naphthyl. In some embodiments, R is optionally substituted biaryl wherein one aryl group is optionally substituted naphthyl, and the other aryl group is an optionally substituted 8-10 membered bicyclic heteroaryl ring having 1-5 heteroatoms independently selected from nitrogen, oxygen, or sulfur.

In some embodiments, R is an optionally substituted 5-6 membered monocyclic heteroaryl ring having 1-4 heteroatoms independently selected from nitrogen, oxygen, or sulfur. In some embodiments, R is a substituted 5-6 membered monocyclic heteroaryl ring having 1-4 heteroatoms independently selected from nitrogen, oxygen, or sulfur. In some embodiments, R is an unsubstituted 5-6 membered monocyclic heteroaryl ring having 1-4 heteroatoms independently selected from nitrogen, oxygen, or sulfur.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, or sulfur.

In some embodiments, R is an optionally substituted 5-membered monocyclic heteroaryl ring having one heteroatom selected from nitrogen, oxygen, or sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, or sulfur. In certain embodiments, R is an optionally substituted 5-membered heteroaryl ring having one nitrogen atom, and an additional heteroatom selected from sulfur or oxygen. Exemplary R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, or sulfur. Exemplary R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, or sulfur. Exemplary R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Exemplary R groups include but are not limited to optionally substituted pyridinyl, pyrimidinyl, pyrazinyl, pyridazinyl, triazinyl, or tetrazinyl.

In some embodiments, R is an optionally substituted 3-7 membered saturated or partially unsaturated heterocyclic ring having 1-3 heteroatoms independently selected from nitrogen, oxygen, or sulfur. In some embodiments, R is a substituted 3-7 membered saturated or partially unsaturated heterocyclic ring having 1-3 heteroatoms independently selected from nitrogen, oxygen, or sulfur. In some embodiments, R is an unsubstituted 3-7 membered saturated or partially unsaturated heterocyclic ring having 1-3 heteroatoms independently selected from nitrogen, oxygen, or sulfur.

In certain embodiments, R is an optionally substituted 5-7 membered partially unsaturated monocyclic ring having 1-3 heteroatoms independently selected from nitrogen, oxygen, or sulfur. In certain embodiments, R is an optionally substituted 5-6 membered partially unsaturated monocyclic ring having 1-3 heteroatoms independently selected from nitrogen, oxygen, or sulfur. In certain embodiments, R is an optionally substituted 5-membered partially unsaturated monocyclic ring having 1-3 heteroatoms independently selected from nitrogen, oxygen, or sulfur. Exemplary R groups include but are not limited to optionally substituted dihydroimidazolyl, dihydrothiazolyl, dihydrooxazolyl, or oxazolinyl. In certain embodiments, R is an optionally substituted 6-membered partially unsaturated monocyclic ring having 1-3 heteroatoms independently selected from nitrogen, oxygen, or sulfur. Exemplary R groups include but are not limited to optionally substituted dihydropyridinyl, tetrahydropyridinyl, dihydropyrimidinyl, tetrahydropyrimidinyl, dihydropyrazinyl, tetrahydropyrazinyl, dihydrotriazinyl, tetrahydrotriazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, R is an optionally substituted 7-membered partially unsaturated monocyclic ring having 1-3 heteroatoms independently selected from nitrogen, oxygen, or sulfur. Exemplary R groups include but are not limited to optionally substituted azepinyl, oxepinyl, thiepinyl, diazepinyl, oxazepinyl, thiazepinyl, triazepinyl, oxadiazepinyl, thiadiazepinyl, dihydroazepinyl, dihydrooxepinyl, dihydrothiepinyl, dihydrodiazepinyl, dihydrooxazepinyl, dihydrothiazepinyl, dihydrotriazepinyl, dihydrooxadiazepinyl, dihydrothiadiazepinyl, tetrahydroazepinyl, tetrahydrooxepinyl, tetrahydrothiepinyl, tetrahydrodiazepinyl, tetrahydrooxazepinyl, tetrahydrothiazepinyl, tetrahydrotriazepinyl, tetrahydrooxadiazepinyl, or tetrahydrothiadiazepinyl.

In some embodiments, R is optionally substituted 3-membered heterocyclic ring having one heteroatom selected from nitrogen, oxygen or sulfur. Exemplary R groups include but are not limited to optionally substituted aziridinyl, thiiranyl or oxiranyl. In some embodiments, R is optionally substituted 4-membered heterocyclic ring having 1-3 heteroatoms independently selected from nitrogen, oxygen, or sulfur. Exemplary R groups include but are not limited to optionally substituted azetidinyl, oxetanyl, thietanyl, oxazetidinyl, thiazetidinyl, or diazetidinyl. In some embodiments, R is optionally substituted 5-membered heterocyclic ring having 1-3 heteroatoms independently selected from nitrogen, oxygen, or sulfur. Exemplary R groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, isothiazolidinyl, triazolidinyl, oxadiazolidinyl, thiadiazolidinyl, oxadiazolidinyl, dioxazolidinyl, oxathiazolidinyl, thiadiazolidinyl or dithiazolidinyl. In some embodiments, R is optionally substituted 6-membered heterocyclic ring having 1-3 heteroatoms independently selected from nitrogen, oxygen, or sulfur. Exemplary R groups include but are not limited to optionally substituted piperidinyl, tetrahydropyranyl, tetrahydrothiopyranyl, piperazinyl, morpholinyl, thiomorpholinyl, dithianyl, dioxanyl, oxathianyl, triazinanyl, oxadiazinanyl, thiadiazinanyl, dithiazinanyl, dioxazinanyl, oxathiazinanyl, oxadithianyl, trioxanyl, dioxathianyl or trithianyl. In some embodiments, R is optionally substituted 7-membered heterocyclic ring having 1-3 heteroatoms independently selected from nitrogen, oxygen, or sulfur. Exemplary R groups include but are not limited to optionally substituted azepanyl, oxepanyl, thiepanyl, diazepanyl, oxazepanyl, thiazepanyl, dioxepanyl, oxathiepanyl, dithiepanyl, triazepanyl, oxadiazepanyl, thiadiazepanyl, dioxazepanyl, oxathiazepanyl, dithiazepanyl, trioxepanyl, dioxathiepanyl, oxadithiepanyl or trithiepanyl.

In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothienyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothienyl, or tetrahydrothiopyranyl.

In some embodiments, R is an optionally substituted 7-10 membered bicyclic saturated or partially unsaturated heterocyclic ring having 1-5 heteroatoms independently selected from nitrogen, oxygen, or sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, or sulfur.

In some embodiments, R is an optionally substituted 5,6-fused heteroaryl ring having 1-5 heteroatoms independently selected from nitrogen, oxygen, or sulfur. In some embodiments, R is an optionally substituted 5,6-fused heteroaryl ring having 1-4 heteroatoms independently selected from nitrogen, oxygen, or sulfur. In some embodiments, R is an optionally substituted 5,6-fused heteroaryl ring having 1-3 heteroatoms independently selected from nitrogen, oxygen, or sulfur. In some embodiments, R is an optionally substituted 5,6-fused heteroaryl ring having two heteroatoms independently selected from nitrogen, oxygen, or sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, or sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, or sulfur. In some embodiments, R is an optionally substituted 5,6-fused heteroaryl ring having five heteroatoms independently selected from nitrogen, oxygen, or sulfur.

In some embodiments, R is an optionally substituted 5,6-fused heteroaryl ring having 1-5 heteroatoms independently selected from nitrogen, oxygen, or sulfur. In other embodiments, R is an optionally substituted 5,6-fused heteroaryl ring having 1-2 heteroatoms independently selected from nitrogen, oxygen, or sulfur. In certain embodiments, R is an optionally substituted 5,6-fused heteroaryl ring having one heteroatom independently selected from nitrogen, oxygen, or sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, or sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, or sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, or sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, or sulfur.

In certain embodiments, R is an optionally substituted 6,6-fused heteroaryl ring having 1-5 heteroatoms independently selected from nitrogen, oxygen, or sulfur. In some embodiments, R is an optionally substituted 6,6-fused heteroaryl ring having 1-2 heteroatoms independently selected from nitrogen, oxygen, or sulfur. In other embodiments, R is an optionally substituted 6,6-fused heteroaryl ring having one heteroatom selected from nitrogen, oxygen, or sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, or sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, or sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, or sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, or sulfur.

In some embodiments, R is optionally substituted heterobiaryl wherein each heteroaryl group is independently an optionally substituted group selected from a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, R is optionally substituted heterobiaryl wherein each aryl group is an optionally substituted 8-10 membered bicyclic heteroaryl ring having 1-5 heteroatoms independently selected from nitrogen, oxygen, or sulfur.

In some embodiments, two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur. In some embodiments, two R groups on the same carbon atom are optionally taken together with the carbon atom to form an optionally substituted 3-10 membered, saturated, partially unsaturated, or aryl ring having 0-4 heteroatoms independently selected from nitrogen, oxygen, or sulfur. In some embodiments, two R groups on the same nitrogen atom are optionally taken together with the nitrogen atom to form an optionally substituted 3-10 membered, saturated, partially unsaturated, or aryl ring having 1-5 heteroatoms independently selected from nitrogen, oxygen, or sulfur. In some embodiments, two R groups on the same sulfur atom are optionally taken together with the sulfur atom to form an optionally substituted 3-10 membered, saturated, partially unsaturated, or aryl ring having 1-5 heteroatoms independently selected from nitrogen, oxygen, or sulfur. In some embodiments, two R groups on the same oxygen atom are optionally taken together with the oxygen atom to form an optionally substituted 3-10 membered, saturated, partially unsaturated, or aryl ring having 1-5 heteroatoms independently selected from nitrogen, oxygen, or sulfur. In some embodiments, two R groups on the same selenium atom are optionally taken together with the selenium atom to form an optionally substituted 3-10 membered, saturated, partially unsaturated, or aryl ring having, in addition to the selenium atom, 0-4 heteroatoms independently selected from nitrogen, oxygen, or sulfur. In some embodiments, two R groups on the same phosphorus atom are optionally taken together with the phosphorus atom to form an optionally substituted 3-10 membered, saturated, partially unsaturated, or aryl ring having, in addition to the phosphorus atom, 0-4 heteroatoms independently selected from nitrogen, oxygen, or sulfur. In some embodiments, three R groups on the same phosphorus atom, e.g., the three R groups of a phosphine ligand having the structure of $P(R)_3$, are taken together with the phosphorus atom to form an optionally substituted 3-10 membered, saturated or partially unsaturated, monocyclic, bicyclic or polycyclic ring having, in addition to the phosphorus atom, 0-4 heteroatoms independently selected from nitrogen, oxygen, or sulfur.

As generally defined above, $R^{14}$ is a carbene. In some embodiments, $R^{14}$ is a non-chelating carbene. In some embodiments, $R^{14}$ is a chelating carbene. In some embodiments, $R^{14}$ is a carbene bonded to M via a double bond. In some embodiments, $R^{14}$ is alkylidene, arylidene, vinylidene, or allenylidene. In some embodiments, $R^{14}$ is alkylidene. In some embodiments, $R^{14}$ is arylidene. In some embodiments, $R^{14}$ is vinylidene. In some embodiments, $R^{14}$ is allenylidene. In some embodiments, $R^{14}$ is indenylidene. Exemplary $R^{14}$ groups are extensively described in the art, including but not limited to those described in Samojlowicz, C.; Bieniek, M.; Grela, K. Ruthenium-based olefin metathesis catalysts bearing N-heterocyclic carbene ligands, *Chem. Rev.* 2009, 109, 3708-3742, Vougioukalakis, G. C.; Grubbs, R. H. Ruthenium-based heterocyclic carbene-coordinated olefin metathesis catalysts, *Chem. Rev.* 2010, 110, 1746-1787, and Lozano-Vila, A. M.; Monsaert, S.; Bajek, A.; Verpoort, F. *Chem. Rev.* 2010, 110, 4865-4909.

In some embodiments, $R^{14}$ is optionally substituted $H_2C=$. In some embodiments, $R^{14}$ is optionally taken together with one or more other ligands to form a bidentate or polydentate ligand. In some embodiments, $R^{14}$ is optionally linked to a tag or support.

In some embodiments, $R^{14}$ has the structure of:

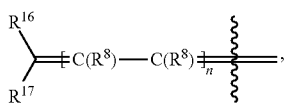

wherein:
each of $R^{16}$ and $R^{17}$ is independently $R^8$;
n is 0-3; and
each $R^8$ is independently as defined above and described herein. In some embodiments, $R^{14}$ is optionally taken together with one or more other ligands to form a bidentate or polydentate ligand, via one or more of $R^8$, $R^{16}$ and $R^{17}$. In some embodiments, $R^{14}$ is optionally linked to a tag or support, via one or more of $R^8$, $R^{16}$ and $R^7$.

In some embodiments, n is 0. In some embodiments, n is 1-3. In some embodiments, n is 1. In some embodiments, n is 2. In some embodiments, n is 3.

In some embodiments, $R^{16}$ is $R^x$, and $R^{17}$ is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, n is 0, and $R^{14}$ has the structure of:

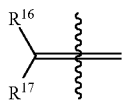

wherein each of $R^{16}$ and $R^{17}$ is independently as defined above and described herein. In some embodiments, $R^{14}$ is

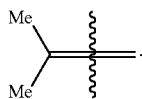

In some embodiments, $R^{16}$ and $R^{17}$ are taken together to form an optionally substituted 3-10 membered, saturated, partially unsaturated, or aryl ring having 0-4 heteroatoms independently selected from nitrogen, oxygen, or sulfur.

In some embodiments, two $R^8$ on the adjacent carbon atoms are taken together to form a double bond. In some embodiments, $R^{14}$ has the structure of:

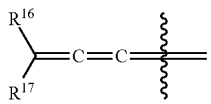

wherein each of $R^{16}$ and $R^{17}$ is independently as defined above and described herein. In some embodiments, $R^{14}$ is

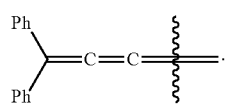

In some embodiments, $R^{14}$ has the structure of:

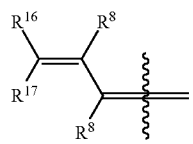

wherein each of $R^8$, $R^{16}$ and $R^{17}$ is independently as defined above and described herein. In some embodiments, each $R^8$ is hydrogen. In some embodiments, $R^{14}$ has the structure of

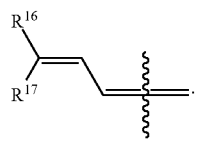

In some embodiments, $R^{14}$ has the structure of

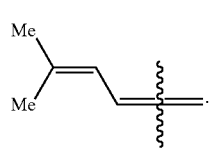

In some embodiments, $R^{14}$ has the structure of:

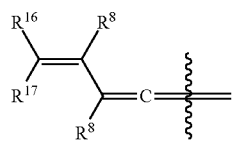

wherein each of $R^8$, $R^{16}$ and $R^{17}$ is independently as defined above and described herein. In some embodiments, each $R^8$ is hydrogen. In some embodiments, $R^{14}$ has the structure of

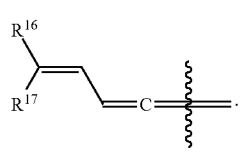

In some embodiments, $R^{14}$ has the structure of:

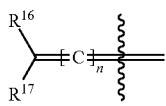

wherein each of n, $R^{16}$ and $R^{17}$ is independently as defined above and described herein.

In some embodiments, $R^{14}$ is optionally taken together with one or more other ligands to form a bidentate or polydentate ligand, via one or more of $R^{16}$ and $R^{17}$. In some embodiments, $R^{14}$ is optionally linked to a tag or support, via one or more of $R^{16}$ and $R^{17}$. In some embodiments, $R^{14}$ has the structure of

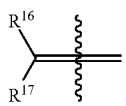

In some embodiments, $R^{14}$ has the structure of

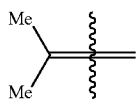

In some embodiments, $R^{14}$ has the structure of

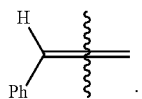

In some embodiments, $R^{14}$ has the structure of

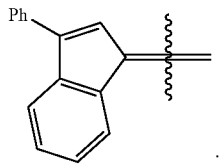 [SMILES: *=C1C=C(c2ccccc2)c2ccccc21]

In some embodiments, $R^{14}$ has the structure of

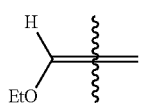

In some embodiments, $R^{14}$ has the structure of

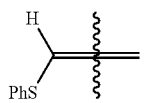

In some embodiments, $R^{14}$ has the structure of

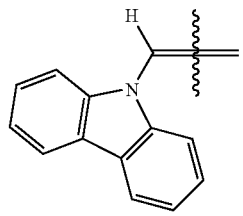

In some embodiments, $R^{14}$ has the structure of

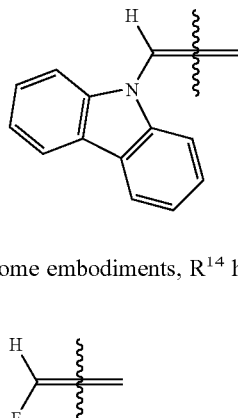

In some embodiments, $R^{14}$ has the structure of

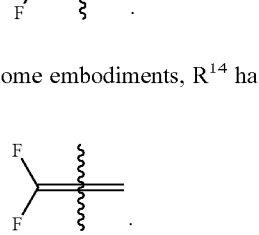

In some embodiments, $R^{14}$ has the structure of

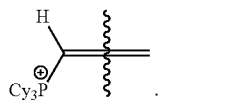

In some embodiments, $R^{14}$ has the structure of

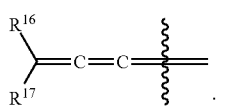

In some embodiments, $R^{14}$ has the structure

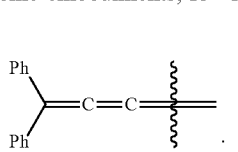

In some embodiments, $R^{14}$ has the structure of:

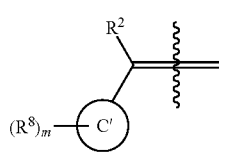

wherein:
Ring C' is an optionally substituted group selected from phenyl, a 3-7 membered saturated or partially unsaturated carbocyclic ring, an 8-14 membered bicyclic or polycyclic saturated, partially unsaturated or aryl ring, a 5-6- membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;

each of m, $R^2$, and $R^8$ is independently as defined above and described herein.

In some embodiments, $R^{14}$ is optionally taken together with one or more other ligands to form a bidentate or polydentate ligand, via one or more of $R^2$, $R^8$ and Ring C'. In some embodiments, $R^{14}$ is optionally linked to a tag or support, via one or more of $R^2$, $R^8$ and Ring C'.

In some embodiments, Ring C' is optionally substituted phenyl. In some embodiments, Ring C' is an optionally substituted group having the following structure:

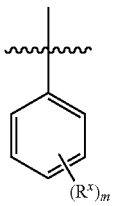

wherein each of $R^x$ and m is independently as defined above and described herein.

In some embodiments, Ring C' is an optionally substituted 3-7 membered saturated carbocyclic ring. In some embodiments, Ring C' is an optionally substituted 5-6 membered saturated carbocyclic ring. In some embodiments, Ring C' is an optionally substituted 3-7 membered partially unsaturated carbocyclic ring. In some embodiments, Ring C' is an optionally substituted 5-6 membered partially unsaturated carbocyclic ring.

In some embodiments, Ring C' is an optionally substituted 8-14 membered bicyclic or polycyclic saturated carbocyclic ring. In some embodiments, Ring C' is an optionally substituted 8-14 membered bicyclic or polycyclic partially unsaturated carbocyclic ring. In some embodiments, Ring C' is an optionally substituted 8-14 membered bicyclic saturated carbocyclic ring. In some embodiments, Ring C' is an optionally substituted 8-10 membered bicyclic saturated carbocyclic ring. In some embodiments, Ring C' is an optionally substituted 8-14 membered bicyclic or polycyclic partially unsaturated carbocyclic ring. In some embodiments, Ring C' is an optionally substituted 8-10 membered bicyclic partially unsaturated carbocyclic ring. In some embodiments, Ring C' is an optionally substituted 10-membered bicyclic aryl ring. In some embodiments, Ring C' is an optionally substituted 14 membered tricyclic aryl ring.

In some embodiments, Ring C' is an optionally substituted 5-6 membered monocyclic heteroaryl ring having 1-4 heteroatoms independently selected from nitrogen, oxygen, or sulfur. In some embodiments, Ring C' is an optionally substituted 5-6 membered monocyclic heteroaryl ring having 1-2 heteroatoms independently selected from nitrogen, oxygen, or sulfur. In some embodiments, Ring C' is an optionally substituted 5-membered monocyclic heteroaryl ring having 1-4 heteroatoms independently selected from nitrogen, oxygen, or sulfur. In some embodiments, Ring C' is an optionally substituted 5-membered monocyclic heteroaryl ring having 1-2 heteroatoms independently selected from nitrogen, oxygen, or sulfur. In some embodiments, Ring C' is an optionally substituted 6-membered monocyclic heteroaryl ring having 1-4 heteroatoms independently selected from nitrogen, oxygen, or sulfur. In some embodiments, Ring C' is an optionally substituted 6-membered monocyclic heteroaryl ring having 1-2 heteroatoms independently selected from nitrogen, oxygen, or sulfur.

In some embodiments, Ring C' is an optionally substituted 3-7 membered saturated heterocyclic ring having 1-3 heteroatoms independently selected from nitrogen, oxygen, or sulfur. In some embodiments, Ring C' is an optionally substituted 5-6 membered saturated heterocyclic ring having 1-2 heteroatoms independently selected from nitrogen, oxygen, or sulfur. In some embodiments, Ring C' is an optionally substituted 3-7 membered partially unsaturated heterocyclic ring having 1-3 heteroatoms independently selected from nitrogen, oxygen, or sulfur. In some embodiments, Ring C' is an optionally substituted 5-6 membered partially unsaturated heterocyclic ring having 1-2 heteroatoms independently selected from nitrogen, oxygen, or sulfur.

In some embodiments, Ring C' is an optionally substituted 7-14 membered bicyclic or polycyclic saturated heterocyclic ring having 1-5 heteroatoms independently selected from nitrogen, oxygen, or sulfur. In some embodiments, Ring C' is an optionally substituted 7-10 membered bicyclic saturated heterocyclic ring having 1-5 heteroatoms independently selected from nitrogen, oxygen, or sulfur. In some embodiments, Ring C' is an optionally substituted 8-10 membered bicyclic saturated heterocyclic ring having 1-2 heteroatoms independently selected from nitrogen, oxygen, or sulfur. In some embodiments, Ring C' is an optionally substituted 7-10 membered bicyclic partially unsaturated heterocyclic ring having 1-5 heteroatoms independently selected from nitrogen, oxygen, or sulfur. In some embodiments, Ring C' is an optionally substituted 8-10 membered bicyclic partially unsaturated heterocyclic ring having 1-2 heteroatoms independently selected from nitrogen, oxygen, or sulfur.

In some embodiments, Ring C' is an optionally substituted 8-14 membered bicyclic or tricyclic heteroaryl ring having 1-5 heteroatoms independently selected from nitrogen, oxygen, or sulfur. In some embodiments, Ring C' is an optionally substituted 8-10 membered bicyclic heteroaryl ring having 1-5 heteroatoms independently selected from nitrogen, oxygen, or sulfur. In some embodiments, Ring C' is an optionally substituted 8-membered bicyclic heteroaryl ring having 1-3 heteroatoms independently selected from nitrogen, oxygen, or sulfur. In some embodiments, Ring C' is an optionally substituted 9-membered bicyclic heteroaryl ring having 1-3 heteroatoms independently selected from nitrogen, oxygen, or sulfur. In some embodiments, Ring C' is an optionally substituted 10-membered bicyclic heteroaryl ring having 1-3 heteroatoms independently selected from nitrogen, oxygen, or sulfur. In some embodiments, Ring C' is an optionally substituted 10-14 membered tricyclic heteroaryl ring having 1-5 heteroatoms independently selected from nitrogen, oxygen, or sulfur.

Exemplary embodiments for Ring C' include but are not limited to those described for R wherein R is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, $R^{14}$ has the structure of

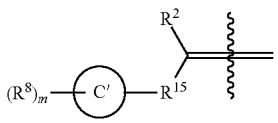

wherein each variable is independently as defined above and described herein.

In some embodiments, $R^{14}$ has the structure of

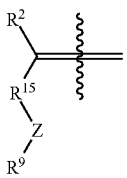

wherein each variable is independently as defined above and described herein. In some embodiments, $R^{14}$ is optionally taken together with one or more other ligands to form a bidentate or polydentate ligand, via one or more of $R^2$, $R^{15}$, Z and $R^{19}$. In some embodiments, $R^{14}$ is optionally linked to a tag or support, via one or more of $R^2$, $R^{15}$, Z and $R^{19}$.

In some embodiments, $R^{14}$ has the structure of

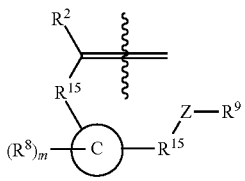

wherein each variable is independently as defined above and described herein. In some embodiments, $R^{14}$ is optionally taken together with one or more other ligands to form a bidentate or polydentate ligand, via one or more of $R^2$, $R^{15}$, $R^8$, Ring C, $R^{15}$, Z and $R^x$. In some embodiments, $R^{14}$ is optionally linked to a tag or support, via one or more of $R^2$, $R^{15}$, $R^8$, Ring C, $R^{15}$, Z and $R^x$.

In some embodiments, Ring C is optionally substituted phenyl. In some embodiments, Ring C is an optionally substituted group having the following structure:

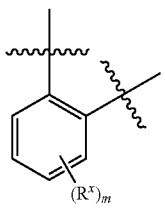

wherein each of $R^x$ and m is independently as defined above and described herein.

In some embodiments, Ring C is an optionally substituted 3-7 membered saturated carbocyclic ring. In some embodiments, Ring C is an optionally substituted 5-6 membered saturated carbocyclic ring. In some embodiments, Ring C is an optionally substituted 3-7 membered partially unsaturated carbocyclic ring. In some embodiments, Ring C is an optionally substituted 5-6 membered partially unsaturated carbocyclic ring.

In some embodiments, Ring C is an optionally substituted 8-14 membered bicyclic or polycyclic saturated carbocyclic ring. In some embodiments, Ring C is an optionally substituted 8-14 membered bicyclic or polycyclic partially unsaturated carbocyclic ring. In some embodiments, Ring C is an optionally substituted 8-10 membered bicyclic saturated carbocyclic ring. In some embodiments, Ring C is an optionally substituted 8-14 membered bicyclic or polycyclic partially unsaturated carbocyclic ring. In some embodiments, Ring C is an optionally substituted 8-10 membered bicyclic partially unsaturated carbocyclic ring. In some embodiments, Ring C is an optionally substituted 10-membered bicyclic aryl ring. In some embodiments, Ring C is an optionally substituted 14 membered tricyclic aryl ring.

In some embodiments, Ring C is an optionally substituted 5-6 membered monocyclic heteroaryl ring having 1-4 heteroatoms independently selected from nitrogen, oxygen, or sulfur. In some embodiments, Ring C is an optionally substituted 5-6 membered monocyclic heteroaryl ring having 1-2 heteroatoms independently selected from nitrogen, oxygen, or sulfur. In some embodiments, Ring C is an optionally substituted 5-membered monocyclic heteroaryl ring having 1-4 heteroatoms independently selected from nitrogen, oxygen, or sulfur. In some embodiments, Ring C is an optionally substituted 5-membered monocyclic heteroaryl ring having 1-2 heteroatoms independently selected from nitrogen, oxygen, or sulfur. In some embodiments, Ring C is an optionally substituted 6-membered monocyclic heteroaryl ring having 1-4 heteroatoms independently selected from nitrogen, oxygen, or sulfur. In some embodiments, Ring C is an optionally substituted 6-membered monocyclic heteroaryl ring having 1-2 heteroatoms independently selected from nitrogen, oxygen, or sulfur.

In some embodiments, Ring C is an optionally substituted 3-7 membered saturated heterocyclic ring having 1-3 heteroatoms independently selected from nitrogen, oxygen, or sulfur. In some embodiments, Ring C is an optionally substituted 5-6 membered saturated heterocyclic ring having 1-2 heteroatoms independently selected from nitrogen, oxygen, or sulfur. In some embodiments, Ring C is an optionally substituted 3-7 membered partially unsaturated heterocyclic ring having 1-3 heteroatoms independently selected from nitrogen, oxygen, or sulfur. In some embodiments, Ring C is an optionally substituted 5-6 membered partially unsaturated heterocyclic ring having 1-2 heteroatoms independently selected from nitrogen, oxygen, or sulfur.

In some embodiments, Ring C is an optionally substituted 7-14 membered bicyclic or polycyclic saturated heterocyclic ring having 1-5 heteroatoms independently selected from nitrogen, oxygen, or sulfur. In some embodiments, Ring C is an optionally substituted 7-10 membered bicyclic saturated heterocyclic ring having 1-5 heteroatoms independently selected from nitrogen, oxygen, or sulfur. In some embodiments, Ring C is an optionally substituted 8-10 membered bicyclic saturated heterocyclic ring having 1-2 heteroatoms independently selected from nitrogen, oxygen, or sulfur. In some embodiments, Ring C is an optionally substituted 7-10 membered bicyclic partially unsaturated heterocyclic ring having 1-5 heteroatoms independently selected from nitrogen, oxygen, or sulfur. In some embodiments, Ring C is an optionally substituted 8-10 membered bicyclic partially unsaturated heterocyclic ring having 1-2 heteroatoms independently selected from nitrogen, oxygen, or sulfur.

In some embodiments, Ring C is an optionally substituted 8-14 membered bicyclic or tricyclic heteroaryl ring having 1-5 heteroatoms independently selected from nitrogen, oxygen, or sulfur. In some embodiments, Ring C is an optionally substituted 8-10 membered bicyclic heteroaryl ring having 1-5 heteroatoms independently selected from nitrogen, oxygen, or sulfur. In some embodiments, Ring C is an optionally substituted 8-membered bicyclic heteroaryl ring having 1-3 heteroatoms independently selected from nitrogen, oxygen, or sulfur. In some embodiments, Ring C is an optionally substituted 9-membered bicyclic heteroaryl ring having 1-3 heteroatoms independently selected from nitrogen, oxygen, or sulfur. In some embodiments, Ring C is an optionally substituted 10-membered bicyclic heteroaryl ring having 1-3 heteroatoms independently selected from nitrogen, oxygen, or sulfur. In some embodiments, Ring C is an optionally substituted 10-14 membered tricyclic heteroaryl ring having 1-5 heteroatoms independently selected from nitrogen, oxygen, or sulfur.

In some embodiments, Ring C is Ring A.

Exemplary embodiments for Ring C include but are not limited to those described for R wherein R is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, Ring C is

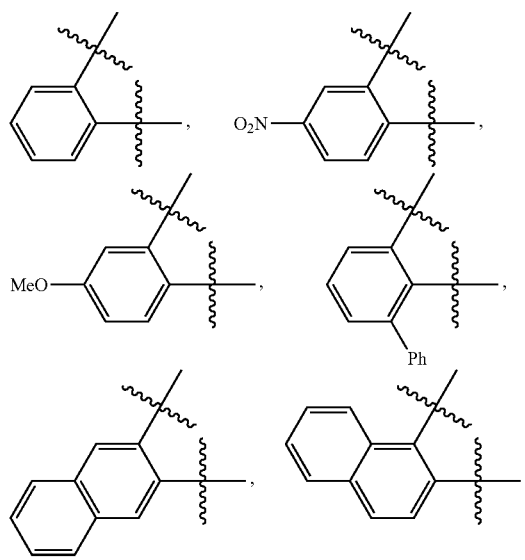

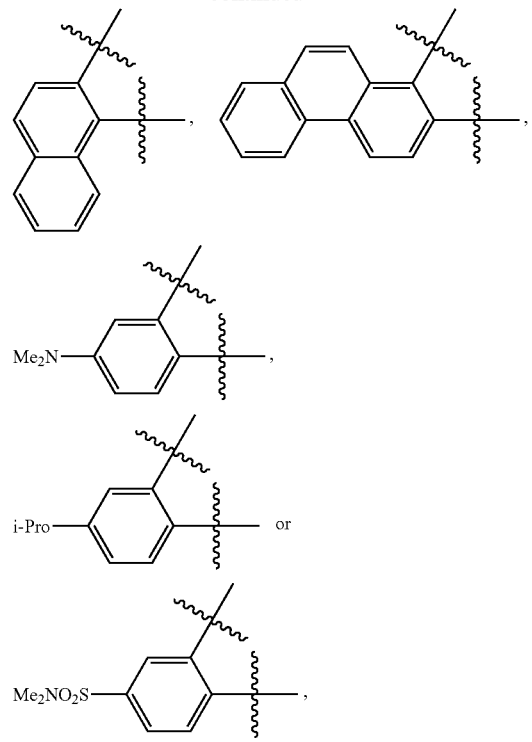

In some embodiments, $R^{14}$ has the structure of

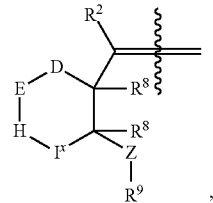

wherein each variable is independently as defined above and described herein. In some embodiments, $R^{14}$ is

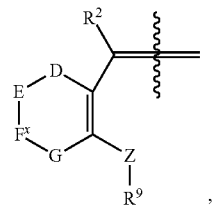

wherein each variable is independently as defined above and described herein. In some embodiments, $R^{14}$ is

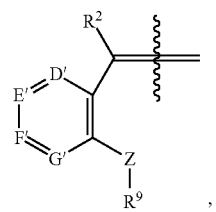

wherein each of D', E', F', and G' is independently —N=, or —C(R$^8$)=, and each of R$^2$, Z and R$^x$ is independently as defined above and described herein.

In some embodiments, R$^{14}$ is

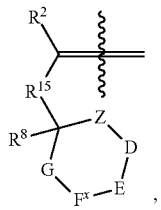

wherein each variable is independently as defined above and described herein. In some embodiments, R$^{14}$ is an optionally substituted group having the structure of

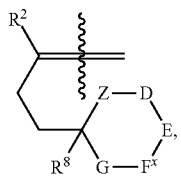

wherein each variable is independently as defined above and described herein. In some embodiments, R$^{14}$ is

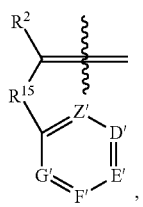

wherein Z' is —N=, or —C(R$^8$)=, and each of R$^2$, R$^{15}$, D', E', F' and G' is independently as defined above and described herein. In some embodiments, R$^{14}$ is an optionally substituted group having the structure of

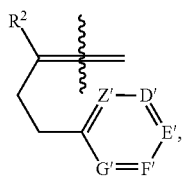

wherein each variable is independently as defined above and described herein.

In some embodiments, R$^{14}$ has the structure of

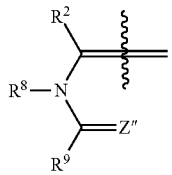

wherein Z" is =C(R$^8$)$_2$, =Si(R$^8$)$_2$, =O, =S, =NR$^8$, =PR$^8$, or =P(O)R$^8$, and each of R$^2$, R$^8$ and R$^9$ is independently as defined above and described herein. In some embodiments, R$^{14}$ has the structure of

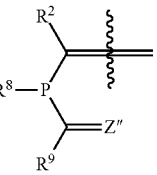

wherein Z" is =C(R$^8$)$_2$, =Si(R$^8$)$_2$, =O, =S, =NR$^8$, =PR$^8$, or =P(O)R$^8$, and each of R$^2$, R$^8$ and R$^9$ is independently as defined above and described herein.

In some embodiments, R$^{14}$ is

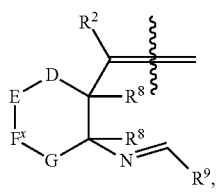

wherein each variable is independently as defined above and described herein. In some embodiments, R$^{14}$ is

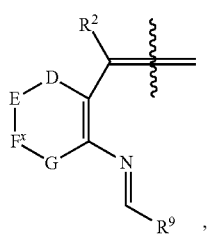

wherein each variable is independently as defined above and described herein. In some embodiments, R$^{14}$ is

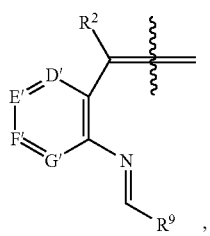

wherein each variable is independently as defined above and described herein.

In some embodiments, R$^{14}$ is

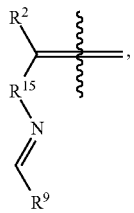

wherein each variable is independently as defined above and described herein. In some embodiments, $R^{14}$ is

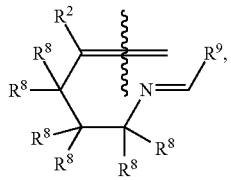

wherein each variable is independently as defined above and described herein. In some embodiments, $R^{14}$ is

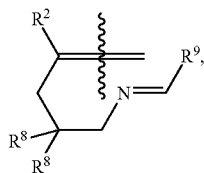

wherein each variable is independently as defined above and described herein.

In some embodiments, $R^{14}$ is

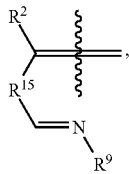

wherein each variable is independently as defined above and described herein. In some embodiments, $R^{14}$ is

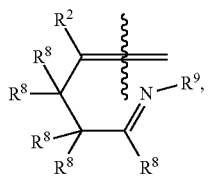

wherein each variable is independently as defined above and described herein. In some embodiments, $R^{14}$ is

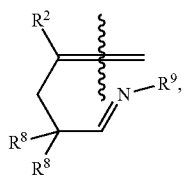

wherein each variable is independently as defined above and described herein.

In some embodiments, $R^{14}$ and L are covalently linked. In some embodiments, $R^{14}$ and L are taken together to form a bidentate ligand. A bidentate ligand formed by $R^{14}$ and L, such as those described herein, is optionally taken together with one or more of $R^1$, $R^4$ and $R^5$ to form a polydentate ligand. In some embodiments, a formed bidentate or polydentate ligand is optionally linked to a tag or solid support. In some embodiments, $R^{14}$ and L are covalently linked, and they coordinate with M to form a 6-membered ring structure. For example, see exemplary compound B-1o. In some embodiments, L is bonded to M through a nitrogen atom.

In some embodiments, $R^{14}$ and L are taken together to form a bidentate ligand having the structure of

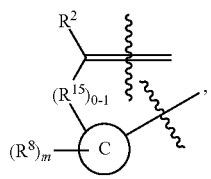

wherein each variable is independently as defined above and described herein.

In some embodiments, Ring C comprises one or more Z, and is bond to M through Z. In some embodiments, Z is in the ring system of Ring C. In some embodiments, Z is —N=. In some embodiments, Z is in a substituent of Ring C. In some embodiments, $R^{14}$ is optionally taken together with one or more other ligands to form a bidentate or polydentate ligand, via one or more of $R^2$, $R^{15}$, $R^8$, and Ring C. In some embodiments, $R^{14}$ is optionally linked to a tag or support, via one or more of $R^2$, $R^{15}$, $R^8$, and Ring C.

In some embodiments, Ring C comprises one or more Z, and is bond to M through Z. In some embodiments, Z is in the ring system of Ring C. In some embodiments, Z is in a substituent of Ring C. In some embodiments, $R^{14}$ is optionally taken together with one or more other ligands to form a bidentate or polydentate ligand, via one or more of $R^2$, $R^{15}$, $R^8$, and Ring C. In some embodiments, $R^{14}$ is optionally linked to a tag or support, via one or more of $R^2$, $R^{15}$, $R^8$, and Ring C.

In some embodiments, $R^{14}$ and L are taken together to form a bidentate ligand having the structure of

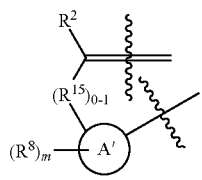

wherein:
Ring A' comprises one or more Z and is an optionally substituted ring selected from a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur, wherein Ring A' is bonded to M through Z; and
wherein each of $R^2$, $R^{t5}$, $R^x$ and m is independently as defined above and described herein.

In some embodiments, $R^{14}$ is optionally taken together with one or more other ligands to form a bidentate or polydentate ligand, via one or more of $R^2$, $R^{15}$, $R^8$, and Ring A'. In some embodiments, $R^{14}$ is optionally linked to a tag or support, via one or more of $R^2$, $R^{15}$, $R^8$, and Ring A'.

In some embodiments, Z is in the ring system of Ring A'. In some embodiments, Z is in a substituent of Ring A'. In some embodiments, $R^{14}$ and L are taken together to form a bidentate ligand having the structure of

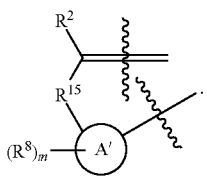

In some embodiments, Ring A' is optionally substituted pyridyl, wherein the nitrogen atom of the pyridyl ring is bonded to the metal atom. In some embodiments, Ring A' is 2-pyridyl. In some embodiments, Ring A' is optionally substituted quinolinyl, wherein the nitrogen atom the quinolinyl ring is bonded to the metal atom. In some embodiments, Ring A' is optionally substituted

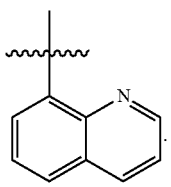 [SMILES: *c1cccc2cccnc12]

In some embodiments, Ring A' is

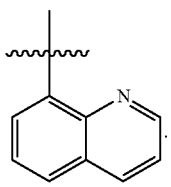 [SMILES: *c1cccc2cccnc12]

In some embodiments, $R^{14}$ and L are taken together to form a bidentate ligand having the structure of:

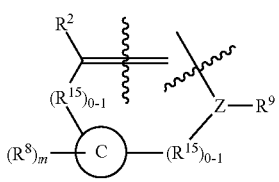

wherein each variable is independently as defined above and described herein.

In some embodiments, $R^{14}$ is optionally taken together with one or more other ligands to form a bidentate or polydentate ligand, via one or more of $R^2$, $R^{15}$, $R^8$, Ring C, Z and $R^9$. In some embodiments, $R^{14}$ is optionally linked to a tag or support, via one or more of $R^2$, $R^{15}$, $R^8$, Ring C, Z and $R^9$.

In some embodiments, $R^{14}$ and L are taken together to form a bidentate ligand having the structure of:

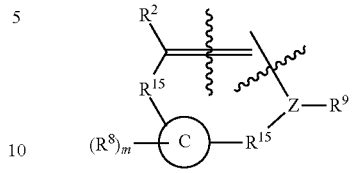

wherein each variable is independently as defined above and described herein. In some embodiments, $R^{14}$ and L are taken together to form a bidentate ligand having the structure of:

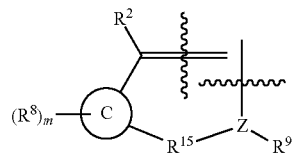

wherein each variable is independently as defined above and described herein. In some embodiments, $R^{14}$ and L are taken together to form a bidentate ligand having the structure of:

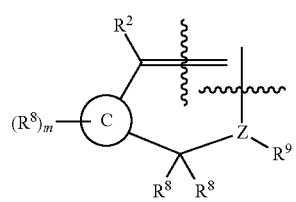

wherein each variable is independently as defined above and described herein. In some embodiments, $R^{14}$ and L are taken together to form a bidentate ligand having the structure of:

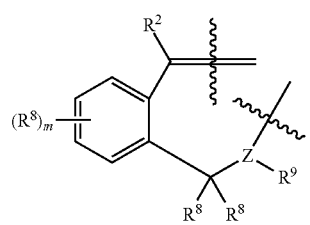

wherein each variable is independently as defined above and described herein. In some embodiments, $R^{14}$ and L are taken together to form a bidentate ligand having the structure of:

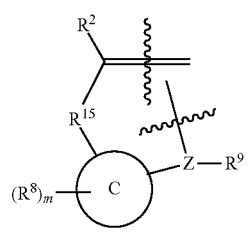

wherein each variable is independently as defined above and described herein. In some embodiments, $R^{14}$ and L are taken together to form a bidentate ligand having the structure of:

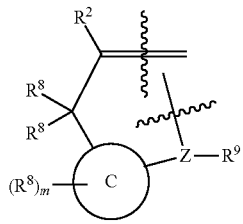

wherein each variable is independently as defined above and described herein.

In some embodiments, $R^{14}$ and L are taken together to form a bidentate ligand having the structure of

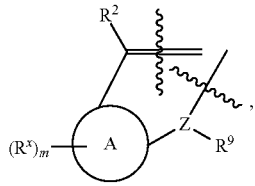

wherein each variable is independently as defined above and described herein. In some embodiments, $R^{14}$ is optionally taken together with one or more other ligands to form a bidentate or polydentate ligand, via one or more of $R^2$, $R^x$, Ring A, Z and $R^9$. In some embodiments, $R^{14}$ is optionally linked to a tag or support, via one or more of $R^2$, $R^x$, Ring A, Z and $R^9$. In some embodiments, $R^{14}$ and L are taken together to form a bidentate ligand having the structure of

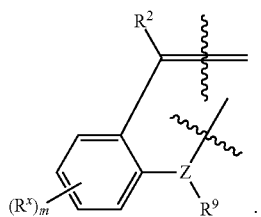

In some embodiments, $R^{14}$ and L are taken together to form a bidentate ligand having the structure of

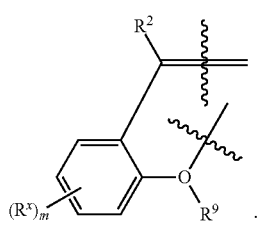

In some embodiments, $R^{14}$ and L are taken together to form a bidentate ligand having the structure of

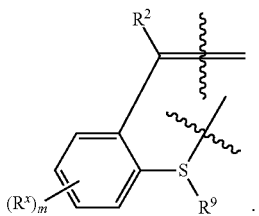

In some embodiments, $R^{14}$ and L are taken together to form a bidentate ligand having the structure of

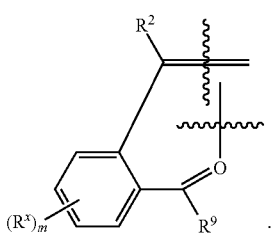

In some embodiments, $R^{14}$ and L are taken together to form a bidentate ligand having the structure of

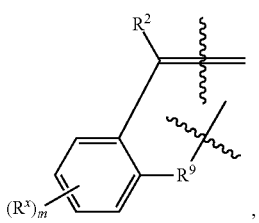

wherein $R^9$ is halogen. In some embodiments, $R^9$ is —I.

In some embodiments, $R^{14}$ and L are taken together to form a bidentate ligand having the structure of

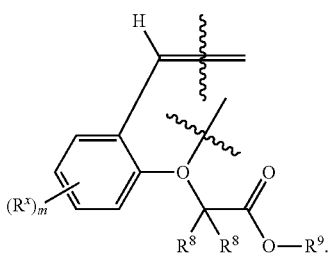

In some embodiments, $R^{14}$ and L are taken together to form a bidentate ligand having the structure of

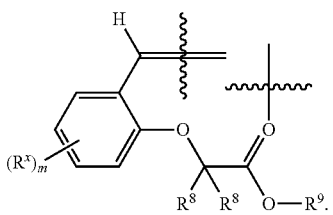

In some embodiments, $R^{14}$ and L are taken together to form a bidentate ligand having the structure of

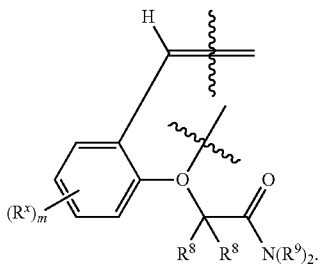

In some embodiments, $R^{14}$ and L are taken together to form a bidentate ligand having the structure of

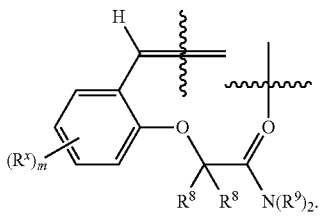

In some embodiments, $R^{14}$ is optionally taken together with one or more other ligands to form a bidentate or polydentate ligand, via one or more of $R^x$, $R^8$, and $R^9$. In some embodiments, $R^{14}$ is optionally linked to a tag or support, via one or more of $R^x$, $R^8$, and $R^9$.

In some embodiments, $R^{14}$ and L are taken together to form a bidentate ligand having the structure of

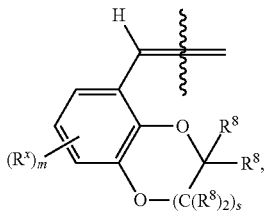

wherein one of the two oxygen atoms is coordinated to M, and s is 0-6. In some embodiments, $R^{14}$ and L are taken together to form a bidentate ligand having the structure of

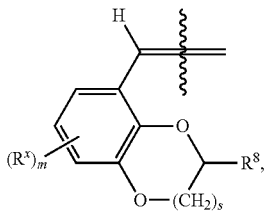

wherein one of the two oxygen atoms is coordinated to M, s is 0-6, and each of the methylene group is optionally substituted. In some embodiments, s is 0-5. In some embodiments, s is 0-4. In some embodiments, s is 0-3. In some embodiments, s is 0-2. In some embodiments, s is 0-1. In some embodiments, s is 0. In some embodiments, s is 1. In some embodiments, s is 2. In some embodiments, s is 3. In some embodiments, s is 4. In some embodiments, s is 5. In some embodiments, s is 6. In some embodiments, $R^{14}$ is optionally taken together with one or more other ligands to form a bidentate or polydentate ligand, via one or more of $R^x$ and $R^8$. In some embodiments, $R^{14}$ is optionally linked to a tag or support, via one or more of $R^x$ and $R^8$.

In some embodiments, $R^{14}$ and L are taken together to form a bidentate ligand having the structure of:

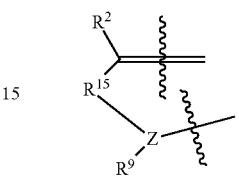

wherein each variable is independently as defined above and described herein. In some embodiments, $R^{14}$ is optionally taken together with one or more other ligands to form a bidentate or polydentate ligand, via one or more of $R^2$, $R^{15}$, Z and $R^9$. In some embodiments, $R^{14}$ is optionally linked to a tag or support, via one or more of $R^2$, $R^{15}$, Z and $R^9$.

In some embodiments, $R^{14}$ and L are taking together to form a bidentate ligand having the structure of:

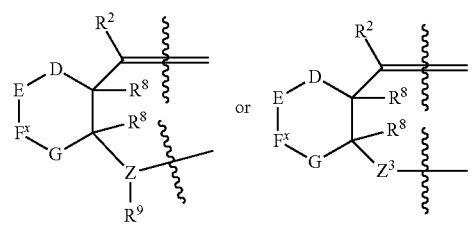

A1 wherein:
$Z^3$ is halogen;
each variable is independently as defined above and described herein. In some embodiments, A1 is

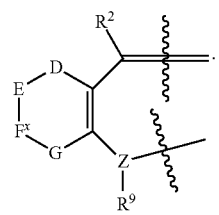

In some embodiments, A1 is

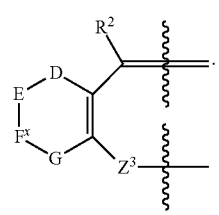

In some embodiments, A1 is

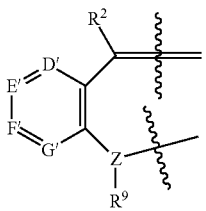

wherein each of D', E', F', and G' is independently —N=, or —C(R$^8$)=, and each of R$^2$, Z and R$^x$ is independently as defined above and described herein. In some embodiments, A1 is

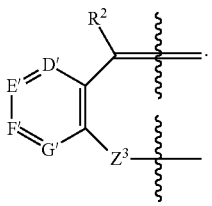

In some embodiments, R$^{14}$ and L are taken together to form a bidentate ligand having the structure of:

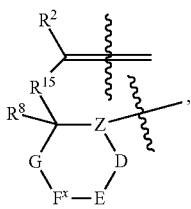

wherein each variable is independently as defined above and described herein. In some embodiments, A2 is

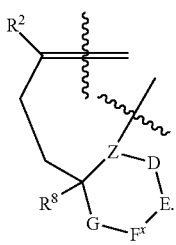

In some embodiments, A2 is

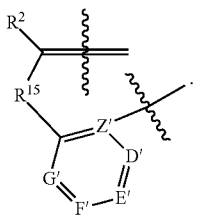

In some embodiments, A2 is

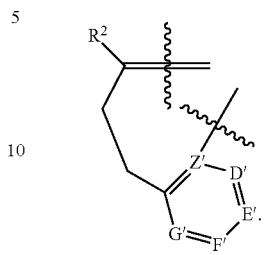

In some embodiments, R$^{14}$ and L are taken together to form a bidentate ligand having the structure of (A3-a)

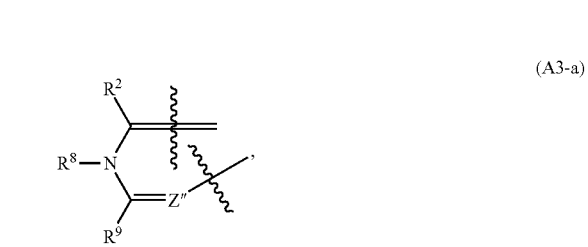

wherein Z" is =O, =S, =NR, =PR$^8$, or =P(O)R$^8$, and each of R$^2$, R$^8$ and R$^9$ is independently as defined above and described herein. In some embodiments, R$^{14}$ and L are taken together to form a bidentate ligand having the structure of (A3-b)

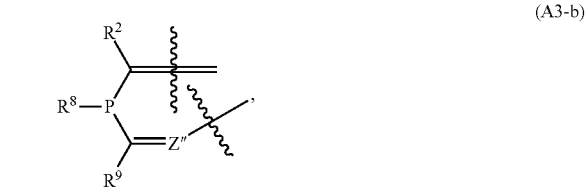

wherein Z" is =O, =S, =NR$^8$, =PR$^8$, or =P(O)R$^8$, and each of R$^2$, R$^8$ and R$^9$ is independently as defined above and described herein.

In some embodiments, R$^{14}$ and L are taken together to form a bidentate ligand having the structure of:

A4

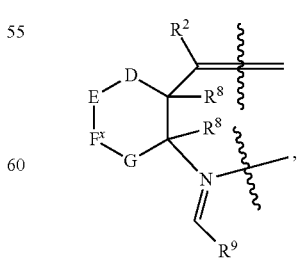

wherein each variable is independently as defined above and described herein. In some embodiments, A4 is

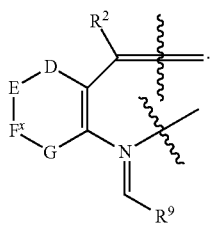

In some embodiments, A4 is

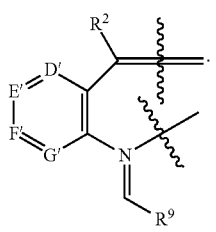

In some embodiments, $R^{14}$ and L are taken together to form a bidentate ligand having the structure of:

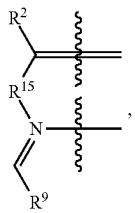
A5 wherein each variable is independently as defined above and described herein. In some embodiments, A5 is

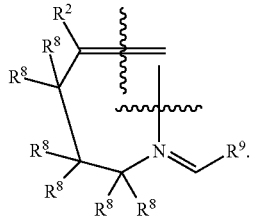

In some embodiments, A5 is

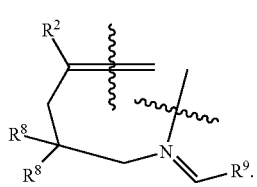

In some embodiments, $R^{14}$ and L are taken together to form a bidentate ligand having the structure of:

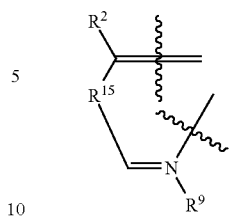
A6 wherein each variable is independently as defined above and described herein. In some embodiments, A6 is

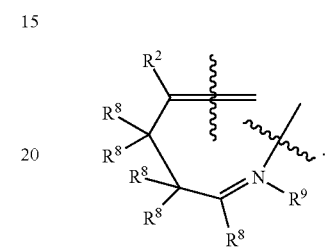

In some embodiments, A6 is

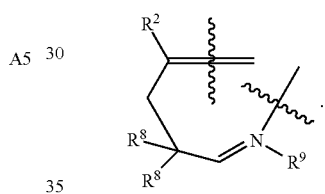

Exemplary $R^{14}$ embodiments are depicted below:

Monodentate Carbenes (for Example):

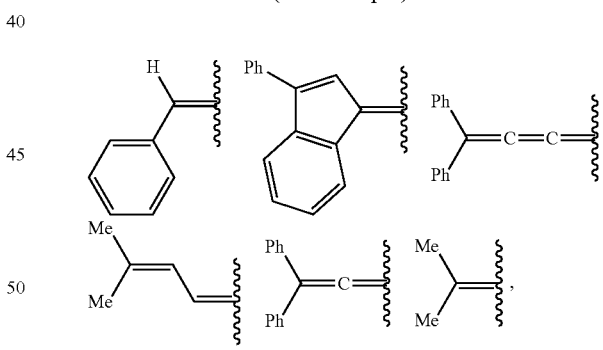

and

Fischer Type Carbenes (for Example):

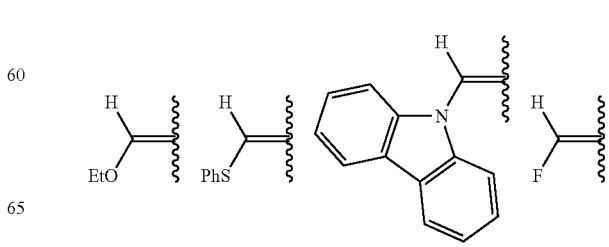

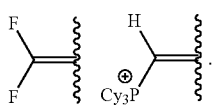
Exemplary bidentate ligands formed by $R^{14}$ and L taken together are depicted below:
Carbenes with Chelating Donor Groups A1 (for Example):
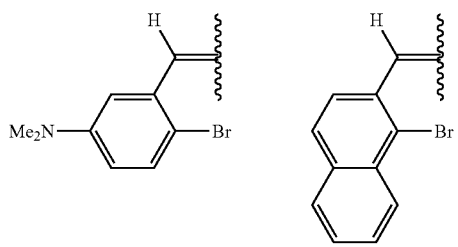
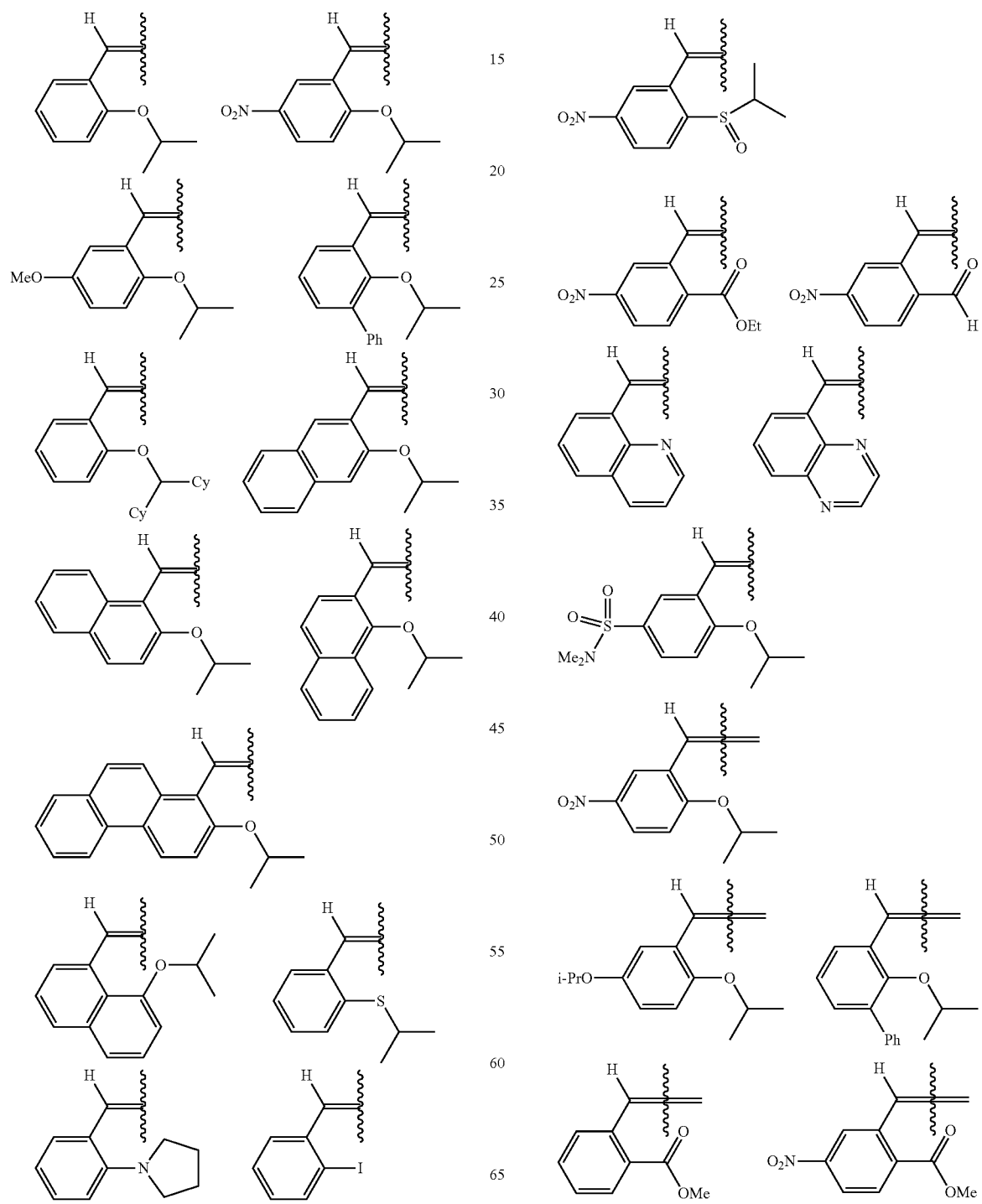

-continued

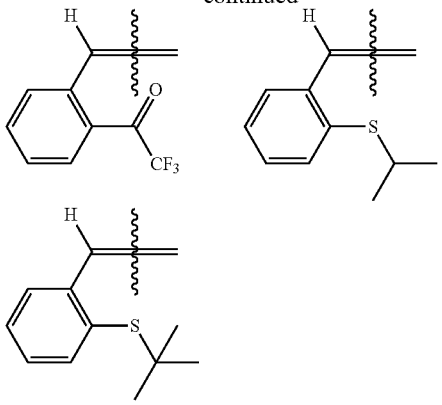

Carbenes with Chelating Donor Groups A2-A6 (for Example):

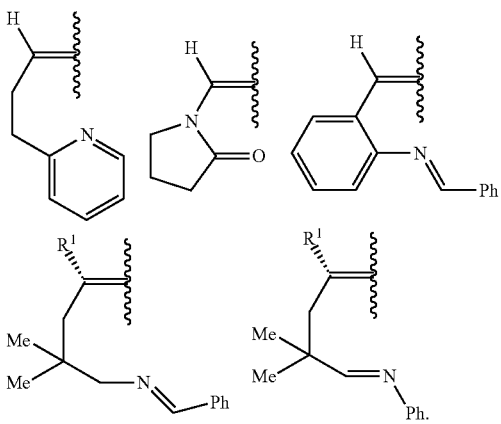

As generally defined above, $R^2$ is $R^x$. In some embodiments, $R^2$ is R. In some embodiments, $R^2$ is hydrogen or an optionally substituted group selected from $C_{1-20}$ aliphatic or $C_{1-20}$ heteroaliphatic.

In some embodiments, $R^2$ is hydrogen. In some embodiments $R^2$ is optionally substituted $C_{1-20}$ aliphatic or $C_{1-20}$ heteroaliphatic.

In some embodiments, $R^2$ is optionally substituted $C_{1-20}$ aliphatic. In some embodiments, $R^2$ is optionally substituted $C_{1-15}$ aliphatic. In some embodiments, $R^2$ is optionally substituted $C_{1-10}$ aliphatic. In some embodiments, $R^2$ is optionally substituted $C_{1-6}$ aliphatic. In some embodiments, $R^2$ is optionally substituted $C_{1-6}$ alkyl. In some embodiments, $R^2$ is optionally substituted hexyl, pentyl, butyl, propyl, ethyl or methyl. In some embodiments, $R^2$ is optionally substituted hexyl. In some embodiments, $R^2$ is optionally substituted pentyl. In some embodiments, $R^2$ is optionally substituted butyl. In some embodiments, $R^2$ is optionally substituted propyl. In some embodiments, $R^2$ is optionally substituted ethyl. In some embodiments, $R^2$ is optionally substituted methyl. In some embodiments, $R^2$ is hexyl. In some embodiments, $R^2$ is pentyl. In some embodiments, $R^2$ is butyl. In some embodiments, $R^2$ is propyl. In some embodiments, $R^2$ is ethyl. In some embodiments, $R^2$ is methyl. In some embodiments, $R^2$ is isopropyl. In some embodiments, $R^2$ is n-propyl. In some embodiments, $R^2$ is tert-butyl. In some embodiments, $R^2$ is sec-butyl. In some embodiments, $R^2$ is n-butyl.

In some embodiments, $R^2$ is $C_{1-20}$ heteroaliphatic. In some embodiments, $R^2$ is $C_{1-20}$ heteroaliphatic having 1-6 heteroatoms independently selected from nitrogen, sulfur, phosphorus or selenium. In some embodiments, $R^2$ is $C_{1-20}$ heteroaliphatic having 1-6 heteroatoms independently selected from nitrogen, sulfur, phosphorus or selenium, optionally including one or more oxidized forms of nitrogen, sulfur, phosphorus or selenium. In some embodiments, $R^2$ is $C_{1-20}$ heteroaliphatic comprising 1-6 groups independently selected from

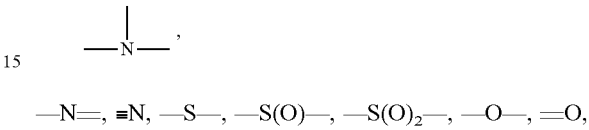

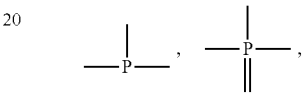

—Se—, and —Se(O)—.

As generally defined above, $R^3$ is hydrogen or an optionally substituted group selected from $C_{1-20}$ aliphatic, $C_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur, or —Z—$R^3$ is halogen. In some embodiments, $R^3$ is hydrogen or an optionally substituted group selected from $C_{1-20}$ aliphatic, $C_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur. In some embodiments, —Z—$R^3$ is halogen.

In some embodiments, $R^3$ is hydrogen. In some embodiments, $R^3$ is an optionally substituted group selected from $C_{1-20}$ aliphatic, $C_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur.

In some embodiments, $R^3$ is optionally substituted $C_{1-20}$ aliphatic. In some embodiments, $R^3$ is optionally substituted $C_{1-15}$ aliphatic. In some embodiments, $R^3$ is optionally substituted $C_{1-10}$ aliphatic. In some embodiments, $R^3$ is optionally substituted $C_{1-6}$ aliphatic. In some embodiments, $R^3$ is optionally substituted $C_{1-6}$ alkyl. In some embodiments, $R^3$ is optionally substituted hexyl, pentyl, butyl, propyl, ethyl or methyl. In some embodiments, $R^3$ is optionally substituted hexyl. In some embodiments, $R^3$ is optionally substituted pentyl. In some embodiments, $R^3$ is optionally substituted butyl. In some embodiments, $R^3$ is optionally substituted propyl. In some embodiments, $R^3$ is optionally substituted ethyl. In some embodiments, $R^3$ is optionally substituted methyl. In some embodiments, $R^3$ is hexyl. In some embodiments, $R^3$ is pentyl. In some embodiments, $R^3$ is butyl. In some embodiments, $R^3$ is propyl. In some embodiments, $R^3$ is ethyl. In some embodiments, $R^3$ is methyl. In some embodiments, $R^3$ is isopropyl. In some embodiments, $R^3$ is n-propyl. In some embodiments, $R^3$ is tert-butyl. In some embodiments, $R^3$ is sec-butyl. In some embodiments, $R^3$ is n-butyl.

In some embodiments, $R^3$ is $C_{1-20}$ heteroaliphatic. In some embodiments, $R^3$ is $C_{1-20}$ heteroaliphatic having 1-6 heteroatoms independently selected from nitrogen, sulfur, phosphorus or selenium. In some embodiments, $R^3$ is $C_{1-20}$ heteroaliphatic having 1-6 heteroatoms independently selected from nitrogen, sulfur, phosphorus or selenium, optionally including one or more oxidized forms of nitrogen, sulfur, phosphorus or selenium. In some embodiments, $R^3$ is $C_{1-20}$ heteroaliphatic comprising 1-6 groups independently selected from

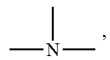

—N=, =N, —S—, —S(O)—, —S(O)$_2$—, —O—, =O,

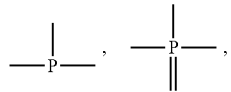

—Se—, and —Se(O)—. In some embodiments, $R^3$ is —OR, —SR, or —N(R)$_2$. In some embodiments, $R^3$ is —OR.

In some embodiments, $R^3$ is optionally substituted phenyl. In some embodiments, $R^3$ is optionally substituted phenyl wherein one or more substituents are halogen. In some embodiments, $R^3$ is optionally substituted phenyl wherein one or more substituents are —F. In some embodiments, $R^3$ is optionally substituted phenyl wherein one or more substituents are —Cl. In some embodiments, $R^3$ is optionally substituted phenyl wherein one or more substituents are —Br. In some embodiments, $R^3$ is optionally substituted phenyl wherein one or more substituents are —I. In some embodiments, $R^3$ is phenyl.

In some embodiments, $R^3$ is an optionally substituted 3-7 membered saturated or partially unsaturated carbocyclic ring. In some embodiments, $R^3$ is an optionally substituted 3-membered saturated or partially unsaturated carbocyclic ring. In some embodiments, $R^3$ is an optionally substituted 4-membered saturated or partially unsaturated carbocyclic ring. In some embodiments, $R^3$ is an optionally substituted 5-membered saturated or partially unsaturated carbocyclic ring. In some embodiments, $R^3$ is an optionally substituted 6-membered saturated or partially unsaturated carbocyclic ring. In some embodiments, $R^3$ is an optionally substituted 7-membered saturated or partially unsaturated carbocyclic ring. In some embodiments, $R^3$ is optionally substituted cycloheptyl. In some embodiments, $R^3$ is cycloheptyl. In some embodiments, $R^3$ is optionally substituted cyclohexyl. In some embodiments, $R^3$ is cyclohexyl. In some embodiments, $R^3$ is optionally substituted cyclopentyl. In some embodiments, $R^3$ is cyclopentyl. In some embodiments, $R^3$ is optionally substituted cyclobutyl. In some embodiments, $R^3$ is cyclobutyl. In some embodiments, $R^3$ is optionally substituted cyclopropyl. In some embodiments, $R^3$ is cyclopropyl.

In some embodiments, $R^3$ is an optionally substituted 5-6 membered monocyclic heteroaryl ring having 1-4 heteroatoms independently selected from nitrogen, oxygen, or sulfur. In some embodiments, $R^3$ is a substituted 5-6 membered monocyclic heteroaryl ring having 1-4 heteroatoms independently selected from nitrogen, oxygen, or sulfur. In some embodiments, $R^3$ is an unsubstituted 5-6 membered monocyclic heteroaryl ring having 1-4 heteroatoms independently selected from nitrogen, oxygen, or sulfur.

In some embodiments, $R^3$ is an optionally substituted 5-membered monocyclic heteroaryl ring having 1-4 heteroatoms independently selected from nitrogen, oxygen or sulfur. In some embodiments, $R^3$ is an optionally substituted 6-membered monocyclic heteroaryl ring having 1-4 heteroatoms independently selected from nitrogen, oxygen, or sulfur.

In some embodiments, $R^3$ is an optionally substituted 5-membered monocyclic heteroaryl ring having one heteroatom selected from nitrogen, oxygen, or sulfur. In some embodiments, $R^3$ is selected from optionally substituted pyrrolyl, furanyl, or thienyl.

In some embodiments, $R^3$ is an optionally substituted 5-membered heteroaryl ring having two heteroatoms independently selected from nitrogen, oxygen, or sulfur. In certain embodiments, $R^3$ is an optionally substituted 5-membered heteroaryl ring having one nitrogen atom, and an additional heteroatom selected from sulfur or oxygen. Exemplary $R^3$ groups include but are not limited to optionally substituted pyrazolyl, imidazolyl, thiazolyl, isothiazolyl, oxazolyl or isoxazolyl.

In some embodiments, $R^3$ is an optionally substituted 5-membered heteroaryl ring having three heteroatoms independently selected from nitrogen, oxygen, or sulfur. Exemplary $R^3$ groups include but are not limited to optionally substituted triazolyl, oxadiazolyl or thiadiazolyl.

In some embodiments, $R^3$ is an optionally substituted 5-membered heteroaryl ring having four heteroatoms independently selected from nitrogen, oxygen, or sulfur. Exemplary $R^3$ groups include but are not limited to optionally substituted tetrazolyl, oxatriazolyl and thiatriazolyl.

In some embodiments, $R^3$ is an optionally substituted 6-membered heteroaryl ring having 1-4 nitrogen atoms. In some embodiments, $R^3$ is an optionally substituted 6-membered heteroaryl ring having 1-3 nitrogen atoms. In other embodiments, $R^3$ is an optionally substituted 6-membered heteroaryl ring having 1-2 nitrogen atoms. In some embodiments, $R^3$ is an optionally substituted 6-membered heteroaryl ring having four nitrogen atoms. In some embodiments, $R^3$ is an optionally substituted 6-membered heteroaryl ring having three nitrogen atoms. In some embodiments, $R^3$ is an optionally substituted 6-membered heteroaryl ring having two nitrogen atoms. In certain embodiments, $R^3$ is an optionally substituted 6-membered heteroaryl ring having one nitrogen atom. Exemplary $R^3$ groups include but are not limited to optionally substituted pyridinyl, pyrimidinyl, pyrazinyl, pyridazinyl, triazinyl, or tetrazinyl.

In some embodiments, $R^3$ is an optionally substituted 3-7 membered saturated or partially unsaturated heterocyclic ring having 1-3 heteroatoms independently selected from nitrogen, oxygen, or sulfur. In some embodiments, $R^3$ is a substituted 3-7 membered saturated or partially unsaturated heterocyclic ring having 1-3 heteroatoms independently selected from nitrogen, oxygen, or sulfur. In some embodiments, $R^3$ is an unsubstituted 3-7 membered saturated or partially unsaturated heterocyclic ring having 1-3 heteroatoms independently selected from nitrogen, oxygen, or sulfur.

In certain embodiments, $R^3$ is an optionally substituted 5-7 membered partially unsaturated monocyclic ring having 1-3 heteroatoms independently selected from nitrogen, oxygen, or sulfur. In certain embodiments, $R^3$ is an optionally substituted 5-6 membered partially unsaturated monocyclic ring having 1-3 heteroatoms independently selected from nitrogen, oxygen, or sulfur. In certain embodiments, $R^3$ is an optionally substituted 5-membered partially unsaturated monocyclic ring having 1-3 heteroatoms independently selected from nitrogen, oxygen, or sulfur. Exemplary $R^3$ groups include but are not limited to optionally substituted dihydroimidazolyl, dihydrothiazolyl, dihydrooxazolyl, or oxazolinyl. In certain embodiments, $R^3$ is an optionally substituted 6-membered partially unsaturated monocyclic ring having 1-3 heteroatoms independently selected from nitrogen, oxygen, or sulfur. Exemplary $R^3$ groups include but are not limited to optionally substituted dihydropyridinyl, tetrahydropyridinyl, dihydropyrimidinyl, tetrahydropyrimidinyl, dihydropyrazinyl, tetrahydropyrazinyl, dihydrotriazinyl, tetrahydrotriazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, $R^3$ is an optionally substituted 7-membered partially unsaturated monocyclic ring having 1-3 heteroatoms independently selected from nitrogen, oxygen, or sulfur. Exemplary $R^3$ groups include but are not limited to optionally substituted azepinyl, oxepinyl, thiepinyl, diazepinyl, oxazepinyl, thiazepinyl, triazepinyl, oxadiazepinyl, thiadiazepinyl, dihydroazepinyl, dihydrooxepinyl, dihydrothiepinyl, dihydrodiazepinyl, dihydrooxazepinyl, dihydrothiazepinyl, dihydrotriazepinyl, dihydrooxadiazepinyl, dihydrothiadiazepinyl, tetrahydroazepinyl, tetrahydrooxepinyl, tetrahydrothiepinyl, tetrahydrodiazepinyl, tetrahydrooxazepinyl, tetrahydrothiazepinyl, tetrahydrotriazepinyl, tetrahydrooxadiazepinyl, or tetrahydrothiadiazepinyl.

In some embodiments, $R^3$ is optionally substituted 3-membered heterocyclic ring having one heteroatom selected from nitrogen, oxygen or sulfur. Exemplary $R^3$ groups include but are not limited to optionally substituted aziridinyl, thiiranyl or oxiranyl. In some embodiments, $R^3$ is optionally substituted 4-membered heterocyclic ring having 1-3 heteroatoms independently selected from nitrogen, oxygen, or sulfur. Exemplary $R^3$ groups include but are not limited to optionally substituted azetidinyl, oxetanyl, thietanyl, oxazetidinyl, thiazetidinyl, or diazetidinyl. In some embodiments, $R^3$ is optionally substituted 5-membered heterocyclic ring having 1-3 heteroatoms independently selected from nitrogen, oxygen, or sulfur. Exemplary $R^3$ groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, isothiazolidinyl, triazolidinyl, oxadiazolidinyl, thiadiazolidinyl, oxadiazolidinyl, dioxazolidinyl, oxathiazolidinyl, thiadiazolidinyl or dithiazolidinyl. In some embodiments, $R^3$ is optionally substituted 6-membered heterocyclic ring having 1-3 heteroatoms independently selected from nitrogen, oxygen, or sulfur. Exemplary $R^3$ groups include but are not limited to optionally substituted piperidinyl, tetrahydropyranyl, tetrahydrothiopyranyl, piperazinyl, morpholinyl, thiomorpholinyl, dithianyl, dioxanyl, oxathianyl, triazinanyl, oxadiazinanyl, thiadiazinanyl, dithiazinanyl, dioxazinanyl, oxathiazinanyl, oxadithianyl, trioxanyl, dioxathianyl or trithianyl. In some embodiments, $R^3$ is optionally substituted 7-membered heterocyclic ring having 1-3 heteroatoms independently selected from nitrogen, oxygen, or sulfur. Exemplary $R^3$ groups include but are not limited to optionally substituted azepanyl, oxepanyl, thiepanyl, diazepanyl, oxazepanyl, thiazepanyl, dioxepanyl, oxathiepanyl, dithiepanyl, triazepanyl, oxadiazepanyl, thiadiazepanyl, dioxazepanyl, oxathiazepanyl, dithiazepanyl, trioxepanyl, dioxathiepanyl, oxadithiepanyl or trithiepanyl.

In certain embodiments, $R^3$ is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothienyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothienyl, or tetrahydrothiopyranyl.

As generally defined above, Ring A is an optionally substituted ring selected from phenyl, an 8-14 membered bicyclic or polycyclic aryl ring, a 5-6 membered monocyclic heteroaryl ring having 1-4 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur. Exemplary substituents are extensively described herein, including but not limited to those monovalent substituents listed for a substitutable carbon atom of an "optionally substituted" group.

In some embodiments, Ring A is an optionally substituted phenyl ring. In some embodiments, Ring A is an unsubstituted phenyl ring.

In some embodiments, Ring A is an unsubstituted phenyl ring having the structure of

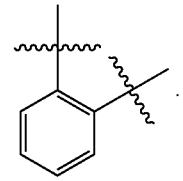 [SMILES: *c1ccccc1*]

In some embodiments, Ring A is a substituted phenyl. In some embodiments, Ring A is a substituted phenyl having the structure of

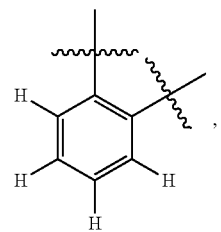 [SMILES: *c1ccccc1*]

wherein at least one hydrogen atom is substituted.

In some embodiments, Ring A has the structure of

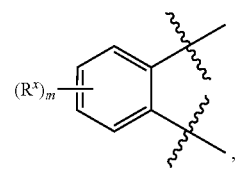

wherein each of $R^x$ and m is independently as defined above and described herein.

In some embodiments Ring A is an optionally substituted 8-14 membered bicyclic or polycyclic aryl ring. In some embodiments Ring A is an optionally substituted 8-10 membered bicyclic aryl ring. In some embodiments, Ring A is an optionally substituted 8-membered aryl ring. In some embodiments, Ring A is an optionally substituted 9-membered aryl ring. In some embodiments, Ring A is an optionally substituted 10-membered aryl ring. In some embodiments, Ring A is optionally substituted naphthyl.

In some embodiments, Ring A is optionally substituted 5-6 membered monocyclic heteroaryl ring having 1-4 heteroatoms independently selected from nitrogen, oxygen, or sulfur. In some embodiments, Ring A is a substituted 5-6 membered monocyclic heteroaryl ring having 1-4 heteroatoms independently selected from nitrogen, oxygen, or sulfur. In some embodiments, Ring A is an unsubstituted 5-6 membered monocyclic heteroaryl ring having 1-4 heteroatoms independently selected from nitrogen, oxygen, or sulfur.

In some embodiments, Ring A is an optionally substituted 5-membered monocyclic heteroaryl ring having 1-4 heteroatoms independently selected from nitrogen, oxygen or sulfur. In some embodiments, Ring A is an optionally substituted 6-membered monocyclic heteroaryl ring having 1-4 heteroatoms independently selected from nitrogen, oxygen, or sulfur.

In some embodiments, Ring A is an optionally substituted 5-membered monocyclic heteroaryl ring having one heteroatom selected from nitrogen, oxygen, or sulfur. In some embodiments, Ring A is selected from an optionally substituted pyrrolyl, furanyl, or thienyl ring.

In some embodiments, Ring A is an optionally substituted 5-membered heteroaryl ring having two heteroatoms independently selected from nitrogen, oxygen, or sulfur. In certain embodiments, Ring A is an optionally substituted 5-membered heteroaryl ring having one nitrogen atom, and an additional heteroatom selected from sulfur or oxygen. Exemplary Ring A groups include but are not limited to optionally substituted pyrazolyl, imidazolyl, thiazolyl, isothiazolyl, oxazolyl or isoxazolyl ring.

In some embodiments, Ring A is an optionally substituted 5-membered heteroaryl ring having three heteroatoms independently selected from nitrogen, oxygen, or sulfur. Exemplary Ring A groups include but are not limited to optionally substituted triazolyl, oxadiazolyl or thiadiazolyl ring.

In some embodiments, Ring A is an optionally substituted 5-membered heteroaryl ring having four heteroatoms independently selected from nitrogen, oxygen, or sulfur. Exemplary Ring A groups include but are not limited to optionally substituted tetrazolyl, oxatriazolyl and thiatriazolyl ring.

In some embodiments, Ring A is an optionally substituted 6-membered heteroaryl ring having 1-4 nitrogen atoms. In some embodiments, Ring A is an optionally substituted 6-membered heteroaryl ring having 1-3 nitrogen atoms. In other embodiments, Ring A is an optionally substituted 6-membered heteroaryl ring having 1-2 nitrogen atoms. In some embodiments, Ring A is an optionally substituted 6-membered heteroaryl ring having four nitrogen atoms. In some embodiments, Ring A is an optionally substituted 6-membered heteroaryl ring having three nitrogen atoms. In some embodiments, Ring A is an optionally substituted 6-membered heteroaryl ring having two nitrogen atoms. In certain embodiments, Ring A is an optionally substituted 6-membered heteroaryl ring having one nitrogen atom. Exemplary Ring A groups include but are not limited to optionally substituted pyridinyl, pyrimidinyl, pyrazinyl, pyridazinyl, triazinyl, or tetrazinyl group.

In some embodiments, Ring A is an optionally substituted 8-14 membered bicyclic or polycyclic heteroaryl ring having 1-5 heteroatoms independently selected from nitrogen, oxygen, or sulfur. In some embodiments, Ring A is an optionally substituted 8-10 membered bicyclic heteroaryl ring having 1-5 heteroatoms independently selected from nitrogen, oxygen, or sulfur.

In some embodiments, Ring A is an optionally substituted 5,6-fused heteroaryl ring having 1-5 heteroatoms independently selected from nitrogen, oxygen, or sulfur. In some embodiments, Ring A is an optionally substituted 5,6-fused heteroaryl ring having 1-4 heteroatoms independently selected from nitrogen, oxygen, or sulfur. In some embodiments, Ring A is an optionally substituted 5,6-fused heteroaryl ring having 1-3 heteroatoms independently selected from nitrogen, oxygen, or sulfur. In some embodiments, Ring A is an optionally substituted 5,6-fused heteroaryl ring having two heteroatoms independently selected from nitrogen, oxygen, or sulfur. In some embodiments, Ring A is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl ring. In some embodiments, Ring A is an optionally substituted 5,6-fused heteroaryl ring having three heteroatoms independently selected from nitrogen, oxygen, or sulfur. In some embodiments, Ring A is optionally substituted dihydropyrroloimidazolyl, 1H-furoimidazolyl, 1H-thienoimidazolyl, furooxazolyl, furoisoxazolyl, 4H-pyrroloxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl ring. In some embodiments, Ring A is an optionally substituted 5,6-fused heteroaryl ring having four heteroatoms independently selected from nitrogen, oxygen, or sulfur. In some embodiments, Ring A is an optionally substituted 5,6-fused heteroaryl ring having five heteroatoms independently selected from nitrogen, oxygen, or sulfur.

In some embodiments, Ring A is an optionally substituted 5,6-fused heteroaryl ring having 1-5 heteroatoms independently selected from nitrogen, oxygen, or sulfur. In other embodiments, Ring A is an optionally substituted 5,6-fused heteroaryl ring having 1-2 heteroatoms independently selected from nitrogen, oxygen, or sulfur. In certain embodiments, Ring A is an optionally substituted 5,6-fused heteroaryl ring having one heteroatom independently selected from nitrogen, oxygen, or sulfur. In some embodiments, Ring A is optionally substituted indolyl ring. In some embodiments, Ring A is optionally substituted benzofuranyl ring. In some embodiments, Ring A is optionally substituted benzo[b]thienyl ring. In certain embodiments, Ring A is an optionally substituted 5,6-fused heteroaryl ring having two heteroatoms independently selected from nitrogen, oxygen, or sulfur. In some embodiments, Ring A is optionally substituted azaindolyl ring. In some embodiments, Ring A is optionally substituted benzimidazolyl ring. In some embodiments, Ring A is optionally substituted benzothiazolyl ring. In some embodiments, Ring A is optionally substituted benzoxazolyl ring. In some embodiments, Ring A is an optionally substituted indazolyl ring. In certain embodiments, Ring A is an optionally substituted 5,6-fused heteroaryl ring having three heteroatoms independently selected from nitrogen, oxygen, or sulfur. In some embodiments, Ring A is optionally substituted oxazolopyridiyl, thiazolopyridinyl or imidazopyridinyl ring. In certain embodiments, Ring A is an optionally substituted 5,6-fused heteroaryl ring having four heteroatoms independently selected from nitrogen, oxygen, or sulfur. In some embodiments, Ring A is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl ring. In certain embodiments, Ring A is an optionally substituted 5,6-fused heteroaryl ring having five heteroatoms independently selected from nitrogen, oxygen, or sulfur.

In certain embodiments, Ring A is an optionally substituted 6,6-fused heteroaryl ring having 1-5 heteroatoms independently selected from nitrogen, oxygen, or sulfur. In some embodiments, Ring A is an optionally substituted 6,6-fused heteroaryl ring having 1-2 heteroatoms independently selected from nitrogen, oxygen, or sulfur. In other embodiments, Ring A is an optionally substituted 6,6-fused heteroaryl ring having one heteroatom selected from nitrogen, oxygen, or sulfur. In some embodiments, Ring A is optionally substituted quinolinyl ring. In some embodiments, Ring A is optionally substituted isoquinolinyl ring. In some embodiments, Ring A is an optionally substituted 6,6-fused heteroaryl ring having two heteroatoms independently selected from nitrogen, oxygen, or sulfur. In some embodiments, Ring A is optionally substituted quinazolinyl, phthalazinyl, quinoxalinyl or naphthyridinyl ring. In some embodiments, Ring A is an optionally substituted 6,6-fused heteroaryl ring having three heteroatoms independently selected from nitrogen, oxygen, or sulfur. In some embodiments, Ring A is optionally substituted pyridopyrimidinyl, pyridopyridazinyl, pyridopyrazinyl, or benzotriazinyl ring. In some embodiments, Ring A is an optionally substituted 6,6-fused heteroaryl ring having four heteroatoms independently selected from nitrogen, oxygen, or sulfur. In some embodiments, Ring A is optionally substituted pyridotriazinyl, pteridinyl, pyrazinopyrazinyl, pyrazinopyridazinyl, pyridazinopyridazinyl, pyrimidopyridazinyl or pyrimidopyrimidinyl ring. In some embodiments, Ring A is an optionally substituted 6,6-fused heteroaryl ring having five heteroatoms independently selected from nitrogen, oxygen, or sulfur.

In some embodiments, Ring A is optionally substituted heterobiaryl wherein each heteroaryl group is independently an optionally substituted group selected from a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, Ring A is optionally substituted heterobiaryl wherein each aryl group is an optionally substituted 8-10 membered bicyclic heteroaryl ring having 1-5 heteroatoms independently selected from nitrogen, oxygen, or sulfur.

In some embodiments, Ring A is

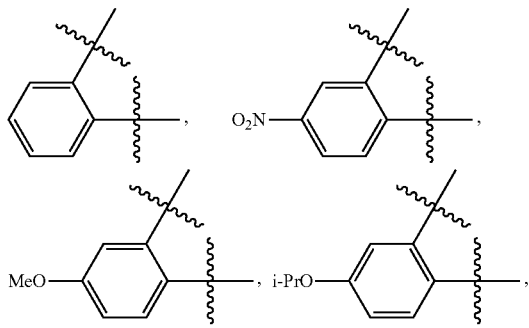

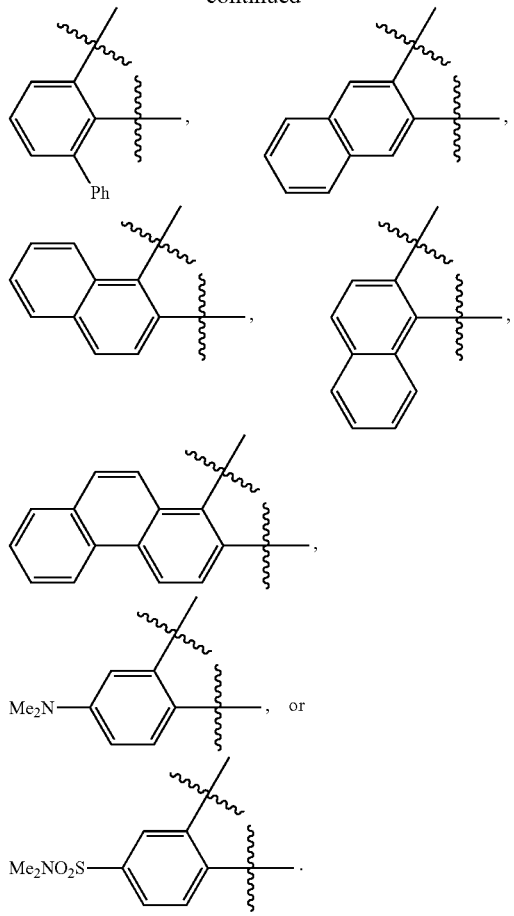

As generally defined above, each $R^x$ is independently halogen, R, —CN, —C(O)N(R')$_2$, —C(O)R, —C(O)OR, —OR, —OC(O)R, —OC(O)OR, —OC(O)N(R')$_2$, —OSi(R)$_3$, —N(R')$_2$, —N(R')$_3^+$, —NR'C(O)R, —NR'C(O)OR, —NR'C(O)N(R')$_2$, —NR'SO$_2$R, —NR'SO$_2$N(R')$_2$, —NR'OR, —NO$_2$, —Si(R)$_3$, —P(R)$_2$, —P(O)(R)$_2$, —P(O)(OR)$_2$, —SR, —SC(O)R, —S(O)R, —SO$_2$R, —SO$_3$R, —SO$_2$N(R')$_2$, or —SeR.

In some embodiments, $R^x$ is halogen. In some embodiments, $R^x$ is —F. In some embodiments, $R^x$ is —Cl. In some embodiments, $R^x$ is —Br. In some embodiments, $R^x$ is —I.

In some embodiments, $R^x$ is R, wherein R is as defined above and described herein.

In some embodiments, $R^x$ is hydrogen. In some embodiments, $R^x$ is an optionally substituted group selected from $C_{1-20}$ aliphatic, $C_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur.

In some embodiments, $R^x$ is optionally substituted $C_{1-20}$ aliphatic. In some embodiments, $R^x$ is optionally substituted $C_{1-15}$ aliphatic. In some embodiments, $R^x$ is optionally substituted $C_{1-10}$ aliphatic. In some embodiments, $R^x$ is optionally substituted $C_{1-6}$ aliphatic. In some embodiments, $R^x$ is optionally substituted $C_{1-6}$ alkyl. In some embodiments, $R^x$ is optionally substituted hexyl, pentyl, butyl, propyl, ethyl or methyl. In some embodiments, $R^x$ is optionally substituted hexyl. In some embodiments, $R^x$ is optionally substituted pentyl. In some embodiments, $R^x$ is optionally substituted butyl. In some embodiments, $R^x$ is optionally substituted propyl. In some embodiments, $R^x$ is optionally substituted ethyl. In some embodiments, $R^x$ is optionally substituted methyl. In some embodiments, $R^x$ is hexyl. In some embodiments, $R^x$ is pentyl. In some embodiments, $R^x$ is butyl. In some embodiments, $R^x$ is propyl. In some embodiments, $R^x$ is ethyl. In some embodiments, $R^x$ is methyl. In some embodiments, $R^x$ is isopropyl. In some embodiments, $R^x$ is n-propyl. In some embodiments, $R^x$ is tert-butyl. In some embodiments, $R^x$ is sec-butyl. In some embodiments, $R^x$ is n-butyl.

In some embodiments, $R^x$ is $C_{1-20}$ heteroaliphatic. In some embodiments, $R^x$ is $C_{1-20}$ heteroaliphatic having 1-6 heteroatoms independently selected from nitrogen, sulfur, phosphorus or selenium. In some embodiments, $R^x$ is $C_{1-20}$ heteroaliphatic having 1-6 heteroatoms independently selected from nitrogen, sulfur, phosphorus or selenium, optionally including one or more oxidized forms of nitrogen, sulfur, phosphorus or selenium. In some embodiments, $R^x$ is $C_{1-20}$ heteroaliphatic comprising 1-6 groups independently selected from

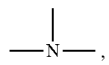

—N=, ≡N, —S—, —S(O)—, —S(O)$_2$—, —O—, =O,

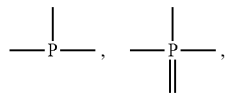

—Se—, and —Se(O)—.

In some embodiments, $R^x$ is optionally substituted phenyl. In some embodiments, $R^x$ is optionally substituted phenyl wherein one or more substituents are halogen. In some embodiments, $R^x$ is optionally substituted phenyl wherein one or more substituents are —F. In some embodiments, $R^x$ is optionally substituted phenyl wherein one or more substituents are —Cl. In some embodiments, $R^x$ is optionally substituted phenyl wherein one or more substituents are —Br. In some embodiments, $R^x$ is optionally substituted phenyl wherein one or more substituents are —I. In some embodiments, $R^x$ is phenyl.

In some embodiments, $R^x$ is an optionally substituted 3-7 membered saturated or partially unsaturated carbocyclic ring. In some embodiments, $R^x$ is an optionally substituted 3-membered saturated or partially unsaturated carbocyclic ring. In some embodiments, $R^x$ is an optionally substituted 4-membered saturated or partially unsaturated carbocyclic ring. In some embodiments, $R^x$ is an optionally substituted 5-membered saturated or partially unsaturated carbocyclic ring. In some embodiments, $R^x$ is an optionally substituted 6-membered saturated or partially unsaturated carbocyclic ring. In some embodiments, $R^x$ is an optionally substituted 7-membered saturated or partially unsaturated carbocyclic ring. In some embodiments, $R^x$ is optionally substituted cycloheptyl. In some embodiments, $R^x$ is cycloheptyl. In some embodiments, $R^x$ is optionally substituted cyclohexyl. In some embodiments, $R^x$ is cyclohexyl. In some embodiments, $R^x$ is optionally substituted cyclopentyl. In some embodiments, $R^x$ is cyclopentyl. In some embodiments, $R^x$ is optionally substituted cyclobutyl. In some embodiments, $R^x$ is cyclobutyl. In some embodiments, $R^x$ is optionally substituted cyclopropyl. In some embodiments, $R^x$ is cyclopropyl.

In some embodiments, $R^x$ is an optionally substituted 5-6 membered monocyclic heteroaryl ring having 1-4 heteroatoms independently selected from nitrogen, oxygen, or sulfur. In some embodiments, $R^x$ is a substituted 5-6 membered monocyclic heteroaryl ring having 1-4 heteroatoms independently selected from nitrogen, oxygen, or sulfur. In some embodiments, $R^x$ is an unsubstituted 5-6 membered monocyclic heteroaryl ring having 1-4 heteroatoms independently selected from nitrogen, oxygen, or sulfur.

In some embodiments, $R^x$ is an optionally substituted 5-membered monocyclic heteroaryl ring having 1-4 heteroatoms independently selected from nitrogen, oxygen or sulfur. In some embodiments, $R^x$ is an optionally substituted 6-membered monocyclic heteroaryl ring having 1-4 heteroatoms independently selected from nitrogen, oxygen, or sulfur.

In some embodiments, $R^x$ is an optionally substituted 5-membered monocyclic heteroaryl ring having one heteroatom selected from nitrogen, oxygen, or sulfur. In some embodiments, $R^x$ is selected from optionally substituted pyrrolyl, furanyl, or thienyl.

In some embodiments, $R^x$ is an optionally substituted 5-membered heteroaryl ring having two heteroatoms independently selected from nitrogen, oxygen, or sulfur. In certain embodiments, $R^x$ is an optionally substituted 5-membered heteroaryl ring having one nitrogen atom, and an additional heteroatom selected from sulfur or oxygen. Exemplary $R^x$ groups include but are not limited to optionally substituted pyrazolyl, imidazolyl, thiazolyl, isothiazolyl, oxazolyl or isoxazolyl.

In some embodiments, $R^x$ is an optionally substituted 5-membered heteroaryl ring having three heteroatoms independently selected from nitrogen, oxygen, or sulfur. Exemplary $R^x$ groups include but are not limited to optionally substituted triazolyl, oxadiazolyl or thiadiazolyl.

In some embodiments, $R^x$ is an optionally substituted 5-membered heteroaryl ring having four heteroatoms independently selected from nitrogen, oxygen, or sulfur. Exemplary $R^x$ groups include but are not limited to optionally substituted tetrazolyl, oxatriazolyl and thiatriazolyl.

In some embodiments, $R^x$ is an optionally substituted 6-membered heteroaryl ring having 1-4 nitrogen atoms. In some embodiments, $R^x$ is an optionally substituted 6-membered heteroaryl ring having 1-3 nitrogen atoms. In other embodiments, $R^x$ is an optionally substituted 6-membered heteroaryl ring having 1-2 nitrogen atoms. In some embodiments, $R^x$ is an optionally substituted 6-membered heteroaryl ring having four nitrogen atoms. In some embodiments, $R^x$ is an optionally substituted 6-membered heteroaryl ring having three nitrogen atoms. In some embodiments, $R^x$ is an optionally substituted 6-membered heteroaryl ring having two nitrogen atoms. In certain embodiments, $R^x$ is an optionally substituted 6-membered heteroaryl ring having one nitrogen atom. Exemplary $R^x$ groups include but are not limited to optionally substituted pyridinyl, pyrimidinyl, pyrazinyl, pyridazinyl, triazinyl, or tetrazinyl.

In some embodiments, $R^x$ is an optionally substituted 3-7 membered saturated or partially unsaturated heterocyclic ring having 1-3 heteroatoms independently selected from nitrogen, oxygen, or sulfur. In some embodiments, $R^x$ is a substituted 3-7 membered saturated or partially unsaturated heterocyclic ring having 1-3 heteroatoms independently selected from nitrogen, oxygen, or sulfur. In some embodiments, $R^x$ is an unsubstituted 3-7 membered saturated or partially unsaturated heterocyclic ring having 1-3 heteroatoms independently selected from nitrogen, oxygen, or sulfur.

In certain embodiments, $R^x$ is an optionally substituted 5-7 membered partially unsaturated monocyclic ring having 1-3 heteroatoms independently selected from nitrogen, oxygen, or sulfur. In certain embodiments, $R^x$ is an optionally substituted 5-6 membered partially unsaturated monocyclic ring having 1-3 heteroatoms independently selected from nitrogen, oxygen, or sulfur. In certain embodiments, $R^x$ is an optionally substituted 5-membered partially unsaturated monocyclic ring having 1-3 heteroatoms independently selected from nitrogen, oxygen, or sulfur. Exemplary $R^x$ groups include but are not limited to optionally substituted dihydroimidazolyl, dihydrothiazolyl, dihydrooxazolyl, or oxazolinyl. In certain embodiments, $R^x$ is an optionally substituted 6-membered partially unsaturated monocyclic ring having 1-3 heteroatoms independently selected from nitrogen, oxygen, or sulfur. Exemplary $R^x$ groups include but are not limited to optionally substituted dihydropyridinyl, tetrahydropyridinyl, dihydropyrimidinyl, tetrahydropyrimidinyl, dihydropyrazinyl, tetrahydropyrazinyl, dihydrotriazinyl, tetrahydrotriazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, $R^x$ is an optionally substituted 7-membered partially unsaturated monocyclic ring having 1-3 heteroatoms independently selected from nitrogen, oxygen, or sulfur. Exemplary $R^x$ groups include but are not limited to optionally substituted azepinyl, oxepinyl, thiepinyl, diazepinyl, oxazepinyl, thiazepinyl, triazepinyl, oxadiazepinyl, thiadiazepinyl, dihydroazepinyl, dihydrooxepinyl, dihydrothiepinyl, dihydrodiazepinyl, dihydrooxazepinyl, dihydrothiazepinyl, dihydrotriazepinyl, dihydrooxadiazepinyl, dihydrothiadiazepinyl, tetrahydroazepinyl, tetrahydrooxepinyl, tetrahydrothiepinyl, tetrahydrodiazepinyl, tetrahydrooxazepinyl, tetrahydrothiazepinyl, tetrahydrotriazepinyl, tetrahydrooxadiazepinyl, or tetrahydrothiadiazepinyl.

In some embodiments, $R^x$ is optionally substituted 3-membered heterocyclic ring having one heteroatom selected from nitrogen, oxygen or sulfur. Exemplary $R^x$ groups include but are not limited to optionally substituted aziridinyl, thiiranyl or oxiranyl. In some embodiments, $R^x$ is optionally substituted 4-membered heterocyclic ring having 1-3 heteroatoms independently selected from nitrogen, oxygen, or sulfur. Exemplary $R^x$ groups include but are not limited to optionally substituted azetidinyl, oxetanyl, thietanyl, oxazetidinyl, thiazetidinyl, or diazetidinyl. In some embodiments, $R^x$ is optionally substituted 5-membered heterocyclic ring having 1-3 heteroatoms independently selected from nitrogen, oxygen, or sulfur. Exemplary $R^x$ groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, isothiazolidinyl, triazolidinyl, oxadiazolidinyl, thiadiazolidinyl, oxadiazolidinyl, dioxazolidinyl, oxathiazolidinyl, thiadiazolidinyl or dithiazolidinyl. In some embodiments, $R^x$ is optionally substituted 6-membered heterocyclic ring having 1-3 heteroatoms independently selected from nitrogen, oxygen, or sulfur. Exemplary $R^x$ groups include but are not limited to optionally substituted piperidinyl, tetrahydropyranyl, tetrahydrothiopyranyl, piperazinyl, morpholinyl, thiomorpholinyl, dithianyl, dioxanyl, oxathianyl, triazinanyl, oxadiazinanyl, thiadiazinanyl, dithiazinanyl, dioxazinanyl, oxathiazinanyl, oxadithianyl, trioxanyl, dioxathianyl or trithianyl. In some embodiments, $R^x$ is optionally substituted 7-membered heterocyclic ring having 1-3 heteroatoms independently selected from nitrogen, oxygen, or sulfur. Exemplary $R^x$ groups include but are not limited to optionally substituted azepanyl, oxepanyl, thiepanyl, diazepanyl, oxazepanyl, thiazepanyl, dioxepanyl, oxathiepanyl, dithiepanyl, triazepanyl, oxadiazepanyl, thiadiazepanyl, dioxazepanyl, oxathiazepanyl, dithiazepanyl, trioxepanyl, dioxathiepanyl, oxadithiepanyl or trithiepanyl.

In certain embodiments, $R^x$ is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothienyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothienyl, or tetrahydrothiopyranyl.

In some embodiments, $R^x$ is —CN. In some embodiments, $R^x$ is —C(O)N(R')$_2$, wherein each R is independently as defined above and described herein. In some embodiments, $R^x$ is —C(O)R, wherein R is as defined above and described herein. In some embodiments, $R^x$ is —C(O)OR, wherein R is as defined above and described herein. In some embodiments, $R^x$ is —OR, wherein R is as defined above and described herein. In some embodiments, $R^x$ is —OC(O)R, wherein R is as defined above and described herein. In some embodiments, $R^x$ is —OC(O)N(R')$_2$, wherein each R is independently as defined above and described herein. In some embodiments, $R^x$ is —OSi(R)$_3$, wherein each R is independently as defined above and described herein. In some embodiments, $R^x$ is —N(R')$_2$, wherein each R is independently as defined above and described herein. In some embodiments, $R^x$ is —N(R')$_3^+$, wherein each and R is independently as defined above and described herein. In some embodiments, $R^x$ is —NR'C(O)R, wherein each of R and R' is independently as defined above and described herein. In some embodiments, $R^x$ is —NR'C(O)OR, wherein each of R and R' is independently as defined above and described herein. In some embodiments, $R^x$ is —NR'C(O)N(R')$_2$, wherein each R' is independently as defined above and described herein. In some embodiments, $R^x$ is —NR'SO$_2$R, wherein each of R and R' is independently as defined above and described herein. In some embodiments, $R^x$ is —NR'SO$_2$N(R')$_2$, wherein each R' is independently as defined above and described herein. In some embodiments, $R^x$ is —NR'OR, wherein each of R and R' is independently as defined above and described herein. In some embodiments, $R^x$ is —NO$_2$. In some embodiments, $R^x$ is —Si(R)$_3$, wherein each R is independently as defined above and described herein. In some embodiments, $R^x$ is —P(R)$_2$, wherein each R is independently as defined above and described herein. In some embodiments, $R^x$ is —P(O)(R)$_2$, wherein each R is independently as defined above and described herein. In some embodiments, R$^x$ is —P(O)(OR)$_2$, wherein each R is independently as defined above and described herein. In some embodiments, R$^x$ is —SR, wherein R is as defined above and described herein. In some embodiments, R$^x$ is —SC(O)R, wherein R is as defined above and described herein. In some embodiments, R$^x$ is —S(O)R, wherein R is as defined above and described herein. In some embodiments, R$^x$ is —SO$_2$R, wherein R is as defined above and described herein. In some embodiments, R$^x$ is —SO$_3$R, wherein R is as defined above and described herein. In some embodiments, R$^x$ is —SO$_2$N(R')$_2$, wherein each R is independently as defined above and described herein. In some embodiments, R$^x$ is —SO$_2$NMe$_2$. In some embodiments, R$^x$ is —SeR.

In some embodiments, R$^x$ is —NHC(O)R, wherein R is as defined above and described herein. In some embodiments, R$^x$ is —NHC(O)C$_6$F$_5$. In some embodiments, R$^x$ is —NHC(O)CF$_3$. In some embodiments, R$^x$ is —NHC(O)C(O)OEt. In some embodiments, R$^x$ is —NHC(O)Ot-Bu. In some embodiments, R$^x$ is —NHC(O)Oi-Bu. In some embodiments, R$^x$ is —NHC(O)C$_{15}$H$_{31}$.

In some embodiments, R$^x$ is —N(R')$_3$$^+$. As understood by a person of ordinary skill in the art, an anion is need to make the overall compound neutral. In some embodiments, an anion is F$^-$. In some embodiments, an anion is Cl$^-$. In some embodiments, an anion is Br$^-$. In some embodiments, an anion is I$^-$. In some embodiments, an —N(R')$_3$$^+$ group facilitates the removal of a metal compound comprising said —N(R')$_3$$^+$ group after a reaction, for example, via chromatograph and/or extraction with aqueous solution.

In some embodiments, at least one R$^x$ is an electron-withdrawing group. In some embodiments, at least one R$^x$ is an electron-donating group. In some embodiments, each R$^x$ is an electron-withdrawing group. In some embodiments, R$^x$ is —NO$_2$. In some embodiments, R$^x$ is —F. In some embodiments, each R$^x$ is —F. In some embodiments, R$^x$ is —Cl. In some embodiments, R$^x$ is —Br. In some embodiments, R$^x$ is —I. In some embodiments, R$^x$ is —CF$_3$. In some embodiments, at least one R$^x$ group is an electron-donating group.

As generally defined above, m is 0-6. In some embodiments, m is 0. In some embodiments, m is 0, and Ring A is an optionally substituted ring selected from phenyl, a 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, m is 0-5. In some embodiments, m is 0-4. In some embodiments, m is 0-3. In some embodiments, m is 0-2. In some embodiments, m is 1-6. In some embodiments, m is 1-5. In some embodiments, m is 1-4. In some embodiments, m is 1-3. In some embodiments, m is 1-2. In some embodiments, m is 1. In some embodiments, m is 2. In some embodiments, m is 3. In some embodiments, m is 4. In some embodiments, m is 5. In some embodiments, m is 6.

In some embodiments, m is 1, and Ring A is

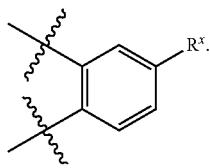

In some embodiments, Ring A is

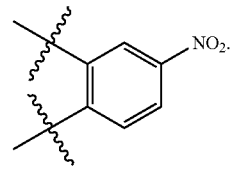 [SMILES: *c1ccc([N+](=O)[O-])cc1*]

In some embodiments, Ring A is

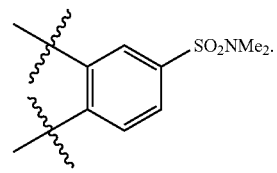

In some embodiments, Ring A is

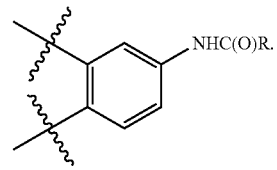

In some embodiments, Ring A is

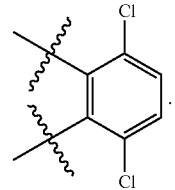 [SMILES: *c1c(Cl)ccc(Cl)c1*]

In some embodiments, Ring A is

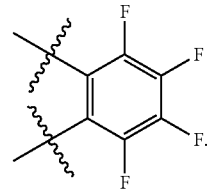 [SMILES: *c1c(*)c(F)c(F)c(F)c1F]

As generally defined above, X is —O—, —S—, —Se—, —OC(O)—, —OC(S)—, —SC(O)—, —SC(S)—, —P(R$^x$)—, —P(O)(R$^x$)—, or —N(R$^x$)—, wherein R$^x$ is independently as defined above and described herein. In some embodiments, X is —O— or —S—. In some embodiments, X is —O—. In some embodiments, X is —S—. In some embodiments, X is —Se—. In some embodiments, X is —N(R$^x$)—, wherein R$^x$ is as defined above and described herein.

As generally defined above, Y is —O—, —S—, —Se—, —OC(O)—, —OC(S)—, —SC(O)—, —SC(S)—, —P(R$^x$)—, —P(O)(R$^x$)—, or —N(R$^x$)—, wherein R$^x$ is independently as defined above and described herein. In some embodiments, Y is —O— or —S—. In some embodiments, Y is —O—. In some embodiments, Y is —S—. In some embodiments, Y is —Se—. In some embodiments, Y is —N(R$^x$)—, wherein R$^x$ is as defined above and described herein.

In some embodiments, each of X and Y is independently —O— or —S—. In some embodiments, each of X and Y is —O—. In some embodiments, at least one of X and Y is —S—. In some embodiments, each of X and Y is —S—. In some embodiments, one of X and Y is —O— and the other is —S—. In some embodiments, one of X and Y is not —O—.

As generally defined above, Z is —O—, —S—, —Se—, —N(R$^x$)—, —N═, —P(R$^x$)—, —C(O)—, —C(S)—, —S(O)—, or —Se(O)—, or —Z—R$^9$ is halogen, wherein R$^x$ is independently as defined above and described herein.

In some embodiments, Z is —O—, —S—, —Se—, —N(R$^x$)—, —N═, —P(R$^x$)—, —C(O)—, —C(S)—, —S(O)—, or —Se(O)—, wherein R$^x$ is independently as defined above and described herein. In some embodiments, Z is —O—. In some embodiments, Z is —S—. In some embodiments, Z is —Se—. In some embodiments, Z is —N(R$^x$)—, wherein R$^x$ is as defined above and described herein. In some embodiments, Z is —N═. In some embodiments, Z is —P(R$^x$)—, wherein R$^x$ is as defined above and described herein. In some embodiments, Z is —C(O)—, and Z is boned to M through the oxygen atom. In some embodiments, Z is —C(S)—, and Z is boned to M through the sulfur atom. In some embodiments, Z is —S(O)—, and Z is boned to M through the oxygen atom. In some embodiments, Z is —Se(O)—, and Z is boned to M through the oxygen atom.

In some embodiments, —Z—R$^9$ is halogen. In some embodiments, —Z—R$^9$ is —F. In some embodiments, —Z—R$^9$ is —Cl. In some embodiments, —Z—R$^9$ is —Br. In some embodiments, —Z—R$^9$ is —I. In some embodiments, —Z—R$^9$ is halogen, wherein R$^9$ is R$^3$. In some embodiments, —Z—R$^3$ is halogen. In some embodiments, —Z—R$^3$ is —F. In some embodiments, —Z—R$^3$ is —Cl. In some embodiments, —Z—R$^3$ is —Br. In some embodiments, —Z—R$^3$ is —I.

As generally defined above, each R' is independently R, —C(O)R, —C(O)N(R)$_2$, —C(O)OR, —SO$_2$R, —SO$_2$N(R)$_2$, —P(O)(OR)$_2$, or —OR.

In some embodiments, R' is R, wherein R is as defined above and described herein. In some embodiments, R' is hydrogen. In some embodiments, R' is R, wherein R is not hydrogen. In some embodiments, R' is optionally substituted C$_{1-20}$ aliphatic. In some embodiments, R' is optionally substituted C$_{1-20}$ heteroaliphatic. Exemplary embodiments for R' include but are not limited to those described for R above.

In some embodiments, R' is —C(O)R. In some embodiments, R' is —C(O)N(R)$_2$. In some embodiments, R' is —C(O)OR. In some embodiments, R' is —SO$_2$R. In some embodiments, R' is —SO$_2$N(R)$_2$. In some embodiments, R' is —P(O)(OR)$_2$. In some embodiments, R' is —OR.

As generally defined above, each of R$^4$ and R$^5$ is independently bonded to M through an oxygen, nitrogen, sulfur or selenium atom, and R$^4$ and R$^5$ are taken together to form a bidentate ligand, or R$^4$ and R$^5$ are taken together with one or more of R$^1$, L and R$^{14}$ to form a polydentate ligand. In some embodiments, each of R$^4$ and R$^5$ is independently bonded to Ru through an oxygen, nitrogen, sulfur or selenium atom, and R$^4$ and R$^5$ are taken together to form a bidentate ligand, or R$^4$ and R$^5$ are taken together with one or more of R$^1$, L and R$^{14}$ to form a polydentate ligand. In some embodiments, R$^4$ and R$^5$ are taken together to form a bidentate dianionic ligand. In some embodiments, R$^4$ and R$^5$ are taken together with one or more of R$^1$, R$^{14}$ and L to form a polydentate ligand. In some embodiments, a bidentate ligand formed by R$^4$ and R$^5$, such as those described herein, is optionally taken together with one or more of R$^1$, R$^{14}$ and L to form a polydentate ligand. In some embodiments, one or both of R$^4$ and R$^5$ are linked to a tag or support. In some embodiments, R$^4$ is linked to a tag or support. In some embodiments, R$^5$ is linked to a tag or support.

In some embodiments, at least one of R$^4$ and R$^5$ is bonded to M through a sulfur atom. In some embodiments, each of R$^4$ and R$^5$ is bonded to M through a sulfur atom. In some embodiments, at least one of R$^4$ and R$^5$ is bonded to M through —S—. In some embodiments, each of R$^4$ and R$^5$ is bonded to M through —S—.

In some embodiments, each of R$^4$ and R$^5$ is independently selected from —OR, —SR, —SeR, or —N(R')$_2$, and one R group of R$^4$ and one R group of R$^5$ are taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR, —SR, —SeR, or —N(R')$_2$, and one R group of R$^4$ and one R group of R$^5$ are taken together with their intervening atoms to form an optionally substituted 3-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR, —SR, —SeR, or —N(R')$_2$, and one R group of R$^4$ and one R group of R$^5$ are taken together with their intervening atoms to form an optionally substituted 4-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR, —SR, —SeR, or —N(R')$_2$, and one R group of R$^4$ and one R group of R$^5$ are taken together with their intervening atoms to form an optionally substituted 5-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR, —SR, —SeR, or —N(R')$_2$, and one R group of R$^4$ and one R group of R$^5$ are taken together with their intervening atoms to form an optionally substituted 6-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR, —SR, —SeR, or —N(R')$_2$, and one R group of R$^4$ and one R group of R$^5$ are taken together with their intervening atoms to form an optionally substituted 7-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR, —SR, —SeR, or —N(R')$_2$, and one R group of R$^4$ and one R group of R$^5$ are taken together with their intervening atoms to form an optionally substituted 8-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR, —SR, —SeR, or —N(R')$_2$, and one R group of R$^4$ and one R group of R$^5$ are taken together with their intervening atoms to form an optionally substituted 9-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR, —SR, —SeR, or —N(R')$_2$, and one R group of R$^4$ and one R group of R$^5$ are taken together with their intervening atoms to form an optionally substituted 10-membered, saturated, partially unsaturated, or aryl ring having, in addition to the intervening atoms, 0-4 heteroatoms independently selected from nitrogen, oxygen, or sulfur.

In some embodiments, each of R$^4$ and R$^5$ is independently selected from —OR or —SR, and the R group of R$^4$ and the R group of R$^5$ are taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR or —SR, and the R group of R$^4$ and the R group of R$^5$ are taken together with their intervening atoms to form an optionally substituted 3-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR or —SR, and the R group of R$^4$ and the R group of R$^5$ are taken together with their intervening atoms to form an optionally substituted 4-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR or —SR, and the R group of R$^4$ and the R group of R$^5$ are taken together with their intervening atoms to form an optionally substituted 5-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR or —SR, and the R group of R$^4$ and the R group of R$^5$ are taken together with their intervening atoms to form an optionally substituted 6-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR or —SR, and the R group of R$^4$ and the R group of R$^5$ are taken together with their intervening atoms to form an optionally substituted phenyl ring. In some embodiments, each of R$^4$ and R$^5$ is independently selected from —OR or —SR, and the R group of R$^4$ and the R group of R$^5$ are taken together with their intervening atoms to form an optionally substituted 7-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR or —SR, and the R group of R$^4$ and the R group of R$^5$ are taken together with their intervening atoms to form an optionally substituted 8-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR or —SR, and the R group of R$^4$ and the R group of R$^5$ are taken together with their intervening atoms to form an optionally substituted 9-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently selected from —OR or —SR, and the R group of R$^4$ and the R group of R$^5$ are taken together with their intervening atoms to form an optionally substituted 10-membered, saturated, partially unsaturated, or aryl ring having, in addition to the intervening atoms, 0-4 heteroatoms independently selected from nitrogen, oxygen, or sulfur.

In some embodiments, each of R$^4$ and R$^5$ is independently —OR, and the R group of R$^4$ and the R group of R$^5$ are taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently —OR, and the R group of R$^4$ and the R group of R$^5$ are taken together with their intervening atoms to form an optionally substituted 3-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently —OR, and the R group of R$^4$ and the R group of R$^5$ are taken together with their intervening atoms to form an optionally substituted 4-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently —OR, and the R group of R$^4$ and the R group of R$^5$ are taken together with their intervening atoms to form an optionally substituted 5-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently —OR, and the R group of R$^4$ and the R group of R$^5$ are taken together with their intervening atoms to form an optionally substituted 6-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently —OR, and the R group of R$^4$ and the R group of R$^5$ are taken together with their intervening atoms to form an optionally substituted phenyl ring. In some embodiments, each of R$^4$ and R$^5$ is independently —OR, and the R group of R$^4$ and the R group of R$^5$ are taken together with their intervening atoms to form an optionally substituted 7-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently —OR, and the R group of R$^4$ and the R group of R$^5$ are taken together with their intervening atoms to form an optionally substituted 8-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently —OR, and the R group of R$^4$ and the R group of R$^5$ are taken together with their intervening atoms to form an optionally substituted 9-membered, saturated, partially unsaturated, or aryl ring having, in addition to the intervening atoms, 0-4 heteroatoms independently selected from nitrogen, oxygen, or sulfur. In some embodiments, each of R$^4$ and R$^5$ is independently —OR, and the R group of R$^4$ and the R group of R$^5$ are taken together with their intervening atoms to form an optionally substituted 10-membered, saturated, partially unsaturated, or aryl ring having, in addition to the intervening atoms, 0-4 heteroatoms independently selected from nitrogen, oxygen, or sulfur.

In some embodiments, each of $R^4$ and $R^5$ is independently —SR, and the R group of $R^4$ and the R group of $R^5$ are taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur. In some embodiments, each of $R^4$ and $R^5$ is independently —SR, and the R group of $R^4$ and the R group of $R^5$ are taken together with their intervening atoms to form an optionally substituted 3-membered, saturated, partially unsaturated, or aryl ring having, in addition to the intervening atoms, 0-4 heteroatoms independently selected from nitrogen, oxygen, or sulfur. In some embodiments, each of $R^4$ and $R^5$ is independently —SR, and the R group of $R^4$ and the R group of $R^5$ are taken together with their intervening atoms to form an optionally substituted 4-membered, saturated, partially unsaturated, or aryl ring having, in addition to the intervening atoms, 0-4 heteroatoms independently selected from nitrogen, oxygen, or sulfur. In some embodiments, each of $R^4$ and $R^5$ is independently —SR, and the R group of $R^4$ and the R group of $R^5$ are taken together with their intervening atoms to form an optionally substituted 5-membered, saturated, partially unsaturated, or aryl ring having, in addition to the intervening atoms, 0-4 heteroatoms independently selected from nitrogen, oxygen, or sulfur. In some embodiments, each of $R^4$ and $R^5$ is independently —SR, and the R group of $R^4$ and the R group of $R^5$ are taken together with their intervening atoms to form an optionally substituted 6-membered, saturated, partially unsaturated, or aryl ring having, in addition to the intervening atoms, 0-4 heteroatoms independently selected from nitrogen, oxygen, or sulfur. In some embodiments, each of $R^4$ and $R^5$ is independently —SR, and the R group of $R^4$ and the R group of $R^5$ are taken together with their intervening atoms to form an optionally substituted phenyl ring. In some embodiments, each of $R^4$ and $R^5$ is independently —SR, and the R group of $R^4$ and the R group of $R^5$ are taken together with their intervening atoms to form an optionally substituted 7-membered, saturated, partially unsaturated, or aryl ring having, in addition to the intervening atoms, 0-4 heteroatoms independently selected from nitrogen, oxygen, or sulfur. In some embodiments, each of $R^4$ and $R^5$ is independently —SR, and the R group of $R^4$ and the R group of $R^5$ are taken together with their intervening atoms to form an optionally substituted 8-membered, saturated, partially unsaturated, or aryl ring having, in addition to the intervening atoms, 0-4 heteroatoms independently selected from nitrogen, oxygen, or sulfur. In some embodiments, each of $R^4$ and $R^5$ is independently —SR, and the R group of $R^4$ and the R group of $R^5$ are taken together with their intervening atoms to form an optionally substituted 9-membered, saturated, partially unsaturated, or aryl ring having, in addition to the intervening atoms, 0-4 heteroatoms independently selected from nitrogen, oxygen, or sulfur. In some embodiments, each of $R^4$ and $R^5$ is independently —SR, and the R group of $R^4$ and the R group of $R^5$ are taken together with their intervening atoms to form an optionally substituted 10-membered, saturated, partially unsaturated, or aryl ring having, in addition to the intervening atoms, 0-4 heteroatoms independently selected from nitrogen, oxygen, or sulfur.

In some embodiments, each of $R^4$ and $R^5$ is independently bonded to Ru through an oxygen, nitrogen, sulfur or selenium atom, and $R^4$ and $R^5$ are taken together with Ru to form an optionally substituted 3-10 membered, saturated, partially unsaturated, or aryl ring having 0-6 heteroatoms independently selected from nitrogen, oxygen, sulfur or selenium. In some embodiments, each of $R^4$ and $R^5$ is independently bonded to Ru through an oxygen, nitrogen, sulfur or selenium atom, and $R^4$ and $R^5$ are taken together with Ru to form an optionally substituted 3-membered, saturated, partially unsaturated, or aryl ring having 0-6 heteroatoms independently selected from nitrogen, oxygen, sulfur or selenium. In some embodiments, each of $R^4$ and $R^5$ is independently bonded to Ru through an oxygen, nitrogen, sulfur or selenium atom, and $R^4$ and $R^5$ are taken together with Ru to form an optionally substituted 4-membered, saturated, partially unsaturated, or aryl ring having 0-6 heteroatoms independently selected from nitrogen, oxygen, sulfur or selenium. In some embodiments, each of $R^4$ and $R^5$ is independently bonded to Ru through an oxygen, nitrogen, sulfur or selenium atom, and $R^4$ and $R^5$ are taken together with Ru to form an optionally substituted 5-membered, saturated, partially unsaturated, or aryl ring having 0-6 heteroatoms independently selected from nitrogen, oxygen, sulfur or selenium. In some embodiments, each of $R^4$ and $R^5$ is independently bonded to Ru through an oxygen, nitrogen, sulfur or selenium atom, and $R^4$ and $R^5$ are taken together with Ru to form an optionally substituted 6-membered, saturated, partially unsaturated, or aryl ring having 0-6 heteroatoms independently selected from nitrogen, oxygen, sulfur or selenium. In some embodiments, each of $R^4$ and $R^5$ is independently bonded to Ru through an oxygen, nitrogen, sulfur or selenium atom, and $R^4$ and $R^5$ are taken together with Ru to form an optionally substituted phenyl ring. In some embodiments, each of $R^4$ and $R^5$ is independently bonded to Ru through an oxygen, nitrogen, sulfur or selenium atom, and $R^4$ and $R^5$ are taken together with Ru to form an optionally substituted 7-membered, saturated, partially unsaturated, or aryl ring having 0-6 heteroatoms independently selected from nitrogen, oxygen, sulfur or selenium. In some embodiments, each of $R^4$ and $R^5$ is independently bonded to Ru through an oxygen, nitrogen, sulfur or selenium atom, and $R^4$ and $R^5$ are taken together with Ru to form an optionally substituted 8-membered, saturated, partially unsaturated, or aryl ring having 0-6 heteroatoms independently selected from nitrogen, oxygen, sulfur or selenium. In some embodiments, each of $R^4$ and $R^5$ is independently bonded to Ru through an oxygen, nitrogen, sulfur or selenium atom, and $R^4$ and $R^5$ are taken together with Ru to form an optionally substituted 9-membered, saturated, partially unsaturated, or aryl ring having 0-6 heteroatoms independently selected from nitrogen, oxygen, sulfur or selenium. In some embodiments, each of $R^4$ and $R^5$ is independently bonded to Ru through an oxygen, nitrogen, sulfur or selenium atom, and $R^4$ and $R^5$ are taken together with Ru to form an optionally substituted 10-membered, saturated, partially unsaturated, or aryl ring having 0-6 heteroatoms independently selected from nitrogen, oxygen, sulfur or selenium.

In some embodiments, $R^4$ and $R^5$ are taken together to form a bidentate ligand having the structure of —X—$R^{15}$—Y—, wherein each of X, Y and $R^{15}$ is independently as defined above and described herein. In some embodiments, $R^4$ and $R^5$ are optionally taken together with one or more of $R^1$, $R^{14}$ and L to form a polydentate ligand via one or more of X, Y and $R^{15}$. In some embodiments, $R^4$ and $R^5$ are linked to a tag or support via one or more of X, Y and $R^5$.

In some embodiments, $R^4$ and $R^5$ are taken together to form a bidentate ligand having the structure of —X—B$^x$—Y—, wherein B$^x$ is:

B1
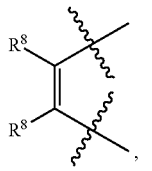,

B2
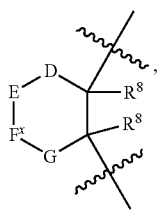,

B3
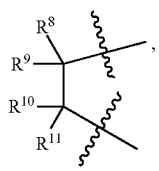,

B4
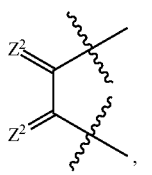,

B5
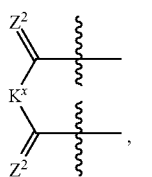,

B6
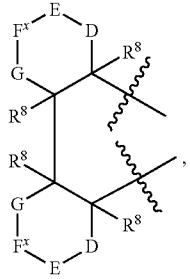, or

B7
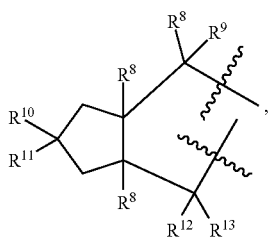, wherein:
each $Z^2$ is independently =C(R$^x$)$_2$, =O, =S, =Se, =N(R$^x$), =P(R$^x$), =C=O, =C=S, =S=O, or =Se=O;

each of D, E, F, G, $R^8$, $R^9$, $R^{10}$, $R^{11}$, $R^{12}$, $R^{13}$, and $R^{15}$ is independently as defined above and described herein. In some embodiments, $R^4$ and $R^5$ are optionally taken together with one or more of $R^1$, $R^{14}$ and L to form a polydentate ligand via one or more of X, Y and B$^x$. In some embodiments, $R^4$ and $R^5$ are linked to a tag or support via one or more of X, Y and B$^x$. In some embodiments, B2 has the structure of

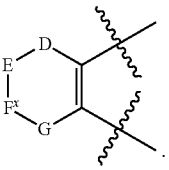.

In some embodiments, B2 has the structure of

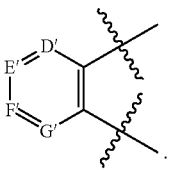.

In some embodiments, B2 is optionally substituted

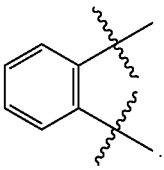 [SMILES: *c1ccccc1*].

In some embodiments, B6 has the structure of

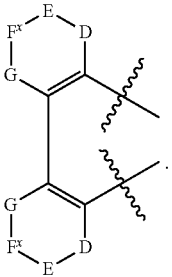.

In some embodiments, B6 has the structure of

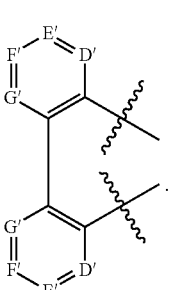.

In some embodiments, B6 has the structure of

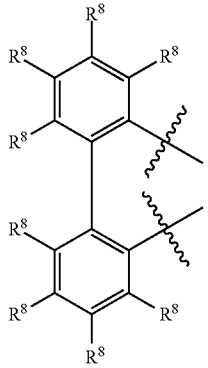

In some embodiments, $Z^2$ is independently $=C(R^x)_2$, $=O$, $=S$, $=Se$, $=N(R^x)$, $=P(R^x)$, $=C=O$, $=C=S$, $=S=O$, or $=Se=O$. In some embodiments, $Z^2$ is independently $=C(R^x)_2$, $=O$, $=S$, $=Se$, $=N(R^x)$, or $=P(R^x)$. In some embodiments, $Z^2$ is independently $=C(R^x)_2$, $=O$, $=S$, $=Se$, or $=N(R^x)$. In some embodiments, $Z^2$ is independently $=O$, $=S$ or $=N(R^x)$. In some embodiments, $Z^2$ is independently $=O$, or $=S$.

In some embodiments, $R^4$ and $R^5$ are taken together to form a bidentate ligand the structure of

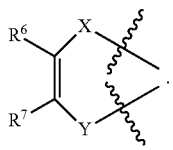

In some embodiments, $R^4$ and $R^5$ are optionally taken together with one or more of $R^1$, $R^{14}$ and L to form a polydentate ligand via one or more of X, Y, $R^6$ and $R^7$. In some embodiments, $R^4$ and $R^5$ are linked to a tag or support via one or more of X, Y, $R^6$ and $R^7$.

In some embodiments, $R^4$ and $R^5$ are taken together to form a bidentate ligand having the structure of

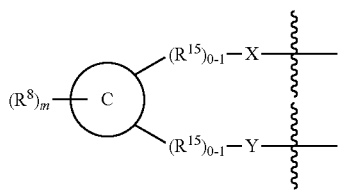

In some embodiments, $R^4$ and $R^5$ are optionally taken together with one or more of $R^1$, $R^{14}$ and L to form a polydentate ligand via one or more of X, Y, $R^5$, Ring C and $R^8$. In some embodiments, $R^4$ and $R^5$ are linked to a tag or support via one or more of X, Y, $R^{15}$, Ring C and $R^8$. In some embodiments, $R^4$ and $R^5$ are taken together to form a bidentate ligand having the structure of

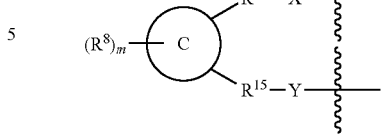

In some embodiments, $R^4$ and $R^5$ are taken together to form a bidentate ligand having the structure of

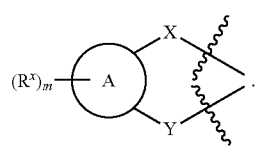

In some embodiments, $R^4$ and $R^5$ are optionally taken together with one or more of $R^1$, $R^{14}$ and L to form a polydentate ligand via one or more of X, Y, Ring A and $R^8$. In some embodiments, $R^4$ and $R^5$ are linked to a tag or support via one or more of X, Y, Ring A and $R^8$. In some embodiments, $R^4$ and $R^5$ are taken together to form a bidentate ligand having the structure of

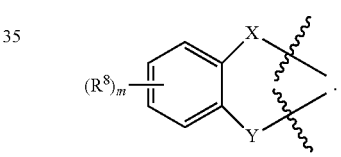

In some embodiments, $R^4$ and $R^5$ are taken together to form a bidentate ligand having the structure of

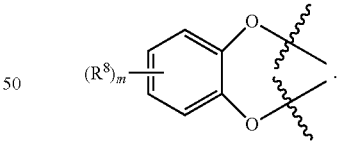

In some embodiments, $R^4$ and $R^5$ are taken together to form a bidentate ligand having the structure of

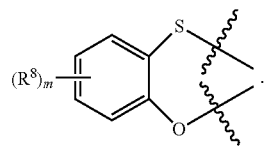

In some embodiments, $R^4$ and $R^5$ are taken together to form a bidentate ligand having the structure of

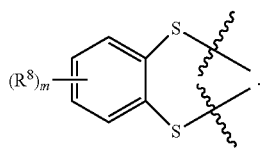

In some embodiments, $R^4$ and $R^5$ are taken together to form a bidentate ligand having the structure of

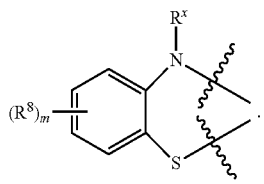

In some embodiments, $R^4$ and $R^5$ are taken together to form optionally substituted

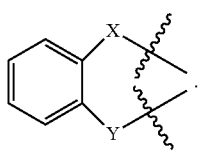

In some embodiments, $R^4$ and $R^5$ are taken together to form optionally substituted

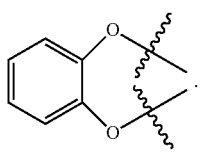 [SMILES: *Oc1ccccc1O*]

In some embodiments, $R^4$ and $R^5$ are taken together to form optionally substituted

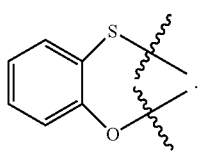 [SMILES: *Oc1ccccc1S*]

In some embodiments, $R^4$ and $R^5$ are taken together to form a bidentate ligand having the structure of

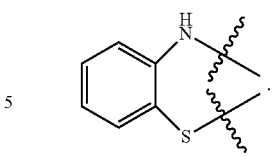

In some embodiments, $R^4$ and $R^5$ are taken together to form a bidentate ligand having the structure of

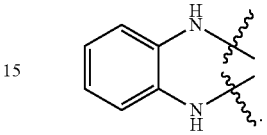

In some embodiments, $R^4$ and $R^5$ are taken together to form a 1,4-dianionic ligand. In some embodiments, $R^4$ and $R^5$ are taken together to form a 1,4 dianionic ligand having the structure of

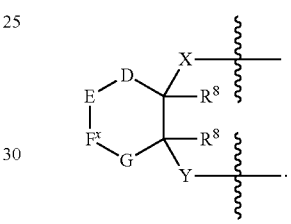

In some embodiments, $R^4$ and $R^5$ are taken together to form a 1,4 dianionic ligand having the structure of

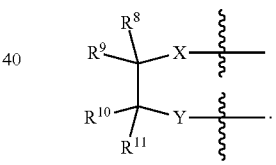

In some embodiments, $R^4$ and $R^5$ are taken together to form a 1,4 dianionic ligand having the structure of

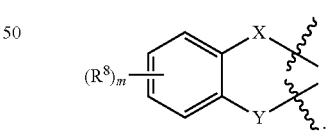

In some embodiments, $R^4$ and $R^5$ are taken together to form a 1,4 dianionic ligand having the structure of

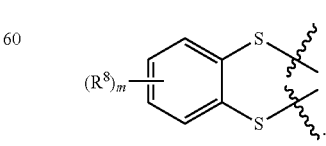

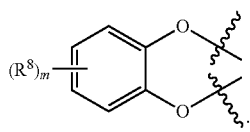

In some embodiments, $R^4$ and $R^5$ are taken together to form a 1,4 dianionic ligand having the structure of

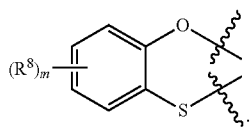

In some embodiments, $R^4$ and $R^5$ are taken together to form a 1,4 dianionic ligand having the structure of

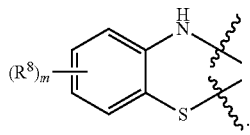

In some embodiments, $R^4$ and $R^5$ are taken together to form a 1,4 dianionic ligand having the structure of

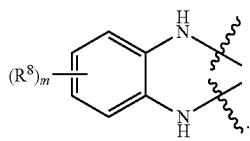

In some embodiments, $R^4$ and $R^5$ are taken together to form a 1,5-dianionic ligand. In some embodiments, $R^4$ and $R^5$ are taken together to form a 1,5 dianionic ligand having the structure of

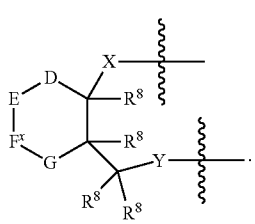

In some embodiments, $R^4$ and $R^5$ are taken together to form a 1,5 dianionic ligand having the structure of

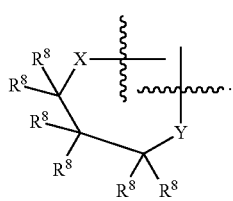

In some embodiments, $R^4$ and $R^5$ are taken together to form a 1,5 dianionic ligand having the structure of

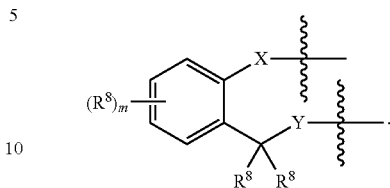

In some embodiments, $R^4$ and $R^5$ are taken together to form a 1,5 dianionic ligand having the structure of

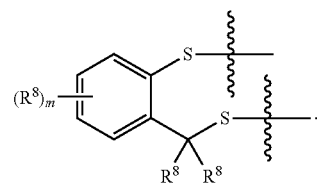

In some embodiments, $R^4$ and $R^5$ are taken together to form a 1,5 dianionic ligand having the structure of

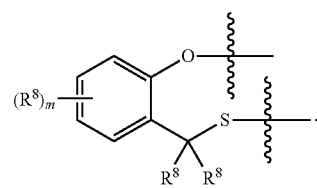

In some embodiments, $R^4$ and $R^5$ are taken together to form a 1,5 dianionic ligand having the structure of

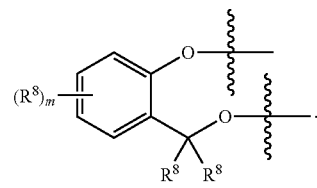

In some embodiments, $R^4$ and $R^5$ are taken together to form a 1,5 dianionic ligand having the structure of

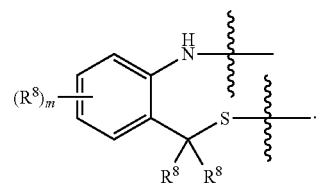

In some embodiments, $R^4$ and $R^5$ are taken together to form a 1,5 dianionic ligand having the structure of

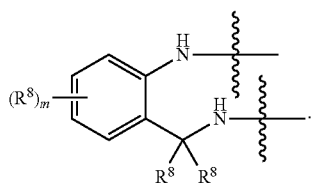

In some embodiments, R⁴ and R⁵ are taken together to form a 1,6-dianionic ligand. In some embodiments, R⁴ and R⁵ are taken together to form a 1,6 dianionic ligand having the structure of

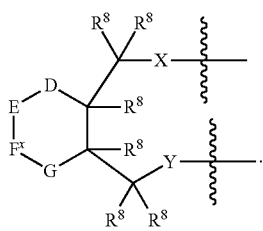

In some embodiments, R⁴ and R⁵ are taken together to form a 1,6 dianionic ligand having the structure of

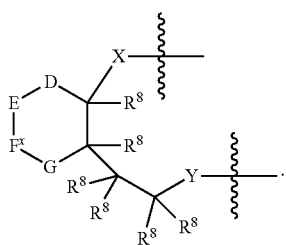

In some embodiments, R⁴ and R⁵ are taken together to form a 1,6 dianionic ligand having the structure of

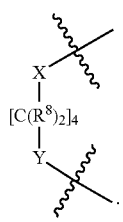

In some embodiments, R⁴ and R⁵ are taken together to form a 1,6 dianionic ligand having the structure of

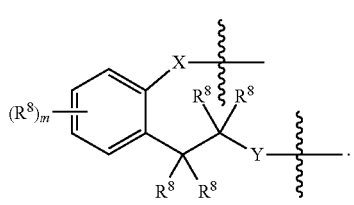

In some embodiments, R⁴ and R⁵ are taken together to form a 1,6 dianionic ligand having the structure of

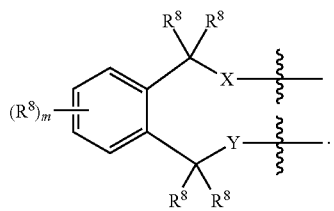

In some embodiments, R⁴ and R⁵ are taken together to form a 1,6 dianionic ligand having the structure of

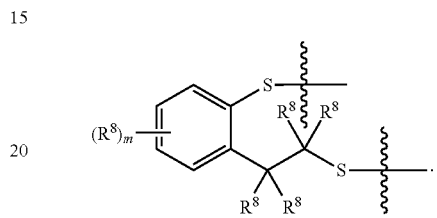

In some embodiments, R⁴ and R⁵ are taken together to form a 1,6 dianionic ligand having the structure of

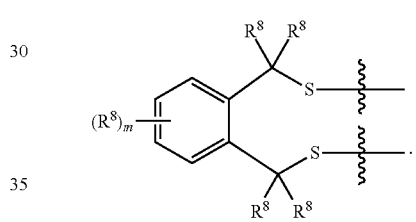

In some embodiments, R⁴ and R⁵ are taken together to form a 1,6 dianionic ligand having the structure of

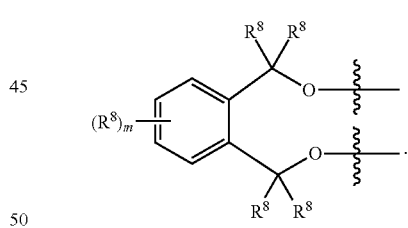

In some embodiments, R⁴ and R⁵ are taken together to form a 1,6 dianionic ligand having the structure of

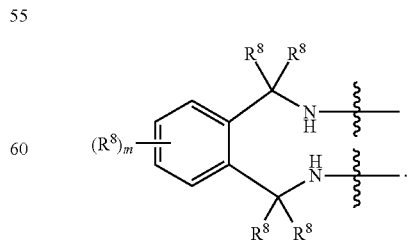

In some embodiments, R⁴ and R⁵ are taken together to form a bidentate ligand having the structure of

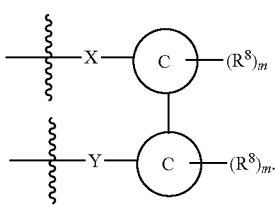

In some embodiments, $R^4$ and $R^5$ are taken together to form a bidentate ligand having the structure

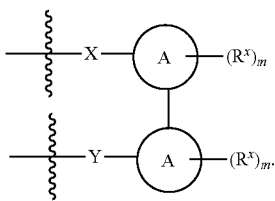

In some embodiments, $R^4$ and $R^5$ are optionally taken together with one or more of $R^1$, $R^{14}$ and L to form a polydentate ligand via one or more of X, Y, Ring A and $R^x$. In some embodiments, $R^4$ and $R^5$ are linked to a tag or support via one or more of X, Y, Ring A and $R^x$. In some embodiments, a formed bidentate ligand is optionally substituted

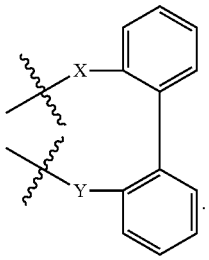

In some embodiments,

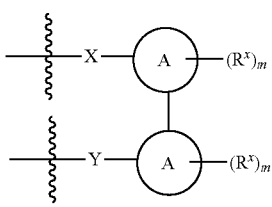

is optionally substituted

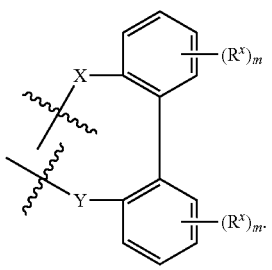

In some embodiments,

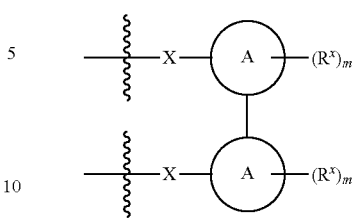

is optionally substituted

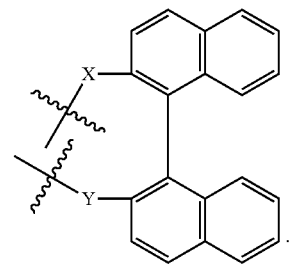

In some embodiments,

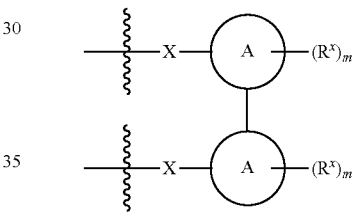

is optionally substituted

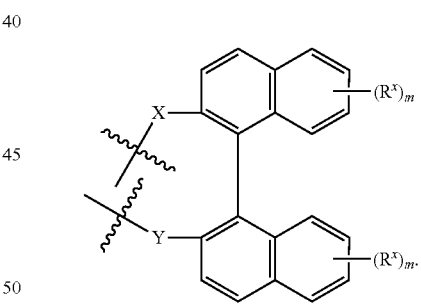

In some embodiments, $R^4$ and $R^5$ are taken together to form a bidentate ligand having the structure of

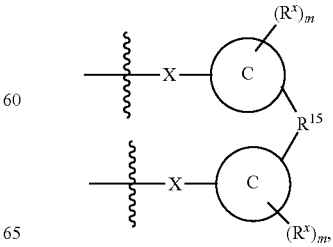

wherein each variable is independently as defined above and described herein. In some embodiments, $R^4$ and $R^5$ are taken together to form a bidentate ligand having the structure of

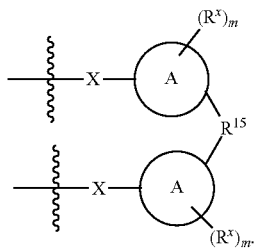

In some embodiments, $R^4$ and $R^5$ are taken together to form a bidentate ligand having the structure of

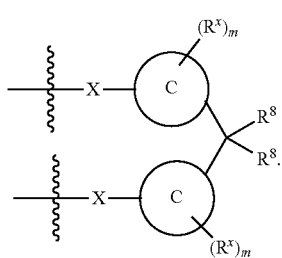

In some embodiments, $R^4$ and $R^5$ are taken together to form a bidentate ligand having the structure of

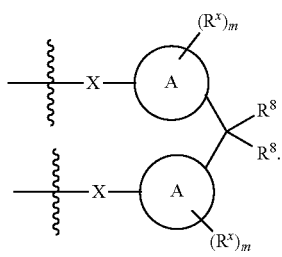

In some embodiments, $R^4$ and $R^5$ are taken together to form a bidentate ligand having the structure of

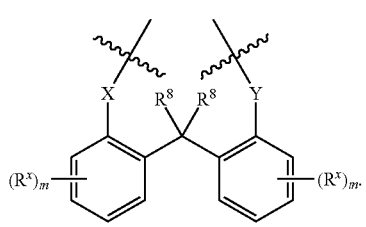

In some embodiments, $R^4$ and $R^5$, or a bidentate or polydentate ligand formed by $R^4$ and $R^5$ taken together optionally with other ligands, are electron-rich. In some embodiments, $R^4$ and $R^5$, or a bidentate or polydentate ligand formed by $R^4$ and $R^5$ taken together optionally with other ligands, are electron-donating.

Exemplary dianionic ligands formed by $R^4$ and $R^5$ taken together are depicted below:

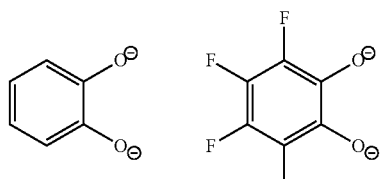
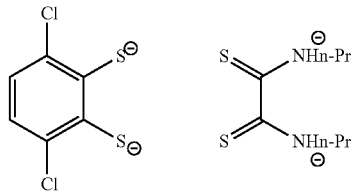
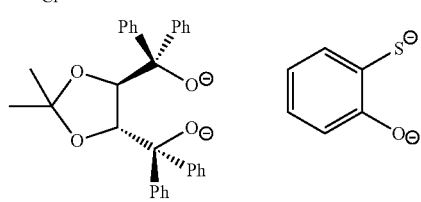
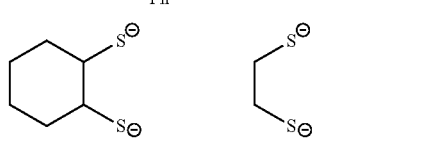
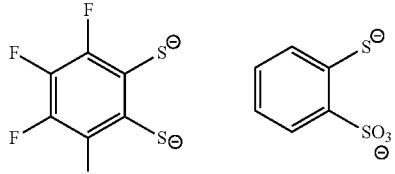
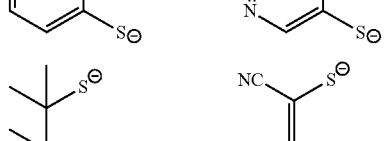
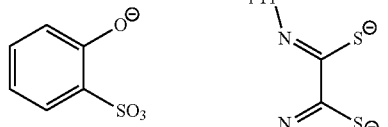
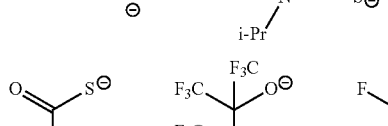
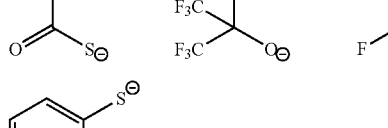
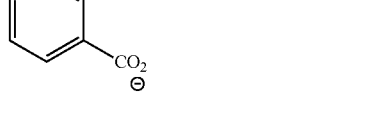

-continued

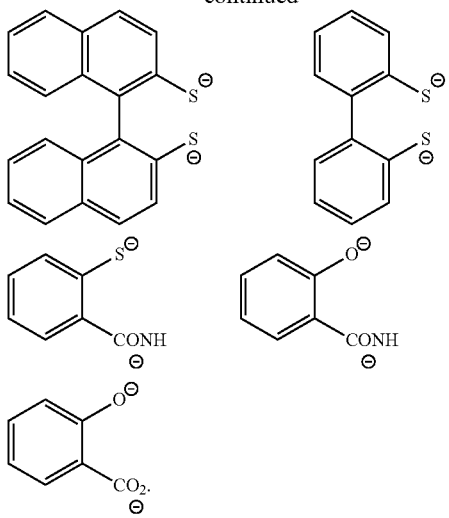

As generally defined above, $R^{15}$ is —$B^x$—, or an optionally substituted bivalent $C_{1-20}$ aliphatic or $C_{1-20}$ heteroaliphatic group, wherein 0-6 methylene units are optionally and independently replaced by —O—, —N(R')—, —S—, —C(O)—, —OC(O)—, —C(O)O—, —OC(O)O—, —C(S)—, —OC(S)—, —SC(O)—, —SC(S)—, —S(O)—, —S(O)$_2$—, —OS(O)$_2$O—, —N(R')C(O)—, —C(O)N(R')—, —N(R')C(O)O—, —OC(O)N(R')—, —N(R')C(O)N(R')—, —P(R$^x$)—, —P(O)(R$^x$)—, or -Cy$^1$-, wherein each of R, R$^x$ and Cy$^1$ is independently as defined above and described herein.

In some embodiments, $R^{15}$ is —$B^x$—, wherein —$B^x$— is:

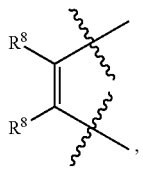 B1

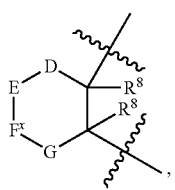 B2

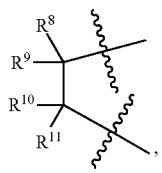 B3

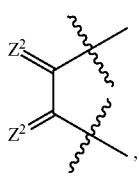 B4

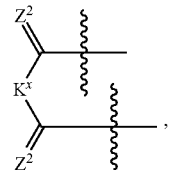 B5

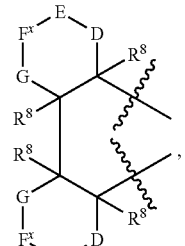 B6

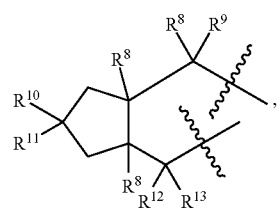 B7 wherein:

each $Z^2$ is independently =C(R$^x$)$_2$, =O, =S, =Se, =N(R$^x$), =P(R$^x$), =C=O, =C=S, =S=O, or =Se=O;

each of D, E, F, G, R$^8$, R$^9$, R$^{10}$, R$^{11}$, R$^{12}$, R$^{13}$, and R$^{15}$ is independently as defined above and described herein.

In some embodiments, —$B^x$— is B1. In some embodiments, —$B^x$— is B2. In some embodiments, B2 has the structure of

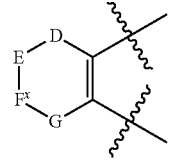

In some embodiments, B2 has the structure of

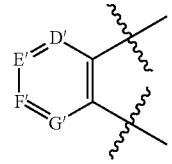

In some embodiments, —$B^x$— is B3. In some embodiments, —$B^x$— is B4. In some embodiments, —$B^x$— is B5. In some embodiments, —$B^x$— is B6. In some embodiments, B6 has the structure of

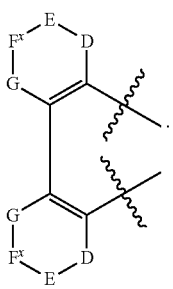

In some embodiments, B6 has the structure of

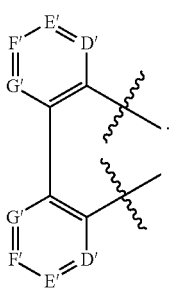

In some embodiments, B6 has the structure of

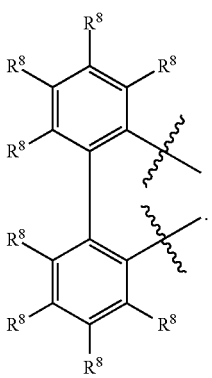

In some embodiments, —B$^x$— is B7.

In some embodiments, R$^{15}$ is an optionally substituted bivalent C$_{1-20}$ aliphatic group. In some embodiments, R$^{15}$ is an optionally substituted bivalent C$_{1-20}$ aliphatic group. In some embodiments, R$^{15}$ is an optionally substituted bivalent C$_{1-6}$ aliphatic group. In some embodiments, R$^{15}$ is an optionally substituted C$_{1-6}$ alkanediyl group. In some embodiments, R$^{15}$ is an optionally substituted C$_{1-6}$ alkenediyl group. In some embodiments, R$^{15}$ is optionally substituted —CH$_2$CH$_2$—. In some embodiments, R$^{15}$ is optionally substituted —CH=CH—. In some embodiments, R$^{15}$ is

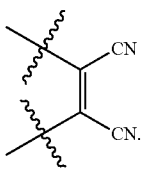 [SMILES: */C(C#N)=C(\*)C#N]

In some embodiments, R$^{15}$ is an optionally substituted bivalent C$_{1-20}$ heteroaliphatic group. In some embodiments, R$^{15}$ is an optionally substituted C$_{1-20}$ heteroaliphatic group having 1-6 heteroatoms independently selected from nitrogen, sulfur, phosphorus or selenium. In some embodiments, R$^{15}$ is an optionally substituted C$_{1-20}$ heteroaliphatic group having 1-6 heteroatoms independently selected from nitrogen, sulfur, phosphorus or selenium, optionally including one or more oxidized forms of nitrogen, sulfur, phosphorus or selenium. In some embodiments, R$^{15}$ is optionally substituted C$_{1-20}$ heteroaliphatic comprising 1-6 groups independently selected from

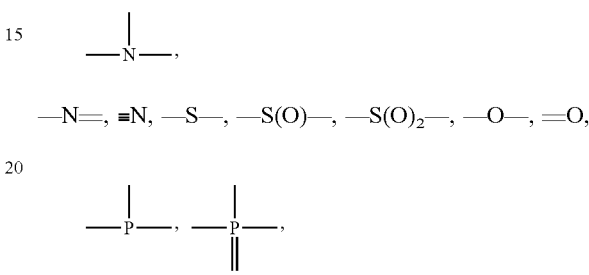

—Se—, and —Se(O)—.

In some embodiments, R$^5$ is an optionally substituted bivalent C$_{1-20}$ aliphatic or C$_{1-20}$ heteroaliphatic group. In some embodiments, R$^{15}$ is an optionally substituted bivalent C$_{1-20}$ aliphatic or C$_{1-20}$ heteroaliphatic group, wherein 1-6 methylene units are optionally and independently replaced by —O—, —N(R')—, —S—, —C(O)—, —OC(O)—, —C(O)O—, —OC(O)O—, —C(S)—, —OC(S)—, —SC(O)—, —SC(S)—, —S(O)—, —S(O)$_2$—, —OS(O)$_2$O—, —N(R')C(O)—, —C(O)N(R')—, —N(R')C(O)O—, —OC(O)N(R')—, —N(R')C(O)N(R')—, —P(R$^x$)—, —P(O)(R$^x$)—, or -Cy$^1$-. In some embodiments, a methylene unit is replaced by —O—. In some embodiments, a methylene unit is replaced by —N(R')—. In some embodiments, a methylene unit is replaced by —S—. In some embodiments, a methylene unit is replaced by —C(O)—. In some embodiments, a methylene unit is replaced by —OC(O)—. In some embodiments, a methylene unit is replaced by —C(O)O—. In some embodiments, a methylene unit is replaced by —OC(O)O—. In some embodiments, a methylene unit is replaced by —C(S)—. In some embodiments, a methylene unit is replaced by —OC(S)—. In some embodiments, a methylene unit is replaced by —SC(O)—. In some embodiments, a methylene unit is replaced by —SC(S)—. In some embodiments, a methylene unit is replaced by —S(O)—. In some embodiments, a methylene unit is replaced by —S(O)$_2$—. In some embodiments, a methylene unit is replaced by —OS(O)$_2$O—. In some embodiments, a methylene unit is replaced by —N(R')C(O)—. In some embodiments, a methylene unit is replaced by —C(O)N(R')—. In some embodiments, a methylene unit is replaced by —N(R')C(O)O—. In some embodiments, a methylene unit is replaced by —OC(O)N(R')—. In some embodiments, a methylene unit is replaced by —N(R')C(O)N(R')—. In some embodiments, a methylene unit is replaced by —P(R$^x$)—. In some embodiments, a methylene unit is replaced by —P(O)(R$^x$)—.

In some embodiments, a methylene unit is replaced by -Cy$^1$-. In some embodiments, a methylene unit is replaced with an optionally substituted phenylene. In some embodiments, a methylene unit is replaced with an optionally substituted 3-8 membered saturated or partially unsaturated carbocyclylene. In some embodiments, a methylene unit is replaced with an optionally substituted 5-6 membered heteroarylene having 1-4 heteroatoms independently selected from nitrogen, oxygen, or sulfur. In some embodiments, a methylene unit is replaced with an optionally substituted 3-8 membered saturated or partially unsaturated heterocyclylene having 1-4 heteroatoms independently selected from nitrogen, oxygen, or sulfur. In some embodiments, a methylene unit is replaced with an optionally substituted 8-14 membered arylene. In some embodiments, a methylene unit is replaced with an optionally substituted 7-14 membered saturated or partially unsaturated carbocyclylene. In some embodiments, a methylene unit is replaced with an optionally substituted 8-14 membered heteroarylene having 1-5 heteroatoms independently selected from nitrogen, oxygen, or sulfur. In some embodiments, a methylene unit is replaced with an optionally substituted 7-14 membered saturated or partially unsaturated heterocyclylene having 1-5 heteroatoms selected from nitrogen, oxygen, or sulfur.

In some embodiments, -$Cy^1$- is a bivalent optionally substituted monocyclic ring.

In certain embodiments, -$Cy^1$- is bivalent optionally substituted phenylene.

In certain embodiments, -$Cy^1$- is a bivalent optionally substituted 3-8 membered saturated carbocyclylene. In certain embodiments, -$Cy^1$- is a bivalent optionally substituted 3-8 membered partially unsaturated carbocyclylene. In certain embodiments, -$Cy^1$- is a bivalent optionally substituted 5-6 membered saturated carbocyclylene. In certain embodiments, -$Cy^1$- is a bivalent optionally substituted 5-6 membered partially unsaturated carbocyclylene.

In certain embodiments, -$Cy^1$- is a bivalent optionally substituted 5-membered heteroarylene having 1-4 heteroatoms independently selected from nitrogen, oxygen, or sulfur.

In certain embodiments, -$Cy^1$- is a bivalent optionally substituted 5-membered heteroarylene having 1-2 heteroatoms independently selected from nitrogen, oxygen, or sulfur. In certain embodiments, -$Cy^1$- is a bivalent optionally substituted 6-membered heteroarylene having 1-4 heteroatoms independently selected from nitrogen, oxygen, or sulfur. In certain embodiments, -$Cy^1$- is a bivalent optionally substituted 6-membered heteroarylene having 1-2 heteroatoms independently selected from nitrogen, oxygen, or sulfur.

In certain embodiments, -$Cy^1$- is a bivalent optionally substituted 3-8 membered saturated heterocyclylene having 1-4 heteroatoms independently selected from nitrogen, oxygen, or sulfur. In certain embodiments, -$Cy^1$- is a bivalent optionally substituted 3-8 membered saturated heterocyclylene having 1-2 heteroatoms independently selected from nitrogen, oxygen, or sulfur. In certain embodiments, -$Cy^1$- is a bivalent optionally substituted 5-6 membered saturated heterocyclylene having 1-4 heteroatoms independently selected from nitrogen, oxygen, or sulfur. In certain embodiments, -$Cy^1$- is a bivalent optionally substituted 5-6 membered saturated heterocyclylene having 1-2 heteroatoms independently selected from nitrogen, oxygen, or sulfur. In certain embodiments, -$Cy^1$- is a bivalent optionally substituted 5-membered saturated heterocyclylene having 1-2 heteroatoms independently selected from nitrogen, oxygen, or sulfur. In certain embodiments, -$Cy^1$- is a bivalent optionally substituted 6-membered saturated heterocyclylene having 1-2 heteroatoms independently selected from nitrogen, oxygen, or sulfur.

In certain embodiments, -$Cy^1$- is a bivalent optionally substituted 3-8 membered unsaturated heterocyclylene having 1-4 heteroatoms independently selected from nitrogen, oxygen, or sulfur. In certain embodiments, -$Cy^1$- is a bivalent optionally substituted 3-8 membered unsaturated heterocyclylene having 1-2 heteroatoms independently selected from nitrogen, oxygen, or sulfur. In certain embodiments, -$Cy^1$- is a bivalent optionally substituted 5-6 membered unsaturated heterocyclylene having 1-4 heteroatoms independently selected from nitrogen, oxygen, or sulfur. In certain embodiments, -$Cy^1$- is a bivalent optionally substituted 5-6 membered unsaturated heterocyclylene having 1-2 heteroatoms independently selected from nitrogen, oxygen, or sulfur. In certain embodiments, -$Cy^1$- is a bivalent optionally substituted 5-membered unsaturated heterocyclylene having 1-2 heteroatoms independently selected from nitrogen, oxygen, or sulfur. In certain embodiments, -$Cy^1$- is a bivalent optionally substituted 6-membered unsaturated heterocyclylene having 1-2 heteroatoms independently selected from nitrogen, oxygen, or sulfur.

In some embodiments, -$Cy^1$- is a bivalent optionally substituted naphthylene. In some embodiments, -$Cy^1$- is a bivalent optionally substituted 10-14 membered tricyclic aryl ring. In some embodiments, -$Cy^1$- is a bivalent optionally substituted 10-membered tricyclic aryl ring. In some embodiments, -$Cy^1$- is a bivalent optionally substituted 11-membered tricyclic aryl ring. In some embodiments, -$Cy^1$- is a bivalent optionally substituted 12-membered tricyclic aryl ring. In some embodiments, -$Cy^1$- is a bivalent optionally substituted 13-membered tricyclic aryl ring. In some embodiments, -$Cy^1$- is a bivalent optionally substituted 14-membered tricyclic aryl ring.

In some embodiments, -$Cy^1$- is a bivalent optionally substituted bicyclic or polycyclic 7-14 membered saturated carbocyclylene. In some embodiments, -$Cy^1$- is a bivalent optionally substituted bicyclic 7-10 membered saturated carbocyclylene. In some embodiments, -$Cy^1$- is a bivalent optionally substituted bicyclic 7-membered saturated carbocyclylene. In some embodiments, -$Cy^1$- is a bivalent optionally substituted bicyclic 8-membered saturated carbocyclylene. In some embodiments, -$Cy^1$- is a bivalent optionally substituted bicyclic 9-membered saturated carbocyclylene. In some embodiments, -$Cy^1$- is a bivalent optionally substituted bicyclic 10-membered saturated carbocyclylene. In some embodiments, -$Cy^1$- is a bivalent optionally substituted tricyclic 7-14 membered saturated carbocyclylene.

In some embodiments, -$Cy^1$- is a bivalent optionally substituted bicyclic or polycyclic 7-14 membered partially unsaturated carbocyclylene. In some embodiments, -$Cy^1$- is a bivalent optionally substituted bicyclic 7-10 membered partially unsaturated carbocyclylene. In some embodiments, -$Cy^1$- is a bivalent optionally substituted bicyclic 7-membered partially unsaturated carbocyclylene. In some embodiments, -$Cy^1$- is a bivalent optionally substituted bicyclic 8-membered partially unsaturated carbocyclylene. In some embodiments, -$Cy^1$- is a bivalent optionally substituted bicyclic 9-membered partially unsaturated carbocyclylene. In some embodiments, -$Cy^1$- is a bivalent optionally substituted bicyclic 10-membered partially unsaturated carbocyclylene. In some embodiments, -$Cy^1$- is a bivalent optionally substituted tricyclic 7-14 membered partially unsaturated carbocyclylene.

In some embodiments, -$Cy^1$- is a bivalent optionally substituted bicyclic or tricyclic 8-14 membered heteroarylene having 1-5 heteroatoms independently selected from nitrogen, oxygen, or sulfur. In some embodiments, -$Cy^1$- is a bivalent optionally substituted bicyclic 8-10 membered heteroarylene having 1-5 heteroatoms independently selected from nitrogen, oxygen, or sulfur. In some embodiments, -Cy$^1$- is a bivalent optionally substituted bicyclic 8-10 membered heteroarylene having 1-2 heteroatoms independently selected from nitrogen, oxygen, or sulfur. In some embodiments, -Cy$^1$- is a bivalent optionally substituted bicyclic 8-membered heteroarylene having 1-5 heteroatoms independently selected from nitrogen, oxygen, or sulfur. In some embodiments, -Cy$^1$- is a bivalent optionally substituted bicyclic 8-membered heteroarylene having 1-2 heteroatoms independently selected from nitrogen, oxygen, or sulfur. In some embodiments, -Cy$^1$- is a bivalent optionally substituted bicyclic 9-membered heteroarylene having 1-5 heteroatoms independently selected from nitrogen, oxygen, or sulfur. In some embodiments, -Cy$^1$- is a bivalent optionally substituted bicyclic 9-membered heteroarylene having 1-2 heteroatoms independently selected from nitrogen, oxygen, or sulfur. In some embodiments, -Cy$^1$- is a bivalent optionally substituted bicyclic 10-membered heteroarylene having 1-5 heteroatoms independently selected from nitrogen, oxygen, or sulfur. In some embodiments, -Cy$^1$- is a bivalent optionally substituted bicyclic 10-membered heteroarylene having 1-2 heteroatoms independently selected from nitrogen, oxygen, or sulfur. In some embodiments, -Cy$^1$- is a bivalent optionally substituted tricyclic 10-14 membered heteroarylene having 1-5 heteroatoms independently selected from nitrogen, oxygen, or sulfur. In some embodiments, -Cy$^1$- is a bivalent optionally substituted tricyclic 10-membered heteroarylene having 1-5 heteroatoms independently selected from nitrogen, oxygen, or sulfur. In some embodiments, -Cy$^1$- is a bivalent optionally substituted tricyclic 10-membered heteroarylene having 1-5 heteroatoms independently selected from nitrogen, oxygen, or sulfur. In some embodiments, -Cy$^1$- is a bivalent optionally substituted tricyclic 11-membered heteroarylene having 1-5 heteroatoms independently selected from nitrogen, oxygen, or sulfur. In some embodiments, -Cy$^1$- is a bivalent optionally substituted tricyclic 12-membered heteroarylene having 1-5 heteroatoms independently selected from nitrogen, oxygen, or sulfur. In some embodiments, -Cy$^1$- is a bivalent optionally substituted tricyclic 13-membered heteroarylene having 1-5 heteroatoms independently selected from nitrogen, oxygen, or sulfur. In some embodiments, -Cy$^1$- is a bivalent optionally substituted 14-membered tricyclic aryl ring.

In some embodiments, -Cy$^1$- is a bivalent optionally substituted bicyclic or polycyclic 7-14 membered saturated heterocyclylene having 1-5 heteroatoms selected from nitrogen, oxygen, or sulfur. In some embodiments, -Cy$^1$- is a bivalent optionally substituted bicyclic or tricyclic 7-14 membered saturated heterocyclylene having 1-5 heteroatoms selected from nitrogen, oxygen, or sulfur. In some embodiments, -Cy$^1$- is a bivalent optionally substituted bicyclic 7-10 membered saturated heterocyclylene having 1-5 heteroatoms selected from nitrogen, oxygen, or sulfur. In some embodiments, -Cy$^1$- is a bivalent optionally substituted bicyclic 7-10 membered saturated heterocyclylene having 1-2 heteroatoms selected from nitrogen, oxygen, or sulfur. In some embodiments, -Cy$^1$- is a bivalent optionally substituted bicyclic 7-membered saturated heterocyclylene having 1-5 heteroatoms selected from nitrogen, oxygen, or sulfur. In some embodiments, -Cy$^1$- is a bivalent optionally substituted bicyclic 7-membered saturated heterocyclylene having 1-2 heteroatoms selected from nitrogen, oxygen, or sulfur. In some embodiments, -Cy$^1$- is a bivalent optionally substituted bicyclic 8-membered saturated heterocyclylene having 1-5 heteroatoms selected from nitrogen, oxygen, or sulfur. In some embodiments, -Cy$^1$- is a bivalent optionally substituted bicyclic 8-membered saturated heterocyclylene having 1-2 heteroatoms selected from nitrogen, oxygen, or sulfur. In some embodiments, -Cy$^1$- is a bivalent optionally substituted bicyclic 9-membered saturated heterocyclylene having 1-5 heteroatoms selected from nitrogen, oxygen, or sulfur. In some embodiments, -Cy$^1$- is a bivalent optionally substituted bicyclic 9-membered saturated heterocyclylene having 1-2 heteroatoms selected from nitrogen, oxygen, or sulfur. In some embodiments, -Cy$^1$- is a bivalent optionally substituted bicyclic 10-membered saturated heterocyclylene having 1-5 heteroatoms selected from nitrogen, oxygen, or sulfur. In some embodiments, -Cy$^1$- is a bivalent optionally substituted bicyclic 10-membered saturated heterocyclylene having 1-2 heteroatoms selected from nitrogen, oxygen, or sulfur. In some embodiments, -Cy$^1$- is a bivalent optionally substituted tricyclic 7-14 membered saturated heterocyclylene having 1-5 heteroatoms selected from nitrogen, oxygen, or sulfur.

In some embodiments, -Cy$^1$- is a bivalent optionally substituted bicyclic or polycyclic 7-14 membered partially unsaturated heterocyclylene having 1-5 heteroatoms selected from nitrogen, oxygen, or sulfur. In some embodiments, -Cy$^1$- is a bivalent optionally substituted bicyclic or tricyclic 7-14 membered partially unsaturated heterocyclylene having 1-5 heteroatoms selected from nitrogen, oxygen, or sulfur. In some embodiments, -Cy$^1$- is a bivalent optionally substituted bicyclic 7-10 membered partially unsaturated heterocyclylene having 1-5 heteroatoms selected from nitrogen, oxygen, or sulfur. In some embodiments, -Cy$^1$- is a bivalent optionally substituted bicyclic 7-10 membered partially unsaturated heterocyclylene having 1-2 heteroatoms selected from nitrogen, oxygen, or sulfur. In some embodiments, -Cy$^1$- is a bivalent optionally substituted bicyclic 7-membered partially unsaturated heterocyclylene having 1-5 heteroatoms selected from nitrogen, oxygen, or sulfur. In some embodiments, -Cy$^1$- is a bivalent optionally substituted bicyclic 7-membered partially unsaturated heterocyclylene having 1-2 heteroatoms selected from nitrogen, oxygen, or sulfur. In some embodiments, -Cy$^1$- is a bivalent optionally substituted bicyclic 8-membered partially unsaturated heterocyclylene having 1-5 heteroatoms selected from nitrogen, oxygen, or sulfur. In some embodiments, -Cy$^1$- is a bivalent optionally substituted bicyclic 8-membered partially unsaturated heterocyclylene having 1-2 heteroatoms selected from nitrogen, oxygen, or sulfur. In some embodiments, -Cy$^1$- is a bivalent optionally substituted bicyclic 9-membered partially unsaturated heterocyclylene having 1-5 heteroatoms selected from nitrogen, oxygen, or sulfur. In some embodiments, -Cy$^1$- is a bivalent optionally substituted bicyclic 9-membered partially unsaturated heterocyclylene having 1-2 heteroatoms selected from nitrogen, oxygen, or sulfur. In some embodiments, -Cy$^1$- is a bivalent optionally substituted bicyclic 10-membered partially unsaturated heterocyclylene having 1-5 heteroatoms selected from nitrogen, oxygen, or sulfur. In some embodiments, -Cy$^1$- is a bivalent optionally substituted bicyclic 10-membered partially unsaturated heterocyclylene having 1-2 heteroatoms selected from nitrogen, oxygen, or sulfur. In some embodiments, -Cy$^1$- is a bivalent optionally substituted tricyclic 7-14 membered partially unsaturated heterocyclylene having 1-5 heteroatoms selected from nitrogen, oxygen, or sulfur.

As generally defined above, L is a neutral ligand.

In some embodiments, L is a neutral phosphorus-containing ligand, wherein L is bonded to M through a phosphorus atom. In some embodiments, L is a neutral phosphorus-containing ligand, wherein L is bonded to Ru through a phosphorus atom. In some embodiments, L is a phosphine ligand. In some embodiments, L is a phosphite ligand. In some embodiments, L is a phosphoramidite. In some embodiments, L has the structure of P(R$^x$)$_3$, wherein each R$^x$ is independently as defined above and described herein. In some embodiments, L has the structure of P(R)$_3$, wherein each R is independently as defined above and described herein. In some embodiments, L is tricyclohexylphosphine (PCy$_3$). In some embodiments, L is PPh$_3$. In some embodiments, L is P(Oi-Pr)$_3$. In some embodiments, L is P(OTMS)$_3$. In some embodiments, L is P(OMe)$_3$.

In some embodiments, L is R$^8$CN or R$^8$—Z—R$^9$, wherein each of R$^8$, R$^9$ and Z is independently as defined above and described herein. In some embodiments, L is R$^8$CN. In some embodiments, L is R$^8$—Z—R$^9$. In some embodiments, L is R$^8$—Z—R$^9$, wherein Z is —O—, —S—, —Se—, —N(R$^x$)—, or —P(R$^x$)—. In some embodiments, L is R$^8$—Z—R$^9$, wherein Z is —O—. In some embodiments, L is R$^8$—Z—R$^9$, wherein Z is —S—. In some embodiments, L is R$^8$—Z—R$^9$, wherein Z is —Se—. In some embodiments, L is R$^8$—Z—R$^9$, wherein Z is —N(R$^x$)—. In some embodiments, L is R$^8$—Z—R$^9$, wherein Z is —P(R$^x$)—. In some embodiments, L is R$^8$—Z—R$^9$, wherein Z is —C(O)—, —C(S)—, —S(O)— or —Se(O)—, and L is bonded to M through the oxygen atom.

In some embodiments, L is a neutral nitrogen-containing ligand.

In some embodiments, L is a nitrile. In some embodiments, L is a nitrile coordinated to M through the nitrogen atom of the nitrile group. In some embodiments, L is R$^8$—CN. In some embodiments, L is optionally substituted pyridine. In some embodiments, L is pyridine.

In some embodiments, R$^1$ is a nitrile. In some embodiments, R$^1$ is a nitrile coordinated to M through the nitrogen atom of the nitrile group. In some embodiments, R$^1$ is R$^8$—CN.

Exemplary suitable L ligands are extensively known and used in the art, including but not limited to those described in de Fremont, P. et al, *Coordination Chemistry Reviews* 253 (2009), 862-892, Colacino, E. et al, *Coordination Chemistry Reviews* 251 (2007), 726-764, Herrmann, W. A., *Angew. Chem. Int. Ed.* 2002, 41, 1290-1309, Samojlowicz, C.; Bieniek, M.; Grela, K. Ruthenium-based olefin metathesis catalysts bearing N-heterocyclic carbene ligands, *Chem. Rev.* 2009, 109, 3708- 3742, Vougioukalakis, G. C.; Grubbs, R. H. Ruthenium-based heterocyclic carbene-coordinated olefin metathesis catalysts, *Chem. Rev.* 2010, 110, 1746-1787, and Lozano-Vila, A. M.; Monsaert, S.; Bajek, A.; Verpoort, F. *Chem. Rev.* 2010, 110, 4865-4909.

In some embodiments, a compound of formula I has the structure of formula I-c:

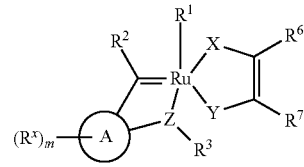

wherein each variable is independently as defined above and described herein. In some embodiments, a compound of formula I has the structure of:

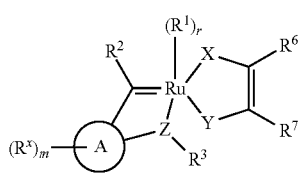

wherein each variable is independently as defined above and described herein.

In some embodiments, a compound of formula I has the structure of formula I-c':

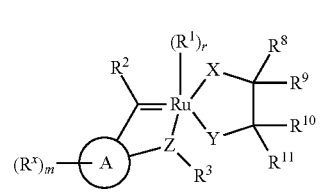

wherein each variable is independently as defined above and described herein. In some embodiments, a compound of formula I has the structure:

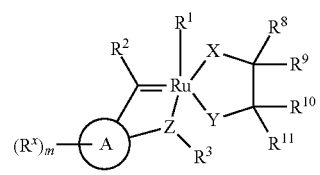

wherein each variable is independently as defined above and described herein.

In some embodiments, a compound of formula I has the structure of formula I-d:

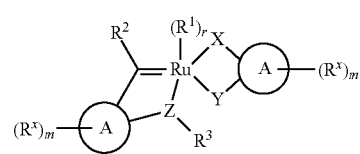

wherein each variable is independently as defined above and described herein. In some embodiments, a compound of formula I has the structure:

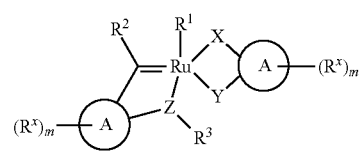

wherein each variable is independently as defined above and described herein.

In some embodiments, a compound of formula I has the structure of formula I-e:

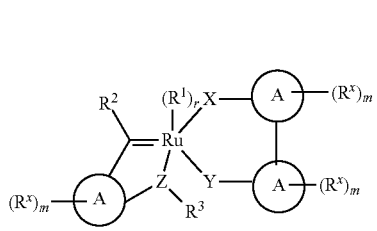

I-e wherein each variable is independently as defined above and described herein. In some embodiments, a compound of formula I has the structure of:

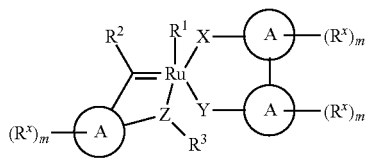

wherein each variable is independently as defined above and described herein. In some embodiments,

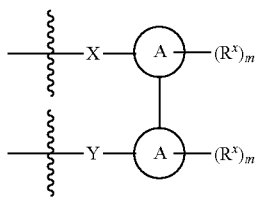

is optionally substituted

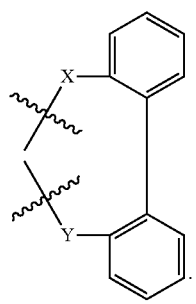

In some embodiments,

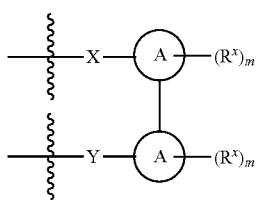

is optionally substituted

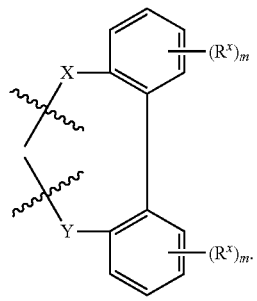

In some embodiments,

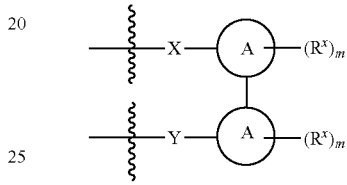

is optionally substituted

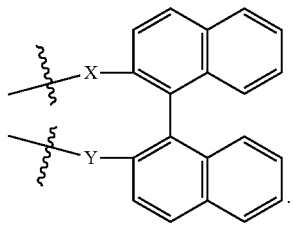

In some embodiments,

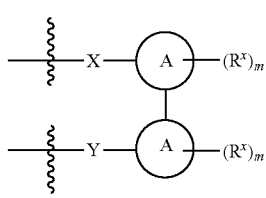

is optionally substituted

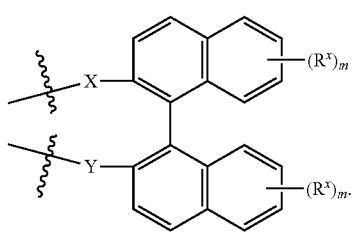

In some embodiments, a compound of formula I has the structure of formula I-f:

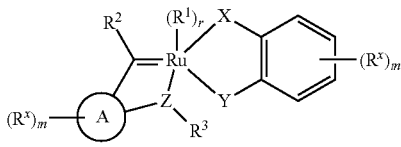

wherein each variable is independently as defined above and described herein. In some embodiments, a compound of formula I has the structure:

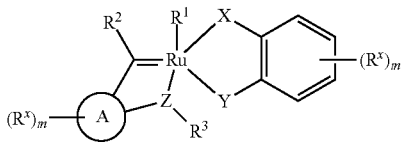

wherein each variable is independently as defined above and described herein.

In some embodiments, a compound of formula I has the structure of formula I-g:

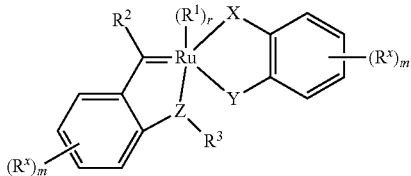

wherein each variable is independently as defined above and described herein. In some embodiments, a compound of formula I has the structure of:

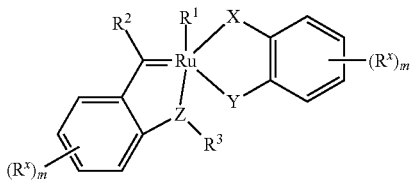

wherein each variable is independently as defined above and described herein.

As generally defined above, each of $R^6$ and $R^7$ is independently R, —CN, halogen, —OR, —OC(O)R, —OSi(R)$_3$, —SR, —S(O)R, —S(O)$_2$R, —NO$_2$, —N(R')$_2$, —NR'C(O)R, —NR'C(O)OR, —NR'C(O)N(R')$_2$, —NR'SO$_2$R, —NR'SO$_2$N(R')$_2$, —NR'OR, —SeR, —Si(R)$_3$, or:

R$^6$ and R$^7$ are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur.

In some embodiments, $R^6$ is R, wherein R is as defined above and described herein.

In some embodiments, $R^6$ is hydrogen.

In some embodiments, $R^6$ is optionally substituted $C_{1-20}$ aliphatic. In some embodiments, $R^6$ is optionally substituted $C_{1-20}$ heteroaliphatic.

In some embodiments, $R^6$ is optionally substituted phenyl. In some embodiments, $R^6$ is phenyl. In some embodiments, $R^6$ is substituted phenyl.

In some embodiments, $R^6$ is an optionally substituted 3-7 membered saturated or partially unsaturated carbocyclic ring. In some embodiments, $R^6$ is optionally substituted cyclohexyl. In some embodiments, $R^6$ is cyclohexyl.

In some embodiments, $R^6$ is an optionally substituted 8-10 membered bicyclic saturated, partially unsaturated or aryl ring. In some embodiments, $R^6$ is an optionally substituted 8-10 membered bicyclic saturated ring. In some embodiments, $R^6$ is an optionally substituted 8-10 membered bicyclic partially unsaturated ring. In some embodiments, $R^6$ is an optionally substituted 8-10 membered bicyclic aryl ring. In some embodiments, $R^6$ is optionally substituted naphthyl. In some embodiments, $R^6$ is naphthyl. In some embodiments, $R^6$ is optionally substituted anthracenyl. In some embodiments, $R^6$ is anthracenyl.

In some embodiments, $R^6$ is an optionally substituted 5-6 membered monocyclic heteroaryl ring having 1-4 heteroatoms independently selected from nitrogen, oxygen, or sulfur. In some embodiments, $R^6$ is an optionally substituted 3-7 membered saturated or partially unsaturated heterocyclic ring having 1-3 heteroatoms independently selected from nitrogen, oxygen, or sulfur. In some embodiments, $R^6$ is an optionally substituted 7-10 membered bicyclic saturated or partially unsaturated heterocyclic ring having 1-5 heteroatoms independently selected from nitrogen, oxygen, or sulfur. In some embodiments, $R^6$ is an optionally substituted 8-10 membered bicyclic heteroaryl ring having 1-5 heteroatoms independently selected from nitrogen, oxygen, or sulfur.

In some embodiments, $R^6$ is —CN. In some embodiments, $R^6$ is halogen. In some embodiments, $R^6$ is —F. In some embodiments, $R^6$ is —Cl. In some embodiments, $R^6$ is —Br. In some embodiments, $R^6$ is —I.

In some embodiments, $R^6$ is —OR. In some embodiments, $R^6$ is —OC(O)R. In some embodiments, $R^6$ is —OSi(R)$_3$. In some embodiments, $R^6$ is —SR. In some embodiments, $R^6$ is —S(O)R. In some embodiments, $R^6$ is —S(O)$_2$R. In some embodiments, $R^6$ is —NO$_2$. In some embodiments, $R^6$ is —N(R')$_2$. In some embodiments, $R^6$ is —N(R')C(O)R. In some embodiments, $R^6$ is —N(R')C(O)OR. In some embodiments, $R^6$ is —N(R')C(O)N(R')$_2$. In some embodiments, $R^6$ is —N(R')SO$_2$R. In some embodiments, $R^6$ is —N(R')SO$_2$N(R')$_2$. In some embodiments, $R^6$ is —NR'OR. In some embodiments, $R^6$ is —SeR. In some embodiments, $R^6$ is —Si(R)$_3$.

In some embodiments, $R^7$ is R, wherein R is as defined above and described herein.

In some embodiments, $R^7$ is hydrogen.

In some embodiments, $R^7$ is optionally substituted $C_{1-20}$ aliphatic. In some embodiments, $R^7$ is optionally substituted $C_{1-20}$ heteroaliphatic.

In some embodiments, $R^7$ is optionally substituted phenyl. In some embodiments, $R^7$ is phenyl. In some embodiments, $R^7$ is substituted phenyl.

In some embodiments, $R^7$ is an optionally substituted 3-7 membered saturated or partially unsaturated carbocyclic ring. In some embodiments, $R^7$ is optionally substituted cyclohexyl. In some embodiments, $R^7$ is cyclohexyl.

In some embodiments, $R^7$ is an optionally substituted 8-10 membered bicyclic saturated, partially unsaturated or aryl ring. In some embodiments, $R^7$ is an optionally substituted 8-10 membered bicyclic saturated ring. In some embodiments, $R^7$ is an optionally substituted 8-10 membered bicyclic partially unsaturated ring. In some embodiments, $R^7$ is an optionally substituted 8-10 membered bicyclic aryl ring. In some embodiments, $R^7$ is optionally substituted naphthyl. In some embodiments, $R^7$ is naphthyl. In some embodiments, $R^7$ is optionally substituted anthracenyl. In some embodiments, $R^7$ is anthracenyl.

In some embodiments, $R^7$ is an optionally substituted 5-6 membered monocyclic heteroaryl ring having 1-4 heteroatoms independently selected from nitrogen, oxygen, or sulfur. In some embodiments, $R^7$ is an optionally substituted 3-7 membered saturated or partially unsaturated heterocyclic ring having 1-3 heteroatoms independently selected from nitrogen, oxygen, or sulfur. In some embodiments, $R^7$ is an optionally substituted 7-10 membered bicyclic saturated or partially unsaturated heterocyclic ring having 1-5 heteroatoms independently selected from nitrogen, oxygen, or sulfur. In some embodiments, $R^7$ is an optionally substituted 8-10 membered bicyclic heteroaryl ring having 1-5 heteroatoms independently selected from nitrogen, oxygen, or sulfur.

In some embodiments, $R^7$ is —CN. In some embodiments, $R^7$ is halogen. In some embodiments, $R^7$ is —F. In some embodiments, $R^7$ is —Cl. In some embodiments, $R^7$ is —Br. In some embodiments, $R^7$ is —I.

In some embodiments, $R^7$ is —OR. In some embodiments, $R^7$ is —OC(O)R. In some embodiments, $R^7$ is —OSi(R)$_3$. In some embodiments, $R^7$ is —SR. In some embodiments, $R^7$ is —S(O)R. In some embodiments, $R^7$ is —S(O)$_2$R. In some embodiments, $R^7$ is —NO$_2$. In some embodiments, $R^7$ is —N(R')$_2$. In some embodiments, $R^7$ is —N(R')C(O)R. In some embodiments, $R^7$ is —N(R')C(O)OR. In some embodiments, $R^7$ is —N(R')C(O)N(R')$_2$. In some embodiments, $R^7$ is —N(R')SO$_2$R. In some embodiments, $R^7$ is —N(R')SO$_2$N(R')$_2$. In some embodiments, $R^7$ is —NR'OR. In some embodiments, $R^7$ is —SeR. In some embodiments, $R^7$ is —Si(R)$_3$.

In some embodiments, both $R^6$ and $R^7$ are —CN.

In some embodiments, $R^6$ and $R^7$ are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur. In some embodiments, $R^6$ and $R^7$ are optionally taken together with their intervening atoms to form an optionally substituted 3-10 membered saturated monocyclic or bicyclic ring having 0-4 heteroatoms independently selected from nitrogen, oxygen, or sulfur. In some embodiments, $R^6$ and $R^7$ are optionally taken together with their intervening atoms to form an optionally substituted 3-10 membered partially unsaturated monocyclic or bicyclic ring having 0-4 heteroatoms independently selected from nitrogen, oxygen, or sulfur.

In some embodiments, $R^6$ and $R^7$ are taken together with their intervening atoms to form an optionally substituted 5-6 membered monocyclic heteroaryl ring having 1-4 heteroatoms independently selected from nitrogen, oxygen, or sulfur.

In some embodiments, $R^6$ and $R^7$ are taken together with their intervening atoms to form optionally substituted phenyl. In some embodiments, $R^6$ and $R^7$ are taken together with their intervening atoms to form substituted phenyl. In some embodiments, $R^6$ and $R^7$ are taken together with their intervening atoms to form unsubstituted phenyl. In some embodiments, $R^6$ and $R^7$ are taken together with their intervening atoms to form substituted phenyl, wherein at least one substituent on the phenyl ring is electron-withdrawing. In some embodiments, $R^6$ and $R^7$ are taken together with their intervening atoms to form substituted phenyl, wherein at least one substituent on the phenyl ring is —F. In some embodiments, $R^6$ and $R^7$ are taken together with their intervening atoms to form substituted phenyl, wherein each substituent on the phenyl ring is —F. In some embodiments, $R^6$ and $R^7$ are taken together with their intervening atoms to form substituted phenyl, wherein each hydrogen atom on the phenyl ring is substituted with —F.

In some embodiments, $R^6$ and $R^7$ are taken together with their intervening atoms to form an optionally substituted 8-10 membered bicyclic aryl ring having 0-4 heteroatoms independently selected from nitrogen, oxygen, or sulfur. In some embodiments, $R^6$ and $R^7$ are taken together with their intervening atoms to form an optionally substituted naphthyl ring. In some embodiments, $R^6$ and $R^7$ are taken together with their intervening atoms to form an optionally substituted 8-10 membered bicyclic heteroaryl ring having 1-4 heteroatoms independently selected from oxygen, nitrogen or sulfur. In some embodiments, $R^6$ and $R^7$ are taken together with their intervening atoms to form an optionally substituted 8-membered bicyclic heteroaryl ring having 1-4 heteroatoms independently selected from oxygen, nitrogen or sulfur. In some embodiments, $R^6$ and $R^7$ are taken together with their intervening atoms to form an optionally substituted 9-membered bicyclic heteroaryl ring having 1-4 heteroatoms independently selected from oxygen, nitrogen or sulfur. In some embodiments, $R^6$ and $R^7$ are taken together with their intervening atoms to form an optionally substituted 10-membered bicyclic heteroaryl ring having 1-4 heteroatoms independently selected from oxygen, nitrogen or sulfur.

As generally defined above, each of $R^8$, $R^9$, $R^{10}$, $R^{11}$, $R^{12}$, and $R^{13}$ is independently $R^x$, or
one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ on the same atom to form an =C($R^x$)$_2$, =N($R^x$), =P($R^x$), =O, =S, or =Se group; or
one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ on an adjacent atom to form a double bond; or
one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms.

In some embodiments, $R^8$ is $R^x$, wherein $R^x$ is as defined above and described herein. In some embodiments, one $R^8$ is taken together with another $R^8$ or $R^9$, $R^{10}$, $R^{11}$, $R^{12}$, or $R^{13}$ on the same atom to form an =C($R^x$)$_2$, =N($R^x$), =P($R^x$), =O, =S, or =Se group. In some embodiments, one $R^8$ is taken together with another $R^8$ or $R^9$, $R^{10}$, $R^{11}$, $R^{12}$, or $R^{13}$ on an adjacent atom to form a double bond. In some embodiments, one $R^8$ is taken together with another $R^8$ or $R^9$, $R^{10}$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms. In some embodiments, a moiety or compound has more than one $R^8$, wherein at least one $R^8$ is $R^x$, and at least one $R^8$ is taken together with another $R^8$ or $R^9$, $R^{10}$, $R^{11}$, $R^{12}$, or $R^{13}$ on the same atom to form an =C($R^x$)$_2$, =N($R^x$), =P($R^x$), =O, =S, or =Se group, or at least one $R^8$ is taken together with another $R^8$ or $R^9$, $R^{10}$, $R^{11}$, $R^{12}$, or $R^{13}$ on an adjacent atom to form a double bond, or one $R^8$ is taken together with another $R^8$ or $R^9$, $R^{10}$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms.

In some embodiments, $R^8$ is R, wherein R is as defined above and described herein. Exemplary embodiments of $R^8$ include but are not limited to those described for R.

In some embodiments, $R^8$ is hydrogen.

In some embodiments, $R^8$ is optionally substituted $C_{1-20}$ aliphatic. In some embodiments, $R^8$ is —$(CH_2)_3CH$=$CH_2$, —$(CH_2)_4CH$=$CH_2$, —$(CH_2)_6CH$=$CH_2$, —$(CH_2)_2O(t\text{-}BuSi(CH_3)_2)$, —$(CH_2)_2OSi(CH_3)_3$, —$(CH_2)_3OSi(CH_3)_3$, —$(CH_2)_6OSi(CH_3)_3$, —$(CH_2)_2C(CH_3)_2OSi(CH_3)_3$, —$CH_2CH_2(CF_2)_5CF_3$, —$CH(CH_3)COEt$, —$(CH_2)_5CN$, —$(CH_2)_2OH$, —$(CH_2)_2OCH_3$, —$CH_2Mes$, —$(CH_2)_3OH$, —$(CH_2)_6OH$, —$(CH_2)_2C(CH_3)_2OH$, adamantyl, MeAd, t-Bu, cyclohexyl, —$(CH_2)_7CH_3$, —$CH_3$, —$CH_2CH_3$, or isopinocampheyl. In some embodiments, $R^8$ is isopropyl. In some embodiments, $R^8$ is 1-phenylethyl. In some embodiments, $R^8$ is 1-naphthylethyl. In some embodiments, $R^8$ is cyclohexyl. In some embodiments, $R^8$ is adamantyl. In some embodiments, $R^8$ is isopinocampheyl.

In some embodiments, $R^8$ is optionally substituted $C_{1-20}$ heteroaliphatic.

Exemplary $R^8$ include but are not limited to —$(CH_2)_2O$ $(t\text{-}BuSi(CH_3)_2)$, —$(CH_2)_2OSi(CH_3)_3$, —$(CH_2)_3OSi(CH_3)_3$, —$(CH_2)_6OSi(CH_3)_3$, —$(CH_2)_2C(CH_3)_2OSi(CH_3)_3$, —$CH(CH_3)COEt$, —$(CH_2)_5CN$, —$(CH_2)_2OH$, —$(CH_2)_2OCH_3$, —$(CH_2)_3OH$, —$(CH_2)_6OH$, or —$(CH_2)_2C(CH_3)_2OH$.

In some embodiments, $R^8$ is optionally substituted phenyl. In some embodiments, $R^8$ is phenyl. In some embodiments, $R^8$ is substituted phenyl. In some embodiments, $R^8$ is 2,4,6-trimethylphenyl (mesityl). In some embodiments, $R^8$ is 2,4-dimethylphenyl. In some embodiments, $R^8$ is 2,6-dimethylphenyl. In some embodiments, $R^8$ is 2,4-dimethylphenyl. In some embodiments, $R^8$ is 4-methylphenyl. In some embodiments, $R^8$ is 4-chlorophenyl. In some embodiments, $R^8$ is 2,6-diisopropylphenyl. In some embodiments, $R^8$ is 2-methylphenyl. In some embodiments, $R^8$ is 2-isopropylphenyl. In some embodiments, $R^8$ is naphthyl. In some embodiments, $R^8$ is anthracenyl.

In some embodiments, $R^8$ is an optionally substituted 3-7 membered saturated or partially unsaturated carbocyclic ring. In some embodiments, $R^8$ is optionally substituted cyclohexyl. In some embodiments, $R^8$ is cyclohexyl.

In some embodiments, $R^8$ is an optionally substituted 8-10 membered bicyclic saturated, partially unsaturated or aryl ring. In some embodiments, $R^8$ is an optionally substituted 8-10 membered bicyclic saturated ring. In some embodiments, $R^8$ is an optionally substituted 8-10 membered bicyclic partially unsaturated ring. In some embodiments, $R^8$ is an optionally substituted 8-10 membered bicyclic aryl ring. In some embodiments, $R^8$ is optionally substituted naphthyl. In some embodiments, $R^8$ is naphthyl. In some embodiments, $R^8$ is optionally substituted anthracenyl. In some embodiments, $R^8$ is anthracenyl.

In some embodiments, $R^8$ is an optionally substituted 5-6 membered monocyclic heteroaryl ring having 1-4 heteroatoms independently selected from nitrogen, oxygen, or sulfur. In some embodiments, $R^8$ is an optionally substituted 3-7 membered saturated or partially unsaturated heterocyclic ring having 1-3 heteroatoms independently selected from nitrogen, oxygen, or sulfur. In some embodiments, $R^8$ is an optionally substituted 7-10 membered bicyclic saturated or partially unsaturated heterocyclic ring having 1-5 heteroatoms independently selected from nitrogen, oxygen, or sulfur. In some embodiments, $R^8$ is an optionally substituted 8-10 membered bicyclic heteroaryl ring having 1-5 heteroatoms independently selected from nitrogen, oxygen, or sulfur.

In some embodiments, $R^9$ is $R^x$, wherein $R^x$ is as defined above and described herein. In some embodiments, one $R^9$ is taken together with another $R^9$ or $R^8$, $R^{10}$, $R^{11}$, $R^{12}$, or $R^{13}$ on the same atom to form an =$C(R^x)_2$, =$N(R^x)$, =$P(R^x)$, =O, =S, or =Se group. In some embodiments, one $R^9$ is taken together with another $R^9$ or $R^8$, $R^{10}$, $R^{11}$, $R^{12}$, or $R^{13}$ on an adjacent atom to form a double bond. In some embodiments, one $R^9$ is taken together with another $R^9$ or $R^8$, $R^{10}$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms. In some embodiments, a moiety or compound has more than one $R^9$, wherein at least one $R^9$ is $R^x$, and at least one $R^9$ is taken together with another $R^9$ or $R^8$, $R^{10}$, $R^{11}$, $R^{12}$, or $R^{13}$ on the same atom to form an =$C(R^x)_2$, =$N(R^x)$, =$P(R^x)$, =O, =S, or =Se group, or at least one $R^9$ is taken together with another $R^9$ or $R^8$, $R^{10}$, $R^{11}$, $R^{12}$, or $R^{13}$ on an adjacent atom to form a double bond, or one $R^9$ is taken together with another $R^9$ or $R^8$, $R^{10}$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms. In some embodiments, —Z—$R^9$ is halogen.

In some embodiments, $R^9$ is R, wherein R is as defined above and described herein. In some embodiments, $R^9$ is $R^3$.

In some embodiments, $R^9$ is hydrogen.

In some embodiments, $R^9$ is optionally substituted $C_{1-20}$ aliphatic. In some embodiments, $R^9$ is optionally substituted $C_{1-20}$ heteroaliphatic.

In some embodiments, $R^9$ is optionally substituted phenyl. In some embodiments, $R^9$ is phenyl. In some embodiments, $R^9$ is substituted phenyl.

In some embodiments, $R^9$ is an optionally substituted 3-7 membered saturated or partially unsaturated carbocyclic ring. In some embodiments, $R^9$ is optionally substituted cyclohexyl. In some embodiments, $R^9$ is cyclohexyl.

In some embodiments, $R^9$ is an optionally substituted 8-10 membered bicyclic saturated, partially unsaturated or aryl ring. In some embodiments, $R^9$ is an optionally substituted 8-10 membered bicyclic saturated ring. In some embodiments, $R^9$ is an optionally substituted 8-10 membered bicyclic partially unsaturated ring. In some embodiments, $R^9$ is an optionally substituted 8-10 membered bicyclic aryl ring. In some embodiments, $R^9$ is optionally substituted naphthyl. In some embodiments, $R^9$ is naphthyl. In some embodiments, $R^9$ is optionally substituted anthracenyl. In some embodiments, $R^9$ is anthracenyl.

In some embodiments, $R^9$ is an optionally substituted 5-6 membered monocyclic heteroaryl ring having 1-4 heteroatoms independently selected from nitrogen, oxygen, or sulfur. In some embodiments, $R^9$ is an optionally substituted 3-7 membered saturated or partially unsaturated heterocyclic ring having 1-3 heteroatoms independently selected from nitrogen, oxygen, or sulfur. In some embodiments, $R^9$ is an optionally substituted 7-10 membered bicyclic saturated or partially unsaturated heterocyclic ring having 1-5 heteroatoms independently selected from nitrogen, oxygen, or sulfur. In some embodiments, $R^9$ is an optionally substituted 8-10 membered bicyclic heteroaryl ring having 1-5 heteroatoms independently selected from nitrogen, oxygen, or sulfur.

In some embodiments, $R^9$ is halogen. In some embodiments, $R^9$ is —F. In some embodiments, $R^9$ is —Cl. In some embodiments, $R^9$ is —Br. In some embodiments, $R^9$ is —I.

In some embodiments, $R^9$ is —NO$_2$. In some embodiments, $R^9$ is —CN. In some embodiments, $R^9$ is —OR. In some embodiments, $R^9$ is —SR. In some embodiments, $R^9$ is —N(R')$_2$. In some embodiments, $R^9$ is —C(O)R. In some embodiments, $R^9$ is —C(O)N(R')$_2$. In some embodiments, $R^9$ is —OC(O)N(R')$_2$. In some embodiments, $R^9$ is —N(R')C(O)N(R')$_2$. In some embodiments, $R^9$ is —C(O)OR. In some embodiments, $R^9$ is —OC(O)R. In some embodiments, $R^9$ is —N(R')C(O)R. In some embodiments, $R^9$ is —N(R')C(O)OR. In some embodiments, $R^9$ is —SO$_2$R. In some embodiments, $R^9$ is —N(R')SO$_2$R. In some embodiments, $R^9$ is —SO$_2$N(R')$_2$. In some embodiments, $R^9$ is —P(O)(OR)$_2$.

In some embodiments, $R^{10}$ is $R^x$, wherein $R^x$ is as defined above and described herein. In some embodiments, one $R^{10}$ is taken together with another $R^{10}$ or $R^8$, $R^9$, $R^{11}$, $R^{12}$, or $R^{13}$ on the same atom to form an =C($R^x$)$_2$, =N($R^x$), =P($R^x$), =O, =S, or =Se group. In some embodiments, one $R^{10}$ is taken together with another $R^{10}$ or $R^8$, $R^9$, $R^{11}$, $R^{12}$, or $R^{13}$ on an adjacent atom to form a double bond. In some embodiments, one $R^{10}$ is taken together with another $R^{10}$ or $R^8$, $R^9$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms. In some embodiments, a moiety or compound has more than one $R^{10}$, wherein at least one $R^{10}$ is $R^x$, and at least one $R^{10}$ is taken together with another $R^{10}$ or $R^8$, $R^9$, $R^{11}$, $R^{12}$, or $R^{13}$ on the same atom to form an =C($R^x$)$_2$, =N($R^x$), =P($R^x$), =O, =S, or =Se group, or at least one $R^{10}$ is taken together with another $R^{10}$ or $R^8$, $R^9$, $R^{11}$, $R^{12}$, or $R^{13}$ on an adjacent atom to form a double bond, or one $R^{10}$ is taken together with another $R^{10}$ or $R^8$, $R^9$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms.

In some embodiments, $R^{10}$ is R, wherein R is as defined above and described herein.

In some embodiments, $R^{10}$ is hydrogen.

In some embodiments, $R^{10}$ is optionally substituted $C_{1-20}$ aliphatic. In some embodiments, $R^{10}$ is optionally substituted $C_{1-20}$ heteroaliphatic.

In some embodiments, $R^{10}$ is optionally substituted phenyl. In some embodiments, $R^{10}$ is phenyl. In some embodiments, $R^{10}$ is substituted phenyl.

In some embodiments, $R^{10}$ is an optionally substituted 3-7 membered saturated or partially unsaturated carbocyclic ring. In some embodiments, $R^{10}$ is optionally substituted cyclohexyl. In some embodiments, $R^{10}$ is cyclohexyl.

In some embodiments, $R^{10}$ is an optionally substituted 8-10 membered bicyclic saturated, partially unsaturated or aryl ring. In some embodiments, $R^{10}$ is an optionally substituted 8-10 membered bicyclic saturated ring. In some embodiments, $R^{10}$ is an optionally substituted 8-10 membered bicyclic partially unsaturated ring. In some embodiments, $R^{10}$ is an optionally substituted 8-10 membered bicyclic aryl ring. In some embodiments, $R^{10}$ is optionally substituted naphthyl. In some embodiments, $R^{10}$ is naphthyl. In some embodiments, $R^{10}$ is optionally substituted anthracenyl. In some embodiments, $R^{10}$ is anthracenyl.

In some embodiments, $R^{10}$ is an optionally substituted 5-6 membered monocyclic heteroaryl ring having 1-4 heteroatoms independently selected from nitrogen, oxygen, or sulfur. In some embodiments, $R^{10}$ is an optionally substituted 3-7 membered saturated or partially unsaturated heterocyclic ring having 1-3 heteroatoms independently selected from nitrogen, oxygen, or sulfur. In some embodiments, $R^{10}$ is an optionally substituted 7-10 membered bicyclic saturated or partially unsaturated heterocyclic ring having 1-5 heteroatoms independently selected from nitrogen, oxygen, or sulfur. In some embodiments, $R^{10}$ is an optionally substituted 8-10 membered bicyclic heteroaryl ring having 1-5 heteroatoms independently selected from nitrogen, oxygen, or sulfur.

In some embodiments, $R^{10}$ is halogen. In some embodiments, $R^{10}$ is —F. In some embodiments, $R^{10}$ is —Cl. In some embodiments, $R^{10}$ is —Br. In some embodiments, $R^{10}$ is —I.

In some embodiments, $R^{10}$ is —NO$_2$. In some embodiments, $R^{10}$ is —CN. In some embodiments, $R^{10}$ is —OR. In some embodiments, $R^{10}$ is —SR. In some embodiments, $R^{10}$ is —N(R')$_2$. In some embodiments, $R^{10}$ is —C(O)R. In some embodiments, $R^{10}$ is —C(O)N(R')$_2$. In some embodiments, $R^{10}$ is —OC(O)N(R')$_2$. In some embodiments, $R^{10}$ is —N(R')C(O)N(R')$_2$. In some embodiments, $R^{10}$ is —C(O)OR. In some embodiments, $R^{10}$ is —OC(O)R. In some embodiments, $R^{10}$ is —N(R')C(O)R. In some embodiments, $R^{10}$ is —N(R')C(O)OR. In some embodiments, $R^{10}$ is —SO$_2$R. In some embodiments, $R^{10}$ is —N(R')SO$_2$R. In some embodiments, $R^{10}$ is —SO$_2$N(R')$_2$. In some embodiments, $R^{10}$ is —P(O)(OR)$_2$.

In some embodiments, $R^{11}$ is $R^x$, wherein $R^x$ is as defined above and described herein. In some embodiments, one $R^{11}$ is taken together with another $R^{11}$ or $R^8$, $R^9$, $R^{10}$, $R^{12}$, or $R^{13}$ on the same atom to form an =C($R^x$)$_2$, =N($R^x$), =P($R^x$), =O, =S, or =Se group. In some embodiments, one $R^{11}$ is taken together with another $R^{11}$ or $R^8$, $R^9$, $R^{10}$, $R^{12}$, or $R^{13}$ on an adjacent atom to form a double bond. In some embodiments, one $R^{11}$ is taken together with another $R^{11}$ or $R^8$, $R^9$, $R^{10}$, $R^{12}$, or $R^{13}$ and their intervening atoms to form an optionally substituted 3-10 membered, saturated, partially unsaturated, or aryl ring having, in addition to the intervening atoms, 0-4 heteroatoms. In some embodiments, a moiety or compound has more than one $R^{11}$, wherein at least one $R^{11}$ is $R^x$, and at least one $R^{11}$ is taken together with another $R^{11}$ or $R^8$, $R^9$, $R^{10}$, $R^{12}$, or $R^{13}$ on the same atom to form an =C($R^x$)$_2$, =N($R^x$), =P($R^x$), =O, =S, or =Se group, or at least one $R^{11}$ is taken together with another $R^{11}$ or $R^8$, $R^9$, $R^{10}$, $R^{12}$, or $R^{13}$ on an adjacent atom to form a double bond, or one $R^{11}$ is taken together with another $R^{11}$ or $R^8$, $R^9$, $R^{10}$, $R^{12}$, or $R^{13}$ and their intervening atoms to form an optionally substituted 3-10 membered, saturated, partially unsaturated, or aryl ring having, in addition to the intervening atoms, 0-4 heteroatoms.

In some embodiments, $R^{11}$ is R, wherein R is as defined above and described herein.

In some embodiments, $R^{11}$ is hydrogen.

In some embodiments, $R^{11}$ is optionally substituted $C_{1-20}$ aliphatic. In some embodiments, $R^{11}$ is optionally substituted $C_{1-20}$ heteroaliphatic.

In some embodiments, $R^{11}$ is optionally substituted phenyl. In some embodiments, $R^{11}$ is phenyl. In some embodiments, $R^{11}$ is substituted phenyl.

In some embodiments, $R^{11}$ is an optionally substituted 3-7 membered saturated or partially unsaturated carbocyclic ring. In some embodiments, $R^{11}$ is optionally substituted cyclohexyl. In some embodiments, $R^{11}$ is cyclohexyl.

In some embodiments, $R^{11}$ is an optionally substituted 8-10 membered bicyclic saturated, partially unsaturated or aryl ring. In some embodiments, $R^{11}$ is an optionally substituted 8-10 membered bicyclic saturated ring. In some embodiments, $R^{11}$ is an optionally substituted 8-10 membered bicyclic partially unsaturated ring. In some embodiments, $R^{11}$ is an optionally substituted 8-10 membered bicyclic aryl ring. In some embodiments, $R^{11}$ is optionally substituted naphthyl. In some embodiments, $R^{11}$ is naphthyl. In some embodiments, $R^{11}$ is optionally substituted anthracenyl. In some embodiments, $R^{11}$ is anthracenyl.

In some embodiments, $R^{11}$ is an optionally substituted 5-6 membered monocyclic heteroaryl ring having 1-4 heteroatoms independently selected from nitrogen, oxygen, or sulfur. In some embodiments, $R^{11}$ is an optionally substituted 3-7 membered saturated or partially unsaturated heterocyclic ring having 1-3 heteroatoms independently selected from nitrogen, oxygen, or sulfur. In some embodiments, $R^{11}$ is an optionally substituted 7-10 membered bicyclic saturated or partially unsaturated heterocyclic ring having 1-5 heteroatoms independently selected from nitrogen, oxygen, or sulfur. In some embodiments, $R^{11}$ is an optionally substituted 8-10 membered bicyclic heteroaryl ring having 1-5 heteroatoms independently selected from nitrogen, oxygen, or sulfur.

In some embodiments, $R^{11}$ is halogen. In some embodiments, $R^{11}$ is —F. In some embodiments, $R^{11}$ is —Cl. In some embodiments, $R^{11}$ is —Br. In some embodiments, $R^{11}$ is —I.

In some embodiments, $R^{11}$ is —NO$_2$. In some embodiments, $R^{11}$ is —CN. In some embodiments, $R^{11}$ is —OR. In some embodiments, $R^{11}$ is —SR. In some embodiments, $R^{11}$ is —N(R')$_2$. In some embodiments, $R^{11}$ is —C(O)R. In some embodiments, $R^{11}$ is —C(O)N(R')$_2$. In some embodiments, $R^{11}$ is —OC(O)N(R')$_2$. In some embodiments, $R^{11}$ is —N(R')C(O)N(R')$_2$. In some embodiments, $R^{11}$ is —C(O)OR. In some embodiments, $R^{11}$ is —OC(O)R. In some embodiments, $R^{11}$ is —N(R')C(O)R. In some embodiments, $R^{11}$ is —N(R')C(O)OR. In some embodiments, $R^{11}$ is —SO$_2$R. In some embodiments, $R^{11}$ is —N(R')SO$_2$R. In some embodiments, R is —SO$_2$N(R')$_2$. In some embodiments, $R^{11}$ is —P(O)(OR)$_2$.

In some embodiments, $R^{12}$ is $R^x$, wherein $R^x$ is as defined above and described herein. In some embodiments, one $R^{12}$ is taken together with another $R^{12}$ or $R^8$, $R^9$, $R^{10}$, $R^{11}$ or $R^{13}$ on the same atom to form an =C(R$^x$)$_2$, =N(R$^x$), =P(R$^x$), =O, =S, or =Se group. In some embodiments, one $R^{12}$ is taken together with another $R^{12}$ or $R^8$, $R^9$, $R^{10}$, $R^{11}$ or $R^{13}$ on an adjacent atom to form a double bond. In some embodiments, one $R^{12}$ is taken together with another $R^{12}$ or $R^8$, $R^9$, $R^{10}$, $R^{11}$ or $R^{13}$ and their intervening atoms to form an optionally substituted 3-10 membered, saturated, partially unsaturated, or aryl ring having, in addition to the intervening atoms, 0-4 heteroatoms. In some embodiments, a moiety or compound has more than one $R^{12}$, wherein at least one $R^{12}$ is $R^x$, and at least one $R^{12}$ is taken together with another $R^{12}$ or $R^8$, $R^9$, $R^{10}$, $R^1$ or $R^{13}$ on the same atom to form an =C(R$^x$)$_2$, =N(R$^x$), =P(R$^x$), =O, =S, or =Se group, or at least one $R^{12}$ is taken together with another $R^{12}$ or $R^8$, $R^9$, $R^{10}$, $R^{11}$ or $R^{13}$ on an adjacent atom to form a double bond, or one $R^{12}$ is taken together with another $R^{12}$ or $R^8$, $R^9$, $R^{10}$, $R^{11}$ or $R^{13}$ and their intervening atoms to form an optionally substituted 3-10 membered, saturated, partially unsaturated, or aryl ring having, in addition to the intervening atoms, 0-4 heteroatoms.

In some embodiments, $R^{12}$ is R, wherein R is as defined above and described herein.

In some embodiments, $R^{12}$ is hydrogen.

In some embodiments, $R^{12}$ is optionally substituted $C_{1-20}$ aliphatic. In some embodiments, $R^{12}$ is optionally substituted $C_{1-20}$ heteroaliphatic.

In some embodiments, $R^{12}$ is optionally substituted phenyl. In some embodiments, $R^{12}$ is phenyl. In some embodiments, $R^{12}$ is substituted phenyl.

In some embodiments, $R^{12}$ is an optionally substituted 3-7 membered saturated or partially unsaturated carbocyclic ring. In some embodiments, $R^{12}$ is optionally substituted cyclohexyl. In some embodiments, $R^{12}$ is cyclohexyl.

In some embodiments, $R^{12}$ is an optionally substituted 8-10 membered bicyclic saturated, partially unsaturated or aryl ring. In some embodiments, $R^{12}$ is an optionally substituted 8-10 membered bicyclic saturated ring. In some embodiments, $R^{12}$ is an optionally substituted 8-10 membered bicyclic partially unsaturated ring. In some embodiments, $R^{12}$ is an optionally substituted 8-10 membered bicyclic aryl ring. In some embodiments, $R^{12}$ is optionally substituted naphthyl. In some embodiments, $R^{12}$ is naphthyl. In some embodiments, $R^{12}$ is optionally substituted anthracenyl. In some embodiments, $R^{12}$ is anthracenyl.

In some embodiments, $R^{12}$ is an optionally substituted 5-6 membered monocyclic heteroaryl ring having 1-4 heteroatoms independently selected from nitrogen, oxygen, or sulfur. In some embodiments, $R^{12}$ is an optionally substituted 3-7 membered saturated or partially unsaturated heterocyclic ring having 1-3 heteroatoms independently selected from nitrogen, oxygen, or sulfur. In some embodiments, $R^{12}$ is an optionally substituted 7-10 membered bicyclic saturated or partially unsaturated heterocyclic ring having 1-5 heteroatoms independently selected from nitrogen, oxygen, or sulfur. In some embodiments, $R^{12}$ is an optionally substituted 8-10 membered bicyclic heteroaryl ring having 1-5 heteroatoms independently selected from nitrogen, oxygen, or sulfur.

In some embodiments, $R^{12}$ is halogen. In some embodiments, $R^{12}$ is —F. In some embodiments, $R^{12}$ is —Cl. In some embodiments, $R^{12}$ is —Br. In some embodiments, $R^{12}$ is —I.

In some embodiments, $R^{12}$ is —NO$_2$. In some embodiments, $R^{12}$ is —CN. In some embodiments, $R^{12}$ is —OR. In some embodiments, $R^{12}$ is —SR. In some embodiments, $R^{12}$ is —N(R')$_2$. In some embodiments, $R^{12}$ is —C(O)R. In some embodiments, $R^{12}$ is —C(O)N(R')$_2$. In some embodiments, $R^{12}$ is —OC(O)N(R')$_2$. In some embodiments, $R^{12}$ is —N(R')C(O)N(R')$_2$. In some embodiments, $R^{12}$ is —C(O)OR. In some embodiments, $R^{12}$ is —OC(O)R. In some embodiments, $R^{12}$ is —N(R')C(O)R. In some embodiments, $R^{12}$ is —N(R')C(O)OR. In some embodiments, $R^{12}$ is —SO$_2$R. In some embodiments, $R^{12}$ is —N(R')SO$_2$R. In some embodiments, $R^{12}$ is —SO$_2$N(R')$_2$. In some embodiments, $R^{12}$ is —P(O)(OR)$_2$.

In some embodiments, $R^{13}$ is $R^x$, wherein $R^x$ is as defined above and described herein. In some embodiments, one $R^{13}$ is taken together with another $R^{13}$ or $R^8$, $R^9$, $R^{10}$, $R^{11}$ or $R^{12}$ on the same atom to form an =C(R$^x$)$_2$, =N(R$^x$), =P(R$^x$), =O, =S, or =Se group. In some embodiments, one $R^{13}$ is taken together with another $R^{13}$ or $R^8$, $R^9$, $R^\circ$, $R^{11}$ or $R^{12}$ on an adjacent atom to form a double bond. In some embodiments, one $R^{13}$ is taken together with another $R^{13}$ or $R^8$, $R^9$, $R^{10}$, $R^{11}$ or $R^{12}$ and their intervening atoms to form an optionally substituted 3-10 membered, saturated, partially unsaturated, or aryl ring having, in addition to the intervening atoms, 0-4 heteroatoms. In some embodiments, a moiety or compound has more than one $R^{13}$, wherein at least one $R^{13}$ is $R^x$, and at least one $R^{13}$ is taken together with another $R^{13}$ or $R^8$, $R^9$, $R^{10}$, $R^{11}$ or $R^{12}$ on the same atom to form an =C(R$^x$)$_2$, =N(R$^x$), =P(R$^x$), =O, =S, or =Se group, or at least one $R^{13}$ is taken together with another $R^{13}$ or $R^8$, $R^9$, $R^\circ$, $R^{11}$ or $R^{12}$ on an adjacent atom to form a double bond, or one $R^{13}$ is taken together with another $R^{13}$ or $R^8$, $R^9$, $R^{10}$, $R^{11}$ or $R^{12}$ and their intervening atoms to form an optionally substituted 3-10 membered, saturated, partially unsaturated, or aryl ring having, in addition to the intervening atoms, 0-4 heteroatoms.

In some embodiments, $R^{13}$ is R, wherein R is as defined above and described herein. Exemplary embodiments of $R^{13}$ include but are not limited to those described for R.

In some embodiments, $R^{13}$ is hydrogen.

In some embodiments, $R^{13}$ is optionally substituted $C_{1-20}$ aliphatic. In some embodiments, $R^{13}$ is —$(CH_2)_3CH$=$CH_2$, —$(CH_2)_4CH$=$CH_2$, —$(CH_2)_6CH$=$CH_2$, —$(CH_2)_2O(t$-$BuSi(CH_3)_2)$, —$(CH_2)_{20}Si(CH_3)_3$, —$(CH_2)_3OSi(CH_3)_3$, —$(CH_2)_6OSi(CH_3)_3$, —$(CH_2)_2C(CH_3)_2OSi(CH_3)_3$, —$CH_2CH_2(CF_2)_5CF_3$, —$CH(CH_3)COEt$, —$(CH_2)_5CN$, —$(CH_2)_2OH$, —$(CH_2)_2OCH_3$, —$CH_2Mes$, —$(CH_2)_3OH$, —$(CH_2)_6OH$, —$(CH_2)_2C(CH_3)_2OH$, adamantyl, MeAd, t-Bu, cyclohexyl, —$(CH_2)_7CH_3$, —$CH_3$, —$CH_2CH_3$, or isopinocampheyl. In some embodiments, $R^{13}$ is isopropyl. In some embodiments, $R^{13}$ is 1-phenylethyl. In some embodiments, $R^{13}$ is 1-naphthylethyl. In some embodiments, $R^{13}$ is cyclohexyl. In some embodiments, $R^{13}$ is adamantyl. In some embodiments, $R^{13}$ is isopinocampheyl.

In some embodiments, $R^{13}$ is optionally substituted $C_{1-20}$ heteroaliphatic. Exemplary $R^{13}$ include but are not limited to —$(CH_2)_2O(t$-$BuSi(CH_3)_2)$, —$(CH_2)_2OSi(CH_3)_3$, —$(CH_2)_3OSi(CH_3)_3$, —$(CH_2)_6OSi(CH_3)_3$, —$(CH_2)_2C(CH_3)_2OSi(CH_3)_3$, —$CH(CH_3)COEt$, —$(CH_2)_5CN$, —$(CH_2)_2OH$, —$(CH_2)_2OCH_3$, —$(CH_2)_3OH$, —$(CH_2)_6OH$, or —$(CH_2)_2C(CH_3)_2OH$.

In some embodiments, $R^{13}$ is optionally substituted phenyl. In some embodiments, $R^{13}$ is phenyl. In some embodiments, $R^{13}$ is substituted phenyl. In some embodiments, $R^{13}$ is 2,4,6-trimethylphenyl (mesityl). In some embodiments, $R^{13}$ is 2,4-dimethylphenyl. In some embodiments, $R^{13}$ is 2,6-dimethylphenyl. In some embodiments, $R^{13}$ is 2,4-dimethylphenyl. In some embodiments, $R^{13}$ is 4-methylphenyl. In some embodiments, $R^{13}$ is 4-chlorophenyl. In some embodiments, $R^{13}$ is 2,6-diisopropylphenyl. In some embodiments, $R^{13}$ is 2-methylphenyl. In some embodiments, $R^{13}$ is 2-isopropylphenyl. In some embodiments, $R^{13}$ is naphthyl. In some embodiments, $R^{13}$ is anthracenyl.

In some embodiments, $R^{13}$ is an optionally substituted 3-7 membered saturated or partially unsaturated carbocyclic ring. In some embodiments, $R^{13}$ is optionally substituted cyclohexyl. In some embodiments, $R^{13}$ is cyclohexyl.

In some embodiments, $R^{13}$ is an optionally substituted 8-10 membered bicyclic saturated, partially unsaturated or aryl ring. In some embodiments, $R^{13}$ is an optionally substituted 8-10 membered bicyclic saturated ring. In some embodiments, $R^{13}$ is an optionally substituted 8-10 membered bicyclic partially unsaturated ring. In some embodiments, $R^{13}$ is an optionally substituted 8-10 membered bicyclic aryl ring. In some embodiments, $R^{13}$ is optionally substituted naphthyl. In some embodiments, $R^{13}$ is naphthyl. In some embodiments, $R^{13}$ is optionally substituted anthracenyl. In some embodiments, $R^{13}$ is anthracenyl.

In some embodiments, $R^{13}$ is an optionally substituted 5-6 membered monocyclic heteroaryl ring having 1-4 heteroatoms independently selected from nitrogen, oxygen, or sulfur. In some embodiments, $R^{13}$ is an optionally substituted 3-7 membered saturated or partially unsaturated heterocyclic ring having 1-3 heteroatoms independently selected from nitrogen, oxygen, or sulfur. In some embodiments, $R^{13}$ is an optionally substituted 7-10 membered bicyclic saturated or partially unsaturated heterocyclic ring having 1-5 heteroatoms independently selected from nitrogen, oxygen, or sulfur. In some embodiments, $R^{13}$ is an optionally substituted 8-10 membered bicyclic heteroaryl ring having 1-5 heteroatoms independently selected from nitrogen, oxygen, or sulfur.

In some embodiments, $R^9$ is hydrogen and $R^{10}$ is R, halogen, nitro, cyano, —OR, —SR, —$N(R)_2$, —$C(O)R$, —$C(O)N(R)_2$, —$OC(O)N(R)_2$, —$N(R)C(O)N(R)_2$, —$C(O)OR$, —$OC(O)R$, —$N(R)C(O)R$, —$N(R)C(O)OR$, —$SO_2R$, —$N(R)SO_2R$, —$SO_2N(R)_2$, or —$P(O)(OR)_2$.

In some embodiments, $R^{11}$ is hydrogen and $R^{12}$ is R, halogen, nitro, cyano, —OR, —SR, —$N(R)_2$, —$C(O)R$, —$C(O)N(R)_2$, —$OC(O)N(R)_2$, —$N(R)C(O)N(R)_2$, —$C(O)OR$, —$OC(O)R$, —$N(R)C(O)R$, —$N(R)C(O)OR$, —$SO_2R$, —$N(R)SO_2R$, —$SO_2N(R)_2$, or —$P(O)(OR)_2$.

A ligand (for example, $R^1$, $R^4$, $R^5$, L, $R^{14}$, and their embodiments) can be taken together with one or more other ligands (for example, $R^1$, $R^4$, $R^5$, L, $R^{14}$, and their embodiments) to form a bidentate or polydentate ligand via any of the suitable variables described herein, such as $R^3$, $R^6$, $R^7$, $R^8$, $R^9$, $R^{10}$, $R^{11}$, $R^{12}$, $R^{13}$, $R^{15}$, R, $R^x$, X, Y, Z, D, E, $F^x$, G, $K^x$, $Z^2$, Ring A, Ring A' and Ring C', or their combinations thereof.

A ligand (for example, $R^1$, $R^4$, $R^5$, L, $R^{14}$, and their embodiments) can be linked to a tag or support via any of the suitable variables described herein, such as $R^3$, $R^6$, $R^7$, $R^8$, $R^9$, $R^{10}$, $R^{11}$, $R^{12}$, $R^{13}$, $R^{15}$, R, $R^x$, X, Y, Z, D, E, $F^x$, G, $K^x$, $Z^2$, Ring A, Ring A' and Ring C', or their combinations thereof.

Exemplary compounds of formula I include but are not limited to those listed below:

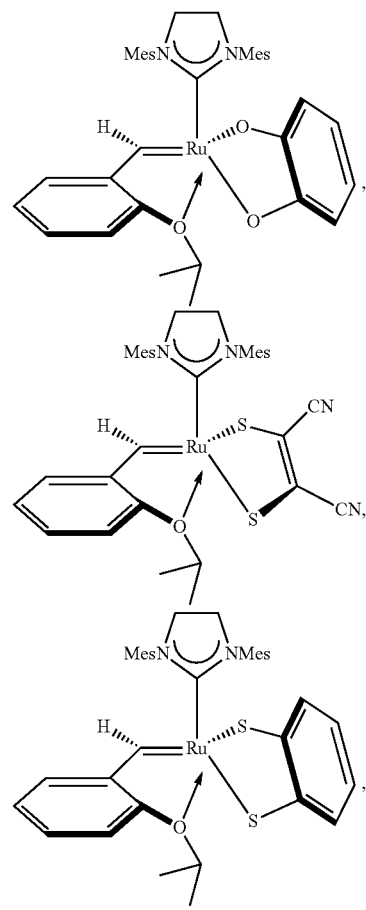

145
-continued
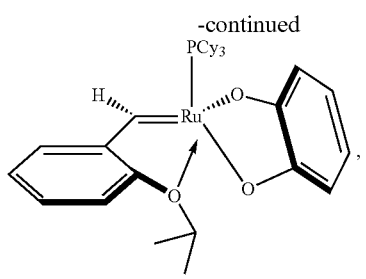
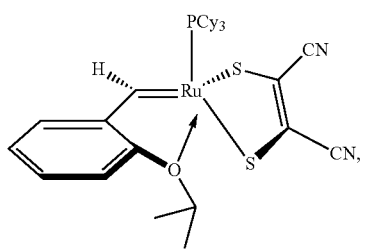
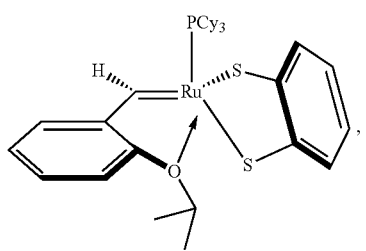
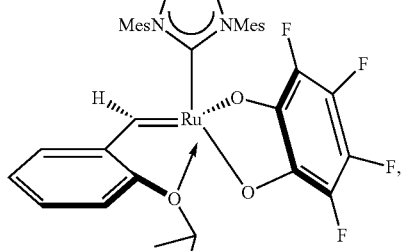
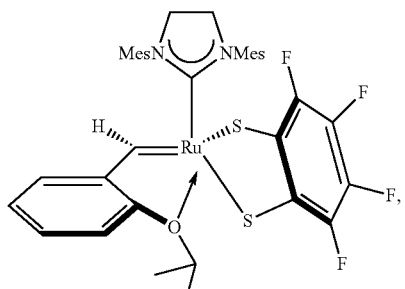
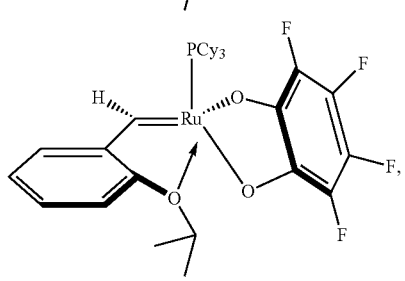
146
-continued
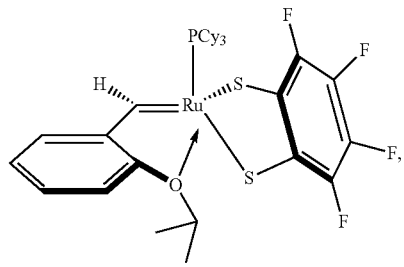
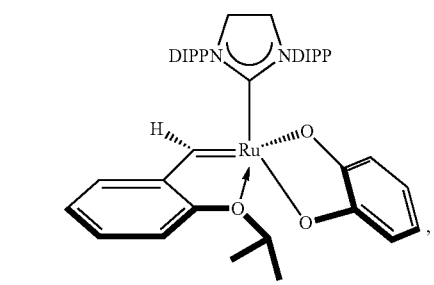
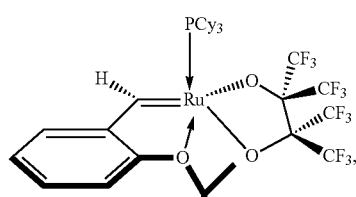
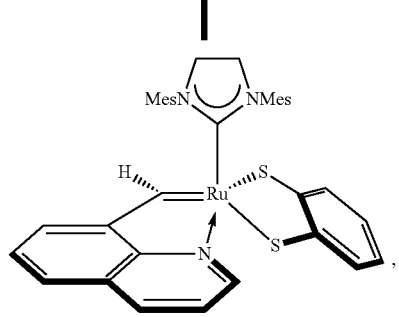
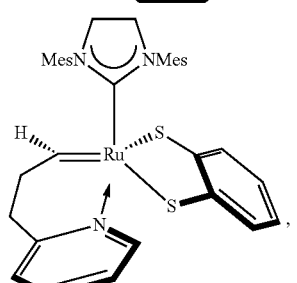
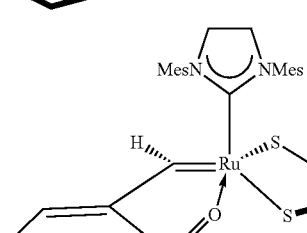

147
-continued
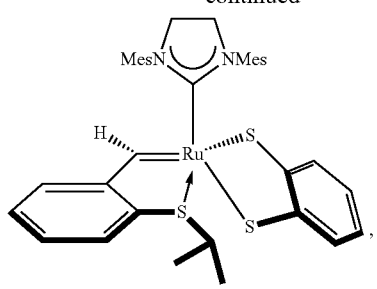
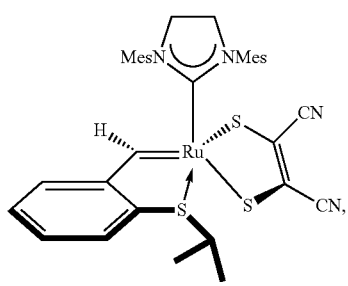
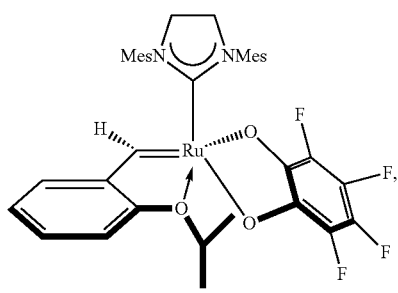
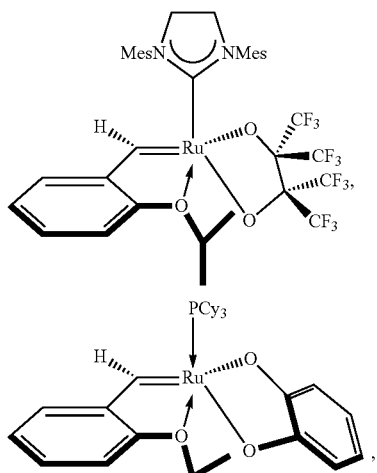
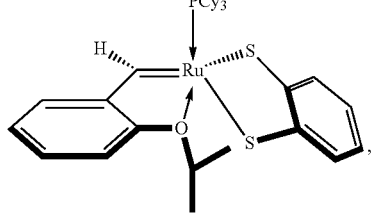
148
-continued
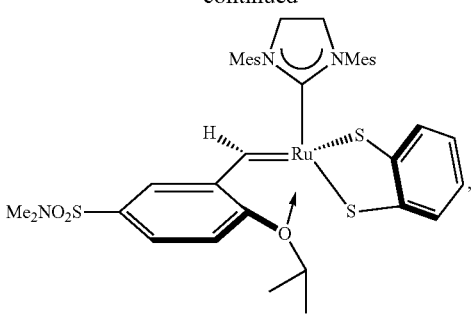
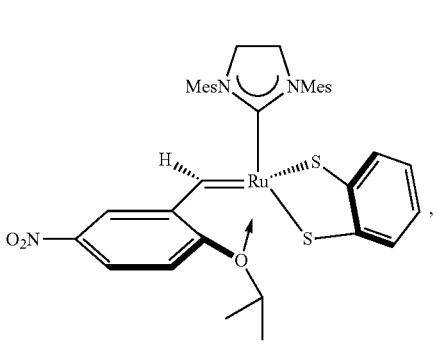
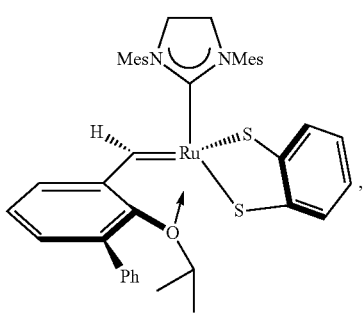
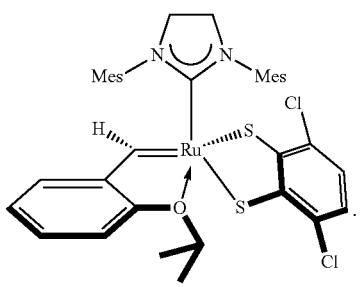
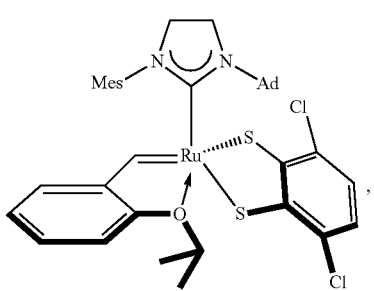

-continued
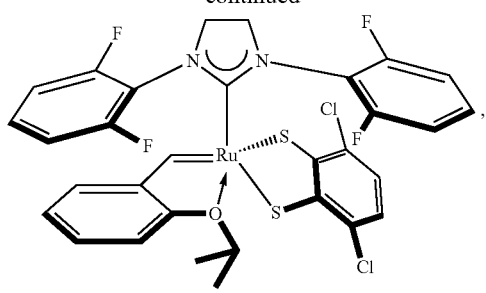
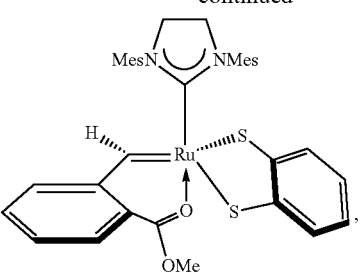,
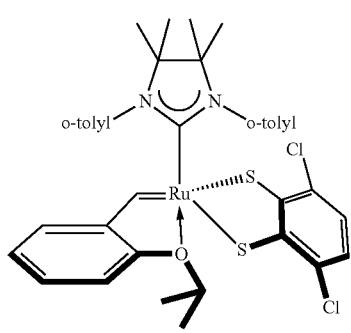
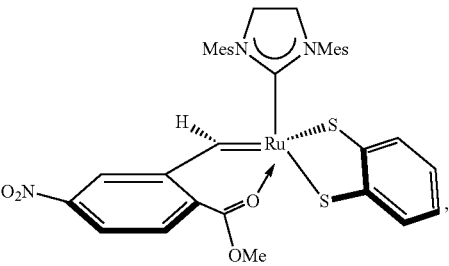,
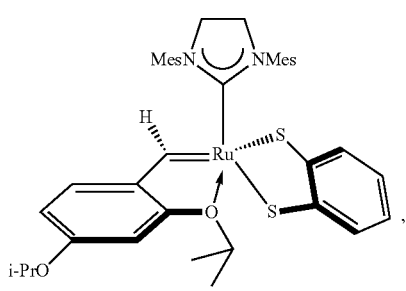,
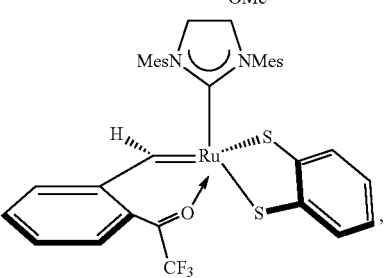,
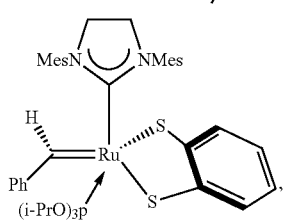,
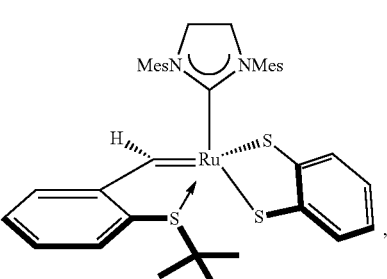,
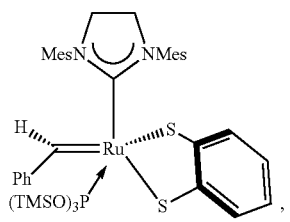,
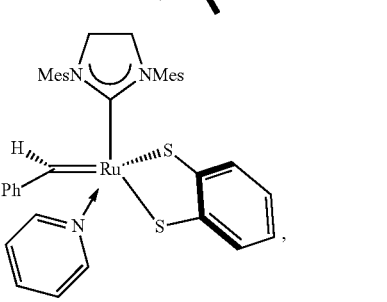,
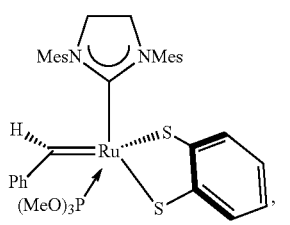,
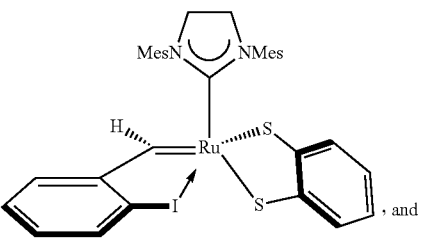, and -continued

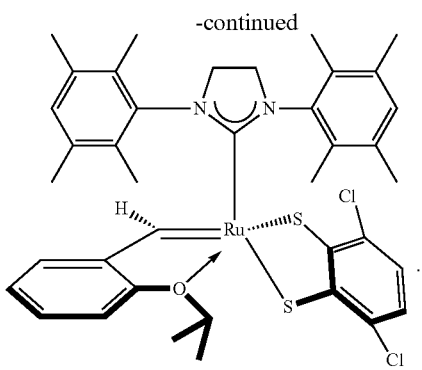

In some embodiments, a compound of formula I is linked to a tag or support. In some embodiments, a compound of formula I is linked to a tag ("tagged"). In some embodiments, a compound of formula I is linked to a support ("immobilized"). In some embodiments, a compound of formula I, when tagged or immobilized, can be recovered from reaction mixtures and recycled. In some embodiments, a compound of formula I, when tagged or immobilized, can be recovered from reaction mixtures by simple filtration, phase separation and/or extraction. In some embodiments, a compound of formula I, when tagged or immobilized, can be readily removed from the reaction mixture. Methods of tagging and/or immobilization are widely known in the art, for example but not limited to, Buchmeiser, M. R., *New. J. Chem.* 28 (2004) 549; Colacino, E. et al, *Coordination Chemistry Reviews* 251 (2007), 726; WO2013010676; WO2012154827; US20100145086; and WO2011069134.

In some embodiments, a compound of formula I is tagged. In some embodiments, a tagged compound of formula I is active for e.g., promoting metathesis reactions. In some embodiments, a tagged compound of formula I is active for e.g., promoting metathesis reactions without separation from the tag. Exemplary tags are widely known n the art, for example but not limited to those described in Buchmeiser, M. R., *New. J. Chem.* 28 (2004) 549; Colacino, E. et al, *Coordination Chemistry Reviews* 251 (2007), 726 and WO2013010676. In some embodiments, a tag is a redox-switchable tag. In some embodiments, a tag improves the solubility of a compound of formula I in aqueous phase. In some embodiments, a tag is an ionic liquid tag. In some embodiments, a tag is a substituted with multiple halogen atoms. In some embodiments, a tag is a substituted with multiple fluorine atoms. In some embodiments, a tag is perfluorinated. In some embodiments, a compound of formula I is active in fluorous media. In some embodiments, a compound of formula I is active in fluorous media without excessive degradation or unwanted side-reactions. In some embodiments, a tag comprises one or more linkers, which are used to attach a provided compound to the tag.

In some embodiments, a compound of formula I is tagged via one or more of $R^1$, $R^4$, $R^5$, $R^{14}$ and L. A compound of formula I can be tagged via any suitable part of a ligand, such as $R^3$, $R^6$, $R^7$, $R^8$, $R^9$, $R^{10}$, $R^{11}$, $R^{12}$, $R^{13}$, $R^{15}$, R, $R^x$, X, Y, Z, D, E, $F^x$, G, $K^x$, $Z^2$, Ring A, Ring A' and Ring C', or any combinations thereof. In some embodiments, a compound of formula I is tagged via one of $R^1$, $R^4$, $R^5$, $R^{14}$ and L. In some embodiments, a compound of formula I is tagged through $R^1$. In some embodiments, a compound of formula I is tagged through $R^1$, wherein $R^1$ is an NHC. In some embodiments, a compound of formula I is tagged through $R^4$ or $R^5$. In some embodiments, a compound of formula I is tagged through $R^4$ or $R^5$, wherein $R^4$ and $R^5$ are taken together to form a bidentate ligand having the structure of —X—$R^{15}$—Y—. In some embodiments, a compound of formula I is tagged through $R^{14}$. In some embodiments, a compound of formula I is tagged through $R^{14}$. In some embodiments, a compound of formula I is tagged through L. In some embodiments, a compound of formula I is tagged through $R^{14}$ or L. In some embodiments, a compound of formula I is tagged through $R^{14}$ or L, wherein $R^{14}$ and L are taken together to form a bidentate ligand. In some embodiments, a compound of formula I is tagged through $R^{14}$ or L, wherein $R^{14}$ and L are taken together to form

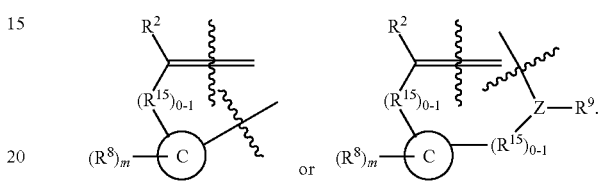

In some embodiments, a compound of formula I is tagged through Ring A.

In some embodiments, a compound of formula I is linked to one tag. In some embodiments, a compound of formula I is linked to more than one tag. In some embodiments, a compound of formula I is linked to more than one tag, wherein each tag has the same structure. In some embodiments, a compound of formula I is linked to more than one tag, wherein at least one tag has a different structure than the others. In some embodiments, a compound of formula I is linked to more than one tag, wherein each tag belongs to the same type, e.g., each tag is an ionic liquid tag. In some embodiments, tags of the same type have the same structures. In some embodiments, tags of the same type have different structures. In some embodiments, a compound of formula I is linked to more than one tag, wherein the more than one tag belongs to two or more types. For example, in some embodiments, one tag is an ionic tag, and the other is a perfluorinated tag.

In some embodiments, a compound of formula I is linked to a support ("immobilized"). A compound of formula I can be linked to a support via any suitable part of a ligand, such as $R^3$, $R^6$, $R^7$, $R^8$, $R^9$, $R^{10}$, $R^{11}$, $R^{12}$, $R^{13}$, $R^{15}$, R, $R^x$, X, Y, Z, D, E, $F^x$, G, $K^x$, $Z^2$, Ring A, Ring A' and Ring C', or their combinations thereof. In some embodiments, a compound of formula I immobilized on a support is active for e.g., promoting metathesis reactions. In some embodiments, a compound of formula I immobilized on a support is active for e.g., promoting metathesis reactions, without separation from the sold support. Suitable supports are widely known in the art, for example but not limited to those described in Buchmeiser, M. R., *New. J. Chem.* 28 (2004) 549; Colacino, E. et al, *Coordination Chemistry Reviews* 251 (2007), 726; WO2013010676; WO2012154827; US20100145086; and WO2011069134. Suitable supports for any of the compounds described herein may be of synthetic, semisynthetic, or naturally occurring materials, which may be organic or inorganic, and may be polymeric, ceramic, or metallic, or any of their combinations thereof. Attachment to the support will generally, although not necessarily, be covalent, and the covalent linkage may be direct or indirect. Indirect covalent linkages are typically, though not necessarily, through a functional group on a support surface. Ionic attachments are also suitable, including combinations of one or more anionic groups on the metal complexes coupled with supports containing cationic groups, or combinations of one or more cationic groups on the metal complexes coupled with supports containing anionic groups. In some embodiments, a suitable mode of attachment would be via a Lewis acid/Lewis base interaction as described in Huang, Z.; Brookhart, M.; Goldman, A. S.; Kundu, S.; Ray, A.; Scott, S. L.; Vicente, B. C. Adv. Synth. Catal, 351, 188-206 (2009). This type of attachment could include combinations of one or more Lewis basic groups on the metal complexes coupled with supports containing Lewis acid groups, or combinations of one or more Lewis acid groups on the metal complexes coupled with supports containing Lewis basic groups. In some embodiments, a support is selected from silicas, silicates, aluminas, aluminum oxides, silica-aluminas, aluminosilicates, zeolites, titanias, titanium dioxide, magnetite, magnesium oxides, boron oxides, clays, zirconias, zirconium dioxide, carbon, polymers, cellulose, cellulosic polymers amylose, amylosic polymers, or a combination thereof. In some embodiments, a support comprises silica, a silicate, or a combination thereof. In some embodiments, a support is Sepharose™, glass beads, magnetic beads, polystyrene, or polystyrene-divinylbenzene polymer (PS-DVB). In some embodiments, a support comprises one or more linkers, which are used to attach a provided compound to the support.

In some embodiments, a compound of formula I is immobilized on a support via one or more of $R^1$, $R^4$, $R^5$, $R^{14}$ and L. In some embodiments, a compound of formula I is immobilized on a support via one of $R^1$, $R^4$, $R^5$, $R^{14}$ and L. In some embodiments, a compound of formula I is immobilized on a support through $R^1$. In some embodiments, a compound of formula I is immobilized on a support through $R^1$, wherein $R^1$ is an NHC. In some embodiments, a compound of formula I is immobilized on a support through $R^4$ or $R^5$. In some embodiments, a compound of formula I is immobilized on a support through $R^4$ or $R^5$, wherein $R^4$ and $R^5$ are taken together to form a bidentate ligand having the structure of —X—$R^{15}$—Y—. In some embodiments, a compound of formula I is immobilized on a support through $R^{14}$. In some embodiments, a compound of formula I is immobilized on a support through $R^{14}$. In some embodiments, a compound of formula I is immobilized on a support through L. In some embodiments, a compound of formula I is immobilized on a support through $R^{14}$ or L. In some embodiments, a compound of formula I is immobilized on a support through $R^{14}$ or L, wherein $R^{14}$ and L are taken together to form a bidentate ligand. In some embodiments, a compound of formula I is immobilized on a support through $R^{14}$ or L, wherein $R^{14}$ and L are taken together to form

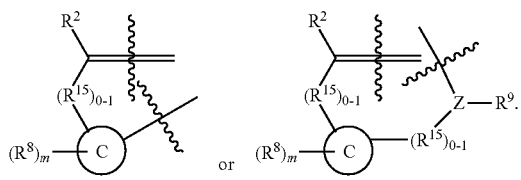

In some embodiments, a compound of formula I is immobilized on a support through Ring A.

In some embodiments, a compound of formula I dimerizes to form dimers. In some embodiments, a compound of formula I polymerizes to form polymers. Unless otherwise specified, "a compound of formula I" used herein encompasses such dimers and polymers.

In some embodiments, a provided compound, such as a compound of formula I, has surprisingly improved properties compared to previously known compounds in terms of, for example but not limited to, stability and/or reactivity. In some embodiments, a provided compound is unexpectedly stable and reactive. In some embodiments, a provided compound of formula I is unexpectedly easier to prepare. In some embodiments, due to the significantly improved stability, a provided compound of formula I is much easier to handle; for example, a provided compound of formula I can be weighed in open air, which contrasts sharply with previously known compounds that often need to be handled under inert atmosphere, for example, in a glove box and/or decompose quickly in solution. In some embodiments, a provided compound is surprisingly efficient in promoting metathesis reactions (0.002% catalyst loading, TON up to about 43,000).

In some embodiments, a provided compound is surprisingly efficient in promoting metathesis reactions. In some embodiments, a compound of formula I can be used at a concentration of no more than about 100 ppm in a metathesis reaction. In some embodiments, a compound of formula I can be used at a concentration of no more than about 50 ppm in a metathesis reaction. In some embodiments, a compound of formula I is used at no more than 0.1 mol % loading to the substrate in a metathesis reaction. In some embodiments, a compound of formula I is used at no more than 0.05 mol % loading to the substrate in a metathesis reaction. In some embodiments, a compound of formula I is used at no more than 0.01 mol % loading to the substrate in a metathesis reaction. In some embodiments, a compound of formula I is used at no more than 0.005 mol % loading to the substrate in a metathesis reaction. In some embodiments, a compound of formula I is used at no more than 0.002 mol % loading to the substrate in a metathesis reaction. In some embodiments, a compound of formula I is used at no more than 0.001 mol % loading to the substrate in a metathesis reaction. In some embodiments, when used at one of the concentrations or loadings described herein, the conversion of the substrate is greater than about 50%. In some embodiments, when used at one of the concentrations or loadings described herein, the conversion of the substrate is greater than about 60%. In some embodiments, when used at one of the concentrations or loadings described herein, the conversion of the substrate is greater than about 70%. In some embodiments, when used at one of the concentrations or loadings described herein, the conversion of the substrate is greater than about 80%. In some embodiments, when used at one of the concentrations or loadings described herein, the conversion of the substrate is greater than about 90%. In some embodiments, a compound of formula I has a TON of greater than 500 in a metathesis reaction. In some embodiments, a compound of formula I has a TON of greater than 1000 in a metathesis reaction. In some embodiments, a compound of formula I has a TON of greater than 3000 in a metathesis reaction. In some embodiments, a compound of formula I has a TON of greater than 5000 in a metathesis reaction. In some embodiments, a compound of formula I has a TON of greater than 9000 in a metathesis reaction. In some embodiments, a compound of formula I has a TON of greater than 10,000 in a metathesis reaction. In some embodiments, a compound of formula I has a TON of greater than 15,000 in a metathesis reaction. In some embodiments, a compound of formula I has a TON of greater than 20,000 in a metathesis reaction. In some embodiments, a compound of formula I has a TON of greater than 30,000 in a metathesis reaction. In some embodiments, a compound of formula I has a TON of greater than 40,000 in a metathesis reaction. In some embodiments, a compound of formula I has a TON of up to 43,000 in a metathesis reaction. In some embodiments, a reaction for measuring the efficiency of a compound of formula I is ROMP. In some embodiments, a reaction for measuring the efficiency of a compound of formula I is ROMP of norbornene. In some embodiments, a reaction for measuring the efficiency of a compound of formula I is ROMP of (1Z,5Z)-cycloocta-1,5-diene.

Compared to other metal complexes, such as previously known Ru-based metathesis catalysts, a compound of formula I can efficiently promote ROCM involving cross partners other than enol ethers. In some embodiments, a compound of formula I efficiently promotes ROCM involving sterically hindered cross partners such as vinylcyclohexane. In some embodiments, a compound of formula I efficiently promotes ROCM of norbornene and vinylcyclohexane.

In some embodiments, a compound of formula I efficiently promotes metathesis reactions in the presence of unprotected hydroxyl group. Non-limiting examples are illustrated in Table 2.

In some embodiments, the present invention provides methods for preparing a provided compound. In some embodiments, the present invention provides methods for preparing a provided compound of formula I. In some embodiments, the present invention provides a method for preparing a compound of formula I, comprising a step of:
providing a compound of formula II:

wherein:
each of $R^{4'}$ and $R^{5'}$ is independently halogen or —OR; and
each of $R^1$, $R^2$, Ring A, Z, and $R^3$ is independently as defined above and described herein.

In some embodiments, each of $R^{4'}$ and $R^{5'}$ is independently halogen. In some embodiments, each of $R^{4'}$ and $R^{5'}$ is —Cl.

In some embodiments, each of $R^{4'}$ and $R^{5'}$ is independently —OR, wherein R is as defined above and described herein. In some embodiments, each of $R^{4'}$ and $R^{5'}$ is independently —OR, wherein R is optionally substituted $C_{1-20}$ aliphatic. In some embodiments, each of $R^{4'}$ and $R^{5'}$ is independently t-BuO.

In some embodiments, $R^1$ is a phosphine ligand. In some embodiments, $R^1$ is $PCy_3$.

In some embodiments, a provided method for preparing a compound of formula I comprises steps of:
a) providing a compound of formula II; and
b) reacting the compound of formula II with a ligand or ligand precursor to replace $R^{4'}$ and $R^{5'}$ with $R^4$ and $R^5$.

Exemplary methods are depicted below:

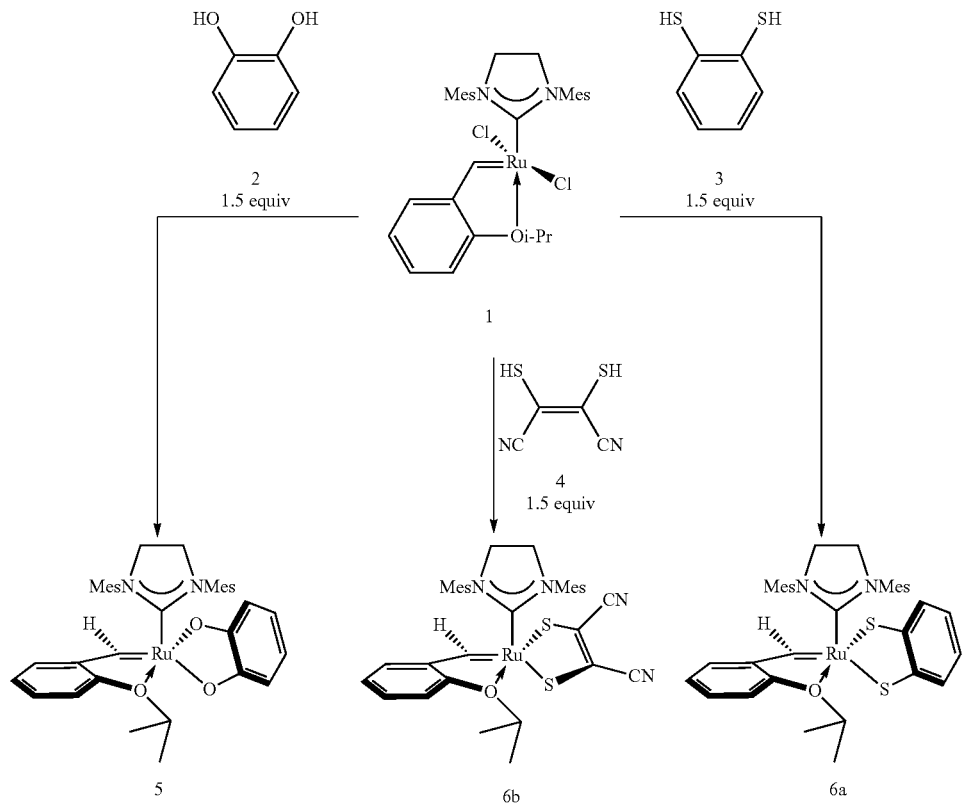

In some embodiments, a provided method comprises steps of:
a) providing a first compound of formula II, wherein $R^1$ is a phosphine ligand;
b) optionally reacting the first compound of formula II with a ligand or ligand precursor to replace the phosphine ligand with $R^1$ to produce a second compound; and
c) reacting the second compound with a ligand or ligand precursor to replace $R^{4'}$ and $R^{5'}$ with $R^4$ and $R^5$ to produce a compound of formula I.

Ligands or ligand precursors used to introduce a carbene ligand is widely known in the art, for example but not limited to those described in Colacino, E. et al, *Coordination Chemistry Reviews* 251 (2007), 726-764, Herrmann, W. A., *Angew. Chem. Int. Ed.* 2002, 41, 1290-1309, Samojlowicz, C.; Bieniek, M.; Grela, K. Ruthenium-based olefin metathesis catalysts bearing N-heterocyclic carbene ligands, *Chem. Rev.* 2009, 109, 3708- 3742, Vougioukalakis, G. C.; Grubbs, R. H. Ruthenium-based heterocyclic carbene-coordinated olefin metathesis catalysts, *Chem. Rev.* 2010, 110, 1746- 1787, and Lozano-Vila, A. M.; Monsaert, S.; Bajek, A.; Verpoort, F. *Chem. Rev.* 2010, 110, 4865-4909. In some embodiments, a ligand or ligand precursor is a salt of optionally substituted

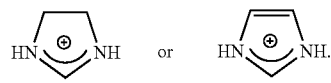

In some embodiments, the counterion is Cl⁻. In some embodiments, the counterion is Br⁻. In some embodiments, a ligand or ligand precursor to introduce a carbene ligand is

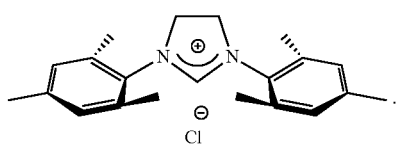

Exemplary methods are depicted below:

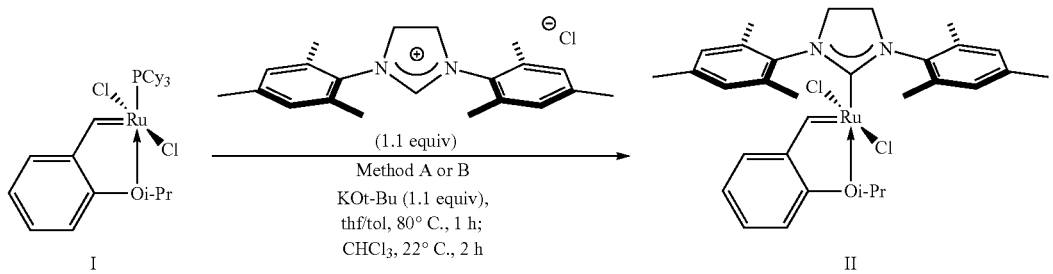

Method A (*Encyc. Rreag. Org.Synth.* HG-I/HG-II):

Method B (Fogg, D. E. *ChemCatChem.* 2012, 4, 2020):

75% yield (Method A)
98% yield (Method B)

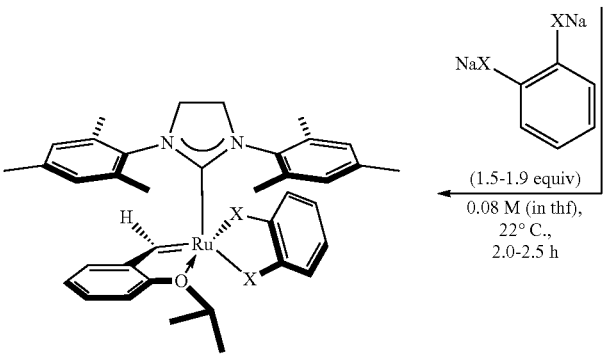

III: X = O; 65% yield
IV$_a$: X = S; 68% yield
IV$_b$: X = S$_{CN}$; 82% yield

In some embodiments, a provided method comprises steps of:
a) providing a first compound of formula II, wherein $R^1$ is a phosphine ligand;
b) reacting the first compound of formula II with a ligand or ligand precursor to replace $R^{4\prime}$ and $R^{5\prime}$ with $R^4$ and $R^5$ to produce a second compound; and
c) optionally reacting the second compound with a ligand or ligand precursor to replace the phosphine ligand with $R^1$ to produce a compound for formula I.

Exemplary methods are depicted below:

b) reacting the first compound of formula II with a ligand or ligand precursor to replace $R^{4\prime}$ and/or $R^{5\prime}$ with two other ligands to produce a second compound;
c) reacting the second compound with a ligand or ligand precursor to replace the two other ligands with $R^4$ and $R^5$ to produce a third compound; and
d) reacting the third compound with a ligand or ligand precursor to replace the phosphine ligand with $R^1$.

In some embodiments, the two other ligands in step b is independently —OR. In some embodiments, a ligand or ligand precursor of step b is ROH or its salt thereof. In some

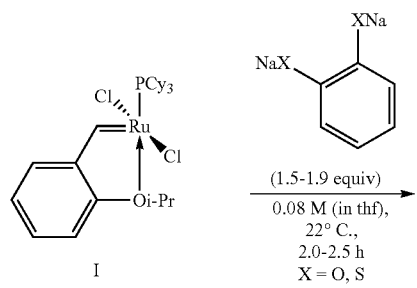

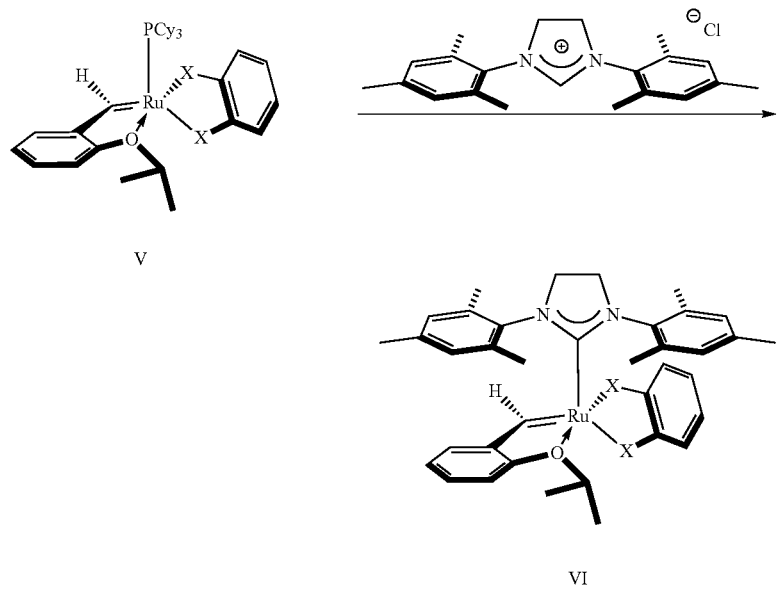

In some embodiments, a provided method comprises steps of:
a) providing a first compound of formula II;
b) reacting the first compound of formula II with a ligand or ligand precursor to replace $R^{4\prime}$ and/or $R^{5\prime}$ with two other ligands to produce a second compound; and
c) reacting the second compound with a ligand or ligand precursor to replace the two other ligands with $R^4$ and $R^5$ to produce a compound for formula I.

In some embodiments, a provided method comprises steps of:
a) providing a first compound of formula II, wherein $R^1$ is a phosphine ligand;

embodiments, ROH is t-BuOH. In some embodiments, a salt of ROH is t-BuOK. In some embodiments, a second compound is

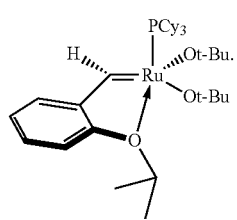

Exemplary methods are depicted below:

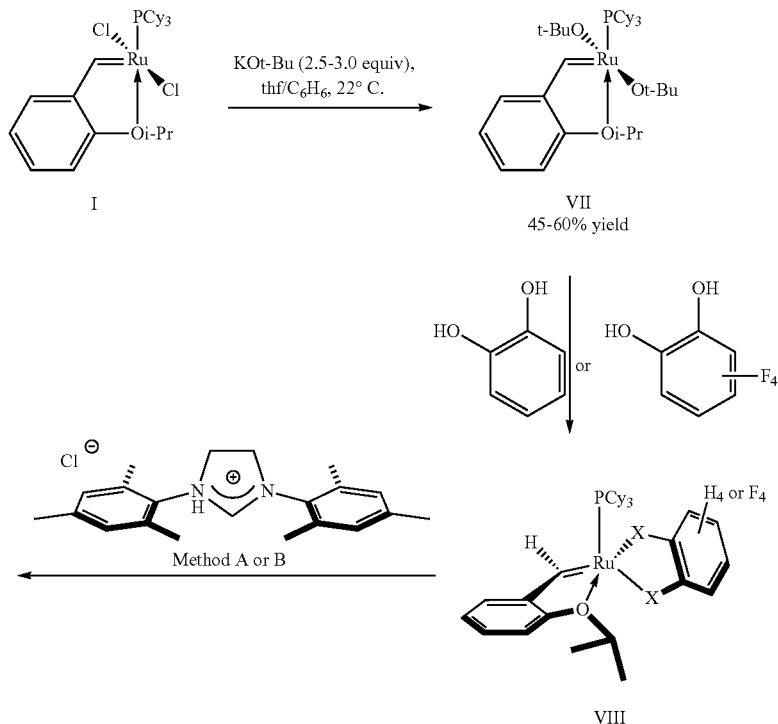

In some embodiments, a provided method comprises steps of:
a) providing a first compound of formula II, wherein $R^1$ is a phosphine ligand;
b) reacting the first compound of formula II with a ligand or ligand precursor to replace $R^{4'}$ and/or $R^{5'}$ with two other ligands to produce a second compound;
c) optionally reacting the second compound with a ligand or ligand precursor to replace the phosphine ligand with $R^1$ to produce a third compound; and
d) reacting the third compound with a ligand or ligand precursor to replace the two other ligands with $R^4$ and $R^5$.

In some embodiments, the two other ligands in step b is independently —OR. In some embodiments, a third compound is

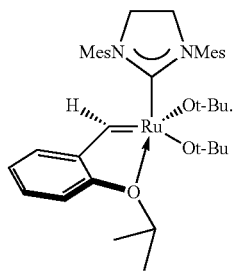

Exemplary methods are depicted below:

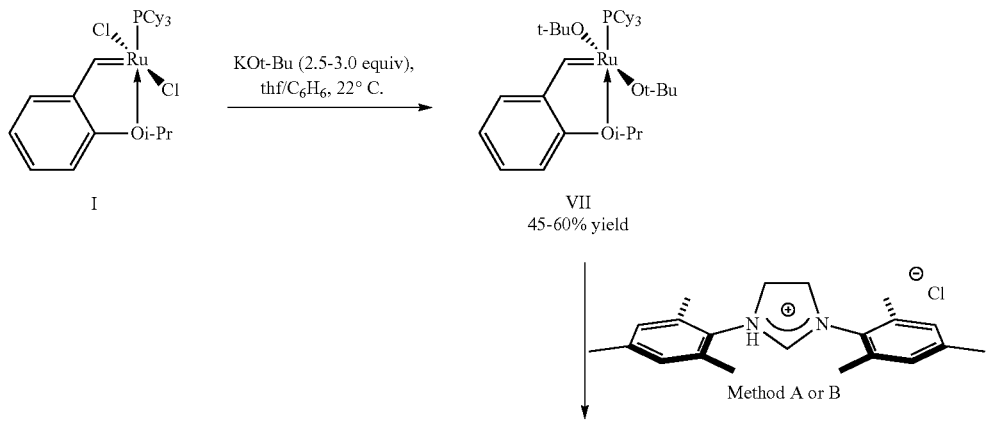

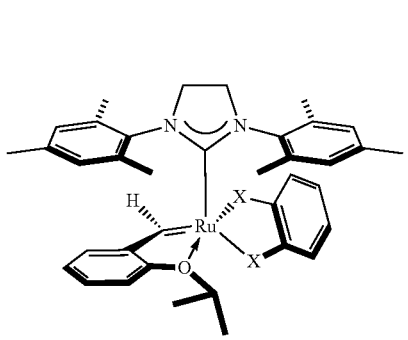
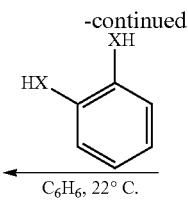
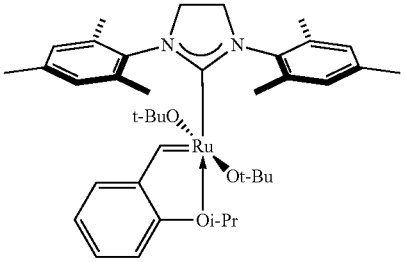

-continued

XI

In some embodiments, a provided method comprises steps of:
a) providing a first compound having the structure of formula III:

$$Ru(R^{1\prime})_3(R^{4\prime})(R^{5\prime}),\qquad \text{III}$$

wherein:
each $R^{1\prime}$ is independently a phosphine ligand; and
each of $R^{4\prime}$ and $R^{5\prime}$ is independently as defined above and described herein;
b) reacting the first compound of formula III with a ligand or ligand precursor to replace $R^{4\prime}$ and $R^{5\prime}$ with $R^4$ and $R^5$ to produce a second compound;
c) reacting the second compound with a ligand or ligand precursor to replace two $R^{1\prime}$ with $R^4$ and L; and
d) optionally reacting the third compound with a ligand or ligand precursor to replace $R^{1\prime}$ with $R^1$.

In some embodiments, a ligand or ligand precursor in step c has the structure of

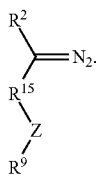

In some embodiments, a ligand or ligand precursor in step c has the structure of

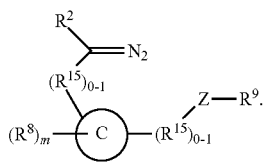

In some embodiments, a ligand or ligand precursor in step c has the structure of

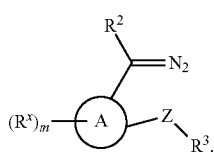

Exemplary methods are depicted below:

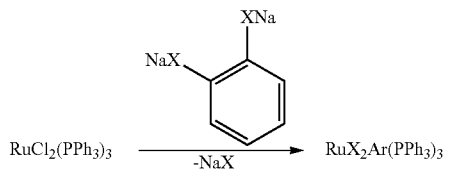

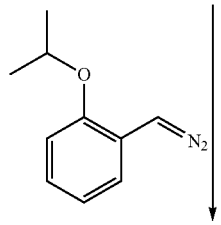

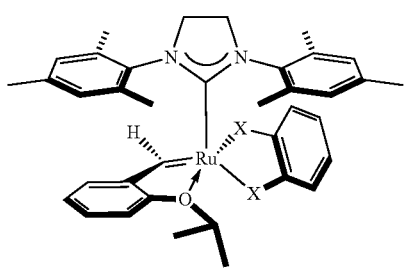
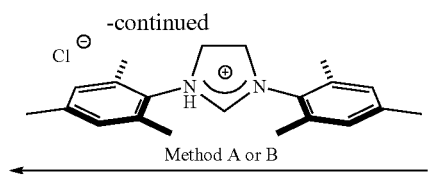
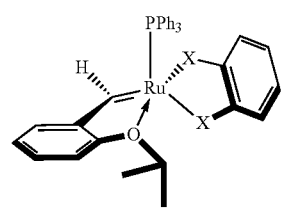

XIV

In some embodiments, a ligand or ligand precursor used to introduce $R^4$ and $R^5$ is $R^4$—H and $R^5$—H, respectively, or salts thereof. In some embodiments, $R^4$ and $R^5$ are taken together to form one ligand, and one ligand or ligand precursor is used to introduce both $R^4$ and $R^5$. In some embodiments, a salt is utilized to introduce $R^4$ and $R^5$. In some embodiments, a salt is a sodium salt. In some embodiments, a salt is a zinc salt.

In some embodiments, a ligand or ligand precursor used to introduce $R^4$ and $R^5$ has the structure of HX—$R^{15}$—YH, or a salt thereof. In some embodiments, a ligand or ligand precursor used to introduce $R^4$ and $R^5$ has the structure of (X—$R^{15}$—Y)Na$_2$. In some embodiments, a ligand or ligand precursor used to introduce $R^4$ and $R^5$ has the structure of (X—$R^{15}$—Y)Zn. In some embodiments, a ligand or ligand precursor used to introduce $R^4$ and $R^5$ has the structure of

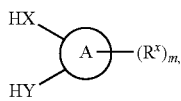

or its salt thereof. In some embodiments, a ligand or ligand precursor used to introduce $R^4$ and $R^5$ is

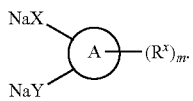

In some embodiments, a ligand or ligand precursor used to introduce $R^4$ and $R^5$ is

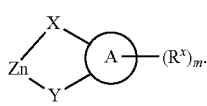

In some embodiments, a ligand or ligand precursor used to introduce $R^4$ and $R^5$ has the structure of

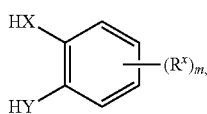

or its salt thereof. In some embodiments, a ligand or ligand precursor used to introduce $R^4$ and $R^5$ is

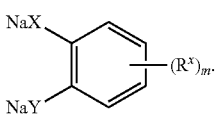

In some embodiments, a ligand or ligand precursor used to introduce $R^4$ and $R^5$ is

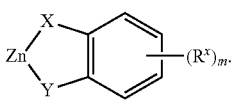

In some embodiments, a ligand or ligand precursor used to introduce $R^4$ and $R^5$ is

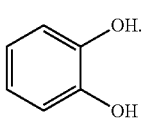

In some embodiments, a ligand or ligand precursor used to introduce $R^4$ and $R^5$ is

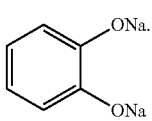

In some embodiments, a ligand or ligand precursor used to introduce $R^4$ and $R^5$ is

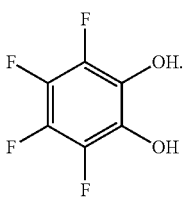

In some embodiments, a ligand or ligand precursor used to introduce $R^4$ and $R^5$ is

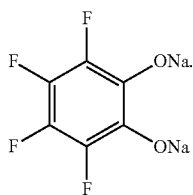

In some embodiments, a ligand or ligand precursor used to introduce $R^4$ and $R^5$ is

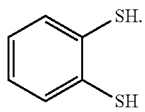

In some embodiments, a ligand or ligand precursor used to introduce $R^4$ and $R^5$ is

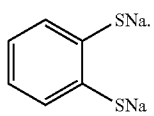

In some embodiments, a ligand or ligand precursor used to introduce $R^4$ and $R^5$ is

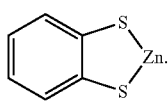

In some embodiments, a ligand or ligand precursor used to introduce $R^4$ and $R^5$ is

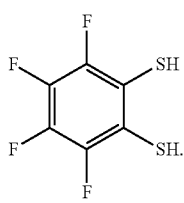 [SMILES: Oc1c(O)c(F)c(F)c(F)c1F]

In some embodiments, a ligand or ligand precursor used to introduce $R^4$ and $R^5$ is

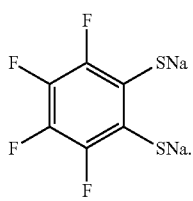

In some embodiments, a ligand or ligand precursor used to introduce $R^4$ and $R^5$ is

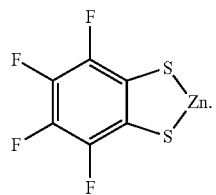

In some embodiments, a ligand or ligand precursor used to introduce $R^4$ and $R^5$ is

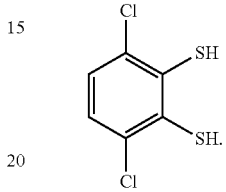

In some embodiments, a ligand or ligand precursor used to introduce $R^4$ and $R^5$ is

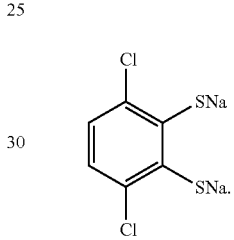

In some embodiments, a ligand or ligand precursor used to introduce $R^4$ and $R^5$ is

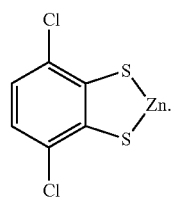

In some embodiments, a ligand or ligand precursor used to introduce $R^4$ and $R^5$ is

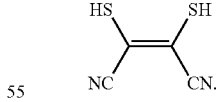

In some embodiments, a ligand or ligand precursor used to introduce $R^4$ and $R^5$ is

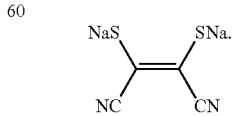

In some embodiments, a ligand or ligand precursor used to introduce $R^4$ and $R^5$ is

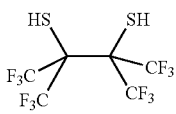

or its salt thereof. In some embodiments, a ligand or ligand precursor used to introduce $R^4$ and $R^5$ is

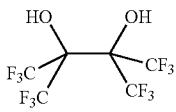

or its salt thereof. In some embodiments, a ligand or ligand precursor used to introduce $R^4$ and $R^5$ is

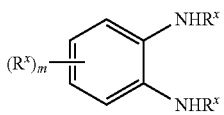

or its salt thereof. In some embodiments, a ligand or ligand precursor used to introduce $R^4$ and $R^5$ is

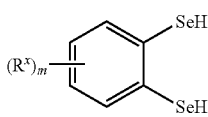

or its salt thereof. In some embodiments, a ligand or ligand precursor used to introduce $R^4$ and $R^5$ is

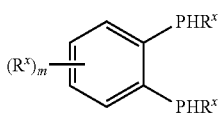

or its salt thereof. In some embodiments, a ligand or ligand precursor used to introduce $R^4$ and $R^5$ is

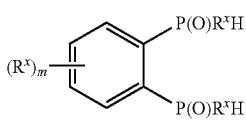

or its salt thereof. In some embodiments, a ligand or ligand precursor used to introduce $R^4$ and $R^5$ is

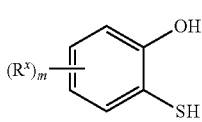

or its salt thereof. In some embodiments, a ligand or ligand precursor used to introduce $R^4$ and $R^5$ is

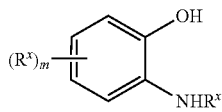

or its salt thereof. In some embodiments, a ligand or ligand precursor used to introduce $R^4$ and $R^5$ is

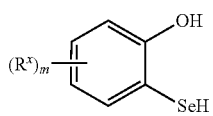

or its salt thereof. In some embodiments, a ligand or ligand precursor used to introduce $R^4$ and $R^5$ is

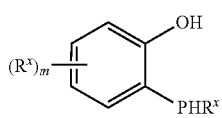

or its salt thereof. In some embodiments, a ligand or ligand precursor used to introduce $R^4$ and $R^5$ is

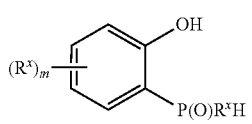

or its salt thereof. In some embodiments, a ligand or ligand precursor used to introduce $R^4$ and $R^5$ is

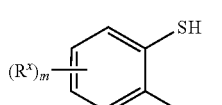

or its salt thereof. In some embodiments, a ligand or ligand precursor used to introduce $R^4$ and

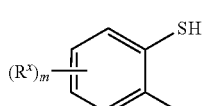

or its salt thereof. In some embodiments, a ligand or ligand precursor used to introduce $R^4$ and $R^5$ is

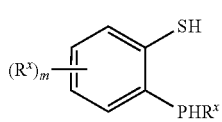

or its salt thereof. In some embodiments, a ligand or ligand precursor used to introduce $R^4$ and $R^5$ is

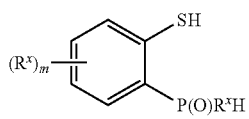

or its salt thereof.

In some embodiments, the present invention provides a method for preparing a compound of formula I, comprising steps of:
a) providing a first compound of formula I;
b) react the first compound of formula I with one or more ligand or ligand precursor to replace the $R^{14}$ and L of the first compound to provide a compound of formula I.

In some embodiments, $R^{14}$ and L of the first compound of formula I are taken together to form one ligand. In some embodiments, $R^{14}$ and L of a target compound of formula I are taken together to form one ligand. In some embodiments, $R^{14}$ and L of both the first compound and the target compound of formula I are taken together to form one ligand.

In some other embodiments, the present invention provides methods for metathesis reactions. In some embodiments, a provided method comprises providing a compound provided by this invention. In some embodiments, a provided method comprises providing a compound of formula I.

In some embodiments, a metathesis reaction is olefin metathesis. In some embodiments, the present invention provides a method for Z-selective metathesis, comprising steps of:
a) providing a compound of formula I;
b) reacting a first carbon-carbon double bond with a second carbon-carbon double bond to produce a compound comprising a carbon-carbon double bond, wherein the carbon-carbon double bond in the product comprises one carbon atom from the first carbon-carbon double bond and one carbon atom from the second carbon-carbon double bond.

In some embodiments, a metathesis reaction promoted by a compound of formula I is ring-opening metathesis polymerization (ROMP). In some embodiments, a metathesis reaction is cross metathesis. In some embodiments, a metathesis reaction promoted by a compound of formula I is ring-opening cross metathesis (ROCM). In some embodiments, a metathesis reaction is Z-selective olefin metathesis. In some embodiments, a metathesis reaction promoted by a compound of formula I is Z-selective ring-opening metathesis polymerization (ROMP). In some embodiments, a metathesis reaction promoted by a compound of formula I is Z-selective ring-opening cross metathesis (ROCM). In some embodiments, a metathesis reaction is ring-closing metathesis (RCM). In some embodiments, a metathesis reaction is ring closing metathesis. In some embodiments, a metathesis reaction is ethenolysis.

In some embodiments, the present invention provides a method for olefin metathesis comprising providing a compound having the structure of formula I, wherein the metathesis product is produced with greater than 50% Z selectivity. In some embodiments, the present invention provides a method for ring-opening metathesis polymerization (ROMP) comprising providing a compound having the structure of formula I, wherein the ROMP polymer product is produced with greater than 50% Z selectivity. In some embodiments, the present invention provides a method for ring-opening cross metathesis (ROCM) comprising providing a compound having the structure of formula I, wherein the ROCM product is produced with greater than 50% Z selectivity.

In some embodiments, a metathesis product is produced with greater than about 50% Z selectivity. In some embodiments, a metathesis product is produced with greater than about 60% Z selectivity. In some embodiments, a metathesis product is produced with greater than about 70% Z selectivity. In some embodiments, a metathesis product is produced with greater than about 80% Z selectivity. In some embodiments, a metathesis product is produced with greater than about 85% Z selectivity. In some embodiments, a metathesis product is produced with greater than about 90% Z selectivity. In some embodiments, a metathesis product is produced with greater than about 91% Z selectivity. In some embodiments, a metathesis product is produced with greater than about 92% Z selectivity. In some embodiments, a metathesis product is produced with greater than about 93% Z selectivity. In some embodiments, a metathesis product is produced with greater than about 94% Z selectivity. In some embodiments, a metathesis product is produced with greater than about 95% Z selectivity. In some embodiments, a metathesis product is produced with greater than about 96% Z selectivity. In some embodiments, a metathesis product is produced with greater than about 97% Z selectivity. In some embodiments, a metathesis product is produced with greater than about 98% Z selectivity. In some embodiments, a metathesis product is produced with greater than about 99% Z selectivity.

In some embodiments, a provided method produces a product with unexpected Z selectivity. For example, ROMP of norbornene promoted by a compound of formula I produces polymers with exceptional Z selectivity (>98% Z).

In some embodiments, a polymer product of a ROMP reaction is produced with high cis, syndiotactic selectivity.

In some embodiments, a provided method has unexpected high efficiency. In some embodiments, a compound of formula I is used at a concentration of no more than about 1,000 ppm in a metathesis reaction. In some embodiments, a compound of formula I is used at a concentration of no more than about 500 ppm in a metathesis reaction. In some embodiments, a compound of formula I is used at a concentration of no more than about 400 ppm in a metathesis reaction. In some embodiments, a compound of formula I is used at a concentration of no more than about 300 ppm in a metathesis reaction. In some embodiments, a compound of formula I is used at a concentration of no more than about 200 ppm in a metathesis reaction. In some embodiments, a compound of formula I is used at a concentration of no more than about 100 ppm in a metathesis reaction. In some embodiments, a compound of formula I is used at a concentration of no more than about 90 ppm in a metathesis reaction. In some embodiments, a compound of formula I is used at a concentration of no more than about 80 ppm in a metathesis reaction. In some embodiments, a compound of formula I is used at a concentration of no more than about 70 ppm in a metathesis reaction. In some embodiments, a compound of formula I is used at a concentration of no more than about 60 ppm in a metathesis reaction. In some embodiments, a compound of formula I is used at a concentration of no more than about 50 ppm in a metathesis reaction. In some embodiments, a compound of formula I is used at a concentration of no more than about 40 ppm in a metathesis reaction. In some embodiments, a compound of formula I is used at a concentration of no more than about 30 ppm in a metathesis reaction. In some embodiments, a compound of formula I is used at a concentration of no more than about 20 ppm in a metathesis reaction. In some embodiments, a compound of formula I is used at a concentration of no more than about 10 ppm in a metathesis reaction. In some embodiments, a compound of formula I is used at no more than 10 mol % loading to the substrate in a metathesis reaction. In some embodiments, a compound of formula I is used at no more than 8 mol % loading to the substrate in a metathesis reaction. In some embodiments, a compound of formula I is used at no more than 6 mol % loading to the substrate in a metathesis reaction. In some embodiments, a compound of formula I is used at no more than 5 mol % loading to the substrate in a metathesis reaction. In some embodiments, a compound of formula I is used at no more than 4 mol % loading to the substrate in a metathesis reaction. In some embodiments, a compound of formula I is used at no more than 3 mol % loading to the substrate in a metathesis reaction. In some embodiments, a compound of formula I is used at no more than 2 mol % loading to the substrate in a metathesis reaction. In some embodiments, a compound of formula I is used at no more than 1 mol % loading to the substrate in a metathesis reaction. In some embodiments, a compound of formula I is used at no more than 0.8 mol % loading to the substrate in a metathesis reaction. In some embodiments, a compound of formula I is used at no more than 0.6 mol % loading to the substrate in a metathesis reaction. In some embodiments, a compound of formula I is used at no more than 0.5 mol % loading to the substrate in a metathesis reaction. In some embodiments, a compound of formula I is used at no more than 0.4 mol % loading to the substrate in a metathesis reaction. In some embodiments, a compound of formula I is used at no more than 0.3 mol % loading to the substrate in a metathesis reaction. In some embodiments, a compound of formula I is used at no more than 0.2 mol % loading to the substrate in a metathesis reaction. In some embodiments, a compound of formula I is used at no more than 0.1 mol % loading to the substrate in a metathesis reaction. In some embodiments, a compound of formula I is used at no more than 0.05 mol % loading to the substrate in a metathesis reaction. In some embodiments, a compound of formula I is used at no more than 0.01 mol % loading to the substrate in a metathesis reaction. In some embodiments, a compound of formula I is used at no more than 0.005 mol % loading to the substrate in a metathesis reaction. In some embodiments, a compound of formula I is used at no more than 0.002 mol % loading to the substrate in a metathesis reaction. In some embodiments, a compound of formula I is used at no more than 0.001 mol % loading to the substrate in a metathesis reaction. In some embodiments, when used at one of the concentrations or loadings described herein, the conversion of the substrate is greater than about 50%. In some embodiments, when used at one of the concentrations or loadings described herein, the conversion of the substrate is greater than about 60%. In some embodiments, when used at one of the concentrations or loadings described herein, the conversion of the substrate is greater than about 70%. In some embodiments, when used at one of the concentrations or loadings described herein, the conversion of the substrate is greater than about 80%. In some embodiments, when used at one of the concentrations or loadings described herein, the conversion of the substrate is greater than about 90%. In some embodiments, the turnover number of a compound of formula I (TON) is greater than about 500. In some embodiments, the turnover number (TON) is greater than about 600. In some embodiments, the turnover number (TON) is greater than about 700. In some embodiments, the turnover number (TON) is greater than about 800. In some embodiments, the turnover number (TON) is greater than about 900. In some embodiments, the turnover number (TON) is greater than about 1,000. In some embodiments, the turnover number (TON) is greater than about 2,000. In some embodiments, the turnover number (TON) is greater than about 3,000. In some embodiments, the turnover number (TON) is greater than about 4,000. In some embodiments, the turnover number (TON) is greater than about 5,000. In some embodiments, the turnover number (TON) is greater than about 6,000. In some embodiments, the turnover number (TON) is greater than about 7,000. In some embodiments, the turnover number (TON) is greater than about 8,000. In some embodiments, the turnover number (TON) is greater than about 9,000. In some embodiments, the turnover number (TON) is greater than about 10,000. In some embodiments, the turnover number (TON) is greater than about 15,000. In some embodiments, the turnover number (TON) is greater than about 20,000. In some embodiments, the turnover number (TON) is greater than about 25,000. In some embodiments, the turnover number (TON) is greater than about 30,000. In some embodiments, the turnover number (TON) is greater than about 35,000. In some embodiments, the turnover number (TON) is greater than about 40,000. In some embodiments, the turnover number (TON) is up to about 43,000.

In some embodiments, a provided compound of formula I is exceptionally efficient and Z-selective in promoting metathesis reactions. In some embodiments, complete conversion is achieved with as low as 0.002% loading in 1 hour, producing the desired product with >98:2 Z:E.

In some embodiments, a provided method has surprising functional group tolerance. In some embodiments, protection of hydroxyl group is not required in a provided method.

In some embodiments, a double bond used in a metathesis reaction is sterically hindered. In some embodiments, a sterically hindered double bond has one or more substituents at an allylic position. It is well known in the art that sterically hindered double bonds represent a significant challenge for cross metathesis, leading to slow reaction, low conversion and/or poor stereoselectivity. Surprisingly, provided compounds of this invention promote metathesis reactions involving sterically hindered olefins, such as vinylcyclohexane and styrene, with high conversion and exceptional Z-selectivity, in some embodiments, up to >98:2 Z:E.

Up until now, ROCM transformations have been limited to enol ether cross partners when Ru catalysts are used (Khan, R. K. M.; O'Brien, R. V.; Torker, S.; Li, B.; Hoveyda, A. H. *J. Am. Chem. Soc.* 2012, 134, 12774). In some embodiments, a provided compound and/or a provided method enables new types of cross partners, other than enol ether, to be used. In some embodiments, one of the metathesis partners is not a double bond of a vinyl ether. In some embodiments, one of the metathesis partners is $CH_2=CHR$, wherein R is an optionally substituted 3-10 membered, saturated, partially unsaturated, or aryl ring having 0-4 heteroatoms. In some embodiments, one of the metathesis partners is $CH_2=CHR$, wherein R is an optionally substituted 3-10 membered, saturated, partially unsaturated, or aryl ring having 0-4 heteroatoms independently selected from nitrogen, oxygen, or sulfur. In some embodiments, one of the metathesis partners is $CH_2=CHR$, wherein R is an optionally substituted 3-10 membered, saturated, partially unsaturated, or aryl ring. In some embodiments, one of the metathesis partners is $CH_2=CHR$, wherein R is an optionally substituted 3-10 membered saturated or partially unsaturated carbocyclic ring. In some embodiments, one of the metathesis partners is $CH_2=CHR$, wherein R is an optionally substituted 3-10 membered saturated carbocyclic ring.

In some embodiments, one of the metathesis partners is $CH_2$=CHR, wherein R is an optionally substituted 3-10 membered partially unsaturated carbocyclic ring. In some embodiments, one of the metathesis partners is $CH_2$=CHR, wherein R is an optionally substituted phenyl ring. In some embodiments, one of the metathesis partners is styrene. In some embodiments, one of the metathesis partners is vinylcyclohexane.

In some embodiments, a provided method provides an allyl alcohol as a metathesis product. In some embodiments, a substrate comprising a first double bond comprises an allyl alcohol. In some embodiments, a substrate comprising a first double bond comprises two allylic hydroxyl groups. In some embodiments, a hydroxyl group is optionally protected. In some embodiments, an allylic hydroxyl group is protected. In some embodiments, an allylic hydroxyl group is unprotected.

In some embodiments, a substrate of a provided method is an aliphatic olefin. In some embodiments, a substrate of a provided method is a heteroaryl olefin. In some embodiments, a heteroaryl olefin comprises an optionally substituted heteroaryl group conjugated to a double bond, wherein the double bond is one of the two double bonds participated in a metathesis reaction. In some embodiments, a substrate of a provided method is a 1,3-diene. In some embodiments, a 1,3-diene is optionally substituted. In some embodiments, a substrate of a provided method comprises a 1,3-diene. In some embodiments, a substrate of a provided method is an O-substituted alkene. In some embodiments, a substrate of a provided method is a S-substituted alkene. In some embodiments, a substrate of a provided method is an allylic alcohol. In some embodiments, a substrate of a provided method is a homoallylic alcohol. In some embodiments, a provided method provides a product with high Z- and diastereomeric selectivity.

With their unexpected efficiency, selectivity, functional group tolerance and substrate scope, provided compounds and methods are particularly useful in industrially important processes. For example, a provided compound of formula I and/or a provided method is particularly useful in the cross metathesis of homoallylic alcohol and 1-butene to produce (Z)-3-hexen-1-ol.

Conditions

In some embodiments, a ligand is provided in a molar ratio of about 10:1, 9:1, 8:1, 7:1, 6:1, 5:1, 4:1, 3:1, 2:1, or 1:1 relative to the metal. In some embodiments, a ligand is provided in a molar ratio of about 0.9:1, 0.8:1, 0.7:1, 0.6:1, 0.5:1, 0.4:1, 0.3:1, 0.2:1, or 0.1:1 relative to the metal. In certain embodiments, a ligand is provided in a molar ratio of about 1:1 relative to the metal. One of skill in the art will appreciate that the optimal molar ratio of ligand to metal will depend on, inter alia, whether the ligand is mono- or polydentate. In some embodiments, a ligand or ligand precursor having the structure of formula I is provided in a molar ratio of about 1:1 to M.

Suitable conditions for performing provided methods generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane and chloroform, or polar aprotic solvents, such as ethereal solvents including ether, tetrahydrofuran (THF), or dioxanes, or protic solvents, such as alcohols, or mixtures thereof. In certain embodiments, one or more solvents are deuterated.

In some embodiments, a single solvent is used. In certain embodiments, a solvent is benzene. In certain embodiments, a solvent is ether. In some embodiments, a solvent is a nitrile. In some embodiments, a solvent is acetonitrile.

In some embodiments, mixtures of two or more solvents are used, and in some cases may be preferred to a single solvent. In certain embodiments, the solvent mixture is a mixture of an ethereal solvent and a hydrocarbon. Exemplary such mixtures include, for instance, an ether/benzene mixture. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. In certain embodiments wherein a solvent mixture comprises an ethereal solvent and a hydrocarbon, the solvents may be present in a ratio of about 20:1, about 10:1, about 9:1, about 8:1, about 7:1, about 6:1, about 5:1, about 4:1, about 3:1, about 2:1, or about 1:1 ethereal solvent: hydrocarbon. In certain embodiments, the solvent mixture comprises a mixture of ether and benzene in a ratio of about 5:1. One of skill in the art would appreciate that other solvent mixtures and/or ratios are contemplated herein, that the selection of such other solvent mixtures and/or ratios will depend on the solubility of species present in the reaction (e.g., substrates, additives, etc.), and that experimentation required to optimized the solvent mixture and/or ratio would be routine in the art and not undue.

Suitable conditions, in some embodiments, employ ambient temperatures. In some embodiments, a suitable temperature is about 15° C., about 20° C., about 25° C., or about 30° C. In some embodiments, a suitable temperature is from about 15° C. to about 25° C. In certain embodiments, a suitable temperature is about 20° C., 21° C., 22° C., 23° C., 24° C., or 25° C.

In certain embodiments, a provided method is performed at elevated temperature. In some embodiments, a suitable temperature is from about 25° C. to about 110° C. In certain embodiments, a suitable temperature is from about 40° C. to about 100° C., from about 50° C. to about 100° C., from about 60° C. to about 100° C., from about 70° C. to about 100° C., from about 80° C. to about 100° C., or from about 90° C. to about 100° C. In some embodiments, a suitable temperature is about 80° C. In some embodiments, a suitable temperature is about 30° C. In some embodiments, a suitable temperature is about 40° C. In some embodiments, a suitable temperature is about 50° C. In some embodiments, a suitable temperature is about 60° C. In some embodiments, a suitable temperature is about 70° C. In some embodiments, a suitable temperature is about 80° C. In some embodiments, a suitable temperature is about 90° C. In some embodiments, a suitable temperature is about 100° C. In some embodiments, a suitable temperature is about 110° C.

In certain embodiments, a provided method is performed at temperature lower than ambient temperatures. In some embodiments, a suitable temperature is from about −100° C. to about 10° C. In certain embodiments, a suitable temperature is from about −80° C. to about 0° C. In certain embodiments, a suitable temperature is from about −70° C. to about 10° C. In certain embodiments, a suitable temperature is from about −60° C. to about 10° C. In certain embodiments, a suitable temperature is from about −50° C. to about 10° C. In certain embodiments, a suitable temperature is from about −40° C. to about 10° C. In certain embodiments, a suitable temperature is or from about −30° C. to about 10° C. In some embodiments, a suitable temperature is below 0° C. In some embodiments, a suitable temperature is about −100° C. In some embodiments, a suitable temperature is about −90° C. In some embodiments, a suitable temperature is about −80° C. In some embodiments, a suitable temperature is about −70° C. In some embodiments, a suitable temperature is about −60° C. In some embodiments, a suitable temperature is about −50° C. In some embodiments, a suitable temperature is about −40° C. In some embodiments, a suitable temperature is about −30° C. In some embodiments, a suitable temperature is about −20° C. In some embodiments, a suitable temperature is about −10° C. In some embodiments, a suitable temperature is about 0° C. In some embodiments, a suitable temperature is about 10° C.

In some embodiments, a provided method is performed at different temperatures. In some embodiments, temperature changes in a provided method. In some embodiments, a provided method involves temperature increase from a lower suitable temperature to a higher suitable temperature. In some embodiments, a provided method comprises temperature increase from about −80° C., about −70° C., about −60° C., about −50° C., about −40° C., about −30° C., about −20° C., about −10° C., and about 0° C. to about 0° C., about 10° C., about 20° C., ambient temperature, about 22° C., about 25° C., about 30° C., about 40° C., about 50° C., about 60° C., about 70° C., about 80° C., about 90° C., about 100° C. and about 110° C. In some embodiments, a provided method comprises temperature increase from about −30° C. to 22° C. In some embodiments, a provided method comprises temperature decrease from a higher suitable temperature to a lower suitable temperature. In some embodiments, a provided method comprises temperature increase from about 110° C., about 100° C., about 90° C., about 80° C., about 70° C., about 60° C., about 50° C., about 40° C., about 30° C., about 25° C., about 22° C., ambient temperature, about 20° C., about 10° C., and about 0° C. to about 0° C., about −10° C., about −20° C., about −30° C., about −40° C., about −50° C., about −60° C., about −70° C., about −80° C., about −90° C., and about −100° C.

Suitable conditions typically involve reaction times of about 1 minute to about one or more days. In some embodiments, the reaction time ranges from about 0.5 hour to about 20 hours. In some embodiments, the reaction time ranges from about 0.5 hour to about 15 hours. In some embodiments, the reaction time ranges from about 1.0 hour to about 12 hours. In some embodiments, the reaction time ranges from about 1 hour to about 10 hours. In some embodiments, the reaction time ranges from about 1 hour to about 8 hours. In some embodiments, the reaction time ranges from about 1 hour to about 6 hours. In some embodiments, the reaction time ranges from about 1 hour to about 4 hours. In some embodiments, the reaction time ranges from about 1 hour to about 2 hours. In some embodiments, the reaction time ranges from about 2 hours to about 8 hours. In some embodiments, the reaction time ranges from about 2 hours to about 4 hours. In some embodiments, the reaction time ranges from about 2 hours to about 3 hours. In certain embodiments, the reaction time is about 1, 2, 3, 4, 5, 6, 7, 8, 9, 10, 11, or 12, 24, 48, 96 or 120 hours. In some embodiments, the reaction time ranges from about 0.05 hour to about 5 hours. In some embodiments, the reaction time ranges from about 0.1 hour to about 2 hours. In certain embodiments, the reaction time is about 1 hour. In certain embodiments, the reaction time is about 2 hours. In certain embodiments, the reaction time is about 3 hours. In certain embodiments, the reaction time is about 4 hours. In certain embodiments, the reaction time is about 5 hours. In certain embodiments, the reaction time is about 6 hours. In some embodiments, the reaction time is about 12 hours. In some embodiments, the reaction time is about 24 hours. In some embodiments, the reaction time is about 48 hours. In some embodiments, the reaction time is about 96 hours. In some embodiments, the reaction time is about 120 hours. In certain embodiments, the reaction time is less than about 1 hour. In certain embodiments, the reaction time is about 5, 10, 15, 20, 25, 30, 35, 40, 45, 50, or 55 minutes. In some embodiments, the reaction time is about 5 minutes. In some embodiments, the reaction time is about 10 minutes. In some embodiments, the reaction time is about 15 minutes. In some embodiments, the reaction time is about 20 minutes. In some embodiments, the reaction time is about 25 minutes. In some embodiments, the reaction time is about 30 minutes. In some embodiments, the reaction time is about 35 minutes. In some embodiments, the reaction time is about 40 minutes. In some embodiments, the reaction time is about 100 minutes. In some embodiments, the reaction time is about 110 minutes. In some embodiments, the reaction time is about 200 minutes. In some embodiments, the reaction time is about 300 minutes. In some embodiments, the reaction time is about 400 minutes.

In some embodiments, a provided metal complex compound, e.g. a compound of formula I, or an active catalyst formed from a provided compound, is stable under metathesis conditions. In some embodiments, a provided compound, or an active catalyst formed from a provided compound, decomposes under metathesis conditions. In some embodiments, a provided compound, or an active catalyst formed from a provided compound, decomposes under metathesis conditions within about 1 hour. In some embodiments, a provided compound, or an active catalyst formed from a provided compound, decomposes under metathesis conditions within about 2 hours. In some embodiments, a provided compound, or an active catalyst formed from a provided compound, decomposes under metathesis conditions within about 6 hours. In some embodiments, a provided compound, or an active catalyst formed from a provided compound, decomposes under metathesis conditions within about 12 hours. In some embodiments, a provided compound, or an active catalyst formed from a provided compound, decomposes under metathesis conditions within about 24 hours. In some embodiments, a provided compound, or an active catalyst formed from a provided compound, decomposes under metathesis conditions within about 48 hours. In some embodiments, a provided compound, or an active catalyst formed from a provided compound, decomposes under metathesis conditions within about 96 hours.

Some embodiments may provide the ability to selectively synthesize, via a metathesis reaction, products having a Z or E configuration about a double bond. In some embodiments, a method of the present invention provides the ability to synthesize compounds comprising a Z-olefin. In some embodiments, such methods are useful when applied to a wide range of olefin substrates, including those having sterically small or large groups adjacent the olefin. In some embodiments, the substrate olefins are terminal olefins. In some embodiments, at least one substrate olefin is not a terminal olefin. In some embodiments, at least one substrate olefin is a sterically hindered olefin. In some embodiments, at least one substrate olefin has at least one allylic substituent.

In some embodiments, the present invention provides a method for Z-selective metathesis reactions. In some embodiments, a provided method produces a double bond in a Z:E ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC or NMR). In some cases, about 100% of the double bond produced in the metathesis reaction may have a Z configuration. The Z or cis selectivity may also be expressed as a percentage of product formed. In some cases, the product may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or, in some cases, greater than about 99.5% Z.

In some embodiments, a metathesis reaction using a compound of the present invention produces a polymer wherein the polymer is >50% cis, >50% syndiotactic. In some embodiments, a metathesis reaction using a compound of the present invention produces a polymer wherein the polymer is >60% cis, >60% syndiotactic. In some embodiments, a metathesis reaction using a compound of the present invention produces a polymer wherein the polymer is >70% cis, >70% syndiotactic. In some embodiments, a metathesis reaction using a compound of the present invention produces a polymer wherein the polymer is 80% cis, >80% syndiotactic. In some embodiments, a metathesis reaction using a compound of the present invention produces a polymer wherein the polymer is >90% cis, 90% syndiotactic. In some embodiments, a metathesis reaction using a compound of the present invention produces a polymer wherein the polymer is >95% cis, 90% syndiotactic. In some embodiments, a metathesis reaction using a compound of the present invention produces a polymer wherein the polymer is >99% cis, 90% syndiotactic. In some embodiments, a metathesis reaction using a compound of the present invention produces a polymer wherein the polymer is >90% cis, >95% syndiotactic. In some embodiments, a metathesis reaction using a compound of the present invention produces a polymer wherein the polymer is >95% cis, >95% syndiotactic. In some embodiments, a metathesis reaction using a compound of the present invention produces a polymer wherein the polymer is >99% cis, >90% syndiotactic. In some embodiments, a metathesis reaction using a compound of the present invention produces a polymer wherein the polymer is >99% cis, >95% syndiotactic. In some embodiments, a metathesis reaction using a compound of the present invention produces a polymer wherein the polymer is >99% cis, >97% syndiotactic. In some embodiments, a metathesis reaction using a compound of the present invention produces a polymer wherein the polymer is >99% cis, >99% syndiotactic.

In some embodiments, an ROMP product is greater than about 50% isotactic. In some embodiments, an ROMP product is greater than about 60% isotactic. In some embodiments, an ROMP product is greater than about 70% isotactic. In some embodiments, an ROMP product is greater than about 80% isotactic. In some embodiments, an ROMP product is greater than about 85% isotactic. In some embodiments, an ROMP product is greater than about 90% isotactic. In some embodiments, an ROMP product is greater than about 91% isotactic. In some embodiments, an ROMP product is greater than about 92% isotactic. In some embodiments, an ROMP product is greater than about 93% isotactic. In some embodiments, an ROMP product is greater than about 94% isotactic. In some embodiments, an ROMP product is greater than about 95% isotactic. In some embodiments, an ROMP product is greater than about 96% isotactic. In some embodiments, an ROMP product is greater than about 97% isotactic. In some embodiments, an ROMP product is greater than about 98% isotactic. In some embodiments, an ROMP product is greater than about 99% isotactic.

In some embodiments, an ROMP product is greater than about 50% cis. In some embodiments, an ROMP product is greater than about 60% cis. In some embodiments, an ROMP product is greater than about 70% cis. In some embodiments, an ROMP product is greater than about 80% cis. In some embodiments, an ROMP product is greater than about 85% cis. In some embodiments, an ROMP product is greater than about 90% cis. In some embodiments, an ROMP product is greater than about 91% cis. In some embodiments, an ROMP product is greater than about 92% cis. In some embodiments, an ROMP product is greater than about 93% cis. In some embodiments, an ROMP product is greater than about 94% cis. In some embodiments, an ROMP product is greater than about 95% cis. In some embodiments, an ROMP product is greater than about 96% cis. In some embodiments, an ROMP product is greater than about 97% cis. In some embodiments, an ROMP product is greater than about 98% cis. In some embodiments, an ROMP product is greater than about 99% cis.

In some embodiments, an ROMP product is greater than about 50% cis and greater than about 50% isotactic. In some embodiments, an ROMP product is greater than about 60% cis and greater than about 50% isotactic. In some embodiments, an ROMP product is greater than about 70% cis and greater than about 50% isotactic. In some embodiments, an ROMP product is greater than about 80% cis and greater than about 50% isotactic. In some embodiments, an ROMP product is greater than about 85% cis and greater than about 50% isotactic. In some embodiments, an ROMP product is greater than about 90% cis and greater than about 50% isotactic. In some embodiments, an ROMP product is greater than about 95% cis and greater than about 50% isotactic. In some embodiments, an ROMP product is greater than about 98% cis and greater than about 50% isotactic. In some embodiments, an ROMP product is greater than about 90% cis and greater than about 60% isotactic. In some embodiments, an ROMP product is greater than about 90% cis and greater than about 70% isotactic. In some embodiments, an ROMP product is greater than about 90% cis and greater than about 80% isotactic. In some embodiments, an ROMP product is greater than about 90% cis and greater than about 90% isotactic. In some embodiments, an ROMP product is greater than about 95% cis and greater than about 90% isotactic. In some embodiments, an ROMP product is greater than about 98% cis and greater than about 90% isotactic. In some embodiments, an ROMP product is greater than about 95% cis and greater than about 95% isotactic.

In some embodiments, a metathesis reaction using a compound of the present invention produces a polymer wherein the polymer is >50% cis, >50% isotactic. In some embodiments, a metathesis reaction using a compound of the present invention produces a polymer wherein the polymer is >60% cis, >60% isotactic. In some embodiments, a metathesis reaction using a compound of the present invention produces a polymer wherein the polymer is >70% cis, >70% isotactic. In some embodiments, a metathesis reaction using a compound of the present invention produces a polymer wherein the polymer is 80% cis, >80% isotactic. In some embodiments, a metathesis reaction using a compound of the present invention produces a polymer wherein the polymer is >90% cis, 90% isotactic. In some embodiments, a metathesis reaction using a compound of the present invention produces a polymer wherein the polymer is >95% cis, 90% isotactic. In some embodiments, a metathesis reaction using a compound of the present invention produces a polymer wherein the polymer is >99% cis, 90% isotactic. In some embodiments, a metathesis reaction using a compound of the present invention produces a polymer wherein the polymer is >90% cis, >95% isotactic. In some embodiments, a metathesis reaction using a compound of the present invention produces a polymer wherein the polymer is >95% cis, >95% isotactic. In some embodiments, a metathesis reaction using a compound of the present invention produces a polymer wherein the polymer is >99% cis, >90% isotactic. In some embodiments, a metathesis reaction using a compound of the present invention produces a polymer wherein the polymer is >99% cis, >95% isotactic. In some embodiments, a metathesis reaction using a compound of the present invention produces a polymer wherein the polymer is >99% cis, >97% isotactic. In some embodiments, a metathesis reaction using a compound of the present invention produces a polymer wherein the polymer is >99% cis, >99% isotactic.

In some embodiments, a provided method requires an amount of a provided compound (e.g., a metal complex having the structure of formula I) such that the loading is from about 0.0001 mol % to about 20 mol % of the provided compound relative to substrate (e.g., a first or second double bond). In certain embodiments, a provided compound is used in an amount of between about 0.0001 mol % to about 10 mol %. In certain embodiments, a provided compound is used in an amount of between about 0.001 mol % to about 6 mol %. In certain embodiments, a provided compound is used in an amount of between about 0.001 mol % to about 5 mol %. In certain embodiments, a provided compound is used in an amount of between about 0.001 mol % to about 4 mol %. In certain embodiments, a provided compound is used in an amount of between about 0.001 mol % to about 3 mol %. In certain embodiments, a provided compound is used in an amount of between about 0.001 mol % to about 1 mol %. In certain embodiments, a provided compound is used in an amount of between about 0.001 mol % to about 0.5 mol %. In certain embodiments, a provided compound is used in an amount of between about 0.001 mol % to about 0.2 mol %. In certain embodiments, a provided compound is used in an amount of about 0.0001 mol %, 0.0002 mol %, 0.0005 mol %, 0.001 mol %, 0.002 mol %, 0.005 mol %, 0.01 mol %, 0.02 mol %, 0.03 mol %, 0.04 mol %, 0.05 mol %, 0.1 mol %, 0.2 mol %, 0.5 mol %, 1 mol %, 2 mol %, 3 mol %, 4 mol %, 5 mol %, 6 mol %, 7 mol %, 8 mol %, 9 mol %, or 10 mol %. In some embodiments, a provided compound is used in an amount of about 0.0002% mol. In some embodiments, a provided compound is used in an amount of about 0.01% mol. In some embodiments, a provided compound is used in an amount of about 1% mol. In some embodiments, a provided compound is used in an amount of about 2% mol. In some embodiments, a provided compound is used in an amount of about 3% mol. In some embodiments, a provided compound is used in an amount of about 4% mol. In some embodiments, a provided compound is used in an amount of about 5% mol. In some embodiments, a provided compound is used in an amount of about 6% mol. In some embodiments, a provided compound is used in an amount of about 7% mol. In some embodiments, a provided compound is used in an amount of about 8% mol. In some embodiments, a provided compound is used in an amount of about 9% mol. A provided compound is used in an amount of no more than about 10%. In some embodiments, a provided compound is used in an amount of no more than about 8%. In some embodiments, a provided compound is used in an amount of no more than about 6%. In some embodiments, a provided compound is used in an amount of no more than about 5%. In some embodiments, a provided compound is used in an amount of no more than about 4%. In some embodiments, a provided compound is used in an amount of no more than about 3%. In some embodiments, a provided compound is used in an amount of no more than about 2%. In some embodiments, a provided compound is used in an amount of no more than about 1%. In some embodiments, a provided compound is used in an amount of no more than about 0.5%. In some embodiments, a provided compound is used in an amount of no more than about 0.2%. In some embodiments, a provided compound is used in an amount of no more than about 0.1%. In some embodiments, a provided compound is used in an amount of no more than about 0.05%. In some embodiments, a provided compound is used in an amount of no more than about 0.02%. In some embodiments, a provided compound is used in an amount of no more than about 0.01%. In some embodiments, a provided compound is used in an amount of no more than about 0.005%. In some embodiments, a provided compound is used in an amount of no more than about 0.002%. In some embodiments, a provided compound is used in an amount of no more than about 0.001%. In some embodiments, a provided compound is used in an amount of no more than about 0.0005%. In some embodiments, a provided compound is used in an amount of no more than about 0.0002%. In some embodiments, a provided compound is used in an amount of no more than about 0.0001%.

In some embodiments, a method of the present invention requires an amount of solvent such that the concentration of the reaction is between about 0.01 M and about 1 M. In some embodiments, the concentration of the reaction is between about 0.01 M and about 0.5 M. In some embodiments, the concentration of the reaction is between about 0.01 M and about 0.1 M. In some embodiments, the concentration of the reaction is between about 0.01 M and about 0.05 M. In some embodiments, the concentration of the reaction is about 0.01 M. In some embodiments, the concentration of the reaction is about 0.02 M. In some embodiments, the concentration of the reaction is about 0.03 M. In some embodiments, the concentration of the reaction is about 0.04 M. In some embodiments, the concentration of the reaction is about 0.05 M. In some embodiments, the concentration of the reaction is about 0.1 M. In some embodiments, the concentration of the reaction is about 0.3 M.

In some embodiments, a method of the present invention is performed at ambient pressure. In some embodiments, a method of the present invention is performed at reduced pressure. In some embodiments, a method of the present invention is performed at a pressure of less than about 20 torr. In some embodiments, a method of the present invention is performed at a pressure of less than about 15 torr. In some embodiments, a method of the present invention is performed at a pressure of less than about 10 torr. In some embodiments, a method of the present invention is performed at a pressure of about 9, 8, 7, 6, 5, 4, 3, 2, or 1 torr. In certain embodiments, a method of the present invention is performed at a pressure of about 7 torr. In certain embodiments, a method of the present invention is performed at a pressure of about 1 torr.

In some embodiments, a method of the present invention is performed at increased pressure. In some embodiments, a method of the present invention is performed at greater than about 1 atm. In some embodiments, a method of the present invention is performed at greater than about 2 atm. In some embodiments, a method of the present invention is performed at greater than about 3 atm. In some embodiments, a method of the present invention is performed at greater than about 5 atm. In some embodiments, a method of the present invention is performed at greater than about 10 atm. In some embodiments, a method of the present invention is performed at about 2 atm. In some embodiments, a method of the present invention is performed at about 3 atm. In some embodiments, a method of the present invention is performed at about 5 atm. In some embodiments, a method of the present invention is performed at about 10 atm.

As mentioned above, provided compounds are useful for metathesis reactions.

Exemplary such methods and reactions are described below.

In some embodiments, the present invention provides the following exemplary compounds and methods:

1. A compound of formula I:

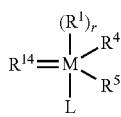

I wherein:
M is a metal selected from Group VIII;
each of $R^1$ and L is independently a neutral ligand;
r is 1-3;
each of $R^4$ and $R^5$ is independently bonded to M through an oxygen, nitrogen, sulfur, phosphorus or selenium atom;
$R^{14}$ is a carbene;
$R^4$ and $R^5$ are taken together to form a bidentate ligand, or $R^4$ and $R^5$ are taken together with one or more of $R^1$, L and $R^{14}$ to form a polydentate ligand;
two or more of $R^1$, L and $R^{14}$ are optionally taken together to form a bidentate or polydentate ligand; and
each of $R^1$, $R^4$, $R^5$, L and $R^{14}$ is independently and optionally linked to a tag or support.

2. The compound of example 1, wherein the compound has the structure of formula I-a:

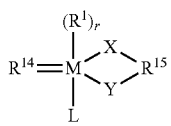

I-a wherein:
M is a metal selected from Group VIII;
each of $R^1$ and L is independently a neutral ligand;
r is 1-3;
each of X and Y is independently —O—, —S—, —Se—, —OC(O)—, —OC(S)—, —SC(O)—, —SC(S)—, —P($R^x$)—, —P(O)($R^x$)—, or —N($R^x$)—;
$R^{14}$ is a carbene;
$R^{15}$ is —$B^x$—, or an optionally substituted bivalent $C_{1-20}$ aliphatic or $C_{1-20}$ heteroaliphatic group, wherein 0-6 methylene units are optionally and independently replaced by —O—, —N(R')—, —S—, —C(O)—, —OC (O)—, —C(O)O—, —OC(O)O—, —C(S)—, —OC(S)—, —SC(O)—, —SC(S)—, —S(O)—, —S(O)$_2$—, —OS(O)$_2$O—, —N(R')C(O)—, —C(O)N(R')—, —N(R') C(O)O—, —OC(O)N(R')—, —N(R')C(O)N(R')—, —P($R^x$)—, —P(O)($R^x$)—, or -$Cy^1$-;

each -$Cy^1$- is independently:
a bivalent optionally substituted monocyclic ring independently selected from phenylene, a 3-8 membered saturated or partially unsaturated carbocyclylene, a 5-6 membered heteroarylene having 1-4 heteroatoms independently selected from nitrogen, oxygen, or sulfur, or a 3-8 membered saturated or partially unsaturated heterocyclylene having 1-4 heteroatoms independently selected from nitrogen, oxygen, or sulfur; or
a bivalent optionally substituted bicyclic or polycyclic ring independently selected from an 8-14 membered arylene, a 7-14 membered saturated or partially unsaturated carbocyclylene, an 8-14 membered heteroarylene having 1-5 heteroatoms independently selected from nitrogen, oxygen, or sulfur, or a 7-14 membered saturated or partially unsaturated heterocyclylene having 1-5 heteroatoms selected from nitrogen, oxygen, or sulfur;

$B^x$ is:

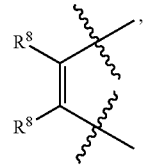

B1

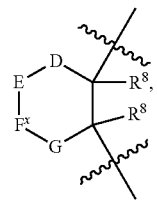

B2

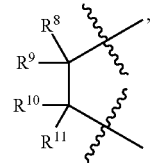

B3

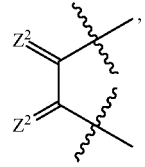

B4

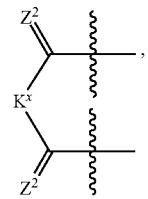

B5

-continued

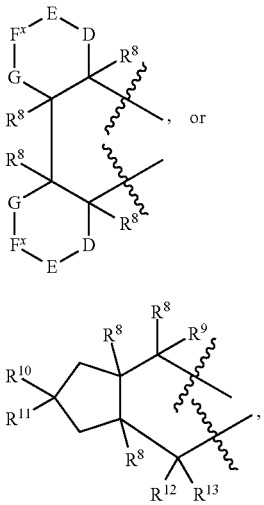

wherein:
each $Z^2$ is independently $=C(R)_2$, $=O$, $=S$, $=Se$, $=N(R^x)$, $=P(R^x)$, $=C=O$, $=C=S$, $=S=O$, or $=Se=O$;
each of D, E, $F^x$, G is independently —$N(R^8)$—, —$C(R^8)_2$—, —S—, —O—, —$P(R^8)$—, —Se—, —C(O)—, —S(O)—, or —Se(O)—;
each of $R^8$, $R^9$, $R^{10}$, $R^{11}$, $R^{12}$, and $R^{13}$ is independently $R^x$, or
  one $R^8$, $R^9$, R, $R^{11}$, $R^{12}$, or $R^{13}$ is independently taken together with another $R^8$, $R^9$, $R^{10}$, $R^{11}$, $R^{12}$, or $R^{13}$ on the same atom to form a $=C(R^x)_2$, $=N(R^x)$, $=P(R^x)$, $=O$, $=S$, or $=Se$ group; or
  one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ on an adjacent atom to form a double bond; or
  one $R^8$, $R^9$, $R^{10}$, $R^{11}$, $R^{12}$, or $R^{13}$ is independently taken together with another $R^8$, $R^9$, $R^{10}$, $R^{11}$, $R^{12}$, or $R^{13}$ and their intervening atoms to form an optionally substituted 3-10 membered, saturated, partially unsaturated, or aryl ring having, in addition to the intervening atoms, 0-4 heteroatoms; and
$K^x$ is an optionally substituted bivalent $C_{1-20}$ aliphatic or $C_{1-20}$ heteroaliphatic group, wherein 0-6 methylene units are optionally and independently replaced by —O—, —N(R')—, —S—, —C(O)—, —OC(O)—, —C(O)O—, —OC(O)O—, —C(S)—, —OC(S)—, —SC(O)—, —SC(S)—, —S(O)—, —$S(O)_2$—, —$OS(O)_2O$—, —N(R')C(O)—, —C(O)N(R')—, —N(R')C(O)O—, —OC(O)N(R')—, —N(R')C(O)N(R')—, —$P(R^x)$—, —$P(O)(R^x)$—, or -$Cy^1$-;
each $R^x$ is independently halogen, R, —CN, —C(O)N(R')$_2$, —C(O)R, —C(O)OR, —OR, —OC(O)R, —OC(O)OR, —OC(O)N(R')$_2$, —OSi(R)$_3$, —N(R')$_2$, —N(R')$_3^+$, —NR'C(O)R, —NR'C(O)OR, —NR'C(O)N(R')$_2$, —NR'SO$_2$R, —NR'SO$_2$N(R')$_2$, —NR'OR, —NO$_2$, —Si(R)$_3$, —P(R)$_2$, —P(O)(R)$_2$, —P(O)(OR)$_2$, —SR, —SC(O)R, —S(O)R, —SO$_2$R, —SO$_3$R, —SO$_2$N(R')$_2$, or —SeR;
each R' is independently R, —C(O)R, —C(O)N(R)$_2$, —C(O)OR, —SO$_2$R, —SO$_2$N(R)$_2$, —P(O)(OR)$_2$, or —OR; and
each R is independently hydrogen or an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:
  two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;
two or more of $R^1$, —X—$R^{15}$—Y—, L and $R^{14}$ are optionally taken together to form a bidentate or polydentate ligand; and
each of $R^1$, X, $R^{15}$, Y, L and $R^{14}$ is independently and optionally linked to a tag or support.

3. The compound of any one of the preceding examples, wherein $R^{14}$ and L are covalently linked.

4. The compound of any one of the preceding examples, wherein $R^{14}$ and L are taken together to form a bidentate ligand.

5. The compound of any one of the preceding examples, wherein the compound has the structure of formula I':

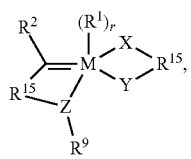

wherein:
each of $R^2$ and $R^9$ is independently $R^x$; and
Z is —O—, —S—, —Se—, —$N(R^x)$—, —N=, —$P(R^x)$—, —C(O)—, —C(S)—, —S(O)—, or —Se(O)—, or —Z—$R^9$ is halogen.

6. The compound of example 2, wherein the compound has the structure of formula I":

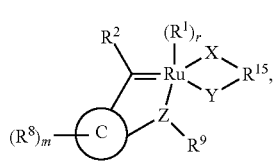

wherein:
each of $R^2$, $R^8$, and $R^9$ is independently $R^x$;
Ring C is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;

m is 0-6; and

Z is —O—, —S—, —Se—, —N(R$^x$)—, —N═, —P(R$^x$)—, —C(O)—, —C(S)—, —S(O)—, or —Se(O)—, or —Z—R$^9$ is halogen.

7. The compound of example 1, wherein the compound has the structure of formula I-b:

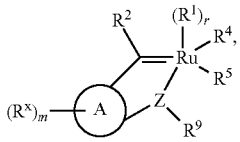

wherein:

each of R$^2$ and R$^9$ is independently R$^x$;

Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur.

8. The compound of any one of the preceding examples, wherein Z is —O—, —S—, —Se—, —N(R$^x$)—, —N═, —P(R$^x$)—, —C(O)—, —C(S)—, —S(O)—, or —Se(O)—, and R$^9$ is R$^x$.

9. The compound of any one of the preceding examples, wherein —Z—R$^9$ is halogen.

10. The compound of example 7, wherein the compound has the structure of formula I-c:

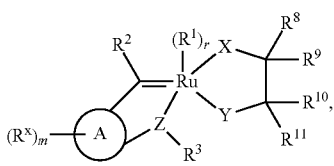

each of R$^8$, R$^9$, R$^{10}$, R$^{11}$, R$^{12}$, and R$^{13}$ is independently R$^x$, or one R$^8$, R$^9$, R$^{10}$, R$^{11}$, R$^{12}$, or R$^{13}$ is independently taken together with another R$^8$, R$^9$, R$^{10}$, R$^{11}$, R$^{12}$, or R$^{13}$ on the same atom to form a ═C(R$^x$)$_2$, ═N(R$^x$), ═P(R$^x$), ═O, ═S, or ═Se group; or one R$^8$, R$^9$, R$^{10}$, R$^{11}$, R$^{12}$, or R$^{13}$ is independently taken together with another R$^8$, R$^9$, R$^{10}$, R$^{11}$, R$^{12}$, or R$^{13}$ on an adjacent atom to form a double bond; or one R$^8$, R$^9$, R$^{10}$, R$^{11}$, R$^{12}$, or R$^{13}$ is independently taken together with another R$^8$, R$^9$, R$^{10}$, R$^{11}$, R$^{12}$, or R$^{13}$ and their intervening atoms to form an optionally substituted 3-10 membered, saturated, partially unsaturated, or aryl ring having, in addition to the intervening atoms, 0-4 heteroatoms; and R$^3$ is hydrogen or an optionally substituted group selected from C$_{1-20}$ aliphatic, C$_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur; or —Z—R$^3$ is halogen.

11. The compound of example 7, wherein the compound has the structure of formula I-c:

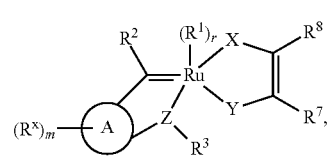

wherein:

each of R$^6$ and R$^7$ is independently R, —CN, halogen, —OR, —OC(O)R, —OSi(R)$_3$, —SR, —S(O)R, —S(O)$_2$R, —NO$_2$, —N(R')$_2$, —NR'C(O)R, —NR'C(O)OR, —NR'C(O)N(R')$_2$, —NR'SO$_2$R, —NR'SO$_2$N(R')$_2$, —NR'OR, —SeR, —Si(R)$_3$, or:

R$^6$ and R$^7$ are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur.

12. The compound of example 7, wherein the compound has the structure of formula I-d:

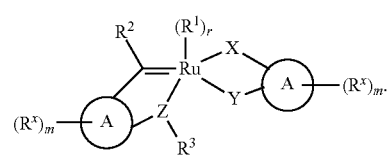

13. The compound of example 7, wherein the compound has the structure of formula I-e:

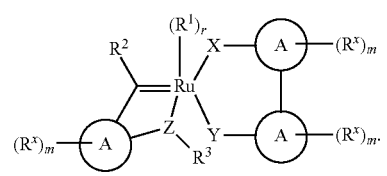

14. The compound of example 7, wherein the compound has the structure of formula I-f:

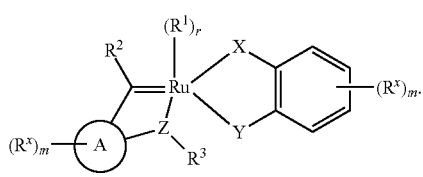

I-f

15. The compound of example 14, wherein the compound has the structure of formula I-g:

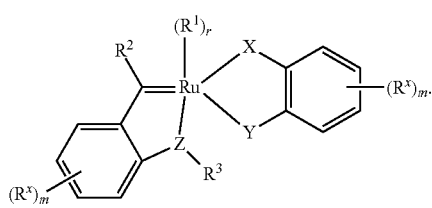

I-g

16. The compound of any one of examples 10-15, wherein —Z—R$^3$ is halogen.
17. The compound of example 1 or 7, wherein R$^4$ and R$^5$ are taken together to form a bidentate ligand.
18. The compound of example 1 or 7, wherein at least one of R$^4$ and R$^5$ is bonded to M through —S—.
19. The compound of example 1 or 7, wherein each of R$^4$ and R$^5$ is bonded to M through —S—.
20. The compound of any one of the preceding examples, wherein r is 1.
21. The compound of any one of the preceding examples, wherein at least one R$^1$ is a carbene.
22. The compound of any one of the preceding examples, wherein R$^1$ is NHC.
23. The compound of any one of the preceding examples, wherein R$^2$ is hydrogen.
24. The compound of any one of the preceding examples, wherein Z is —O—, —S—, =N—, —C(O)—, —S(O)— or —N(R$^x$)—.
25. The compound of any one of the preceding examples, wherein Z is —O—.
26. The compound of any one of the preceding examples, wherein Z is —S—.
27. The compound of any one of the preceding examples, wherein at least one of X and Y is —S—.
28. The compound of any one of the preceding examples, wherein each of X and Y is —S—.
29. The compound of any one of the preceding examples, wherein R$^4$ and L are taken together to form a bidentate ligand having the structure of

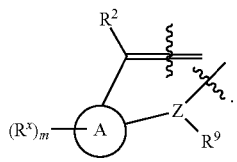

30. The compound of any one of the preceding examples, wherein R$^4$ and L are taken together to form a bidentate ligand having the structure of

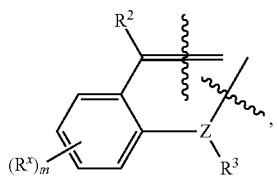

wherein m is 0-4.

31. The compound of any one of the preceding examples, wherein R$^4$ and R$^5$ are taken together to form a bidentate ligand having the structure of

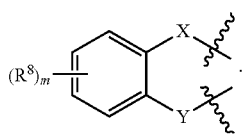

32. The compound of any one of the preceding examples, wherein R$^4$ and R$^5$ are taken together to form optionally substituted

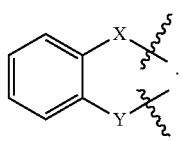

33. The compound of any one of the preceding examples, wherein R$^4$ and R$^5$ are taken together to form

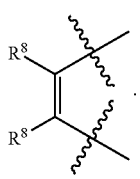

34. The compound of example 1, wherein the compound is selected from

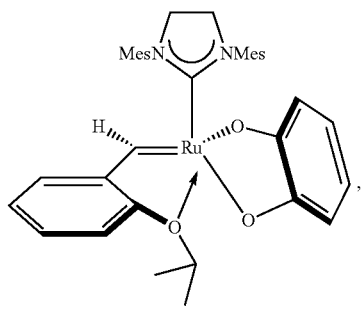

191
-continued
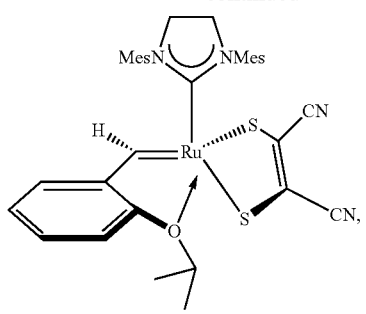
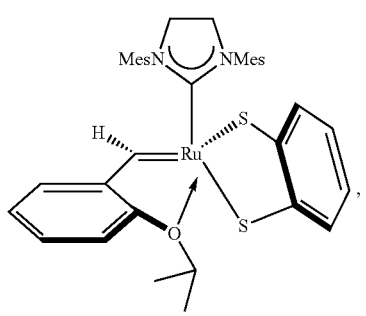
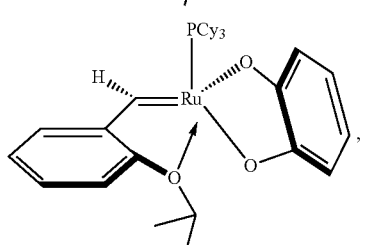
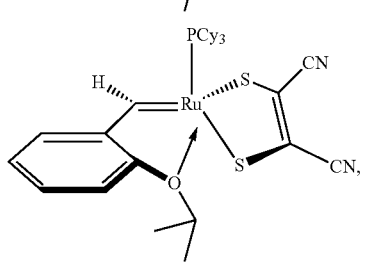
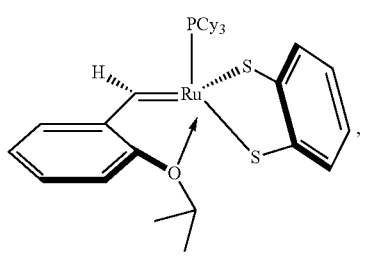
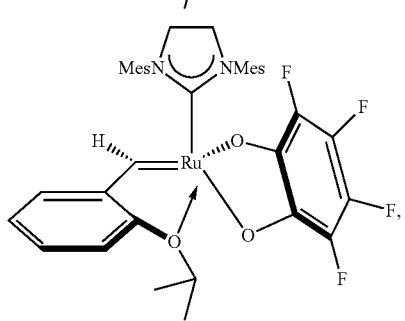
192
-continued
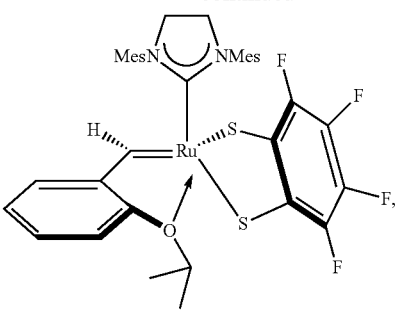
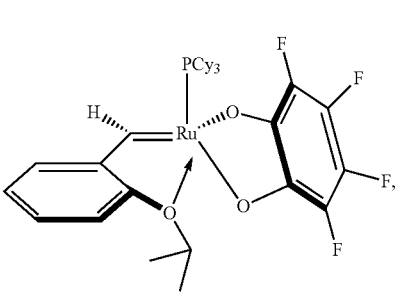
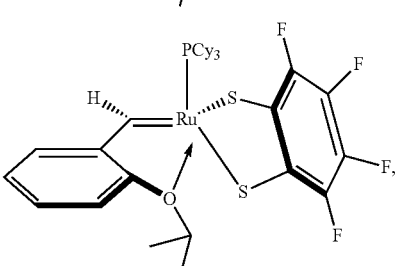
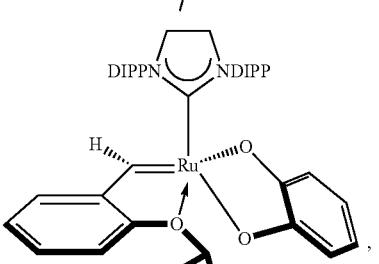
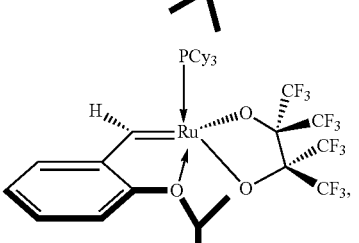
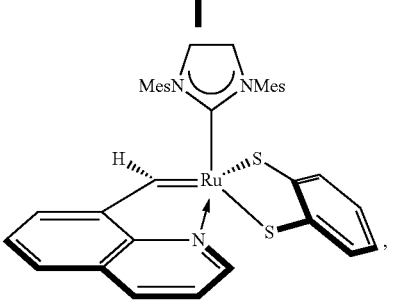

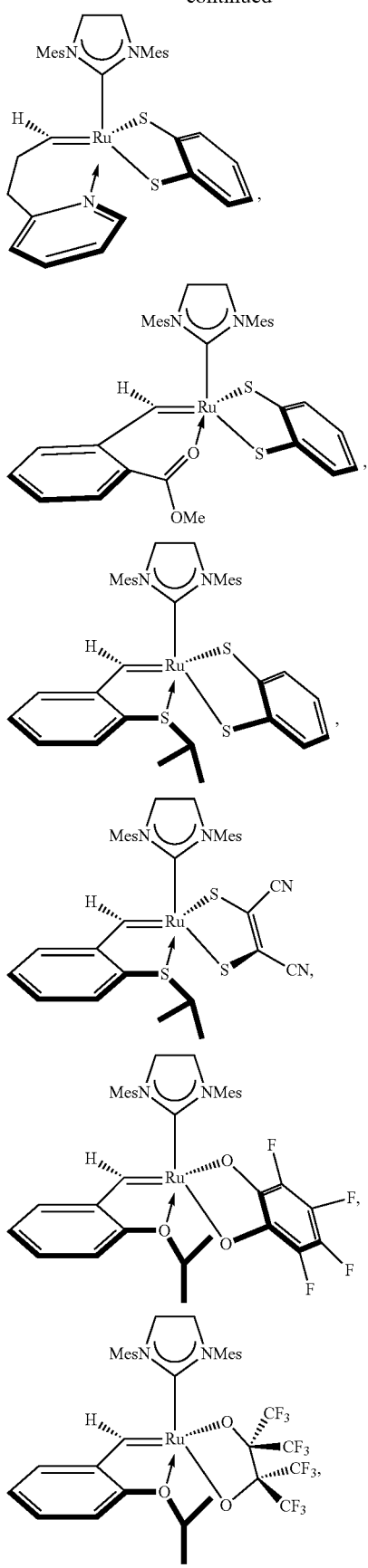
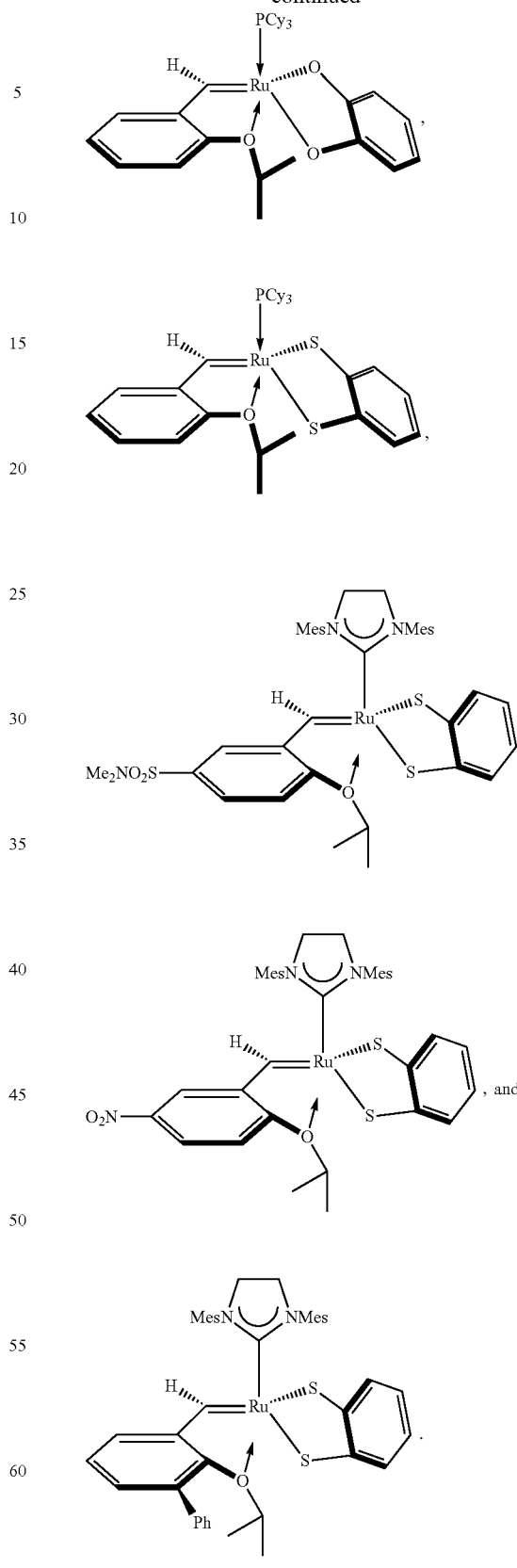
35. The compound of example 1, wherein the compound is selected from

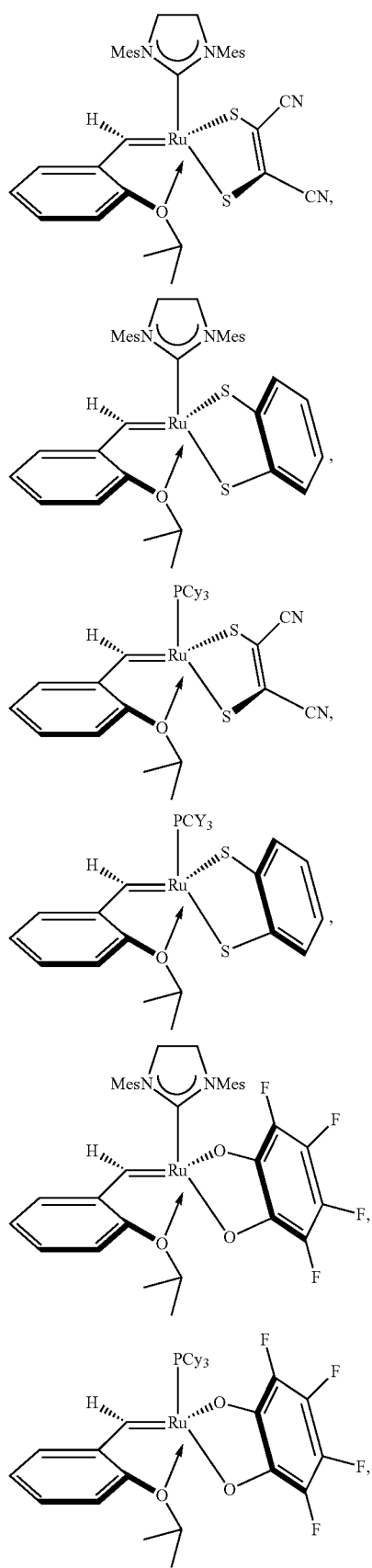
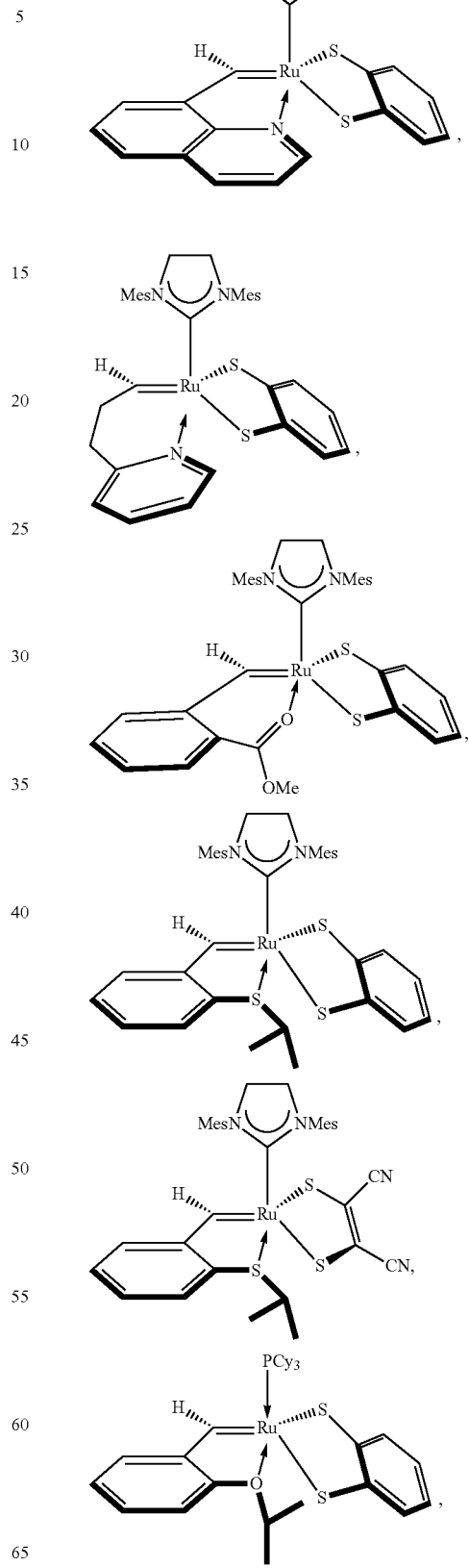

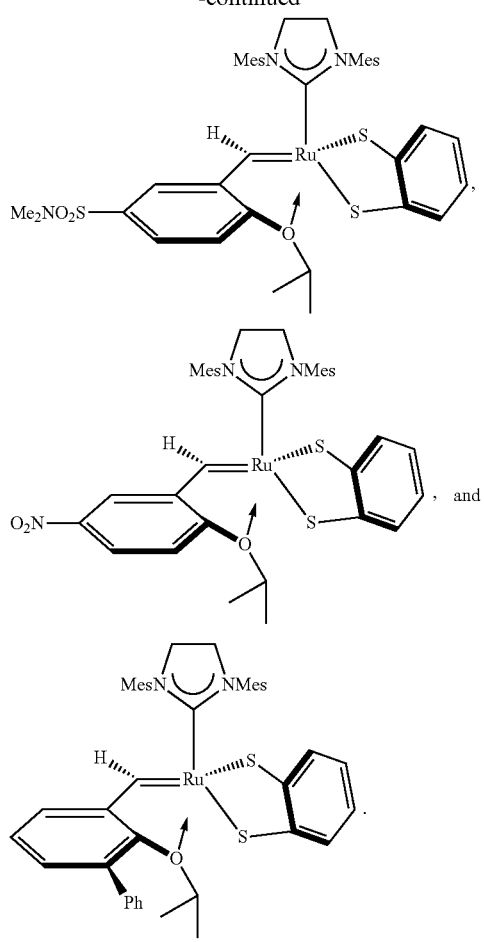
36. The compound of example, wherein the compound is selected from:
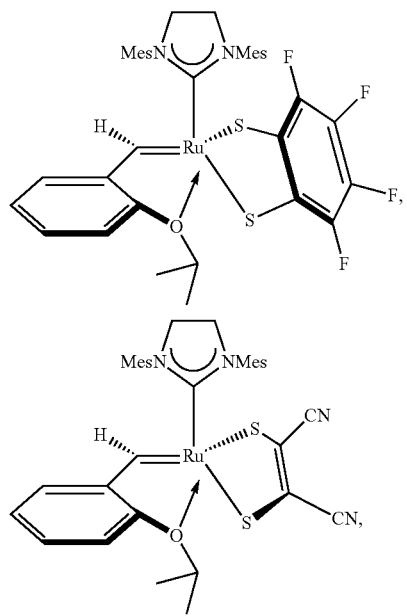
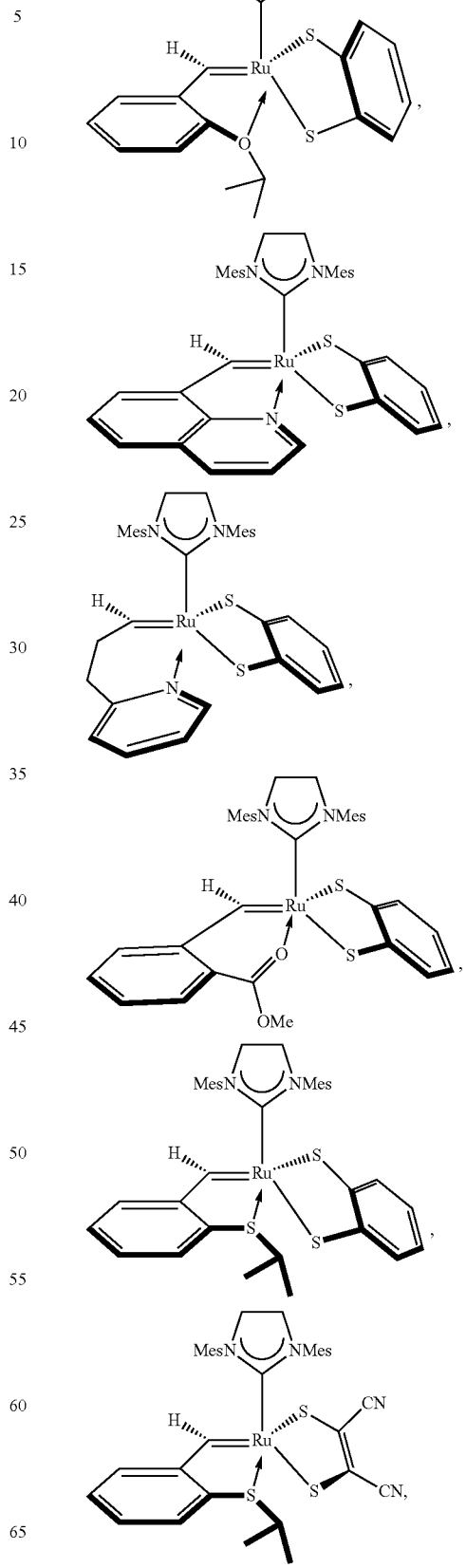

-continued

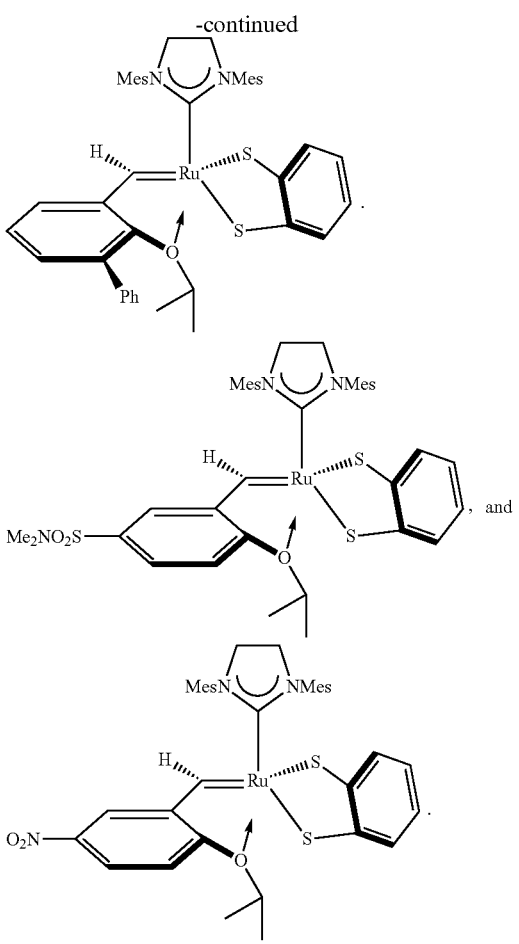

37. The compound of any of the preceding examples, wherein the compound, when used in a ROMP reaction, has a TON greater than about 10,000.
38. The compound of any of the preceding examples, wherein the compound, when used in a ROMP reaction, has a TON greater than about 40,000.
39. The compound of any of the preceding examples, wherein the compound, when used in a ROMP reaction, provides greater than 50% conversion at 0.1 mol % loading.
40. The compound of any of the preceding examples, wherein the compound, when used in a ROMP reaction, provides greater than 50% conversion at 0.05 mol % loading.
41. The compound of any of the preceding examples, wherein the compound, when used in a ROMP reaction, provides greater than 50% conversion at 0.01 mol % loading.
42. The compound of any of the preceding examples, wherein the compound, when used in a ROMP reaction, provides greater than 90% conversion at 0.1 mol % loading.
43. The compound of any of the preceding examples, wherein the compound, when used in a ROMP reaction, provides greater than 90% conversion at 0.05 mol % loading.
44. The compound of any of the preceding examples, wherein the compound, when used in a ROMP reaction, provides greater than 90% conversion at 0.01 mol % loading.
45. The compound of any of the preceding examples, wherein the compound, when used in a ROMP reaction, provides greater than 90% conversion at 0.005 mol % loading.
46. The compound of any of the preceding examples, wherein the compound, when used in a ROMP reaction, provides greater than 95% conversion at 0.005 mol % loading.
47. The compound of any one of examples 37-46, wherein the ROMP reaction is ROMP of norbornene.
48. The compound of any one of the preceding examples, wherein the compound, when used in a metathesis reaction, tolerates unprotected hydroxyl group.
49. The compound of any one of the preceding examples, wherein the compound provides >50% conversion in 24 hours in ROCM between norbornene and vinyl cyclohexane with 1.0 mol % catalyst loading.
50. The compound of any one of the preceding examples, wherein the compound provides >50% conversion in 2 hours in ROCM between norbornene and vinyl cyclohexane with 1.0 mol % catalyst loading.
51. The compound of any one of the preceding examples, wherein the compound provides >80% conversion in 2 hours in ROCM between norbornene and vinyl cyclohexane with 1.0 mol % catalyst loading.
52. The compound of any one of the preceding examples, wherein the compound provides >95% conversion in 2 hours in ROCM between norbornene and vinyl cyclohexane with 1.0 mol % catalyst loading.
53. A method for preparing a compound of any one of examples 1-52 and 92-104, comprising providing a compound having the structure of formula II:

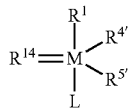

wherein each of $R^{4'}$ and $R^{5'}$ is independently halogen or —OR.

54. The method of example 53, further comprising a step of reacting the compound of formula II with a ligand or ligand precursor to replace $R^{4'}$ and $R^{5'}$ with $R^4$ and $R^5$.
55. The method of example 53, comprising steps of:
    a) providing a first compound of formula II, wherein $R^1$ is a phosphine ligand;
    b) optionally reacting the first compound of formula II with a ligand or ligand precursor to replace the phosphine ligand with $R^1$ to produce a second compound; and
    c) reacting the second compound with a ligand or ligand precursor to replace $R^{4'}$ and $R^{5'}$ with $R^4$ and $R^5$ to produce a compound of formula I.
56. The method of example 53, comprising steps of:
    a) providing a first compound of formula II, wherein $R^1$ is a phosphine ligand;
    b) reacting the first compound of formula II with a ligand or ligand precursor to replace $R^{4'}$ and $R^{5'}$ with $R^4$ and $R^5$ to produce a second compound; and
    c) optionally reacting the second compound with a ligand or ligand precursor to replace the phosphine ligand with $R^1$ to produce a compound for formula I.

57. The method of example 53, comprising steps of:
   a) providing a first compound of formula II;
   b) reacting the first compound of formula II with a ligand or ligand precursor to replace $R^{4'}$ and/or $R^{5'}$ with two other ligands to produce a second compound; and
   c) reacting the second compound with a ligand or ligand precursor to replace the two other ligands with $R^4$ and $R^5$ to produce a compound for formula I.

58. The method of example 53, comprising steps of:
   a) providing a first compound of formula II, wherein $R^1$ is a phosphine ligand;
   b) reacting the first compound of formula II with a ligand or ligand precursor to replace $R^{4'}$ and/or $R^{5'}$ with two other ligands to produce a second compound;
   c) reacting the second compound with a ligand or ligand precursor to replace the two other ligands with $R^4$ and $R^5$ to produce a third compound; and
   d) reacting the third compound with a ligand or ligand precursor to replace the phosphine ligand with $R^1$.

59. The method of example 53, comprising steps of:
   a) providing a first compound of formula II, wherein $R^1$ is a phosphine ligand;
   b) reacting the first compound of formula II with a ligand or ligand precursor to replace $R^{4'}$ and/or $R^{5'}$ with two other ligands to produce a second compound;
   c) optionally reacting the second compound with a ligand or ligand precursor to replace the phosphine ligand with $R^1$ to produce a third compound; and
   d) reacting the third compound with a ligand or ligand precursor to replace the two other ligands with $R^4$ and $R^5$.

60. The method of example 53, comprising steps of:
   a) providing a first compound having the structure of formula III:

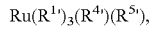   III wherein:
      each $R^{1'}$ is independently a phosphine ligand; and
      each of $R^{4'}$ and $R^{5'}$ is independently as defined above and described herein;
   b) reacting the first compound of formula III with a ligand or ligand precursor to replace $R^{4'}$ and $R^{5'}$ with $R^4$ and $R^5$ to produce a second compound;
   c) reacting the second compound with a ligand or ligand precursor to replace two $R^{1'}$ with $R^4$ and L; and
   d) optionally reacting the third compound with a ligand or ligand precursor to replace $R^{1'}$ with $R^1$.

61. The method of any one of examples 53-60, wherein each of $R^{4'}$ and $R^{5'}$ is independently halogen.

62. The method of any one of examples 53-61, wherein each of $R^{4'}$ and $R^{5'}$ is independently —Cl.

63. The method of any one of examples 53-61, wherein each of $R^{4'}$ and $R^{5'}$ is independently —OR.

64. A method for performing a metathesis reaction, comprising providing a compound of any one of examples 1-52 and 92-104.

65. The method of example 64, wherein the metathesis reaction is ROMP.

66. The method of example 64, wherein the metathesis reaction is cross metathesis.

67. The method of example 64, wherein the metathesis reaction is ROCM.

68. The method of example 64, wherein the metathesis reaction is ring closing metathesis.

69. The method of any one of examples 64-68, wherein the provided compound has a TON greater than about 500.

70. The method of any one of examples 64-69, wherein the provided compound has a TON greater than about 1,000.

71. The method of any one of examples 64-70, wherein the provided compound has a TON greater than about 5,000.

72. The method of any one of examples 64-71, wherein the provided compound has a TON greater than about 10,000.

73. The method of any one of examples 64-72, wherein the provided compound has a TON greater than about 20,000.

74. The method of any one of examples 64-73, wherein the provided compound has a TON greater than about 40,000.

75. The method of any one of examples 64-74, wherein the provided compound is used at 0.1 mol % loading, and the metathesis reaction has a conversion greater than 50%.

76. The method of any one of examples 64-75, wherein the provided compound is used at 0.05 mol % loading, and the metathesis reaction has a conversion greater than 50%.

77. The method of any one of examples 64-76, wherein the provided compound is used at 0.01 mol % loading, and the metathesis reaction has a conversion greater than 50%.

78. The method of any one of examples 64-76, wherein the provided compound is used at 0.05 mol % loading, and the metathesis reaction has a conversion greater than 90%.

79. The method of any one of examples 64-76, wherein the provided compound is used at 0.01 mol % loading, and the metathesis reaction has a conversion greater than 90%.

80. The method of any one of examples 64-76, wherein the provided compound is used at 0.005 mol % loading, and the metathesis reaction has a conversion greater than 90%.

81. The method of any one of examples 64-80, wherein the reaction time is less than about 24 hours.

82. The method of any one of examples 64-81, wherein the reaction time is less than about 12 hours.

83. The method of any one of examples 64-82, wherein the reaction time is less than about 6 hours.

84. The method of any one of examples 64-83, wherein the reaction is Z-selective.

85. The method of any one of examples 64-84, wherein the product is greater than 50:50 Z:E.

86. The method of any one of examples 64-85, wherein the product is greater than 60:40 Z:E.

87. The method of any one of examples 64-86, wherein the product is greater than 70:30 Z:E.

88. The method of any one of examples 64-87, wherein the product is greater than 80:20 Z:E.

89. The method of any one of examples 64-88, wherein the product is greater than 90:10 Z:E.

90. The method of any one of examples 64-89, wherein the product is greater than 95:5 Z:E.

91. The method of any one of examples 64-90, wherein the method tolerates unprotected hydroxyl group.

92. The compound of any one of examples 1-52, wherein $R^1$ is an NHC having the structure of

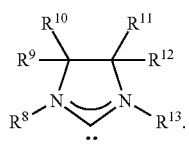

93. The compound of any one of examples 1-52 and 92, wherein $R^1$ is an NHC having the structure of

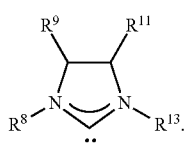
94. The compound of any one of examples 1-52 and 92-93, wherein R¹ is optionally substituted
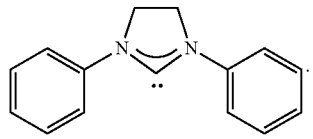
95. The compound of any one of examples 1-52 and 92, wherein R¹ is an NHC having the structure of
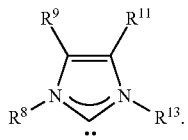
96. The compound of any one of examples 1-33, 37-52 and 92-94, wherein the compound is selected from:
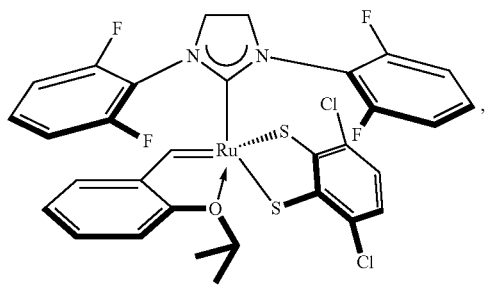
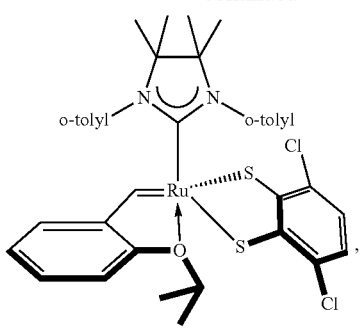
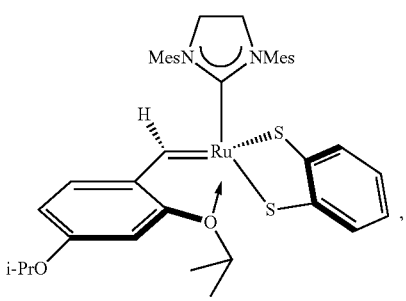
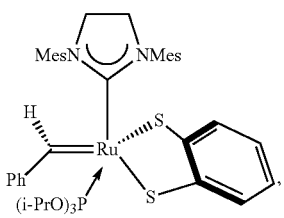
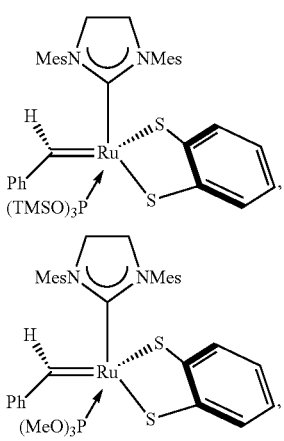
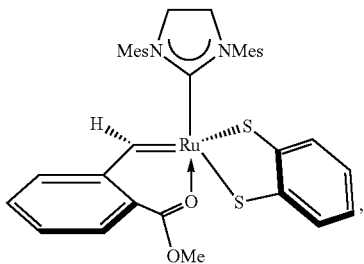

-continued

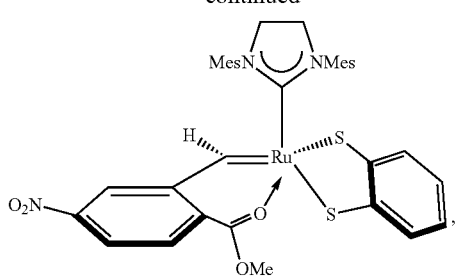

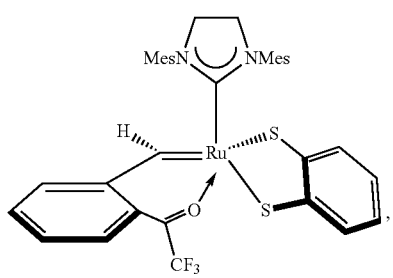

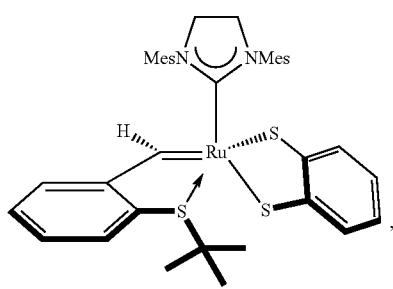

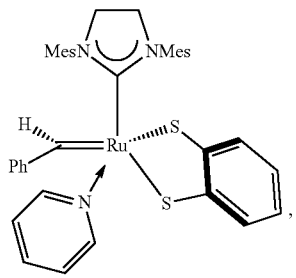

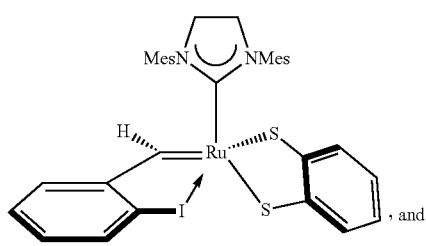, and

-continued

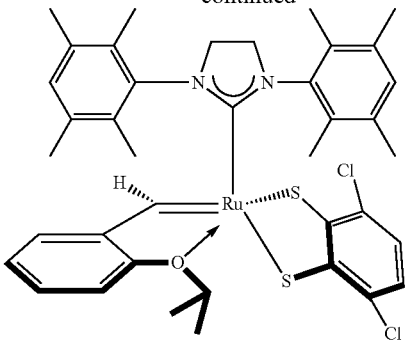

97. The compound of any one of examples 1-52 and 92-96, wherein the compound is dimerized or polymerized.
98. The compound of any one of examples 1-52 and 92-97, wherein M is Ru.
99. The compound of any one of examples 1-52 and 92-98, wherein the compound is linked to a tag.
100. The compound of any one of examples 1-52 and 92-98, wherein the compound is linked to a support.
101. The compound of example 99 or 100, wherein the compound is linked via a linker.
102. The compound of example 100, wherein the support is selected from silicas, silicates, aluminas, aluminum oxides, silica-aluminas, aluminosilicates, zeolites, titanias, titanium dioxide, magnetite, magnesium oxides, boron oxides, clays, zirconias, zirconium dioxide, carbon, polymers, cellulose, cellulosic polymers amylose, amylosic polymers, or a combination thereof.
103. The compound of example 100, wherein the support is selected from SEPHAROSE, glass beads, magnetic beads, polystyrene, or polystyrene-divinylbenzene polymer (PS-DVB).
104. The compound of any one of examples 1-52 and 92-98, wherein the compound is not linked to a tag or solid support.
105. A method for preparing a compound of any one of examples 1-52 and 92-104, comprising steps of:
  a) providing a first compound of formula I; and
  b) replacing the $R^{14}$ and L groups of the first compound to provide a second compound of formula I, wherein the first compound and the second compound are different.
106. The method of example 105, wherein $R^{14}$ and L are covalently linked.
107. The method of any one of examples 64-91, wherein the product is greater than about 98:2 Z:E.
108. The method of any one of examples 64-91 and 107, wherein one substrate of the metathesis reaction is an aliphatic olefin.
109. The method of any one of examples 64-91 and 107, wherein one substrate of the metathesis reaction is a heteroaryl olefin.
110. The method of any one of examples 64-91 and 107, wherein one substrate of the metathesis reaction is a heteroaryl olefin, wherein the heteroaryl olefin comprises an optionally substituted heteroaryl group conjugated to a double bond, wherein the double bond is one of the two double bonds participated in a metathesis reaction.

111. The method of any one of examples 64-91 and 107, wherein a substrate of the metathesis reaction comprises a 1,3-diene.
112. The method of any one of examples 64-91 and 107, wherein a substrate of the metathesis reaction is a 1,3-diene.
113. The method of any one of examples 64-91 and 107, wherein a substrate of the metathesis reaction is an O-substituted alkene.
114. The method of any one of examples 64-91 and 107, wherein a substrate of the metathesis reaction is a S-substituted alkene.
115. The method of any one of examples 64-91 and 107, wherein a substrate of the metathesis reaction is an allylic alcohol.
116. The method of any one of examples 64-91 and 107, wherein a substrate of the metathesis reaction is a homoallylic alcohol.
117. The method of any one of examples 108-116, wherein the substrate is a terminal olefin.
118. The method of any one of examples 53-63, further comprising providing a zinc salt.
119. The method of claim 118, wherein the zinc salt has the structure of $R^4$—Zn—$R^5$.
120. The method of claim 119, wherein the zinc salt is a ligand or ligand precursor that replaces $R^{4\prime}$ and $R^{5\prime}$ with $R^4$ and $R^5$.

It will be appreciated that, in certain embodiments, each variable recited is as defined above and described in embodiments, herein, both singly and in combination.

EXEMPLIFICATION

The present invention recognizes, among other things, that there is a continuing demand for compounds and methods for highly efficient and stereoselective metathesis reactions. In some embodiments, the present invention provides novel compounds for metathesis reactions, their preparation methods and uses thereof. In some embodiments, the prevent invention provides novel methods for metathesis. Exemplary but non-limiting examples are depicted herein.

Provided Compounds and Methods for Metathesis Reactions

Herein, we developed new stereogenic-at-Ru complexes, in some embodiments, having the structure of formula I, easily accessed from commercially available sources in a single step, which can be used to promote Z-selective metathesis reactions. In some embodiments, a metathesis reaction is ROMP. In some embodiments, a metathesis reaction is ROCM. In some embodiments, a provided compound catalyzes Z-selective ROMP and ROCM reactions efficiently, with turnover numbers (TONs) of as high as 43,000. Transformations are exceptionally Z-selective, typically delivering >98:2 Z:E values at >90% conversion levels. The presence of hydroxyl groups does not have an adverse effect on catalyst activity. We provided the first examples of Z-selective Ru-catalyzed ROCM reactions that involve styrenes or other sterically hindered olefins, such as vinylcyclohexane, as cross partners.

To devise a practical and efficient route for certain new metal complexes, we tested transformation between the robust and commercially available phosphine-free Ru complex 1 and disodium catecholate of 2 (Scheme 1). Double-displacement of the chlorides proceeds to completion in two hours (22° C., THF), affording stereogenic-at-Ru complex 5 in 65% yield after purification. Similarly, dithio-based carbenes 6a and 6b can be synthesized and isolated in ca. 60% yields. The higher polarity of Ru carbenes 5, 6a and 6b (calculated values: 7.9, 7.7, 17.3 Debye, respectively) allows for ease of purification and removal of trace impurities, including any unreacted 3 (2.0 Debye), which is highly active and typically gives rise to E-selective reactions. Without the intention to be limited by theory, the latter characteristics minimize the possibility of competitive non-selective side reactions by any catalytically active contaminants.

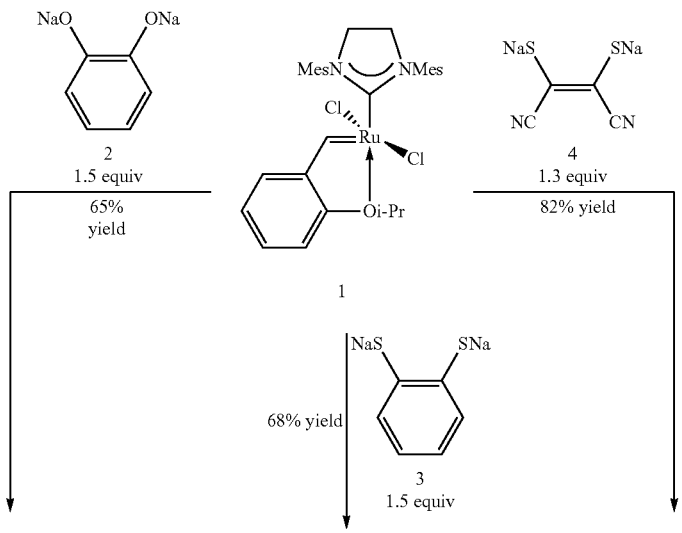

Scheme 1. Preparation of Ru-Based complexes 5 and 6a-b.

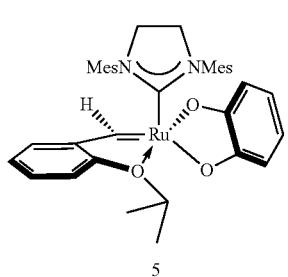 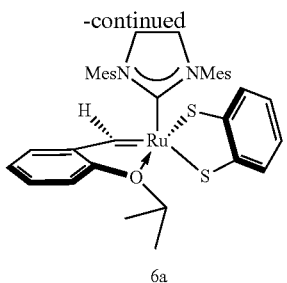 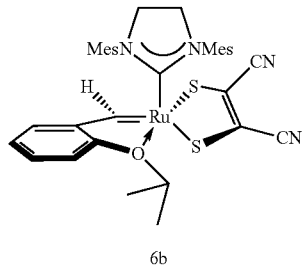

5            6a            6b

Figure 2:
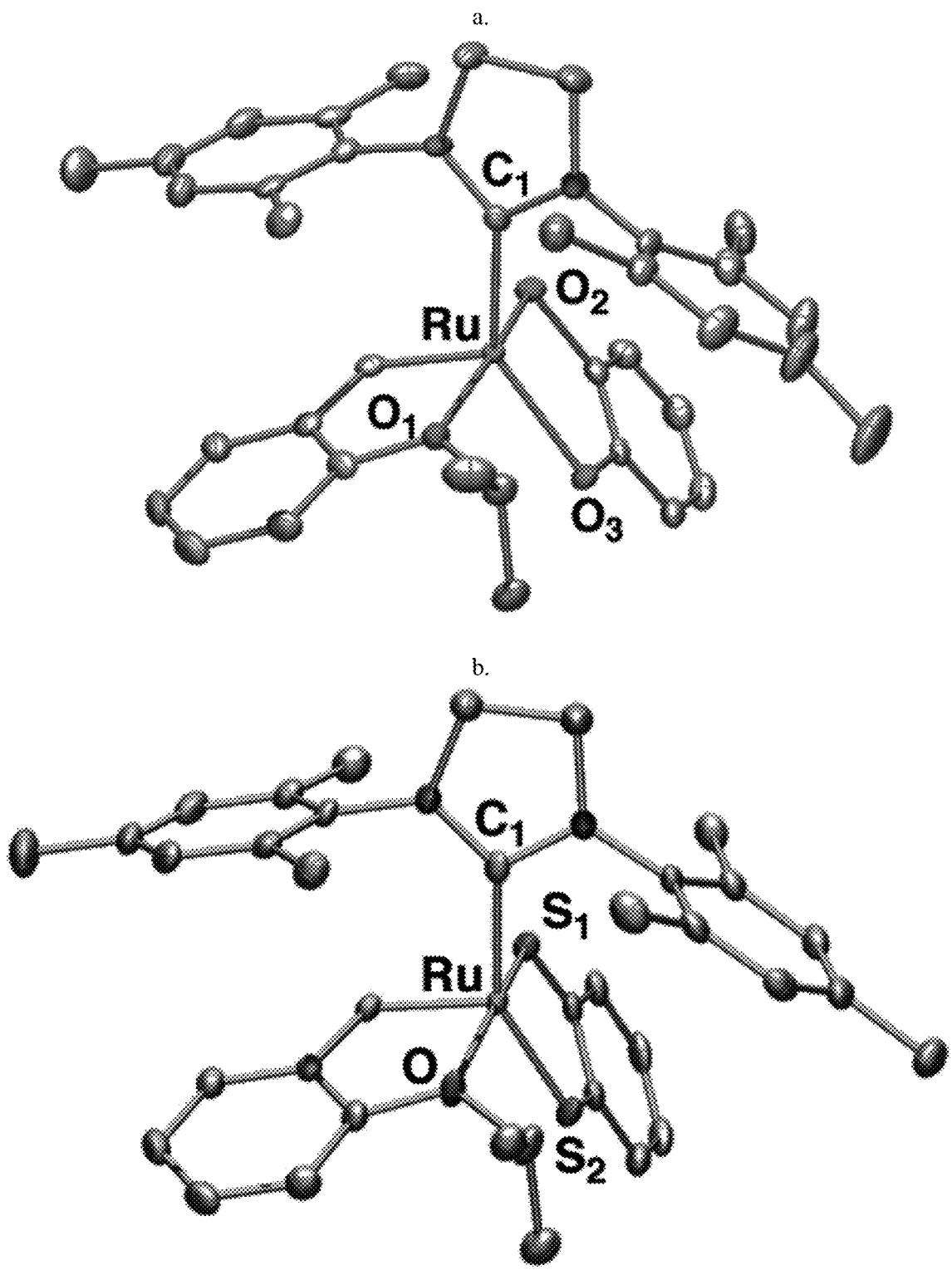
FIG. 2. ORTEP representation of X-ray structures of the Ru complexes. (a) X-ray of 5: $C_1$—Ru: 2.015 Å; $O_1$—Ru: 2.192 Å; $C_1$—Ru—$O_3$: 149.2°; O—Ru—$O_2$: 169.3°; (b) X-ray of 6a: $C_1$—Ru: 2.061 Å; $O_1$—Ru: 2.277 Å; $C_1$—Ru—$S_2$: 143.4°; O—Ru—$S_1$: 169.8°.

We have obtained X-ray structures for complexes 5 and 6a (FIG. 2). The isopropoxy ligands are chelated syn to the NHC moiety, and there is significant deviation from linearity of the $C_1$—Ru—$O_3$ (149.2°) and $C_1$—Ru—$S_2$ (143.4°) angles (FIG. 2). The $C_1$—Ru and $O_1$—Ru bonds are longer in 6a (vs 5).

Figure 42:
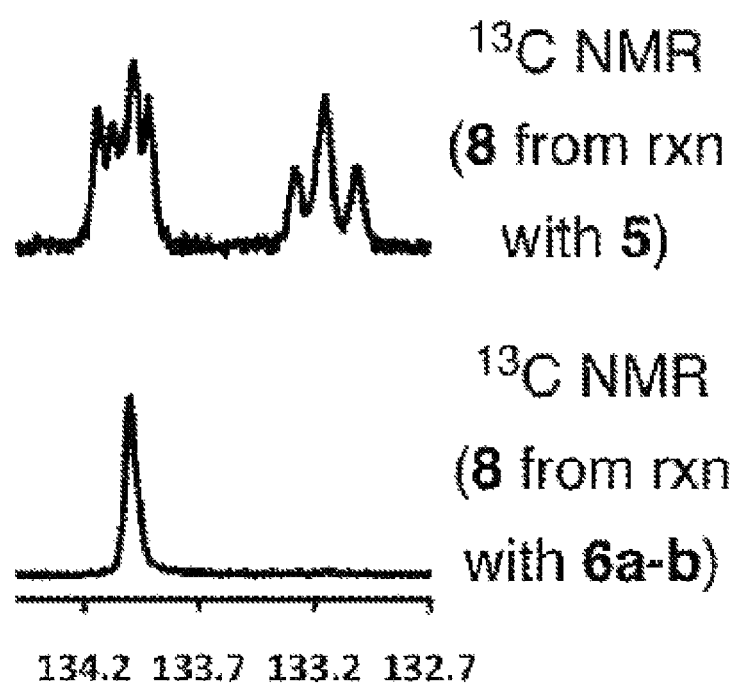
FIG. 42. $^{13}$C NMR spectra of Table 1.

Evaluation of the ability of Ru carbenes 6 and 7b to promote ROMP processes was presented in Table 1. Polymerization of norbornene (7) took place readily in the presence of 0.1 mol % 5 at 22° C. in dichloromethane (96% yield of 8 after 1 hour) with preference for the Z isomers (58:42 Z:E; entry 1, Table 1). The S-containing complexes 6a-b provide similarly high efficiency but are exceptionally Z-selective (>98% Z; entries 2 and 3, Table 1). To evaluate the robustness of the catalytic system, we carried out these latter transformations without purification of the norbornene monomer. The high stereo-regularity of poly-norbornene 8, generated through the use of 6a or 6b is clearly illustrated by comparison of the olefin region of the corresponding $^{13}C$ NMR spectra (FIG. 42). A similar trend in the Z content is observed in 10 obtained from ROMP of the less strained cyclooctadiene 9: 72% Z selectivity is obtained with Ru carbene 5, and complete preference for the higher energy Z isomer with 6a or 6b (>98% Z; entries 4-6, Table 1).

TABLE 1

Z-Selective Ru-Catalyzed ROMP Reactions.[a]

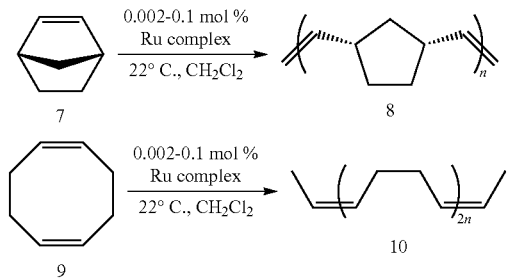

| entry | monomer | complex; mol % | time (h); yield[b] | Z:E[b] | TON |
|---|---|---|---|---|---|
| 1 | 7 | 5; 0.1 | 1.0; 96 | 58:42 | 960 |
| 2 | 7 | 6a; 0.1 | 1.0; 93 | >98:2 | 930 |
| 3 | 7 | 6b; 0.1 | 1.0; 90 | >98:2 | 900 |
| 4 | 9[c] | 5; 0.1 | 24; 88 | 72:38 | 880 |
| 5 | 9[c] | 6a; 0.1 | 24; 75 | >98:2 | 750 |
| 6 | 9[c] | 6b; 0.1 | 24; 75 | >98:2 | 750 |
| 7 | 7[c] | 6b; 0.01 | 1.0; 92 | >98:2 | 9,200 |
| 8 | 7[c] | 6b; 0.002 | 1.0; 86 | >98:2 | 43,000 |
| 9 | 9[c] | 6b; 0.01 | 24; 35 | >98:2 | 3,500 |
| 10 | 9[c] | 6b; 0.01 | 48; 54 | >98:2 | 5,400 |

[a]Experimental details described below.
[b]Determined by analysis of $^1H$ NMR spectra of the purified product.
[c]Substrate was first passed through a short column of basic alumina prior to use.

To gain further insight into the activity levels that can be provided by complex 6b, we performed the aforementioned polymerizations with reduced catalyst loadings (entries 7-10, Table 1), thus determining that with as little as 0.002 mol % 6b, poly-norbornene is generated with a turnover number (TON) of 43,000 in one hour (entry 8). Equally notable is the TON of 3,500 achieved for polymerization of cyclooctadiene after 24 h at 0.01 mol % loading (entry 9), a value that is increased to 5,400 after 48 h (entry 10), underlining the considerable longevity of the catalytically active Ru carbene. These results are unexpected, and much better than the Z selectivities (e.g., 86:14 Z:E for polynorbornene and 92% Z for cyclooctadiene) and TON values (e.g., TON=38 for cyclooctadiene in 72 h) reported recently for the same ROMP process catalyzed by known Ru-based catalysts ((a) Endo, K.; Grubbs, R. H. J. Am. Chem. Soc. 2011, 133, 8525. (b) Keitz, B. K.; Endo, K.; Herbert, M. B.; Grubbs, R. H. J. Am. Chem. Soc. 2011, 133, 9686. (c) Keitz, B. K.; Endo, K.; Patel, P. R.; Herbert, M. B.; Grubbs, R. H. J. Am. Chem. Soc. 2012, 134, 693. (d) Liu, P.; Xu, X.; Dong, X.; Keitz, B. K.; Herbert, M. B.; Grubbs, R. H.; Houk, K. N. J. Am. Chem. Soc. 2012, 134, 1464).

We tested Z-selective ROCM, which, up until now, has been limited to enol ether cross partners when Ru catalysts are involved (Khan, R. K. M.; O'Brien, R. V.; Torker, S.; Li, B.; Hoveyda, A. H. J. Am. Chem. Soc. 2012, 134, 12774). ROCM of norbornene with styrene in the presence of 1.0 mol % 6a generates 11a in 75% yield and 97:3 Z:E (entry 1, Table 2). Without the intention to be limited by theory, such exceptional stereoselectivity underscores the efficient control induced by the Ru catalyst, disfavoring the corresponding E alkene, which is 2.9 kcal/mol lower in energy than the Z isomer ((a) Monfette, S.; Fogg, D. E. Organometallics 2006, 25, 1940. (b) Monfette, S.; Camm, K. D.; Gorelsky, S. I.; Fogg, D. E. Organometallics 2009, 28, 944. (c) Monfette, S.; Silva, J. A. D.; Gorelsky, S. I.; Dalgarno, S. J.; dos Santos, E. N.; Araujo, M. H.; Fogg, D. E. Can. J. Chem. 2009, 87, 361). Catalytic ROCM with the more hindered and less reactive vinyl cyclohexane delivers 11b in 59% yield and complete Z selectivity (<2% E, entry 2). The disulfide Ru complexes are fully tolerant of alcohols, as evidenced by the highly efficient ROCM shown in entry 3 of Table 2, which proceeds readily to afford the disubstituted styrene 13a in 92% yield and, again, with high Z selectivity (98% Z; entry 3, Table 2). ROCM reactions promoted by the provided compounds are exceptionally Z-selective with different cross partners, regardless of their electronic or steric attributes (entries 3-6, Table 2). Transformations with 2,3-dibenzyloxy cyclobutene 14 with styrene proceeds to completion in 12 h at 40 OC in the presence of 3.0 mol % 6a to afford the desired 1,5-diene in 87% yield and 93:7 Z:E ratio. The provided Ru-catalyzed olefin metathesis reactions are operationally simple to perform; for example, when a sample of 6a (1.0 mol %) was weighed in air and the ROCM in entry 3 of Table 2 was performed under $N_2$ atmosphere in a typical fume hood, the transformation proceeded to >98% conversion (1.0 h, 22° C., thf), affording the desired product in 98% Z selectivity.

TABLE 2

Z-Selective ROCM with Styrenes and Vinylcyclohexane [a]

| entry | substrate | G | time (h) | product | conv (%);[b] yield (%)[c] | Z:E[b] |
|---|---|---|---|---|---|---|
| 1 | 7 | a C$_6$H$_5$ | 1.0 | 11 | >98; 75 | 97:3 |
| 2 | 7 | b Cy | 2.0 | 11 | >98; 59 | >98:2 |
| 3 | 12 | a C$_6$H$_5$ | 1.0 | 13 | >98; 85 | 98:2 |
| 4 | 12 | b m-FC$_6$H$_4$ | 1.0 | 13 | >98; 81 | 98:2 |
| 5 | 12 | c p-MeOC$_6$H$_4$ | 1.0 | 13 | >98; 93 | 96:4 |
| 6 | 12 | d Cy | 8.0 | 13 | 88; 62 | >98:2 |
| 7 | 14 | C$_6$H$_5$ | 12 | 15 | 94; 67 | 93:7 |

[a] For experimental details described below; 3.0 mol % 6a and 40° C. for entry 7.
[b] Determined by analysis of $^1$H NMR spectra of the unpurified mixtures.
[c] Yield of isolated and purified products.

Figure 3:
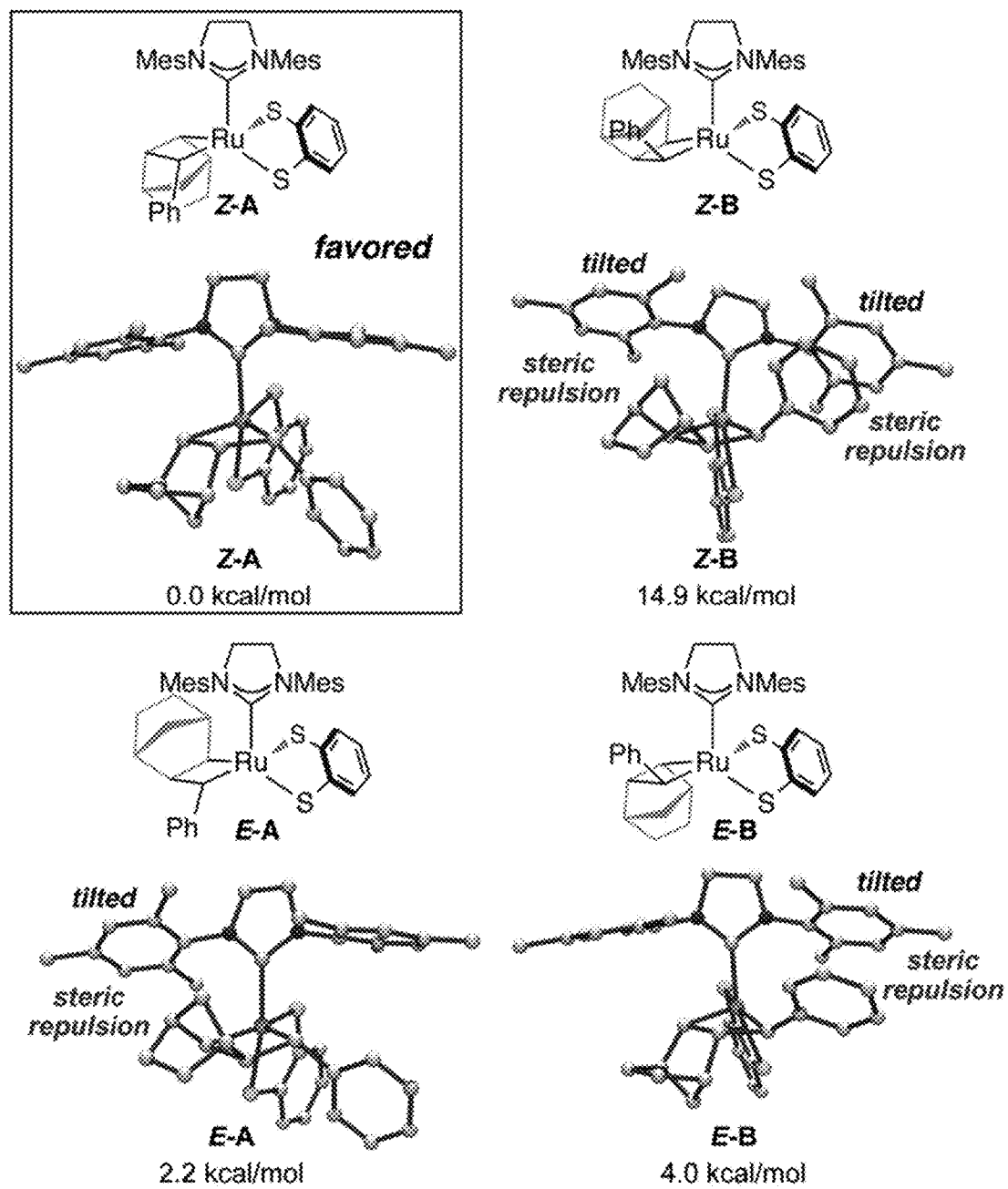
FIG. 3. Proposed stereochemical model and calculation results.
Figure 3:
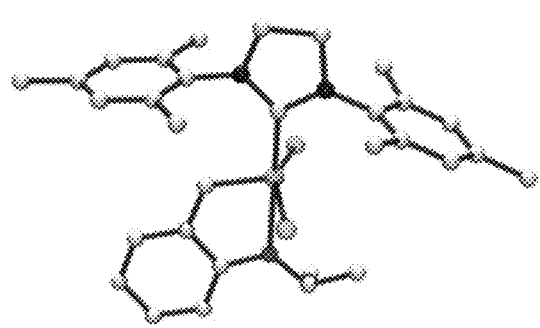
Figure 3:
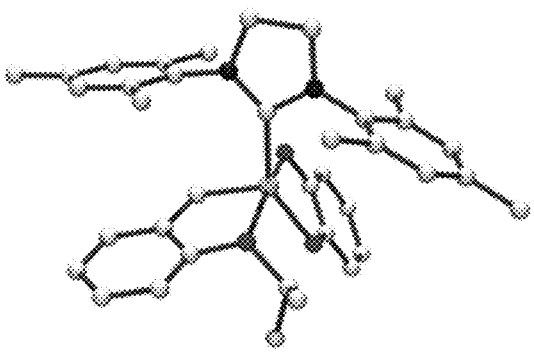
Figure 3:
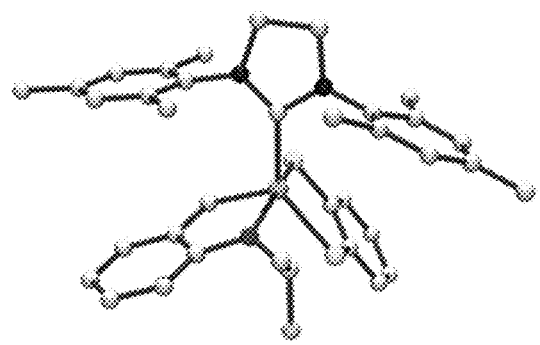
Figure 3:
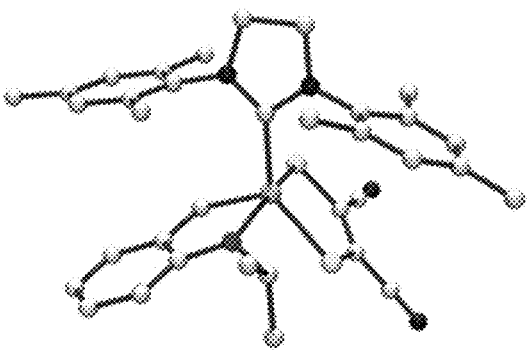
Figure 3:
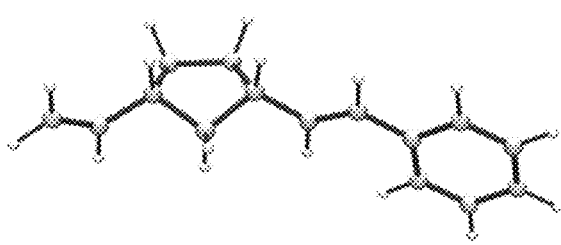
Figure 3:
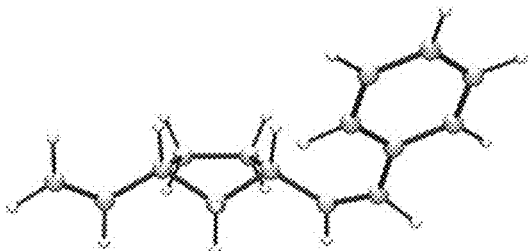
Figure 4:
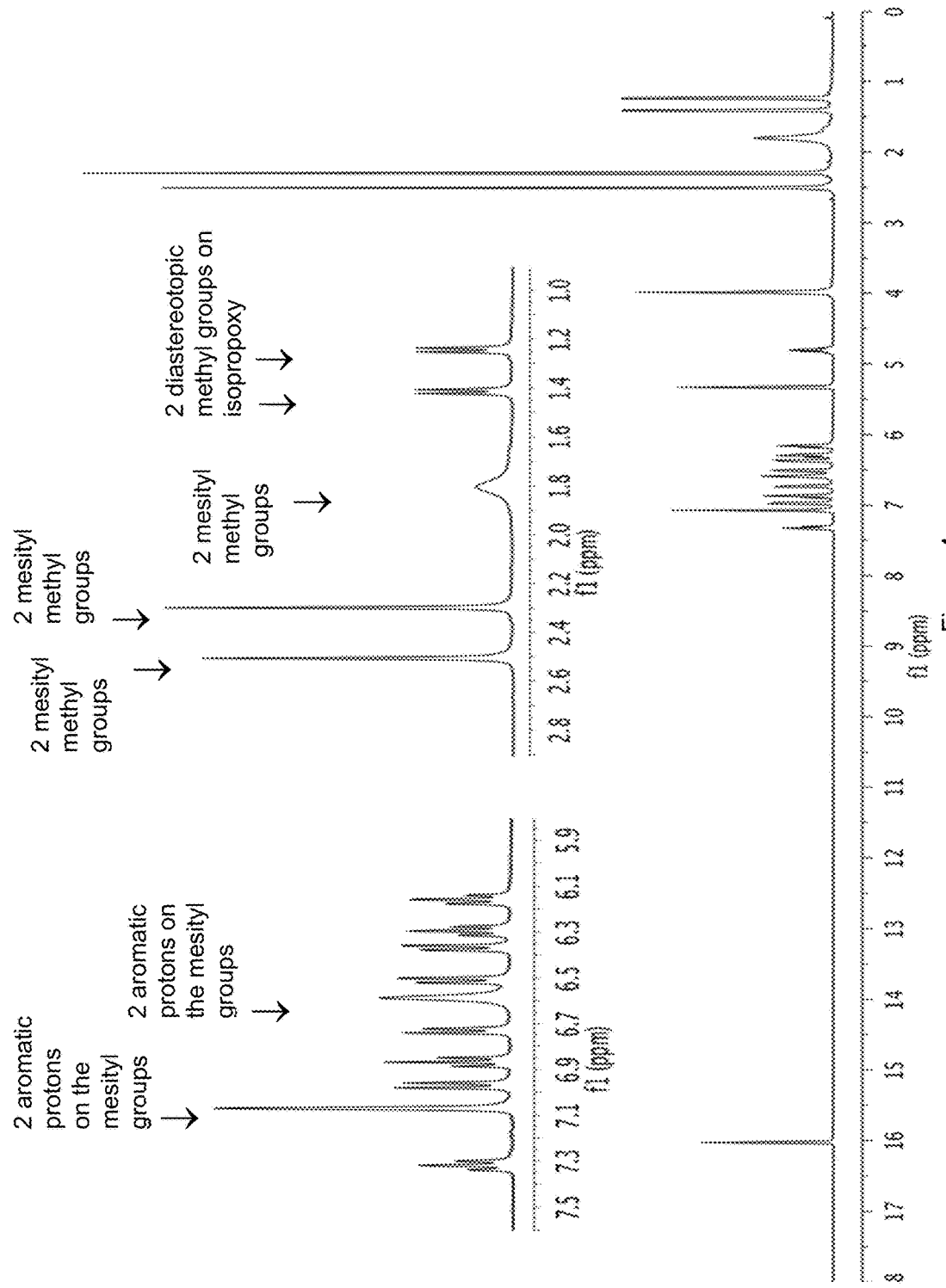
FIG. 4. $^1$H NMR of complex 5.
Figure 5:
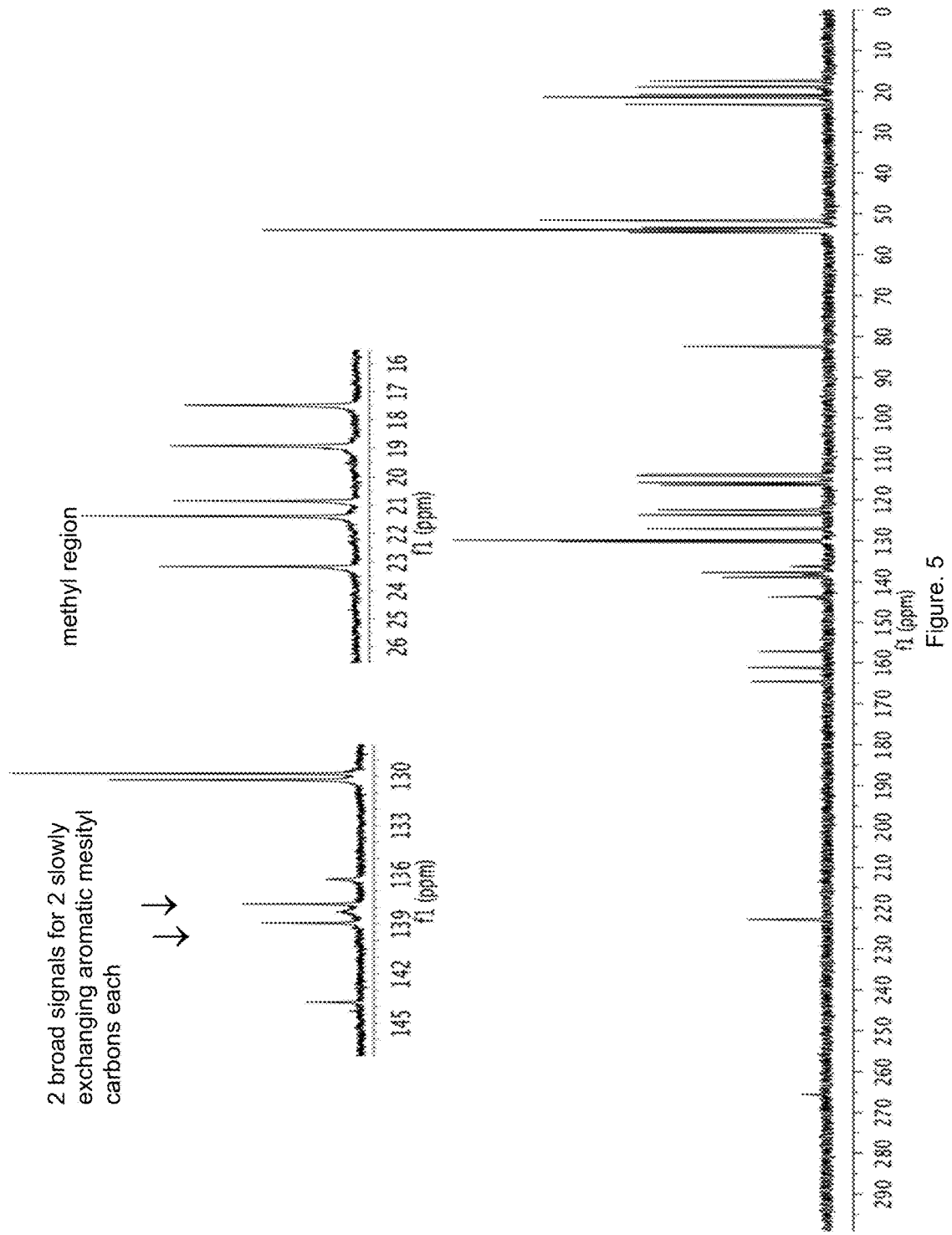
FIG. 5. $^{13}$C NMR of complex 5.
Figure 6:
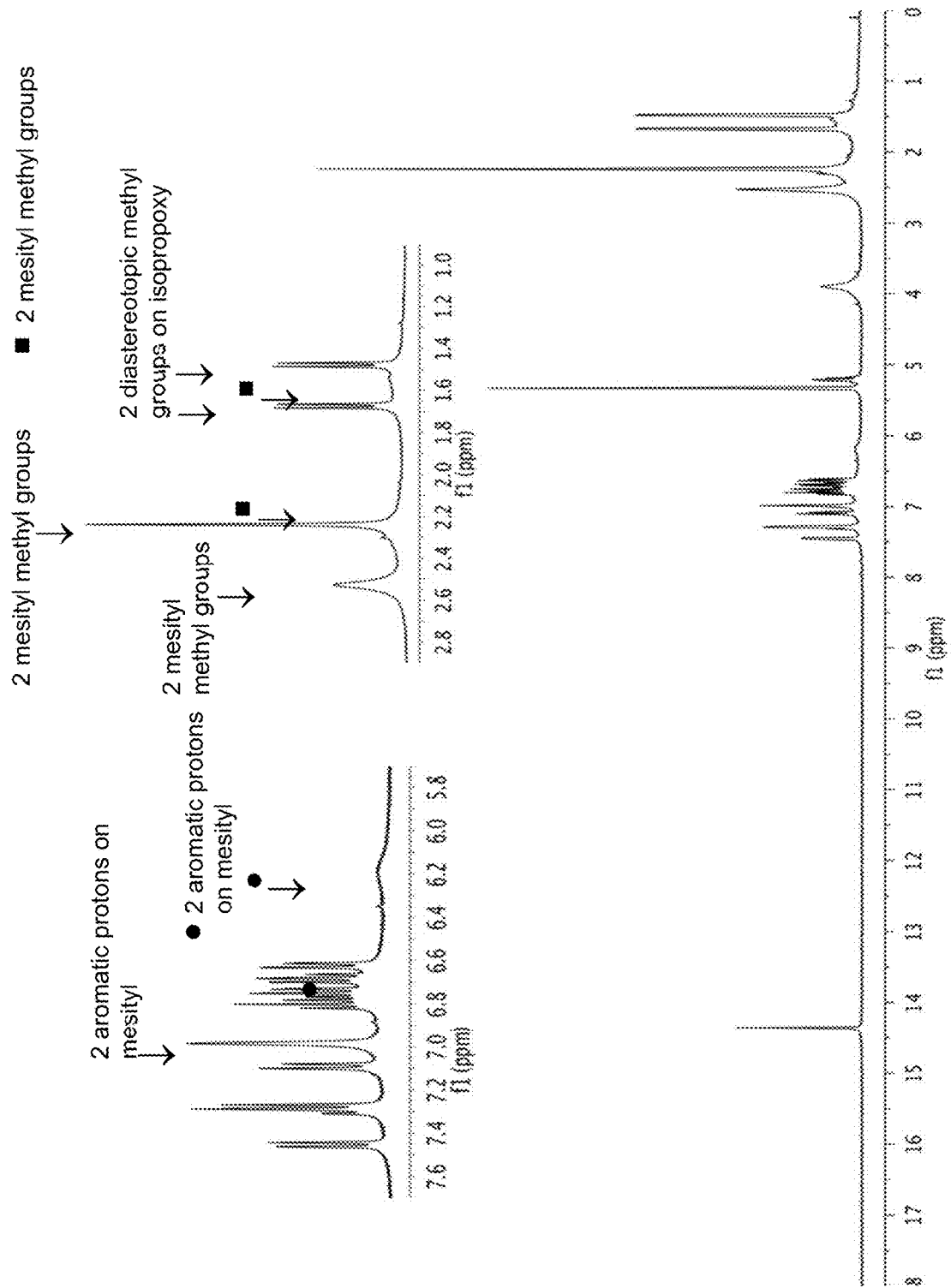
Figure 7:
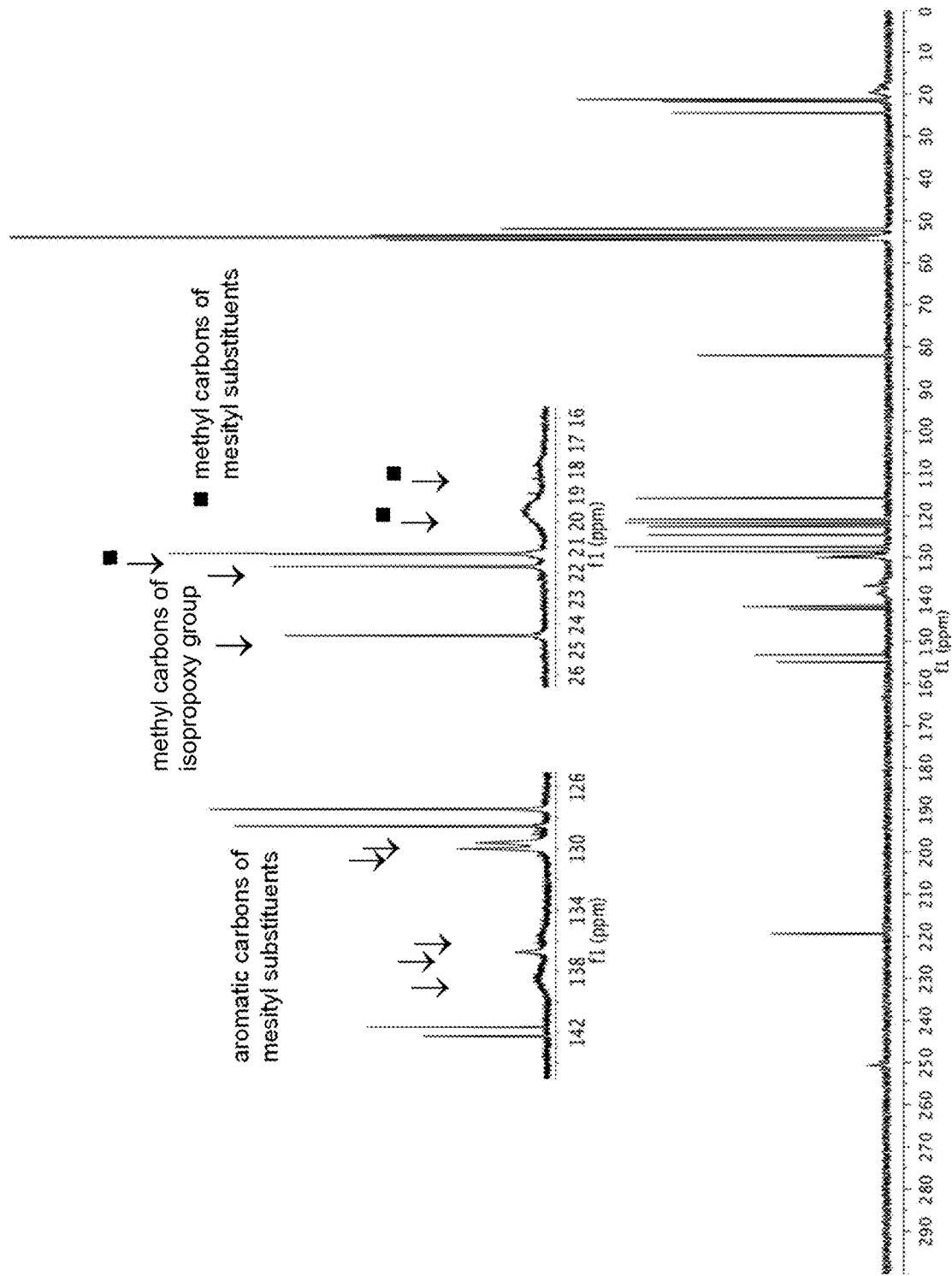
Figure 8:
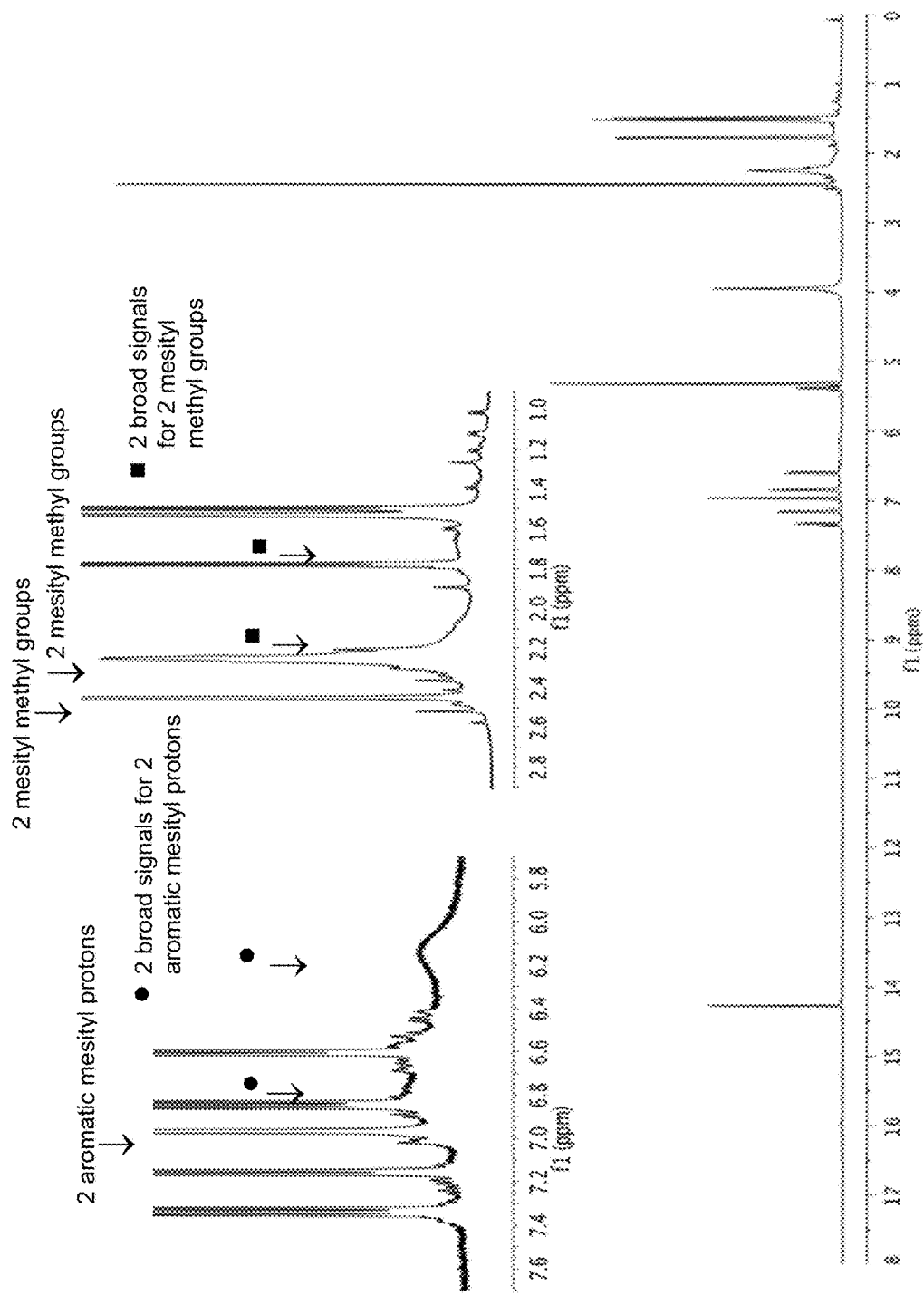
FIG. 8. $^1$H NMR of complex 6b (2 mg/mL conc.). Aggregation of 6b is observed at higher concentration, in some embodiments, due to intermolecular coordination of CN-substituents to Ru centers. The monomeric species of 6b was observed at low concentration (2 mg/mL) as shown here.
Figure 9:
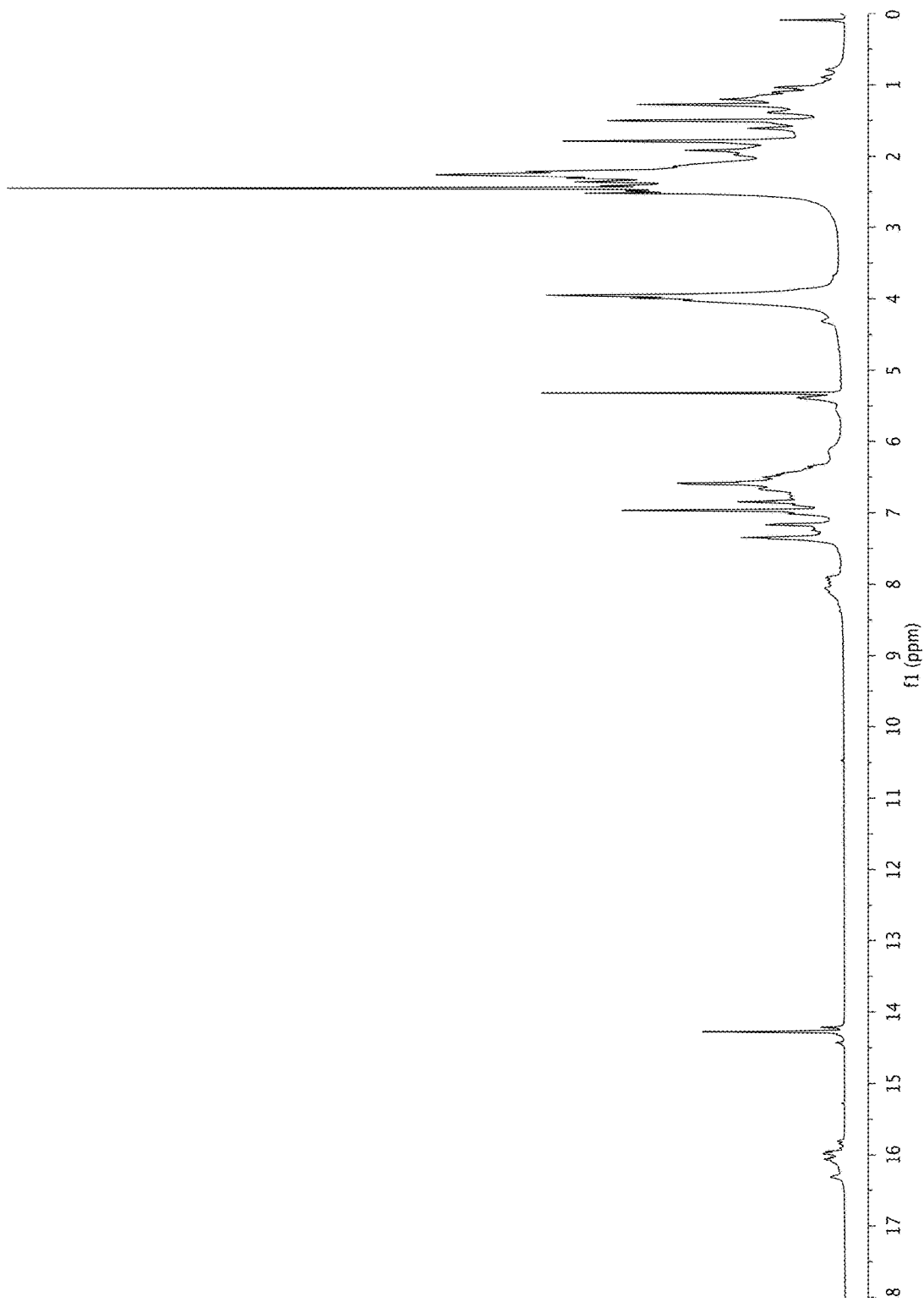
FIG. 9. $^1$H NMR of complex 6b (70 mg/mL conc.).

While not wishing to be limited by theory, based on the calculated Gibbs free energies of the four possible ruthenacycle intermediates associated with the ROCM involving complex 6a, norbornene and styrene (cf. Table 2, entry 1), as outlined in FIG. 3, we propose the stereochemical model, below, for the surprising results. The ruthenacycle originating from approach of norbornene to Ru benzylidene is denoted as Z-A; here, the carbene's phenyl moiety and the bridgehead segment of the bicyclic alkene are oriented away from the NHC ligand, and is calculated to be 2.2 kcal/mol lower in energy than metallacyclobutane E-A. In the latter mode of approach, there is unfavorable steric interaction between the norbornene and the NHC ligand, such that one of the mesityl substituents is forced to undergo a tilt. Norbornene modes of association with ruthenobenzylidene labeled as Z-B and E-B are more strongly disfavored, corresponding to ruthenacycle energies of 14.9 and 4.0 kcal/mol, respectively.

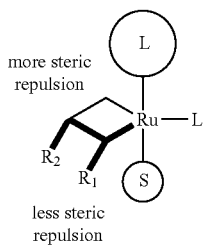

As shown above, provided complexes of this invention catalyze ROMP and ROCM efficiently and often with >98% Z selectivity. Additional features, such as tolerance of hydroxyl units, high turnover numbers (e.g., 43,000 for norbornene polymerization), and the ease of operation (rigorous purification of alkenes obviated) further expand the scope of utility of provided compounds.

Procedures

General: Unless otherwise noted, all reactions were performed with distilled and degassed solvents under an atmosphere of dry N$_2$ in oven (135° C.) or flame-dried glassware with standard dry box or vacuum line techniques. Infrared (IR) spectra were recorded on a Bruker FTIR Alpha (ATR Mode) spectrometer, $\nu_{max}$ in cm$^{-1}$. Bands are characterized as broad (br), strong (s), medium (m), or weak (w). $^1$H NMR spectra were recorded on a Varian Unity INOVA 400 (400 MHz) or a Varian Unity INOVA 500 (500 MHz) spectrometer. Chemical shifts are reported in ppm from tetramethylsilane with the solvent resonance resulting from incomplete deuterium incorporation as the internal standard (CDCl$_3$: δ 7.26 ppm, C$_6$D$_6$: δ 7.16 ppm, CD$_2$Cl$_2$: δ 5.32 ppm). Data are reported as follows: chemical shift, integration, multiplicity (s=singlet, d=doublet, t=triplet, q=quartet, br=broad, m=multiplet), and coupling constants (Hz). $^{13}$C NMR spectra were recorded on a Varian Unity INOVA 400 (100 MHz) or Varian Unity INOVA 500 (125 MHz) spectrometer with complete proton decoupling. Chemical shifts are reported in ppm from tetramethylsilane with the solvent resonance as the internal standard (CDCl$_3$: δ 77.16 ppm, CD$_2$Cl$_2$: δ 54.00 ppm). High-resolution mass spectrometry was performed on a Micromass LCT ESI-MS and JEOL Accu TOF Dart (positive mode) at the Boston College Mass Spectrometry Facility. Values for Z:E ratios of products were determined by analysis of $^1$H NMR spectra or $^{13}$C NMR spectra (in the case of poly-cyclooctadiene 10).

X-Ray Data Collection: Selected single crystals suitable for X-ray crystallographic analysis were used for structural determination. The X-ray intensity data were measured at 100(2) K (Oxford Cryostream 700) on a Bruker Kappa APEX Duo diffractometer system equipped with a sealed Mo-target X-ray tube (λ=0.71073 Å) and a high brightness IμS copper source (λ=1.54178 Å). The crystals were mounted on a goniometer head with paratone oil. The detector was placed at a distance of 5.000 or 6.000 cm from the crystal. For each experiment, data collection strategy was determined by APEX software package and all frames were collected with a scan width of 0.5° in ω and φ with an exposure time of 10 or 20 s/frame. The frames were integrated with the Bruker SAINT Software package using a narrow-frame integration algorithm to a maximum 2θ angle of 56.54° (0.75 Å resolution) for Mo data and of 134° (0.84 Å resolution) for Cu data. The final cell constants are based upon the refinement of the XYZ-centroids of several thousand reflections above 20 σ(I). Analysis of the data showed negligible decay during data collection. Data were corrected for absorption effects using the empirical method (SAD-ABS). The structures were solved and refined by full-matrix least squares procedures on |F$^2$| using the Bruker SHELXTL (version 6.12) software package. All hydrogen atoms were included in idealized positions for structure factor calculations except for those forming hydrogen bonds or on a chiral center. Anisotropic displacement parameters were assigned to all non-hydrogen atoms, except those disordered.

Solvents: Solvents (CH$_2$Cl$_2$, pentane, benzene) were purified under a positive pressure of dry Ar by a modified Innovative Technologies purification system. Tetrahydrofuran was distilled under a nitrogen atmosphere from Na/benzophenone. Methanol was distilled from CaH$_2$ under nitrogen atmosphere. Work-up of Ru complexes was performed in a glove box filled with nitrogen using dry and degassed solvents. All other purification procedures of ROMP and ROCM products were carried out with reagent grade solvents (purchased from Fisher) under bench-top conditions.

Deuterated solvents: CDCl$_3$, CD$_2$Cl$_2$, C$_6$D$_6$ were purchased from Cambridge Isotope Laboratories and used as received.

Reagents: Ru-based complex 1 (Aldrich), sodium maleonitriledithiolate 4 (TCI America), 1,2-dihydroxybenzene (Aldrich) and benezene-1,2-dithiol (Aldrich) were used as received. Styrene (Aldrich), vinylcylcohexane (Aldrich), 1,5-cyclooctadiene 9 (Aldrich), p-methoxystyrene (Aldrich) and 3-fluorostyrene (Aldrich) were passed through a plug of basic alumina prior to the experiment. Unless otherwise indicated, norbornene 7 (Aldrich) was used without purification but purified for polymerization experiments with low catalyst loading (see below). 5-Norbornene-2-exo,3-exo-dimethanol 12 (Aldrich) was used as received. Cyclobutene 14 was prepared in analogy to a previously reported procedure involving the use of benzyl alcohol (Khan, R. K. M.; Zhugralin, A. R.; Torker, S.; O'Brien, R. V.; Lombardi, P. J.; Hoveyda, A. H. J. Am. Chem. Soc. 2012, 134, 12438).

Exemplary Compound Synthesis

Disodium Catecholate 2

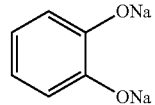

In an N$_2$ filled glove box, a solution of sodium tert-butoxide (948 mg, 9.86 mmol, 2.40 equiv) in methanol (8.2 mL) is transferred to a vial containing 1,2-dihydroxybenzene (453 mg, 4.11 mmol, 1.00 equiv), and the resulting mixture is allowed to stir for 30 minutes at 50 OC. The mixture is cooled to 22° C. followed by evaporation of solvent under vacuum. The residue is transferred to a fritted funnel and washed with tetrahydrofuran (25 mL). After removal of solvents in vacuo, disodium catecholate 2 is obtained as white solid (602 mg, 3.91 mmol, 95% yield) and used directly without purification.

Ru Complex 5

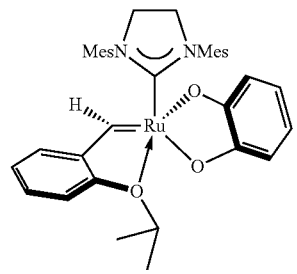

To a 2-dram vial charged with a stir bar and disodium catecholate 2 (37.0 mg, 0.240 mmol, 1.50 equiv) under N$_2$ atmosphere, a solution of Ru complex 1 (100 mg, 0.160 mmol, 1.00 equiv) in tetrahydrofuran (2.0 mL) is added. The resulting mixture is allowed to stir at 22° C. for three hours, at which time the solvent is evaporated under vacuum. Residual tetrahydrofuran is removed through co-evaporation with pentane (2×4 mL). The resulting solid is dissolved in dichloromethane and passed through a short column of Celite (4 cm in height), placed in a pipette (~0.5 cm diameter), with dichloromethane (10 mL). The filtrate is adsorbed onto fresh Celite and subjected to vacuum until complete dryness. The adsorbed material is loaded onto a second short column of Celite (4 cm in height) and washed with Et$_2$O (20 mL), after which complex 5 is collected upon elution with dichloromethane. After removal of solvents and co-evaporation with pentane, Ru-based catecholate 5 is isolated as an orange-brown solid (68.9 mg, 0.104 mmol, 65% yield). $^1$H NMR (400 MHz, CD$_2$Cl$_2$): δ 16.03 (1H, s), 7.32 (1H, td, J=7.8, 1.6 Hz), 7.07 (2H, s), 6.97 (1H, d, J=8.4 Hz), 6.87 (1H, t, J=7.4 Hz), 6.73 (1H, dd, J=7.2, 1.6 Hz), 6.59 (2H, br s), 6.51 (1H, dd, J=7.6, 1.6 Hz), 6.37 (1H, dd, J=7.6, 1.6 Hz), 6.30 (1H, td, J=7.4, 1.6 Hz), 6.16 (1H, td, J=7.4, 1.6 Hz), 4.86-4.76 (1H, m), 3.99 (4H, apparent br s), 2.51 (6H, s), 2.30 (6H, s), 1.80 (6H, br s), 1.41 (3H, d, J=6.4 Hz), 1.24 (3H, d, J=6.4 Hz); $^{13}$C NMR (100 MHz, CD$_2$Cl$_2$): δ 265.6, 222.8, 164.6, 161.1, 157.2, 143.7, 138.9, 138.2 (very br), 137.8, 136.3 (br), 130.2, 129.8, 127.1, 123.7, 122.4, 116.4, 115.8, 114.1, 114.0, 113.8, 82.4, 51.6, 23.2, 21.4, 20.8, 18.9, 17.5.

Disodium benzenedithiolate 3

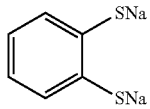

In an $N_2$ filled glove box, a solution of sodium tert-butoxide (455 mg, 4.73 mmol, 2.40 equiv) in methanol (4.0 mL) is transferred to a vial containing benzene-1,2-dithiol (280 mg, 1.97 mmol, 1.00 equiv), and the resulting solution is allowed to stir for 30 minutes at 50 OC. The mixture is allowed to cool to 22° C. followed by solvent evaporation under vacuum. The residue is transferred to a fritted funnel and washed with tetrahydrofuran (25 mL). After removal of solvent in vacuo, disodium benzenedithiolate 3 is obtained as white solid (338 mg, 1.82 mmol, 92% yield) and used directly without purification.

Ru Complex 6a

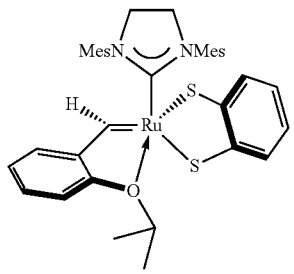

To a 2-dram vial equipped with a stir bar and charged with disodium benzenedithiolate 3 (44.6 mg, 0.240 mmol, 1.50 equiv) under $N_2$ atmosphere, a solution of Ru complex 1 (100 mg, 0.160 mmol, 1.00 equiv) in tetrahydrofuran (2.0 mL) is added. The resulting mixture is allowed to stir at 22° C. for three hours, at which time the solvent is evaporated under vacuum. Residual tetrahydrofuran is removed through co-evaporation with pentane (2×4 mL). The obtained solid is dissolved in dichloromethane and passed through a short column of Celite (4 cm in height) in a pipette (~0.5 cm diameter) with dichloromethane (10 mL). The filtrate is adsorbed onto fresh Celite and subjected to vacuum until complete dryness. The adsorbed material is loaded onto another short column of Celite (4 cm in height) and washed with diethyl ether (20 mL), after which complex 6a is collected upon elution with dichloromethane. After removal of solvents and co-evaporation with pentane, 6a is isolated as an orange-brown solid (75.6 mg, 0.109 mmol, 68% yield). $^1$H NMR (400 MHz, $CD_2Cl_2$): δ 14.36 (1H, s), 7.45 (1H, dd, J=7.2, 1.6 Hz), 7.31-7.26 (2H, m), 7.09 (1H, d, J=8.8 Hz), 6.99 (2H, s), 6.9-6.4 (1H, very br s, overlapping), 6.80 (1H, td, J=7.4, 0.8 Hz), 6.75 (1H, ddd, J=8.0, 7.2, 1.6 Hz), 6.68 (1H, ddd, J=7.6, 6.8, 1.6 Hz), 6.62 (1H, dd, J=7.6, 1.6 Hz), 6.4-5.9 (1H, very br s), 5.25-5.17 (1H, m), 3.90 (4H, apparent br s), 2.53 (6H, br s), 2.5-2.0 (3H, very br s), 2.24 (6H, s), 1.9-1.5 (3H, very br s), 1.67 (3H, d, J=6.8 Hz), 1.48 (3H, d, J=6.4 Hz); $^{13}$C NMR (100 MHz, $CD_2Cl_2$): δ 250.7, 219.4, 154.9, 153.2, 142.3, 141.6, 138.5 (very br), 136.7 (br), 135.6 (very br), 130.0 (br), 129.6 (br), 128.6, 127.48, 127.45, 124.7, 122.6, 121.7, 120.8, 115.9, 82.0, 51.9, 24.4, 21.8, 21.3, 19.6 (very br), 17.8 (very br).

Ru Complex 6b

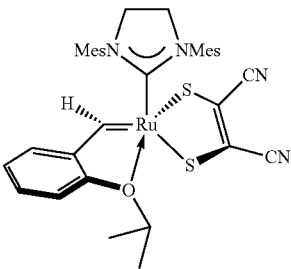

Under an atmosphere of dry $N_2$, a suspension of Ru complex 1 (100 mg, 0.160 mmol, 1.00 equiv) and sodium maleonitriledithiolate 4 (38.7 mg, 0.208 mmol, 1.30 equiv) is allowed to stir in tetrahydrofuran (1.5 mL) for 3 hours, during which a color change from green to reddish brown is observed. The solvent is evaporated and the residual tetrahydrofuran is removed through co-evaporation with pentane. The residue is taken up in dichloromethane and the solution filtered through a glass microfiber filter (Whatman™). After removal of the solvent in vacuo, dichloromethane (1.0 mL) is added and the complex precipitated while stirring by slow addition of diethyl ether (10 mL). The resulting suspension is transferred onto a short column of Celite (4 cm in height) placed in a pipette (~0.5 cm diameter) and washed with a 1:10 mixture of dichloromethane/diethyl ether (5.5 mL). The first filtrate is collected and left for crystallization (see below). The complex is then eluted with dichloromethane until the second filtrate is colorless. After removal of the solvent and co-evaporation of dichloromethane with pentane, complex 6b is obtained as an orange-brown solid (75.0 mg, 0.109 mmol, 68% yield). After two days, the crystals from the first filtrate were collected and washed with diethyl ether to give an overall yield of 6b of 82% (90.0 mg, 0.131 mmol). $^1$H NMR (500 MHz, $CD_2Cl_2$): δ 14.28 (1H, s), 7.34 (1H, td, J=7.8, 1.6 Hz), 7.16 (1H, d, J=8.4 Hz), 7.0-6.4 (1H, very br s), 6.97 (2H, s), 6.85 (1H, t, J=7.4 Hz), 6.60 (1H, dd, J=7.6, 1.6 Hz), 6.4-5.9 (1H, br s), 5.38 (1H, m), 3.95 (4H, apparent br s), 2.5-1.9 (3H, very br s), 2.45 (6H, s), 2.25 (6H, br s), 1.9-1.4 (3H, very br s), 1.78 (3H, d, J=6.7 Hz), 1.49 (3H, d, J=6.6 Hz).

Ring-Opening Polymerization (ROMP) Reactions

Representative procedure for polymerization of norbornene (7) at 0.1 mol % catalyst loading of 6b: In an $N_2$ filled glove box, norbornene (7; 94.2 mg, 1.00 mmol, not rigorously purified) is dissolved in $CH_2Cl_2$ (1.8 mL) upon which a solution of 6b (0.70 mg, 0.0010 mmol) in $CH_2Cl_2$ (0.2 mL) is added. The resulting solution is allowed to stir at 22° C. for one hour, after which the polymer is precipitated by addition of MeOH (4.0 mL). The polymer is washed again with MeOH (2.0 mL) and dried under high vacuum ($1.0 \times 10^{-1}$ torr) to yield poly-norbornene 8 in 90% yield (85.0 mg). A 30 mg sample of the polymer is dissolved in an NMR tube for 12 hours in $CDCl_3$. IR (neat): 2996 (m), 2939 (s), 2861 (m), 1710 (w), 1652 (w), 1463 (w), 1445 (m), 1404 (w), 1296 (w), 1265 (w), 1040 (w), 954 (w), 731 (s); $^1$H NMR (500 MHz, $CDCl_3$): δ 5.25-5.19 (2H, m), 2.87-2.75 (2H, m), 1.95-1.87 (1H, m) 1.86-1.76 (2H, m), 1.42-1.33 (2H, m), 1.07-0.98 (1H, m); $^{13}$C NMR (125 MHz, $CDCl_3$): δ 134.0, 42.9, 38.7, 33.4.

Representative procedure for polymerization of cyclooctadiene (9) at 0.1 mol % catalyst loading of 6b: In an $N_2$ filled glove box, a solution of 6b (0.70 mg, 0.0010 mmol) in CH$_2$Cl$_2$ (0.2 mL) is added to 1,5-cyclooctadiene (9; 108 mg, 1.00 mmol, after purification by passing through a plug of basic alumina). The resulting solution is allowed to stir at 22° C. for 24 hours, after which the polymer is precipitated by the addition of MeOH (2.0 mL). The polymer is washed again with MeOH (2.0 mL) and dried under high vacuum (1.0×10$^{-1}$ torr) to yield polycyclooctadiene 10 in 75% yield (80.0 mg). A 30 mg sample of the polymer is dissolved in a common NMR tube for 12 hours in CDCl$_3$. IR (neat): 3005 (m), 2939 (m), 2852 (m), 1655 (w), 1450 (m), 1433 (m), 1404 (w), 1308 (w), 1239 (w), 994 (w), 733 (s); $^1$H NMR (500 MHz, CDCl$_3$): δ 5.41-5.37 (4H, m), 2.11-2.06 (8H, m); $^{13}$C NMR (125 MHz, CDCl$_3$): δ 129.7, 27.6.

Procedures for polymerization reactions at <0.1 mol % catalyst loading (cf. Table 1, entries 7-10): Polymerizations at reduced catalyst loading are performed at a 5.0 mmol scale of substrate (7 or 9), which has been purified by passing a corresponding sample over a plug of basic alumina (either neat in case of 9 or as a solution in CH$_2$Cl$_2$ in case of 7). The amount of solvent is increased accordingly to maintain the monomer concentration from the experiments at 0.1 mol % loading. A corresponding aliquot (0.40 or 0.08 mL) of a solution of complex 6b (2.0 mg, 2.9 mol in 2.3 mL dichloromethane) is added to initiate the polymerization.

Ring-Opening/Cross-Metathesis (ROCM) Reactions

General Procedure: In an N$_2$-filled glove box, an oven-dried 4 mL vial equipped with a magnetic stir bar is charged with strained alkene substrate (1.0 equiv) and terminal olefin cross partner (10-20 equiv). To this vial, a solution of Ru complex 6a (1.0-3.0 mol %) in tetrahydrofuran is added. The resulting mixture is allowed to stir for 1-12 hours at 22-40° C., after which the reaction is quenched by addition of wet diethyl ether and concentrated in vacuo (percent conversion determined by 400 MHz $^1$H NMR analysis). Purification is performed through silica gel chromatography.

((Z)-2-((1S,3R)-3-Vinylcyclopentyl)vinyl)benzene 11a

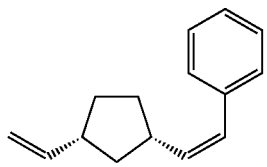

Following the general procedure, a solution of 6a (1.1 mg, 1.5 μmol, 1.0 mol %) in tetrahydrofuran (320 μL) is transferred by syringe to a vial containing norbornene 7 (15.0 mg, 0.159 mmol, 1.00 equiv) and styrene (332 mg, 3.19 mmol, 20.0 equiv). The resulting mixture is allowed to stir for one hour at 22° C. Analysis of the $^1$H NMR (400 MHz) spectrum reveals >98% conversion of norbornene, and the corresponding ROCM product 11a is obtained as a mixture of 98:2 Z:E isomers. The resulting brown oil is purified by silica gel chromatography (100% hexanes) to afford 11a (23.7 mg, 0.119 mmol, 75% yield) as colorless oil. IR (neat): 3079 (w), 3024 (w), 3002 (w), 2944 (s), 2863 (m), 1639 (s), 1600 (w), 1492 (w), 1464 (m), 1446 (m), 1409 (m), 1299 (w), 1074 (w), 1028 (m), 993 (m), 964 (m), 909 (s), 768 (s), 732 (m), 698 (s), 664 (w), 553 (w), 500 (w), 422 (w); $^1$H NMR (400 MHz, CDCl$_3$): δ 7.36-7.32 (2H, m), 7.28-7.21 (3H, m), 6.38 (1H, d, J=11.2 Hz), 5.88-5.79 (1H, m), 5.59 (1H, dd, J=11.6, 10.4 Hz), 5.03-4.98 (1H, m), 4.92-4.89 (1H, m), 3.12-3.02 (1H, m), 2.60-2.50 (1H, m), 2.07-2.00 (1H, m), 1.97-1.80 (2H, m), 1.58-1.45 (2H, m), 1.29-1.22 (1H, m). The coupling constants (J=11.2 and 11.6 Hz, respectively) of the signals at 6.38 and 5.59 ppm are indicative of Z isomer of 11a. $^{13}$C NMR (100 MHz, CDCl$_3$): δ 143.2, 138.1, 138.0, 128.8, 128.3, 127.8, 126.6, 112.7, 44.7, 41.6, 38.8, 33.2, 32.1; HRMS [M+H]$^+$ calcd for C$_{15}$H$_{19}$: 199.1487, found: 199.1479.

((Z)-2-((1S,3R)-3-Vinylcyclopentyl)vinyl)cyclohexane 11b

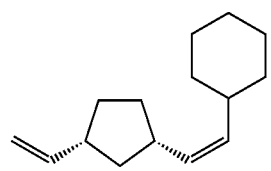

Following the general procedure, a solution of 6a (1.1 mg, 1.5 μmol, 1.0 mol %) in tetrahydrofuran (320 μL) is transferred by syringe to a vial containing norbornene 7 (15.0 mg, 0.159 mmol, 1.00 equiv) and vinyl cyclohexane (351 mg, 3.19 mmol, 20.0 equiv). The resulting mixture is allowed to stir for two hours at 22° C. Analysis of the $^1$H NMR (400 MHz) spectrum reveals >98% conversion of norbornene, and the corresponding ROCM product 11b is obtained as >98% Z isomer. The resulting brown oil is purified by silica gel chromatography (100% hexanes) to afford 11b (19.2 mg, 0.0940 mmol, 59% yield) as colorless oil. IR (neat): 3077 (w), 2994 (w), 2921 (s), 2849 (s), 1640 (m), 1447 (s), 1407 (w), 1269 (w), 1029 (s), 992 (w), 951 (s), 907 (s), 889 (w), 742 (s), 666 (w); $^1$H NMR (500 MHz, CDCl$_3$): δ 5.84-5.77 (1H, m), 5.18 (1H, apparent t with strong roof effect, J=10.0 Hz), 5.13 (1H, apparent t with strong roof effect, 9.8 Hz), 4.98 (1H, d, J=17.0 Hz), 4.88 (1H, d, J=10.5 Hz), 2.85-2.76 (1H, m), 2.56-2.49 (1H, m), 2.29-2.22 (1H, m), 1.94-1.84 (3H, m), 1.71-1.59 (4H, m), 1.49-1.24 (4H, m), 1.21-1.04 (4H, m), 0.89-0.84 (1H, m). The coupling constants (J=10.0 and 9.8 Hz, respectively) of the signals at 5.18 and 5.13 ppm are indicative of Z isomer of 11b. $^{13}$C NMR (100 MHz, CDCl$_3$): δ 143.5, 135.1, 133.2, 112.4, 44.7, 41.6, 38.6, 36.8, 36.7, 33.9, 33.1, 31.9, 26.2; HRMS [M+H]$^+$ calcd for C$_{15}$H$_{25}$: 205.1956, found: 205.1953.

3-((Z)-Styryl)-5-vinylcyclopentane-1,2-diyl)dimethanol 13a

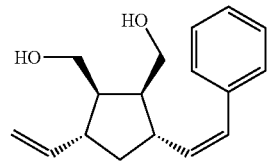 [SMILES: C=C[C@H]1C[C@@H](/C=C\c2ccccc2)[C@H](CO)[C@@H]1CO]

Following the general procedure, a solution of 6a (0.70 mg, 1.0 μmol, 1.0 mol %) in tetrahydrofuran (195 μL) is transferred by syringe to a vial containing 5-norbornene-2-exo, 3-exo-dimethanol 12 (15.0 mg, 0.0970 mmol, 1.00 equiv) and styrene (202 mg, 1.94 mmol, 20.0 equiv). The resulting mixture is allowed to stir for one hour at 22° C. Analysis of the $^1$H NMR (400 MHz) spectrum reveals >98% conv of 12, and the corresponding ROCM product 13a is obtained as a mixture of 97:3 Z:E isomers. The resulting brown oil is purified by silica gel chromatography (100% hexanes followed by 30-70% Et₂O in hexanes) to afford 13a (23.2 mg, 0.0890 mmol, 92% yield) as colorless oil. IR (neat): 3263 (br), 3078 (m), 3023 (m), 3002 (m), 2018 (m), 1639 (s), 1600 (s), 1493 (s), 1447 (m), 1413 (m), 1318 (br), 1252 (m), 1209 (m), 1180 (m), 1132 (m), 1066 (s), 1047 (s), 1027 (s), 993 (s), 913 (s), 875 (s), 809 (s), 770 (s), 736 (s), 700 (s), 673 (s), 563 (s), 494 (m), 449 (m); $^1$H NMR (400 MHz, CDCl₃): δ 7.34-7.30 (2H, m), 7.24-7.21 (3H, m), 6.48 (1H, d, J=11.6 Hz), 5.79-5.70 (1H, m), 5.52 (1H, dd, J=11.6, 10.4 Hz), 5.04-4.99 (1H, m), 4.98-4.95 (1H, m), 3.66-3.52 (5H, m), 3.31 (1H, br s), 2.78-2.69 (1H, m), 2.21-2.07 (3H, m), 2.03-1.97 (1H, m), 1.41-1.32 (1H, m). The coupling constants (J=11.6 and 11.6 Hz, respectively) of the signals at 6.48 and 5.52 ppm are indicative of Z isomer of 13a. $^{13}$C NMR (100 MHz, CDCl₃): δ 141.5, 137.6, 135.9, 129.9, 128.6, 128.4, 126.9, 114.6, 62.05, 62.03, 50.6, 48.6, 46.4, 40.3, 39.9; HRMS [M+H]⁺ calcd for C₁₇H₂₃O₂: 259.1698, found: 259.1694.

3-((Z)-3-Fluorostyryl)-5-vinylcyclopentane-1,2-diyl)dimethanol 13b

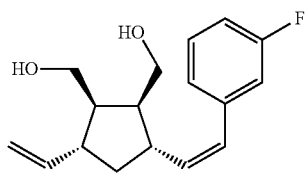 [SMILES: C=C[C@H]1C[C@@H](/C=C\c2cccc(F)c2)[C@H](CO)[C@@H]1CO]

Following the general procedure, a solution of 6a (0.70 mg, 1.0 μmol, 1.0 mol %) in tetrahydrofuran (195 μL) is transferred by syringe to a vial containing 5-norbornene-2-exo, 3-exo-dimethanol 12 (15.0 mg, 0.0970 mmol, 1.00 equiv) and 4-methoxystyrene (237 mg, 1.94 mmol, 20.0 equiv). The resulting mixture is allowed to stir for one hour at 22° C. Analysis of the $^1$H NMR (400 MHz) spectrum reveals >98% conv of 12, and the corresponding ROCM product 13b is obtained as a mixture of 96:4 Z:E isomers. The resulting brown oil is purified by silica gel chromatography (100% hexanes followed by 30-70% diethyl ether in hexanes) to afford 13b (24.9 mg, 0.0900 mmol, 93% yield) as colorless oil. IR (neat): 3285 (br), 3075 (m), 3004 (m), 2919 (m), 1640 (s), 1611 (s), 1580 (s), 1485 (s), 1441 (s), 1375 (m), 1282 (m), 1245 (s), 1136 (s), 1066 (s), 1047 (s), 1024 (s), 994 (s), 914 (s), 875 (s), 795 (s), 756 (s), 697 (s), 673 (s), 604 (m), 522 (s), 443 (w), 424 (w); $^1$H NMR (400 MHz, CDCl₃): δ 7.29-7.24 (1H, m), 7.00-6.98 (1H, m), 6.94-6.89 (2H, m), 6.42 (1H, d, J=11.2 Hz), 5.78-5.69 (1H, m), 5.56 (1H, dd, J=11.2, 10.0 Hz), 5.05-4.99 (1H, m), 4.98-4.96 (1H, m), 3.68-3.52 (4H, m), 3.37 (2H, br s), 2.75-2.66 (1H, m), 2.22-2.10 (3H, m), 2.02-1.96 (1H, m), 1.40-1.31 (1H, m). The coupling constants (J=11.2 and 11.2 Hz, respectively) of the signals at 6.42 and 5.56 ppm are indicative of Z isomer of 13b. $^{13}$C NMR (100 MHz, CDCl₃): δ 162.8 (d, $J_{C,F}$=244.4 Hz), 141.3, 139.7 (d, $J_{C,F}$=7.6 Hz), 137.0, 129.9 (d, $J_{C,F}$=8.3 Hz), 128.8 (d, $J_{C,F}$=2.3 Hz), 124.4 (d, $J_{C,F}$=3.0 Hz), 115.4 (d, $J_{C,F}$=21.2 Hz), 114.8, 113.7 (d, $J_{C,F}$=21.2 Hz), 62.01, 61.99, 50.5, 48.6, 46.4, 40.3, 39.8; HRMS [M+NH₄]⁺ calcd for C₁₇H₂₂FO₂: 277.1604, found: 277.1591.

3-((Z)-4-Methoxystyryl)-5-vinylcyclopentane-1,2-diyl)dimethanol 13c

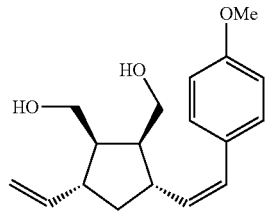 [SMILES: C=C[C@H]1C[C@@H](/C=C\c2ccc(OC)cc2)[C@H](CO)[C@@H]1CO]

Following the general procedure, a solution of 6a (0.70 mg, 1.0 μmol, 1.0 mol %) in tetrahydrofuran (195 μL) is transferred by syringe to a vial containing 5-norbornene-2-exo, 3-exo-dimethanol 12 (15.0 mg, 0.0970 mmol, 1.00 equiv) and 4-methoxystyrene (260 mg, 1.94 mmol, 20.0 equiv). The resulting mixture is allowed to stir for one hour at 22° C. Analysis of the $^1$H NMR (400 MHz) spectrum reveals >98% conv of 12, and the corresponding ROCM product 13c is obtained as a mixture of 98:2 Z:E isomers. The resulting brown oil is purified by silica gel chromatography (100% hexanes followed by 20-70% diethyl ether in hexanes) to afford 13c (23.2 mg, 0.0800 mmol, 82% yield) as colorless oil. IR (neat): 3271 (br), 3074 (m), 2999 (m), 2917 (m), 1639 (s), 1607 (s), 1574 (s), 1509 (s), 1460 (m), 1405 (m), 1300 (m), 1245 (s), 1174 (s), 1108 (m), 1065 (m), 1031 (s), 994 (m), 913 (s), 842 (s), 817 (m), 746 (m), 710 (m), 669 (m), 631 (m), 564 (m), 517 (m), 443 (m); $^1$H NMR (400 MHz, CDCl₃): δ 7.19-7.15 (2H, m), 6.87-6.84 (2H, m), 6.41 (1H, d, J=11.6 Hz), 5.79-5.71 (1H, m), 5.44 (1H, dd, J=11.6, 10.0 Hz), 5.04-4.99 (1H, m), 4.98-4.95 (1H, m), 3.80 (3H, s), 3.68-3.54 (4H, m), 3.45 (1H, br s), 3.18 (1H, br s), 2.79-2.70 (1H, m), 2.27-2.08 (3H, m), 2.03-1.97 (1H, m), 1.39-1.31 (1H, m). The coupling constants (J=11.6 and 11.6 Hz, respectively) of the signals at 6.41 and 5.44 ppm are indicative of Z isomer of 13c. $^{13}$C NMR (100 MHz, CDCl₃): δ 158.5, 141.6, 134.6, 130.1, 129.8, 129.4, 114.6, 113.8, 62.09, 62.08, 55.4, 50.7, 48.6, 46.4, 40.3, 39.9; HRMS [M+H]⁺ calcd for C₁₈H₂₅O₃: 289.1804, found: 289.1809.

3-((Z)-2-Cyclohexylvinyl)-5-vinylcyclopentane-1,2-diyl)dimethanol 13d

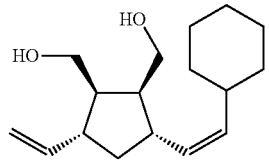 [SMILES: C=C[C@H]1C[C@@H](/C=C\C2CCCCC2)[C@H](CO)[C@@H]1CO]

Following the general procedure, a solution of 6a (0.70 mg, 1.0 μmol, 1.0 mol %) in tetrahydrofuran (195 μL) is transferred by syringe to a vial containing 5-norbornene-2-exo, 3-exo-dimethanol 12 (15.0 mg, 0.0970 mmol, 1.00 equiv) and vinyl cyclohexane (214 mg, 1.94 mmol, 20.0 equiv). The resulting mixture is allowed to stir for 8 hours at 22° C. Analysis of the $^1$H NMR (400 MHz) spectrum reveals >98% conversion of 12, and the corresponding ROCM product 13d is obtained as >98% Z isomer. The resulting brown oil is purified by silica gel chromatography (100% hexanes followed by 30-50% diethyl ether in hexanes) to afford 13d (15.8 mg, 0.0590 mmol, 61% yield) as colorless oil. IR (neat): 3284 (br), 3076 (w), 2990 (w), 2920 (s), 2849 (s), 1639 (m), 1448 (s), 1349 (w), 1258 (w), 1072 (m), 1044 (m), 1028 (m), 993 (m), 947 (s), 911 (s), 890 (w), 748 (m), 675 (w); $^1$H NMR (400 MHz, CDCl$_3$): δ 5.78-5.69 (1H, m), 5.23 (1H, apparent t with roof effect, J=10.8 Hz), 5.11 (1H, apparent t with roof effect, J=10.8 Hz), 5.03-4.98 (1H, m), 4.97-4.94 (1H, m), 3.76-3.60 (4H, m), 3.28 (2H, br s), 2.51-2.42 (1H, m), 2.29-1.98 (4H, m), 1.88-1.82 (1H, m), 1.72-1.53 (5H, m), 1.32-0.99 (6H, m). The coupling constants (J=10.8 and 10.8 Hz, respectively) of the signals at 5.23 and 5.11 ppm are indicative of Z isomer of 13d. $^{13}$C NMR (100 MHz, CDCl$_3$): δ 141.7, 137.0, 131.0, 114.5, 62.35, 62.26, 50.0, 48.6, 46.6, 40.3, 40.1, 36.8, 35.0, 33.9, 33.7, 26.1, 26.0; HRMS [M+H]$^+$ calcd for C$_{17}$H$_{29}$O$_2$: 265.2168, found: 265.2178.

(Z)-(((1-Phenylhexa-1,5-diene-3,4-diyl)bis(oxy))bis(methylene))dibenzene 15

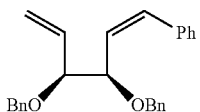 [SMILES: C=C[C@H](OCc1ccccc1)[C@@H](/C=C\c1ccccc1)OCc1ccccc1]

Following the general procedure, a solution of 6a (1.8 mg, 2.5 μmol, 3.0 mol %) in tetrahydrofuran (170 μL) is transferred by syringe to a vial containing cyclobutene 14 (22.4 mg, 0.0840 mmol, 1.00 equiv) and styrene (88.0 mg, 0.845 mmol, 10.0 equiv). The resulting mixture is allowed to stir for 12 hours at 40 OC. Analysis of the $^1$H NMR (400 MHz) spectrum reveals 94% conversion of 14, and the corresponding ROCM product 15 is obtained as a mixture of 93:7 Z:E isomers. The resulting brown oil is purified by silica gel chromatography (100% hexanes to 2% diethyl ether in hexanes) followed by passing through a plug of activated charcoal with 100% dichloromethane to afford 15 (20.9 mg, 0.0560 mmol, 63% yield) as colorless oil. IR (neat): 3062 (w), 3028 (m), 2863 (m), 1641 (m), 1600 (m), 1495 (w), 1454 (w), 1422 (w), 1388 (w), 1368 (w), 1332 (w), 1246 (w), 1205 (w), 1090 (s), 1069 (s), 1028 (s), 991 (m), 928 (m), 804 (w), 779 (w), 736 (s), 697 (s), 606 (w), 459 (w); $^1$H NMR (400 MHz, CDCl$_3$): δ 7.36-7.12 (13H, m), 7.15-7.12 (2H, m), 6.80 (1H, d, J=12.0 Hz), 5.96-5.87 (1H, m), 5.68 (1H, dd, J=12.0, 10.0 Hz), 5.37-5.29 (2H, m), 4.68 (1H, d, J=12.4 Hz), 4.52 (1H, d, J=12.0 Hz), 4.48-4.44 (2H, m), 4.27 (1H, d, J=11.6 Hz), 3.94-3.90 (1H, m). The coupling constants (J=12.0 and 12.0 Hz, respectively) of the signals at 6.80 and 5.68 ppm are indicative of Z isomer of 15. $^{13}$C NMR (100 MHz, CDCl$_3$): δ 138.8, 138.5, 136.8, 135.8, 133.9, 130.1, 128.9, 128.4, 128.3, 128.2, 128.0, 127.8, 127.5, 127.4, 127.3, 119.2, 82.3, 76.2, 70.4, 70.3; HRMS [M+NH$_4$]$^+$ calcd for C$_{26}$H$_{30}$NO$_2$: 388.2277, found: 388.2278.

Density Functional Theory (DFT) Calculations: DFT (For a recent review on the application of DFT to complexes containing transition metals, see: Cramer, C. J.; Truhlar, D. G. *Phys. Chem. Chem. Phys.* 2009, 11, 10757) computations were performed with the Gaussian 09 suite of programs (Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, Jr., J. A.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, J. M.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, Ö.; Foresman, J. B.; Ortiz, J. V.; Cioslowski, J.; Fox, D. J. *Gaussian* 09, Revision A.1, Gaussian, Inc., Wallingford Conn., 2009) by application of the generalized gradient approximation (GGA) functional BP86 ((a) Becke, A. D. *Phys. Rev. A* 1988, 38, 3098. (b) Perdew, J. P.; Yue, W. *Phys. Rev. B* 1986, 33, 8800). The following basis set (termed "basis1") was used for geometry optimizations, calculation of dipole moments and evaluation of thermal corrections to the Gibbs free energy at standard conditions (298.15 K, 1 atm): 6-31G(d,p) basis set for hydrogen and carbon atoms, including additional diffuse functions (+) on heteroatoms (oxygen, nitrogen, sulfur and chloride). A quasi-relativistic effective core potential (ECP) of the Stuttgart-Dresden type (Andrae, D.; Haeussermann, U.; Dolg, M.; Stoll, H.; Preuss, H. *Theor. Chim. Acta* 1990, 77, 123) was used for ruthenium (MWB28 keyword in Gaussian for basis set and ECP). The nature of all stationary points was checked through vibrational analysis. Single point electronic energies of metallacyclobutanes Z-A, Z-B, E-A and E-B in solution (tetrahydrofuran) were performed on the gas phase geometries obtained with basis1 through application of an integral equation formalism variant of the polarizable continuum model (IEFPCM) (Scalmani, G.; Frisch, M. J. *J. Chem. Phys.* 2010, 132, 114110) and the larger basis set termed "basis2": 6-311+G(2df,2pd) on H, C, N, S and MWB28 on ruthenium. The single point electronic energies at the BP86/basis2 level were corrected by addition of thermal corrections to the Gibbs free energy obtained at the BP86/basis1 level.

Geometries and Energies of Computed Structures
Ruthenacyclobutane Z-A
Gas phase electronic energy (basis 1): −2591.06281055 hartree;
Gas phase thermal correction to free energy (basis 1): 0.665857 hartree;
Single point electronic energy in thf (basis 2): −2591.62434465 hartree.
Ruthenacyclobutane Z-B
Gas phase electronic energy (basis 1): −2591.04519743 hartree;
Gas phase thermal correction to free energy (basis 1): 0.669445 hartree;
Single point electronic energy in thf (basis 2): −2591.60424425 hartree
Ruthenacyclobutane E-A
Gas phase electronic energy (basis 1): −2591.06329315 hartree
Gas phase thermal correction to free energy (basis 1): 0.667798 hartree
Single point electronic energy in thf (basis 2): −2591.62280483 hartree
Ruthenacyclobutane E-B
Gas phase electronic energy (basis 1): −2591.05806998 hartree
Gas phase thermal correction to free energy (basis 1): 0.666349 hartree Single point electronic energy in thf (basis 2): −2591.61843404 hartree Ru Complex 1

Gas phase electronic energy (basis 1): −2404.50152636 hartree

Dipole moment: 1.9702 Debye

Ru Complex 5

Gas phase electronic energy (basis 1): −1865.48358042 hartree

Dipole moment: 7.8511 Debye

Ru Complex 6a

Gas phase electronic energy (basis 1): −2511.50014885 hartree

Dipole moment: 7.7302 Debye

Ru Complex 6b

Gas phase electronic energy (basis 1): −2542.34928152 hartree

Dipole moment: 17.2896 Debye

E Isomer of ROCM Product 1La

Gas phase electronic energy (basis 1): −582.390941560 hartree

Sum of electronic and thermal Free Energies (basis 1): −582.156194 hartree

Z Isomer of ROCM Product 11a

Gas phase electronic energy (basis 1): −582.386301883 hartree

Sum of electronic and thermal Free Energies (basis 1): −582.149981 hartree

Compounds and their Synthesis

Figure 10:
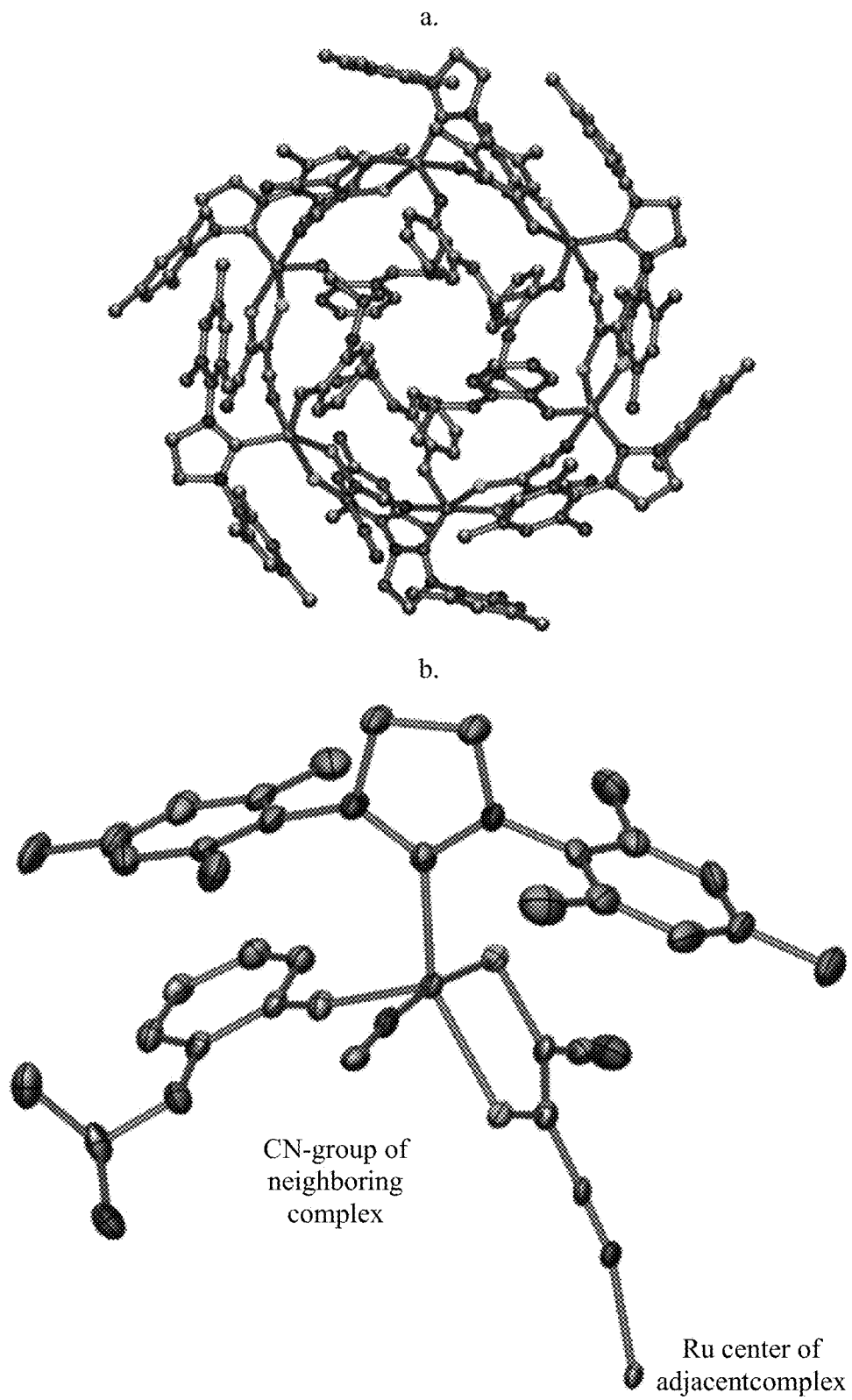
FIG. 10. X-ray structure of complex 6b. Cyclic hexamer (a) and monomer unit showing the connection to the adjacent complexes (b).
Figure 11:
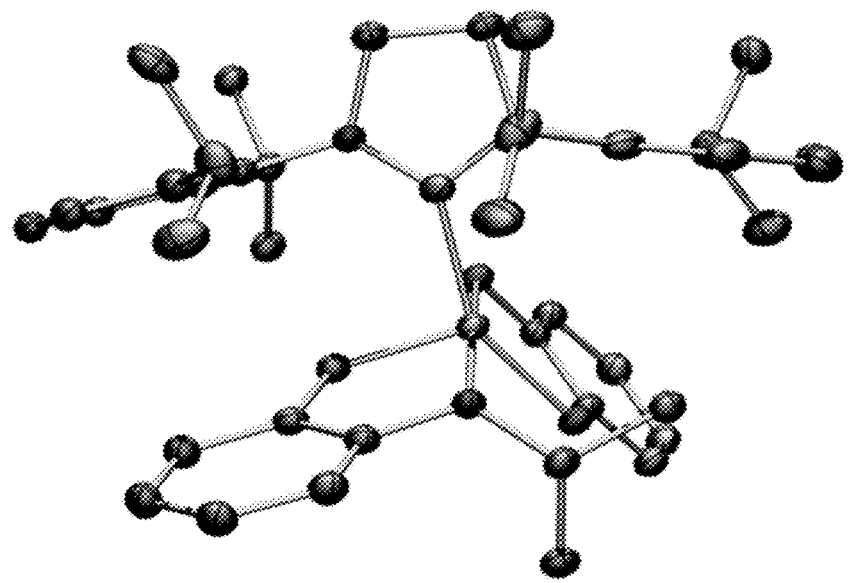
FIG. 11. X-ray structure of complex 6c.

A series of complexes were prepared through different pathways (Scheme X1), from either commercially available (Aldrich; 1, 1a, 1b) or in the literature reported compounds (1e (Ung, T.; Hejl, A.; Grubbs, R. H.; Schrodi, Y. *Organometallics* 2004, 23, 5399), 1d (Barbasiewicz, M.; Szadkowska, A.; Bujok, R.; Grela, K. *Organometallics* 2006, 25, 3599), 1f (Slugovc, C.; Perner, B.; Stelzer, F.; Mereiter, K. *Organometallics* 2004, 23, 3622), 1g (Ben-Asuly, A.; Tzur, E.; Diesendruck, C. E.; Sigalov, M.; Goldberg, I.; Lemcoff; G. N. *Organometallics* 2008, 27, 811)). Alcoholysis of 1c with phenol 2a or pinacol 2b upon liberation of tert-butanol provides access to phosphine based complexes 6d-e. Exchange of the chloride ligands with disodium salts 2-4 (Scheme X2) provides 6a-c and 6f-j. Both bidentate ligands in target complexes 5-6j (i.e. the chelating carbene ligand as well as the dianionic ligand) and also the neutral monodentate donor L (PCy$_3$, SIMes and SIPr) have been altered independently (cf. Scheme X1). Compound 6b appears monomeric in dilute dichloromethane solution and as cyclic hexamer in the solid state (FIG. 10), wherein a nitrile group of the neighboring complex coordinates to the Ru center.

Scheme X1. Exemplary compounds.

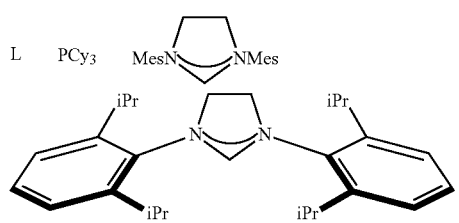

-continued

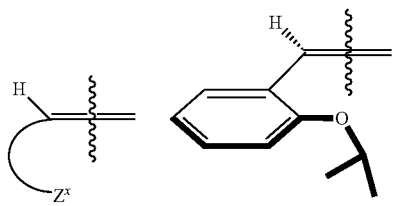

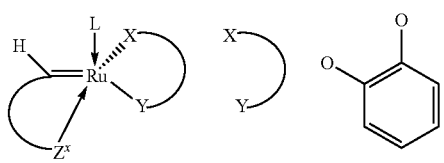

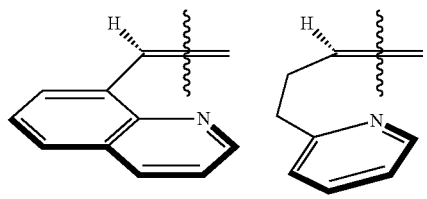

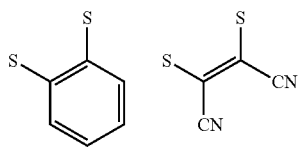

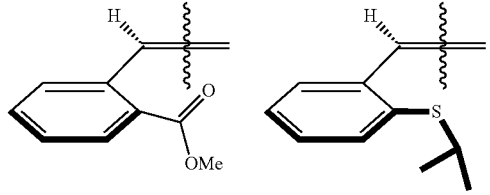

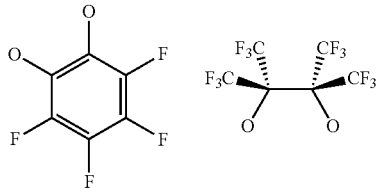

Complex Precursors:

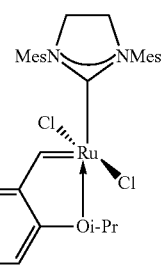

-continued
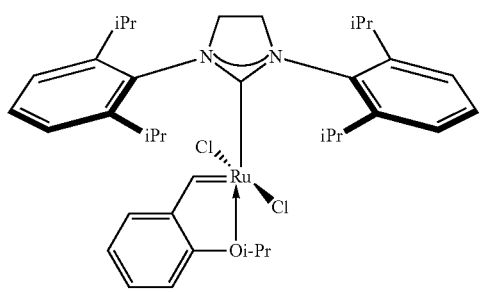 1a
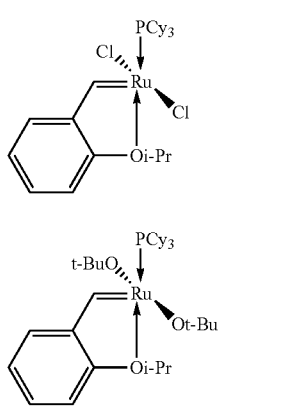 1b
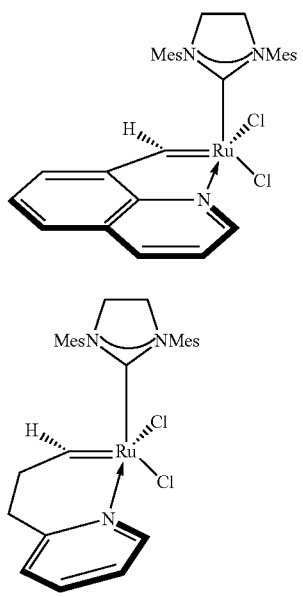 1d
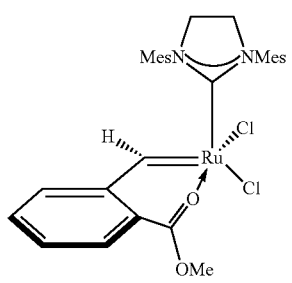 1f
-continued
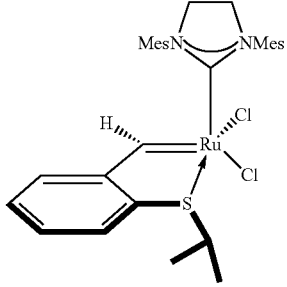 1g
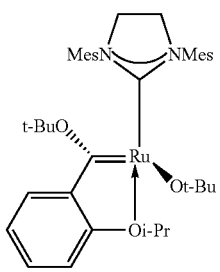 1h
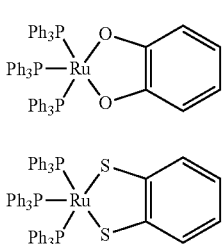 1i
 1j
Bidentate Ligands (Protonated Form or Salt):
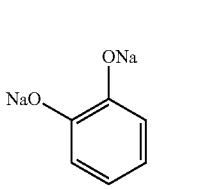 2
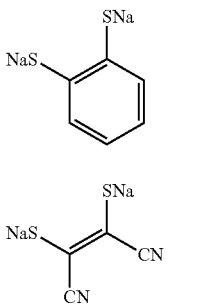 3
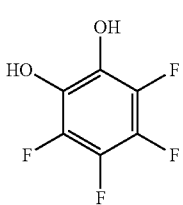 4
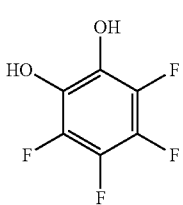 2a 227
-continued
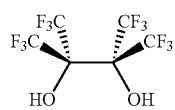
Exemplary Compounds:
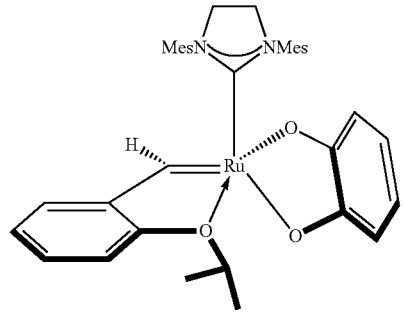
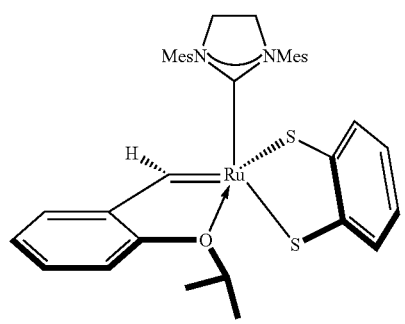
6a
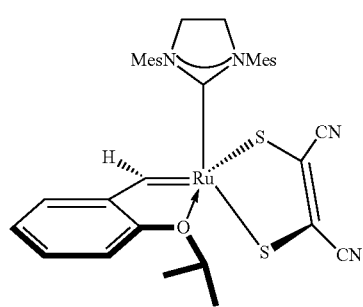
6b
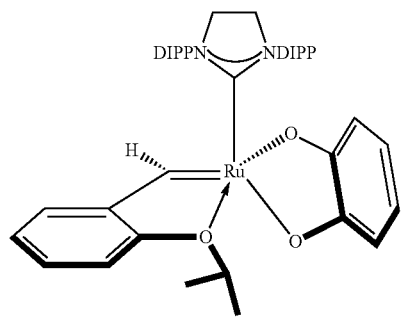
6c
228
-continued
2b
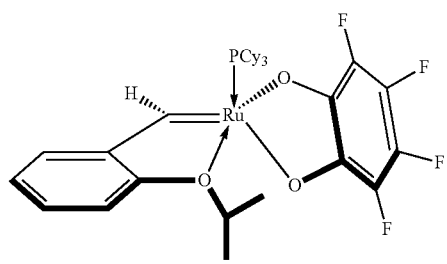
6d
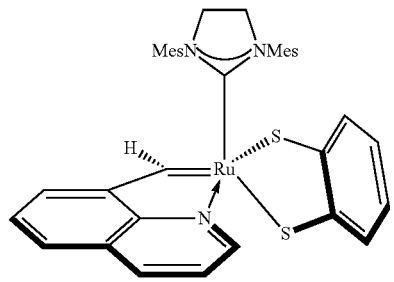
6e
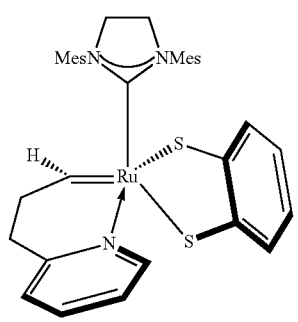
6f
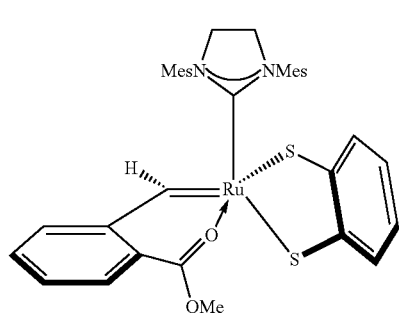
6g
6h 6i
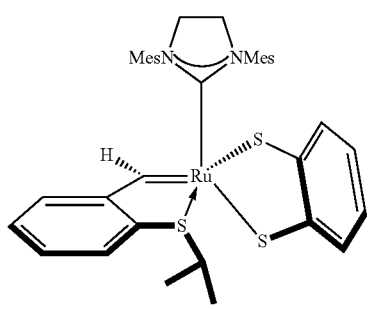

6j
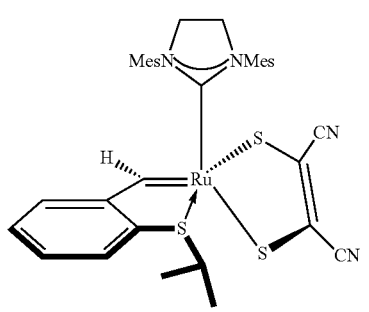

6k
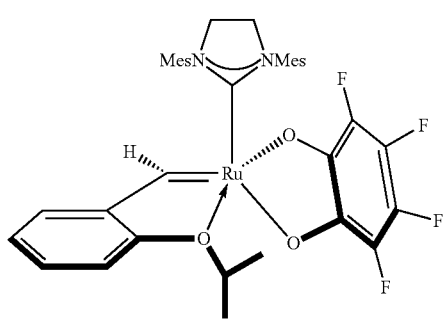

6l
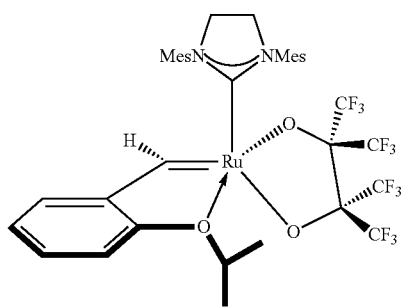

6m
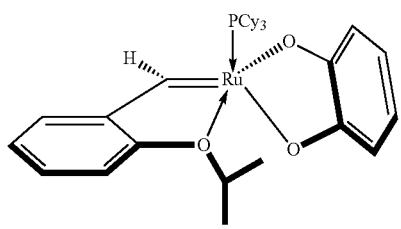

6n
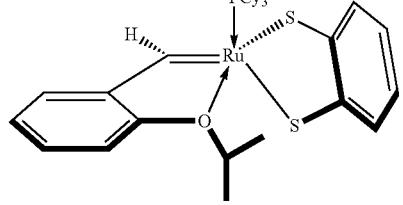

6o
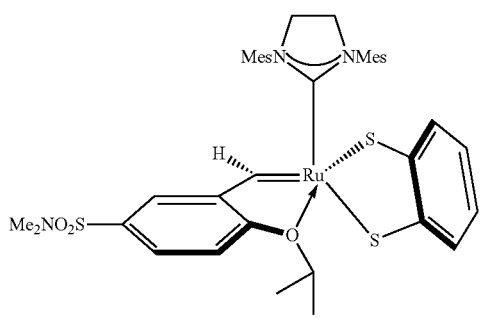

6p
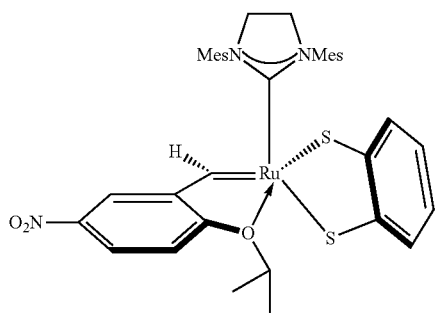

6q
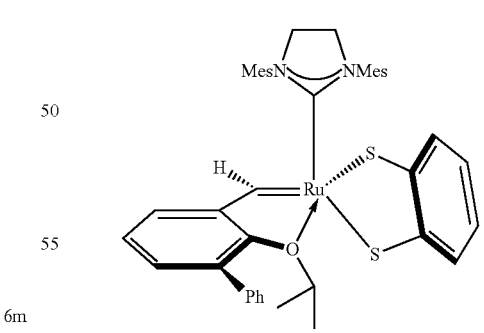

Synthesis of complexes 5-6b and 6f-j: Following the general procedures for 5-6b, complexes 6c and 6f-j have been prepared in >98% conversion to product. Single crystals suitable for x-ray crystallography have been obtained through vapor diffusion from one of the following solvent combinations: dichloromethane and hexane or dichloromethane and diethyl ether (FIGS. 10-11 and 14-18).

Scheme X2. Exemplary synthesis.

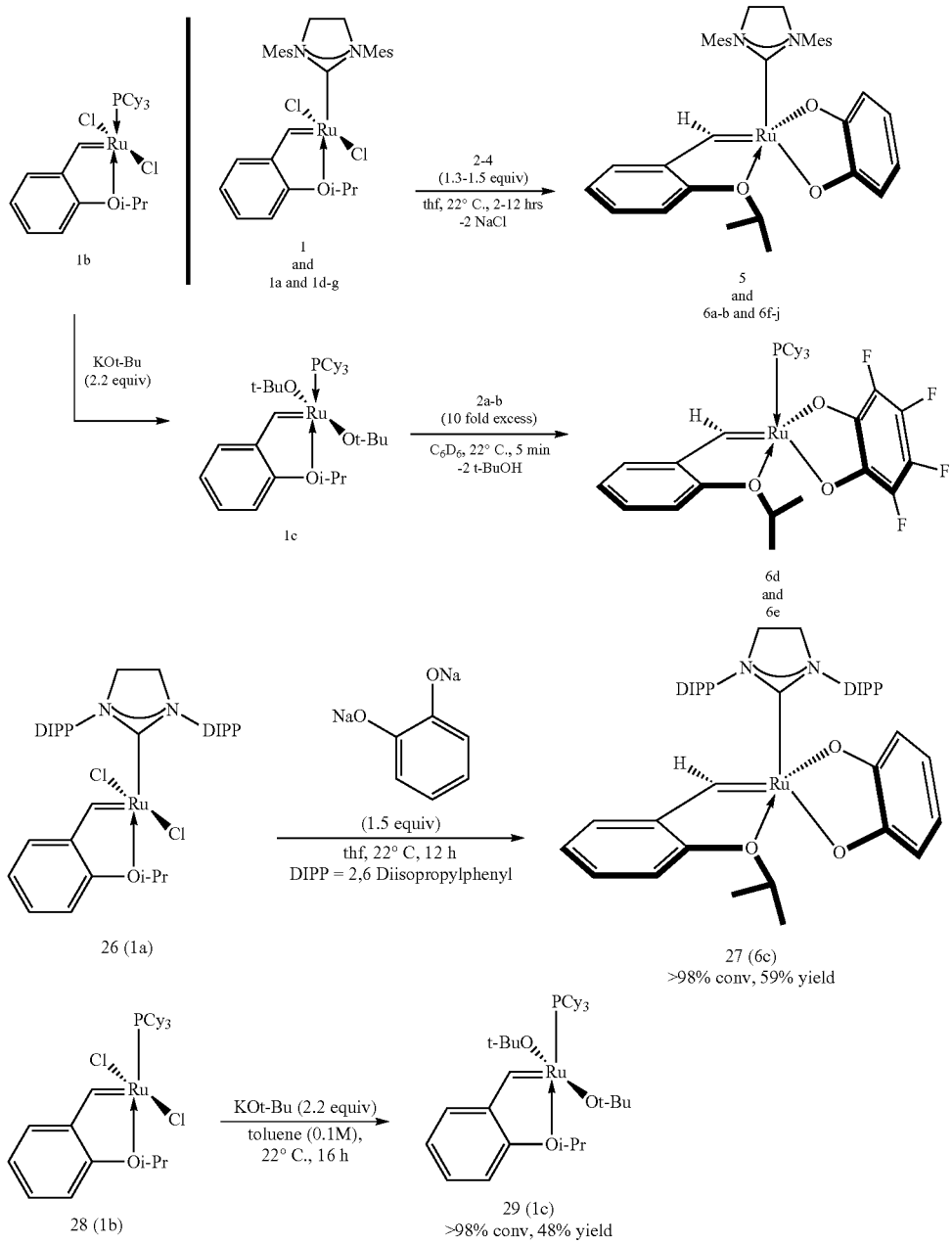

Synthesis of complex 1c: To a 9-dram vial charged with a stir bar and potassium tert-butoxide (559.0 mg, 4.982 mmol, 2.20 equiv) under $N_2$ atmosphere, a solution of dichloride Ru complex 1b (1.359 g, 2.265 mmol, 1.00 equiv) in toluene (22.6 mL) was added. The resulting mixture was allowed to stir at 22° C. for 16 hours, at which time the reaction mixture was passed through a Celite plug and the solvent was evaporated under vacuum. The resulting solid was re-dissolved in toluene and pentane was added until a white-colored precipitate emerges. The mixture was loaded onto a short column prepared with Celite (4 cm in height), placed in a pipette (~0.5 cm diameter), and eluted with 1:1 toluene:pentane (5 mL). After the removal of solvents, the brown-colored solids were recrystallized at −55° C. by layering a toluene solution of the complex with pentane, which afforded 1c (739.2 mg, 1.095 mmol, 48% yield).

Figure 12:
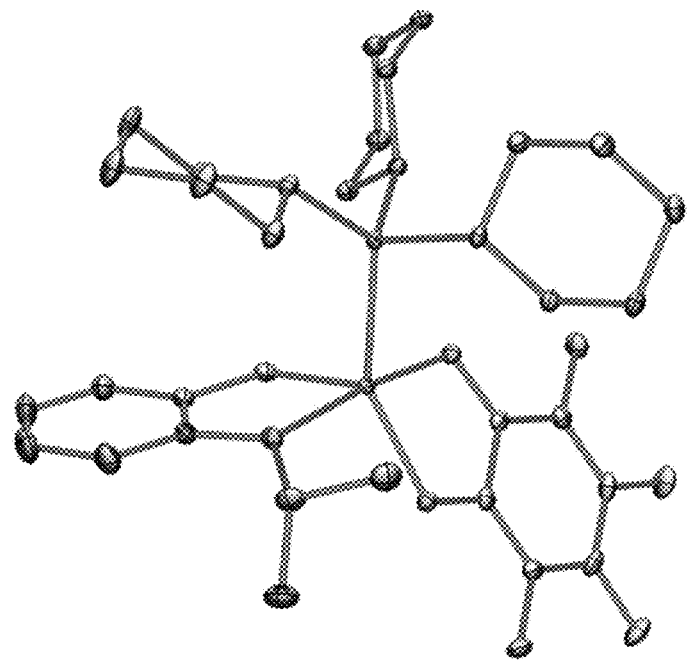
FIG. 12. X-ray structure of complex 6d.
Figure 13:
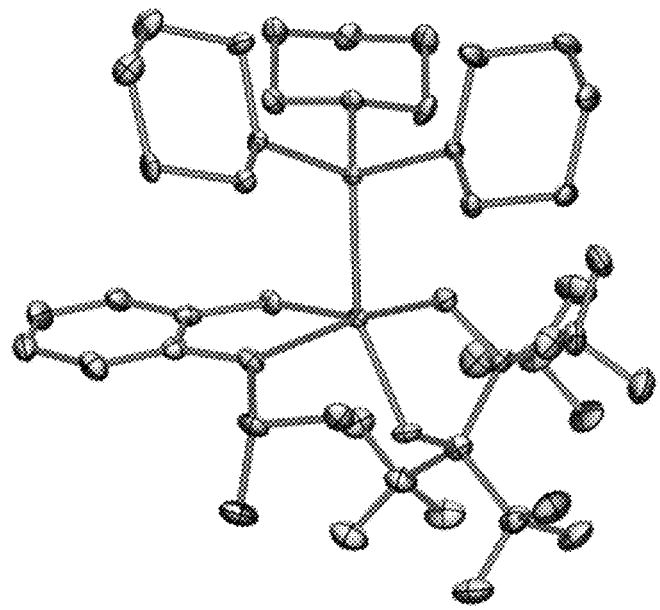
FIG. 13. X-ray structure of complex 6e.
Figure 14:
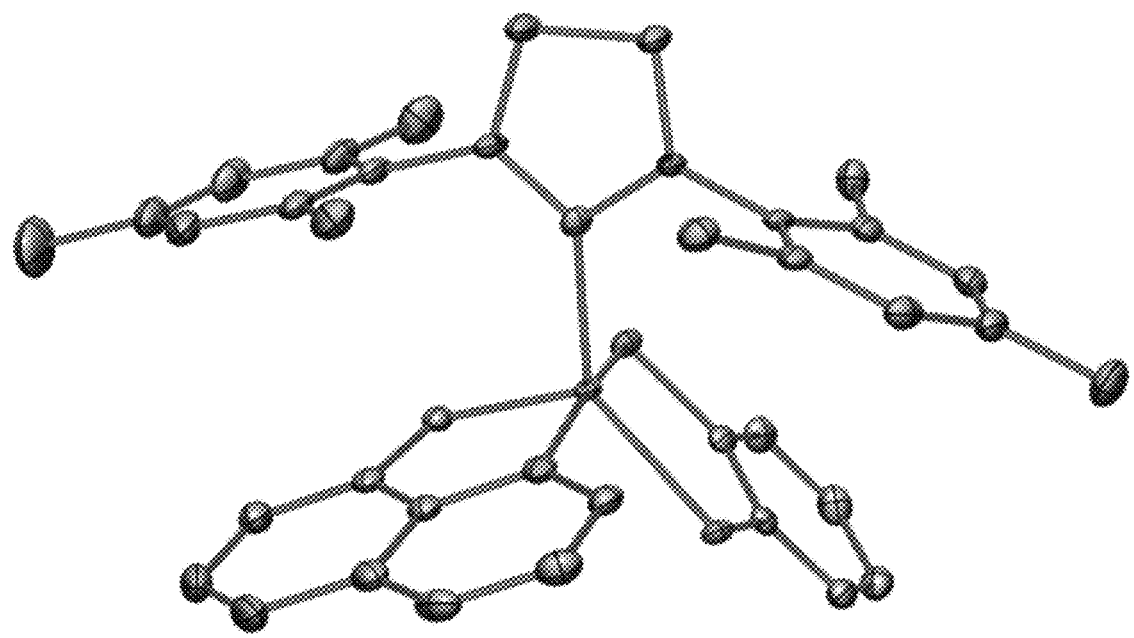
FIG. 14. X-ray structure of complex 6f.
Figure 15:
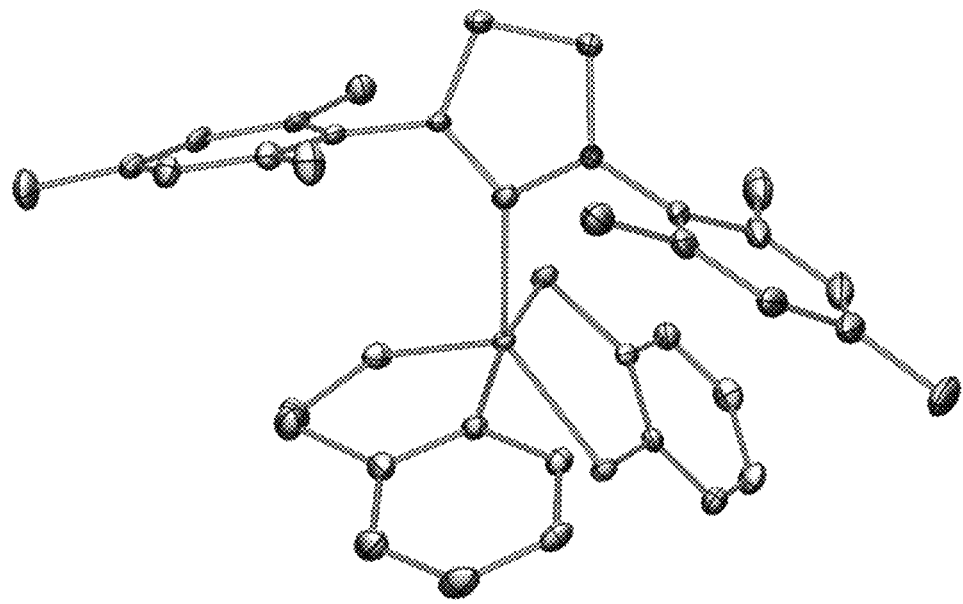
FIG. 15. X-ray structure of complex 6g.
Figure 16:
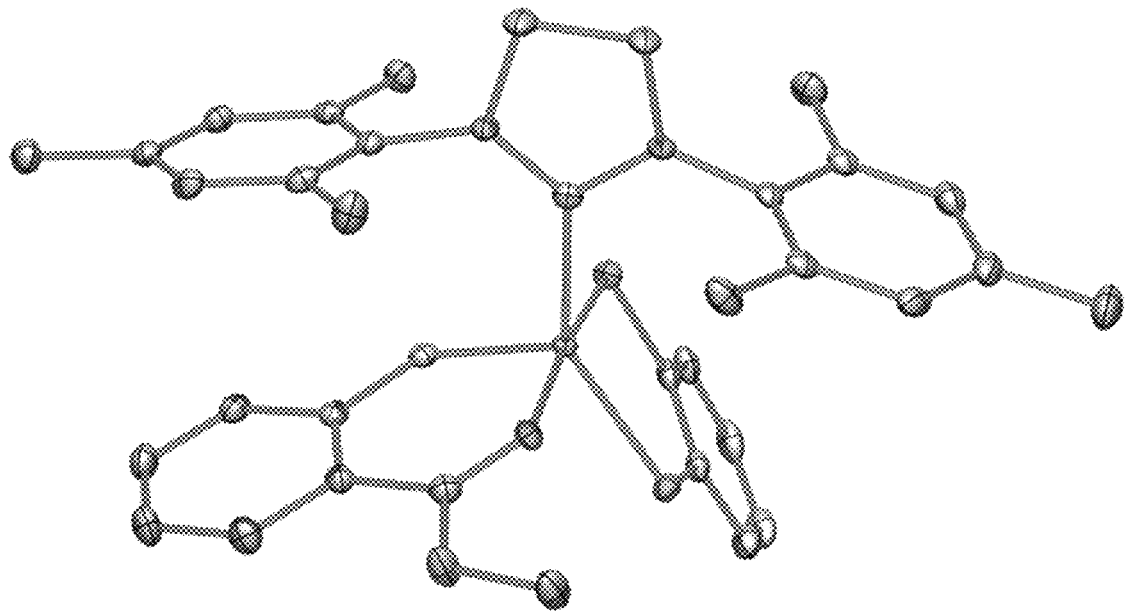
FIG. 16. X-ray structure of complex 6h.
Figure 17:
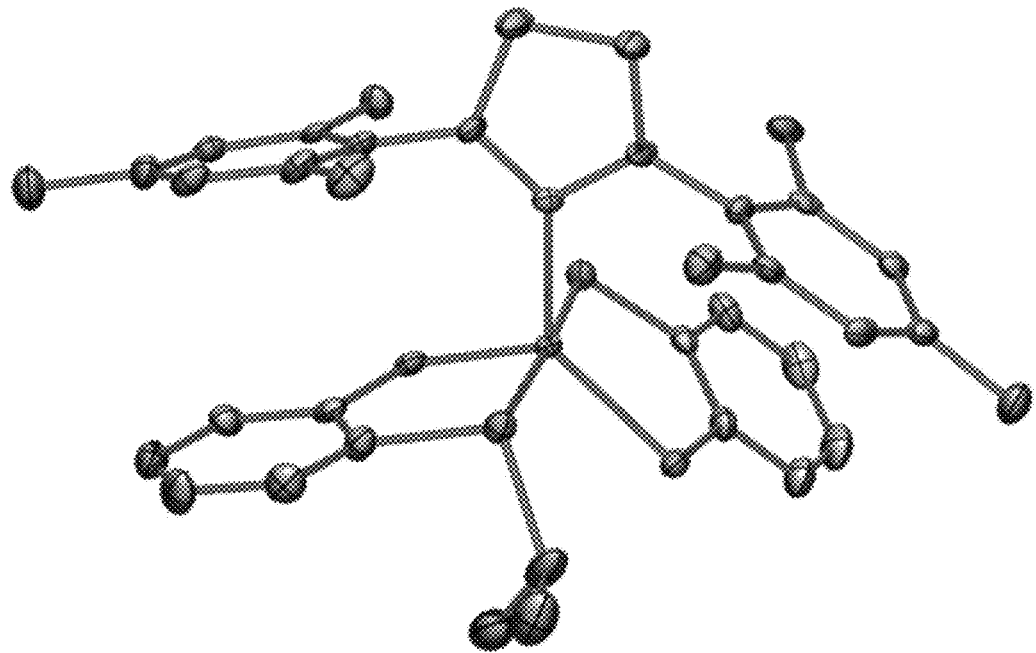
FIG. 17. X-ray structure of complex 6i.
Figure 18:
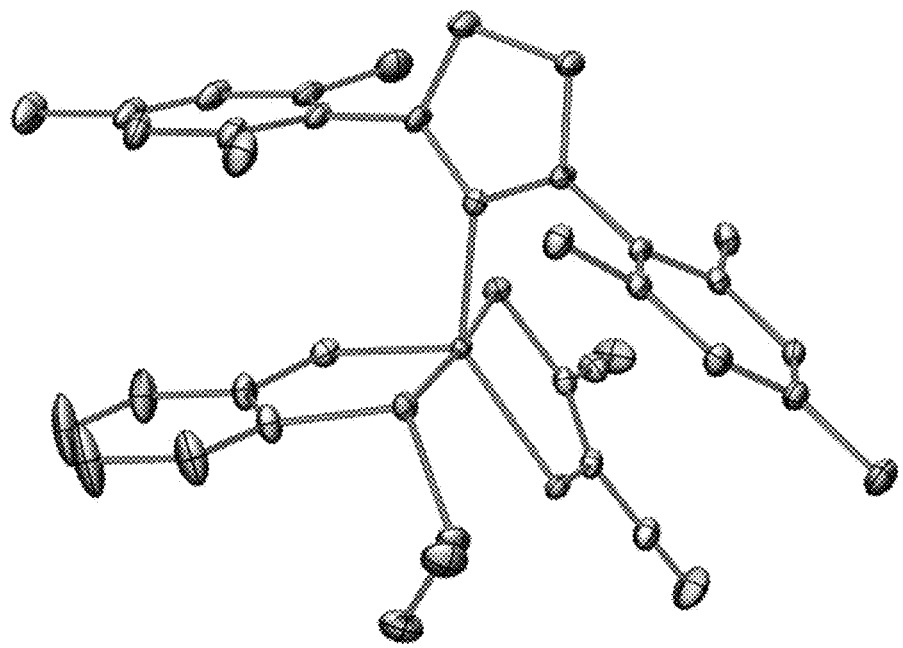
FIG. 18. X-ray structure of complex 6j.
Figure 19:
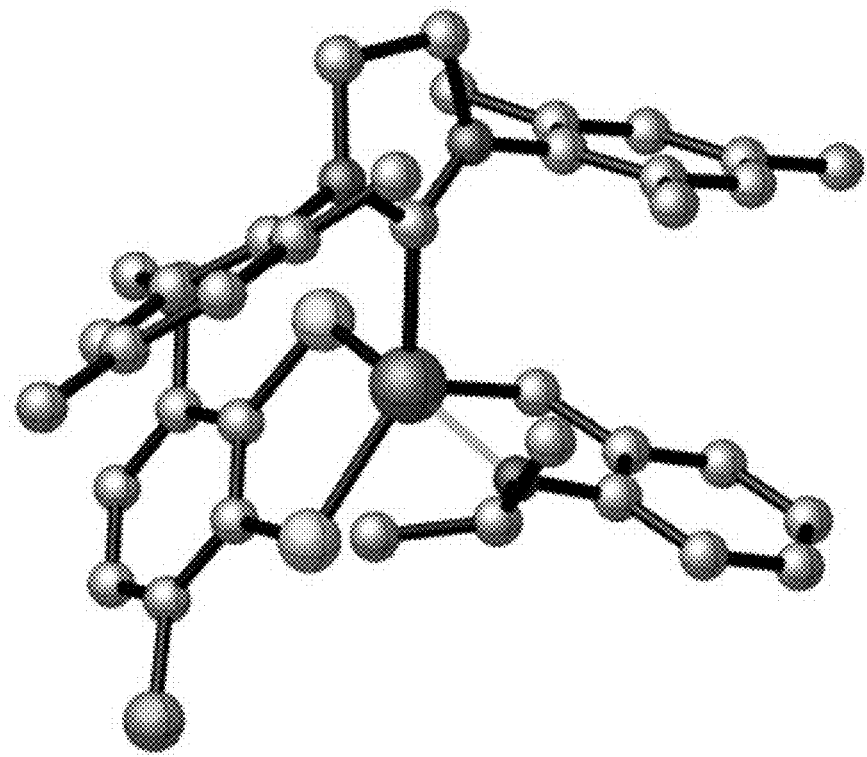
FIG. 19. X-ray structure of complex A-1b.
Figure 20:
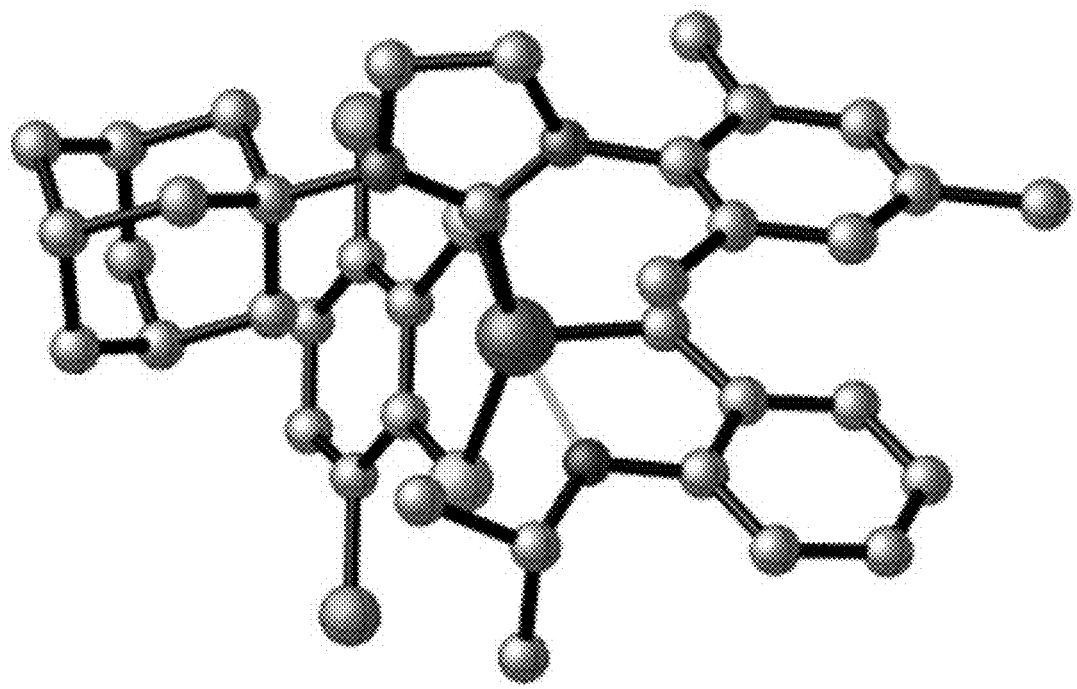
FIG. 20. X-ray structure of complex A-3b.
Figure 21:
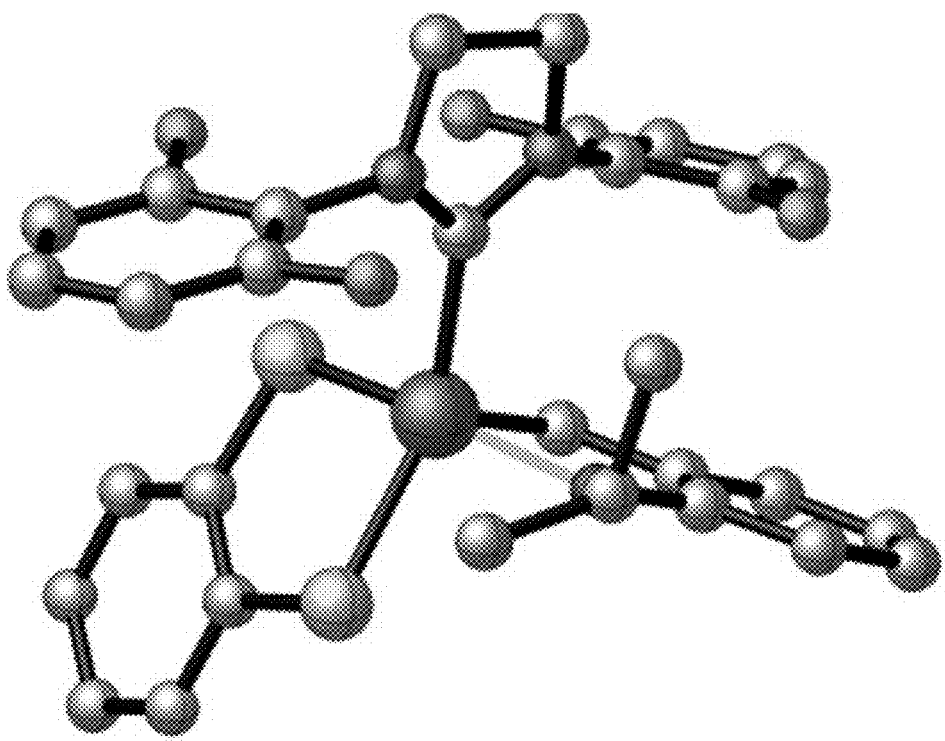
FIG. 21. X-ray structure of complex A-4b.
Figure 22:
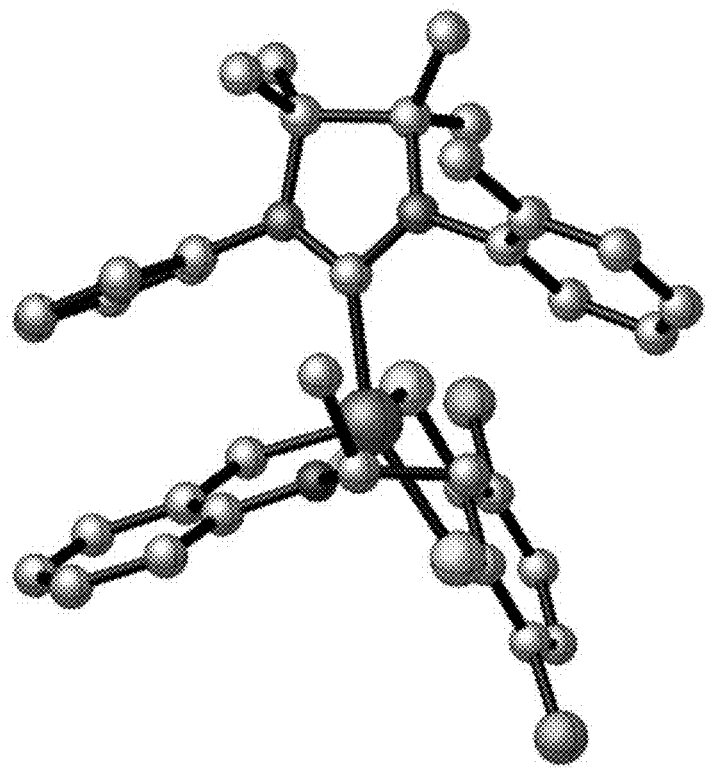
FIG. 22. X-ray structure of complex A-5b.
Figure 23:
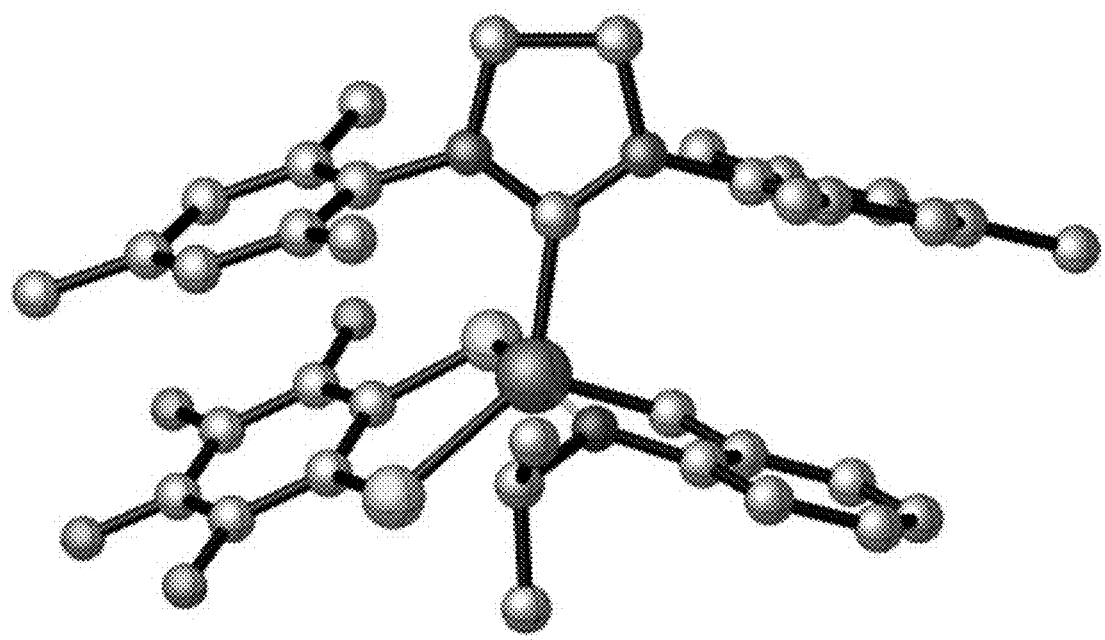
FIG. 23. X-ray structure of complex A-6b.
Figure 24:
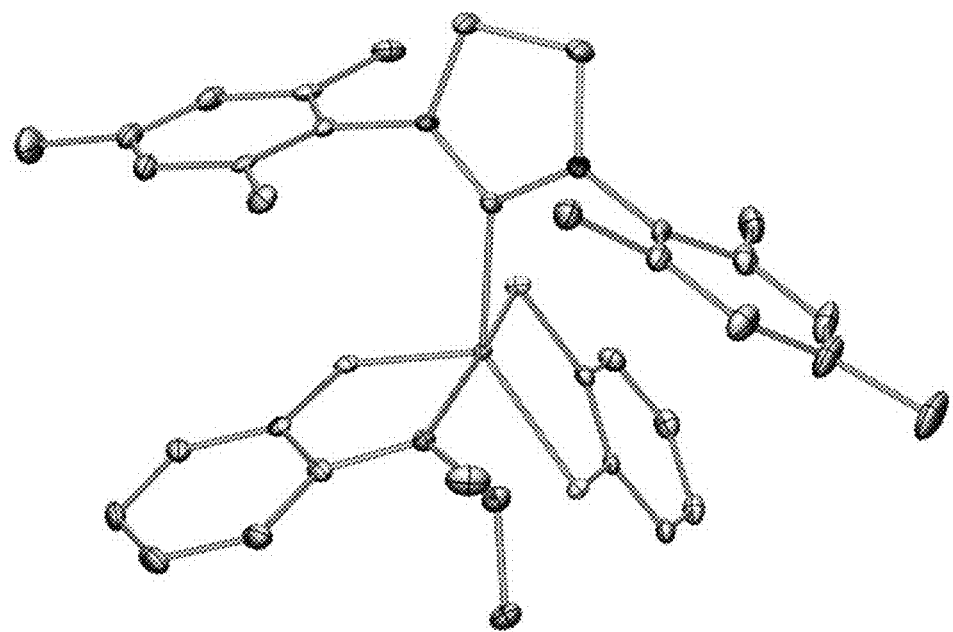
Figure 25:
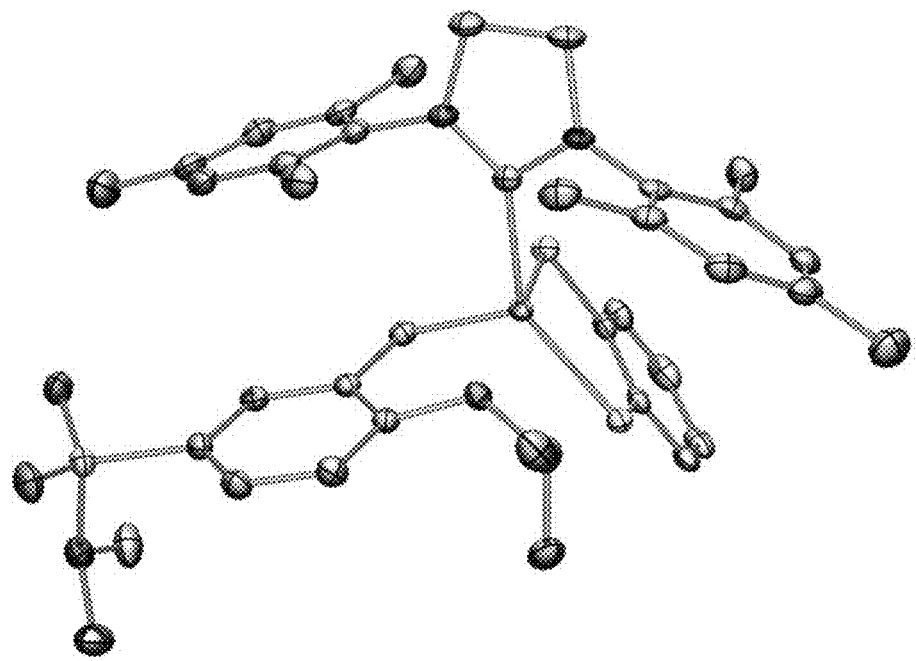
FIG. 25. X-ray structure of complex B-1c.
Figure 26:
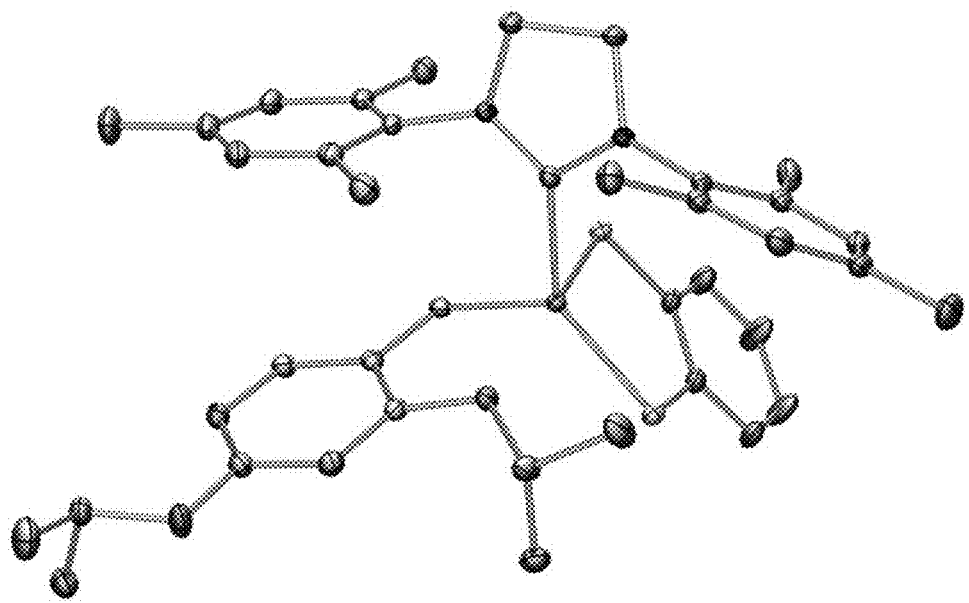
FIG. 26. X-ray structure of complex B-1d.
Figure 27:
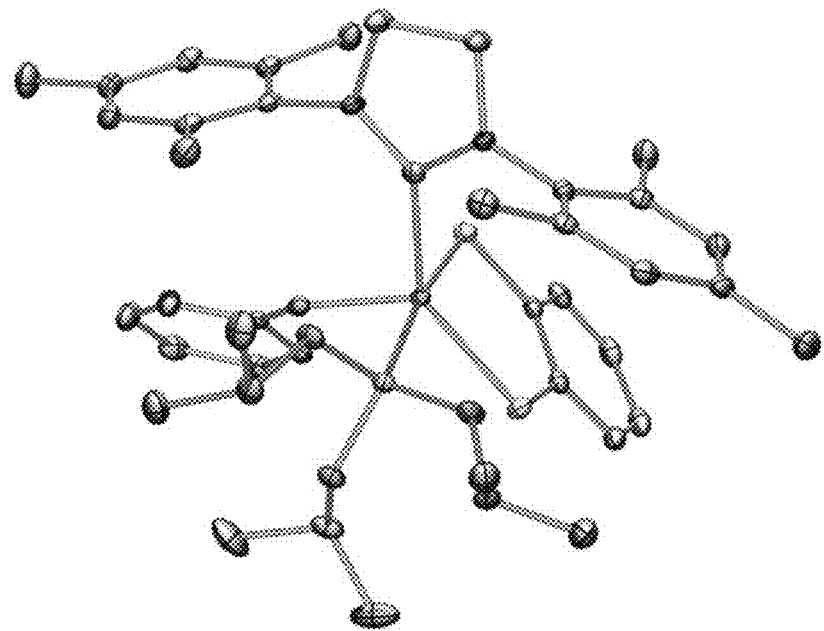
FIG. 27. X-ray structure of complex B-1f.
Figure 28:
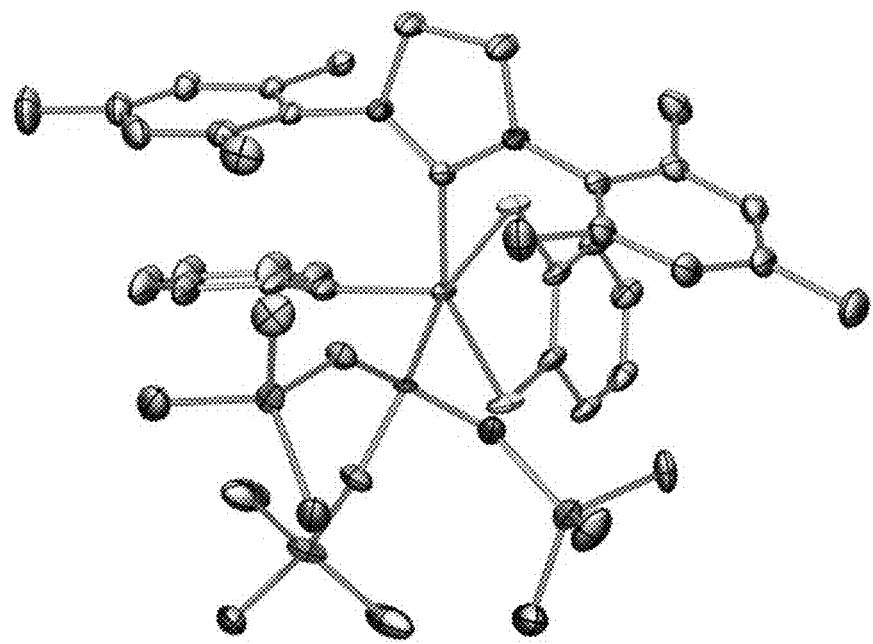
FIG. 28. X-ray structure of complex B-1g.
Figure 29:
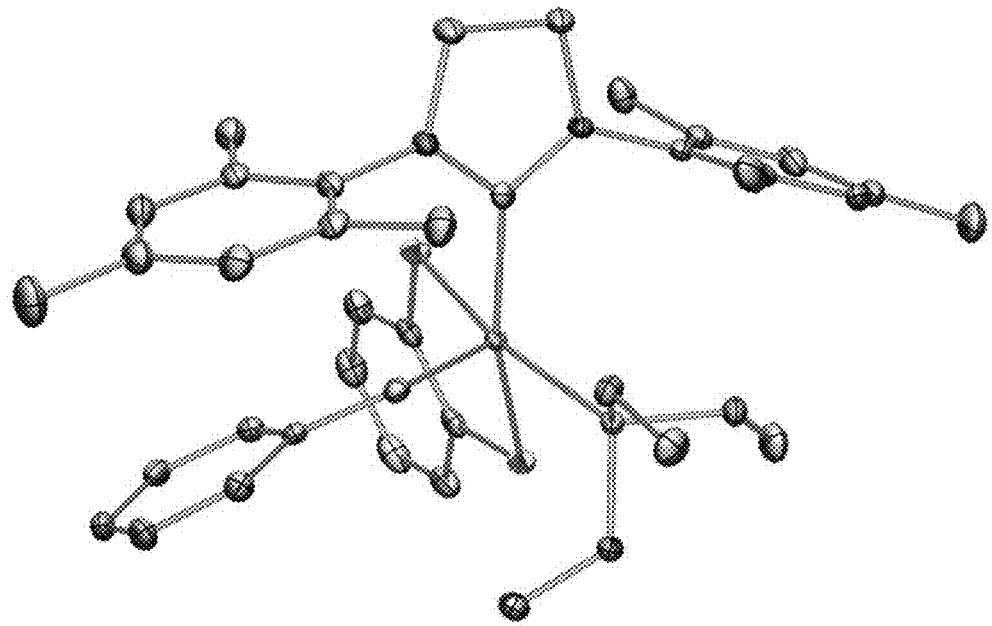
FIG. 29. X-ray structure of complex B-1h.
Figure 30:
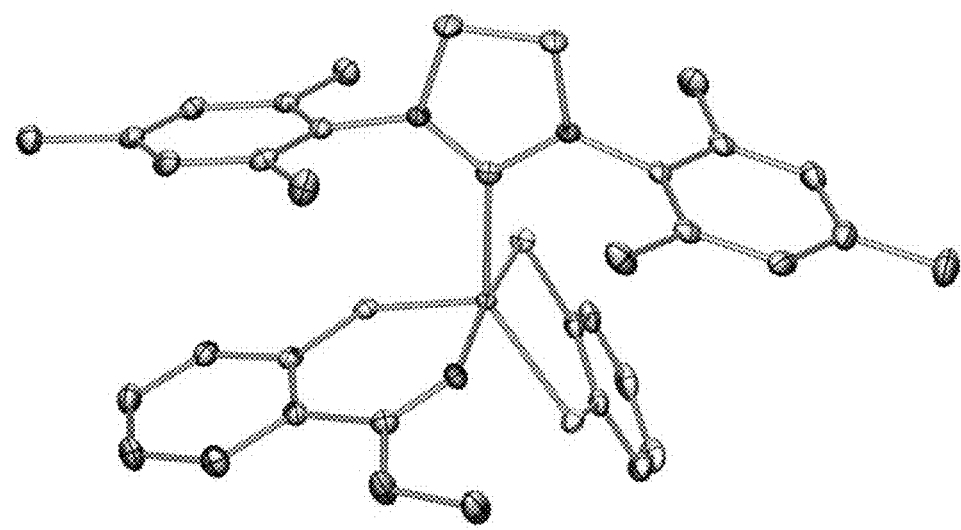
FIG. 30. X-ray structure of complex B-1i.
Figure 31:
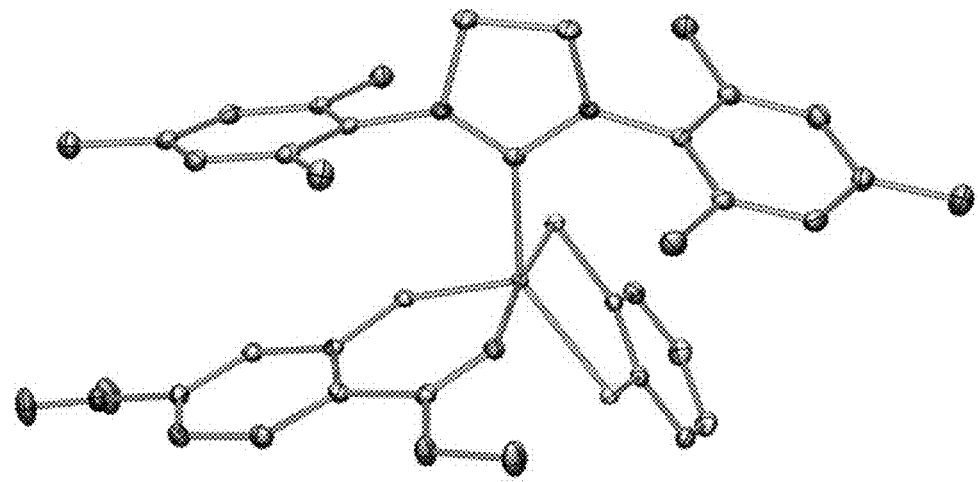
FIG. 31. X-ray structure of complex B-1j.
Figure 32:
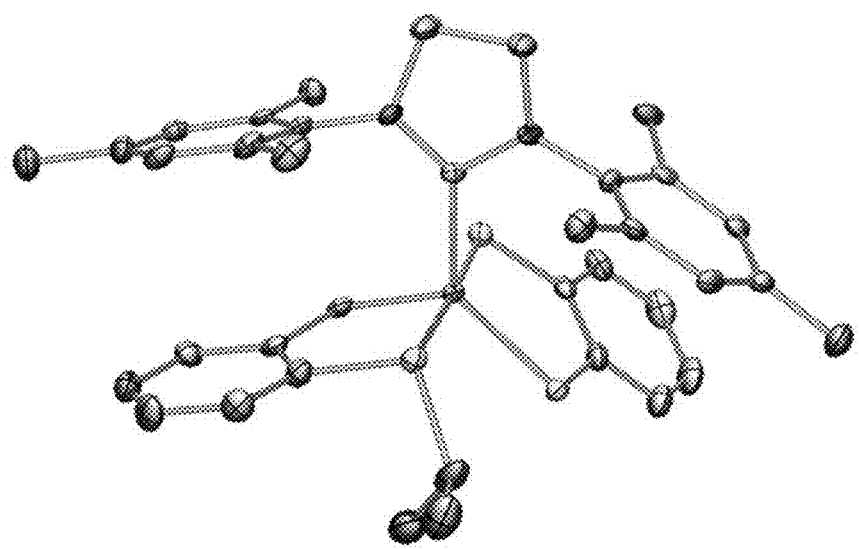
FIG. 32. X-ray structure of complex B-1l.
Figure 33:
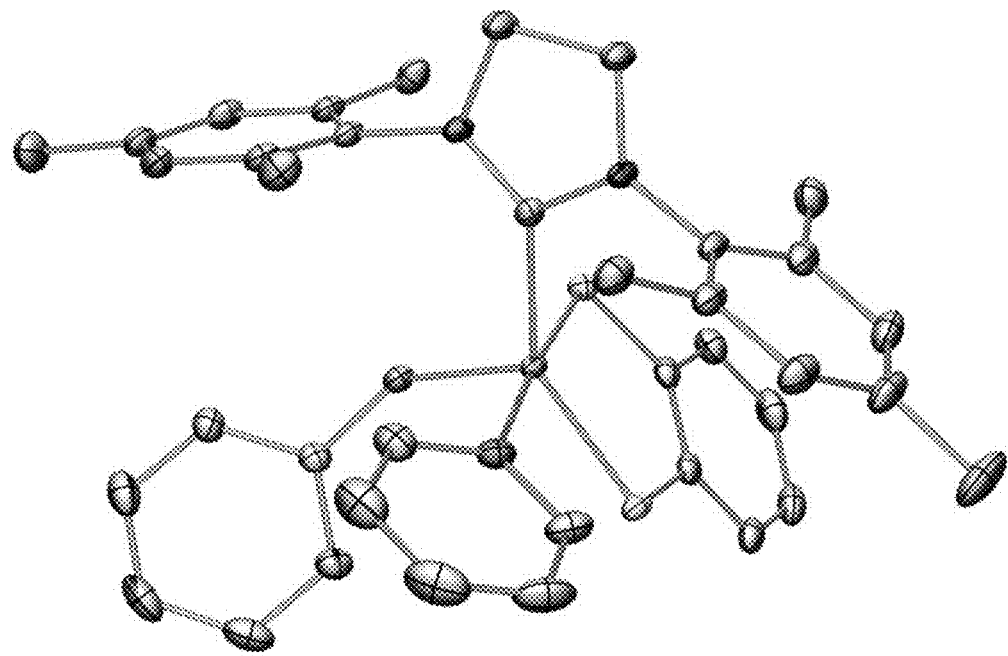
FIG. 33. X-ray structure of complex B-1n.
Figure 34:
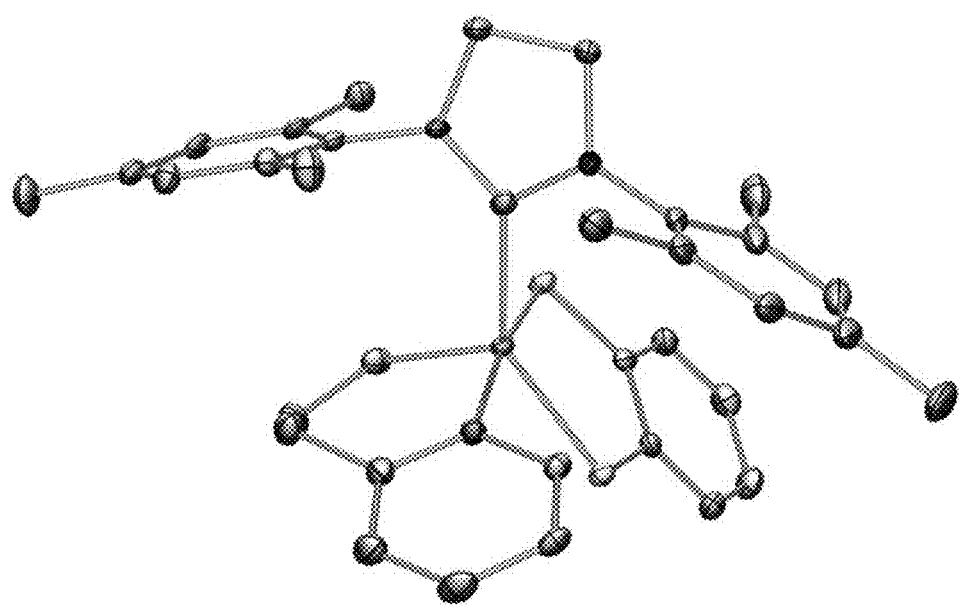
FIG. 34. X-ray structure of complex B-1o.
Figure 35:
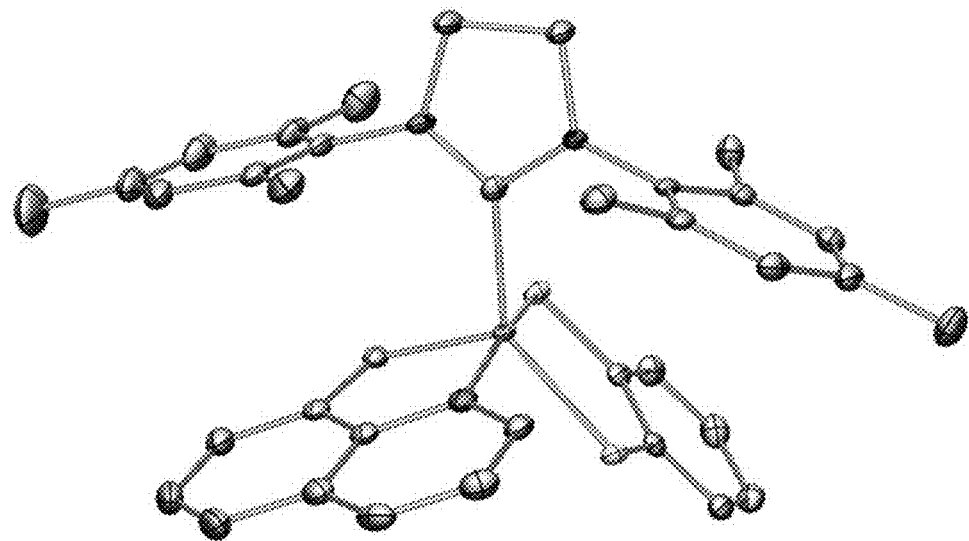
FIG. 35. X-ray structure of complex B-1p.
Figure 36:
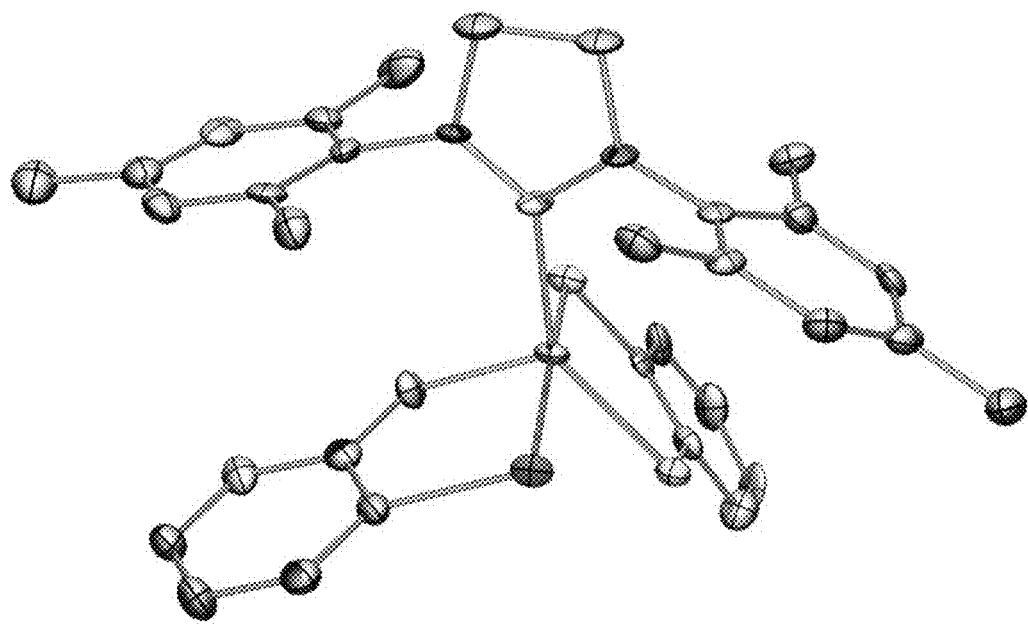
FIG. 36. X-ray structure of complex B-1q.
Figure 37:
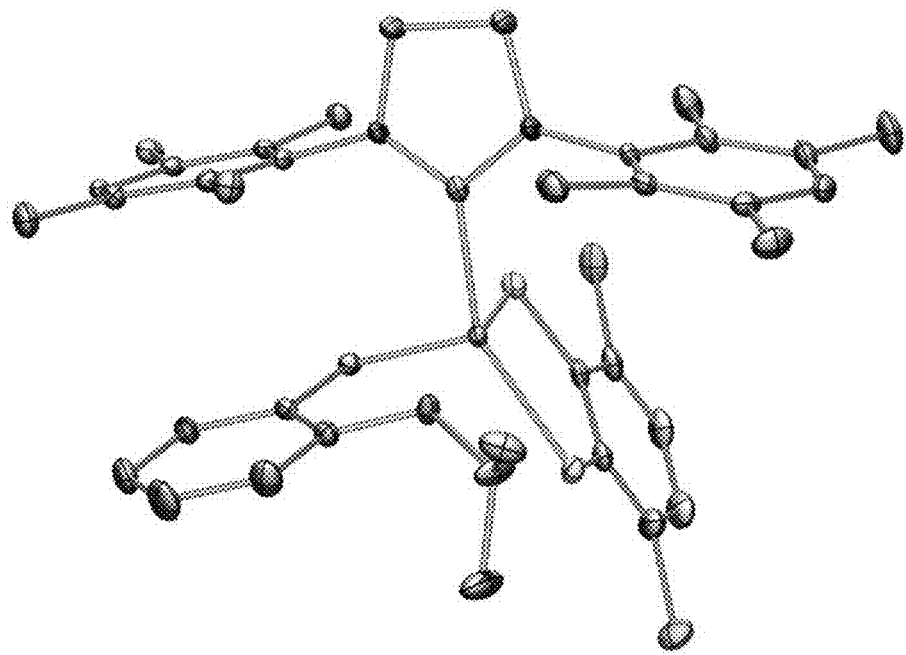
FIG. 37. X-ray structure of complex B-3.
Figure 38:
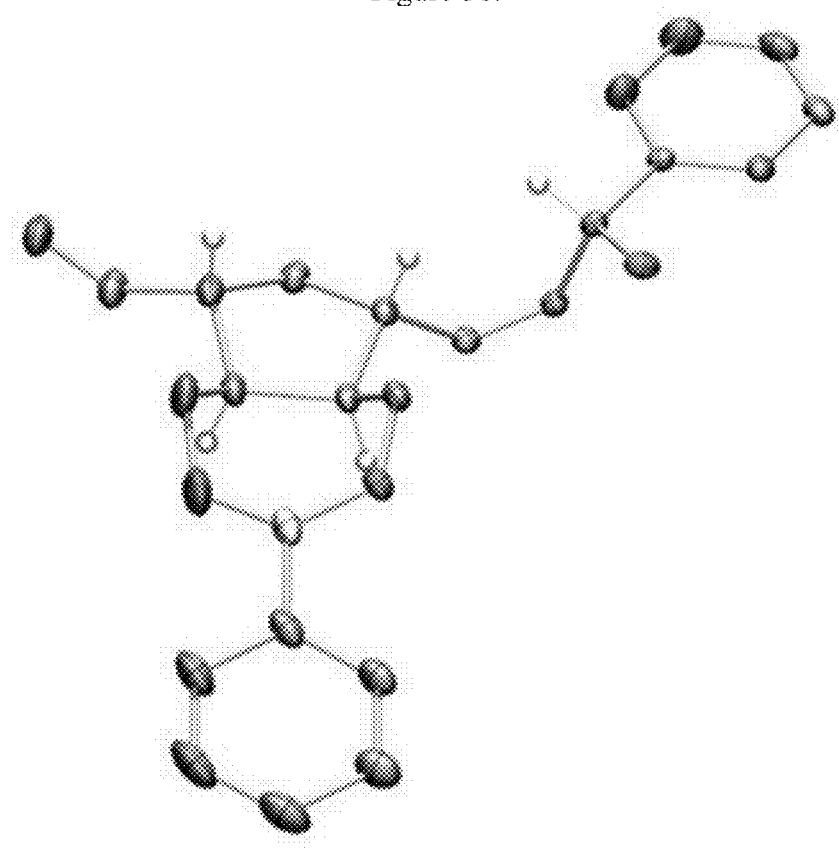
FIG. 38. X-ray structure of complex C27.
Figure 39:
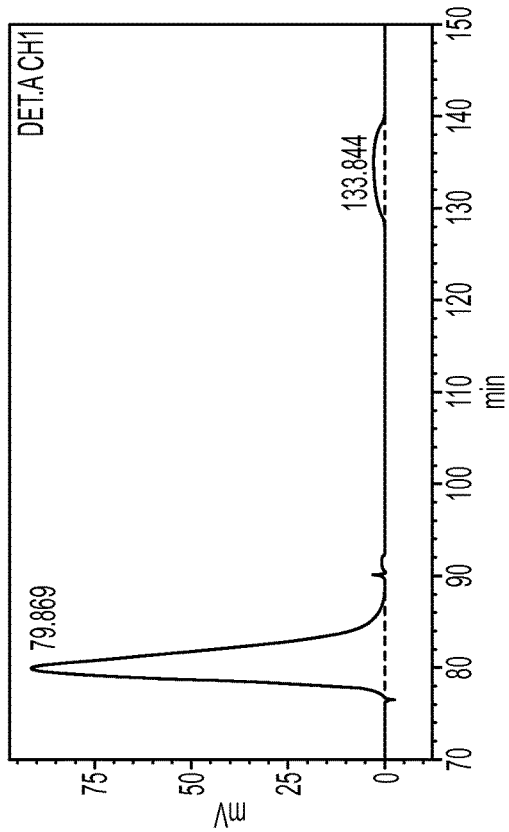
FIG. 39. HPLC analysis of compound C26.
Figure 39:
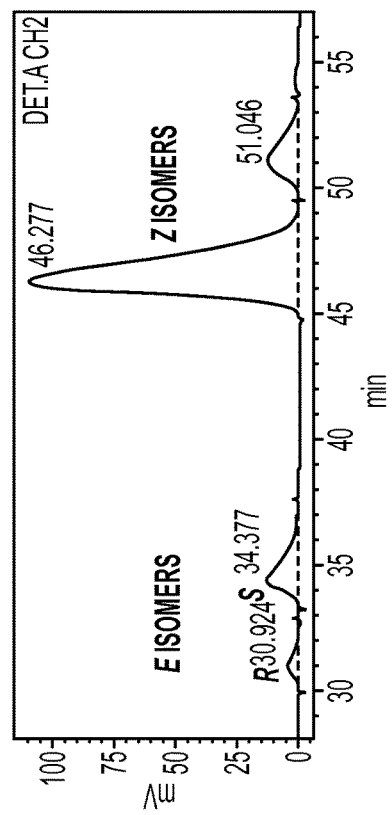
Figure 40:
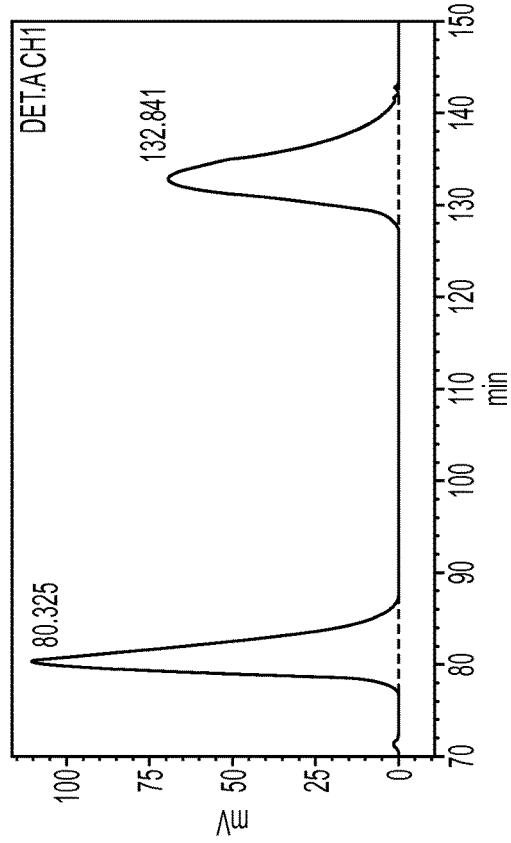
Figure 40:
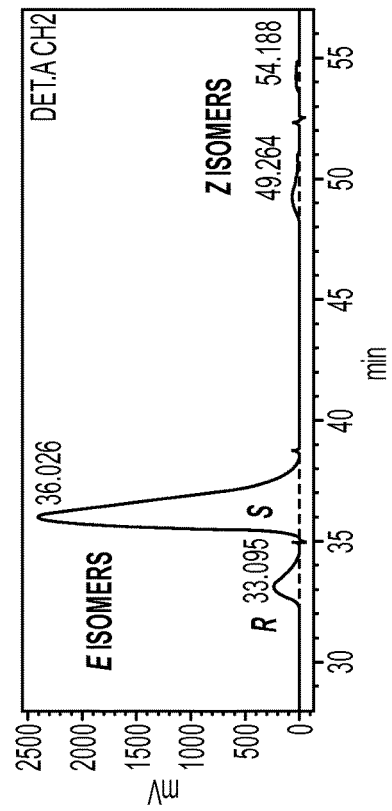
Figure 41:
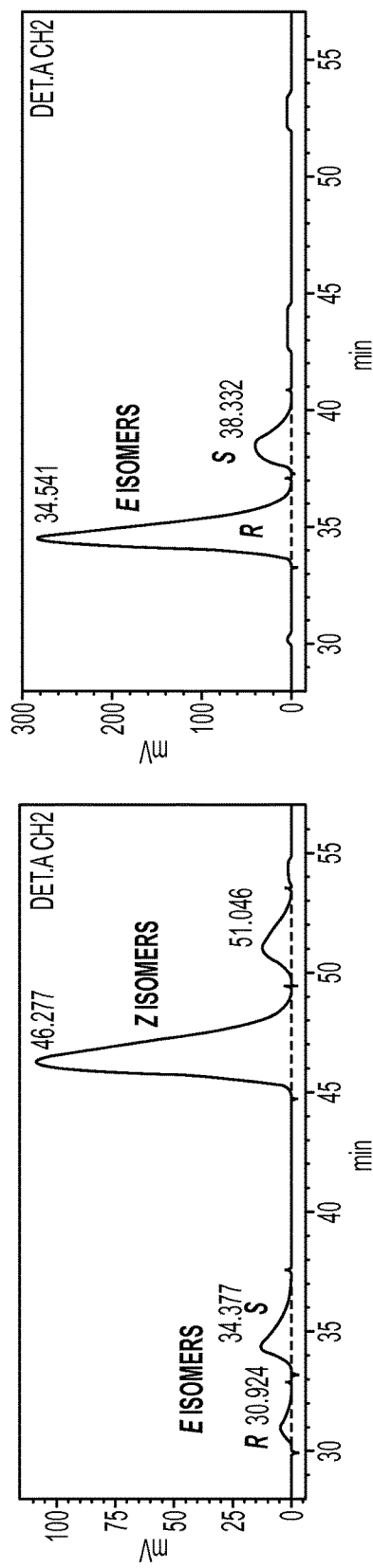
FIG. 41. HPLC analysis of compound C31b.

Synthesis of complexes 6d-e and 6k-l: To a reddish-brown solution of 1c (40.0 mg, 0.0590 mmol, 1.00 equiv.) in dichloromethane (0.5 mL) was added diol 2a or 2b (0.118 mmol, 2.00 equiv.). An immediate color change to dark green was observed. Analysis by $^1H$ NMR indicates >98% conversion after 30 min. Complex 6d or 6e was isolated by precipitation with pentane (3 mL), filtration and washing the solid with pentane. Single crystals suitable for x-ray crystallography have been obtained through vapor diffusion from one of the following solvent combinations: dichloromethane and pentane or dichloromethane and diethyl ether (FIGS. 12 and 13). Complex 6d or 6e is converted to 6k or 6l using known methods.

Synthesis of complexes 6o-6q: Complexes 6o-6q were prepared as illustrated in Scheme X2.

Synthesis of complexes 5 and 6a: Complex 1c, prepared above, is converted to 1h by reacting with

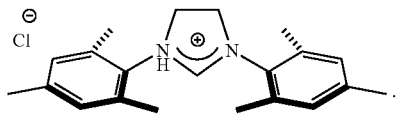

Reaction of 1h with 2 or 3 provides 5 and 6a, respectively.

Synthesis of complexes 6m, 6n, 5 and 6a: RuCl$_2$(PPh$_3$)$_3$ is reacted with 2 or 3 (or the corresponding thallium salt) (Fogg, D. E., *Can. J. Chem.* 2009, 87, 361) to provide complex 1i or 1j, respectively. Reaction of 1i or 1j with

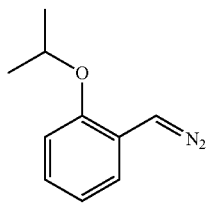

affords 6m or 6n, which is subsequently converted to 5 or 6a by reacting with

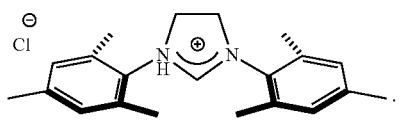

Exemplary Metathesis Reaction

Reagents: (2-(1-(Allyloxy)cyclopent-3-en-1-yl)ethyl)benzene (16) was prepared according to a known procedure (Cefalo, D. R.; Kiely, A. F.; Wuchrer, M.; Jamieson, J. Y.; Schrock, R. R.; Hoveyda, A. H. *J. Am. Chem. Soc.* 2001, 123, 3139).

(R)-1-Phenyl-2-propen-1-ol (18) was purchased from Fluka and purified by column chromatography. Enantiomeric ratio was determined by HPLC analysis to be 96:04 (Chiracel OD column, 98:2 hexanes:propanol, 1 mL/min, 220 nm) in comparison with authentic racemic material.

Cyclopropene (19) was prepared according to a previously reported procedure (Rubin, M.; Gevorgyan, V. *Synthesis* 2004, 796).

Ring-Opening/Ring-Closing Metathesis Reaction

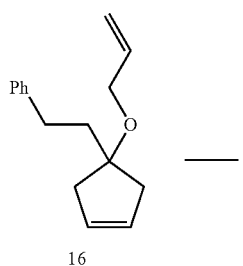

16

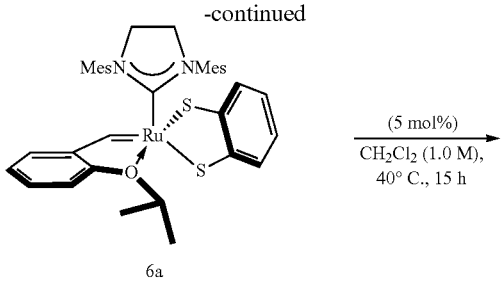

6a

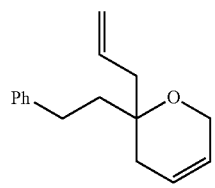

17
>98% conv, 88% yield

2-Allyl-2-phenethyl-3,6-dihydro-2H-pyran (17): A solution of 6a (2.0 mg, 2.9 μmol, 5.0 mol %) in dichloromethane (575 μL, 0.1 M) was transferred by syringe to a vial containing 16 (13.1 mg, 0.0575 mmol, 1.00 equiv). The resulting mixture was allowed to stir for 15 hours at 40 OC. Analysis of the $^1$H NMR (400 MHz) spectrum revealed >98% conv of the substrate, and the resulting mixture was purified by silica gel chromatography (2% Et$_2$O in hexanes to 4% Et$_2$O in hexanes) to afford product 17 (11.5 mg, 0.0504 mmol, 88% yield) as a colorless oil; $^1$H NMR (400 MHz, CDCl$_3$): δ 7.31-7.17 (5H, m), 5.94-5.83 (1H, m), 5.80-5.72 (2H, m), 5.19-5.38 (2H, m), 4.19 (2H, dd, J=2.0, 2.0 Hz), 2.68 (2H, t, J=8.0), 2.46 (1H, dd, J=13.6, 6.8 Hz), 2.34 (1H, dd, J=14.0, 6.8 Hz), 2.13-2.00 (2H, m), 1.97-1.89 (1H, m), 1.80-1.72 (1H, m).

Diastereoselective Ring-Opening/Cross-Metathesis Reaction

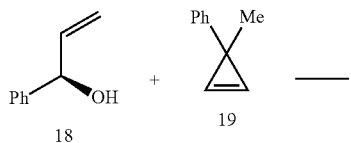

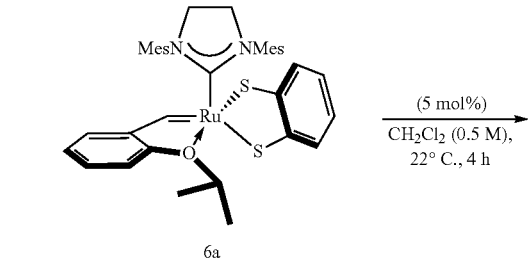

6a

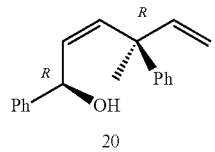

20
>98% conv, 78% yield,
91% Z; 93:07 dr (1R,4R,Z)-4-methyl-1,4-diphenylhexa-2,5-dien-1-ol (20): A solution of 6a (3.9 mg, 5.6 μmol, 5.0 mol %) in dichloromethane (224 μL) was transferred by syringe to a vial containing (R)-1-phenyl-2-propen-1-ol 18 (15 mg, 0.112 mmol, 1.00 equiv) and cyclopropene 19 (29 mg, 0.224 mmol, 2.00 equiv). The resulting mixture was allowed to stir for 4 hours at 22° C. Analysis of the $^1$H NMR (400 MHz) spectrum revealed >98% conv of the substrate, and the corresponding ROCM product was obtained in 91:09 Z/E ratio. The resulting oil was purified by silica gel chromatography (10% Et$_2$O in hexanes to 20% Et$_2$O in hexanes) followed by passing through a plug of activated charcoal with 50% Et$_2$O in pentane to afford product 20 (23.1 mg, 0.087 mmol, 78% yield) as a colorless oil; $^1$H NMR (400 MHz, CDCl$_3$): Z-isomer (major): δ 7.37 (2H, dd, J=8.1, 1.0 Hz), 7.34-7.26 (3H, m), 7.26-7.17 (4H, m), 7.06-7.04 (2H, m), 6.34 (1H, dd, J=17.3, 10.5 Hz), 5.90 (1H, dd, J=11.5, 0.8 Hz), 5.68 (1H, dd, J=11.5, 9.9 Hz), 5.16 (2H, ddd, J=18.4, 13.9, 1.0 Hz), 5.08 (1H, d, J=9.8 Hz), 1.58 (3H, s); $^{13}$C NMR (100 MHz, CDCl$_3$): δ 147.8, 146.0, 142.7, 138.9, 132.9, 128.4, 128.3, 127.4, 127.1, 126.3, 126.1, 112.7, 69.1, 47.3, 29.1.

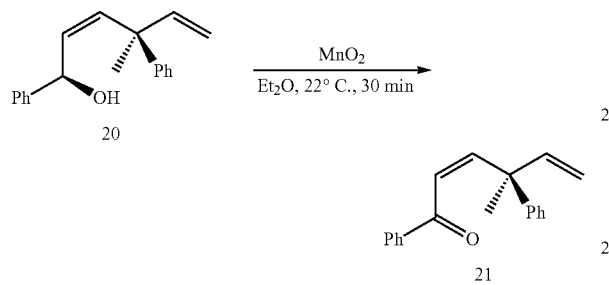

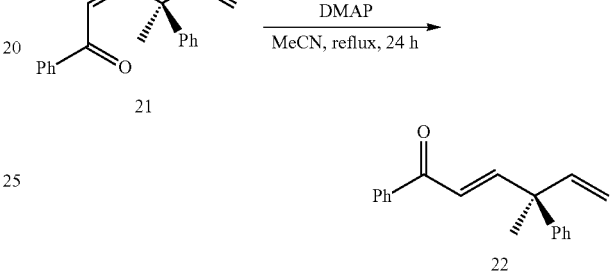

(R,Z)-4-methyl-1,4-diphenylhexa-2,5-dien-1-one (21): This material was prepared based on a previously reported procedure (Hoveyda, A. H. Lombardi, P. J.; O'Brien, R. V.; Zhugralin, A. R. *J. Am. Chem. Soc.* 2009, 131, 8378). An oven-dried vial equipped with a stir bar was charged with 20 (16 mg, 0.061 mmol, 1.00 equiv). Diethyl ether (1.8 mL) was added through a syringe followed by manganese dioxide (160 mg, 10 mg/mg of substrate, ~30 equiv).

The resulting suspension was allowed to stir vigorously until the reaction was determined to be complete according to TLC analysis (30 min). The mixture was filtered through a short pad of celite, which was then washed with diethyl ether (3×5.0 mL). The volatiles were removed in vacuo, affording a yellow oil which was purified by silica gel chromatography (5% Et$_2$O in hexanes). 21 was obtained in 91:09 Z/E ratio as a colorless oil (14.3 mg, 0.055 mmol, 90% yield); $^1$H NMR (400 MHz, CDCl$_3$): Z-isomer (major): δ 7.84-7.79 (2H, m), 7.55-7.49 (1H, m), 7.40 (2H, t, J=7.7 Hz), 7.33-7.28 (m, 2H), 7.17 (2H, t, J=7.6 Hz), 7.12-7.05 (1H, m), 6.49 (1H, d, J=13.1 Hz), 6.23 (1H, d, J=12.0 Hz), 6.20 (1H, dd, J=16.0, 12.0 Hz), 5.09 (1H, d, J=10.6 Hz), 5.05 (1H, d, J=17.4 Hz), 1.55 (s, 3H); $^{13}$C NMR (100 MHz, CDCl$_3$): δ 194.7, 146.0, 145.8, 144.2, 137.3, 133.0, 128.7, 128.3, 128.0, 127.0, 126.7, 126.2, 113.5, 48.7, 26.7. Diastereomeric ratio was established by HPLC analysis in comparison with authentic material prepared according to a previously reported procedure (Rubin, M.; Gevorgyan, V. *Synthesis* 2004, 796) where the absolute stereochemistry of the major E-enone isomers had been established (89.5:10.5 er shown for 21; after correction for 96:04 er of the starting material, results in a diastereoselectivity of 93:07 dr; Chiracel OD-H column (99.5:0.5 hexanes:i-PrOH, 0.7 mL/min, 254 nm) was used.
E-selective DROCM (Hoveyda, A. H. Lombardi, P. J.; O'Brien, R. V.; Zhugralin, A. R. *J. Am. Chem. Soc.* 2009, 131, 8378)

| Peak # | Retention time (min) | Area | Area % |
| --- | --- | --- | --- |
| 1 (E-isomer, R) | 33.10 | 14469688 | 7.42 |
| 2 (E-isomer, S) | 36.03 | 175303050 | 89.84 |
| 3 (Z-isomer) | 49.26 | 4660845 | 2.39 |
| 4 (Z-isomer) | 54.19 | 688395 | 0.35 |

Z-Selective DROCM

| Peak # | Retention time (min) | Area | Area % |
| --- | --- | --- | --- |
| 1 (E-isomer, R) | 30.92 | 296306 | 2.26 |
| 2 (E-isomer, S) | 34.38 | 1131722 | 8.62 |
| 3 (Z-isomer) | 46.28 | 10474729 | 79.80 |
| 4 (Z-isomer) | 51.05 | 1223446 | 9.32 |

Determination of the absolute stereochemical identity of DROCM product

To ascertain the absolute stereochemistry of the DROCM product, Z-enone 21 was isomerized to the corresponding E-isomer through a modified literature procedure (Könning, D.; Hiller, W.; Christmann, M. *Org. Lett.* 2012, 14, 5258). An oven-dried vial equipped with a stir bar was charged with Z-enone 21 (12 mg, 0.046 mmol, 1.00 equiv, 91:09 Z/E). Dry MeCN (0.2 mL) was added through a syringe followed by N,N-dimethylaminopyridine (1.1 mg, 5.6 μmol, 20 mol %). The resulting solution was allowed to reflux for 24 hours in a sealed vial. H$_2$O was then added to the reaction mixture followed by extraction with Et$_2$O (3×2.0 mL). The combined organic layers were dried over anhydrous MgSO$_4$, filtered and concentrated in vacuo to afford E-enone 22 in >98:02 E/Z ratio and as a yellow oil, which was purified by silica gel chromatography (5% Et$_2$O in hexanes) to afford colorless oil (11.3 mg, 0.043 mmol, 94% yield). Comparison of the HPLC retention times for the E-isomers before and after isomerization allowed us to establish the absolute configuration at the all-carbon quaternary stereogenic center of the DROCM product. Chiracel OD-H column (99.5:0.5 hexanes:i-PrOH, 0.7 mL/min, 254 nm) was used.
Before Isomerization:

| Peak # | Retention time (min) | Area | Area % |
| --- | --- | --- | --- |
| 1 (E-isomer, R) | 30.92 | 296306 | 2.26 |
| 2 (E-isomer, S) | 34.38 | 1131722 | 8.62 |
| 3 (Z-isomer) | 46.28 | 10474729 | 79.80 |
| 4 (Z-isomer) | 51.05 | 1223446 | 9.32 |

After Isomerization:

| Peak # | Retention time (min) | Area | Area % |
| --- | --- | --- | --- |
| 1 (E-isomer, R) | 34.54 | 19774970 | 83.09 |
| 2 (E-isomer, S) | 38.33 | 4024481 | 16.91 |
| 3 (Z-isomer) | — | — | — |
| 4 (Z-isomer) | — | — | — |

Z-Selective Cross-Metathesis Reactions

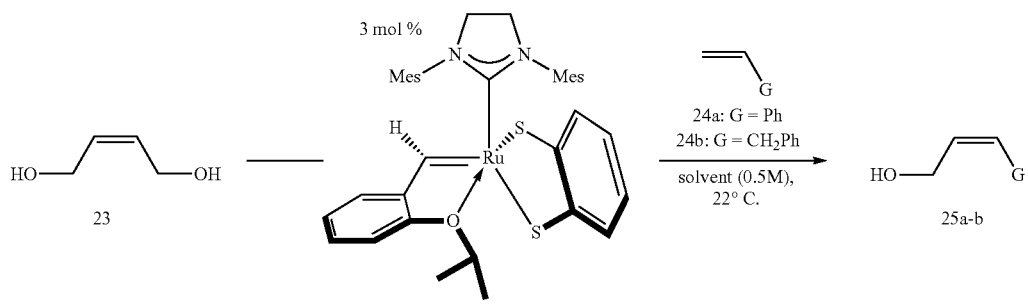

| entry | 23 (equiv) | 24a-b (equiv) | time (h) | solvent | conv (%); yield (%) | Z:E (%) |
|---|---|---|---|---|---|---|
| 1 | 2 | 1 | 12 | $CH_2Cl_2$ | ~50, 31 | >98, 2 |
| 2 | 1 | 3 | 6 | THF | ~50, 40 | >98, 2 |

(Z)-3-phenylprop-2-en-1-ol (25a): A solution of 6a (3.0 mg, 4.3 μmol, 3.0 mol %) in dichloromethane (290 μL) was transferred by syringe to a vial containing 23 (15 mg, 0.144 mmol, 1.00 equiv) and 24a (25.0 mg, 0.288 mmol, 2.00 equiv). The resulting mixture was allowed to stir for 4 hours at 22° C. Analysis of the $^1$H NMR (400 MHz) spectrum revealed ~50% conv of the substrate, and the corresponding CM product was obtained in >98:2 Z/E ratio. The resulting oil was purified by silica gel chromatography (10% EtOAc in hexanes to 40% EtOAc in hexanes) to afford product 25a (6.0 mg, 0.045 mmol, 31% yield) as a colorless oil; $^1$H NMR (400 MHz, $C_6D_6$): Z-isomer (major): δ 7.14-6.99 (5H, m), 6.35 (1H, d, J=11.8 Hz), 5.72 (1H, dt, J=12.4, 6.3 Hz), 4.11 (2H, d, J=6.2 Hz).

(Z)-4-phenylbut-2-en-1-ol (25b) (Z-isomer is confirmed by comparison with the data reported in literature for Z and E-isomers: (a) Stille, J. K. Tetrahedron 1989, 45, 979. (b) Ely, R. J.; Morken, J. P. J. Am. Chem. Soc. 2010, 132, 2534): A solution of 6a (2.4 mg, 3.4 μmol, 3.0 mol %) in tetrahydrofuran (230 μL) was transferred by syringe to a vial containing 23 (10.0 mg, 0.114 mmol, 1.00 equiv) and 24b (40.2 mg, 0.341 mmol, 3.00 equiv). The resulting mixture was allowed to stir for 6 hours at 22° C. Analysis of the $^1$H NMR (400 MHz) spectrum revealed ~50% cony of the substrate, and the corresponding ROCM product 25b was obtained in >98:2 Z/E ratio. The resulting oil was purified by silica gel chromatography (20% EtOAc in hexanes to 40% EtOAc in hexanes) to afford product 25b (6.1 mg, 0.046 mmol, 40% yield) as colorless oil. $^1$H NMR (400 MHz, $CDCl_3$): Z-isomer (major): δ 7.20-7.30 (5H, m), 5.75 (2H, m), 4.32 (2H, d, J=4.4 Hz), δ 3.45 (2H, d, J=5.6 Hz).

Additional Exemplary Compounds for High Efficiency and Z-Selectivity in Olefin Metathesis As described extensively above, additional exemplary compounds can be prepared for highly efficient and selective olefin metathesis. For example, among other things, 1) $R^1$ (depicted as L in Scheme A1, below), 2) Catechothiolate ($X_2$ in Scheme A1 below, and 3) Initiators (Scheme A1) could be varied to provide different stereoelectronic effects.

Scheme A1. Exemplary Compounds for High Activity and Selectivity in Olefin Metathesis (G is a suitable substituent)

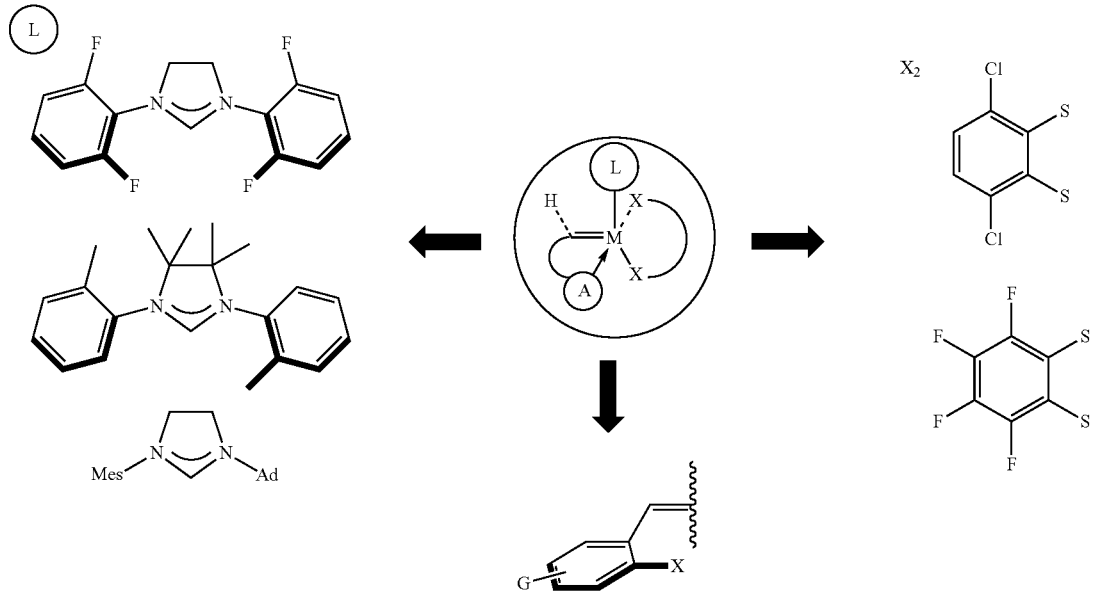

Synthesis of Syn Ru Complexes
Sources for Ru dichloride precursors (A1a and A2a) are purchased from Aldrich and used as received.
i. Ru Dichloride Precursors:
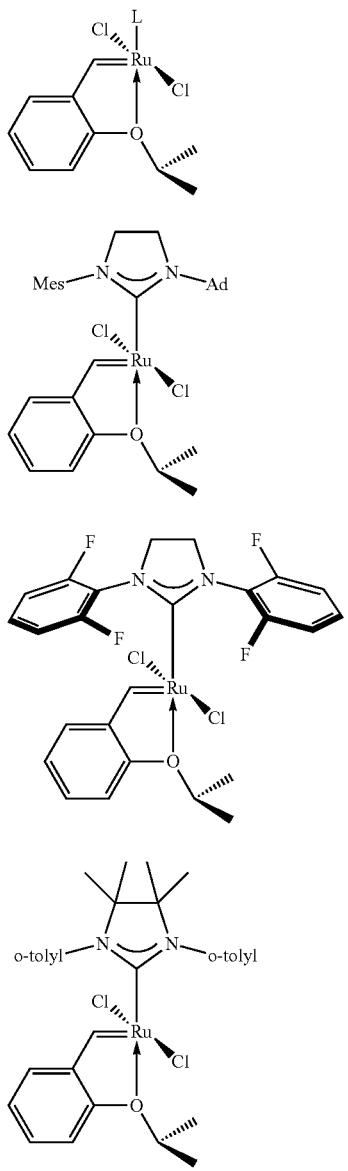
L = SIMe₃ (A1a)
L = PCy₃ (A2a)
ii. Thiocatecholate Zinc Salts
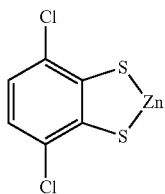
S-1
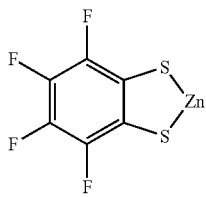
S-2
iii. Syn-Ru Complexes:
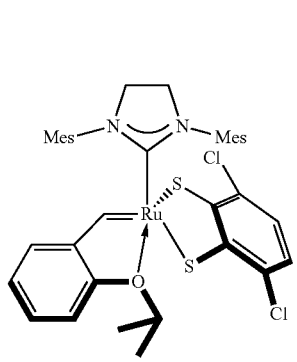
A1b
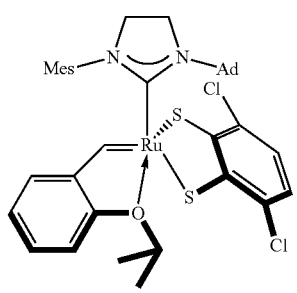
A3b
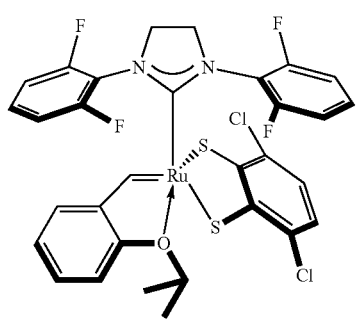
A4b
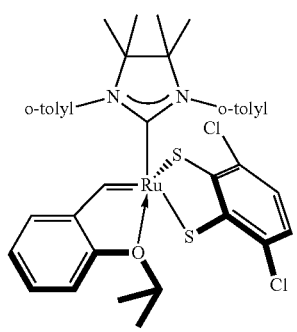
A5b A6b

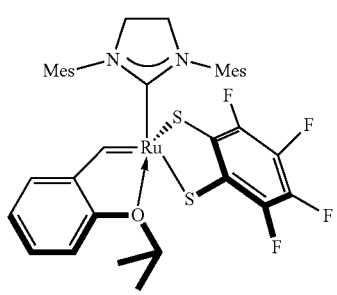

Preparation of Ru Dichloride Precursors (A3a-A5a):

To the corresponding imidazolinium salt (0.15 mmol, 1.5 equiv) and LiHMDS (25.1 mg, 0.15 mmol, 1.5 equiv) in a one-dram vial was added benzene (1.0 ml) at 22° C. The suspension was stirred until almost clear. The solution was filtered through a cotton plug; the one-dram vial and the cotton plug are rinsed with benzene (2×0.5 mL). The filtrate was transferred to a two-dram vial containing A1b (60.0 mg, 0.10 mmol, 1.0 equiv) and the resulting mixture was allowed to stir at 50° C. The reaction progress was monitored by $^1$H NMR spectroscopy. Upon >98% conversion, benzene was removed in vacuo; the residue was dissolved in 2.0 mL tetrahydrofuran and AgCl (70.1 mg, 0.50 mmol, 5.0 equiv) was added to the resulted solution. After stirring for 30 minutes at 22° C., the suspension was filtered through a small plug of Celite and solvents were removed from the filtrate. The residue was dissolved in minimum amount of diethyl ether, and copious amount of n-pentane was added until precipitation took place. The solids were filtered through a small plug of Celite and washed with hexanes followed by collection of the product with dichloromethane. Solvents were removed in vacuo to obtain the product as a green powder (56%, 56%, and 53% yields for A3a, A4a, and A5a, respectively).

Preparation of Thiocatecholate Zinc Salts:

3,6-Dichlorobenzene-1,2-dithiolate Zinc (S-1)

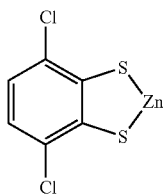

A mixture of 3,6-dichlorobenzene-1,2-dithiol (211 mg, 1.00 mmol, 1.00 equiv) purchased from Aldrich, Zn(OAc)$_2$·2H$_2$O (878 mg, 4.00 mmol, 4.00 equiv) and ethylenediamine (0.40 mL, 6.00 mmol, 6.00 equiv) in i-PrOH (8 mL) was allowed to stir for one hour at 22° C. The precipitated solid was filtered, washed with methanol (5.0 mL) and hot chloroform (5.0 mL), and dried in a vacuum desiccator overnight to afford S-1 (261 mg, 0.95 mmol, 95% yield) as white solid.

3,4,5,6-Tetrafluorobenzene-1,2-dithiolate Zinc (S-2)

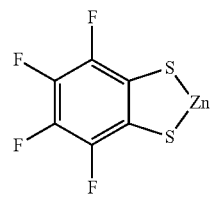

A mixture of dithiol A-b (214 mg, 1.00 mmol, 1.00 equiv), Zn(OAc)$_2$·2H$_2$O (878 mg, 4.00 mmol, 4.00 equiv) and ethylenediamine (0.40 mL, 6.00 mmol, 6.00 equiv) in i-PrOH (8 mL) was allowed to stir for one hour at 22° C. The precipitated solid was filtered, washed with methanol (5.0 mL) and hot chloroform (5.0 mL), and dried in a vacuum desiccator overnight to afford S-2 (155 mg, 0.56 mmol, 56% yield) as white solid.

For the preparation of 3,4,5,6-tetrafluorobenzene-1,2-dithiol (A-b), see below:

2,3,4,5-Tetrafluorobenzenethiol (A-a)

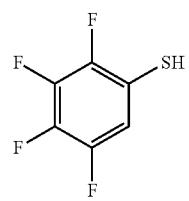 [SMILES: Fc1cc(S)c(F)c(F)c1F]

To a stirred solution of n-BuLi (0.69 mL, 1.10 mmol, 1.10 equiv) in tetrahydrofuran (2 mL) at −78° C. was added 1,2,3,4-tetrafluorobenzene (150 mg, 1.00 mmol, 1.00 equiv) over 30 minutes, after which the solution was allowed to stir for 45 minutes at -78° C. Then, powdered anhydrous sulfur (35.3 mg, 1.10 mmol, 1.10 equiv) was added in portions over 30 minutes followed by vigorous stirring for 30 minutes at −78° C. The reaction was quenched with 6M HCl (1.5 mL) and extracted with Et$_2$O (3×5.0 mL). The combined organic layers were washed with water (10 mL), dried over anhydrous MgSO$_4$, and filtered and concentrated in vacuo to A-a (75.0 mg, 0.41 mmol, 41% yield) as yellow oil, which was used in the next step without further purification.

3,4,5,6-Tetrafluorobenzene- 1,2-dithiol (A-b)

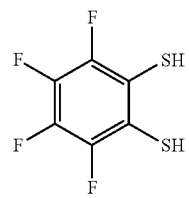 [SMILES: Fc1c(F)c(F)c(S)c(S)c1F]

To a stirred solution of n-BuLi (0.28 mL, 0.45 mmol, 1.10 equiv) in tetrahydrofuran (1 mL) at −78° C. was added A-a (75.0 mg, 0.41 mmol, 1.00 equiv) in tetrahydrofuran (1 mL) over 30 minutes, after which the solution was allowed to stir for 45 minutes at −78° C. Then, powdered anhydrous sulfur (14.4 mg, 0.45 mmol, 1.10 equiv) was added in portions over 30 minutes followed by vigorous stirring for 30 minutes at −78° C. The reaction was quenched with 6M HCl (0.6 mL) and extracted with Et$_2$O (3×3.0 mL). The combined organic layers were washed with water (5.0 mL), dried over anhydrous MgSO$_4$, filtered and concentrated in vacuo to afford A-b (39.5 mg, 0.18 mmol, 45% yield) as brown oil, which was used in the synthesis of S-2 without further purification.

Preparation of Ru Complexes (A1b-A6b)

To a two-dram vial charged with stir bar and zinc dithiolate S-1 or S-2 (0.098 mmol, 2.00 equiv) under N$_2$ atmosphere, a solution of A1a or the corresponding A3a-A5a (0.049 mmol, 1.00 equiv) in tetrahydrofuran (610 μL) was added and allowed to stir at 22° C. Reaction progress was monitored by $^1$H NMR spectroscopy. Upon >98% conversion after three to five hours, the solvent was evaporated under vacuum. Residual tetrahydrofuran was removed through co-evaporation with pentane (2×2 mL). The obtained solid was dissolved in dichloromethane and passed through a short column of Celite (4 cm in height) in a pipette (~0.5 cm diameter) with dichloromethane (10 mL). After removal of dichloromethane from the filtrate and co-evaporation with pentane, complex 1b was isolated as brown solid (31.9 mg, 0.42 mmol, 85% yield). See X-ray data of A1b-A6b below for structural information.

Exemplary Z-Selective Cross-Metathesis to Access Highly Functionalized Allyl Alcohols General Procedure for Cross-Metathesis (CM) Reactions In N$_2$-filled glove box, an oven-dried 8 mL vial equipped with a magnetic stir bar was charged with alkene substrate (1.0 equiv) and cis-2-butene-1,4-diol (2.0 equiv). To this vial, a solution of Ru complex A1b (5.0-7.5 mol %) in tetrahydrofuran or dichloromethane was added. The resulting solution was allowed to stir for 4-12 hours at 22° C., after which the reaction was quenched by addition of wet diethyl ether and concentrated in vacuo (percent conversion was determined by 400 MHz or 500 MHz $^1$H NMR analysis). Purification was performed through Silica Gel Chromatography or Kugelrohr Distillation.

I. Representative Examples of Z-selective CM with Terminal Alkenes (A7a-1):

Z)-2-undecene-1-ol (A7a

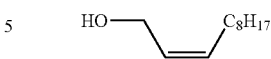

Following the general procedure, a solution of A1b (4.9 mg, 6.3 μmol, 5.0 mol %) in tetrahydrofuran (255 μL) was transferred by syringe to a vial charged with 1-decene (17.8 mg, 0.127 mmol, 1.00 equiv) and cis-2-butene-1,4-diol (22.4 mg, 0.254 mmol, 2.00 equiv). The resulting solution was allowed to stir for four hours at 22° C. Analysis of the unpurified mixture revealed 78% consumption of 1-decene. The resulting brown oil was purified by silica gel chromatography (10% Et$_2$O in hexanes to 40% Et$_2$O in hexanes) to afford A7a (14.0 mg, 0.0822 mmol, 65% yield) as pale yellow oil in 98:02 Z/E ratio. The spectral data for this compound were identical to those reported in the literature.

Z)-4-phenyl-2-butene-1-ol (A7b

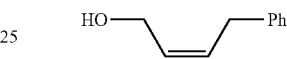

Following the general procedure, a solution of A1b (4.9 mg, 6.3 μmol, 5.0 mol %) in tetrahydrofuran (255 μL) was transferred by syringe to a vial charged with allylbenzene (15.0 mg, 0.127 mmol, 1.00 equiv) and cis-2-butene-1,4-diol (22.4 mg, 0.254 mmol, 2.00 equiv). The resulting solution was allowed to stir for four hours at 22° C. Analysis of the unpurified mixture revealed 84% consumption of allylbenzene. The resulting brown oil was purified by silica gel chromatography (10% Et$_2$O in hexanes to 40% Et$_2$O in hexanes) to afford A7b (13.4 mg, 0.0904 mmol, 71% yield) as pale yellow oil in 96:04 Z/E ratio. The spectral data for this compound were identical to those reported in the literature.

Z)-5-(tert-butyldimethylsiloxy)-2-pentene-1-ol (A7c

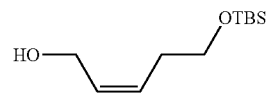 [SMILES: CC(C)(C)[Si](C)(C)OCC/C=C\CO]

Scheme A2. Broadly Applicable Catalyst for High Efficiency and Z-selectivity in Cross-Metathesis Involving Terminal Alkene Substrates to Provide Alcohols

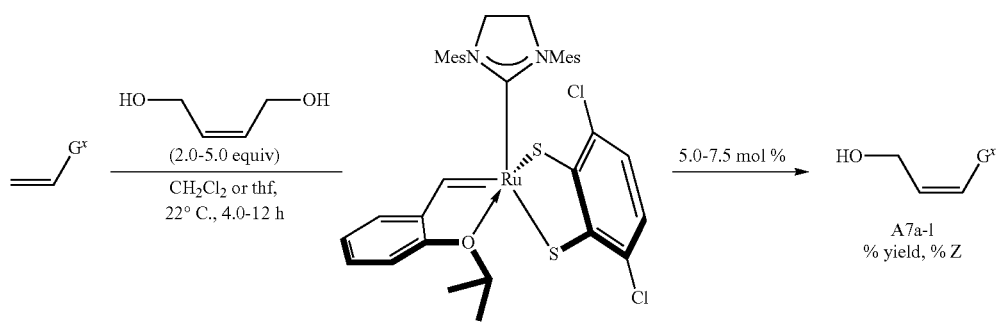

Following the general procedure, a solution of A1b (4.9 mg, 6.3 μmol, 5.0 mol %) in tetrahydrofuran (255 μL) was transferred by syringe to a vial charged with 1-(tert-butyldimethylsilyoxy)-3-butene (23.7 mg, 0.127 mmol, 1.00 equiv) and cis-2-butene-1,4-diol (22.4 mg, 0.254 mmol, 2.00 equiv). The resulting solution was allowed to stir for four hours at 22° C. Analysis of the unpurified mixture revealed 76% consumption of 1-(tert-butyldimethylsilyoxy)-3-butene. The resulting brown oil was purified by silica gel chromatography (10% Et$_2$O in hexanes to 40% Et$_2$O in hexanes) to afford A7c (17.8 mg, 0.0823 mmol, 65% yield) as pale yellow oil in 93:07 Z/E ratio. The spectral data for this compound were identical to those reported in the literature.

Z)-2-(7-hydroxy-5-heptenyl)isoindoline-1,3-dione (A7d

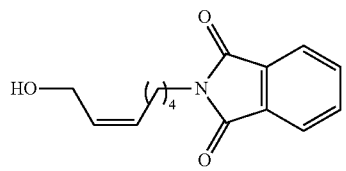

Following the general procedure, a solution of A1b (4.9 mg, 6.3 μmol, 5.0 mol %) in tetrahydrofuran (255 μL) was transferred by syringe to a vial charged with 2-(hex-5-enyl)isoindoline-1,3-dione (29.1 mg, 0.127 mmol, 1.00 equiv) and cis-2-butene-1,4-diol (24.2 mg, 0.254 mmol, 2.00 equiv). The resulting solution was allowed to stir for four hours at 22° C. Analysis of the unpurified mixture revealed 80% consumption of benzyl pent-4-enoate. The resulting brown oil was purified by silica gel chromatography (10% Et$_2$O in hexanes to 40% Et$_2$O in hexanes) to afford A7d (23.4 mg, 0.0902 mmol, 71% yield) as yellow oil in 98:02 Z/E ratio. The spectral data for this compound were identical to those reported in the literature.

Z)-5-phenyl-2-pentene-1,5-diol (A7e

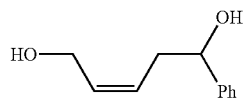

Following the general procedure, a solution of A1b (4.9 mg, 6.3 μmol, 5.0 mol %) in tetrahydrofuran (255 μL) was transferred by syringe to a vial charged with 4-phenyl-1-buten-4-ol (18.8 mg, 0.127 mmol, 1.00 equiv) and cis-2-butene-1,4-diol (24.2 mg, 0.254 mmol, 2.00 equiv). The resulting solution was allowed to stir for four hours at 22° C. Analysis of the unpurified mixture revealed 72% consumption of 4-phenyl-1-buten-4-ol. The resulting brown oil was purified by silica gel chromatography (10% Et$_2$O in hexanes to 40% Et$_2$O in hexanes) to afford A7e (14.5 mg, 0.0814 mmol, 64% yield) as yellow oil in 96:04 Z/E ratio. The spectral data for this compound were identical to those reported in the literature.

(Z)-12-hydroxy-10-dodecenal (A7f

Following the general procedure, a solution of A1b (4.9 mg, 6.3 μmol, 5.0 mol %) in tetrahydrofuran (255 μL) was transferred by syringe to a vial charged with undecylenic aldehyde (21.4 mg, 0.127 mmol, 1.00 equiv) and cis-2-butene-1,4-diol (24.2 mg, 0.254 mmol, 2.00 equiv). The resulting solution was allowed to stir for four hours at 22° C. Analysis of the unpurified mixture revealed 86% consumption of undecylenic aldehyde. The resulting brown oil was purified by silica gel chromatography (10% Et$_2$O in hexanes to 40% Et$_2$O in hexanes) to afford A7f (20.1 mg, 0.101 mmol, 80% yield) as pale yellow oil in 94:06 Z/E ratio; $^1$H NMR (400 MHz, C$_6$D$_6$): Z-isomer (major): δ 9.33 (1H, s), 5.58 (1H, dt, J=11.4, 6.3 Hz), 5.56-5.36 (1H, m), 4.01 (2H, d, J=6.4 Hz), 1.98-1.89 (2H, m), 1.87-1.78 (2H, m), 1.33-1.05 (13H, m). Coupling constant (J=11.4 Hz) of the signal at δ 5.58 ppm is indicative of Z-A7f.

(2Z,4E)-undeca-2,4-dien-1-ol (A7g

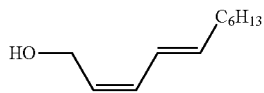

Following the general procedure, a solution of A1b (4.9 mg, 6.3 μmol, 5.0 mol %) in tetrahydrofuran (255 μL) was transferred by syringe to a vial charged with deca-1,3-diene (17.6 mg, 0.127 mmol, 1.00 equiv) and cis-2-butene-1,4-diol (24.2 mg, 0.254 mmol, 2.00 equiv). The resulting solution was allowed to stir for eight hours at 22° C. Analysis of the unpurified mixture revealed 88% consumption of deca-1,3-diene. The resulting brown oil was purified by silica gel chromatography (10% Et$_2$O in hexanes to 40% Et$_2$O in hexanes) to afford 7g (14.1 mg, 0.0838 mmol, 66% yield) as pale yellow oil in 95:05 Z/E ratio; $^1$H NMR (400 MHz, CDCl$_3$): Z-isomer (major): δ 6.35-6.25 (1H, m), 6.07 (1H, t, J=11.0 Hz), 5.76 (1H, dt, J=14.5, 7.0 Hz), 5.49 (1H, dt, J=10.9, 7.0 Hz), 4.30 (2H, d, J=7.0 Hz), 2.15-2.06 (2H, m), 1.42-1.34 (2H, m), 1.32-1.25 (7H, m), 0.88 (3H, t, J=6.8 Hz). Coupling constant (J=11.0 Hz) of the signal at δ 6.07 ppm is indicative of Z-A7g.

(Z)-7-hydroxy-5-heptenoic acid (A7h

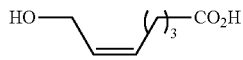

Following the general procedure, a solution of A1b (4.9 mg, 6.3 μmol, 5.0 mol %) in tetrahydrofuran (255 μL) was transferred by syringe to a vial charged with 5-hexenoic acid (14.5 mg, 0.127 mmol, 1.00 equiv) and cis-2-butene-1,4-diol (24.2 mg, 0.254 mmol, 2.00 equiv). The resulting solution was allowed to stir for 4 hours at 22° C. Analysis of the unpurified mixture revealed 85% consumption of 5-hexenoic acid. The resulting brown oil was purified by silica gel chromatography (100% CH$_2$Cl$_2$ to 5% CH$_2$Cl$_2$ in MeOH) to afford A7h (12.8 mg, 0.0890 mmol, 70% yield) as pale yellow oil in 96:04 Z/E ratio. The spectral data were identical to those reported in the literature.

(Z)-4-butoxy-2-butene-1-ol (A7i

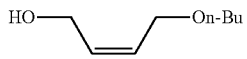

Following the general procedure, a solution of A1b (4.9 mg, 6.3 µmol, 5.0 mol %) in tetrahydrofuran (255 µL) was transferred by syringe to a vial charged with 4-butoxybut-1-ene (14.5 mg, 0.127 mmol, 1.00 equiv) and cis-2-butene-1,4-diol (24.2 mg, 0.254 mmol, 2.00 equiv). The resulting solution was allowed to stir for 12 hours at 22° C. Analysis of the unpurified mixture revealed 65% consumption of 4-butoxybut-1-ene. The resulting brown oil was purified by silica gel chromatography (10% Et$_2$O in hexanes to 40% Et$_2$O in hexanes) to afford A7i (10.5 mg, 0.073 mmol, 57% yield) as pale yellow oil in 91:09 Z/E ratio. The spectral data for this compound were identical to those reported in the literature.

(Z)-1-(4-hydroxy-3-(4-hydroxy-2-butenyl)phenyl)ethanone (A7j

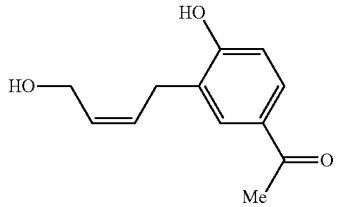 [SMILES: CC(=O)c1ccc(O)c(C/C=C\CO)c1]

Following the general procedure, a solution of A1b (4.9 mg, 6.3 µmol, 5.0 mol %) in tetrahydrofuran (255 µL) was transferred by syringe to a vial charged with 3'-allyl-4'-hydroxyacetophenone (22.4 mg, 0.127 mmol, 1.00 equiv) and cis-2-butene-1,4-diol (24.2 mg, 0.254 mmol, 2.00 equiv). The resulting solution was allowed to stir for four hours at 22° C. Analysis of the unpurified mixture revealed 77% consumption of 3'-allyl-4'-hydroxyacetophenone. The resulting brown residue was purified by silica gel chromatography (10% Et$_2$O in hexanes to 60% Et$_2$O in hexanes) to afford A7j (17.8 mg, 0.0863 mmol, 68% yield) as off-white solid in 98:02 Z/E ratio; mp: 97-99° C.; $^1$H NMR (400 MHz, CDCl$_3$): Z-isomer (major): δ 7.80 (1H, d, J=2.2 Hz), 7.77 (1H, dd, J=8.4, 2.3 Hz), 6.86 (1H, d, J=8.4 Hz), 5.79 (1H, dt, J=10.9, 6.2 Hz), 5.69 (1H, dt, J=10.8, 7.6 Hz),[9] 4.42 (2H, d, J=6.2 Hz), 3.56 (2H, d, J=7.8 Hz), 2.55 (3H, s), 1.25 (2H, br s). Coupling constants (J=10.9 Hz and J=10.8 Hz) of the signals at δ 5.79 and 5.69 ppm are indicative of Z-A7j.

(Z)-3-cyclohexyl-2-propene-1-ol (A7k

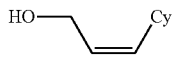

Following the general procedure, a solution of A1b (4.9 mg, 6.3 µmol, 5.0 mol %) in tetrahydrofuran (255 µL) was transferred by syringe to a vial charged with vinylcyclohexane (14.0 mg, 0.127 mmol, 1.00 equiv) and cis-2-butene-1,4-diol (56.0 mg, 0.635 mmol, 5.00 equiv). The resulting solution was allowed to stir for four hours at 22° C. Analysis of the unpurified mixture revealed 65% consumption of vinylcyclohexane. The resulting brown oil was purified by silica gel chromatography (10% Et$_2$O in hexanes to 40% Et$_2$O in hexanes) to afford A7k (10.5 mg, 0.075 mmol, 59% yield) as pale yellow oil in 98:02 Z/E ratio. The spectral data for this compound were identical to those reported in the literature.

(Z)-3-(4-(trifluoromethyl)phenyl)-2-propene-1-ol (A7l

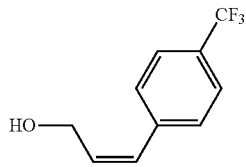

Following the general procedure, a solution of A1b (7.3 mg, 9.5 µmol, 7.5 mol %) in tetrahydrofuran (255 µL) was transferred by syringe to a vial charged with 4-(trifluoromethyl)styrene (21.9 mg, 0.127 mmol, 1.00 equiv) and cis-2-butene-1,4-diol (24.2 mg, 0.254 mmol, 2.00 equiv). The resulting solution was allowed to stir for eight hours at 22° C. Analysis of the unpurified mixture revealed 65% consumption of 4-(trifluoromethyl)styrene. The resulting brown oil was purified by silica gel chromatography (10% Et$_2$O in hexanes to 40% Et$_2$O in hexanes) to afford A7l (14.9 mg, 0.0737 mmol, 58% yield) as pale yellow oil in 92:08 Z/E ratio; $^1$H NMR (400 MHz, CDCl$_3$): Z-isomer (major): δ 7.60 (2H, d, J=8.0 Hz), 7.32 (2H, d, J=8.0 Hz), 6.60 (1H, d, J=11.8 Hz), 6.00 (1H, dt, J=12.4, 6.4 Hz), 4.42 (2H, s), 1.50 (1H, s). Coupling constant (J=11.8 Hz) of the signal at δ 6.60 ppm is indicative of Z-A7l.

Unexpectedly High Group Tolerance, Efficiency, and Z-Selectivity of Catechothiolate A1b (vs A8) in Z-selective Cross-Metathesis As shown below, whereas there was no conversion with complex A8 in the presence of 5-hexenoic acid, the reaction readily took place with A1b to furnish 70% yield of the product in 96% Z-selectivity. Investigation to access products with synthetically useful functional groups (e.g. aldehyde (A7f), diene (A7g), ketone (A7j), and styrenyl (A7l)) unambiguously showed the robustness of A1b in Z-selective CM.

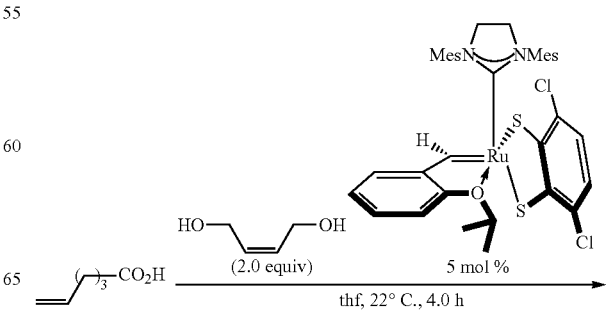

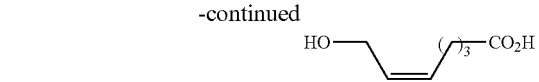

A7h
70% yield, 96:4 Z:E
with 5 mol % A8: <5% yield

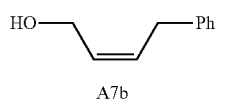

A7b
71% yield, 96:4 Z:E
with 5 mol % A8: <58% yield,
82:18 Z:E

A7f
80% yield, 96:4 Z:E
with 5 mol % A8: 30% yield,
87:13 Z:E

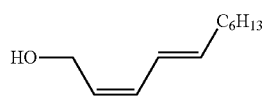

A7g
66% yield, 95:5 Z:E
with 5 mol % A8: 53% yield,
93:7 Z:E

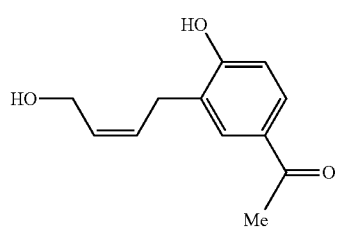

A7j
68% yield, 98:2 Z:E
with 5 mol % A8: 50% yield,
82:18 Z:E

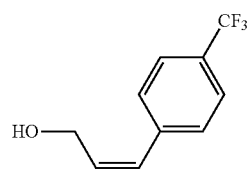 [SMILES: OC/C=C\c1ccc(C(F)(F)F)cc1]

A7l
55% conv., 47% yield, 93:7 Z:E
with 5 mol % A8: 19% conv., yield ND
complicated mix of E/Z

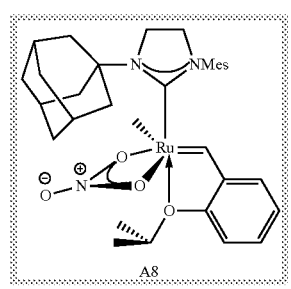

A8

Formal Synthesis of Insect Pheromone (+)-Disparlure

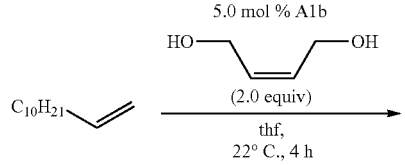

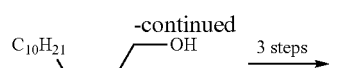

A9
72% yield, 96:4 Z:E

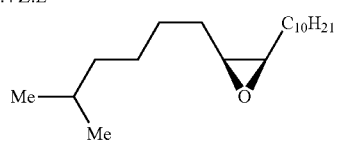

(+)-Disparlure (Z)-2-tridecene-1-ol (A9)

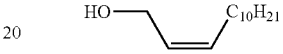

Following the general procedure in Section 2, a solution of 1b (4.9 mg, 6.3 µmol, 5.0 mol %) in tetrahydrofuran (255 µL) was transferred by syringe to a vial charged with 1-dodecene (21.4 mg, 0.127 mmol, 1.00 equiv) and cis-2-butene-1,4-diol (24.2 mg, 0.254 mmol, 2.00 equiv). The resulting solution was allowed to stir for four hours at 22° C. Analysis of the unpurified mixture revealed 81% consumption of 1-dodecene. The resulting brown oil was purified by silica gel chromatography (10% $Et_2O$ in hexanes to 40% $Et_2O$ in hexanes) to afford A9 (18.1 mg, 0.091 mmol, 72% yield) as pale yellow oil in 96:04 Z/E ratio. The spectral data for this compound were identical to those reported in the literature. Insect pheromone precursor 9 has been previously elaborated to (+)-disparlure over three steps in 49% overall yield.

Z-Selective Cross-Metathesis of Oleic Acid to Access Antifungal Agent (A10a) and Fatty Alcohol (A7a) in One Step (Gram-Scale)

Scheme A3. Application of A1b in CM to Access Functionalized Fatty Alcohols from a Renewable Internal Alkene Source

Oleic acid
(1.0 gram scale)

+

(2.0 equiv)

antifungal (A10a)
(isolated from leaves of wild rice)
94% Z, 66% isolated yield

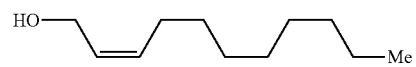

fatty alcohol (A7a)
95% Z, 60% isolated yield (Z)-11-hydroxy-9-undecenoic acid (A10a)

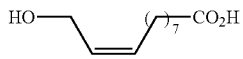

Following the general procedure, a solution of A1b (135 mg, 0.177 mmol, 5.0 mol %) in dichloromethane (3.5 mL) was transferred by syringe to a vial charged with oleic acid (1.00 g, 3.54 mmol, 1.00 equiv) and cis-2-butene-1,4-diol (0.624 g, 7.08 mmol, 2.00 equiv). The resulting solution was allowed to stir for four hours at 22° C. Analysis of the unpurified mixture revealed 75% consumption of oleic acid. The resulting brown oil was purified by silica gel chromatography (10% Et$_2$O in hexanes to 20% Et$_2$O in hexanes to 70% Et$_2$O in hexanes) to afford an inseparable mixture of unreacted oleic acid and A7a (see below for the purification of A7a), as well as A10a (0.470 g, 2.35 mmol, 66% yield) as yellow oil in 94:06 Z/E ratio. The spectral data for A10a were identical to those reported in the literature.

(Z)-2-undecene-1-ol (A7a)

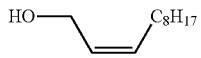

The mixture of oleic acid and A7a was further purified by Kugelrohr distillation to afford A7a (0.363 g, 2.13 mmol, 60% yield) as colorless oil in 95:05 Z/E ratio. The spectral data for A7a were identical to those reported in the literature.

In some embodiments, choice of the right initiator can have a profound impact on the conversion as well. In some embodiments, for certain difficult OM transformation it has been shown that initiator is critical for achieving high conversion, presumably due to, without the intention to be limited by theory, a longer lifetime of the catalyst precursor. In some embodiments, R$^4$ and/or R$^5$, or a bidentate or polydentate ligand formed by taking R$^4$ and R$^5$ and optionally other ligands together, comprise an electron-withdrawing group.

Scheme B1. Electron deficient Ru dithiolate B-2a as efficient catalyst in CM reactions.[a]

B-1a

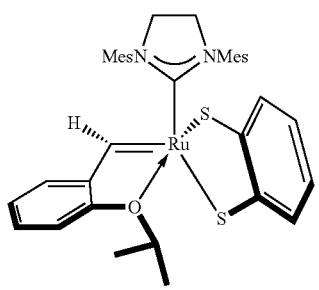

B-2a

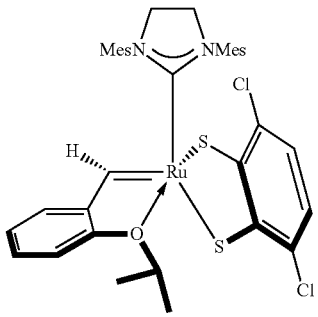

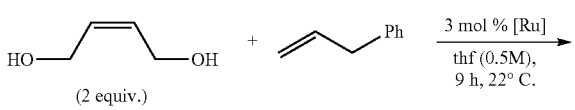

B-1a, 50% conv., 40% yield, 98:2 Z:E

B-2a, 71% conv., 61% yield, 96:4 Z:E

[a] Z:E ratios and conversions to product were determined by $^1$H NMR analysis.

As described, additional compounds (B-1b-B-1q, below) with different chelating or monodentate donor ligands have been prepared through a number of different pathways (Scheme B2) from dichloride precursors.

Dichloride Precursors

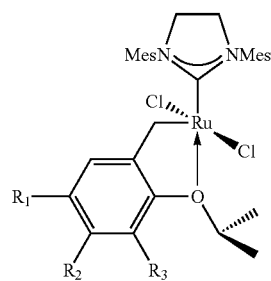

P-a (R$^1$=R$^2$=R$^3$=H)
P-b (R$^1$=NO$_2$, R$^2$=R$^3$=H)
P-c (R$^1$=SO$_2$NMe$_2$, R$^2$=R$^3$=H)
P-d (R$^2$=OiPr, R$^1$=R$^3$=H)
P-e (R$^1$=R$^2$=H, R$^3$=Ph)

P-f

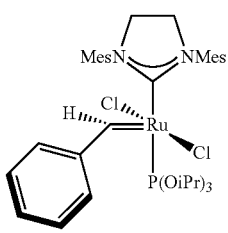

Fast Initiating (B-1a-e, B-1n) and Latent Syn Complexes (B-1f-1m, B-1o-1q)
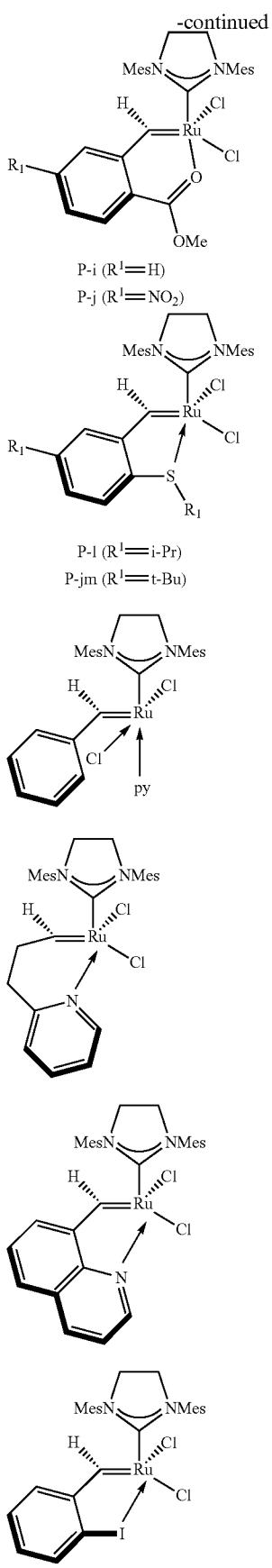
P-i ($R^1$=H)
P-j ($R^1$=$NO_2$)
P-l ($R^1$=i-Pr)
P-jm ($R^1$=t-Bu)
P-n
P-o
P-p
P-q
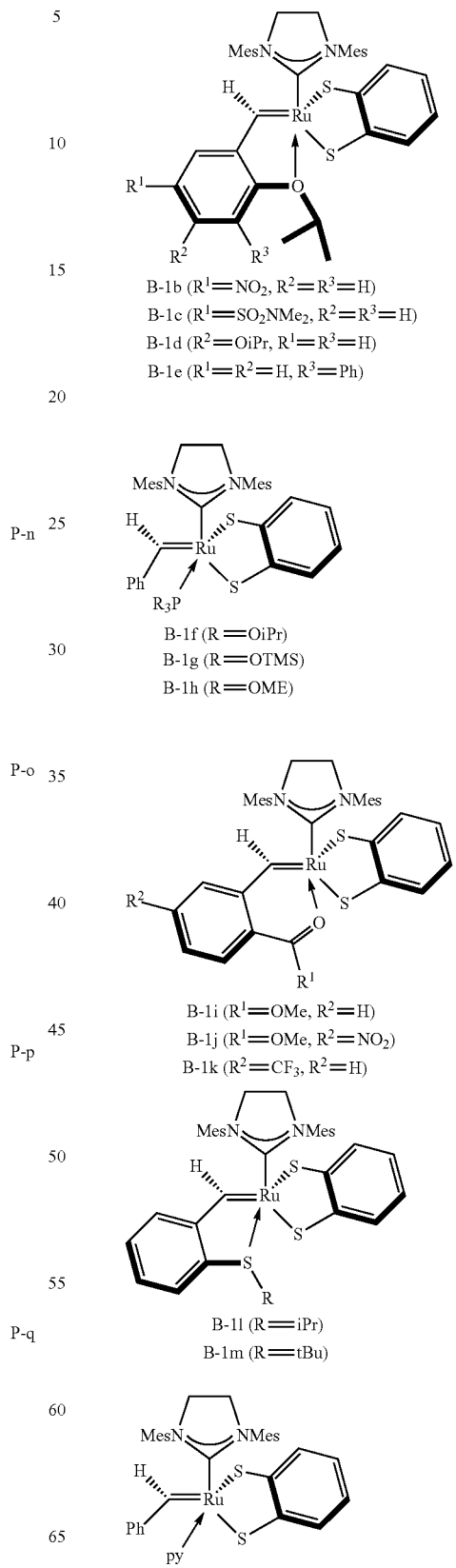
B-1b ($R^1$=$NO_2$, $R^2$=$R^3$=H)
B-1c ($R^1$=$SO_2NMe_2$, $R^2$=$R^3$=H)
B-1d ($R^2$=OiPr, $R^1$=$R^3$=H)
B-1e ($R^1$=$R^2$=H, $R^3$=Ph)
B-1f (R=OiPr)
B-1g (R=OTMS)
B-1h (R=OME)
B-1i ($R^1$=OMe, $R^2$=H)
B-1j ($R^1$=OMe, $R^2$=$NO_2$)
B-1k ($R^2$=$CF_3$, $R^2$=H)
B-1l (R=iPr)
B-1m (R=tBu)
B-1n -continued

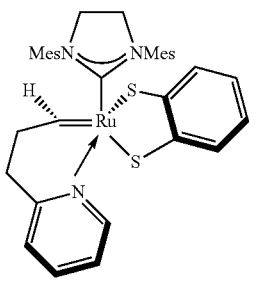

B-1o

B-1p

B-1q

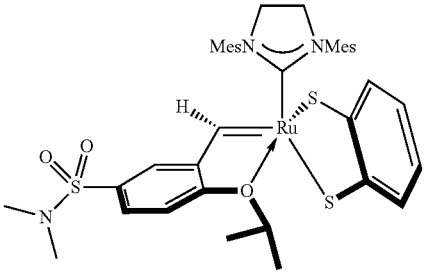

B-1c

Route B

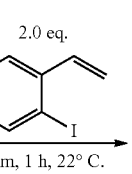

B-1c

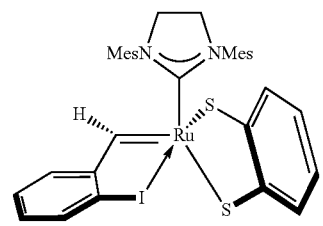

B-1q

Salt metathesis of dichloride precursors containing a bidentate initiator with 2 equiv. Zn-dithiolate in tetrahydrofuran at room temperature (Route A, Scheme B2) yielded the desired sulfur containing complexes B-1b-d,i-m,o,p in good yield (see representative procedures below). Through an analogues procedure, initiators B-1f-h,n with a monodentate neutral donor ligand have been prepared from pyridine or phosphite containing precursors (Route C, Scheme B2). An additionally developed method through styrene exchange provided complexes B-1i-m,q, which feature a stronger chelate ring than the common precursor B-1c (Route B, Scheme B2). All complexes, except for B-1b,e,k,m, have been characterized through X-ray crystallography as monomeric species (see Appendix; FIGS. 23-36).

Scheme B2. Syntheses of syn complexes through salt metathesis from dichloride precursors containing either a bidentate (Route A) or a monodentate initiator group (Route C) or through styrene exchange with a common complex B-1c (Route B).

Route A

Route C

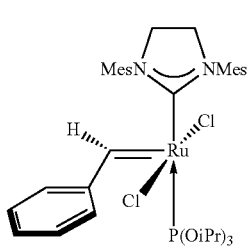

P-f

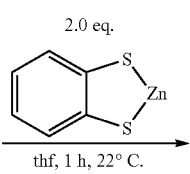

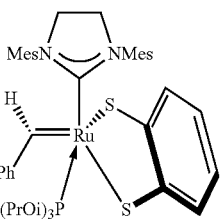

B-1f

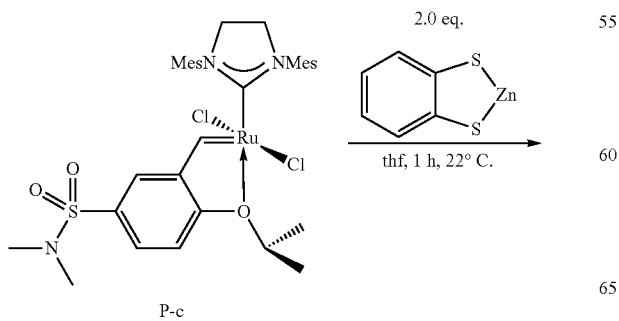

P-c

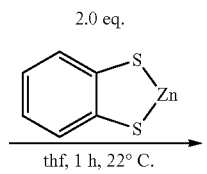

Exemplary Syntheses of Syn Complexes
Synthesis of Complex B-1c (Route A, Scheme B2)

To an oven-dried 2-dram vial charged with a stir bar and zinc catechothiolate (45 mg, 0.216 mmol, 2.10 equiv.) under $N_2$ atmosphere, a solution of P-c (75 mg, 0.102 mmol, 1.00 equiv.) in tetrahydrofuran (2.0 mL) was added. The reaction mixture was stirred for one hour at 22° C. after which the solvent was evaporated in vacuo. Residual tetrahydrofuran was removed through co-evaporation with pentane (3×1 mL). The resulting solid was dissolved in dichloromethane (1 mL) and passed through a short plug of Celite. The product was precipitated through addition of pentane (4 mL). The solid was filtered of over a short column of Celite (4 cm in height), washed with a mixture of dichloromethane and pentane (1:5, 4 mL) and eluted with dichloromethane (1 mL). After co-evaporation with pentane (3×2 mL) the product was isolated as an orange-brown solid (78 mg, 0.097 mmol, 95%). $^1$H NMR (400 MHz, $CD_2Cl_2$): δ 14.23 (d, 1H, J=0.4 Hz), 7.71 (dd, 1H, J=8.7, 2.3 Hz), 7.47 (dd, 1H, J=7.8, 1.0 Hz, 1H), 7.28 (dd, 1H, J=16.0, 5.1 Hz), 7.21 (d, 1H, J=8.8 Hz), 7.02 (br s, 2H), 6.78 (td, 1H, J=7.0, 1.4 Hz), 6.71 (td, 1H, J=7.0, 1.4 Hz), 6.33 (s, 1H), 5.26 (sep, 1H, J=6.6 Hz), 3.94 (s, 4H), 2.55 (br s, 12H), 2.20 (br s, 6H), 1.67 (d, 3H, J=6.6 Hz), 1.55 (d, 3h, J=6.5 Hz). $^{13}$C NMR (400 MHz, $CD_2Cl_2$): δ 246.16 (s), 218.58 (s), 157.84 (s), 152.89 (s), 142.00 (s), 141.04 (s), 139.32 (s), 129.66 (s), 128.43 (s), 126.61 (s), 123.78 (s), 122.09 (s), 121.18 (s), 115.25 (s), 82.85 (s), 52.03 (s), 38.31 (s), 34.69 (s), 24.02 (s), 22.91 (s), 22.00 (s), 21.27 (s), 19.74 (s), 14.39 (s).

Synthesis of B-1q Through Styrene Exchange from B-1c (Route B, Scheme B2)

To an oven-dried 2-dram vial charged with a stir bar and iodostyrene (44 mg, 0.190 mmol, 2.0 equiv.) under $N_2$ atmosphere, a solution of B-1c (76 mg, 0.095 mmol, 1.00 equiv.) in methylenechloride (2.0 mL) was added. The reaction mixture was stirred for two hours at 22° C. after which the solvent was evaporated in vacuo. The solid was dissolved in methylenechloride (0.5 mL) and the product precipitated through addition of hexanes (3 mL). The solid was filtered over a short column of Celite (4 cm in height), washed with a mixture of dichloromethane and pentane (1:5, 4 mL) and eluted with dichloromethane (1 mL). After co-evaporation with pentane (3×2 mL) the product was isolated as an orange-brown solid (52 mg, 0.068 mmol, 71%).

Synthesis of Phosphite Containing Complex B-1f (Route C, Scheme B2)

To an oven-dried 2-dram vial charged with a stir bar and zinc catechothiolate (48 mg, 0.231 mmol, 2.90 equiv.) under $N_2$ atmosphere, a solution of Ru carbene P-f (62 mg, 0.080 mmol, 1.00 equiv.) in tetrahydrofuran (1.5 mL) was added. The reaction mixture was stirred for two hours at 22° C. after which the solvent was evaporated in vacuo. Residual tetrahydrofuran was removed through co-evaporation with pentane (3×1 mL). The resulting solid was dissolved in dichloromethane (1 mL) and passed through a short plug of Celite and the solvent removed under reduced pressure. The solid was taken up in methanol (1 mL) and put into the freezer for 1 h after which the resulting solid was filtered over a short column of Celite (4 cm in height), washed with cold methanol (1 mL) and eluted with methylene chloride (1 mL). Co-evaporation with methanol (1 mL) yielded the product as a green solid (25 mg, 0.029 mmol, 37%).

Structural Analysis of Exemplary Syn Complexes and Reactivity in Polymerization of Norbornene Complexes B-1a-1q were utilized in the ring-opening metathesis polymerization (ROMP) of norbornene (see Tables B1 and B2). Complexes with a five-membered oxygen chelate ring B-1a-1d and pyridyl complex B-1n exhibited high initiation rates at 22° C. (>98% yield, >98% Z) and were still very active at lower temperatures (0.01 mol % B-1a, B-1c or B-1d, 30 min, 0° C., >98% yield, >98% Z) or catalyst loadings (0.002 mol % B-1c, 1h, 22° C., >98% yield, >98% Z). In some embodiments, substitution of the benzylidene moiety with an electron withdrawing substituent as in B-1b and B-1c led to elongation of the Ru—O bond (2.332 Å in B-1c compared to 2.277 Å in B-1a). In some embodiments, without the intention to be limited by theory, Applicant notes that the increased lability of the oxygen chelate ring rendered B-1b and B-1c prone to decomposition. After 1 h at 60° C. in toluene, B-1a showed 36% decomposition compared to >98% with B-1c. The influence of electron-donating substituents was demonstrated in complex B-1d. The isopropoxy group para to the benzylidene led to elongation of the Ru—O bond (2.336 Å vs 2.277 Å in B-a, Table B2a) and the C=Ru double bond (1.847 Å vs 1.838 Å in B-1a) due to, for example, the higher Fischer-carbene character. B-1e decomposed after minutes in solution, possibly due to increased steric pressure exerted through the phenyl group. Complex B-1o exhibited latent behavior at room temperature, but initiated at 40° C. (82% yield, 1 h, >98% Z) and led to quantitative reaction at 60° C. (>98% yield, 1 h, >98% Z). The 6-membered N chelate ring in B-1o led to superior stability (<2% decomposition in toluene at 60° C. for 1 h or in toluene at 22° C. for 10h, whereas B-1a showed >98% decomposition under identical conditions). In agreement with the greater a-donor strength of the nitrogen atom in B-1o, the Ru—S bond in trans position (relative to the pyridyl moiety) elongated to 2.330 Å (Table B2b) compared to 2.276-2.283 Å in complexes B-1a-d (Table B2a). Phosphite complexes B-1f and B-1g initiated even slower and produce reduced amounts of polynorbornene at 40° C. (42% and 52% yield after 1 h) which increases at 60° C. to 72% yield (>98% Z). Both complexes exhibited high stability at increased temperatures (toluene, 60° C.) though they slowly isomerized to other Ru species (about 20% conversion after 1 h). Despite the increased steric bulk of the trimethylsilylphosphine in B-1g (vs B-1f), as evident by the elongation of the Ru—P bond (2.300 vs 2.270 Å, Table B2c) and the shortening of the Ru—$S^{trans}$ bond (2.342 vs 2.373 Å, Table B2c), the initiation rates of both complexes appeared to be very similar. For the tested conditions, 6-membered carbonyl chelate containing B-1k did not produce >6% polymer at 60° C. after 1 h (67% Z). Reaction of ester chelate B-1i was significantly faster (60° C., 1 h, 30% yield, 88% Z). In some embodiments, the introduction of an electron-withdrawing nitro group in B-1j seems to have no effect on initiation (60° C., 1 h, 30% yield, 82% Z), as reflected by the nearly identical Ru—O bond lengths (2.143 Å in B-1i vs 2.146 Å in B-j, Table B2a). Sulfur analogues B-1l and B-1m initiated the reaction most slowly.

TABLE B1
Reactivity trend of syn complexes B-1a-q in polymerization of norbornene at different temperatures.
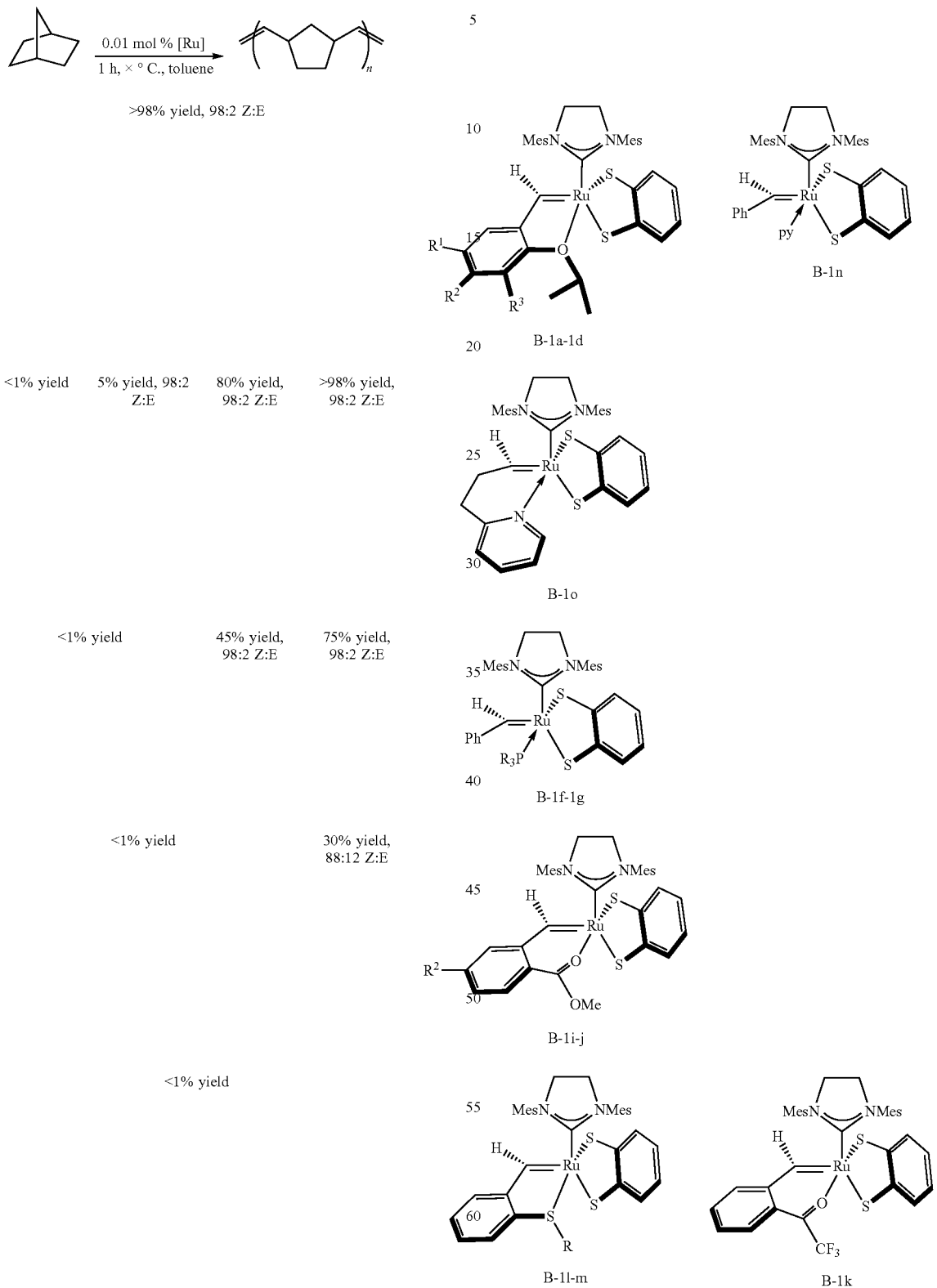

TABLE B2a

Structural parameters of oxygen chelates.[a]

| [Ru] | Ru—O | Ru—S$^{trans}$ | Ru=C$^{carb}$ |
|---|---|---|---|
| B-1a | 2.277 | 2.283 | 1.838 |
| B-1c | 2.332 | 2.276 | 1.827 |
| B-1d | 2.336 | 2.281 | 1.847 |
| B-1i | 2.143 | 2.300 | 1.843 |
| B-1j | 2.146 | 2.301 | 1.842 |

[a]Bond lengths in Å

TABLE B2b

Structural parameters of complexes with nitrogen donors.[a]

| [Ru] | Ru—N | Ru—S$^{trans}$ | Ru = C$^{carb}$ |
|---|---|---|---|
| B-1n | 2.171 | 2.325 | 1.850 |
| B-1o | 2.167 | 2.330 | 1.836 |
| B-1p | 2.127 | 2.319 | 1.854 |

[a]Bond lengths in Å

TABLE B2c

Structural parameters of phosphite complexes.[a]

| [Ru] | Ru—P | RU—S$^{trans}$ | Ru=C$^{carb}$ |
|---|---|---|---|
| B-1h | 2.251 | 2.348 | 1.874 |
| B-1f | 2.270 | 2.373 | 1.881 |
| B-1g | 2.300 | 2.342 | 1.875 |

[a]Bond lengths in Å

TABLE B2d

Structural parameters of complexes with sulfur and iodide ligands.[a]

| [Ru] | Ru—X[b] | Ru—S$^{trans}$ | Ru = C$^{carb}$ |
|---|---|---|---|
| B-1l | 2.371 | 2.324 | 1.857 |
| B-1q | 2.672 | 2.300 | 1.845 |

[a]Bond lengths in Å.
[b]1l (X = S), 1q (X = I)

Representative Procedure for the ROMP of Norbornene with B-1c

To an oven-dried 40 mL vial charged with a stir bar and a solution of norbornene (450 mg, 5.0 mmol, 1.0 equiv.) in toluene (10 mL) under $N_2$ atmosphere, a solution of B-1c (0.40 mg, 0.5 µmol, 0.01 mol %) in toluene (0.40 mL) was added. The reaction mixture was stirred for one hour at 22° C. after which methanol (10 mL) was added to precipitate the polymer. The polymer was washed with methanol (3×10 mL) and dried in vacuo to yield a white solid (445 mg, 98%).

Additional Exemplary ROCM Reactions

As described above, in some embodiments, the present invention provides methods for efficient and stereoselective metathesis reactions, e.g., ROCM reactions. In addition to reactions relating to terminal alkenes of different sizes, provided compounds also promote Z-selective ROCM processes involving heteroaryl olefins, 1,3-dienes, O- and S-substituted alkenes as well as allylic or homoallylic alcohols. Z-Selective transformations with an a-substituted allylic alcohol are shown to afford congested Z alkenes with high diastereoselectivity. Exemplary transformations are performed in the presence of 2.0-5.0 mol % of a provided Ru-based dithiolate complex that can be easily prepared. Among other things, transformations exemplified herewith proceed at ambient temperature and are complete within eight hours; products are obtained in up to 97% yield, >98:2 Z:E and >98:2 diastereomeric ratio. Without the intention to be limited by theory, Applicant proposes a mechanistically significant attribute of the Ru-based dithiolates that arises from electrostatic interactions with anionic S-based ligands.

A transformative development in olefin metathesis is the recent emergence of catalysts for efficient synthesis of Z alkenes. The latest progress notwithstanding, major challenges remain unaddressed. For example, there is a lack of Z-selective reactions with allylic or homoallylic alcohols. There are also no instances of transformations that afford cis heteroaryl-substituted alkenes; Ru-catalyzed Z-selective ROCM with O- and S-substituted olefins, and Z-Selective olefin metathesis with 1,3-dienes are also scarce. Instances of Z- and diastereoselective ROCM are unknown. In some embodiments, the present invention provides solutions to these challenges by providing compounds and methods that deliver unexpected results for these, and other, transformations.

In some embodiments, the present invention provides Ru-catalyzed Z-selective ROCM reactions of aliphatic as well as heteroaryl olefins, 1,3-dienes, O- and S-substituted alkenes and allylic or homoallylic alcohols. In some embodiments, a substrate of a provided method is an aliphatic olefin. In some embodiments, a substrate of a provided method is a heteroaryl olefin. In some embodiments, a heteroaryl olefin comprises an optionally substituted heteroaryl group conjugated to a double bond, wherein the double bond is one of the two double bonds participated in a metathesis reaction. In some embodiments, a substrate of a provided method is a 1,3-diene. In some embodiments, a 1,3-diene is optionally substituted. In some embodiments, a substrate of a provided method comprises a 1,3-diene. In some embodiments, a substrate of a provided method is an O-substituted alkene. In some embodiments, a substrate of a provided method is a S-substituted alkene. In some embodiments, a substrate of a provided method is an allylic alcohol. In some embodiments, a substrate of a provided method is a homoallylic alcohol. In some embodiments, a provided method provides a product with high Z- and diastereomeric selectivity. Provided compounds and catalysts are surprisingly efficient and deliver unexpectedly high yield, Z-selectivity and/or diastereomeric selectivity. In some embodiments, metathesis reactions are performed in the presence of 2.0-5.0 mol % of a provided metal complex compound, typically proceed at ambient temperature and are complete within eight hours; desired products are generated in up to 97% yield, >98:2 Z:E and >98:2 diastereomeric ratio (d.r.). Without the intention to be limited by theory, Applicant proposes that an anionic disulfide ligand may facilitate ROCM by forming a proton bridge with an allylic alcohol-derived carbene.

Ru carbene C1 promotes efficient and exceptionally Z-selective ring-opening metathesis polymerization and ROCM. In some embodiments, reaction rates appear to be similar to those of processes catalyzed by commonly used (non-stereoselective) Ru-based dichlorides. Without the intention to be limited by theory, Applicant reasoned that for dithiolate complex C1, ruthenacyclobutanes would be formed exclusively syn to the N-heterocyclic carbene (NHC) (I vs. II or III, Scheme C1), and that steric repulsion between the metallacycle substituents and the sizeable NHC leads to a preference for cis products. C1 can also be utilized with sterically hindered alkenes (e.g., styrenes).

Scheme C1. Ru dithiolate C1, a proposed model for Z selectivity and exemplary issues addressed.

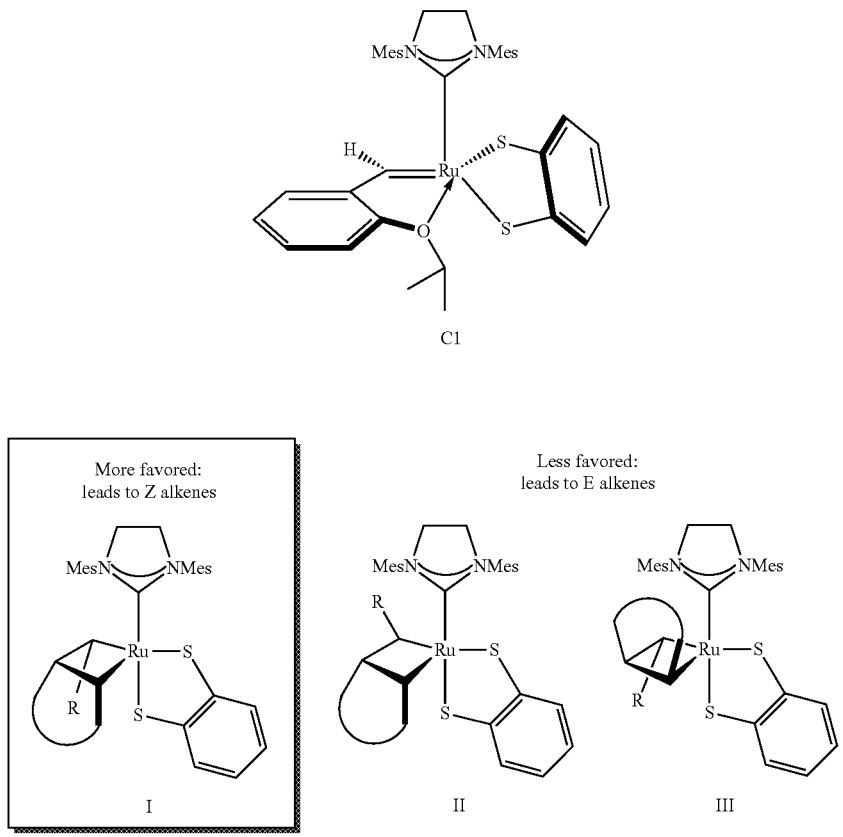

How small can the substituents be for high Z selectivity?
Wide substrate range: allylic or homoallylic alcohols, enol ethers, 1,3-dienes?

Alkenes bearing relatively small groups may lead to reduced steric repulsion with the NHC ligand (cf. II-III, Scheme C1). Unhindered olefins can also undergo more facile homocoupling to generate ethylene and the somewhat unstable methylidene complex. Additionally, processes of the more diminutive substrates afford relatively exposed disubstituted alkenes that are more susceptible to post-metathesis isomerization. Unexpectedly, reactions with alkenes bearing relatively small groups delivered high Z:E ratios when promoted by provided compounds despite all these issues. Reactions with sparsely examined enol ethers, dienes and heteroaryl alkenes also proceeded with unexpected efficiency and stereoselectivity; and it was surprisingly found that allylic and homoallylic alcohols can serve as effective substrates in ROCM with provided compounds. Influence of the size of terminal alkene cross partners on the efficiency and stereoselectivity of ROCM reactions was exemplified with diol C2. With allyltrimethylsilane, where the alkene and the sizeable moiety are linked by a methylene unit (vs. styrenes or vinylcyclohexane), reaction proceeded to >98% conversion, affording Z-C3 in 89% yield as the sole isomer (<2% E); when the β-substituent is the smaller p-methoxyphenyl group, ROCM remained efficient and exceptionally Z selectivity (cf. C4, Scheme C2). γ,δ-Unsaturated amide C5, in which an additional methylene unit separates the C=C and the carbonyl-containing moiety, underwent a fully Z-selective ROCM and the product was obtained in 65% yield. Without the intention to be limited by theory, Applicant notes that in some embodiments, the efficiency with which the ROCM products form likely can suffer due to more competitive homocoupling of the terminal olefins and generation of the less robust methylidene.

Under identical conditions, ROCM of C2 with a homoallylic silyl ether proceeded to 87% conversion, affording C6 in 68% yield and >98:2 Z:E. When the least hindered 1-decene was used, there was 91% conversion (disappearance of C2) and diene C7 was isolated in 58% yield, yet the corresponding E alkene remains undetected. Transformation of cyclobutene C8 to diene C9 (58% yield, >98% Z) provided an additional example with a different cyclic olefin. Without the intention to be limited by theory, the above findings may indicate that exceptional Z selectivity persists despite the diminishing size of the substituent of a cross partner, and steric repulsion with a mesityl moiety of the NHC and the substituents of a ruthenacyclobutane may be sufficient for the intermediacy of II or III to remain non-competitive with I even when R is relatively small.

Scheme C2. Exemplary ROCM reactions.
TBS = t-butyl(dimethyl)silyl.

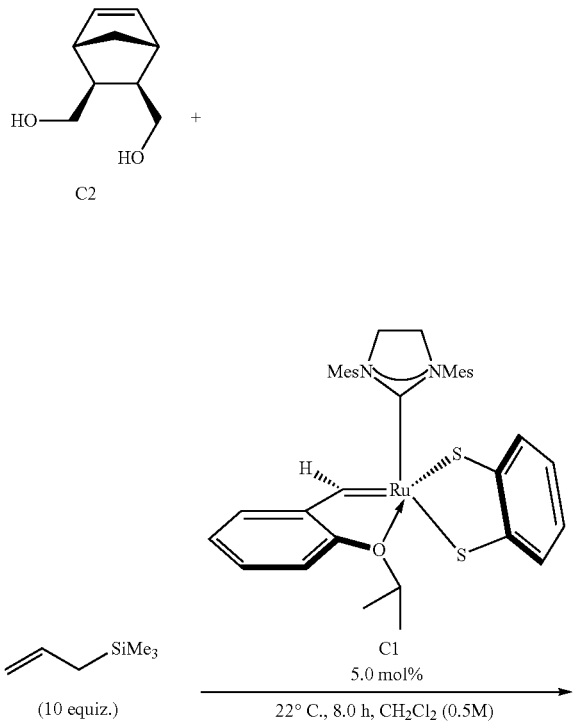

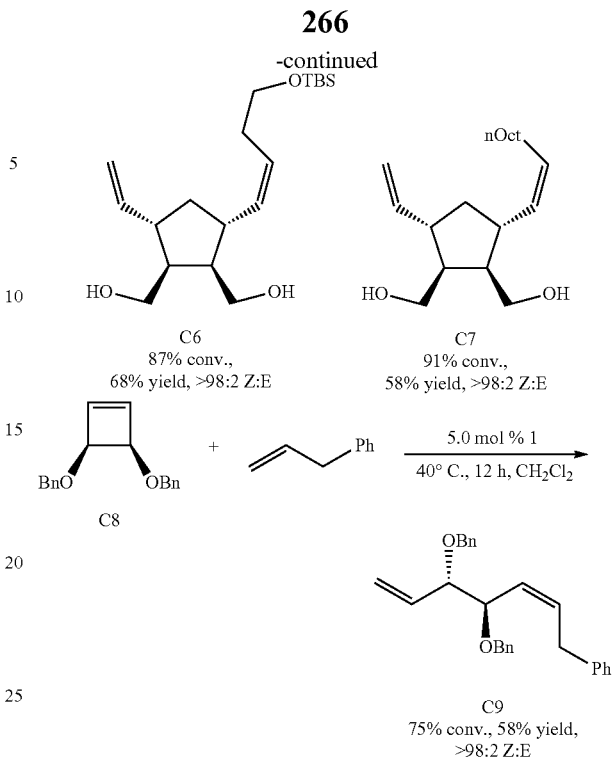

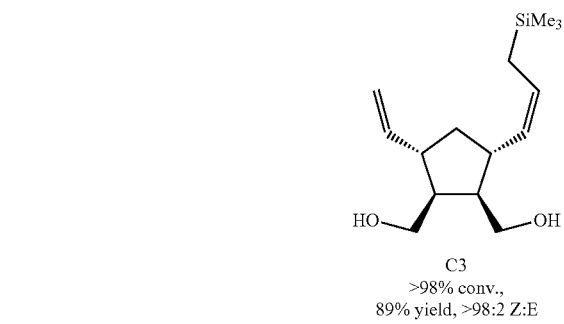

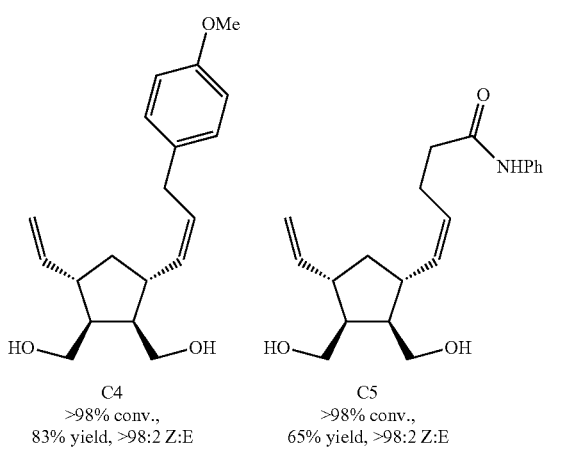

In some embodiments, the present invention provides compounds and methods for producing Z-heterocyclic alkenes. As represented by synthesis of C10 and C11 (Scheme C3), products were obtained in 93-97% yield and 93:7 to >98:2 Z:E in no more than two hours at ambient temperature. We then examined the corresponding transformations with 1,3-dienes. In the presence of 2.0-5.0 mol % C1, use of (E)-1-methoxy-1,3-butadiene generated C12a in 84% yield and 91:9 Z:E, and C12b was isolated in 80% yield and >98% Z selectivity when (E)-deca-1,3-diene was employed; the latter processes proceeded to completion in two hours at 22° C. Two other examples involving cyclobutene C8, delivering C14a and C14b without a trace of the E,E-diene isomer (<2%) are shown in Scheme C3 (88% and 60% yield, respectively). Reactions with 1,3-dienes, such as C13a-b, afforded high Z selectivity in spite of their smaller size compared to aryl-substituted alkenes (cf. C10-C11).

Scheme C3. Exemplary Z-selective ROCM with heteroaryl alkenes and linear 1,3-dienes; same conditions as shown in Scheme C2.

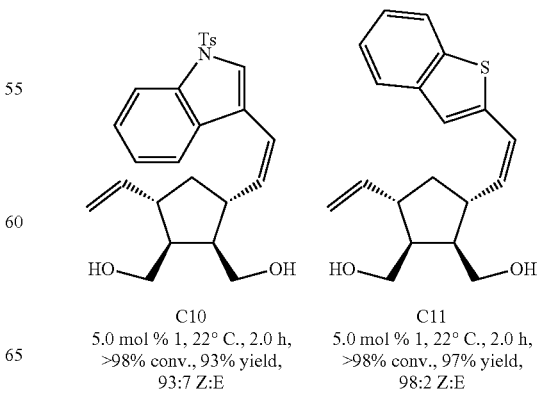

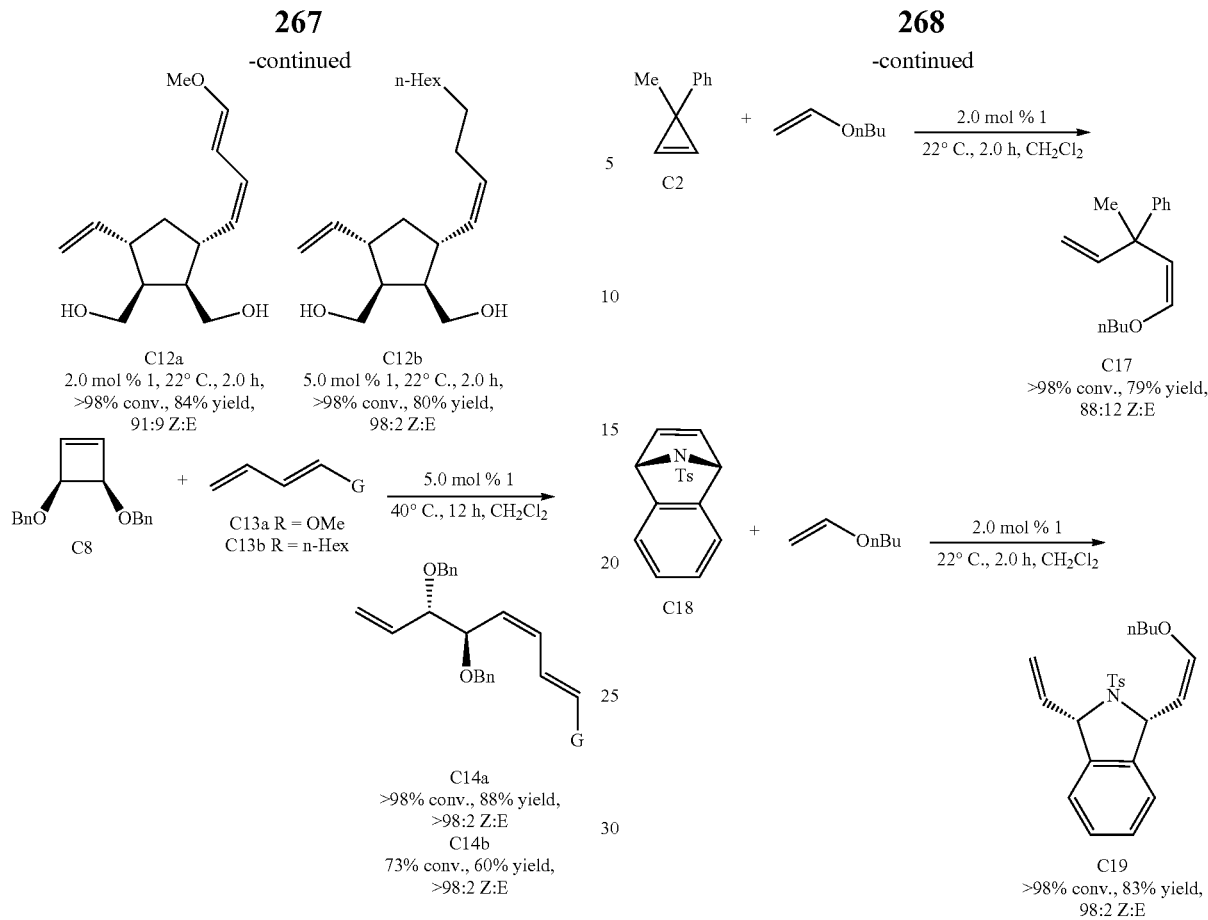

In some embodiments, the present invention provides compounds and methods for generating Z enol ethers (Scheme C4). Transformations are efficient: with 2.0-5.0 mol % C1, the desired O- or S-substituted carbo- or heterocyclic (C15a-b and C19, Scheme C4) as well as acyclic products (C16 and C17) were obtained in 79-95% yield and 88:12 to >98:2 Z:E.

In some embodiments, the present invention provides compounds and methods for using allylic or homoallylic alcohols as cross partners. ROCM of norbornene and allyl alcohol in the presence of 5.0 mol % C1 was complete in two hours (22° C.), affording C20 in 68% yield and 88:12 Z:E (Scheme C5). Likewise, homoallylic alcohol C21 was formed in 84% yield and 87% Z selectivity. Z-Allylboron compounds, precursors to useful organic molecules (e.g., allylic amines) can be readily accessed: ROCM with (pinacolato)allylboron generated C22 in 64% yield and 90:10 Z:E.

Scheme C4. Exemplary ROCM reactions with O- or S-substituted alkenyl ethers.

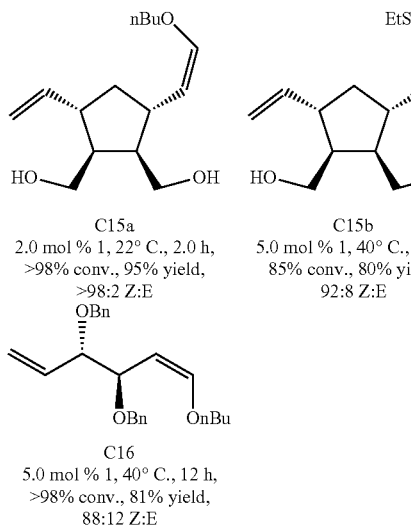

Scheme C5. Exemplary Z-selective ROCM with allyl alcohol and homoallyl alcohol.

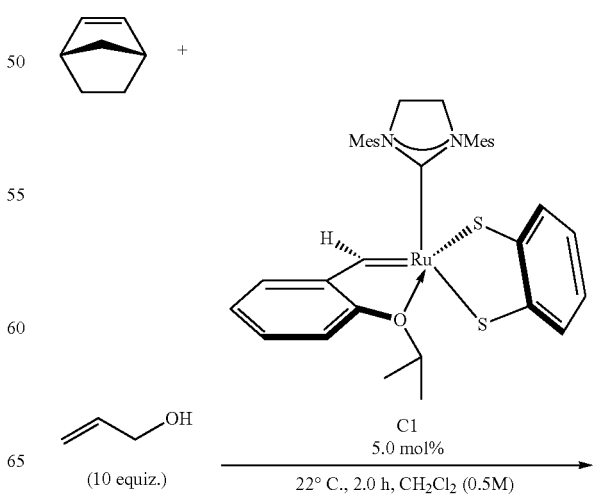

269
-continued

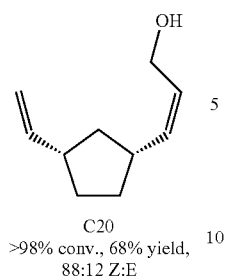

C20
>98% conv., 68% yield,
88:12 Z:E

270
-continued

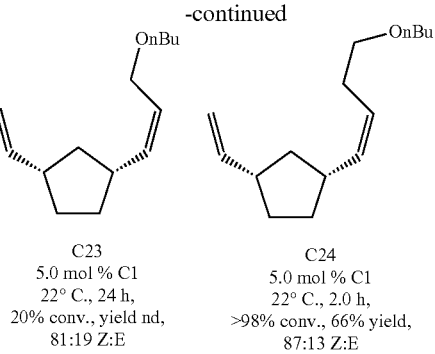

C23
5.0 mol % C1
22° C., 24 h,
20% conv., yield nd,
81:19 Z:E

C24
5.0 mol % C1
22° C., 2.0 h,
>98% conv., 66% yield,
87:13 Z:E

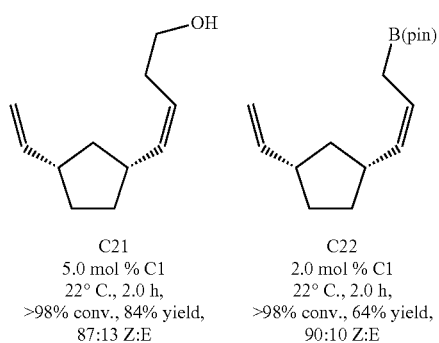

C21
5.0 mol % C1
22° C., 2.0 h,
>98% conv., 84% yield,
87:13 Z:E

C22
2.0 mol % C1
22° C., 2.0 h,
>98% conv., 64% yield,
90:10 Z:E

Reaction of allylic alcohol C25 (96:4 enantiomeric ratio) with cyclic alkene C2 (5:1) in the presence of 5.0 mol % C1 unexpectedly afforded triol C26 in 67% yield as a single diastereomer (>98:2 Z:E and >98:2 d.r.; Scheme C6). The identity of the major isomer was established by the X-ray structure of the phenylboronate derivative C27. When 25 was treated with cyclopropene C28 (1:2), under otherwise the same conditions, the congested cis alkene C29 was obtained in 78% yield, 91% Z selectivity and 93:7 d.r. There was <5% conversion after 24 hours (22° C.) when methyl ether C30 was used with either C2 or C28.

Scheme C6. Exemplary Ru-catalyzed ROCM with enantiomerically enriched allylic alcohol C25.

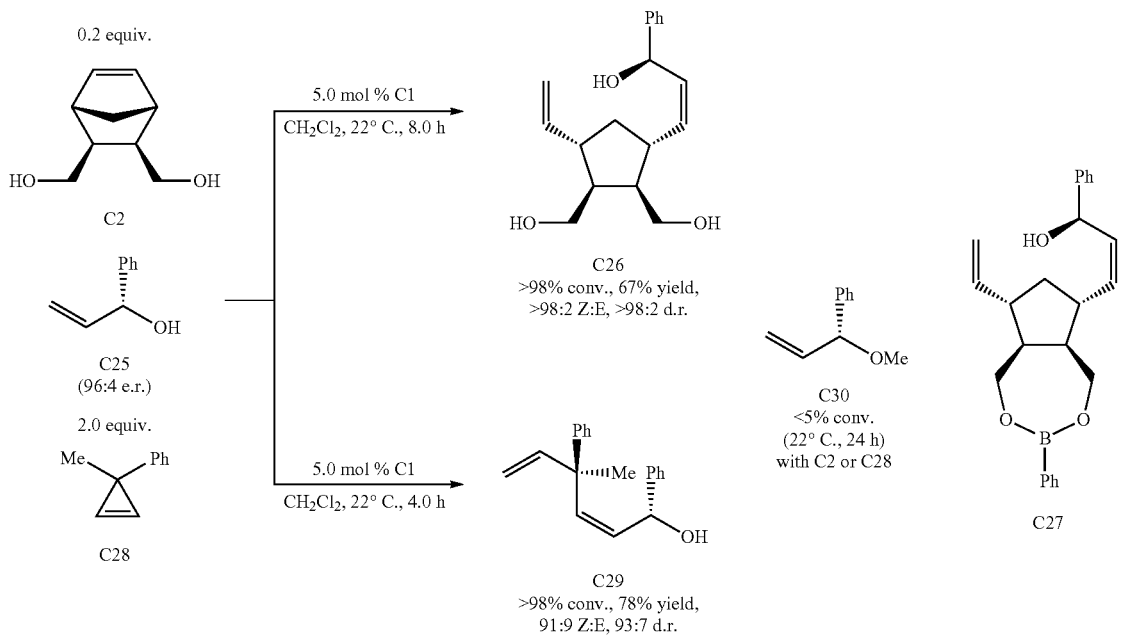

Congested Z alkenes were accessed. e.r. = enantiomeric ratio; d.r. = diastereomeric ratio.

Without the intention to be limited by theory, Applicant notes that in some embodiments, the following mechanistic factors may apply:

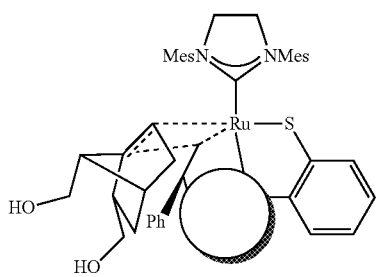

A

S***H Association:
1. Induces structural organization that results in high diastereoselectivity
2. Minimizes O-S e-e repulsion
3. Stabilizes trans influence (minimizes e-e repulsion with trans Ru-C and Ru-S)

While not wishing to be limited by theory, Applicant notes that in some embodiments, the structural organization afforded by H-bonding may lead to high diastereofacial differentiation; additionally, it may stabilize the ruthenacyclobutane and the preceding transition state by minimizing the trans influence that may arise from the placement of the NHC and sulfide groups. In some embodiments, the proton bridge may dispense with the electron-electron repulsion that otherwise may exist between the heteroatom-containing carbene substituent and the nearby sulfide (cf. C23, Scheme 5). In some embodiments, the collective consequence is the distinctive ability of a provided compound to catalyze reactions with alkenes containing a proximal hydroxyl group, without the intention to be limited by theory, likely due to a sulfide group positioned opposite to the donor NHC ligand participating in favorable electrostatic interactions.

Exemplary Experimental Procedures

General: Unless otherwise noted, all transformations were performed with distilled and degassed solvents under an atmosphere of dry $N_2$ in oven- (135° C.) or flame-dried glassware with standard dry box or vacuum line techniques. Infrared (IR) spectra were recorded on a Bruker FTIR Alpha (ATR Mode) spectrometer, $v_{max}$ in $cm^{-1}$. Bands are characterized as broad (br), strong (s), medium (m), or weak (w). $^1$H NMR spectra were recorded on a Varian Unity INOVA 400 (400 MHz) or a Varian Unity INOVA 500 (500 MHz) spectrometer. Chemical shifts are reported in ppm from tetramethylsilane with the solvent resonance resulting from incomplete deuterium incorporation as the internal standard ($CDCl_3$: δ 7.26 ppm, $C_6D_6$: δ 7.16 ppm). Data are reported as follows: chemical shift, integration, multiplicity (s=singlet, d=doublet, t=triplet, q=quartet, br=broad, m=multiplet), and coupling constants (Hz). $^{13}$C NMR spectra were recorded on a Varian Unity INOVA 400 (100 MHz) or Varian Unity INOVA 500 (125 MHz) spectrometer with complete proton decoupling. Chemical shifts are reported in ppm from tetramethylsilane with the solvent resonance as the internal standard ($CDCl_3$: δ 77.16 ppm, $C_6D_6$: δ 128.00 ppm). High-resolution mass spectrometry was performed on a Micromass LCT ESI-MS and JEOL Accu TOF Dart (positive mode) at the Boston College Mass Spectrometry Facility. Values for Z:E ratios of products were determined by analysis of $^1$H NMR spectra.

Solvents ($CH_2Cl_2$, pentane, benzene) were purified under a positive pressure of dry Ar by a modified Innovative Technologies purification system. Tetrahydrofuran was distilled under a nitrogen atmosphere from Na/benzophenone. Methanol was distilled from $CaH_2$ under nitrogen atmosphere. All purification procedures of ROCM products were carried out with reagent grade solvents (purchased from Fisher) under bench-top conditions. $CDCl_3$ and $C_6D_6$ were purchased from Cambridge Isotope Laboratories and used as received.

Styrene (Aldrich), allylbenzene (Aldrich), allyl alcohol (Aldrich), allyl(pinacolato)boronate (Frontier Scientific), 3-buten-1-ol (Aldrich), butyl vinyl ether (Aldrich), allyltrimethylsilane (Aldrich), 4-allylanisole (Aldrich), ethyl vinyl sulfide (Aldrich), 1-decene (Aldrich) and (E)-1-methoxy-1,3-butadiene (Aldrich) were distilled from $CaH_2$ under vacuum prior to use. (E)-Deca-1,3-diene was prepared according to a literature procedure (E. M. Townsend, R. R. Schrock, A. H. Hoveyda, J. Am. Chem. Soc. 2012, 134, 11334-11337) and was distilled from $CaH_2$ under vacuum prior to use. 1-(tert-butyldimethylsilyoxy)-3-butene (M. C. Pirrung, N. J. G. Webster, J. Org. Chem. 1987, 52, 3603-3613), N-phenylpent-4-enamide (S. Nicolai, R. Sedigh-Zadeh, J. Waser, J. Org. Chem. 2013, 78, 3783-3801), 1-tosyl-3-vinyl-1H-indole (J. Waser, B. Gaspar, H. Nambu, E. M. Carreira, J. Am. Chem. Soc. 2006, 128, 11693-11712), 2-vinylbenzo[b]thiophene (A. Marrocchi, L. Minuti, A. Taticchi, H. W. Scheeren, Tetrahedron 2001, 57, 4959-4965) and 4-butoxybut-1-ene (S. Kaur, J. V. Crivello, N. Pascuzzi, J. Polym. Sci. A: Polym. Chem. 1999, 37, 199-209) were prepared according to literature procedures. 5-Norbornene-2-exo,3-exo-dimethanol C2 (Aldrich) and norbornene (Aldrich) were used as received. (R)-1-Phenyl-2-propen-1-ol C25 (Fluka) was purified by column chromatography prior to use; enantiomeric ratio was determined by HPLC analysis to be 96:04 (Chiracel OD-H column, 98:2 hexanes:2-propanol, 1 mL/min, 220 nm) in comparison with authentic racemic material.

Preparation of Cyclic Olefin Substrates

Cyclobutene C8 (R. K. M. Khan, A. R. Zhugralin, S. Torker, R. V. O'Brien, P. J. Lombardi, A. H. Hoveyda, J. Am. Chem. Soc. 2012, 134, 12438-12441) and cyclopropene C28 (M. Rubin, V. Gevorgyan, Synthesis 2004, 796-800) were prepared in analogy to previously reported procedures.

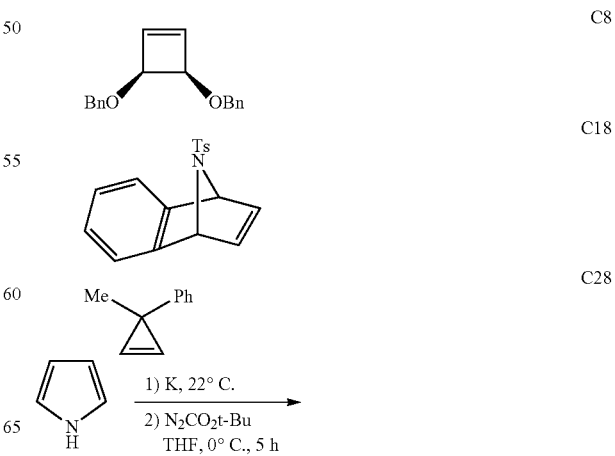

-continued

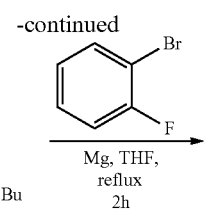

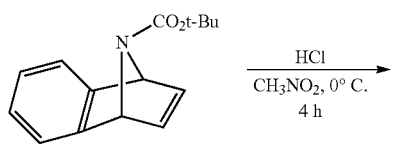

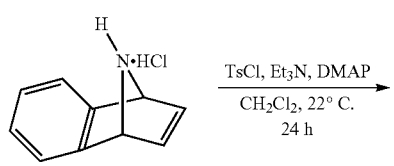

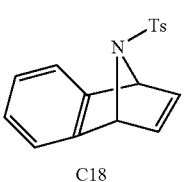

C18

N-Tosyl-2,3-Benzo-7-azabicyclo[2.2.1]hepta-2,5-diene C18

2,3-Benzo-7-azabicyclo[2.2.1]hepta-2,5-diene hydrochloride (precursor to C18) was prepared based on a reported procedure (L. A. Carpino, D. E. Barr, *J. Org. Chem.* 1966, 31, 764-767). The ammonium salt (100 mg, 0.557 mmol, 1.00 equiv) was added to a flame-dried round-bottom flask equipped with a stir bar, followed by p-toluenesulfonyl chloride (159 mg, 0.835 mmol, 1.50 equiv), triethylamine (233 μL, 1.67 mmol, 3.00 equiv), dimethylaminopyridine (6.8 mg, 0.056 mmol, 0.10 equiv) and $CH_2Cl_2$ (3 mL). The mixture was allowed to stir at 22° C. for 24 hours. The resulting mixture was washed with $H_2O$ (3×5 mL). The aqueous layers were combined and back-washed with dichloromethane (2×5 mL). The combined organic layers were dried over anhydrous $MgSO_4$, filtered and concentrated in vacuo to afford a brown residue, which was purified by silica gel chromatography (10% EtOAc in hexanes to 20% EtOAc in hexanes) to afford C18 as brown solid (124 mg, 0.417 mmol, 75% yield); mp: 152-154° C.; IR ($CH_2Cl_2$): 3052 (w), 2920 (w), 1597 (w), 1448 (w), 1339 (m), 1157 (m), 1092 (s), 599 (w); $^1H$ NMR (400 MHz, $CDCl_3$): δ 7.46 (2H, d, J=8.4 Hz), 7.09 (2H, dd, J=8.0, 0.5 Hz), 7.03 (2H, dd, J=5.1, 3.0 Hz), 6.80-6.77 (4H, m), 5.44 (2H, s), 2.34 (3H, s); $^{13}C$ NMR (100 MHz, $CDCl_3$): δ 147.4, 143.4, 142.5, 135.4, 129.5, 128.4, 125.2, 121.3, 67.9, 21.7; HRMS [M+H]$^+$ calcd for $C_{17}H_{16}NO_2S$: 298.0902, found: 298.0893.

Exemplary Ring-Opening/Cross-Metathesis (ROCM) Reactions

General Procedure: In an $N_2$-filled glove box, an oven-dried 4 mL vial equipped with a magnetic stir bar is charged with strained alkene substrate (1.0 equiv) and terminal olefin cross partner (10 equiv). To this vial, a solution of Ru complex C1 (2.0-5.0 mol %) in dichloromethane was added. The resulting solution was allowed to stir for 2-12 hours at 22-40° C., after which the reaction was quenched by addition of wet diethyl ether and concentrated in vacuo (percent conversion determined by 400 MHz or 500 MHz $^1H$ NMR analysis). Purification was performed through silica gel chromatography.

((1S,2R,3R,5S)-3-((Z)-3-(Trimethylsilyl)prop-1-enyl)-5-vinylcyclopentane-1,2-diyl)dimethanol (C3

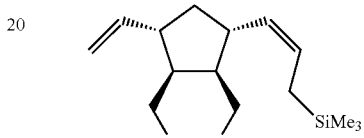

Following the general procedure, a solution of C1 (3.4 mg, 4.9 μmol, 5.0 mol %) in dichloromethane (195 μL) was transferred by syringe to a vial containing 5-norbornene-2-exo,3-exo-dimethanol 2 (15.0 mg, 0.0973 mmol, 1.00 equiv) and allyltrimethylsilane (111 mg, 0.973 mmol, 10.0 equiv). The resulting solution was allowed to stir for 8 hours at 22° C. Analysis of the unpurified mixture revealed >98% consumption of C2, and the ROCM product was obtained in >98:2 Z:E ratio. The resulting brown oil was purified by silica gel chromatography (10% EtOAc in hexanes to 30% EtOAc in hexanes) to afford C3 (23.2 mg, 0.0864 mmol, 89% yield) as colorless oil; IR ($CH_2Cl_2$): 3274 (br), 2951 (w), 2918 (w), 1640 (w), 1398 (w), 1048 (w), 993 (w), 850 (s), 837 (s), 663 (m); $^1H$ NMR (400 MHz, $CDCl_3$): Z-isomer (major): δ 5.74 (1H, ddd, J=17.1, 10.1, 7.9 Hz), 5.48-5.31 (1H, m), 5.15 (1H, dd, J=12.0, 10.8 Hz), 5.00 (1H, ddd, J=17.0, 1.8, 0.9 Hz), 4.95 (1H, dd, J=10.1, 1.3 Hz), 3.75-3.62 (4H, m), 3.32 (2H, s), 2.42 (1H, ddd, J=20.5, 12.7, 7.8 Hz), 2.21- 1.98 (3H, m), 1.85 (1H, dt, J=12.3, 6.1 Hz), 1.53 (1H, ddd, J=13.6, 9.7, 1.3 Hz), 1.36 (1H, ddd, J=13.6, 7.5, 1.5 Hz), 1.22 (1H, t, J=12.0 Hz), 0.00 (9H, s); $^{13}C$ NMR (100 MHz, $CDCl_3$): δ 141.8, 130.9, 126.4, 114.4, 62.3, 62.3, 50.3, 48.6, 46.6, 39.9, 39.5, 18.8, -1.7; HRMS [M+H—$H_2O$]$^+$ calcd for $C_{15}H_{27}OSi$: 251.1831, found: 251.1837. Coupling constant (J=12.0 Hz) of the signal at δ 5.15 ppm is indicative of Z-C3.

((1S,2R,3R,5S)-3-((Z)-3-(4-Methoxyphenyl)prop-1-enyl)-5-vinylcyclopentane-1,2-diyl)dimethanol (C4)

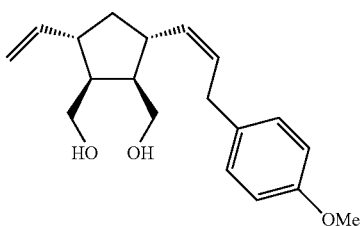 [SMILES: C=C[C@@H]1C[C@H](/C=C\Cc2ccc(OC)cc2)[C@@H](CO)[C@H]1CO]

Following the general procedure, a solution of C1 (3.4 mg, 4.9 μmol, 5.0 mol %) in dichloromethane (195 μL) was transferred by syringe to a vial containing 5-norbornene-2-exo,3-exo-dimethanol C2 (15.0 mg, 0.0973 mmol, 1.00 equiv) and 4-allylanisole (144 mg, 0.973 mmol, 10.0 equiv). The resulting solution was allowed to stir for 8 hours at 22° C. Analysis of the unpurified mixture revealed >98% consumption of C2, and the ROCM product was obtained in >98:2 Z:E ratio. The resulting brown oil was purified by silica gel chromatography (10% EtOAc in hexanes to 40% EtOAc in hexanes) to afford C4 (24.4 mg, 0.0807 mmol, 83% yield) as yellow oil; IR (CH$_2$Cl$_2$): 3286 (br), 2917 (m), 1610 (w), 1509 (s), 1463 (w), 1243 (s), 1175 (m), 1033 (s), 995 (m), 911 (m), 816 (m); $^1$H NMR (400 MHz, CDCl$_3$): Z-isomer (major): δ 7.09 (2H, d, J=8.7 Hz), 6.83 (2H, d, J=8.6 Hz), 5.75 (1H, ddd, J=16.0, 12.0, 8.0 Hz), 5.57 (1H, dt, J=10.7, 7.5 Hz), 5.37 (1H, t, J=10.2 Hz), 5.05-4.99 (1H, m), 4.98-4.95 (1H, m), 3.78 (3H, s), 3.75-3.64 (4H, m), 3.34 (1H, dd, J=10.9, 7.6 Hz), 3.29-3.26 (2H, m), 2.69-2.56 (1H, m), 2.27-2.19 (1H, m), 2.16-2.03 (2H, m), 1.93 (1H, dt, J=12.3, 6.2 Hz), 1.33-1.22 (2H, m); $^{13}$C NMR (100 MHz, C$_6$D$_6$): δ 158.6, 142.1, 134.1, 133.2, 129.5, 129.5, 114.3, 114.2, 61.8, 54.8, 50.3, 48.8, 46.4, 40.1, 39.7, 33.2; HRMS [M+H]$^+$ calcd for C$_{19}$H$_{27}$O$_3$: 303.1960, found: 303.1955. Coupling constants (J=10.7 Hz and J=10.2 Hz) of the signals at δ 5.57 and 5.37 ppm are indicative of Z-C4.

(Z)-5-((1R,2R,3S,4S)-2,3-Bis(hydroxymethyl)-4-vinylcyclopentyl)-N-phenylpent-4-enamide (C5)

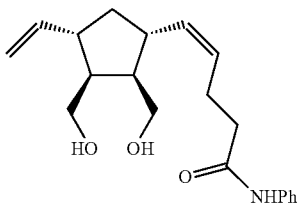

Following the general procedure, a solution of C1 (3.4 mg, 4.9 μmol, 5.0 mol %) in dichloromethane (195 μL) was transferred by syringe to a vial containing 5-norbornene-2-exo,3-exo-dimethanol C2 (15.0 mg, 0.0973 mmol, 1.00 equiv) and N-phenylpent-4-enamide (320 mg, 0.973 mmol, 10.0 equiv). The resulting solution was allowed to stir for 4 hours at 22° C. Analysis of the unpurified mixture revealed >98% conv of C2, and the ROCM product was obtained in >98:02 Z/E ratio. The resulting brown oil was purified by silica gel chromatography (10% EtOAc in hexanes to 50% EtOAc in hexanes) to afford C5 (20.8 mg, 0.0631 mmol, 65% yield) as colorless oil; IR (CH$_2$Cl$_2$): 3299 (br), 2920 (m), 2853 (m), 1663 (m), 1599 (m), 1545 (m), 1443 (s), 1027 (m); $^1$H NMR (400 MHz, CDCl$_3$): Z-isomer (major): δ 7.61 (1H, s), 7.50 (2H, d, J=7.7 Hz), 7.31 (2H, t, J=7.9 Hz), 7.10 (1H, t, J=7.4 Hz), 5.75 (1H, ddd, J=17.1, 10.1, 8.1 Hz), 5.45-5.36 (1H, m), 5.25 (1H, t, J=10.2 Hz), 5.02 (1H, ddd, J=17.1, 1.8, 1.0 Hz), 4.94 (1H, ddd, J=10.1, 1.8, 0.5 Hz), 3.79 (1H, dd, J=11.6, 2.7 Hz), 3.71 (1H, dd, J=12.0, 2.5 Hz), 3.67-3.61 (2H, m), 2.92-2.80 (1H, m), 2.75-2.65 (1H, m), 2.57-2.43 (2H, m), 2.36-2.28 (2H, m), 2.03-1.81 (4H, m), 1.23-1.16 (2H, m); $^{13}$C NMR (100 MHz, CDCl$_3$): δ 171.4, 142.1, 138.0, 135.1, 129.2, 128.5, 124.5, 119.9, 114.1, 61.8, 60.4, 50.1, 48.7, 45.6, 39.8, 39.2, 38.0, 23.9; HRMS [M+H]$^+$ calcd for C$_{20}$H$_{28}$NO$_3$: 330.2069, found: 330.2076. Coupling constant (J=10.2 Hz) of the signal at δ 5.25 ppm is indicative of Z-C5.

((1S,2R,3R,5S)-3-((Z)-4-(tert-Butyldimethylsilyloxy)but-1-enyl)-5-vinylcyclopentane-1,2-diyl)dimethanol (C6)

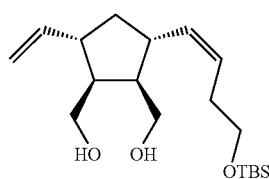 [SMILES: C=C[C@@H]1C[C@H](/C=C\CCO[Si](C)(C)C(C)(C)C)[C@@H](CO)[C@H]1CO]

Following the general procedure, a solution of C1 (3.4 mg, 4.9 μmol, 5.0 mol %) in dichloromethane (195 μL) was transferred by syringe to a vial containing 5-norbornene-2-exo,3-exo-dimethanol C2 (15.0 mg, 0.0973 mmol, 1.00 equiv) and 1-(tert-butyldimethylsilyoxy)-3-butene (181 mg, 0.973 mmol, 10.0 equiv). The resulting solution was allowed to stir for 8 hours at 22° C. Analysis of the unpurified mixture revealed 89% consumption of C2, and the ROCM product was obtained in >98:2 Z:E ratio. The resulting brown oil was purified by silica gel chromatography (10% EtOAc in hexanes to 30% EtOAc in hexanes) to afford C6 (22.5 mg, 0.0661 mmol, 68% yield) as yellow oil; IR (CH$_2$Cl$_2$): 3299 (br), 2926 (s), 2856 (m), 1639 (w), 1463 (w), 1095 (m), 1046 (m), 836 (s); $^1$H NMR (500 MHz, CDCl$_3$): Z-isomer (major): δ 5.76 (1H, ddd, J=17.8, 10.3, 8.3 Hz), 5.43-5.36 (1H, m), 5.30 (1H, t, J=10.3 Hz), 5.04-4.98 (1H, m), 4.94 (1H, ddd, J=10.1, 1.7, 0.8 Hz), 3.75-3.71 (1H, m), 3.69 (1H, d, J=10.6 Hz), 3.67-3.58 (4H, m), 2.67-2.57 (1H, m), 2.42- 2.28 (2H, m), 2.25- 2.16 (2H, m), 2.08-2.00 (1H, m), 1.95 (1H, tdd, J=10.3, 7.7, 2.8 Hz), 1.89 (1H, dt, J=12.3, 6.3 Hz), 1.27-1.19 (2H, m), 0.90 (9H, d, J=0.7 Hz), 0.07 (6H, s); $^{13}$C NMR (125 MHz, CDCl$_3$): δ 142.1, 134.8, 127.2, 114.1, 63.4, 62.3, 61.3, 50.1, 48.6, 46.1, 39.8, 39.7, 31.5, 26.2, -5.1, -5.1; HRMS [M+Na]$^+$ calcd for C$_{19}$H$_{36}$O$_3$NaSi: 363.2326, found: 363.2330. Coupling constant (J=10.3 Hz) of the signal at δ 5.30 ppm is indicative of Z-C6.

((1S,2R,3R,5S)-3-((Z)-Dec-1-enyl)-5-vinylcyclopentane-1,2-diyl)dimethanol (C7)

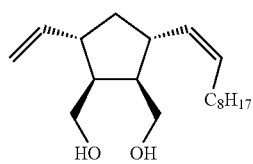

Following the general procedure, a solution of C1 (3.4 mg, 4.9 μmol, 5.0 mol %) in dichloromethane (195 μL) was transferred by syringe to a vial containing 5-norbornene-2- exo,3-exo-dimethanol C2 (15.0 mg, 0.0973 mmol, 1.00 equiv) and 1-decene (136 mg, 0.973 mmol, 10.0 equiv). The resulting solution was allowed to stir for 8 hours at 22° C. Analysis of the unpurified mixture revealed 91% consumption of C2, and the ROCM product was obtained in 92:8 Z:E ratio. The resulting brown oil was purified by silica gel chromatography (10% EtOAc in hexanes to 30% EtOAc in hexanes) to afford C7 (16.6 mg, 0.0564 mmol, 58% yield) as colorless oil; IR (CH$_2$Cl$_2$): 3274 (br), 2921 (s), 2853 (m), 1640 (w), 1458 (w), 1029 (m), 993 (m), 911 (m); $^1$H NMR (400 MHz, CDCl$_3$): Z-isomer (major): δ 5.74 (1H, ddd, J=17.2, 10.1, 7.9 Hz), 5.39 (1H, dt, J=10.8, 7.3 Hz), 5.22 (1H, dd, J=10.8, 9.5 Hz), 5.01 (1H, dd, J=17.0, 1.8, 0.9 Hz), 4.96 (1H, ddd, J=10.1, 1.8, 0.6 Hz), 3.79- 3.58 (4H, m), 2.84 (2H, s), 2.54-2.41 (1H, m), 2.19-1.97 (5H, m), 1.86 (1H, dt, J=12.3, 6.1, Hz), 1.34-1.19 (13H, m), 0.88 (3H, t, J=6.8 Hz); $^{13}$C NMR (100 MHz, CDCl$_3$): δ 141.7, 132.9, 131.0, 114.5, 62.3, 62.3, 50.1, 48.6, 46.6, 40.0, 39.8, 32.1, 30.1, 29.7, 29.5, 29.5, 27.8, 22.8, 14.3; HRMS [M+H]$^+$ calcd for C$_{19}$H$_{35}$O$_2$: 295.2637, found: 295.2634. Coupling constants (J=10.3 and J=10.3 Hz) of the signals at δ 5.39 and 5.22 ppm are indicative of Z-C7.

((3S,4R,Z)-7-Phenylhepta-1,5-diene-3,4-diyl)bis(oxy)bis(methylene)dibenzene (C9)

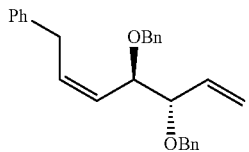 [SMILES: C=C[C@H](OCc1ccccc1)[C@@H](/C=C\Cc1ccccc1)OCc1ccccc1]

Following the general procedure, a solution of C1 (1.9 mg, 2.8 µmol, 5.0 mol %) in dichloromethane (113 µL) was transferred by syringe to a vial containing cyclobutene C8 (15.0 mg, 0.0563 mmol, 1.00 equiv) and allylbenzene (67.0 mg, 0.563 mmol, 10.0 equiv). The resulting solution was allowed to stir for 12 hours at 40 OC. Analysis of the unpurified mixture revealed 75% consumption of C8, and the ROCM product was obtained in >98:2 Z:E ratio. The resulting brown oil was purified by silica gel chromatography (100% hexanes to 10% Et$_2$O in hexanes) followed by passing through a plug of activated charcoal with 50% Et$_2$O in pentane to afford C9 (12.6 mg, 0.0328 mmol, 58% yield) as colorless oil; IR (CH$_2$Cl$_2$): 3027 (w), 2918 (w), 2860 (w), 1602 (w), 1495 (w), 1453 (m), 1088 (s), 1069 (s), 1028 (m), 927 (w); $^1$H NMR (400 MHz, CDCl$_3$): Z-isomer (major): δ 7.36-7.27 (1OH, m), 7.25-7.17 (3H, m), 7.12 (2H, d, J=7.3 Hz), 5.96-5.83 (2H, m), 5.56 (1H, ddt, J=11.0, 9.4, 1.7 Hz), 5.35-5.29 (2H, m), 4.67 (2H, d, J=12.2 Hz), 4.46 (2H, dd, J=12.2, 8.2 Hz), 4.36 (1H, ddd, J=9.4, 4.7, 1.0 Hz), 3.92- 3.85 (1H, m), 3.33 (2H, t, J=6.9 Hz); $^{13}$C NMR (100 MHz, CDCl$_3$): δ 140.4, 138.8, 135.7, 133.5, 128.6, 128.6, 128.4, 128.4, 128.4, 128.3, 127.8, 127.8, 127.5, 127.5, 126.2, 119.0, 82.7, 76.3, 70.6, 70.3, 34.3; HRMS [M+NH$_4$]$^+$ calcd for C$_{27}$H$_{32}$NO$_2$: 402.2433, found: 402.2443. Coupling constant (J=11.0 Hz) of the signal at δ 5.56 ppm is indicative of Z-C9.

((1S,2R,3R,5S)-3-((Z)-2-(1-Tosyl-1H-indol-3-yl)vinyl)-5-vinylcyclopentane-1,2-diyl)dimethanol (C10)

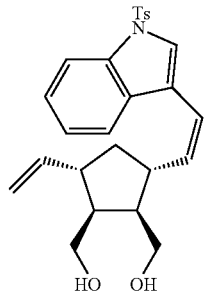 [SMILES: C=C[C@@H]1C[C@H](/C=C\c2cn(S(=O)(=O)c3ccc(C)cc3)c3ccccc23)[C@@H](CO)[C@H]1CO]

Following the general procedure, a solution of C1 (3.4 mg, 4.9 µmol, 5.0 mol %) in dichloromethane (195 µL) was transferred by syringe to a vial containing 5-norbornene-2-exo,3-exo-dimethanol C2 (15.0 mg, 0.0973 mmol, 1.00 equiv) and 1-tosyl-3-vinyl-1H-indole (289 mg, 0.973 mmol, 10.0 equiv). The resulting solution was allowed to stir for 2 hours at 22° C. Analysis of the unpurified mixture revealed >98% consumption of C2, and the ROCM product was obtained in 93:7 Z:E ratio. The resulting brown oil was purified by silica gel chromatography (10% EtOAc in hexanes to 40% EtOAc in hexanes) to afford C10 (40.9 mg, 0.0906 mmol, 93% yield) as off-white wax; IR (CH$_2$Cl$_2$): 3308 (br), 3076 (w), 2922 (m), 1639 (w), 1597 (w), 1447 (m), 1370 (m), 1173 (s), 965 (m); $^1$H NMR (400 MHz, CDCl$_3$): Z-isomer (major): δ 7.99 (1H, d, J=8.3 Hz), 7.76 (2H, d, J=8.4 Hz), 7.59 (1H, s), 7.47 (1H, d, J=7.8 Hz), 7.35-7.30 (1H, m), 7.22 (3H, t, J=7.2 Hz), 6.38 (1H, d, J=11.3 Hz), 5.76 (1H, ddd, J=17.1, 10.1, 8.1 Hz), 5.68 (1H, dd, J=11.3, 10.1 Hz), 5.09-5.02 (1H, m), 5.00 (1H, dd, J=10.1, 1.3 Hz), 3.73-3.68 (2H, m), 3.61-3.59 (2H, m), 3.10 (2H, s), 2.82-2.73 (1H, m), 2.33 (3H, s), 2.32-2.22 (1H, m), 2.17-2.12 (2H, m), 2.00 (1H, dt, J=12.5, 6.3 Hz), 0.90-0.83 (1H, m); $^{13}$C NMR (100 MHz, CDCl$_3$): δ 145.1, 141.4, 138.0, 135.2, 134.9, 131.0, 130.0, 126.9, 125.1, 123.5, 123.3, 119.6, 119.1, 118.5, 114.8, 113.8, 61.9, 61.9, 50.2, 48.6, 46.3, 41.3, 39.7, 21.7; HRMS [M+H]$^+$ calcd for C$_{26}$H$_{30}$NO$_4$S: 452.1896, found: 452.1887. Coupling constants (J=11.3 and J=11.3 Hz) of the signals at δ 6.38 and 5.68 ppm are indicative of Z-C10.

((1S,2R,3R,5S)-3-((Z)-2-(Benzo[b]thiophen-2-yl)-5-vinylcyclopentane-1,2-diyl)dimethanol (C11)

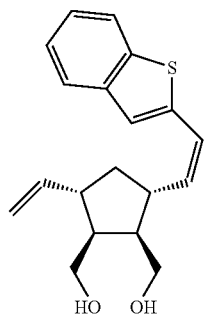 [SMILES: C=C[C@@H]1C[C@H](/C=C\c2cc3ccccc3s2)[C@@H](CO)[C@H]1CO]

Following the general procedure, a solution of C1 (3.4 mg, 4.9 μmol, 5.0 mol %) in dichloromethane (195 μL) was transferred by syringe to a vial containing 5-norbornene-2-exo,3-exo-dimethanol C2 (15.0 mg, 0.0973 mmol, 1.00 equiv) and 2-vinylbenzo[b]thiophene (156 mg, 0.973 mmol, 10.0 equiv). The resulting solution was allowed to stir for 2 hours at 22° C. Analysis of the unpurified mixture revealed >98% consumption of C2, and the ROCM product was obtained in >98:2 Z:E ratio. The resulting brown oil was purified by silica gel chromatography (10% EtOAc in hexanes to 40% EtOAc in hexanes) to afford C11 (29.6 mg, 0.0941 mmol, 97% yield) as yellow oil; IR (CH$_2$Cl$_2$): 3275 (br), 3070 (w), 2917 (m), 2850 (w), 1638 (w), 1456 (w), 1015 (m), 993 (m); $^1$H NMR (400 MHz, CDCl$_3$): Z-isomer (major): δ 7.77 (1H, dd, J=7.6, 0.8 Hz), 7.73-7.68 (1H, m), 7.38-7.26 (2H, m), 7.16 (1H, s), 6.61 (1H, dd, J=11.5, 0.6 Hz), 5.77 (1H, ddd, J=17.4, 10.0, 8.0 Hz), 5.56 (1H, t, J=10.8 Hz), 5.11-5.02 (1H, m), 5.00 (1H, dd, J=10.1, 1.7 Hz), 3.82-3.76 (2H, m), 3.73-3.65 (2H, m), 3.26-2.97 (3H, m), 2.37-2.29 (1H, m), 2.21-2.17 (2H, m), 2.11 (1H, dt, J=12.4, 6.3 Hz), 1.39-1.31 (1H, m); $^{13}$C NMR (100 MHz, CDCl$_3$): δ 141.4, 140.0, 139.8, 139.3, 136.4, 124.7, 124.7, 123.5, 123.0, 122.1, 122.1, 114.8, 62.3, 62.2, 50.8, 48.7, 46.6, 41.6, 39.5; HRMS [M+H]$^+$ calcd for C$_{19}$H$_{32}$O$_2$S: 315.1419, found: 315.1410. Coupling constant (J=10.8 Hz) of the signal at δ 5.56 ppm is indicative of Z-11.

((1S,2R,3R,5S)-3-((1Z,3E)-4-Methoxybuta-1,3-dienyl)-5-vinylcyclopentane-1,2-diyl)dimethanol (C12a)

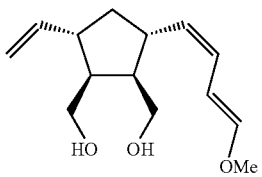 [SMILES: C=C[C@@H]1C[C@H](/C=C\C=C\OC)[C@@H](CO)[C@H]1CO]

Following the general procedure, a solution of C1 (1.4 mg, 1.9 μmol, 2.0 mol %) in dichloromethane (195 μL) was transferred by syringe to a vial containing 5-norbornene-2-exo,3-exo-dimethanol C2 (15.0 mg, 0.0973 mmol, 1.00 equiv) and (E)-1-methoxy-1,3-butadiene (82.0 mg, 0.973 mmol, 10.0 equiv). The resulting solution was allowed to stir for 2 hours at 22° C. Analysis of the $^1$H NMR (400 MHz) spectrum revealed >98% consumption of C2, and the ROCM product was obtained in 91:9 Z:E ratio. The resulting brown oil was purified by silica gel chromatography (10% EtOAc in hexanes to 40% EtOAc in hexanes) to afford C12a (19.5 mg, 0.0818 mmol, 84% yield) as colorless oil; IR (CH$_2$Cl$_2$): 3305 (br), 2920 (m), 1648 (m), 1608 (m), 1452 (w), 1210 (s), 1027 (s), 993 (s), 912 (s); $^1$H NMR (400 MHz, CDCl$_3$): Z-isomer (major): δ 6.56 (1H, d, J=12.3 Hz), 5.88 (1H, t, J=11.0 Hz), 5.80-5.66 (2H, m), 5.09-4.98 (2H, m), 4.96 (1H, dd, J=10.1, 1.7 Hz), 3.76-3.63 (4H, m), 3.60 (3H, s), 3.28 (2H, s), 2.64-2.52 (1H, m), 2.28-2.19 (1H, m), 2.15-1.99 (2H, m), 1.93 (1H, dt, J=12.4, 6.2 Hz), 1.24 (1H, d, J=11.2 Hz); $^{13}$C NMR (100 MHz, CDCl$_3$): δ 152.1, 141.7, 129.9, 125.3, 114.5, 101.7, 62.2, 62.0, 56.9, 50.3, 48.5, 46.5, 40.3, 39.9; HRMS [M+H—H$_2$O]$^+$ calcd for C$_{14}$H$_{21}$O$_2$: 221.1542, found: 221.1545. Coupling constant (J=11.0 Hz) of the signal at δ 5.88 ppm is indicative of Z-C12a.

((1S,2R,3R,5S)-3-((1Z,3E)-Deca-1,3-dienyl)-5-vinylcyclopentane-1,2-diyl)dimethanol (C12b)

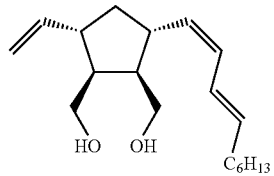

Following the general procedure, a solution of C1 (3.4 mg, 4.9 μmol, 5.0 mol %) in dichloromethane (195 μL) was transferred by syringe to a vial containing 5-norbornene-2-exo,3-exo-dimethanol C2 (15.0 mg, 0.0973 mmol, 1.00 equiv) and (E)-deca-1,3-diene (134 mg, 0.973 mmol, 10.0 equiv). The resulting solution was allowed to stir for 2 hours at 22° C. Analysis of the $^1$H NMR (400 MHz) spectrum revealed >98% consumption of C2, and the ROCM product was obtained in >98:2 Z:E ratio. The resulting brown oil was purified by silica gel chromatography (10% EtOAc in hexanes to 30% EtOAc in hexanes) to afford C12b (22.8 mg, 0.0780 mmol, 80% yield) as colorless oil; IR (CH$_2$Cl$_2$): 3276 (br), 2922 (s), 2854 (m), 1639 (w), 1455 (m), 1027 (s), 983 (s), 946 (s), 910 (s); $^1$H NMR (400 MHz, CDCl$_3$): Z-isomer (major): δ 6.25 (1H, ddd, J=13.6, 11.5, 6.0 Hz), 5.97 (1H, t, J=10.9 Hz), 5.82-5.61 (2H, m), 5.16 (1H, t, J=10.2 Hz), 5.04-4.98 (1H, m), 4.96 (1H, dd, J=10.1, 1.8, Hz), 3.77-3.61 (4H, m), 3.22 (2H, s), 2.70-2.61 (1H, m), 2.28-2.16 (1H, m), 2.15-1.99 (4H, m), 1.93 (1H, dt, J=12.3, 6.2 Hz), 1.42-1.24 (9H, m), 0.88 (3H, t, J=6.8 Hz); $^{13}$C NMR (100 MHz, CDCl$_3$): δ 141.6, 136.0, 132.6, 129.6, 125.5, 114.5, 62.2, 62.1, 50.2, 48.6, 46.5, 40.2, 40.0, 33.1, 31.9, 29.5, 29.1, 22.8, 14.3; HRMS [M+H]$^+$ calcd for C$_{19}$H$_{33}$O$_2$: 293.2481, found: 293.2473. Coupling constants (J=10.9 and 10.2 Hz) of the signals at δ 5.97 and 5.16 ppm are indicative of Z-C12b.

((3S,4R,5Z,7E)-8-Methoxyocta-1,5,7-triene-3,4-diyl)bis(oxy)bis(methylene)dibenzene (C14a)

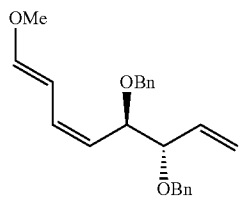 [SMILES: C=C[C@H](OCc1ccccc1)[C@@H](/C=C\C=C\OC)OCc1ccccc1]

Following the general procedure, a solution of C1 (1.9 mg, 2.8 μmol, 5.0 mol %) in dichloromethane (113 μL) was transferred by syringe to a vial containing cyclobutene C8 (15.0 mg, 0.0563 mmol, 1.00 equiv) and (E)-1-methoxy-1,3-butadiene (47.0 mg, 0.563 mmol, 10.0 equiv). The resulting solution was allowed to stir for 12 hours at 40 OC. Analysis of the unpurified mixture revealed >98% consumption of C8, and the ROCM product was obtained in >98:2 Z:E ratio. The resulting brown oil was purified by silica gel chromatography (100% hexanes to 10% Et$_2$O in hexanes) to afford C14a (17.4 mg, 0.0497 mmol, 88% yield) as colorless oil; IR (CH$_2$Cl$_2$): 2918 (w), 2850 (w), 1649 (m), 1608 (w), 1453 (w), 1335 (w), 1210 (s), 1168 (m), 1087 (s), 1065 (s), 925 (m); ¹H NMR (400 MHz, CDCl₃): Z-isomer (major): δ 7.38-7.29 (8H, m), 7.27-7.23 (2H, m), 6.63 (1H, d, J=12.3 Hz), 6.16 (1H, t, J=11.2 Hz), 5.89 (1H, ddd, J=17.3, 10.4, 7.7 Hz), 5.56 (1H, t, J=12.1 Hz), 5.35-5.25 (2H, m), 5.21 (1H, t, J=10.3 Hz), 4.66 (2H, d, J=12.3 Hz), 4.45 (2H, dd, J=12.3, 5.5, Hz), 4.31-4.24 (1H, m), 3.87 (1H, dd, J=7.7, 4.5 Hz), 3.49 (3H, s); ¹³C NMR (100 MHz, CDCl₃): δ 153.3, 138.9, 138.9, 135.7, 129.7, 128.3, 128.3, 127.9, 127.7, 127.4, 127.4, 123.0, 119.0, 101.4, 82.8, 76.5, 70.6, 69.9, 56.6; HRMS [M+NH₄]⁺ calcd for C₂₃H₃₀NO₃: 368.2226, found: 368.2243. Coupling constant (J=10.3 Hz) of the signal at δ 5.21 ppm is indicative of Z-C14a.

3S,4R,5Z,7E)-Tetradeca-1,5,7-triene-3,4-diylbis(oxy)bis(methylene)dibenzene (C14b)

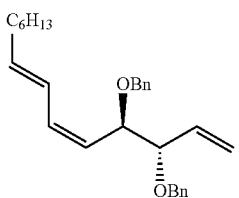

Following the general procedure, a solution of C1 (1.9 mg, 2.8 μmol, 5.0 mol %) in dichloromethane (113 μL) was transferred by syringe to a vial containing cyclobutene C8 (15.0 mg, 0.0563 mmol, 1.00 equiv) and (E)-deca-1,3-diene (78.0 mg, 0.563 mmol, 10.0 equiv).

The resulting solution was allowed to stir for 12 hours at 40 OC. Analysis of the unpurified mixture revealed 73% consumption of C8, and the ROCM product was obtained in >98:2 Z:E ratio. The resulting brown oil was purified by silica gel chromatography (100% hexanes to 5% Et₂O in hexanes) followed by passing through a plug of activated charcoal with 50% Et₂O in pentane to afford C14b (13.7 mg, 0.0339 mmol, 60% yield) as colorless oil; IR (CH₂Cl₂): 3028 (w), 2955 (m), 2925 (s), 2855 (m), 1653 (w), 1496 (w), 1455 (m), 1090 (s), 1070 (s), 1028 (w), 988 (w); ¹H NMR (400 MHz, CDCl₃): Z-isomer (major): δ 7.37-7.26 (10H, m), 6.24 (1H, t, J=11.0 Hz), 6.18-6.07 (1H, m), 5.87 (1H, ddd, J=16.0, 12.0, 8.0 Hz), 5.74 (1H, dt, J=14.2, 6.9 Hz), 5.34-5.25 (3H, m), 4.64 (2H, dd, J=12.3, 2.2 Hz), 4.44 (2H, dd, J=12.2, 9.0 Hz), 4.35 (1H, dd, J=9.3, 4.6 Hz), 3.86 (1H, dd, J=7.7, 4.6 Hz), 2.05 (2H, q, J=7.0 Hz), 1.38-1.25 (8H, m), 0.89 (3H, t, J=6.7 Hz); ¹³C NMR (100 MHz, CDCl₃): δ 138.8, 138.8, 137.8, 135.6, 133.6, 128.3, 128.3, 127.9, 127.7, 127.5, 127.4, 126.0, 125.6, 120.0, 82.8, 76.3, 70.6, 70.1, 33.0, 31.9, 29.3, 29.1, 22.8, 14.3; HRMS [M+NH₄]⁺ calcd for C₂₈H₄₀NO₂: 422.3059, found: 422.3072. Coupling constant (J=11.0 Hz) of the signal at δ 6.24 ppm is indicative of Z-C14b.

((1S,2R,3S,5S)-3-((Z)-2-Butoxyvinyl)-5-vinylcyclopentane-1,2-diyl)dimethanol (C15a)

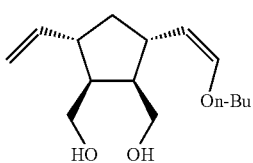

Following the general procedure, a solution of C1 (1.4 mg, 1.9 μmol, 2.0 mol %) in dichloromethane (195 μL) was transferred by syringe to a vial containing 5-norbornene-2-exo,3-exo-dimethanol C2 (15.0 mg, 0.0973 mmol, 1.00 equiv) and butyl vinyl ether (97.0 mg, 0.973 mmol, 10.0 equiv). The resulting solution was allowed to stir for 2 hours at 22° C. Analysis of the unpurified mixture revealed >98% consumption of C2, and the ROCM product was obtained in >98:2 Z:E ratio. The resulting brown oil was purified by silica gel chromatography (10% EtOAc in hexanes to 40% EtOAc in hexanes) to afford C15a (23.5 mg, 0.0924 mmol, 95% yield) as colorless oil; IR (CH₂Cl₂): 3414 (br), 2920 (m), 2987 (m), 1639 (w), 1455 (w), 1367 (w), 1135 (m), 1038 (s), 907 (m); ¹H NMR (400 MHz, CDCl₃): Z-isomer (major): δ 6.00 (1H, dd, J=6.2, 0.8 Hz), 5.76 (1H, ddd, J=17.2, 10.1, 8.1 Hz), 5.00 (1H, ddd, J=17.0, 1.8, 1.0 Hz), 4.94-4.89 (1H, m), 4.27 (1H, dd, J=9.1, 6.2 Hz), 3.77-3.70 (5H, m), 3.60 (1H, dd, J=11.9, 6.7 Hz), 2.79-2.70 (1H, m), 2.42 (1H, dq, J=11.2, 7.9 Hz), 2.03-1.90 (2H, m), 1.87-1.76 (1H, m), 1.68-1.52 (3H, m), 1.43-1.31 (2H, m), 1.28-1.15 (2H, m), 0.93 (3H, t, J=7.4 Hz); ¹³C NMR (100 MHz, CDCl₃): δ 145.7, 142.5, 113.8, 109.6, 72.5, 62.2, 61.1, 50.2, 48.5, 45.6, 39.6, 36.5, 31.8, 19.1, 13.9; HRMS [M+H—H₂O]⁺ calcd for C₁₅H₂₅O₂: 237.1860, found: 237.1855. Coupling constants (J=6.2 and J=6.2 Hz) of the signal at δ 6.00 and 4.27 ppm are indicative of Z-C15a.

(1S,2R,3R,5S)-3-((Z)-2-Ethylthio)vinyl)-5-vinylcyclopentane-1,2-diyl)dimethanol (C15b

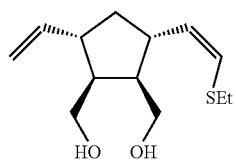

Following the general procedure, a solution of C1 (3.4 mg, 4.9 μmol, 5.0 mol %) in dichloromethane (195 μL) was transferred by syringe to a vial containing 5-norbornene-2-exo,3-exo-dimethanol C2 (15.0 mg, 0.0973 mmol, 1.00 equiv) and ethyl vinyl sulfide (86.0 mg, 0.973 mmol, 10.0 equiv). The resulting solution was allowed to stir for 12 hours at 40° C. Analysis of the unpurified mixture revealed 85% consumption of C2, and the ROCM product was obtained in 92:8 Z:E ratio. The resulting brown oil was purified by silica gel chromatography (10% EtOAc in hexanes to 40% EtOAc in hexanes) to afford C15b (18.9 mg, 0.0780 mmol, 80% yield) as colorless oil; IR (CH₂Cl₂): 3284 (br), 2919 (m), 2871 (w), 1639 (w), 1450 (m), 1047 (s), 1029 (s), 993 (s), 912 (s); ¹H NMR (400 MHz, CDCl₃): Z-isomer (major): δ 5.95 (1H, d, J=9.4 Hz), 5.75 (1H, ddd, J=17.1, 10.1, 8.1 Hz), 5.46 (1H, t, J=9.4 Hz), 5.02 (1H, dd, J=17.1, 1.0 Hz), 4.98-4.92 (1H, m,), 3.76-3.66 (4H, m), 3.27 (1H, s), 2.72-2.54 (3H, m), 2.37-2.26 (1H, m), 2.11-1.95 (3H, m), 1.31-1.25 (5H, m); ¹³C NMR (100 MHz, CDCl₃): δ 141.8, 132.8, 125.3, 114.4, 62.1, 61.7, 50.1, 48.6, 46.0, 41.7, 40.0, 28.1, 15.6; HRMS [M+H—H₂O]⁺ calcd for C₁₃H₂₁OS: 225.1313, found: 225.1324. Coupling constants (J=9.4 and J=9.4 Hz) of the signals at δ 5.95 and 5.46 ppm are indicative of Z-C15b.

((3R,4S,Z)-1-Butoxyhexa-1,5-diene-3,4-diyl)bis(oxy)bis(methylene)dibenzene (C16)

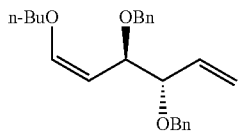

Following the general procedure, a solution of C1 (1.9 mg, 2.8 µmol, 5.0 mol %) in dichloromethane (113 µL) was transferred by syringe to a vial containing cyclobutene C8 (15.0 mg, 0.0563 mmol, 1.00 equiv) and butyl vinyl ether (56.0 mg, 0.563 mmol, 10.0 equiv). The resulting solution was allowed to stir for 12 hours at 40 OC. Analysis of the unpurified mixture revealed >98% consumption of C8, and the ROCM product was obtained in 88:12 Z:E ratio. The resulting brown oil was purified by silica gel chromatography (100% hexanes to 10% $Et_2O$ in hexanes) followed by passing through a plug of activated charcoal with 100% $Et_2O$ to afford C16 (16.7 mg, 0.0456 mmol, 81% yield) as a colorless oil; IR ($CH_2Cl_2$): 2957 (w), 2926 (m), 2858 (w), 1659 (m), 1454 (w), 1377 (m), 1085 (s), 1068 (s), 1028 (m); $^1$H NMR (400 MHz, $CDCl_3$): Z-isomer (major): δ 7.37-7.29 (8H, m), 7.26-7.22 (2H, m), 6.20 (1H, d, J=6.2 Hz), 5.87 (1H, ddd, J=17.1, 10.7, 7.5 Hz), 5.29-5.28 (1H, m), 5.27-5.22 (1H, m), 4.65 (2H, dd, J=12.3, 4.6 Hz), 4.55 (1H, dd, J=9.4, 3.7 Hz), 4.51-4.45 (3H, m), 3.91-3.87 (1H, m), 3.74 (2H, t, J=6.5 Hz), 1.60-1.52 (2H, m), 1.41-1.30 (2H, m), 0.91 (3H, t, J=7.4 Hz); $^{13}$C NMR (100 MHz, $CDCl_3$): δ 149.0, 139.5, 139.1, 135.8, 128.3, 128.2, 127.8, 127.7, 127.3, 127.2, 118.5, 103.3, 82.7, 74.5, 72.5, 70.5, 70.3, 32.0, 19.1, 14.0; HRMS $[M+NH_4]^+$ calcd for $C_{24}H_{34}NO_3$: 384.2539, found: 384.2544. Coupling constant (J=6.2 Hz) of the signal at δ 6.20 ppm is indicative of Z-C16.

(R, Z)-(1-Butoxy-3-methylpenta-1,4-dien-1,3-diyl)dibenzene (C17)

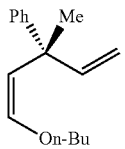

Following the general procedure, a solution of C1 (1.6 mg, 2.3 µmol, 2.0 mol %) in dichloromethane (230 µL) was transferred by syringe to a vial containing cyclopropene C28 (15.0 mg, 0.115 mmol, 1.00 equiv) and butyl vinyl ether (115 mg, 1.15 mmol, 10.0 equiv). The resulting solution was allowed to stir for 2 hours at 22° C. Analysis of the unpurified mixture revealed >98% consumption of C28, and the ROCM product was obtained in 88:12 Z:E ratio. The resulting brown oil was purified by silica gel chromatography (5% $Et_2O$ in hexanes to 10% $Et_2O$ in hexanes) to afford C17 (20.9 mg, 0.0907 mmol, 79% yield) as colorless oil; IR ($CH_2Cl_2$): 2960 (w), 2932 (w), 2872 (w), 1655 (m), 1372 (w), 1095 (s), 909 (m); $^1$H NMR (400 MHz, $CDCl_3$): Z-isomer (major): δ 7.42-7.37 (2H, m), 7.30-7.25 (2H, m), 7.19-7.14 (1H, m), 6.29 (1H, ddd, J=17.7, 10.2, 1.3 Hz), 5.95 (1H, dd, J=6.8, 1.3 Hz), 5.09-5.08 (1H, m), 5.05 (1H, dt, J=4.8, 1.4 Hz), 4.49 (1H, dd, J=6.8, 1.2 Hz), 3.66-3.60 (2H, m), 1.58 (3H, d, J=1.2 Hz), 1.47 (1H, d, J=6.9 Hz), 1.45-1.41 (1H, m), 1.29-1.19 (2H, m), 0.86 (3H, td, J=7.2, 1.0 Hz); $^{13}$C NMR (100 MHz, $CDCl_3$): δ 148.8, 146.1, 145.3, 128.0, 126.8, 125.7, 112.1, 110.8, 72.4, 45.9, 31.9, 27.4, 19.1, 13.9; HRMS $[M+H]^+$ calcd for $C_{1-6}H_{23}O$: 231.1749, found: 231.1752. Coupling constants (J=6.8 and J=6.8 Hz) of the signals at δ 5.95 and 4.49 ppm are indicative of Z-C17.

(1R,3S)— 1-((Z)-2-Butoxyvinyl)-2-tosyl-3-vinylisoindoline (C19)

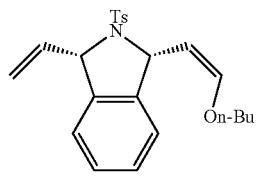

Following the general procedure, a solution of C1 (0.70 mg, 1.0 µmol, 2.0 mol %) in dichloromethane (100 µL) was transferred by syringe to a vial containing 7-azanorbornene C18 (15.0 mg, 0.0504 mmol, 1.00 equiv) and butyl vinyl ether (51.0 mg, 0.504 mmol, 10.0 equiv). The resulting solution was allowed to stir for 2 hours at 22° C. Analysis of the unpurified mixture revealed >98% consumption of C18, and the ROCM product was obtained in >98:2 Z:E ratio. The resulting brown oil was purified by silica gel chromatography (10% $Et_2O$ in hexanes to 40% $Et_2O$ in hexanes) to afford C19 (16.6 mg, 0.0418 mmol, 83% yield) as colorless oil; IR ($CH_2Cl_2$): 2957 (w), 2928 (m), 1661 (m), 1460 (w), 1352 (m), 1164 (s), 1095 (s), 1039 (s), 578 (s), 551 (s); $^1$H NMR (400 MHz, $CDCl_3$): Z-isomer (major): δ 7.80 (2H, d, J=8.3 Hz), 7.26-7.19 (4H, m), 7.17-7.00 (2H, m), 6.14 (1H, dd, J=6.1, 1.1 Hz), 5.99-5.90 (1H, m), 5.88 (1H, d, J=9.8 Hz), 5.42 (1H, dt, J=17.0, 1.0 Hz), 5.28 (1H, d, J=7.5 Hz), 5.22 (1H, dt, J=10.1, 1.0 Hz), 4.56 (1H, dd, J=8.9, 6.1 Hz), 3.97-3.81 (2H, m), 2.38 (3H, s), 1.75-1.68 (2H, m), 1.49 (2H, q, J=8.0 Hz), 1.00 (3H, t, J=7.4 Hz); $^{13}$C NMR (100 MHz, $CDCl_3$): δ 148.9, 139.5, 139.1, 135.8, 128.3, 128.2, 127.8, 127.7, 127.3, 127.2, 118.5, 103.3, 82.7, 74.5, 72.5, 70.5, 70.3, 32.0, 19.1, 14.0; HRMS $[M+H]^+$ calcd for $C_{23}H_{28}NO_3S$: 398.1784, found: 398.1792. Coupling constants (J=6.1 and J=6.1 Hz) of the signals at δ 6.14 and 4.56 ppm are indicative of Z-C19.

(Z)-3-((1R,3S)-3-Vinylcyclopentyl)prop-2-en-1-ol (C20)

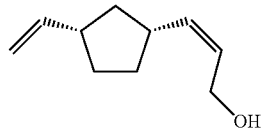

Following the general procedure, a solution of C1 (5.5 mg, 8.0 µmol, 5.0 mol %) in dichloromethane (320 µL) was transferred by syringe to a vial containing norbornene (15.0 mg, 0.159 mmol, 1.00 equiv) and allyl alcohol (93.0 mg, 1.59 mmol, 10.0 equiv). The resulting solution was allowed to stir for 2 hours at 22° C. Analysis of the unpurified mixture revealed >98% consumption of norbornene, and the ROCM product was obtained in 88:12 Z:E ratio. The resulting brown oil was purified by silica gel chromatography (10% Et$_2$O in hexanes to 30% Et$_2$O in hexanes) to afford C20 (16.4 mg, 0.108 mmol, 68% yield) as colorless oil; IR (CH$_2$Cl$_2$): 3319 (br), 2943 (m), 2864 (m), 1639 (w), 1447 (w), 1012 (s), 993 (s), 907 (s); $^1$H NMR (400 MHz, CDCl$_3$): Z-isomer (major): δ 5.79 (1H, ddd, J=17.4, 10.2, 7.5 Hz), 5.53 (1H, dt, J=10.8, 6.8 Hz), 5.43 (1H, dd, J=10.6, 9.4 Hz), 4.98 (1H, ddd, J=17.1, 1.9, 1.2 Hz), 4.88 (1H, ddd, J=10.2, 1.9, 1.0 Hz), 4.20 (2H, d, J=5.6 Hz), 2.89-2.76 (1H, m), 2.61-2.46 (1H, m), 1.96-1.89 (1H, m), 1.87-1.77 (2H, m), 1.51-1.32 (3H, m), 1.12 (1H, dt, J=12.4, 10.5 Hz); $^{13}$C NMR (100 MHz, C$_6$D$_6$): δ 143.1, 137.1, 128.4, 112.7, 58.7, 44.7, 41.4, 38.4, 32.8, 32.0; HRMS [M+H—H$_2$O]$^+$ calcd for C$_{10}$H$_{15}$: 135.1174, found: 135.1179. Coupling constants (J=10.8 and J=10.6 Hz) of the signals at δ 5.53 and 5.43 ppm are indicative of Z-C20.

For the synthesis of C20 from the ROCM reaction of norbornene and allyl(pinacolato)boronate, a solution of C1 (2.2 mg, 3.2 μmol, 2.0 mol %) in dichloromethane (320 μL) was transferred by syringe to a vial containing norbornene (15.0 mg, 0.159 mmol, 1.00 equiv) and allyl(pinacolato)boronate (268 mg, 1.59 mmol, 10.0 equiv). The resulting mixture was allowed to stir for 2 hours at 22° C. Analysis of the unpurified mixture revealed >98% consumption of norbornene; C22 was obtained in 90:10 Z:E ratio. The mixture was concentrated and dissolved in tetrahydrofuran (1 mL) and cooled to 0 OC in an ice bath. A 2.0 M aqueous solution of NaOH (880 μL, 1.75 mmol, 11.0 equiv) was added, followed by H$_2$O$_2$ (170 μL, 1.75 mmol, 11.0 equiv). The mixture was allowed to warm to 22° C. over 0.5 h. The solution was treated with a 2.0 M solution of HCl and washed with CH$_2$Cl$_2$ (3×1 mL). The organic layer was dried over MgSO$_4$, filtered and concentrated in vacuo to afford a yellow oil, which was purified by silica gel chromatography (10% Et$_2$O in hexanes to 30% Et$_2$O in hexanes) to obtain C20 (15.5 mg, 0.102 mmol, 64% yield) as colorless oil. The spectra data for this compound were identical to those reported above.

(Z)-4-((1R,3S)-3-Vinylcyclopentyl)but-3-en-1-ol (C21)

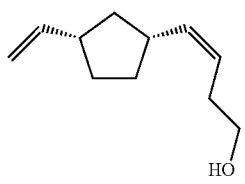

Following the general procedure, a solution of C1 (5.5 mg, 8.0 μmol, 5.0 mol %) in dichloromethane (320 μL) was transferred by syringe to a vial containing norbornene (15.0 mg, 0.159 mmol, 1.00 equiv) and 3-buten-1-ol (115 mg, 1.59 mmol, 10.0 equiv). The resulting solution was allowed to stir for 2 hours at 22° C. Analysis of the unpurified mixture revealed >98% consumption of norbornene, and the product was obtained in 87:13 Z:E ratio. The resulting brown oil was purified by silica gel chromatography (5% Et$_2$O in hexanes to 10% Et$_2$O in hexanes) to afford C21 (23.3 mg, 0.140 mmol, 88% yield) as colorless oil; IR (CH$_2$Cl$_2$): 3334 (br), 2944 (s), 2864 (m), 1639 (w), 1447 (w), 1045 (s), 907 (s); $^1$H NMR (400 MHz, CDCl$_3$): Z-isomer (major): δ 5.80 (1H, ddd, J=17.3, 10.1, 7.5 Hz), 5.50 (1H, t, J=10.1 Hz), 5.29 (1H, dt, J=10.8, 7.5 Hz), 4.97 (1H, dd, J=17.1, 1.1 Hz), 4.91-4.83 (1H, m), 3.63 (2H, t, J=6.3 Hz), 2.90-2.76 (1H, m), 2.62-2.47 (1H, m), 2.34 (2H, qd, J=6.5, 1.3 Hz), 1.99-1.87 (1H, m), 1.86-1.78 (2H, m), 1.49-1.35 (3H, m), 1.18-1.04 (1H, m); $^{13}$C NMR (100 MHz, CDCl$_3$): δ 143.3, 138.8, 123.9, 112.6, 62.5, 44.6, 41.3, 38.3, 32.8, 31.9, 31.2; HRMS [M+H]$^+$ calcd for C$_{11}$H$_{19}$O: 167.1436, found: 167.1431. Coupling constants (J=10.8 and J=10.1 Hz) of the signals at 5.50 and 5.29 ppm are indicative of Z-C21.

(1R,3S)-1-((Z)-4-butoxybut-1-enyl)-3-vinylcyclopentane (C24)

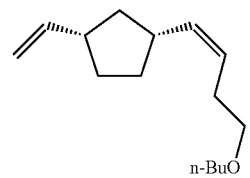

Following the general procedure, a solution of C1 (5.5 mg, 8.0 μmol, 5.0 mol %) in dichloromethane (320 μL) was transferred by syringe to a vial containing norbornene (15.0 mg, 0.159 mmol, 1.00 equiv) and 4-butoxybut-1-ene (204 mg, 1.59 mmol, 10.0 equiv). The resulting solution was allowed to stir for 2 hours at 22° C. Analysis of the unpurified mixture revealed >98% consumption of norbornene, and the product was obtained in 87:13 Z:E ratio. The resulting brown oil was purified by silica gel chromatography (100% hexanes to 10% Et$_2$O in hexanes) to afford C24 (23.4 mg, 0.105 mmol, 66% yield) as colorless oil; IR (CH$_2$Cl$_2$): 3078 (s), 2861 (s), 1640 (w), 1464 (w), 1361 (w), 908 (m); $^1$H NMR (400 MHz, CDCl$_3$): Z-isomer (major): δ 5.80 (1H, ddd, J=17.3, 9.9, 7.6 Hz), 5.39 (1H, t, J=9.9 Hz), 5.30 (1H, dt, J=10.4, 7.1 Hz), 4.97 (1H, d, J=17.2 Hz), 4.87 (1H, d, J=10.2 Hz), 3.47-3.36 (4H, m), 2.87-2.76 (1H, m), 2.58-2.46 (1H, m), 2.34 (2H, q, J=6.9 Hz), 1.96-1.87 (1H, m), 1.82-1.80 (2H, m), 1.62-1.50 (2H, m), 1.40-1.30 (4H, m), 1.14-1.04 (1H, m), 0.92 (3H, t, J=7.3 Hz); $^{13}$C NMR (100 MHz, C$_6$D$_6$): δ 143.4, 136.9, 125.2, 112.6, 71.0, 70.8, 44.8, 41.4, 38.5, 32.8, 32.4, 32.1, 28.9, 19.8, 14.1; HRMS [M+H]$^+$ calcd for C$_{15}$H$_{27}$O: 223.2062, found: 223.2066. Coupling constants (J=10.4 and J=9.9 Hz) of the signals at 5.39 and 5.30 ppm are indicative of Z-C24.

((1S,2R,3R,5S)-3-((R,Z)-3-Hydroxy-3-phenylprop-1-enyl)-5-vinylcyclopentane-1,2-diyl)dimethanol (C26)

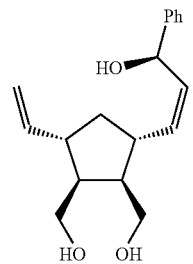 [SMILES: C=C[C@@H]1C[C@H](/C=C\[C@@H](O)c2ccccc2)[C@@H](CO)[C@H]1CO]

Following the general procedure, a solution of C1 (3.4 mg, 4.9 μmol, 5.0 mol %) in dichloromethane (195 μL) was transferred by syringe to a vial containing 5-norbornene-2-exo,3-exo-dimethanol 2 (15.0 mg, 0.0973 mmol, 1.00 equiv) and (R)-1-phenyl-2-propen-1-ol C25 (65.2 mg, 0.486 mmol, 5.0 equiv). The resulting solution was allowed to stir for 8 hours at 22° C. Analysis of the unpurified mixture revealed >98% consumption of C2, and the ROCM product was obtained in >98:2 Z:E ratio. The resulting brown oil was purified by silica gel chromatography (20% EtOAc in hexanes to 80% EtOAc in hexanes) to afford C26 (18.8 mg, 0.0652 mmol, 67% yield) as colorless oil; IR (CH$_2$Cl$_2$): 3299 (br), 2961 (w), 2921 (m), 2856 (m), 1639 (w), 1492 (m), 1021 (m), 913 (m); $^1$H NMR (400 MHz, CDCl$_3$): Z-isomer (major): δ 7.42-7.33 (4H, m), 7.31-7.26 (1H, m), 5.78 (1H, ddd, J=17.6, 10.2, 8.2 Hz), 5.72 (1H, dd, J=10.8, 8.4 Hz), 5.55 (1H, d, J=7.9 Hz), 5.43 (1H, t, J=10.5 Hz), 5.04 (1H, ddt, J=17.1, 1.8, 1.0 Hz), 4.99-4.92 (1H, m), 4.20 (1H, s), 3.82 (3H, s); 3.69-3.50 (2H, m), 3.14-3.03 (2H, m), 2.62-2.52 (1H, m), 2.03-1.94 (2H, m), 1.33-1.23 (2H, m); $^{13}$C NMR (100 MHz, CDCl$_3$): δ 143.7, 142.0, 136.6, 132.9, 128.7, 127.7, 126.1, 114.2, 69.7, 61.9, 60.1, 50.1, 48.4, 45.6, 39.9, 39.5; HRMS [M+H—H$_2$O]$^+$ calcd for C$_{18}$H$_{23}$O$_2$: 271.1698, found: 271.1701; diastereomeric ratio was established by HPLC analysis in comparison with authentic racemic material prepared from C2 and rac-1-phenyl-2-propen-1-ol under standard conditions (97:03 e.r. shown for C26; after correction for 96:04 e.r. of the starting material, results in a diastereoselectivity of >98:02 d.r.; Daicel Chiralpak OD-H column (97:3 hexanes:i-PrOH, 0.5 mL/min, 220 nm) was used.) Coupling constants (J=10.8 and J=10.5 Hz) of the signals at 5.72 and 5.43 ppm are indicative of Z-C26.

(w), 1491 (w), 1446 (w), 1005 (w), 914 (w); $^1$H NMR (400 MHz, CDCl$_3$): Z-isomer (major): δ 7.37 (2H, dd, J=8.1, 1.0 Hz), 7.34-7.26 (3H, m), 7.26-7.17 (4H, m), 7.06-7.04 (2H, m), 6.34 (1H, dd, J=17.3, 10.5 Hz), 5.90 (1H, dd, J=11.5, 0.8 Hz), 5.68 (1H, dd, J=11.5, 9.9 Hz), 5.16 (2H, ddd, J=18.4, 13.9, 1.0 Hz), 5.08 (1H, d, J=9.8 Hz), 1.58 (3H, s); $^{13}$C NMR (100 MHz, CDCl$_3$): δ 148.0, 146.2, 142.9, 139.1, 133.1, 128.6, 128.4, 127.6, 127.3, 126.5, 126.3, 112.9, 69.3, 47.5, 29.3; HRMS [M+H—H$_2$O]$^+$ calcd for C$_{19}$H$_{19}$: 247.1487, found: 247.1485. Coupling constants (J=11.5 and J=11.5 Hz) of the signals at δ 5.90 and 5.68 ppm are indicative of Z-C29.

Stereochemical Identity of ROCM Products C26 and C29

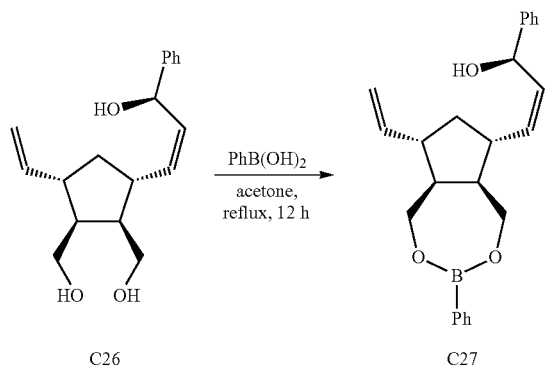

| Peak # | Retention time (min) | Area | Area % | Peak # | Retention time (min) | Area | Area % |
|---|---|---|---|---|---|---|---|
| 1 | 80.33 | 23060079 | 50.39 | 1 | 79.87 | 19429049 | 97.06 |
| 2 | 132.84 | 22706960 | 49.61 | 2 | 133.84 | 588688 | 2.94 |

(1R,4R,Z)-4-Methyl-1,4-diphenylhexa-2,5-dien-1-ol (C29)

(R,Z)-1-Phenyl-3-((5 aR,6R,8S,8aS)-3-phenyl-8-vinylhexahydro-1H cyclopenta[e][1,3,2]dioxaborepin-6-yl)prop-2-en-1-ol(C27)

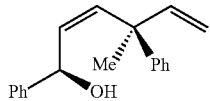 [SMILES: C=C[C@](C)(/C=C\[C@@H](O)c1ccccc1)c1ccccc1]

Following the general procedure, a solution of C1 (3.9 mg, 5.6 μmol, 5.0 mol %) in dichloromethane (224 μL) was transferred by syringe to a vial containing (R)-1-phenyl-2-propen-1-ol C25 (15.0 mg, 0.112 mmol, 1.00 equiv) and cyclopropene C28 (29.0 mg, 0.224 mmol, 2.00 equiv). The resulting solution was allowed to stir for 4 hours at 22° C. Analysis of the unpurified mixture revealed >98% consumption of C28, and the product was obtained in 91:9 Z:E ratio. The resulting brown oil was purified by silica gel chromatography (10% Et$_2$O in hexanes to 20% Et$_2$O in hexanes) after which it was passed through a plug of activated charcoal with 50% Et$_2$O in pentane to afford 29 (23.1 mg, 0.0870 mmol, 78% yield) as colorless oil; IR (CH$_2$Cl$_2$): 3408 (br), 2961 (w), 2924 (m), 2852 (w), 1616 (w), 1579

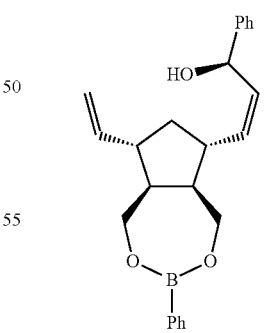

A previously reported procedure was adopted (J. M. Sugihara, C. M. Bowman, *J. Am. Chem. Soc.* 1958, 80, 2443-2446). A flame-dried round-bottom flask, equipped with a stir bar and reflux condenser, was charged with C26 (20.0 mg, 0.069 mmol, 1.00 equiv), phenylboronic acid (20.0 mg, 0.069 mmol, 1.00 equiv) and acetone (0.5 mL). The solution was allowed to stir at reflux for 12 hours. The resulting mixture was concentrated in vacuo to afford C27 as yellow solid, which was recrystallized from hexane, affording colorless crystals (24.4 mg, 0.0652 mmol, 94% yield); mp: 84-86° C.; IR (CH$_2$Cl$_2$): 3386 (br), 3075 (w), 2919 (w), 1640 (w), 1599 (w), 1479 (m), 1439 (m), 1141 (m), 1030 (m), 915 (w); $^1$H NMR (400 MHz, CDCl$_3$): Z-isomer (major): δ 7.84-7.79 (2H, m), 7.44-7.37 (1H, m), 7.36-7.32 (2H, m), 7.32-7.30 (3H, m), 7.26-7.25 (2H, m), 5.80-5.69 (2H, m), 5.52-5.47 (1H, m), 5.43 (1H, t, J=10.3 Hz), 5.08 (1H, ddd, J=17.1, 1.7, 1.0 Hz), 5.01 (1H, ddd, J=10.1, 1.7, 0.6 Hz), 4.42 (1H, d, J=12.2 Hz), 4.37 (1H, d, J=12.1 Hz), 4.30-4.22 (1H, m), 4.20-4.13 (1H, m), 2.98-2.84 (1H, m), 2.58-2.44 (1H, m), 2.27 (2H, s), 2.15-2.09 (1H, m), 1.86 (1H, dt, J=11.6, 5.7 Hz), 1.34 (1H, q, J=12.0 Hz); $^{13}$C NMR (100 MHz, CDCl$_3$): δ 143.7, 140.6, 134.4, 134.0, 133.7, 130.7, 128.7, 127.7, 127.6, 126.1, 115.3, 69.9, 64.3, 64.1, 49.6, 48.4, 46.3, 40.3, 39.9; HRMS [M+H—H$_2$O]$^+$ calcd for C$_{24}$H$_{26}$BO$_2$: 357.2026, found: 357.2021. Coupling constant (J=10.3 Hz) of the signal at δ 5.43 ppm is indicative of Z-C27.

Hz), 7.33-7.28 (2H, m), 7.17 (2H, t, J=7.6 Hz), 7.12-7.05 (1H, m), 6.49 (1H, d, J=13.2 Hz), 6.23 (1H, d, J=12.8 Hz), 6.20 (1H, dd, J=17.2, 10.8 Hz), 5.09 (1H, d, J=10.6 Hz), 5.05 (1H, d, J=17.4 Hz), 1.55 (s, 3H); $^{13}$C NMR (100 MHz, CDCl$_3$): δ 194.9, 146.2, 146.0, 144.4, 137.4, 133.1, 128.9, 128.5, 128.2, 127.2, 126.9, 126.3, 113.7, 48.9, 26.8; HRMS [M+H]$^+$ calcd for C$_{19}$H$_{19}$O: 263.1436, found: 263.1438; diastereomeric ratio was established by HPLC analysis in comparison with authentic material prepared according to a previously reported procedure (A. H. Hoveyda, P. J. Lombardi, R. V. O'Brien, A. R. Zhugralin, *J. Am. Chem. Soc.* 2009 131, 8378-8379) where the absolute stereochemistry of the major E-enone isomers had been formerly established [89.5:10.5 e.r. shown for C31a; after correction for 96:4 e.r. of the starting material, diastereoselectivity is measured to be 93:7 d.r.; Daicel Chiralpak OD-H column (99.5:0.5 hexanes:i-PrOH, 0.7 mL/min, 254 nm) was used]. Coupling constants (J=13.2 and J=12.8 Hz) of the signals at δ 6.49 and 6.23 ppm are indicative of Z-C31a.

| Peak # | Retention time (min) | Area | Area % | Peak # | Retention time (min) | Area | Area % |
|---|---|---|---|---|---|---|---|
| 1 | 33.10 | 14469688 | 7.42 | 1 | 30.92 | 296306 | 2.26 |
| 2 | 36.03 | 175303050 | 89.84 | 2 | 34.38 | 1131722 | 8.62 |
| 3 | 49.26 | 4660845 | 2.39 | 3 | 46.28 | 10474729 | 79.80 |
| 4 | 54.19 | 688395 | 0.35 | 4 | 51.05 | 1223446 | 9.32 |

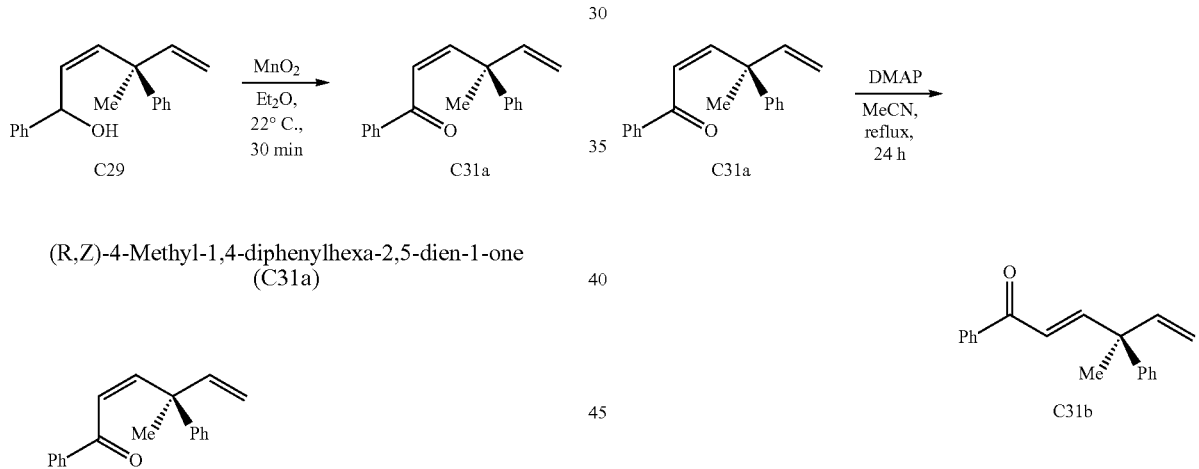

(R,Z)-4-Methyl-1,4-diphenylhexa-2,5-dien-1-one (C31a)

A previously reported procedure was adopted (A. H. Hoveyda, P. J. Lombardi, R. V. O'Brien, A. R. Zhugralin, *J. Am. Chem. Soc.* 2009 131, 8378-8379). An oven-dried vial equipped with a stir bar was charged with C29 (16.0 mg, 0.0610 mmol, 1.00 equiv). Diethyl ether (1.8 mL) was added through a syringe followed by manganese dioxide (160 mg, 10 mg/mg of substrate, ~30 equiv). The resulting suspension was allowed to stir vigorously until the reaction was determined to be complete according to TLC analysis (30 min). The mixture was filtered through a short pad of celite, which was then washed with diethyl ether (3×5.0 mL). The volatiles were removed in vacuo, affording yellow oil which was purified by silica gel chromatography (5% Et$_2$O in hexanes). C31a was obtained in 91:09 Z/E ratio and as colorless oil (14.3 mg, 0.0550 mmol, 90% yield); IR (CH$_2$Cl$_2$): 2965 (w), 2926 (w), 1670 (s), 1580 (w), 1492 (w), 1448 (m), 1007 (m), 919 (w); $^1$H NMR (400 MHz, CDCl$_3$): Z-isomer (major): δ 7.84-7.79 (2H, m), 7.55-7.49 (1H, m), 7.40 (2H, t, J=7.7

Z-enone C31a was isomerized to its corresponding E isomer through a modified reported procedure (D. Könning, W. Hiller, M. Christmann, *Org. Lett.* 2012, 14, 5258-5261). An oven-dried vial equipped with a stir bar was charged with Z-C31a (12.0 mg, 0.046 mmol, 1.00 equiv, 91:09 Z/E). Dry MeCN (0.2 mL) was added through syringe followed by N,N-dimethylaminopyridine (1.1 mg, 5.6 μmol, 20 mol %). The resulting solution was allowed to reflux for 24 hours in a sealed vial. After addition of H$_2$O, the mixture was washed withEt$_2$O (3×2.0 mL). The combined organic layers were dried over anhydrous MgSO$_4$, filtered and concentrated in vacuo to afford E-C31b in >98:2 E:Z as yellow oil, which was purified by silica gel chromatography (5% Et$_2$O in hexanes) to afford colorless oil (11.3 mg, 0.0430 mmol, 94% yield). Comparison of the HPLC retention times for the E isomers before and after isomerization established the absolute configuration at the all-carbon quaternary stereogenic center of the product [Daicel Chiralpak OD-H column (99.5:0.5 hexanes:i-PrOH, 0.7 mL/min 254 nm) was used].

| Peak # | Retention time (min) | Area | Area % | Peak # | Retention time (min) | Area | Area % |
|---|---|---|---|---|---|---|---|
| 1 | 30.92 | 296306 | 2.26 | 1 | 34.54 | 19774970 | 83.09 |
| 2 | 34.38 | 1131722 | 8.62 | 2 | 38.33 | 4024481 | 16.91 |
| 3 | 46.28 | 10474729 | 79.80 | — | — | — | — |
| 4 | 51.05 | 1223446 | 9.32 | — | — | — | — |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A compound, wherein the compound has the structure of formula I-c:

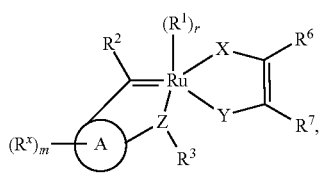

I-c wherein:
each of $R^6$ and $R^7$ is independently R, —CN, halogen, —OR, —OC(O)R, —OSi(R)$_3$, —SR, —S(O)R, —S(O)$_2$R, —NO$_2$, —N(R')$_2$, —NR'C(O)R, —NR'C(O)OR, —NR'C(O)N(R')$_2$, —NR'SO$_2$R, —NR'SO$_2$N(R')$_2$, —NR'OR, —SeR, —Si(R)$_3$, or:
  $R^6$ and $R^7$ are optionally taken together with their intervening atoms to form an optionally substituted 3-10 membered, saturated, partially unsaturated or aryl monocyclic or bicyclic ring having 0-4 heteroatoms independently selected from nitrogen, oxygen, or sulfur;

or wherein the compound has the structure of formula I-d:

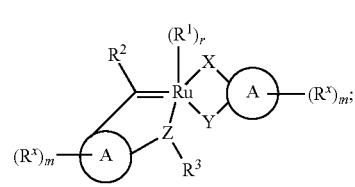

I-d or wherein the compound has the structure of formula I-e:

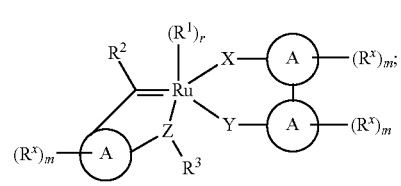

I-e or wherein the compound has the structure of formula I-f:

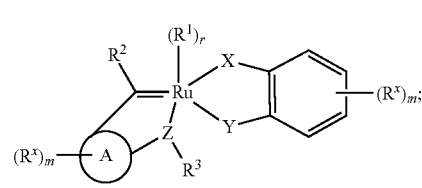

I-f wherein
$R^1$ is a nitrogen-containing heterocyclic carbene;
r is 1;
X and Y is —S—;
Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;
each $R^x$ is independently halogen, R, —CN, —C(O)N(R')$_2$, —C(O)R, —C(O)OR, —OR, —OC(O)R, —OC(O)OR, —OC(O)N(R')$_2$, —OSi(R)$_3$, —N(R')$_2$, —N(R')$_3$$^+$, —NR'C(O)R, —NR'C(O)OR, —NR'C(O)N(R')$_2$, —NR'SO$_2$R, —NR'SO$_2$N(R')$_2$, —NR'OR, —NO$_2$, —Si(R)$_3$, —P(R)$_2$, —P(O)(R)$_2$, —P(O)(OR)$_2$, —SR, —SC(O)R, —S(O)R, —SO$_2$R, —SO$_3$R, —SO$_2$N(R')$_2$, or —SeR;
each R' is independently R, —C(O)R, —C(O)N(R)$_2$, —C(O)OR, —SO$_2$R, —SO$_2$N(R)$_2$, —P(O)(OR)$_2$, or —OR; and
each R is independently hydrogen or an optionally substituted group selected from C$_{1-20}$ aliphatic, C$_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, saturated, partially unsaturated, or aryl ring having, in addition to the intervening atoms, 0-4 heteroatoms independently selected from nitrogen, oxygen, or sulfur;

m is 0-6;

$R^2$ is $R^x$;

$R^3$ is hydrogen or an optionally substituted group selected from $C_{1-20}$ aliphatic, $C_{1-20}$ heteroaliphatic, phenyl, a 3-7 membered saturated or partially unsaturated carbocyclic ring, a 5-6 membered monocyclic heteroaryl ring having 1-4 heteroatoms independently selected from nitrogen, oxygen, or sulfur, or a 3-7 membered saturated or partially unsaturated heterocyclic ring having 1-3 heteroatoms independently selected from nitrogen, oxygen, or sulfur; and Z is —O— or —S—.

2. The compound of claim 1, wherein Z is —O—.

3. The compound of claim 1, wherein the compound is selected from:

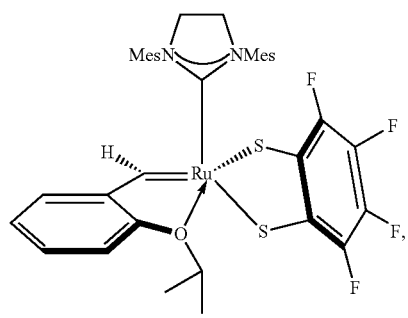

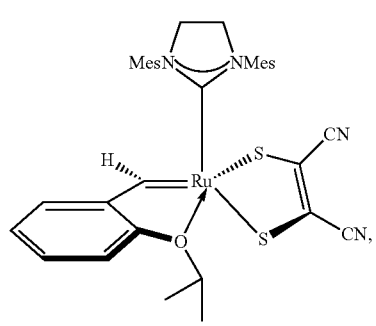

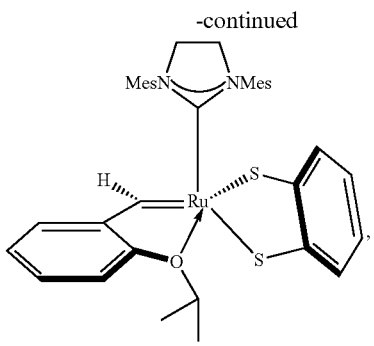

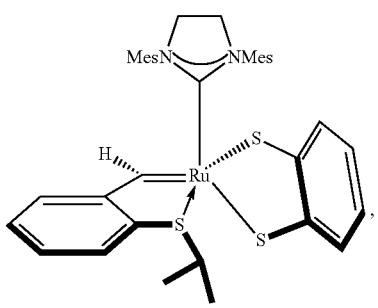

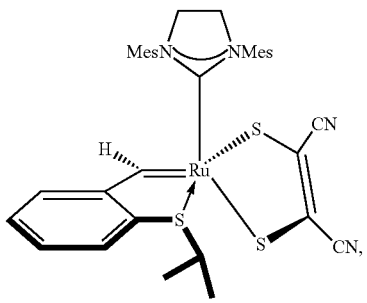

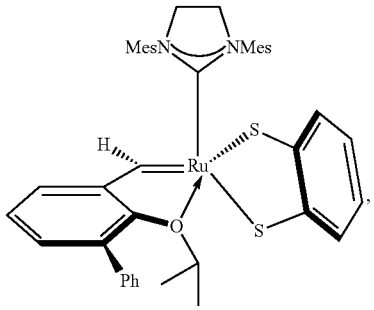

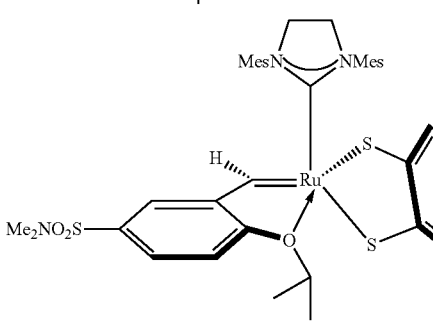

295
-continued

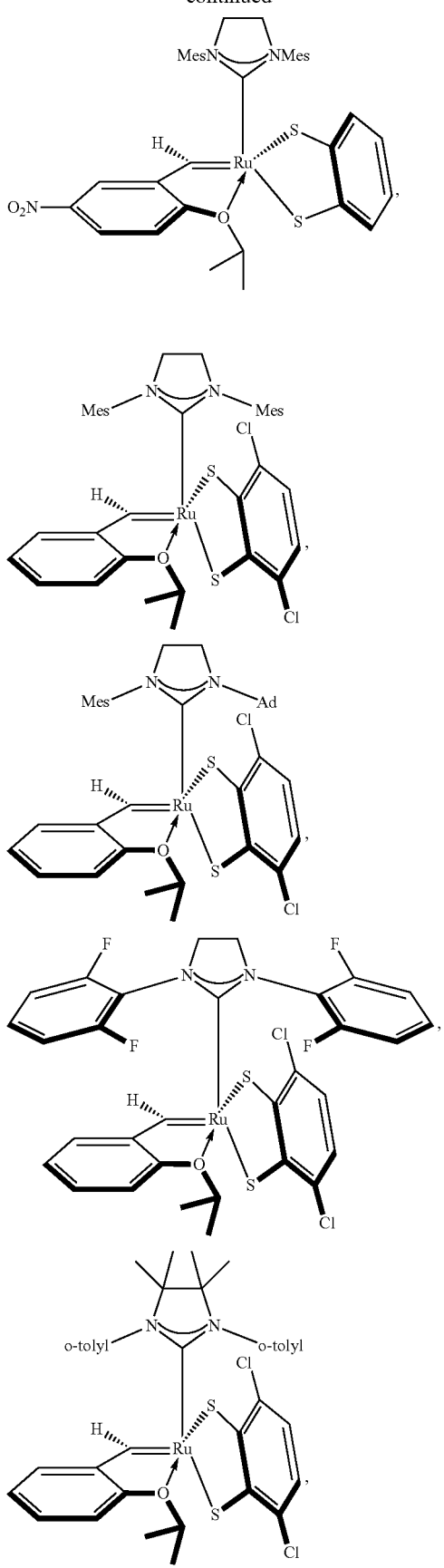

296
-continued

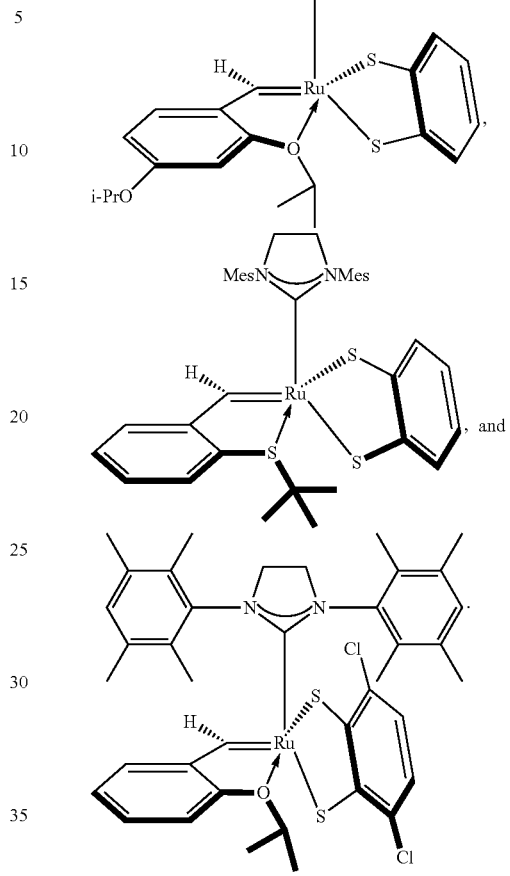

4. The compound of claim 1, wherein the compound is dimerized or polymerized.

5. The compound of claim 1, wherein the compound is linked to a tag or a solid support.

6. A method for performing a metathesis reaction, comprising providing a compound of claim 1.

7. The compound of claim 1, wherein one $R^x$ is —$NO_2$.

8. The compound of claim 1, wherein

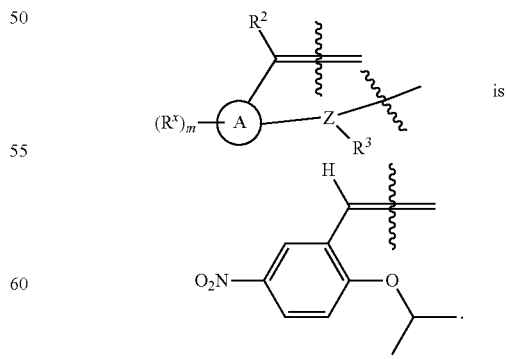

9. The compound of claim 1, wherein one $R^x$ is —$SO_2N(R')_2$, —$SO_2R$, —$S(O)R$, —$C(O)R$, —$C(O)N(R')_2$, or —$NR'SO_2R$.

10. The compound of claim 1, wherein one $R^x$ is —SO$_2$N(R')$_2$.

11. The compound of claim 1, wherein

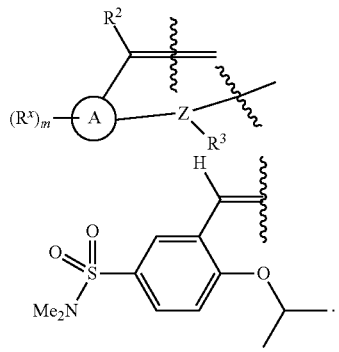

is

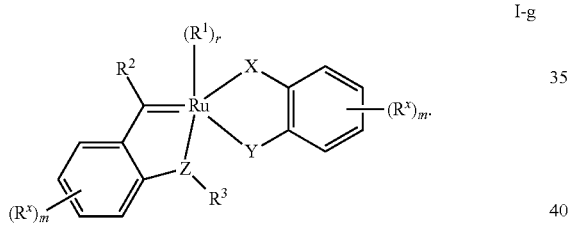

12. The compound of claim 1, wherein one $R^x$ is —NR'C(O)N(R')$_2$.

13. The compound of claim 1, wherein one $R^x$ is —NHC(O)R.

14. The compound of claim 1, wherein one $R^x$ is —NHC(O)C$_6$F$_5$, —NHC(O)CF$_3$, —NHC(O)C(O)OEt, —NHC(O)Ot—Bu, —NHC(O)Oi—Bu, or —NHC(O)C$_{15}$H$_{31}$.

15. The compound of claim 1, wherein the compound has the structure of formula I-g:

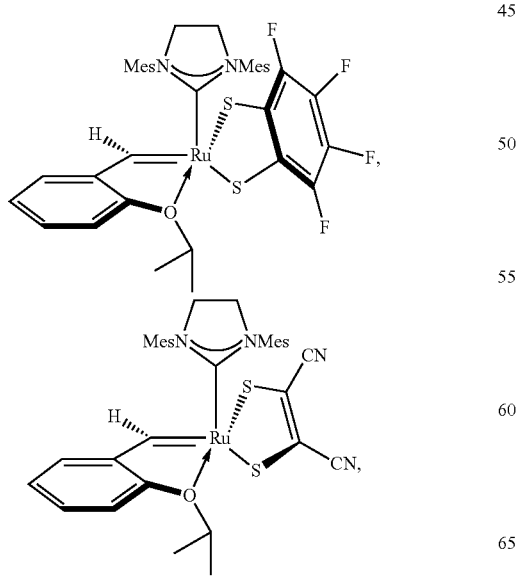

I-g

16. A compound selected from:

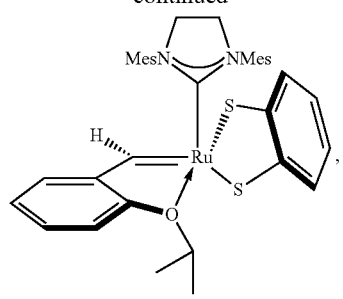

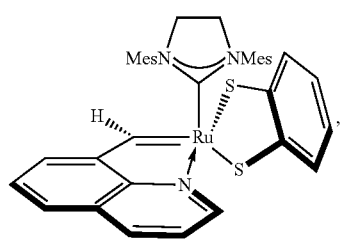

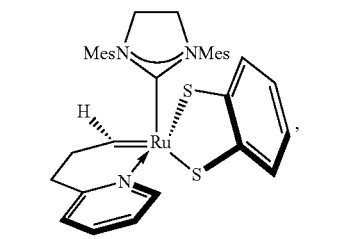

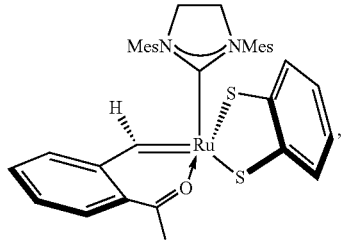

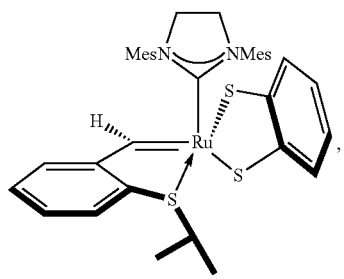

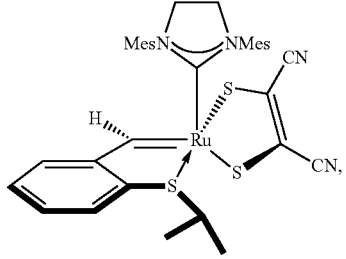

299
-continued
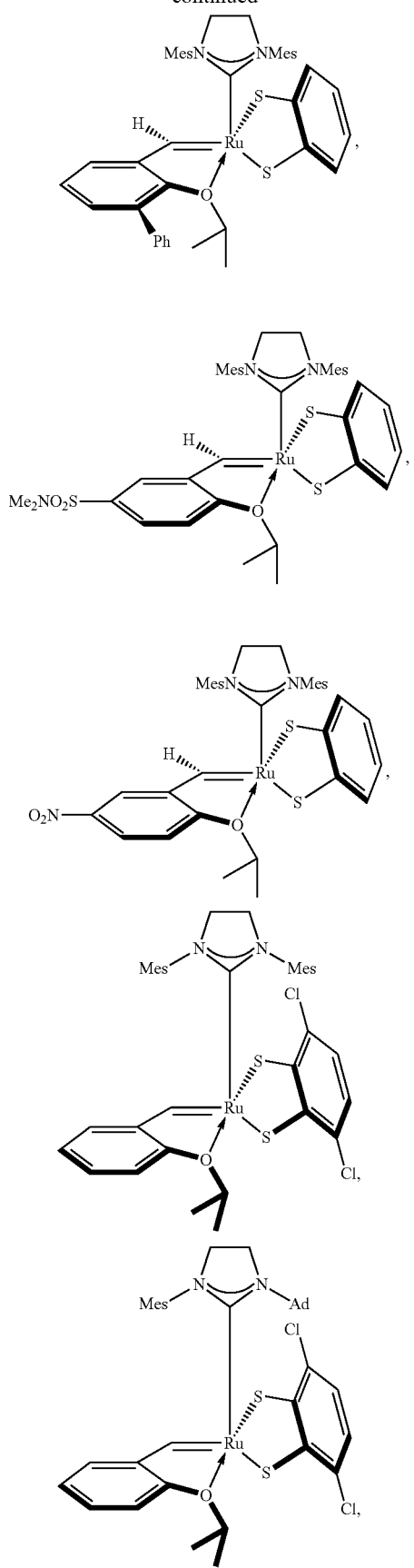
300
-continued
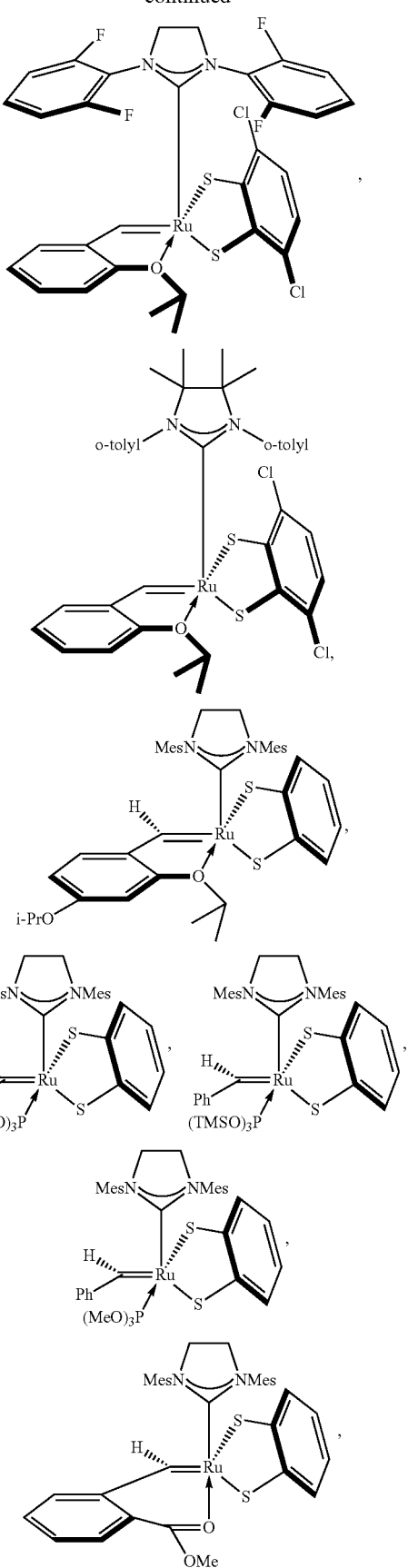

301
-continued
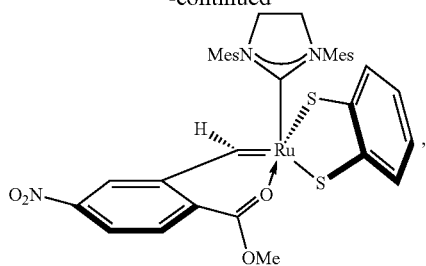
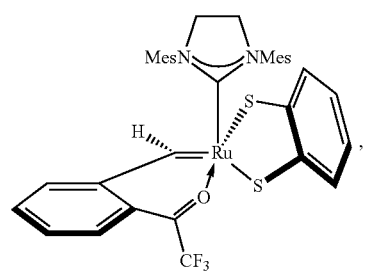
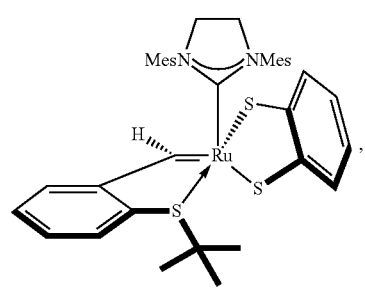
302
-continued
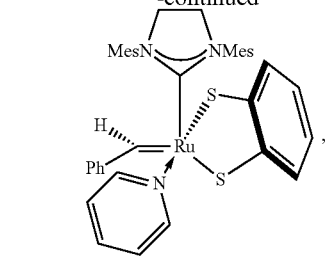
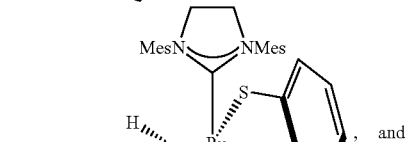
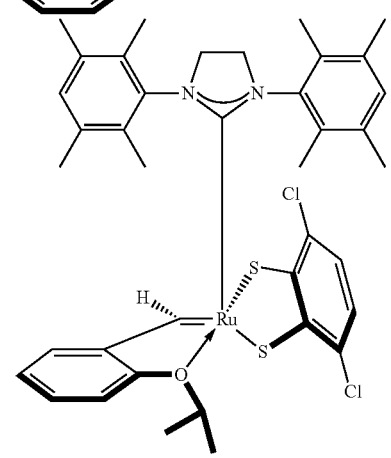
* * * * *